(12) United States Patent
Oguro et al.

(10) Patent No.: US 8,304,557 B2
(45) Date of Patent: Nov. 6, 2012

(54) FUSED HETEROCYCLE DERIVATIVES AND USE THEREOF

(75) Inventors: Yuya Oguro, Tsukuba (JP); Shinichi Imamura, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 781 days.

(21) Appl. No.: 12/133,063

(22) Filed: Jun. 4, 2008

(65) Prior Publication Data

US 2009/0163488 A1   Jun. 25, 2009

(30) Foreign Application Priority Data

Jun. 5, 2007 (JP) ................................ 2007-149781
Aug. 29, 2007 (JP) ................................ 2007-223284

(51) Int. Cl.
C07D 277/62 (2006.01)
A61K 31/428 (2006.01)
(52) U.S. Cl. ........................................ 548/178; 514/367
(58) Field of Classification Search .................. 548/178; 514/367
See application file for complete search history.

(56) References Cited

U.S. PATENT DOCUMENTS

| | | | |
|---|---|---|---|
| 2,399,026 A | 4/1946 | Henzi et al. | |
| 4,096,264 A | 6/1978 | Bochis et al. | |
| 6,797,823 B1 | 9/2004 | Kubo et al. | |
| 2002/0133005 A1 | 9/2002 | Iino et al. | |
| 2004/0058972 A1* | 3/2004 | Davis ............................ | 514/394 |
| 2004/0082583 A1* | 4/2004 | Cheung et al. ................ | 514/243 |
| 2006/0160832 A1 | 7/2006 | Funahashi et al. | |
| 2006/0241301 A1 | 10/2006 | Hoelzemann et al. | |
| 2007/0021456 A1* | 1/2007 | Mitjans et al. ................ | 514/291 |
| 2011/0046169 A1 | 2/2011 | Miyamoto et al. | |

FOREIGN PATENT DOCUMENTS

| | | |
|---|---|---|
| JP | 52-73896 | 6/1977 |
| JP | 2008-189659 | 8/2008 |
| WO | 98/35958 | 8/1998 |
| WO | 99/10325 | 3/1999 |
| WO | 99/16438 | 4/1999 |
| WO | 00/41698 | 7/2000 |
| WO | 00/42012 | 7/2000 |
| WO | 01/02359 | 1/2001 |
| WO | 01/32651 | 5/2001 |
| WO | 01/57008 | 8/2001 |
| WO | 01/60814 | 8/2001 |
| WO | 01/66539 | 9/2001 |
| WO | 01/66540 | 9/2001 |
| WO | 02/24680 | 3/2002 |
| WO | 02/44156 | 6/2002 |
| WO | 02/062763 | 8/2002 |
| WO | 02/094808 | 11/2002 |
| WO | 03/022833 | 3/2003 |
| WO | 03/022836 | 3/2003 |
| WO | 03/022837 | 3/2003 |
| WO | 03/022838 | 3/2003 |
| WO | 03/074515 | 9/2003 |
| WO | 03/082272 | 10/2003 |
| WO | 2004/087153 | 10/2004 |
| WO | 2005/019192 | 3/2005 |
| WO | WO 2005019216 | * 3/2005 |
| WO | WO 20050192216 | * 3/2005 |
| WO | 2005/032548 | 4/2005 |
| WO | 2005/037273 | 4/2005 |
| WO | 2005/112932 | 12/2005 |
| WO | 2006/030031 | 3/2006 |
| WO | 2006/071035 | 7/2006 |
| WO | 2006/076376 | 7/2006 |
| WO | 2007/007886 | 1/2007 |
| WO | 2007/030377 | 3/2007 |
| WO | 2007/041365 | 4/2007 |
| WO | 2007/058482 | 5/2007 |
| WO | 2007/121484 | 10/2007 |

(Continued)

OTHER PUBLICATIONS

Cannon, "Analog Design" in Burgers Medicinal Chemistry and Drug Discovery, 6th ed. 2003, Wiley, pp. 687-714.*

(Continued)

Primary Examiner — Robert Havlin
(74) Attorney, Agent, or Firm — Hamre, Schumann, Mueller & Larson, P.C.

(57) ABSTRACT

A compound represented by the formula (I):

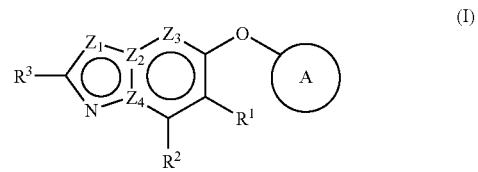

wherein $Z_1$, $Z_2$, $Z_3$ and $Z_4$ are the following combination, $(Z_1,Z_2,Z_3,Z_4)=(CR^4,N,CR^5,C)$, $(N,N,CR^5,C)$, $(N,C,CR^5,N)$, $(S,C,CR^5,C)$ or $(S,C,N,C)$; $R^1$ and $R^2$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom; $R^3$ is an amino optionally having substituent(s); $R^4$ and $R^5$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom; $R^3$ and $R^4$ optionally form a ring optionally having substituent(s); and a group represented by the formula

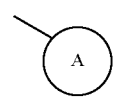

is a cyclic group optionally having substituent(s), or a salt thereof.

6 Claims, No Drawings

FOREIGN PATENT DOCUMENTS

| WO | 2008/016131 | 2/2008 |
|---|---|---|
| WO | 2008/016192 | 2/2008 |
| WO | 2008/084873 | 7/2008 |
| WO | 2008/150015 | 12/2008 |
| WO | 2009/025358 | 2/2009 |
| WO | 2009/028629 | 3/2009 |
| WO | 2009/028655 | 3/2009 |

OTHER PUBLICATIONS

International Search Report (Form PCT/ISA/210) issued in International Application No. PCT/JP2008/065011, mailed Sep. 16, 2008—4 pages.

STN Search Result by Applicants—466 pages.

Lowinger, et al., "Design and Discovery of Small Molecules Targeting Raf-1 Kinase", Current Pharmaceutical Design, vol. 8, 2002, pp. 2269-2278.

Aly, et al., "New polymer syntheses IV. Synthesis and characterization of new polyamides containing bis-benzthiazolyl sulphone units in the main chain" High Perform. Polym., vol. 8, No. 2, 1996, pp. 307-314.

Takubo, et al., "Syntheses of Diaryl Sulfone. IV.", Yakugaku Zasshi, vol. 78, 1958, pp. 482-485.

Srivastava, et al., "Studies in antiparasitic agents: Part 20—Synthesis of probenzimidazoles, benzimidazoles and pyrimido[1,2-α]benzimidazoles as possible anthelmintics", Indian Journal of Chemistry, Section B: Organic Chemistry including Medicinal Chemistry, vol. 32B, No. 10, Oct. 1993, pp. 1035-1044.

Singh, et al., "Chemotherapy of Filariasis—On the Search of New Agents Effective on the Reproductive System of Female Adult Worms", Zeitschrift fuer Naturforschung, C: Journal of Biosciences, vol. 45, No. 11-12, 1990, pp. 1210-1214.

Naim, et al., "Studies in antiparasitic agents: Part 11—Synthesis of 5-substituted 2-aklyl/aryl-carbonylaminobenzimidazoles as orally effective anthelmintics", Indian Journal of Chemistry, Section B: Organic Chemistry including Medicinal Chemistry, vol. 29B, No. 5, 1990, pp. 464-470.

Naim, et al., "Studies in antiparasitic agents: Part 17,—Synthesis of 2-acylamino-6-substituted-benzthiazoles as potential anthelmintic agents", Indian Journal of Chemistry, vol. 30B, May 1991 pp. 494-498.

Folkman, Judah, "Tumor Angiogenesis: Therapeutic Implications", The New England Journal of Medicine, vol. 285, No. 21, Nov. 18, 1971, 1182-1186.

Ferrara, et al., "The Biology of Vascular Endothelial Growth Factor", Endocrine Reviews, vol. 18, No. 1, Feb. 1997, 4-25.

Matter, Alex, "Tumor angiogenesis as a therapeutic target", Drug Discovery Today, vol. 6, No. 19, Oct. 2001, 1005-1024.

Hasegawa, et al., "Discovery of Novel Benzimidazoles as Potent Inhibitors of TIE-2 and VEGFR-2 Tyrosine Kinase Receptors", J. Med. Chem., vol. 50, No. 18, 2007, 4453-4470.

Stella, et al., "Prodrug strategies to overcome poor water solubility", Advanced Drug Delivery Reviews, vol. 59, 2007, pp. 677-694.

Patani, et al., "Bioisosteris: A Rational Approach in Drug Design", Chem. Rev., vol. 96, 1996, pp. 3147-3176.

Pilyugin, et al., "Synthesis of bis [ (aroylamino)—1H-benzimidazol-5-yl] ethers", Russian Journal of General Chemistry, 2006, 76(8), 1327-1330, CA 146:500952.

* cited by examiner

FUSED HETEROCYCLE DERIVATIVES AND USE THEREOF

TECHNICAL FIELD OF THE INVENTION

The present invention relates to fused heterocycle derivatives having potent kinase inhibitory activity and useful for the prophylaxis or treatment of cancer and the like.

BACKGROUND OF THE INVENTION

For a solid tumor to grow to a certain size or above, angiogenesis is essential for ensuring sufficient supply of nutrition and oxygen to cancer cell (see, for example, New England Journal of Medicine, 1971, vol. 285, No. 21, pp. 1182-1186). One of the important factors causing angiogenesis toward tumor, a vascular endothelial growth factor (VEGF) is known. VEGF is bound to a vascular endothelial growth factor receptor (VEGFR) expressed on vascular endothelial cells and transmits signal for cell growth (see, for example, Endocrine Reviews, 1997, vol. 18, No. 1, pp. 4-25). Accordingly, inhibition of the VEGF-VEGFR signal transduction system is considered to enable suppression of angiogenesis and tumor growth (see, for example, Drug Discovery Today, 2001, vol. 6, No. 19, pp. 1005-1024). Moreover, since tumor blood vessels are involved in cancer hematogenous metastasis, inhibition of angiogenesis is considered to be effective for suppression of cancer metastasis.

As compounds inhibiting receptor-type tyrosine kinase including VEGFR, phthalazine derivatives (see, for example, WO 98/35958), pyrrole-substituted 2-indolinone derivatives (see, for example, WO 01/60814), quinazoline derivatives (see, for example, WO 01/32651), ω-carboxyaryl-substituted diphenylurea derivatives (see, for example, WO 00/42012), quinoline derivatives and quinazoline derivatives (see, for example, WO 00/43366), nitrogen-containing aromatic ring derivatives (see, for example, WO 02/32872), benzimidazole derivatives (see, for example, WO 02/44156) and the like are known.

In addition, as an imidazo[1,2-a]pyridine derivative having a similar structure to that of the compound of the present invention, a compound having anthelmintic action is described in JP-A-52-73896.

DISCLOSURE OF THE INVENTION

Problems to be Solved by the Invention

A kinase inhibitor superior in the affinity for kinase, efficacy expression, pharmacokinetics, solubility, interaction with other pharmaceutical products, safety and stability is expected to show a therapeutically superior effect. At present, however, such inhibitor superior in the affinity for kinase, and sufficiently satisfactory in the efficacy expression, pharmacokinetics, solubility, interaction with other pharmaceutical products, safety and stability has not been found. Thus, there is a demand for the development of a compound having a superior kinase inhibitory activity, and sufficiently satisfactory as a pharmaceutical product. Accordingly, an object of the present invention is to provide a compound having a superior kinase inhibitory activity, low toxic and sufficiently satisfactory as a pharmaceutical product.

Means of Solving the Problems

The present inventors have conducted intensive studies in an attempt to solve the above-mentioned problems and found that a compound represented by the following formula or a salt thereof has a superior kinase inhibitory activity, which resulted in the completion of the present invention.

Accordingly, the present invention provides the following.

[1] A compound represented by the formula (I):

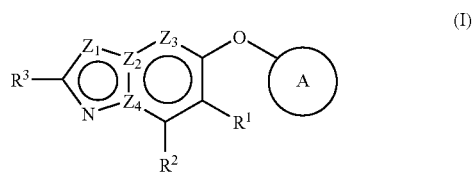

wherein $Z_1$, $Z_2$, $Z_3$ and $Z_4$ show the following combination:
$(Z_1,Z_2,Z_3,Z_4)=(CR^4,N,CR^5,C)$, $(N,N,CR^5,C)$, $(N,C,CR^5,N)$, $(S,C,CR^5,C)$ or $(S,C,N,C)$;

$R^1$ and $R^2$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;

$R^3$ is an amino optionally having substituent(s);

$R^4$ and $R^5$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;

$R^3$ and $R^4$ optionally form a ring optionally having substituent(s);

a group represented by the formula

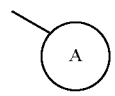

is a cyclic group optionally having substituent(s),
provided that
(1) when $(Z_1,Z_2,Z_3,Z_4)=(S,C,CR^5,C)$, the group represented by the formula

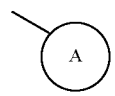

is a group represented by the formula

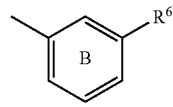

wherein $R^6$ is (1') an amino, (2') a mono-$C_{1-6}$ alkylamino, (3') a di-$C_{1-6}$ alkylamino, (4') a mono($C_{1-6}$ alkyl-carbonyl)amino optionally having 1 to 3 halogen atoms, (5') a mono ($C_{3-6}$ cycloalkyl-carbonyl)amino, (6') a mono($C_{3-6}$ cycloalkenyl-carbonyl)amino, (7') a mono($C_{6-10}$ aryl-carbonyl)amino optionally having 1 to 3 halogen atoms, (8') a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (9') a mono(8- to 12-membered fused aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (10') a mono(3- to 8-membered non-aromatic heterocyclyl-carbonyl)amino, (11') a mono-$C_{1-6}$ alkoxy-carbonylamino, (12') a $C_{1-6}$ alkyl-aminocarbonyl, (13') a di-$C_{1-6}$ alkyl-aminocarbonyl or (14') a nitro, and ring B is a benzene ring optionally further having substituent(s), and (2) when $(Z_1,Z_2,Z_3,Z_4)=(S,C,N,C)$, the group represented by the formula

is an aromatic cyclic group having substituent(s) (excluding 2-methoxycarbonylamino-6-(4-nitrophenoxy)imidazo[1,2-a]pyridine, 2-methoxycarbonylamino-6-(phenoxy)imidazo[1,2-a]pyridine, 6-(4-acetamidophenoxy)-2-methoxycarbonylaminoimidazo[1,2-a]pyridine, 6-(4-aminophenoxy)-2-methoxycarbonylaminoimidazo[1,2-a]pyridine and 6-(4-(2-fluoro-5-(trifluoromethyl)phenyl)aminocarbonylamino)phenoxy-2-methoxycarbonylaminoimidazo[1,2-a]pyridine), or a salt thereof;

[2] the compound of the aforementioned [1], wherein $R^1$ is a hydrogen atom;

[3] the compound of the aforementioned [1], wherein $R^2$ is a hydrogen atom;

[4] the compound of the aforementioned [1], wherein $R^3$ is an amino optionally substituted by an acyl;

[5] the compound of the aforementioned [1], wherein $R^3$ is
(1) an amino,
(2) a mono-$C_{1-6}$ alkylamino-carbonylamino,
(3) a mono-$C_{3-6}$ cycloalkylamino-carbonylamino,
(4) a $C_{1-5}$ alkyl-carbonylamino optionally having 1 to 3 substituents selected from (a) a halogen atom, (b) a hydroxy, (c) a $C_{1-6}$ alkoxy and (d) a 3- to 8-membered non-aromatic heterocyclic group optionally having one $C_{1-6}$ alkyl,
(5) a $C_{3-6}$ cycloalkyl-carbonylamino optionally having 1 to 3 halogen atoms,
(6) a 5- or 6-membered monocyclic aromatic heterocyclyl-carbonylamino optionally having 1 to 3 substituents selected from a halogen atom and a $C_{1-6}$ alkyl,
(7) a $C_{3-6}$ cycloalkyl-sulfonylamino, or
(8) a 5- to 7-membered monocyclic aromatic heterocyclyl-amino optionally having one halogen atom;

[6] the compound of the aforementioned [1], wherein $R^4$ is a hydrogen atom;

[7] the compound of the aforementioned [1], wherein $R^5$ is a hydrogen atom;

[8] the compound of the aforementioned [1], wherein $Z_1$, $Z_2$, $Z_3$ and $Z_4$ show the following combination:
$(Z_1,Z_2,Z_3,Z_4)=(CH,N,CH,C)$, $(N,N,CH,C)$, $(N,C,CH,N)$ or $(S,C,N,C)$; and the group represented by the formula

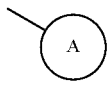

is a phenyl having substituent(s);

[9] the compound of the aforementioned [1], wherein $Z_1$, $Z_2$, $Z_3$ and $Z_4$ show the following combination:
$(Z_1,Z_2,Z_3,Z_4)=(CH,N,CH,C)$, $(N,N,CH,C)$, $(N,C,CH,N)$ or $(S,C,N,C)$; and the group represented by the formula

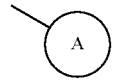

is a phenyl optionally having 1 to 3 substituents selected from
(1) a halogen atom,
(2) a $C_{1-6}$ alkyl optionally having 1 to 3 substituents selected from (a) a halogen atom, and
(b) a 5- or 6-membered monocyclic aromatic heterocyclic group,
(3) a mono-$C_{1-6}$ alkylamino optionally having one substituent selected from (a) a $C_{6-10}$ aryl and (b) a 5- or 6-membered monocyclic aromatic heterocyclic group optionally having one $C_{1-6}$ alkyl,
(4) a 5- or 6-membered monocyclic aromatic heterocyclyl-amino,
(5) a cyclic amino optionally having one oxo and optionally fused with a benzene ring,
(6) a $C_{1-6}$ alkyl-carbonylamino optionally having a 5- or 6-membered monocyclic aromatic heterocyclic group,
(7) a $C_{3-6}$ cycloalkyl-carbonylamino,
(8) a $C_{3-6}$ cycloalkenyl-carbonylamino,
(9) a $C_{2-6}$ alkynyl-carbonylamino optionally having one $C_{6-10}$ aryl,
(10) a $C_{6-10}$ aryl-carbonylamino optionally having 1 to 3 substituents selected from
(a) a halogen atom,
(b) a cyano,
(c) a hydroxy,
(d) an amino,
(e) a $C_{1-6}$ alkyl optionally having 1 to 3 substituents selected from a halogen atom and a cyano,
(f) a $C_{3-6}$ cycloalkyl optionally having one cyano,
(g) a $C_{1-6}$ alkoxy,
(h) a mono-$C_{1-6}$ alkylamino,
(i) a di-$C_{1-6}$ alkylamino,
(j) a $C_{1-6}$ alkyl-carbonylamino, and
(k) a $C_{1-4}$ alkylenedioxy,
(11) a mono(5- or 6-membered monocyclic aromatic heterocyclyl-carbonyl)amino optionally having 1 to 3 substituents selected from
(a) a halogen atom,
(b) a hydroxy,
(c) an amino,
(d) a $C_{1-6}$ alkyl optionally having 1 to 3 halogen atoms,
(e) a $C_{6-10}$ aryl,
(f) a $C_{1-6}$ alkoxy,
(g) a $C_{1-6}$ alkylsulfanyl, and
(h) a $C_{3-6}$ cycloalkyl,
(12) a mono(8- to 12-membered fused aromatic heterocyclyl-carbonyl)amino optionally having 1 to 3 substituents selected from
(a) a halogen atom,
(b) a $C_{1-6}$ alkyl optionally having 1 to 3 halogen atoms,
(c) a $C_{1-6}$ alkoxy, and
(d) a $C_{3-6}$ cycloalkyl,
(13) a 3- to 8-membered non-aromatic heterocyclyl-carbonylamino,
(14) a $C_{6-10}$ aryl-sulfonylamino optionally having 1 to 3 substituents selected from (a) a halogen atom,
(b) a $C_{1-6}$ alkyl optionally having 1 to 3 halogen atoms, and
(c) a $C_{1-6}$ alkylsulfonyl,
(15) a 5- or 6-membered monocyclic aromatic heterocyclylsulfonylamino optionally having one $C_{1-6}$ alkyl, and
(16) a ureido optionally having substituents selected from
(a) a $C_{1-6}$ alkyl,
(b) a $C_{6-10}$ aryl, and
(c) a 5- or 6-membered monocyclic aromatic heterocyclic group;

[10] N-[3-({2-[(cyclopropylcarbonyl)amino]imidazo[1,2-a]pyridin-6-yl}oxy)phenyl]-1,3-dimethyl-1H-pyrazole-5-carboxamide or a salt thereof;

[11] N-[5-({2-[(cyclopropylcarbonyl)amino]imidazo[1,2-a]pyridin-6-yl}oxy)-2-fluorophenyl]-1,3-dimethyl-1H-pyrazole-5-carboxamide or a salt thereof;

[12] N-[3-({2-[(cyclopropylcarbonyl)amino][1,2,4]triazolo[1,5-a]pyridin-6-yl}oxy)phenyl]-1,3-dimethyl-1H-pyrazole-5-carboxamide or a salt thereof;

[13] N-[5-({2-[(cyclopropylcarbonyl)amino][1,2,4]triazolo[1,5-a]pyridin-6-yl}oxy)-2-methylphenyl]-1,3-dimethyl-1H-pyrazole-5-carboxamide or a salt thereof;

[14] N-[3-({2-[(cyclopropylcarbonyl)amino][1,2,4]triazolo[1,5-a]pyridin-6-yl}oxy)phenyl]-2-methyl-5-(trifluoromethyl)-1,3-oxazole-4-carboxamide or a salt thereof;

[15] N-[5-({2-[(cyclopropylcarbonyl)amino][1,2,4]triazolo[1,5-a]pyridin-6-yl}oxy)-2-fluorophenyl]-1,3-dimethyl-1H-pyrazole-5-carboxamide or a salt thereof;

[16] N-[5-({2-[(cyclopropylcarbonyl)amino][1,2,4]triazolo[1,5-a]pyridin-6-yl}oxy)-2-fluorophenyl]-1-ethyl-3-methyl-1H-pyrazole-5-carboxamide or a salt thereof;

[17] N-[3-({2-[(cyclopropylcarbonyl)amino][1,2,4]triazolo[1,5-a]pyridin-7-yl}oxy)phenyl]-1,3-dimethyl-1H-pyrazole-5-carboxamide or a salt thereof;

[18] N-[3-({2-[(cyclopropylcarbonyl)amino]-1,3-benzothiazol-6-yl}oxy)phenyl]-1,3-dimethyl-1H-pyrazole-5-carboxamide or a salt thereof;

[19] N-[3-({2-[(cyclopropylcarbonyl)amino][1,3]thiazolo[5,4-b]pyridin-5-yl}oxy)phenyl]-1,3-dimethyl-1H-pyrazole-5-carboxamide or a salt thereof;

[20] a prodrug of the compound of the aforementioned [1];
[21] a pharmaceutical agent comprising the compound of the aforementioned [1] or a prodrug thereof;
[22] the pharmaceutical agent of the aforementioned [21], which is a kinase inhibitor;
[23] the pharmaceutical agent of the aforementioned [21], which is a vascular endothelial growth factor receptor (VEGFR) inhibitor;
[24] the pharmaceutical agent of the aforementioned [21], which is a vascular endothelial growth factor receptor (VEGFR) 2 inhibitor;
[25] the pharmaceutical agent of the aforementioned [21], which is a platelet-derived growth factor receptor (PDGFR) inhibitor;
[26] the pharmaceutical agent of the aforementioned [21], which is a Raf inhibitor;
[27] the pharmaceutical agent of the aforementioned [21], which is an angiogenesis inhibitor;
[28] the pharmaceutical agent of the aforementioned [21], which is an agent for the prophylaxis or treatment of cancer;
[29] the pharmaceutical agent of the aforementioned [21], which is a cancer growth inhibitor;
[30] the pharmaceutical agent of the aforementioned [21], which is a cancer metastasis suppressor;

[31] a method for the prophylaxis or treatment of cancer, which comprises administering, to a mammal, an effective amount of a compound represented by the formula (I):

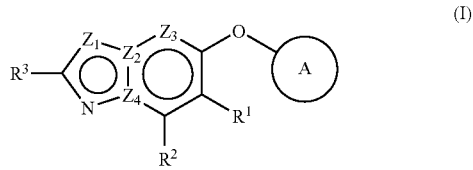

(I)

wherein $Z_1$, $Z_2$, $Z_3$ and $Z_4$ show the following combination: $(Z_1,Z_2,Z_3,Z_4)$=$(CR^4,N,CR^5,C)$, $(N,N,CR^5,C)$, $(N,C,CR^5,N)$, $(S,C,CR^5,C)$ or $(S,C,N,C)$;

$R^1$ and $R^2$ are the same or different and each is (1) a hydrogen atom, (2) a group bonded via a carbon atom, (3) a group bonded via a nitrogen atom, (4) a group bonded via an oxygen atom or (5) a group bonded via a sulfur atom;

$R^3$ is an amino optionally having substituent(s);

$R^4$ and $R^5$ are the same or different and each is (1) a hydrogen atom, (2) a group bonded via a carbon atom, (3) a group bonded via a nitrogen atom, (4) a group bonded via an oxygen atom or (5) a group bonded via a sulfur atom;

$R^3$ and $R^4$ optionally form a ring optionally having substituent(s); a group represented by the formula

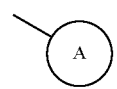

is a cyclic group optionally having substituent(s),
provided that
(1) when $(Z_1,Z_2,Z_3,Z_4)$=$(S,C,CR^5,C)$, the group represented by the formula

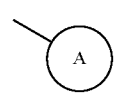

is a group represented by the formula

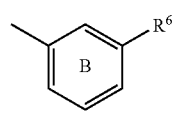

wherein $R^6$ is (1') an amino, (2') a mono-$C_{1-6}$ alkylamino, (3') a di-$C_{1-6}$ alkylamino, (4') a mono($C_{1-6}$ alkyl-carbonyl)amino optionally having 1 to 3 halogen atoms, (5') a mono ($C_{3-6}$ cycloalkyl-carbonyl)amino, (6') a mono($C_{3-6}$ cycloalkenyl-carbonyl)amino, (7') a mono($C_{6-10}$ aryl-carbonyl)amino optionally having 1 to 3 halogen atoms, (8') a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (9') a mono(8- to 12-membered fused aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (10') a mono(3- to 8-membered non-aromatic heterocyclyl-carbonyl)amino, (11') a mono-$C_{1-6}$ alkoxy-carbonylamino, (12') a $C_{1-6}$ alkyl-aminocarbonyl, (13') a di-$C_{1-6}$ alkyl-aminocarbonyl or (14') a nitro, and ring B is a benzene ring optionally further having substituent(s), and (2) when $(Z_1,Z_2,Z_3,Z_4)$=(S,C,N,C), the group represented by the formula

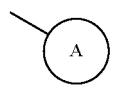

is an aromatic cyclic group having substituent(s), (excluding 2-methoxycarbonylamino-6-(4-nitrophenoxy)imidazo[1,2-a]pyridine, 2-methoxycarbonylamino-6-(phenoxy)imidazo[1,2-a]pyridine, 6-(4-acetamidophenoxy)-2-methoxycarbonylaminoimidazo[1,2-a]pyridine, 6-(4-aminophenoxy)-2-methoxycarbonylaminoimidazo[1,2-a]pyridine and 6-(4-(2-fluoro-5-(trifluoromethyl)phenyl)aminocarbonylamino)phenoxy-2-methoxycarbonylaminoimidazo[1,2-a]pyridine), or a salt thereof or a prodrug thereof;

[32] use of a compound represented by the formula (I):

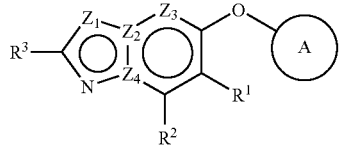

wherein $Z_1$, $Z_2$, $Z_3$ and $Z_4$ show the following combination: $(Z_1,Z_2,Z_3,Z_4)$=($CR^4$,N,$CR^5$,C), (N,N,$CR^5$,C), (N,C,$CR^5$,N), (S,C,$CR^5$,C) or (S,C,N,C);

$R^1$ and $R^2$ are the same or different and each is (1) a hydrogen atom, (2) a group bonded via a carbon atom, (3) a group bonded via a nitrogen atom, (4) a group bonded via an oxygen atom or (5) a group bonded via a sulfur atom;

$R^3$ is an amino optionally having substituent(s);

$R^4$ and $R^5$ are the same or different and each is (1) a hydrogen atom, (2) a group bonded via a carbon atom, (3) a group bonded via a nitrogen atom, (4) a group bonded via an oxygen atom or (5) a group bonded via a sulfur atom;

$R^3$ and $R^4$ optionally form a ring having substituent(s);

a group represented by the formula

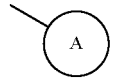

is a cyclic group optionally having substituent(s), provided that (1) when $(Z_1,Z_2,Z_3,Z_4)$=(S,C,$CR^5$,C), the group represented by the formula

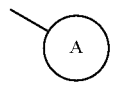

is a group represented by the formula

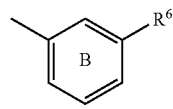

wherein $R^6$ is (1') an amino, (2') a mono-$C_{1-6}$ alkylamino, (3') a di-$C_{1-6}$ alkylamino, (4') a mono($C_{1-6}$ alkyl-carbonyl)amino optionally having 1 to 3 halogen atoms, (5') a mono ($C_{3-6}$ cycloalkyl-carbonyl)amino, (6') a mono($C_{3-6}$ cycloalkenyl-carbonyl)amino, (7') a mono($C_{6-10}$ aryl-carbonyl)amino optionally having 1 to 3 halogen atoms, (8') a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (9') a mono(8- to 12-membered fused aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (10') a mono(3- to 8-membered non-aromatic heterocyclyl-carbonyl)amino, (11') a mono-$C_{1-6}$ alkoxy-carbonylamino, (12') a $C_{1-6}$ alkyl-aminocarbonyl (e.g., methylaminocarbonyl, ethylaminocarbonyl, propylaminocarbonyl etc.), (13') a di-$C_{1-6}$ alkyl-aminocarbonyl (e.g., dimethylaminocarbonyl, diethylaminocarbonyl, dipropylaminocarbonyl etc.) or (14') a nitro, and ring B is a benzene ring optionally further having substituent(s), and (2) when $(Z_1,Z_2,Z_3,Z_4)$=(S,C,N,C), the group represented by the formula

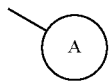

is an aromatic cyclic group having substituent(s), (excluding 2-methoxycarbonylamino-6-(4-nitrophenoxy)imidazo[1,2-a]pyridine, 2-methoxycarbonylamino-6-(phenoxy)imidazo[1,2-a]pyridine, 6-(4-acetamidophenoxy)-2-methoxycarbonylaminoimidazo[1,2-a]pyridine, 6-(4-aminophenoxy)-2-methoxycarbonylaminoimidazo[1,2-a]pyridine and 6-(4-(2-fluoro-5-(trifluoromethyl)phenyl)aminocarbonylamino)phenoxy-2-methoxycarbonylaminoimidazo[1,2-a]pyridine), or a salt thereof or a prodrug thereof, for the production of an agent for the prophylaxis or treatment of cancer; and the like.

EFFECT OF THE INVENTION

Compound (I) or salts thereof or prodrugs thereof have strong inhibitory activity against kinases such as vascular endothelial growth factor receptor, platelet-derived growth factor receptor and the like, and have strong angiogenesis inhibitory activity and strong Raf inhibitory activity (particularly, B-Raf inhibitory activity). Therefore, they can provide a clinically useful agent for the prophylaxis or treatment of cancer, a cancer growth inhibitor, or a cancer metastasis suppressor. Furthermore, Compound (I) or salts thereof or prodrugs thereof can provide clinically useful agents for the prophylaxis or treatment for applications on diseases other than cancer such as chronic rheumatism, diabetic retinopathy and the like, and have excellent efficacy expression, pharmacokinetics, solubility, interaction with other pharmaceutical products, safety and stability.

BEST MODE FOR CARRYING OUT THE INVENTION

The present invention is explained in detail in the following.

In the present specification, the term "halogen atom" is a fluorine atom, a chlorine atom, a bromine atom and an iodine atom.

In the present specification, examples of the term "group bonded via a carbon atom" include a cyano, a hydrocarbon group optionally having substituent(s), a heterocyclic group bonded via a carbon atom and optionally having substituent(s) and the like.

Examples of the "hydrocarbon group optionally having substituent(s)" include an alkyl optionally having substituent(s), an alkenyl optionally having substituent(s), an alkynyl optionally having substituent(s), a cycloalkyl optionally having substituent(s), a cycloalkenyl optionally having substituent(s), an aryl optionally having substituent(s), a cycloalkyl-alkyl optionally having substituent(s), a cycloalkenyl-alkyl optionally having substituent(s), an aryl-alkyl optionally having substituent(s), a cycloalkanedienyl optionally having substituent(s) and the like.

The "alkyl optionally having substituent(s)" is a $C_{1-6}$ alkyl (e.g., methyl, ethyl, propyl, isopropyl, butyl, isobutyl, sec-butyl, tert-butyl, pentyl, hexyl etc.) optionally having 1 to 3 substituents selected from the following substituent group (hereinafter to be abbreviated as substituent group A).

Substituent Group A:
(1) a halogen atom;
(2) a cyano;
(3) a nitro;
(4) a hydroxy;
(5) a $C_{1-6}$ alkoxy (e.g., methoxy, ethoxy, propoxy, isopropoxy, butoxy, isobutoxy, tert-butoxy etc.) optionally having 1 to 3 halogen atoms;
(6) a $C_{2-6}$ alkenyloxy (e.g., ethenyloxy, propenyloxy, butenyloxy, pentenyloxy, hexenyloxy etc.) optionally having 1 to 3 halogen atoms;
(7) a $C_{2-6}$ alkynyloxy (e.g., ethynyloxy, propynyloxy, butynyloxy, pentynyloxy, hexynyloxy etc.) optionally having 1 to 3 halogen atoms;
(8) a $C_{3-6}$ cycloalkyloxy (e.g., cyclopropyloxy, cyclobutyloxy, cyclopentyloxy, cyclohexyloxy etc.) optionally having 1 to 3 halogen atoms;
(9) a $C_{3-6}$ cycloalkenyloxy (e.g., cyclopropenyloxy, cyclobutenyloxy, cyclopentenyloxy, cyclohexenyloxy etc.) optionally having 1 to 3 halogen atoms;
(10) a $C_{6-10}$ aryloxy (e.g., phenyloxy, 1-naphthyloxy, 2-naphthyloxy etc.) optionally having 1 to 3 substituents (except an oxo) selected from the substituent group B and the substituent group C;
(11) a $C_{3-6}$ cycloalkyl-$C_{1-6}$ alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms;
(12) a $C_{3-6}$ cycloalkenyl-$C_{1-6}$ alkoxy (e.g., cyclopentenylmethyloxy, cyclohexenylmethyloxy, cyclohexenylethyloxy, cyclohexenylpropyloxy etc.) optionally having 1 to 3 halogen atoms;
(13) a $C_{6-10}$ aryl-$C_{1-6}$ alkoxy (e.g., phenylmethyloxy, phenylethyloxy etc.) optionally having 1 to 3 substituents (except an oxo) selected from the substituent group B and the substituent group C;
(14) a $C_{1-6}$ alkylsulfamoyl (e.g., methylsulfamoyl, ethylsulfamoyl, propylsulfamoyl etc.);
(15) a di-$C_{1-6}$ alkylsulfamoyl (e.g., dimethylsulfamoyl, diethylsulfamoyl, dipropylsulfamoyl etc.);
(16) a $C_{1-6}$ alkylamino-carbonyl (e.g., methylaminocarbonyl, ethylaminocarbonyl, propylaminocarbonyl etc.);
(17) a di-$C_{1-6}$ alkylamino-carbonyl (e.g., dimethylaminocarbonyl, diethylaminocarbonyl, dipropylaminocarbonyl etc.);
(18) a formyl;
(19) a $C_{1-6}$ alkyl-carbonyl (e.g., acetyl, ethylcarbonyl, propylcarbonyl, isopropylcarbonyl etc.);
(20) a $C_{2-6}$ alkenyl-carbonyl (e.g., ethenylcarbonyl, propenylcarbonyl, butenylcarbonyl, pentenylcarbonyl, hexenylcarbonyl etc.);
(21) a $C_{2-6}$ alkynyl-carbonyl (e.g., ethynylcarbonyl, propynylcarbonyl, butynylcarbonyl, pentynylcarbonyl, hexynylcarbonyl etc.);
(22) a $C_{3-6}$ cycloalkyl-carbonyl (e.g., cyclopropylcarbonyl, cyclobutylcarbonyl, cyclopentylcarbonyl, cyclohexylcarbonyl etc.);
(23) a $C_{3-6}$ cycloalkenyl-carbonyl (e.g., cyclopropenylcarbonyl, cyclobutenylcarbonyl, cyclopentenylcarbonyl, cyclohexenylcarbonyl etc.);
(24) a $C_{6-10}$ aryl-carbonyl (e.g., benzoyl, 1-naphthylcarbonyl, 2-naphthylcarbonyl etc.);
(25) a $C_{3-6}$ cycloalkyl-$C_{1-6}$ alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);
(26) a $C_{3-6}$ cycloalkenyl-$C_{1-6}$ alkyl-carbonyl (e.g., cyclopentenylmethylcarbonyl, cyclohexenylmethylcarbonyl, cyclohexenylethylcarbonyl, cyclohexenylpropylcarbonyl etc.);
(27) a $C_{6-10}$ aryl-$C_{1-6}$ alkyl-carbonyl (e.g., benzylcarbonyl, phenylethylcarbonyl etc.);
(28) a 5- or 6-membered monocyclic aromatic heterocyclyl-carbonyl (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl etc.);
(29) a 8- to 12-membered fused aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.);
(30) a 3- to 8-membered non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl etc.);
(31) a $C_{1-6}$ alkylsulfonyl (e.g., methylsulfonyl, ethylsulfonyl etc.);
(32) a $C_{2-6}$ alkenylsulfonyl (e.g., ethenylsulfonyl, propenylsulfonyl etc.);
(33) a $C_{2-6}$ alkynylsulfonyl (e.g., ethynylsulfonyl, propynylsulfonyl, butynylsulfonyl, pentynylsulfonyl, hexynylsulfonyl etc.);
(34) a $C_{3-6}$ cycloalkylsulfonyl (e.g., cyclopropylsulfonyl, cyclobutylsulfonyl etc.);
(35) a $C_{3-6}$ cycloalkenylsulfonyl (e.g., cyclopropenylsulfonyl, cyclobutenylsulfonyl etc.);
(36) a $C_{6-10}$ arylsulfonyl (e.g., phenylsulfonyl etc.);

(37) a $C_{3-6}$ cycloalkyl-$C_{1-6}$ alkylsulfonyl (e.g., cyclopropylmethylsulfonyl etc.);
(38) a $C_{3-6}$ cycloalkenyl-$C_{1-6}$ alkylsulfonyl (e.g., cyclopentenylmethylsulfonyl etc.);
(39) a $C_{6-10}$ aryl-$C_{1-6}$ alkylsulfonyl (e.g., benzylsulfonyl etc.);
(40) a 5- or 6-membered monocyclic aromatic heterocyclylsulfonyl (e.g., furylsulfonyl, thienylsulfonyl, pyridylsulfonyl etc.);
(41) a 8- to 12-membered fused aromatic heterocyclyl-sulfonyl (e.g., benzofurylsulfonyl, isobenzofurylsulfonyl etc.);
(42) a 3- to 8-membered non-aromatic heterocyclyl-sulfonyl (e.g., oxiranylsulfonyl, azetidinylsulfonyl etc.);
(43) an amino;
(44) a mono-$C_{1-6}$ alkylamino (e.g., methylamino, ethylamino, propylamino, isopropylamino, butylamino, isobutylamino, tert-butylamino etc.) optionally having one substituent selected from (a) a $C_{6-10}$ aryl (e.g., phenyl, naphthyl etc.) and (b) a 5- or 6-membered monocyclic aromatic heterocyclic group (e.g., pyridyl etc.) optionally having one $C_{1-6}$ alkyl (e.g., methyl, ethyl, propyl etc.);
(45) a di-$C_{1-6}$ alkylamino (e.g., dimethylamino, diethylamino, dipropylamino, diisopropylamino, dibutylamino, diisobutylamino, di-tert-butylamino etc.);
(46) a $C_{1-6}$ alkyl-carbonylamino (e.g., acetylamino, ethylcarbonylamino, propylcarbonylamino, isobutylcarbonylamino, tert-butylcarbonylamino etc.) optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.);
(47) a ($C_{3-6}$ cycloalkyl-carbonyl)amino (e.g., cyclopropylcarbonylamino, cyclobutylcarbonylamino, cyclopentylcarbonylamino, cyclohexylcarbonylamino etc.);
(48) a ($C_{3-6}$ cycloalkenyl-carbonyl)amino (e.g., cyclopropenylcarbonylamino, cyclobutenylcarbonylamino, cyclopentenylcarbonylamino, cyclohexenylcarbonylamino etc.);
(49) a ($C_{6-10}$ aryl-carbonyl)amino (e.g., benzoylamino etc.) optionally having 1 to 3 substituents (except an oxo) selected from the substituent group B and the substituent group C;
(50) a mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino, pyrazinylcarbonylamino, pyridazinylcarbonylamino etc.) optionally having 1 to 3 substituents (except an oxo) selected from the substituent group B and the substituent group C;
(51) a mono(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino, benzopyrazolylcarbonylamino, indolylcarbonylamino etc.) optionally having 1 to 3 substituents (except an oxo) selected from the substituent group B and the substituent group C;
(52) a mono(3- to 8-membered non-aromatic heterocyclyl-carbonyl)amino (e.g., oxiranylcarbonylamino, azetidinylcarbonylamino, oxetanylcarbonylamino, thietanylcarbonylamino, pyrrolidinylcarbonylamino, tetrahydrofurylcarbonylamino, thiolanylcarbonylamino, piperidinylcarbonylamino etc.) optionally having 1 to 3 substituents (except an oxo) selected from the substituent group B and the substituent group C;
(53) a mono-$C_{1-6}$ alkoxycarbonylamino (e.g., methoxycarbonylamino, ethoxycarbonylamino, tert-butoxycarbonylamino etc.)
(54) a mercapto;
(55) a $C_{1-6}$ alkylsulfanyl (e.g., methylsulfanyl, ethylsulfanyl etc.);
(56) a $C_{2-6}$ alkenylsulfanyl (e.g., ethenylsulfanyl, propenylsulfanyl etc.);
(57) a $C_{2-6}$ alkynylsulfanyl (e.g., ethynylsulfanyl, propynylsulfanyl, butynylsulfanyl, pentynylsulfanyl, hexynylsulfanyl etc.);
(58) a $C_{3-6}$ cycloalkylsulfanyl (e.g., cyclopropylsulfanyl, cyclobutylsulfanyl etc.);
(59) a $C_{3-6}$ cycloalkenylsulfanyl (e.g., cyclopropenylsulfanyl, cyclobutenylsulfanyl etc.);
(60) a $C_{6-10}$ arylsulfanyl (e.g., phenylsulfanyl etc.);
(61) a $C_{3-6}$ cycloalkyl-$C_{1-6}$ alkylsulfanyl (e.g., cyclopropylmethylsulfanyl etc.);
(62) a $C_{3-6}$ cycloalkenyl-$C_{1-6}$ alkylsulfanyl (e.g., cyclopentenylmethylsulfanyl etc.);
(63) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.);
(64) a 8- to 12-membered fused aromatic heterocyclic group (e.g., benzofuryl, isobenzofuryl, benzothienyl, isobenzothienyl, indolyl, isoindolyl, 1H-indazolyl, benzimidazolyl, benzoxazolyl etc.);
(65) a 3- to 8-membered non-aromatic heterocyclic group (e.g., oxiranyl, azetidinyl, oxetanyl, thietanyl, pyrrolidinyl, tetrahydrofuryl, thiolanyl, piperidinyl, morpholino, piperazino etc.) optionally having 1 to 3 substituents selected from the substituent group B and the substituent group C;
(66) a 5- or 6-membered monocyclic aromatic heterocyclyl-oxy (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy etc.) optionally having 1 to 3 substituents (except an oxo) selected from the substituent group B and the substituent group C;
(67) a 8- to 12-membered fused aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.) optionally having 1 to 3 substituents (except an oxo) selected from the substituent group B and the substituent group C;
(68) a 3- to 8-membered non-aromatic heterocyclyl-oxy (e.g., oxiranyloxy, azetidinyloxy, oxetanyloxy, thietanyloxy, pyrrolidinyloxy, tetrahydrofuryloxy, thiolanyloxy, piperidinyloxy etc.) optionally having 1 to 3 substituents selected from the substituent group B and the substituent group C;
(69) an oxo;
(70) a $C_{1-6}$ alkylsulfinyl (e.g., methylsulfinyl, ethylsulfinyl etc.);
(71) a $C_{2-6}$ alkenylsulfinyl (e.g., ethenylsulfinyl, propenylsulfinyl etc.);
(72) a $C_{2-6}$ alkynylsulfinyl (e.g., ethynylsulfinyl, propynylsulfinyl, butynylsulfinyl, pentynylsulfinyl, hexynylsulfinyl etc.);
(73) a $C_{3-6}$ cycloalkylsulfinyl (e.g., cyclopropylsulfinyl, cyclobutylsulfinyl etc.);
(74) a $C_{3-6}$ cycloalkenylsulfinyl (e.g., cyclopropenylsulfinyl, cyclobutenylsulfinyl etc.);
(75) a $C_{6-10}$ arylsulfinyl (e.g., phenylsulfinyl etc.);
(76) a $C_{3-6}$ cycloalkyl-$C_{1-6}$ alkylsulfinyl (e.g., cyclopropylmethylsulfinyl etc.);

(77) a $C_{3-6}$ cycloalkenyl-$C_{1-6}$ alkylsulfinyl (e.g., cyclopentenylmethylsulfinyl etc.);
(78) a $C_{1-6}$ alkylamino-thiocarbonyl (e.g., methylaminothiocarbonyl, ethylaminothiocarbonyl, propylaminothiocarbonyl etc.);
(79) a di-$C_{1-6}$ alkylamino-thiocarbonyl (e.g., dimethylaminothiocarbonyl, diethylaminothiocarbonyl, dipropylaminothiocarbonyl etc.);
(80) a carboxy;
(81) a $C_{1-6}$ alkoxycarbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);
(82) a $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);
(83) a $C_{2-6}$ alkynyloxy-carbonyl (e.g., ethynyloxycarbonyl, propynyloxycarbonyl, butynyloxycarbonyl, pentynyloxycarbonyl, hexynyloxycarbonyl etc.);
(84) a $C_{3-6}$ cycloalkyloxy-carbonyl (e.g., cyclopropyloxycarbonyl, cyclobutyloxycarbonyl, cyclopentyloxycarbonyl, cyclohexyloxycarbonyl etc.);
(85) a $C_{3-6}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);
(86) a $C_{6-10}$ aryloxy-carbonyl (e.g., phenyloxycarbonyl, 1-naphthyloxycarbonyl, 2-naphthyloxycarbonyl etc.);
(87) a $C_{3-6}$ cycloalkyl-$C_{1-6}$ alkoxycarbonyl (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl etc.);
(88) a $C_{3-6}$ cycloalkenyl-$C_{1-6}$ alkoxycarbonyl (e.g., cyclopentenylmethyloxycarbonyl, cyclohexenylmethyloxycarbonyl, cyclohexenylethyloxycarbonyl, cyclohexenylpropyloxycarbonyl etc.);
(89) a $C_{6-10}$ aryl-$C_{1-6}$ alkoxycarbonyl (e.g., phenylmethyloxycarbonyl, phenylethyloxycarbonyl etc.);
(90) a sulfamoyl;
(91) a carbamoyl;
(92) a mono($C_{6-10}$ aryl-$C_{1-6}$ alkyl-carbonyl)amino (e.g., phenylmethylcarbonylamino etc.) optionally having 1 to 3 substituents selected from the substituent group B and the substituent group C;
(93) a mono(5- or 6-membered monocyclic aromatic heterocyclyl-$C_{1-6}$ alkyl-carbonyl)amino (e.g., furylmethylcarbonylamino, thienylmethylcarbonylamino, pyrrolylmethylcarbonylamino, oxazolylmethylcarbonylamino, isoxazolylmethylcarbonylamino, thiazolylmethylcarbonylamino, isothiazolylmethylcarbonylamino, imidazolylmethylcarbonylamino, tetrazolylmethylcarbonylamino, pyridylmethylcarbonylamino, pyrazolylmethylcarbonylamino etc.) optionally having 1 to 3 substituents selected from the substituent group B and the substituent group C;
(94) a mono(8- to 12-membered fused aromatic heterocyclyl-$C_{1-6}$ alkyl-carbonyl)amino (e.g., benzofurylmethylcarbonylamino, isobenzofurylmethylcarbonylamino, benzothienylmethylcarbonylamino, isobenzothienylmethylcarbonylamino, benzopyrazolylmethylcarbonylamino etc.) optionally having 1 to 3 substituents selected from the substituent group B and the substituent group C;
(95) a mono(3- to 8-membered non-aromatic heterocyclyl-$C_{1-6}$ alkyl-carbonyl)amino (e.g., oxiranylmethylcarbonylamino, azetidinylmethylcarbonylamino, oxetanylmethylcarbonylamino, thietanylmethylcarbonylamino, pyrrolidinylmethylcarbonylamino, tetrahydrofurylmethylcarbonylamino, thiolanylmethylcarbonylamino, piperidinylmethylcarbonylamino etc.) optionally having 1 to 3 substituents selected from the substituent group B and the substituent group C;
(96) a mono-$C_{6-10}$ aryl-ureido (e.g., phenylureido etc.) optionally having 1 to 3 substituents selected from the substituent group B and the substituent group C;
(97) a mono-5- or 6-membered monocyclic aromatic heterocyclyl-ureido (e.g., furylureido, thienylureido, pyrrolylureido, oxazolylureido, isoxazolylureido, thiazolylureido, isothiazolylureido, imidazolylureido, tetrazolylureido, pyridylureido, pyrazolylureido etc.) optionally having 1 to 3 substituents selected from the substituent group B and the substituent group C;
(98) a mono-8- to 12-membered fused aromatic heterocyclyl-ureido (e.g., benzofurylureido, isobenzofurylureido, benzothienylureido, isobenzothienylureido, benzopyrazolylureido etc.) optionally having 1 to 3 substituents selected from the substituent group B and the substituent group C;
(99) a mono-3- to 8-membered non-aromatic heterocyclyl-ureido (e.g., oxiranylureido, azetidinylureido, oxetanylureido, thietanylureido, pyrrolidinylureido, tetrahydrofurylureido, thiolanylureido, piperidinylureido etc.) optionally having 1 to 3 substituents selected from the substituent group B and the substituent group C;
(100) a mono($C_{6-10}$ aryl-$C_{1-6}$ alkyl)ureido (e.g., phenylmethylureido etc.) optionally having 1 to 3 substituents selected from the substituent group B and the substituent group C;
(101) a mono(5- or 6-membered monocyclic aromatic heterocyclyl-$C_{1-6}$ alkyl)ureido (e.g., furylmethylureido, thienylmethylureido, pyrrolylmethylureido, oxazolylmethylureido, isoxazolylmethylureido, thiazolylmethylureido, isothiazolylmethylureido, imidazolylmethylureido, tetrazolylmethylureido, pyridylmethylureido, pyrazolylmethylureido etc.) optionally having 1 to 3 substituents selected from the substituent group B and the substituent group C;
(102) a mono(8- to 12-membered fused aromatic heterocyclyl-$C_{1-6}$ alkyl)ureido (e.g., benzofurylmethylureido, isobenzofurylmethylureido, benzothienylmethylureido, isobenzothienylmethylureido, benzopyrazolylmethylureido etc.) optionally having 1 to 3 substituents selected from the substituent group B and the substituent group C;
(103) a mono(3- to 8-membered non-aromatic heterocyclyl-$C_{1-6}$ alkyl)ureido (e.g., oxiranylmethylureido, azetidinylmethylureido, oxetanylmethylureido, thietanylmethylureido, pyrrolidinylmethylureido, tetrahydrofurylmethylureido, thiolanylmethylureido, piperidinylmethylureido etc.) optionally having 1 to 3 substituents selected from the substituent group B and the substituent group C;
(104) a mono-$C_{6-10}$ aryl-aminocarbonyl (e.g., phenylaminocarbonyl etc.) optionally having 1 to 3 substituents selected from the substituent group B and the substituent group C;
(105) a mono-5- or 6-membered monocyclic aromatic heterocyclyl-aminocarbonyl (e.g., furylaminocarbonyl, thienylaminocarbonyl, pyrrolylaminocarbonyl, oxazolylaminocarbonyl, isoxazolylaminocarbonyl, thiazolylaminocarbonyl, isothiazolylaminocarbonyl, imidazolylaminocarbonyl, tetrazolylaminocarbonyl, pyridylaminocarbonyl, pyrazolylaminocarbonyl etc.) optionally having 1 to 3 substituents selected from the substituent group B and the substituent group C;
(106) a mono-8- to 12-membered fused aromatic heterocyclyl-aminocarbonyl (e.g., benzofurylaminocarbonyl, isobenzofurylaminocarbonyl, benzothienylaminocarbonyl, isobenzothienylaminocarbonyl, benzopyrazolylaminocarbonyl etc.) optionally having 1 to 3 substituents selected from the substituent group B and the substituent group C;
(107) a mono-3- to 8-membered non-aromatic heterocyclyl-aminocarbonyl (e.g., oxiranylaminocarbonyl, azetidinylaminocarbonyl, oxetanylaminocarbonyl, thietanylaminocarbonyl, pyrrolidinylaminocarbonyl, tetrahydrofurylaminocarbonyl, thiolanylaminocarbonyl, piperidinylaminocarbonyl etc.) optionally having 1 to 3 substituents selected from the substituent group B and the substituent group C;
(108) a mono($C_{6-10}$ aryl-$C_{1-6}$ alkyl)aminocarbonyl (e.g., phenylmethylaminocarbonyl etc.) optionally having 1 to 3 substituents selected from the substituent group B and the substituent group C;
(109) a mono(5- or 6-membered monocyclic aromatic heterocyclyl-$C_{1-6}$ alkyl)aminocarbonyl (e.g., furylmethylaminocarbonyl, thienylmethylaminocarbonyl, pyrrolylmethylaminocarbonyl, oxazolylmethylaminocarbonyl, isoxazolylmethylaminocarbonyl, thiazolylmethylaminocarbonyl, isothiazolylmethylaminocarbonyl, imidazolylmethylaminocarbonyl, tetrazolylmethylaminocarbonyl, pyridylmethylaminocarbonyl, pyrazolylmethylaminocarbonyl etc.) optionally having 1 to 3 substituents selected from the substituent group B and the substituent group C;
(110) a mono(8- to 12-membered fused aromatic heterocyclyl-$C_{1-6}$ alkyl)aminocarbonyl (e.g., benzofurylmethylaminocarbonyl, isobenzofurylmethylaminocarbonyl, benzothienylmethylaminocarbonyl, isobenzothienylmethylaminocarbonyl, benzopyrazolylmethylaminocarbonyl etc.) optionally having 1 to 3 substituents selected from the substituent group B and the substituent group C;
(111) a mono(3- to 8-membered non-aromatic heterocyclyl-$C_{1-6}$ alkyl)aminocarbonyl (e.g., oxiranylmethylaminocarbonyl, azetidinylmethylaminocarbonyl, oxetanylmethylaminocarbonyl, thietanylmethylaminocarbonyl, pyrrolidinylmethylaminocarbonyl, tetrahydrofurylmethylaminocarbonyl, thiolanylmethylaminocarbonyl, piperidinylmethylaminocarbonyl etc.) optionally having 1 to 3 substituents selected from the substituent group B and the substituent group C;
(112) a mono-5- or 6-membered monocyclic aromatic heterocyclyl-amino (e.g., furylamino, thienylamino, pyrrolylamino, oxazolylamino, isoxazolylamino, thiazolylamino, isothiazolylamino, imidazolylamino, tetrazolylamino, pyridylamino, pyrazolylamino etc.) optionally having 1 to 3 substituents selected from the substituent group B and the substituent group C;
(113) a cyclic amino (e.g., pyrrolidino, piperidino, piperazino, morpholino, thiomorpholino etc.) optionally having one oxo and optionally fused with a benzene ring;
(114) a $C_{2-6}$ alkynyl-carbonylamino (e.g., ethynylcarbonylamino, propynylcarbonylamino, butynylcarbonylamino, pentynylcarbonylamino, hexynylcarbonylamino etc.) optionally having one $C_{6-10}$ aryl (e.g., phenyl etc.);
(115) a $C_{6-10}$ aryl-sulfonylamino (e.g., phenylsulfonylamino, naphthylsulfonylamino etc.) optionally having one substituent selected from (a) a halogen atom, (b) a $C_{1-6}$ alkyl (e.g., methyl, ethyl, propyl) optionally having 1 to 3 halogen atoms and (c) a $C_{1-6}$ alkylsulfonyl (e.g., methylsulfonyl, ethylsulfonyl etc.);
(116) a 5- or 6-membered monocyclic aromatic heterocyclyl-sulfonylamino (e.g., furylsulfonylamino, thienylsulfonylamino, pyrrolylsulfonylamino, oxazolylsulfonylamino, isoxazolylsulfonylamino, thiazolylsulfonylamino, isothiazolylsulfonylamino, imidazolylsulfonylamino, tetrazolylsulfonylamino, pyridylsulfonylamino, pyrazolylsulfonylamino etc.) optionally having one $C_{1-6}$ alkyl (e.g., methyl, ethyl, propyl);
(117) a ureido; and
(118) a $C_{1-6}$ alkyl-ureido (e.g., methylureido, ethylureido, propylureido, isopropylureido etc.).

Substituent Group B:
(1) a halogen atom;
(2) a cyano;
(3) a hydroxy;
(4) a 3- to 8-membered non-aromatic heterocyclyl-oxy (e.g., oxiranyloxy, azetidinyloxy, oxetanyloxy, thietanyloxy, pyrrolidinyloxy, tetrahydrofuryloxy, thiolanyloxy, piperidinyloxy etc.);
(5) an amino;
(6) a mono-$C_{1-6}$ alkyl-amino (e.g., methylamino, ethylamino, propylamino, isopropylamino, butylamino, isobutylamino, tert-butylamino etc.);
(7) a di-$C_{1-6}$ alkyl-amino (e.g., dimethylamino, diethylamino, dipropylamino, diisopropylamino, dibutylamino, diisobutylamino, di-tert-butylamino, N-ethyl-N-methylamino, N-methyl-N-propylamino, N-ethyl-N-propylamino etc.);
(8) a mono-$C_{3-6}$ cycloalkyl-amino (e.g., cyclopropylamino, cyclobutylamino, cyclopentylamino, cyclohexylamino etc.);
(9) a mono($C_{1-6}$ alkyl-carbonyl)amino (e.g., acetylamino, ethylcarbonylamino, propylcarbonylamino, isobutylcarbonylamino, tert-butylcarbonylamino etc.);
(10) a mono($C_{3-6}$ cycloalkyl-carbonyl)amino (e.g., cyclopropylcarbonylamino, cyclobutylcarbonylamino, cyclopentylcarbonylamino, cyclohexylcarbonylamino etc.);
(11) a mercapto;
(12) a $C_{1-6}$ alkyl-sulfanyl (e.g., methylsulfanyl, ethylsulfanyl etc.);
(13) a $C_{3-6}$ cycloalkyl-sulfanyl (e.g., cyclopropylsulfanyl, cyclobutylsulfanyl etc.);
(14) a 3- to 8-membered non-aromatic heterocyclyl-sulfanyl (e.g., oxiranylsulfanyl, azetidinylsulfanyl etc.);
(15) a $C_{1-6}$ alkyl-sulfinyl (e.g., methylsulfinyl, ethylsulfinyl etc.);
(16) a $C_{3-6}$ cycloalkyl-sulfinyl (e.g., cyclopropylsulfinyl, cyclobutylsulfinyl etc.);
(17) a 3- to 8-membered non-aromatic heterocyclyl-sulfinyl (e.g., oxiranylsulfinyl, azetidinylsulfinyl etc.);
(18) a $C_{1-6}$ alkyl-sulfonyl (e.g., methylsulfonyl, ethylsulfonyl etc.);
(19) a $C_{3-6}$ cycloalkyl-sulfonyl (e.g., cyclopropylsulfonyl, cyclobutylsulfonyl etc.);
(20) a 3- to 8-membered non-aromatic heterocyclyl-sulfonyl (e.g., oxiranylsulfonyl, azetidinylsulfonyl etc.);
(21) an oxo;
(22) a formyl;
(23) a $C_{1-6}$ alkyl-carbonyl (e.g., acetyl, ethylcarbonyl, propylcarbonyl, isopropylcarbonyl etc.);
(24) a $C_{3-6}$ cycloalkyl-carbonyl (e.g., cyclopropylcarbonyl, cyclobutylcarbonyl, cyclopentylcarbonyl, cyclohexylcarbonyl etc.);
(25) a 3- to 8-membered non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl etc.);
(26) a carboxy;
(27) a carbamoyl
(28) a mono($C_{1-6}$ alkyl-amino)carbonyl (e.g., methylaminocarbonyl, ethylaminocarbonyl, propylaminocarbonyl etc.);

(29) a di-($C_{1-6}$ alkyl-amino)carbonyl (e.g., dimethylaminocarbonyl, diethylaminocarbonyl, dipropylaminocarbonyl etc.);
(30) a sulfo;
(31) a sulfamoyl;
(32) a mono-$C_{1-6}$ alkylsulfamoyl (e.g., methylsulfamoyl, ethylsulfamoyl, propylsulfamoyl etc.);
(33) a di-$C_{1-6}$ alkylsulfamoyl (e.g., dimethylsulfamoyl, diethylsulfamoyl, dipropylsulfamoyl etc.);
(34) a 3- to 8-membered non-aromatic heterocyclic group (e.g., oxiranyl, azetidinyl, oxetanyl, thietanyl, pyrrolidinyl, tetrahydrofuryl, thiolanyl, piperidinyl etc.); and
(35) a $C_{1-4}$ alkylenedioxy (e.g., methylenedioxy, ethylenedioxy, trimethylendioxy etc.)

Substituent Group C:
(1) a $C_{1-6}$ alkyl (e.g., methyl, ethyl, propyl, isopropyl etc.) optionally having 1 to 3 substituents selected from the substituent group B;
(2) a $C_{1-6}$ alkoxy (e.g., methoxy, ethoxy, propoxy etc.) optionally having 1 to 3 substituents selected from the substituent group B;
(3) a $C_{3-6}$ cycloalkyl (e.g., cyclopropyl, cyclobutyl, cyclopentyl, cyclohexyl etc.) optionally having 1 to 3 substituents selected from the substituent group B;
(4) a $C_{3-6}$ cycloalkyloxy (e.g., cyclopropyloxy, cyclobutyloxy, cyclopentyloxy, cyclohexyloxy etc.) optionally having 1 to 3 substituents selected from the substituent group B;
(5) a $C_{3-6}$ cycloalkyl-$C_{1-6}$ alkyl (e.g., cyclopropylmethyl, cyclopropylethyl, cyclobutylmethyl, cyclopentylmethyl, cyclohexylmethyl, cyclohexylethyl etc.) optionally having 1 to 3 substituents selected from the substituent group B;
(6) a $C_{3-6}$ cycloalkyl-$C_{1-6}$ alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 substituents selected from the substituent group B;
(7) a $C_{6-10}$ aryl (e.g., phenyl, 1-naphthyl, 2-naphthyl etc.) optionally having 1 to 3 substituents (except an oxo) selected from the substituent group B;
(8) a $C_{6-10}$ aryloxy (e.g., phenyloxy, 1-naphthyloxy, 2-naphthyloxy etc.) optionally having 1 to 3 substituents (except an oxo) selected from the substituent group B;
(9) a $C_{6-10}$ aryl-$C_{1-6}$ alkyl (e.g., benzyl, phenylethyl etc.) optionally having 1 to 3 substituents selected from the substituent group B;
(10) a $C_{6-10}$ aryl-$C_{1-6}$ alkoxy (e.g., phenylmethyloxy, phenylethyloxy etc.) optionally having 1 to 3 substituents selected from the substituent group B;
(11) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.) optionally having 1 to 3 substituents (except an oxo) selected from the substituent group B;
(12) a 5- or 6-membered monocyclic aromatic heterocyclyloxy (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy etc.) optionally having 1 to 3 substituents (except an oxo) selected from the substituent group B;
(13) a 5- or 6-membered monocyclic aromatic heterocyclyl-$C_{1-6}$ alkyl (e.g., furylmethyl, thienylmethyl, pyrrolylmethyl, oxazolylmethyl, isoxazolylmethyl, thiazolylmethyl, isothiazolylmethyl, imidazolylmethyl, pyridylmethyl, pyrazolylmethyl etc.) optionally having 1 to 3 substituents selected from the substituent group B; and
(14) a 5- or 6-membered monocyclic aromatic heterocyclyl-$C_{1-6}$ alkoxy (e.g., furylmethyloxy, thienylmethyloxy, pyrrolylmethyloxy, oxazolylmethyloxy, isoxazolylmethyloxy, thiazolylmethyloxy, isothiazolylmethyloxy, imidazolylmethyloxy, pyridylmethyloxy, pyrazolylmethyloxy etc.) optionally having 1 to 3 substituents selected from the substituent group B.

The "alkenyl optionally having substituent(s)" is a $C_{2-6}$ alkenyl (e.g., ethenyl, propenyl, butenyl, pentenyl, hexenyl, butadienyl etc.) optionally having 1 to 3 substituents selected from the substituent group A.

The "alkynyl optionally having substituent(s)" is a $C_{2-6}$ alkynyl (e.g., ethynyl, propynyl, butynyl, pentynyl, hexynyl etc.) optionally having 1 to 3 substituents selected from the substituent group A.

The "cycloalkyl optionally having substituent(s)" is a $C_{3-6}$ cycloalkyl (e.g., cyclopropyl, cyclobutyl, cyclopentyl, cyclohexyl etc.) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

The "cycloalkenyl optionally having substituent(s)" is a $C_{3-6}$ cycloalkenyl (e.g., cyclopropenyl, cyclobutenyl, cyclopentenyl, cyclohexenyl etc.) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

The "aryl optionally having substituent(s)" is a $C_{6-10}$ aryl (e.g., phenyl, 1-naphthyl, 2-naphthyl etc.) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A (except an oxo).

The "cycloalkyl-alkyl optionally having substituent(s)" is a $C_{3-6}$ cycloalkyl-$C_{1-4}$ alkyl (e.g., cyclopropylmethyl, cyclopropylethyl, cyclobutylmethyl, cyclopentylmethyl, cyclohexylmethyl, cyclohexylethyl etc.) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

The "cycloalkenyl-alkyl optionally having substituent(s)" is a $C_{3-6}$ cycloalkenyl-$C_{1-4}$ alkyl (e.g., cyclopentenylmethyl, cyclohexenylmethyl, cyclohexenylethyl, cyclohexenylpropyl etc.) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

The "aryl-alkyl optionally having substituent(s)" is a $C_{6-10}$ aryl-$C_{1-4}$ alkyl (e.g., benzyl, phenylethyl etc.) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

The "cycloalkanedienyl optionally having substituent(s)" is a $C_{4-6}$ cycloalkanedienyl (e.g., 2,4-cyclopentadien-1-yl, 2,4-cyclohexadien-1-yl, 2,5-cyclohexadien-1-yl etc.) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

Examples of the "heterocyclic group bonded via a carbon atom and optionally having substituent(s)" include a heterocyclic group bonded via a carbon atom (monocyclic aromatic heterocyclic group, fused aromatic heterocyclic group, non-aromatic heterocyclic group) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

Examples of the "monocyclic aromatic heterocyclic group" include a 5- to 7-membered monocyclic aromatic heterocyclic group containing, as ring-constituting atom besides carbon atom, 1 to 4 hetero atoms selected from oxygen atom, sulfur atom and nitrogen atom (e.g., furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 2-imidazolyl, 4-imidazolyl, 5-imidazolyl), pyrazolyl (e.g., 3-pyrazolyl, 4-pyrazolyl), thiazolyl (e.g., 2-thiazolyl, 4-thiazolyl, 5-thiazolyl), isothiazolyl, oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-3-yl, 1,2,3-triazol-4-yl), tetrazolyl (e.g., tetrazol-5-yl), triazinyl etc.) and the like.

Examples of the "fused aromatic heterocyclic group" include a group formed by fusion of a 5- to 7-membered monocyclic aromatic heterocyclic group containing, as ring-constituting atom besides carbon atom, 1 to 4 hetero atoms selected from oxygen atom, sulfur atom and nitrogen atom, and the like, and a $C_{6-10}$ aryl and the like; a group formed by fusion of the above-mentioned 5- to 7-membered monocyclic aromatic heterocyclic groups (e.g., quinolyl (e.g., 2-quinolyl, 3-quinolyl, 4-quinolyl, isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-2-yl, benzimidazol-5-yl), indolyl (e.g., indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl, benzotriazolyl, pyrazolopyridyl, pyrazolothienyl, pyrazolotriazinyl etc.) and the like.

Examples of the "non-aromatic heterocyclic group" include a 3- to 8-membered saturated or unsaturated non-aromatic heterocyclic group (e.g., oxiranyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl, thiazocanyl, dioxinyl etc.) and the like.

In the present specification, examples of the term "group bonded via a nitrogen atom" include a nitro, an amino optionally having substituent(s), a heterocyclic group bonded via a nitrogen atom and optionally having substituent(s) and the like.

Examples of the substituent of the "amino optionally having substituent(s)" (in the present specification, also the term "amino optionally having substituent(s)" for $R^3$) include a group bonded via a carbon atom, the formulas —(CO)$R^a$, —(CO)NH$R^a$, and —SO$_2R^a$ wherein $R^a$ is a group bonded via a carbon atom, and the like, and the amino may be mono- or di-substituted. When the amino is di-substituted, the substituents may be the same or different.

Examples of the "heterocyclic group bonded via a nitrogen atom and optionally having substituent(s)" include a heterocyclic group bonded via a nitrogen atom (monocyclic aromatic heterocyclic group, fused aromatic heterocyclic group, non-aromatic heterocyclic group) optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

Examples of the "monocyclic aromatic heterocyclic group" include a 5- to 7-membered monocyclic aromatic heterocyclic group optionally containing, as ring-constituting atom besides carbon atom and one nitrogen atom, 1 to 4 hetero atoms selected from oxygen atom, sulfur atom and nitrogen atom (e.g., pyrrolyl (e.g., 1-pyrrolyl), imidazolyl (e.g., 1-imidazolyl), pyrazolyl (e.g., 1-pyrazolyl), triazolyl (e.g., 1,2,4-triazol-1-yl), tetrazolyl (e.g., tetrazol-1-yl) etc.) and the like.

Examples of the "fused aromatic heterocyclic group" include a group formed by fusion of a 5- to 7-membered monocyclic aromatic heterocyclic group optionally containing, as ring-constituting atom besides carbon atom and one nitrogen atom, 1 to 4 hetero atoms selected from oxygen atom, sulfur atom and nitrogen atom, and the like, and a $C_{6-10}$ aryl and the like; a group formed by fusion of the above-mentioned 5- to 7-membered monocyclic aromatic heterocyclic groups (e.g., benzimidazolyl (e.g., benzimidazol-1-yl), indolyl (e.g., indol-1-yl) etc.) and the like.

Examples of the "non-aromatic heterocyclic group" include a 3- to 8-membered saturated or unsaturated non-aromatic heterocyclic group (e.g., azetidinyl, pyrrolidinyl, piperidinyl, morpholinyl, thiomorpholinyl, piperazinyl, azepanyl, oxazepanyl, thiazepanyl, azocanyl etc.) and the like.

In the present specification, examples of the term "group bonded via an oxygen atom" include a hydroxy optionally having a substituent. Examples of the substituent of the "hydroxy optionally having a substituent" include a group bonded via a carbon atom and the like.

In the present specification, the term "group bonded via a sulfur atom" is, for example, a mercapto or a group represented by the formula —S(O)$_nR^b$ wherein n is an integer of 0 to 2, and $R^b$ is a group bonded via a carbon atom or a group bonded via a nitrogen atom.

In the present specification, the term "cyclic group optionally having substituent(s)" is a cyclic group optionally having 1 to 3 substituents selected from (1) a $C_{1-6}$ alkyl (e.g., methyl, ethyl, propyl, isopropyl, butyl, isobutyl, tert-butyl etc.) optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.) and (2) the substituent group A.

Examples of the "cyclic group" include an aromatic hydrocarbon group, an aromatic heterocyclic group (e.g., monocyclic aromatic heterocyclic group, fused aromatic heterocyclic group), a non-aromatic cyclic hydrocarbon group, a non-aromatic heterocyclic group, a fused ring group thereof and the like.

Examples of the aromatic hydrocarbon group include a $C_{6-10}$ aryl and the like. Specific examples include phenyl, 1-naphthyl, 2-naphthyl, biphenylyl, anthryl, phenanthryl, acenaphthyl and the like.

Examples of the "monocyclic aromatic heterocyclic group" include a 5- to 7-membered monocyclic aromatic heterocyclic group containing, as ring-constituting atom besides carbon atom, 1 to 4 hetero atoms selected from oxygen atom, sulfur atom and nitrogen atom (e.g., furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl, oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl etc.) and the like.

Examples of the "fused aromatic heterocyclic group" include a group formed by fusion of a 5- to 7-membered monocyclic aromatic heterocyclic group containing, as ring-constituting atom besides carbon atom, 1 to 4 hetero atoms selected from oxygen atom, sulfur atom and nitrogen atom, and the like, and a $C_{6-10}$ aryl and the like; a group formed by fusion of the above-mentioned 5- to 7-membered monocyclic aromatic heterocyclic groups (e.g., quinolyl (e.g., 2-quinolyl, 3-quinolyl, 4-quinolyl, isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-1-yl, benzimidazol-2-yl, benzimidazol-5-yl), indolyl (e.g., indol-1-yl, indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl, benzotriazolyl, pyrazolopyridyl, pyrazolothienyl, pyrazolotriazinyl etc.).

Examples of the "non-aromatic cyclic hydrocarbon group" include a cycloalkyl, a cycloalkenyl and a cycloalkadienyl, each of which is optionally fused with a benzene ring (e.g., a $C_{3-6}$ cycloalkyl (e.g., cyclopropyl, cyclobutyl, cyclopentyl, cyclohexyl), a $C_{3-6}$ cycloalkenyl (e.g., cyclopropenyl, cyclobutenyl, cyclopentenyl, cyclohexenyl), $C_{4-10}$ cycloalkadienyl (e.g., cyclobutadienyl, cyclopentadienyl, cyclohexadienyl, cycloheptadienyl, cyclooctadienyl, cyclononadienyl, cyclodecadienyl) and the like, a fused ring formed by fusion of these groups and a benzene ring (e.g., indanyl (e.g., 1-indanyl), tetrahydronaphthyl (e.g., 1,2,3,4-tetrahydronaphthalen-1-yl), fluorenyl (e.g., 9-fluorenyl) etc.) etc.) and the like.

Examples of the "non-aromatic heterocyclic group" include a 3- to 8-membered saturated or unsaturated non-aromatic heterocyclic group (e.g., oxiranyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl, thiazocanyl, dioxinyl, tetrahydropyrimidinyl, tetrahydropyridinyl etc.) and the like.

The "ring optionally having substituent(s)" formed together with $R^3$ and $R^4$ is a ring optionally having 1 to 3 substituents selected from a $C_{1-6}$ alkyl (e.g., methyl, ethyl, propyl, isopropyl, butyl, isobutyl, tert-butyl etc.) optionally having 1 to 3 halogen atoms and the substituent group A.

Examples of the "ring" include, among the rings constituting the above-mentioned "cyclic group", those containing the formula —C=C— as a ring constituting part, and a 5- to 8-membered ring is preferable.

In compound (I), preferable respective substituents are shown below.

As $R^1$, a hydrogen atom is preferable.
As $R^2$, a hydrogen atom is preferable.
As $R^3$, an amino optionally substituted (more preferably monosubstituted) by acyl is preferable. Here, acyl is the formula —C(O)$R^7$ wherein $R^7$ is (1) a mono-$C_{1-6}$ alkylamino, (2) a di-$C_{1-6}$ alkylamino, (3) a mono-$C_{3-6}$ cycloalkylamino, (4) a mono($C_{1-6}$ alkyl-carbonyl)amino optionally having 1 to 3 halogen atoms, (5) a mono($C_{3-6}$ cycloalkyl-carbonyl)amino, (6) a mono($C_{6-10}$ aryl-carbonyl)amino optionally having 1 to 3 halogen atoms, (7) a mono(5- or 6-membered monocyclic aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (8) a mono(8- to 12-membered fused aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (9) a mono(3- to 8-membered non-aromatic heterocyclyl-carbonyl)amino, (10) a $C_{1-5}$ alkyl optionally having 1 to 3 substituents selected from the aforementioned substituent group A, (11) a $C_{3-6}$ cycloalkyl optionally having 1 to 3 substituents selected from the aforementioned substituent group A, (12) a $C_{3-6}$ cycloalkyl-$C_{1-3}$ alkyl optionally having 1 to 3 substituents selected from the aforementioned substituent group A, (13) a $C_{3-8}$ cycloalkenyl optionally having 1 to 3 substituents selected from the aforementioned substituent group A, (14) a $C_{3-8}$ cycloalkenyl-$C_{1-3}$ alkyl optionally having 1 to 3 substituents selected from the aforementioned substituent group A, (15) a $C_{6-10}$ aryl optionally having 1 to 3 substituents selected from the aforementioned substituent group A, (16) a $C_{6-10}$ aryl-$C_{1-3}$ alkyl optionally having 1 to 3 substituents selected from the aforementioned substituent group A or (17) a 5- or 6-membered monocyclic aromatic heterocyclic group optionally having 1 to 3 substituents selected from the aforementioned substituent group A and the aforementioned substituent group C, or the formula —S(O)$_2R^8$ wherein $R^8$ is a group bonded via a carbon atom. Particularly, as $R^3$, (1) an amino, (2) a mono-$C_{1-6}$ alkylaminocarbonylamino, (3) a mono-$C_{3-6}$ cycloalkylamino-carbonylamino, (4) a $C_{1-5}$ alkyl-carbonylamino optionally having 1 to 3 substituents selected from (a) a halogen atom, (b) a hydroxy, (c) a $C_{1-6}$ alkoxy and (d) a 3- to 8-membered non-aromatic heterocyclic group optionally having one $C_{1-6}$ alkyl, (5) a $C_{3-6}$ cycloalkyl-carbonylamino optionally having 1 to 3 halogen atoms, (6) a 5- or 6-membered monocyclic aromatic heterocyclyl-carbonylamino optionally having 1 to 3 substituents selected from a halogen atom and a $C_{1-6}$ alkyl or (7) a $C_{3-6}$ cycloalkyl-sulfonylamino is preferable.

In addition, another preferable example of $R^3$ is an amino substituted by a 5- to 7-membered monocyclic aromatic heterocyclic group optionally having one halogen atom (particularly 2-chloropyrimidin-4-ylamino).

As $R^4$, a hydrogen atom is preferable.
As $R^5$, a hydrogen atom is preferable.

As a combination of $Z_1$, $Z_2$, $Z_3$ and $Z_4$, and a group represented by the formula

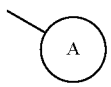

a combination of $Z_1$, $Z_2$, $Z_3$ and $Z_4$ which is the following combination:
$(Z_1,Z_2,Z_3,Z_4)$=(CH,N,CH,C), (N,N,CH,C), (N,C,CH,N) or (S,C,N,C); and
a group represented by the formula

which is a $C_{6-10}$ aryl (particularly phenyl) optionally having substituent(s) is preferable. Particularly, a combination of $Z_1$, $Z_2$, $Z_3$ and $Z_4$ which is the following combination:
$(Z_1,Z_2,Z_3,Z_4)$=(CH,N,CH,C), (N,N,CH,C), (N,C,CH,N) or (S,C,N,C); and a group represented by the formula

which is a phenyl optionally having 1 to 3 substituents selected from
(1) a halogen atom,
(2) a $C_{1-6}$ alkyl optionally having 1 to 3 substituents selected from (a) a halogen atom, and
  (b) a 5- or 6-membered monocyclic aromatic heterocyclic group,
(3) a mono-$C_{1-6}$ alkylamino optionally having one substituent selected from (a) a $C_{6-10}$ aryl and (b) a 5- or 6-membered monocyclic aromatic heterocyclic group optionally having one $C_{1-6}$ alkyl,
(4) a 5- or 6-membered monocyclic aromatic heterocyclyl-amino,
(5) a cyclic amino optionally having one oxo and optionally fused with a benzene ring,
(6) a $C_{1-6}$ alkyl-carbonylamino optionally having a 5- or 6-membered monocyclic aromatic heterocyclic group,
(7) a $C_{3-6}$ cycloalkyl-carbonylamino,
(8) a $C_{3-6}$ cycloalkenyl-carbonylamino,
(9) a $C_{2-6}$ alkynyl-carbonylamino optionally having one $C_{6-10}$ aryl,
(10) a $C_{6-10}$ aryl-carbonylamino optionally having 1 to 3 substituents selected from
  (a) a halogen atom,
  (b) a cyano,
  (c) a hydroxy,
  (d) an amino,
  (e) a $C_{1-6}$ alkyl optionally having 1 to 3 substituents selected from a halogen atom and a cyano,
  (f) a $C_{3-6}$ cycloalkyl optionally having one cyano,
  (g) a $C_{1-6}$ alkoxy,
  (h) a mono-$C_{1-6}$ alkylamino,
  (i) a di-$C_{1-6}$ alkylamino,
  (j) a $C_{1-6}$ alkyl-carbonylamino, and
  (k) a $C_{1-4}$ alkylenedioxy,
(11) a mono(5- or 6-membered monocyclic aromatic heterocyclyl-carbonyl)amino optionally having 1 to 3 substituents selected from
  (a) a halogen atom,
  (b) a hydroxy,
  (c) an amino,
  (d) a $C_{1-6}$ alkyl optionally having 1 to 3 halogen atoms,
  (e) a $C_{6-10}$ aryl,
  (f) a $C_{1-6}$ alkoxy,
  (g) a $C_{1-6}$ alkylsulfanyl, and
  (h) a $C_{3-6}$ cycloalkyl,
(12) a mono(8- to 12-membered fused aromatic heterocyclyl-carbonyl)amino optionally having 1 to 3 substituents selected from
  (a) a halogen atom,
  (b) a $C_{1-6}$ alkyl optionally having 1 to 3 halogen atoms,
  (c) a $C_{1-6}$ alkoxy, and
  (d) a $C_{3-6}$ cycloalkyl,
(13) a 3- to 8-membered non-aromatic heterocyclyl-carbonylamino,
(14) a $C_{6-10}$ aryl-sulfonylamino optionally having 1 to 3 substituents selected from
  (a) a halogen atom,
  (b) a $C_{1-6}$ alkyl optionally having 1 to 3 halogen atoms, and
  (c) a $C_{1-6}$ alkylsulfonyl,
(15) a 5- or 6-membered monocyclic aromatic heterocyclyl-sulfonylamino optionally having one $C_{1-6}$ alkyl, and
(16) a ureido optionally having substituents selected from
  (a) a $C_{1-6}$ alkyl,
  (b) a $C_{6-10}$ aryl, and
  (c) a 5- or 6-membered monocyclic aromatic heterocyclic group,
is preferable.

As compound (I), the compounds described in Examples 1 to 248 are particularly preferable, and specifically, N-[3-({2-[(cyclopropylcarbonyl)amino]imidazo[1,2-a]pyridin-6-yl}oxy)phenyl]-1,3-dimethyl-1H-pyrazole-5-carboxamide, N-[5-({2-[(cyclopropylcarbonyl)amino]imidazo[1,2-a]pyridin-6-yl}oxy)-2-fluorophenyl]-1,3-dimethyl-1H-pyrazole-5-carboxamide, N-[3-({2-[(cyclopropylcarbonyl)amino][1,2,4]triazolo[1,5-a]pyridin-6-yl}oxy)phenyl]-1,3-dimethyl-1H-pyrazole-5-carboxamide, N-[5-({2-[(cyclopropylcarbonyl)amino][1,2,4]triazolo[1,5-a]pyridin-6-yl}oxy)-2-methylphenyl]-1,3-dimethyl-1H-pyrazole-5-carboxamide, N-[3-({2-[(cyclopropylcarbonyl)amino][1,2,4]triazolo[1,5-a]pyridin-6-yl}oxy)phenyl]-2-methyl-5-(trifluoromethyl)-1,3-oxazole-4-carboxamide, N-[5-({2-[(cyclopropylcarbonyl)amino][1,2,4]triazolo[1,5-a]pyridin-6-yl}oxy)-2-fluorophenyl]-1,3-dimethyl-1H-pyrazole-5-carboxamide, N-[5-({2-[(cyclopropylcarbonyl)amino][1,2,4]triazolo[1,5-a]pyridin-6-yl}oxy)-2-fluorophenyl]-1-ethyl-3-methyl-1H-pyrazole-5-carboxamide, N-[3-({2-[(cyclopropylcarbonyl)amino][1,2,4]triazolo[1,5-a]pyridin-7-yl}oxy)phenyl]-1,3-dimethyl-1H-pyrazole-5-carboxamide, N-[3-({2-[(cyclopropylcarbonyl)amino]-1,3-benzothiazol-6-yl}oxy)phenyl]-1,3-dimethyl-1H-pyrazole-5-carboxamide, N-[3-({2-[(cyclopropylcarbonyl)amino][1,3]thiazolo[5,4-b]pyridin-5-yl}oxy)phenyl]-1,3-dimethyl-1H-pyrazole-5-carboxamide, or a salt thereof is preferable.

In compound (I), $Z_1$, $Z_2$, $Z_3$ and $Z_4$ are the following combination:
$(Z_1,Z_2,Z_3,Z_4)$=(CR$^4$,N,CR$^5$,C), (N,N,CR$^5$,C), (N,C,CR$^5$,N), (S,C,CR$^5$,C) or (S,C,N,C).

That is, compound (I) can be subdivided into the compounds represented by the following formulas (Ia) to (Ie) (hereinafter to be sometimes abbreviated as compounds (Ia) to (Ie)).

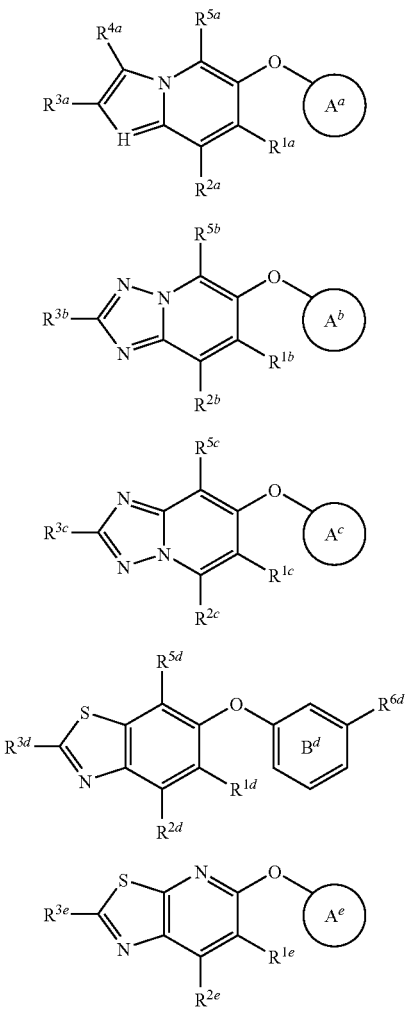

Compounds (Ia) to (Ie) are explained below.
[Compound (Ia)]

imidazo[1,2-a]pyridine derivative

A group represented by the formula

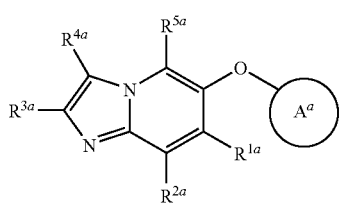
(Ia)

wherein $R^{1a}$ and $R^{2a}$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;

$R^{3a}$ is an amino optionally having substituent(s);

$R^{4a}$ and $R^{5a}$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;

$R^{3a}$ may form, together with $R^{4a}$, a ring optionally having substituent(s);

a group represented by the formula

is a cyclic group optionally having substituent(s), provided that 2-methoxycarbonylamino-6-(4-nitrophenoxy)imidazo[1,2-a]pyridine, 2-methoxycarbonylamino-6-(phenoxy)imidazo[1,2-a]pyridine, 6-(4-acetamidophenoxy)-2-methoxycarbonylaminoimidazo[1,2-a]pyridine, 6-(4-aminophenoxy)-2-methoxycarbonylaminoimidazo[1,2-a]pyridine and 6-(4-(2-fluoro-5-(trifluoromethyl)phenyl)aminocarbonylamino)phenoxy-2-methoxycarbonylaminoimidazo[1,2-a]pyridine are excluded, or a salt thereof.

As $R^{1a}$, a hydrogen atom is preferable.
As $R^{2a}$, a hydrogen atom is preferable.
As $R^{3a}$, an amino optionally monosubstituted by an acyl is preferable. Here, acyl is the formula —C(O)$R^{7a}$ wherein $R^{7a}$ is (1) a mono-$C_{1-6}$ alkylamino, (2) a di-$C_{1-6}$ alkylamino, (3) a mono-$C_{3-6}$ cycloalkylamino, (4) a mono($C_{1-6}$ alkyl-carbonyl)amino optionally having 1 to 3 halogen atoms, (5) a mono ($C_{3-6}$ cycloalkyl-carbonyl)amino, (6) a mono($C_{6-10}$ aryl-carbonyl)amino optionally having 1 to 3 halogen atoms, (7) a mono(5- or 6-membered monocyclic aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (8) a mono(8- to 12-membered fused aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (9) a mono(3- to 8-membered non-aromatic heterocyclyl-carbonyl)amino, (10) a $C_{1-5}$ alkyl optionally having 1 to 3 substituents selected from the aforementioned substituent group A, (11) a $C_{3-6}$ cycloalkyl optionally having 1 to 3 substituents selected from the aforementioned substituent group A, (12) a $C_{3-6}$ cycloalkyl-$C_{1-3}$ alkyl optionally having 1 to 3 substituents selected from the aforementioned substituent group A, (13) a $C_{3-8}$ cycloalkenyl optionally having 1 to 3 substituents selected from the aforementioned substituent group A, (14) a $C_{3-8}$ cycloalkenyl-$C_{1-3}$ alkyl optionally having 1 to 3 substituents selected from the aforementioned substituent group A, (15) a $C_{6-10}$ aryl optionally having 1 to 3 substituents selected from the aforementioned substituent group A, (16) a $C_{6-10}$ aryl-$C_{1-3}$ alkyl optionally having 1 to 3 substituents selected from the aforementioned substituent group A or (17) a 5- or 6-membered monocyclic aromatic heterocyclic group optionally having 1 to 3 substituents selected from the aforementioned substituent group A and the aforementioned substituent group C, or the formula —S(O)$_2$$R^{8a}$ wherein $R^{8a}$ is a group bonded via a carbon atom.

Of these, an amino optionally monosubstituted by an acyl represented by (A) the formula —C(O)$R^{7a'}$ wherein $R^{7a'}$ is (1) a mono-$C_{1-6}$ alkylamino, (2) a mono-$C_{3-6}$ cycloalkylamino, (3) a $C_{1-5}$ alkyl optionally having 1 to 3 substituents selected from the aforementioned substituent group A, (4) a $C_{3-6}$ cycloalkyl optionally having 1 to 3 substituents selected from the aforementioned substituent group A or (5) a 5- or 6-membered monocyclic aromatic heterocyclic group, or (B) a $C_{3-6}$ cycloalkyl-sulfonyl is preferable as $R^{3a}$. Particularly, (1) an amino, (2) a mono-$C_{1-6}$ alkylamino-carbonylamino (particularly ethylaminocarbonylamino), (3) a mono-$C_{3-6}$ cycloalkylamino-carbonylamino (particularly cyclopropylaminocarbonylamino), (4) a $C_{1-5}$ alkyl-carbonylamino optionally having 1 to 3 substituents selected from (a) a halogen atom, (b) a hydroxy, (c) a $C_{1-6}$ alkoxy (methoxy) and (d) a 3- to 8-membered non-aromatic heterocyclic group (morpholino) (particularly trifluoroacetylamino, hydroxyacetylamino, methoxyacetylamino, morpholinoacetylamino, ethylcarbonylamino, acetylamino), (5) a $C_{3-6}$ cycloalkyl-carbonylamino (particularly cyclopropylcarbonylamino), (6) a 5- or 6-membered monocyclic aromatic heterocyclyl-carbonylamino (particularly 3-pyridylcarbonylamino) optionally having 1 to 3 halogen atoms (particularly, chlorine atom), (7) a $C_{3-6}$ cycloalkyl-sulfonylamino (particularly cyclopropylsulfonylamino) and the like are preferable.

In addition, preferable examples of $R^{3a}$ also include an amino substituted by a 5- to 7-membered monocyclic aromatic heterocyclic group optionally having one halogen atom (particularly 2-chloropyrimidin-4-ylamino).

When $R^{3a}$ and $R^{4a}$ in combination form a ring optionally having substituent(s), compound (Ia) is a compound represented by the formula

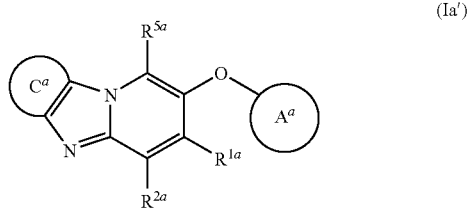

(Ia')

wherein ring $C^a$ is a 5- to 8-membered ring optionally having 1 to 3 substituents selected from a $C_{1-6}$ alkyl optionally having 1 to 3 halogen atoms and the substituent group A, and other symbols are as defined above.

The "5- to 8-membered ring optionally having 1 to 3 substituents selected from a $C_{1-6}$ alkyl optionally having 1 to 3 halogen atoms and the substituent group A" can be selected from those defined above, without particularly limitation. Of these, a tetrahydropyrimidine ring optionally having 1 to 3 substituents selected from a $C_{1-6}$ alkyl and an oxo is preferable.

As $R^{5a}$, a hydrogen atom is preferable.
As the group represented by the formula

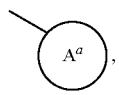

a $C_{6-10}$ aryl optionally having 1 to 3 substituents selected from a $C_{1-6}$ alkyl optionally having 1 to 3 substituents selected from a halogen atom and a 5- or 6-membered monocyclic aromatic heterocyclic group and the substituent group A is preferable. Of these, a $C_{6-10}$ aryl optionally having 1 to 3 substituents selected from (1) a $C_{1-6}$ alkyl optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.), (2) a halogen atom, (3) a mono-$C_{1-6}$ alkylamino (e.g., methylamino, ethylamino, propylamino, isopropylamino, butylamino, isobutylamino, tert-butylamino etc.) optionally having one substituent selected from (a) a $C_{6-10}$ aryl (e.g., phenyl, naphthyl etc.) and (b) a 5- or 6-membered monocyclic aromatic heterocyclic group optionally having one $C_{1-6}$ alkyl (e.g., methyl, ethyl, propyl etc.), (4) a mono-5- or 6-membered monocyclic aromatic heterocyclylamino (e.g., furylamino, thienylamino, pyrrolylamino, oxazolylamino, isoxazolylamino, thiazolylamino, isothiazolylamino, imidazolylamino, tetrazolylamino, pyridylamino, pyrazolylamino etc.) optionally having 1 to 3 substituents selected from the substituent group B and the substituent group C, (5) a cyclic amino (e.g., pyrrolidino, piperidino, piperazino, morpholino, thiomorpholino etc.) optionally having one oxo and optionally fused with a benzene ring, (6) a $C_{1-6}$ alkyl-carbonylamino (e.g., acetylamino, ethylcarbonylamino, propylcarbonylamino, isobutylcarbonylamino, tert-butylcarbonylamino etc.) optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.), (7) a $C_{2-6}$ alkynyl-carbonylamino (e.g., ethynylcarbonylamino, propynylcarbonylamino, butynylcarbonylamino, pentynylcarbonylamino, hexynylcarbonylamino etc.) optionally having one $C_{6-10}$ aryl (e.g., phenyl etc.), (8) a $C_{6-10}$ aryl-carbonylamino (e.g., benzoylamino etc.) optionally having 1 to 3 substituents (except an oxo) selected from the substituent group B and the substituent group C, (9) a mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino, pyrazinylcarbonylamino, pyridazinylcarbonylamino etc.) optionally having 1 to 3 substituents selected from (a) a halogen atom, (b) a hydroxy, (c) an amino, (d) a $C_{1-6}$ alkyl optionally having 1 to 3 halogen atoms (e.g., methyl, ethyl, propyl, isopropyl, trifluoromethyl, 2,2,2-trifluoroethyl etc.), (e) a $C_{6-10}$ aryl (e.g., phenyl), (f) a $C_{1-6}$ alkoxy (e.g., methoxy, ethoxy, propoxy etc.), (g) a $C_{1-6}$ alkylsulfanyl (e.g., methylsulfanyl) and (h) a $C_{3-6}$ cycloalkyl (e.g., cyclopropyl, cyclobutyl, cyclopentyl, cyclohexyl etc.), (10) a mono(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino, benzopyrazolylcarbonylamino, indolylcarbonylamino etc.) optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (11) a $C_{6-10}$ aryl-sulfonylamino (e.g., phenylsulfonylamino, naphthylsulfonylamino etc.) optionally having one substituent selected from (a) a halogen atom, (b) a $C_{1-6}$ alkyl (e.g., methyl, ethyl, propyl) optionally having 1 to 3 halogen atoms and (c) a $C_{1-6}$ alkylsulfonyl (e.g., methylsulfonyl, ethylsulfonyl etc.),

(12) a 5- or 6-membered monocyclic aromatic heterocyclyl-sulfonylamino (e.g., furylsulfonylamino, thienylsulfonylamino, pyrrolylsulfonylamino, oxazolylsulfonylamino, isoxazolylsulfonylamino, thiazolylsulfonylamino, isothiazolylsulfonylamino, imidazolylsulfonylamino, tetrazolylsulfonylamino, pyridylsulfonylamino, pyrazolylsulfonylamino etc.) optionally having one $C_{1-6}$ alkyl (e.g., methyl, ethyl, propyl); and (13) a ureido optionally having substituent(s) selected from (a) a $C_{1-6}$ alkyl (particularly isopropyl), (b) a $C_{6-10}$ aryl (particularly phenyl) and (c) a 5- or 6-membered monocyclic aromatic heterocyclic group (particularly pyridyl) is preferable.

Particularly, a $C_{6-10}$ aryl (particularly phenyl) optionally having 1 to 3 substituents selected from (1) a $C_{1-6}$ alkyl (particularly methyl), (2) a halogen atom (particularly fluorine atom, chlorine atom), (3) a mono-$C_{1-6}$ alkylamino (particularly methylamino) optionally having one substituent selected from (a) a $C_{6-10}$ aryl (particularly phenyl) and (b) a 5- or 6-membered monocyclic aromatic heterocyclic group (particularly pyridyl) optionally having one $C_{1-6}$ alkyl (particularly methyl), (4) a 5- or 6-membered monocyclic aromatic heterocyclyl-amino (particularly pyridylamino), (5) a cyclic amino (particularly pyrrolidinyl) optionally having one oxo and optionally fused with a benzene ring, (6) a $C_{1-6}$ alkyl-carbonylamino (particularly acetylamino) optionally having a 5- or 6-membered monocyclic aromatic heterocyclic group (particularly pyridyl), (7) a $C_{2-6}$ alkynyl-carbonylamino (particularly ethynylcarbonylamino) optionally having one $C_{6-10}$ aryl (particularly phenyl), (8) a $C_{6-10}$ arylcarbonylamino (particularly benzoylamino) optionally having 1 to 3 substituents selected from (a) a halogen atom (particularly fluorine atom, chlorine atom), (b) a cyano, (c) a hydroxy, (d) an amino, (e) a $C_{1-6}$ alkyl (particularly methyl, isopropyl) optionally having 1 to 3 substituents selected from a halogen atom (particularly fluorine atom) and a cyano, (f) a $C_{3-6}$ cycloalkyl (particularly cyclopropyl) optionally having one cyano, (g) a $C_{1-6}$ alkoxy (particularly methoxy), (h) a mono-$C_{1-6}$ alkylamino (particularly methylamino), (i) a di-$C_{1-6}$ alkylamino (particularly dimethylamino), (j) a $C_{1-6}$ alkyl-carbonylamino (particularly acetylamino), (k) a $C_{1-6}$ alkyl-sulfonyl (particularly methylsulfonyl) and (l) a $C_{1-4}$ alkylenedioxy (particularly methylenedioxy), (9) a mono(5- or 6-membered monocyclic aromatic heterocyclyl-carbonyl) amino (particularly furylcarbonylamino, thienylcarbonylamino, imidazolylcarbonylamino, pyrazolylcarbonylamino, tetrazolylcarbonylamino, oxazolylcarbonylamino, pyridylcarbonylamino, pyridazinylcarbonylamino, pyrazinylcarbonylamino) optionally having 1 to 3 substituents selected from (a) a halogen atom (particularly fluorine atom, chlorine atom), (b) a hydroxy, (c) an amino, (d) a $C_{1-6}$ alkyl (particularly methyl, ethyl) optionally having 1 to 3 halogen atoms (particularly fluorine atom), (e) a $C_{6-10}$ aryl (particularly phenyl), (f) a $C_{1-6}$ alkoxy (particularly methoxy, ethoxy) and (g) a $C_{1-6}$ alkylsulfanyl (particularly methylsulfanyl), (10) a mono(8- to 12-membered fused aromatic heterocyclyl-carbonyl)amino (particularly indolylcarbonylamino) optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (11) a $C_{6-10}$ aryl-sulfonylamino (particularly phenylsulfonylamino) optionally having one substituent selected from (a) a halogen atom (particularly fluorine atom), (b) a $C_{1-6}$ alkyl (particularly methyl) optionally having 1 to 3 halogen atoms (particularly fluorine atom) and (c) a $C_{1-6}$ alkylsulfonyl (particularly methylsulfonyl), (12) a 5- or 6-membered monocyclic aromatic heterocyclyl-sulfonylamino (particularly imidazolylsulfonylamino, pyridylsulfonylamino) optionally having one $C_{1-6}$ alkyl (particularly methyl), and (13) a ureido optionally having substituent(s) selected from (a) a $C_{1-6}$ alkyl (particularly isopropyl), (b) a $C_{6-10}$ aryl (particularly phenyl) and (c) a 5- or 6-membered monocyclic aromatic heterocyclic group (particularly pyridyl) is preferable.

As compound (Ia), a compound wherein
$R^{1a}$ is a hydrogen atom;
$R^{2a}$ is a hydrogen atom;
$R^{3a}$ is an amino optionally monosubstituted by an acyl;
$R^{4a}$ is a hydrogen atom;
$R^{5a}$ is a hydrogen atom; and
a group represented by the formula

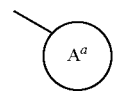

is a $C_{6-10}$ aryl optionally having 1 to 3 substituents selected from a $C_{1-6}$ alkyl optionally having 1 to 3 substituents selected from a halogen atom and a 5- or 6-membered monocyclic aromatic heterocyclic group and the substituent group A is preferable.

Of these, as compound (Ia), a compound wherein
$R^{1a}$ is a hydrogen atom;
$R^{2a}$ is a hydrogen atom;
$R^{3a}$ is an amino optionally monosubstituted by an acyl represented by (A) the formula —C(O)$R^{7a'}$ wherein $R^{7a'}$ is (1) a mono-$C_{1-6}$ alkylamino, (2) a mono-$C_{3-6}$ cycloalkylamino, (3) a $C_{1-5}$ alkyl optionally having 1 to 3 substituents selected from the aforementioned substituent group A, (4) a $C_{3-6}$ cycloalkyl optionally having 1 to 3 substituents selected from the aforementioned substituent group A or (5) a 5- or 6-membered monocyclic aromatic heterocyclic group, or (B) a $C_{3-8}$ cycloalkyl-sulfonyl;
$R^{4a}$ is a hydrogen atom;
$R^{5a}$ is a hydrogen atom; and
a group represented by the formula

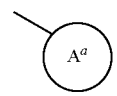

is a $C_{6-10}$ aryl optionally having 1 to 3 substituents selected from (1) a $C_{1-6}$ alkyl optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.), (2) a halogen atom, (3) a mono-$C_{1-6}$ alkylamino (e.g., methylamino, ethylamino, propylamino, isopropylamino, butylamino, isobutylamino, tert-butylamino etc.) optionally having one substituent selected from (a) a $C_{6-10}$ aryl (e.g., phenyl, naphthyl etc.) and (b) a 5- or 6-membered monocyclic aromatic heterocyclic group optionally having one $C_{1-6}$ alkyl (e.g., methyl, ethyl, propyl etc.), (4) a mono-5- or 6-membered monocyclic aromatic heterocyclyl-amino (e.g., furylamino, thienylamino, pyrrolylamino, oxazolylamino, isoxazolylamino, thiazolylamino, isothiazolylamino, imidazolylamino, tetrazolylamino, pyridylamino, pyrazolylamino etc.) optionally having 1 to 3 substituents selected from the substituent group B and the substituent group C, (5) a cyclic amino (e.g., pyrrolidino, piperidino, piperazino, morpholino, thiomorpholino etc.) optionally having one oxo and optionally fused with a benzene ring, (6) a $C_{1-6}$ alkyl-carbonylamino (e.g., acetylamino, ethylcarbonylamino, propylcarbonylamino, isobutylcarbonylamino, tert-butylcarbonylamino etc.) optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.), (7) a $C_{2-6}$ alkynyl-carbonylamino (e.g., ethynylcarbonylamino, propynylcarbonylamino, butynylcarbonylamino, pentynylcarbonylamino, hexynylcarbonylamino etc.) optionally having one $C_{6-10}$ aryl (e.g., phenyl etc.), (8) a $C_{6-10}$ arylcarbonylamino (e.g., benzoylamino etc.) optionally having 1 to 3 substituents (except an oxo) selected from the substituent group B and the substituent group C, (9) a mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino, pyrazinylcarbonylamino, pyridazinylcarbonylamino etc.) optionally having 1 to 3 substituents selected from (a) a halogen atom, (b) a hydroxy, (c) an amino, (d) a $C_{1-6}$ alkyl optionally having 1 to 3 halogen atoms (e.g., methyl, ethyl, propyl, isopropyl, trifluoromethyl, 2,2,2-trifluoroethyl etc.), (e) a $C_{6-10}$ aryl (e.g., phenyl), (f) a $C_{1-6}$ alkoxy (e.g., methoxy, ethoxy, propoxy etc.), (g) a $C_{1-6}$ alkylsulfanyl (e.g., methylsulfanyl) and (h) a $C_{3-6}$ cycloalkyl (e.g., cyclopropyl, cyclobutyl, cyclopentyl, cyclohexyl etc.), (10) a mono(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino, benzopyrazolylcarbonylamino, indolylcarbonylamino etc.) optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (11) a $C_{6-10}$ aryl-sulfonylamino (e.g., phenylsulfonylamino, naphthylsulfonylamino etc.) optionally having one substituent selected from (a) a halogen atom, (b) a $C_{1-6}$ alkyl (e.g., methyl, ethyl, propyl) optionally having 1 to 3 halogen atoms and (c) a $C_{1-6}$ alkylsulfonyl (e.g., methylsulfonyl, ethylsulfonyl etc.), (12) a 5- or 6-membered monocyclic aromatic heterocyclyl-sulfonylamino (e.g., furylsulfonylamino, thienylsulfonylamino, pyrrolylsulfonylamino, oxazolylsulfonylamino, isoxazolylsulfonylamino, thiazolylsulfonylamino, isothiazolylsulfonylamino, imidazolylsulfonylamino, tetrazolylsulfonylamino, pyridylsulfonylamino, pyrazolylsulfonylamino etc.) optionally having one $C_{1-6}$ alkyl (e.g., methyl, ethyl, propyl); and (13) a ureido optionally having substituent(s) selected from (a) a $C_{1-6}$ alkyl (particularly isopropyl), (b) a $C_{6-10}$ aryl (particularly phenyl) and (c) a 5- or 6-membered monocyclic aromatic heterocyclic group (particularly pyridyl) is preferable.

Particularly, as compound (Ia), a compound wherein
$R^{1a}$ is a hydrogen atom;
$R^{2a}$ is a hydrogen atom;
$R^{3a}$ is (1) an amino, (2) a mono-$C_{1-6}$ alkylamino-carbonylamino (particularly ethylaminocarbonylamino), (3) a mono-$C_{3-6}$ cycloalkylamino-carbonylamino (particularly cyclopropylaminocarbonylamino), (4) a $C_{1-5}$ alkyl-carbonylamino optionally having 1 to 3 substituents selected from (a) a halogen atom, (b) a hydroxy, (c) a $C_{1-6}$ alkoxy (methoxy) and (d) a 3- to 8-membered non-aromatic heterocyclic group (morpholino) (particularly trifluoroacetylamino, hydroxyacetylamino, methoxyacetylamino, morpholinoacetylamino, ethylcarbonylamino, acetylamino), (5) a $C_{3-6}$ cycloalkyl-carbonylamino (particularly cyclopropylcarbonylamino), (6) a 5- or 6-membered monocyclic aromatic heterocyclyl-carbonylamino (particularly 3-pyridylcarbonylamino) or (7) a $C_{3-6}$ cycloalkylsulfonylamino (particularly cyclopropylsulfonylamino);
$R^{4a}$ is a hydrogen atom;
$R^{5a}$ is a hydrogen atom; and
a group represented by the formula

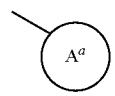

is $C_{6-10}$ aryl (particularly phenyl) optionally having 1 to 3 substituents selected from (1) a $C_{1-6}$ alkyl (particularly methyl), (2) a halogen atom (particularly fluorine atom, chlorine atom), (3) a mono-$C_{1-6}$ alkylamino (particularly methylamino) optionally having one substituent selected from (a) a $C_{6-10}$ aryl (particularly phenyl) and (b) a 5- or 6-membered monocyclic aromatic heterocyclic group (particularly pyridyl) optionally having one $C_{1-6}$ alkyl (particularly methyl), (4) a 5- or 6-membered monocyclic aromatic heterocyclyl-amino (particularly pyridylamino), (5) a cyclic amino (particularly pyrrolidinyl) optionally having one oxo and optionally fused with a benzene ring, (6) a $C_{1-6}$ alkyl-carbonylamino (particularly acetylamino) optionally having a 5- or 6-membered monocyclic aromatic heterocyclic group (particularly pyridyl), (7) a $C_{2-6}$ alkynyl-carbonylamino (particularly ethynylcarbonylamino) optionally having one $C_{6-10}$ aryl (particularly phenyl), (8) a $C_{6-10}$ aryl-carbonylamino (particularly benzoylamino) optionally having 1 to 3 substituents selected from (a) a halogen atom (particularly fluorine atom, chlorine atom), (b) a cyano, (c) a hydroxy, (d) an amino, (e) a $C_{1-6}$ alkyl (particularly methyl, isopropyl) optionally having 1 to 3 substituents selected from a halogen atom (particularly fluorine atom) and a cyano, (f) a $C_{3-6}$ cycloalkyl (particularly cyclopropyl) optionally having one cyano, (g) a $C_{1-6}$ alkoxy (particularly methoxy), (h) a mono-$C_{1-6}$ alkylamino (particularly methylamino), (i) a di-$C_{1-6}$ alkylamino (particularly dimethylamino), (j) a $C_{1-6}$ alkyl-carbonylamino (particularly acetylamino), (k) a $C_{1-6}$ alkyl-sulfonyl (particularly methylsulfonyl) and (l) a $C_{1-4}$ alkylenedioxy (particularly methylenedioxy), (9) a mono (5- or 6-membered monocyclic aromatic heterocyclyl-carbonyl)amino (particularly furylcarbonylamino, thienylcarbonylamino, imidazolylcarbonylamino, pyrazolylcarbonylamino, tetrazolylcarbonylamino, oxazolylcarbonylamino, pyridylcarbonylamino, pyridazinylcarbonylamino, pyrazinylcarbonylamino) optionally having 1 to 3 substituents selected from (a) a halogen atom (particularly fluorine atom, chlorine atom), (b) a hydroxy, (c) an amino, (d) a $C_{1-6}$ alkyl (particularly methyl, ethyl) optionally having 1 to 3 halogen atoms (particularly fluorine atom), (e) a $C_{6-10}$ aryl (particularly phenyl), (f) a $C_{1-6}$ alkoxy (particularly methoxy, ethoxy) and (g) a $C_{1-6}$ alkylsulfanyl (particularly methylsulfanyl), (10) a mono(8- to 12-membered fused aromatic heterocyclyl-carbonyl) amino (particularly indolylcarbonylamino) optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (11) a $C_{6-10}$ arylsulfonylamino (particularly phenylsulfonylamino) optionally having one substituent selected from (a) a halogen atom (particularly fluorine atom), (b) a $C_{1-6}$ alkyl (particularly methyl) optionally having 1 to 3 halogen atoms (particularly fluorine atom) and (c) a $C_{1-6}$ alkylsulfonyl (particularly methylsulfonyl), (12) a 5- or 6-membered monocyclic aromatic heterocyclyl-sulfonylamino (particularly imidazolylsulfonylamino, pyridylsulfonylamino) optionally having one $C_{1-6}$ alkyl (particularly methyl), and (13) a ureido optionally having substituent(s) selected from (a) a $C_{1-6}$ alkyl (particularly isopropyl), (b) a $C_{6-10}$ aryl (particularly phenyl) and (c) a 5- or 6-membered monocyclic aromatic heterocyclic group (particularly pyridyl) is preferable.

More specifically, as compound (Ia), compounds of Example 1-1 to Example 14, and Example 117 to Example 229 and the like are preferable.

Among those, N-[3-({2-[(cyclopropylcarbonyl)amino]imidazo[1,2-a]pyridin-6-yl}oxy)phenyl]-1,3-dimethyl-1H-pyrazole-5-carboxamide (Example 2), N-[2-chloro-5-({2-[(cyclopropylcarbonyl)amino]imidazo[1,2-a]pyridin-6-yl}oxy)phenyl]-1,3-dimethyl-1H-pyrazole-5-carboxamide (Example 3), N-[5-({2-[(cyclopropylcarbonyl)amino]imidazo[1,2-a]pyridin-6-yl}oxy)-2-methylphenyl]-1,3-dimethyl-1H-pyrazole-5-carboxamide (Example 4), N-[3-({2-[(cyclopropylcarbonyl)amino]imidazo[1,2-a]pyridin-6-yl}oxy)phenyl]-1,3-dimethyl-1H-pyrazole-5-carboxamide p-toluenesulfonate (Example 5), N-[3-({2-[(cyclopropylcarbonyl)amino]imidazo[1,2-a]pyridin-6-yl}oxy)phenyl]-3-methylpyridine-2-carboxamide (Example 7-4), N-[5-({2-[(cyclopropylcarbonyl)amino]imidazo[1,2-a]pyridin-6-yl}oxy)-2-fluorophenyl]-1,3-dimethyl-1H-pyrazole-5-carboxamide (Example 9-2), N-{5-[(2-{[(ethylamino)carbonyl]amino}imidazo[1,2-a]pyridin-6-yl)oxy]-2-fluorophenyl}-1,3-dimethyl-1H-pyrazole-5-carboxamide (Example 10), or a salt thereof and the like are preferable, and particularly, N-[3-({2-[(cyclopropylcarbonyl)amino]imidazo[1,2-a]pyridin-6-yl}oxy)phenyl]-1,3-dimethyl-1H-pyrazole-5-carboxamide (Example 2), N-[5-({2-[(cyclopropylcarbonyl)amino]imidazo[1,2-a]pyridin-6-yl}oxy)-2-fluorophenyl]-1,3-dimethyl-1H-pyrazole-5-carboxamide (Example 9-2) and salts thereof are preferable.

[Compound (Ib)]

1,2,4-triazolo[1,5-a]pyridine derivative

A compound represented by the formula

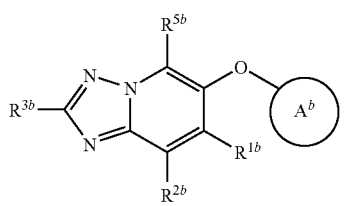

(Ib)

wherein $R^{1b}$ and $R^{2b}$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;

$R^{3b}$ is an amino optionally having substituent(s);
$R^{5b}$ is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom; and
a group represented by the formula

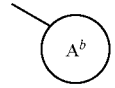

is a cyclic group optionally having substituent(s), or a salt thereof.

As $R^{1b}$, a hydrogen atom is preferable.
As $R^{2b}$, a hydrogen atom is preferable.
As $R^{3b}$, an amino optionally monosubstituted by an acyl is preferable. Here, acyl is the formula —C(O)$R^{7b}$ wherein $R^{7b}$ is (1) a mono-$C_{1-6}$ alkylamino, (2) a di-$C_{1-6}$ alkylamino, (3) a mono($C_{1-6}$ alkyl-carbonyl)amino optionally having 1 to 3 halogen atoms, (4) a mono($C_{3-6}$ cycloalkyl-carbonyl)amino, (5) a mono($C_{6-10}$ aryl-carbonyl)amino optionally having 1 to 3 halogen atoms, (6) a mono(5- or 6-membered monocyclic aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (7) a mono(8- to 12-membered fused aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (8) a mono(3- to 8-membered non-aromatic heterocyclyl-carbonyl)amino, (9) a $C_{1-5}$ alkyl optionally having 1 to 3 substituents selected from the aforementioned substituent group A, (10) a $C_{3-6}$ cycloalkyl optionally having 1 to 3 substituents selected from the aforementioned substituent group A, (11) a $C_{3-6}$ cycloalkyl-$C_{1-3}$ alkyl optionally having 1 to 3 substituents selected from the aforementioned substituent group A, (12) a $C_{3-6}$ cycloalkenyl optionally having 1 to 3 substituents selected from the aforementioned substituent group A, (13) a $C_{3-6}$ cycloalkenyl-$C_{1-3}$ alkyl optionally having 1 to 3 substituents selected from the aforementioned substituent group A, (14) a $C_{6-10}$ aryl optionally having 1 to 3 substituents selected from the aforementioned substituent group A, (15) a $C_{6-10}$ aryl-$C_{1-3}$ alkyl optionally having 1 to 3 substituents selected from the aforementioned substituent group A or (16) a 5- or 6-membered monocyclic aromatic heterocyclic group optionally having 1 to 3 substituents selected from the aforementioned substituent group A and the aforementioned substituent group C, or the formula —S(O)$_2R^{8b}$ wherein $R^{8b}$ is a group bonded via a carbon atom.

Of these, as $R^{3b}$, an amino optionally monosubstituted by an acyl represented by the formula —C(O)$R^{7b'}$ wherein $R^{7b'}$ is (1) a mono-$C_{1-6}$ alkylamino, (2) a $C_{1-5}$ alkyl optionally having 1 to 3 substituents selected from the aforementioned substituent group A, (3) a $C_{3-6}$ cycloalkyl optionally having 1 to 3 substituents selected from the aforementioned substituent group A or (4) a 5- or 6-membered monocyclic aromatic heterocyclic group optionally having 1 to 3 substituents selected from the aforementioned substituent group A and the aforementioned substituent group C is preferable. Particularly, (1) an amino, (2) a mono-$C_{1-6}$ alkylamino-carbonylamino (particularly ethylaminocarbonylamino), (3) a $C_{1-5}$ alkyl-carbonylamino (particularly acetylamino, ethylcarbonylamino, propylcarbonylamino) optionally having one substituent selected from (a) a hydroxy and (b) a 3- to 8-membered non-aromatic heterocyclic group (particularly piperazino, morpholino) optionally having one $C_{1-6}$ alkyl (particularly methyl), (4) a $C_{3-6}$ cycloalkyl-carbonylamino optionally having 1 to 3 halogen atoms (particularly fluorine atom) (particularly cyclopropylcarbonylamino, 2,2-difluorocyclopropylcarbonylamino), (5) a 5- or 6-membered monocyclic aromatic heterocyclyl-carbonylamino (particularly oxazolylcarbonylamino, thiazolylcarbonylamino, pyridylcarbonylamino) optionally having one substituent selected from (a) a halogen atom (particularly bromine atom) and (b) a $C_{1-6}$ alkyl (particularly methyl) and the like is preferable.

As $R^{5b}$, a hydrogen atom is preferable.

As a group represented by the formula

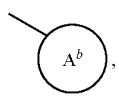

a $C_{6-10}$ aryl optionally having 1 to 3 substituents selected from a $C_{1-6}$ alkyl optionally having 1 to 3 substituents selected from a halogen atom and a 5- or 6-membered monocyclic aromatic heterocyclic group and the substituent group A is preferable. Of these, a $C_{6-10}$ aryl optionally having 1 to 3 substituents selected from (1) a $C_{1-6}$ alkyl optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.), (2) a halogen atom, (3) an amino, (4) a mono($C_{1-6}$ alkyl-carbonyl)amino (e.g., acetylamino, ethylcarbonylamino, propylcarbonylamino, isobutylcarbonylamino, tert-butylcarbonylamino etc.) optionally having 1 to 3 halogen atoms, (5) a mono($C_{3-6}$ cycloalkyl-carbonyl)amino (e.g., cyclopropylcarbonylamino, cyclobutylcarbonylamino, cyclopentylcarbonylamino, cyclohexylcarbonylamino etc.), (6) a mono($C_{3-6}$ cycloalkenyl-carbonyl)amino (e.g., cyclopropenylcarbonylamino, cyclobutenylcarbonylamino, cyclopentenylcarbonylamino, cyclohexenylcarbonylamino etc.), (7) a $C_{6-10}$ aryl-carbonylamino (e.g., benzoylamino etc.) optionally having 1 to 3 substituents (except an oxo) selected from the substituent group B and the substituent group C, (8) a mono-$C_{1-6}$ alkoxy-carbonylamino (e.g., methoxycarbonylamino, ethoxycarbonylamino, tert-butoxycarbonylamino etc.) (9) a mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents selected from (a) a halogen atom (e.g., chlorine atom etc.), (b) a $C_{1-6}$ alkyl optionally having 1 to 3 halogen atoms (e.g., methyl, ethyl, propyl, isopropyl, trifluoromethyl, 2,2,2-trifluoroethyl etc.), (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (10) a mono(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino, benzopyrazolylcarbonylamino etc.) optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.) and (11) a mono(3- to 8-membered non-aromatic heterocyclyl-carbonyl)amino (e.g., oxiranylcarbonylamino, azetidinylcarbonylamino, oxetanylcarbonylamino, tetrahydrofurylcarbonylamino etc.) is preferable.

Of these, a $C_{6-10}$ aryl (particularly phenyl) optionally having 1 to 3 substituents selected from (1) a $C_{1-6}$ alkyl (particularly methyl),
(2) a halogen atom (particularly fluorine atom, chlorine atom),
(3) an amino,
(4) a mono($C_{1-6}$ alkyl-carbonyl)amino (particularly isobutylcarbonylamino),
(5) a mono($C_{3-6}$ cycloalkyl-carbonyl)amino (particularly cyclobutylcarbonylamino),
(6) a mono($C_{3-6}$ cycloalkenyl-carbonyl)amino (particularly cyclopentenylcarbonylamino),
(7) a $C_{6-10}$ aryl-carbonylamino (particularly benzoylamino) optionally having one substituent selected from (a) a $C_{1-6}$ alkyl (particularly methyl, isopropyl) optionally having 1 to 3 substituents selected from a halogen atom (particularly fluorine atom) and a cyano and (b) a $C_{3-6}$ cycloalkyl (particularly cyclopropyl) optionally having a cyano,
(8) a mono-$C_{1-6}$ alkoxy-carbonylamino (particularly tert-butoxycarbonylamino),
(9) a mono(5- or 6-membered monocyclic aromatic heterocyclyl-carbonyl)amino (particularly furylcarbonylamino, thienylcarbonylamino, pyrrolylcarbonylamino, oxazolylcarbonylamino, thiazolylcarbonylamino, pyrazolylcarbonylamino, pyridylcarbonylamino etc.) optionally having 1 to 3 substituents selected from (a) a halogen atom (particularly chlorine atom), (b) a $C_{1-6}$ alkyl optionally having 1 to 3 halogen atoms (particularly fluorine atom) (particularly methyl, ethyl, isopropyl, trifluoromethyl, 2,2,2-trifluoroethyl), (c) a $C_{1-6}$ alkoxy (particularly methoxy) and (d) a $C_{3-6}$ cycloalkyl (particularly cyclopropyl),
(10) a mono(8- to 12-membered fused aromatic heterocyclyl-carbonyl)amino (particularly benzopyrazolylcarbonylamino) optionally having 1 to 3 $C_{1-6}$ alkyl (particularly methyl) and
(11) a mono(3- to 8-membered non-aromatic heterocyclyl-carbonyl)amino (particularly tetrahydrofurylcarbonylamino) is preferable.

As compound (Ib), a compound wherein
$R^{1b}$ is a hydrogen atom;
$R^{2b}$ is a hydrogen atom;
$R^{3b}$ is an amino optionally monosubstituted by an acyl;
$R^{5b}$ is a hydrogen atom; and
a group represented by the formula

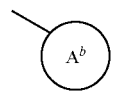

is a $C_{6-10}$ aryl optionally having 1 to 3 substituents selected from a $C_{1-6}$ alkyl optionally having 1 to 3 substituents selected from a halogen atom and a 5- or 6-membered monocyclic aromatic heterocyclic group and the substituent group A is preferable.

Of these, as compound (Ib), a compound wherein
R$^{1b}$ is a hydrogen atom;
R$^{2b}$ is a hydrogen atom;
R$^{3b}$ is an amino optionally monosubstituted by an acyl represented by the formula —C(O)R$^{7b'}$ wherein R$^{7b'}$ is (1) a mono-C$_{1-6}$ alkylamino, (2) a C$_{1-5}$ alkyl optionally having 1 to 3 substituents selected from the aforementioned substituent group A, (3) a C$_{3-6}$ cycloalkyl optionally having 1 to 3 substituents selected from the aforementioned substituent group A or (4) a 5- or 6-membered monocyclic aromatic heterocyclic group optionally having 1 to 3 substituents selected from the aforementioned substituent group A;
R$^{5b}$ is a hydrogen atom; and
a group represented by the formula

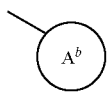

is a C$_{6-10}$ aryl optionally having 1 to 3 substituents selected from (1) a C$_{1-6}$ alkyl optionally having 1 to 3 substituents selected from (a) a halogen atom and (b) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.), (2) a halogen atom, (3) an amino, (4) a mono(C$_{1-6}$ alkyl-carbonyl)amino (e.g., acetylamino, ethylcarbonylamino, propylcarbonylamino, isobutylcarbonylamino, tert-butylcarbonylamino etc.) optionally having 1 to 3 halogen atoms, (5) a mono(C$_{3-6}$ cycloalkyl-carbonyl)amino (e.g., cyclopropylcarbonylamino, cyclobutylcarbonylamino, cyclopentylcarbonylamino, cyclohexylcarbonylamino etc.), (6) a mono(C$_{3-6}$ cycloalkenyl-carbonyl)amino (e.g., cyclopropenylcarbonylamino, cyclobutenylcarbonylamino, cyclopentenylcarbonylamino, cyclohexenylcarbonylamino etc.), (7) a C$_{6-10}$ aryl-carbonylamino (e.g., benzoylamino etc.) optionally having 1 to 3 substituents (except an oxo) selected from the substituent group B and the substituent group C, (8) a mono-C$_{1-6}$ alkoxy-carbonylamino (e.g., methoxycarbonylamino, ethoxycarbonylamino, tert-butoxycarbonylamino etc.), (9) a mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents selected from (a) a halogen atom (e.g., chlorine atom etc.), (b) a C$_{1-6}$ alkyl optionally having 1 to 3 halogen atoms (e.g., methyl, ethyl, propyl, isopropyl, trifluoromethyl, 2,2,2-trifluoroethyl etc.), (c) a C$_{1-6}$ alkoxy (e.g., methoxy, ethoxy, propoxy etc.) and (d) a C$_{3-6}$ cycloalkyl (e.g., cyclopropyl, cyclobutyl, cyclopentyl, cyclohexyl etc.), (10) a mono(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino, benzopyrazolylcarbonylamino etc.) optionally having 1 to 3 substituents selected from (a) a halogen atom, (b) a C$_{1-6}$ alkyl (e.g., methyl, ethyl, propyl etc.) optionally having 1 to 3 halogen atoms, (c) a C$_{1-6}$ alkoxy (e.g., methoxy, ethoxy, propoxy etc.) and (d) a C$_{3-6}$ cycloalkyl (e.g., cyclopropyl, cyclobutyl, cyclopentyl, cyclohexyl etc.) and (11) a mono(3- to 8-membered non-aromatic heterocyclyl-carbonyl)amino (e.g., oxiranylcarbonylamino, azetidinylcarbonylamino, oxetanylcarbonylamino, tetrahydrofurylcarbonylamino etc.) is preferable.

Particularly, as compound (Ib), a compound wherein
R$^{1b}$ is a hydrogen atom;
R$^{2b}$ is a hydrogen atom;
R$^{3b}$ is (1) an amino, (2) a mono-C$_{1-6}$ alkylamino-carbonylamino (particularly ethylaminocarbonylamino), (3) a C$_{1-5}$ alkyl-carbonylamino (particularly acetylamino, ethylcarbonylamino, propylcarbonylamino) optionally having one substituent selected from (a) a hydroxy and (b) a 3- to 8-membered non-aromatic heterocyclic group (particularly piperazino, morpholino) optionally having one C$_{1-6}$ alkyl (particularly methyl), (4) a C$_{3-6}$ cycloalkyl-carbonylamino optionally having 1 to 3 halogen atoms (particularly fluorine atom) (particularly cyclopropylcarbonylamino, 2,2-difluorocyclopropylcarbonylamino) or (5) a 5- or 6-membered monocyclic aromatic heterocyclyl-carbonylamino (particularly oxazolylcarbonylamino, thiazolylcarbonylamino, pyridylcarbonylamino) optionally having one substituent selected from (a) a halogen atom (particularly bromine atom) and (b) a C$_{1-6}$ alkyl (particularly methyl);
R$^{5b}$ is a hydrogen atom; and
a group represented by the formula

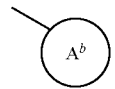

is a C$_{6-10}$ aryl (particularly phenyl) optionally having 1 to 3 substituents selected from
(1) a C$_{1-6}$ alkyl (particularly methyl),
(2) a halogen atom (particularly fluorine atom, chlorine atom),
(3) an amino,
(4) a mono(C$_{1-6}$ alkyl-carbonyl)amino (particularly isobutylcarbonylamino),
(5) a mono(C$_{3-6}$ cycloalkyl-carbonyl)amino (particularly cyclobutylcarbonylamino),
(6) a mono(C$_{3-6}$ cycloalkenyl-carbonyl)amino (particularly cyclopentenylcarbonylamino),
(7) a C$_{6-10}$ aryl-carbonylamino (particularly benzoylamino) optionally having one substituent selected from (a) a C$_{1-6}$ alkyl (particularly methyl, isopropyl) optionally having 1 to 3 substituents selected from a halogen atom (particularly fluorine atom) and a cyano and (b) a C$_{3-6}$ cycloalkyl (particularly cyclopropyl) optionally having a cyano,
(8) a mono-C$_{1-6}$ alkoxy-carbonylamino (particularly tert-butoxycarbonylamino),
(9) a mono(5- or 6-membered monocyclic aromatic heterocyclyl-carbonyl)amino (particularly furylcarbonylamino, thienylcarbonylamino, pyrrolylcarbonylamino, oxazolylcarbonylamino, thiazolylcarbonylamino, pyrazolylcarbonylamino, pyridylcarbonylamino etc.) optionally having 1 to 3 substituents selected from (a) a halogen atom (particularly chlorine atom), (b) a C$_{1-6}$ alkyl optionally having 1 to 3 halogen atoms (particularly fluorine atom) (particularly methyl, ethyl, isopropyl, trifluoromethyl, 2,2,2-trifluoroethyl), (c) a C$_{1-6}$ alkoxy (particularly methoxy) and (d) a C$_{3-6}$ cycloalkyl (particularly cyclopropyl),
(10) a mono(8- to 12-membered fused aromatic heterocyclyl-carbonyl)amino (particularly benzopyrazolylcarbonylamino) optionally having 1 to 3 C$_{1-6}$ alkyl (particularly methyl) and

(11) a mono(3- to 8-membered non-aromatic heterocyclyl-carbonyl)amino (particularly tetrahydrofurylcarbonylamino) is preferable.

As compound (Ib), more specifically, the compounds of Example 15 to Example 95, Example 104 to Example 116, and Example 230 to Example 248 are preferable.

Among those, N-[3-({2-[(cyclopropylcarbonyl)amino][1,2,4]triazolo[1,5-a]pyridin-6-yl}oxy)phenyl]-1,3-dimethyl-1H-pyrazole-5-carboxamide (Example 16), N-[5-({2-[(cyclopropylcarbonyl)amino][1,2,4]triazolo[1,5-a]pyridin-6-yl}oxy)-2-methylphenyl]-1,3-dimethyl-1H-pyrazole-5-carboxamide (Example 17-2), N-[3-({2-[(cyclopropylcarbonyl)amino][1,2,4]triazolo[1,5-a]pyridin-6-yl}oxy)phenyl]-2-methyl-5-(trifluoromethyl)-1,3-oxazole-4-carboxamide (Example 22), N-[5-({2-[(cyclopropylcarbonyl)amino][1,2,4]triazolo[1,5-a]pyridin-6-yl}oxy)-2-fluorophenyl]-1,3-dimethyl-1H-pyrazole-5-carboxamide (Example 23-2), N-[3-({2-[(cyclopropylcarbonyl)amino][1,2,4]triazolo[1,5-a]pyridin-6-yl}oxy)phenyl]-1-methyl-3-(trifluoromethyl)-1H-pyrazole-4-carboxamide (Example 27), N-[3-({2-[(cyclopropylcarbonyl)amino][1,2,4]triazolo[1,5-a]pyridin-6-yl}oxy)phenyl]-1,4-dimethyl-1H-pyrazole-3-carboxamide (Example 33), N-[5-({2-[(cyclopropylcarbonyl)amino][1,2,4]triazolo[1,5-a]pyridin-6-yl}oxy)-2-fluorophenyl]-3-ethyl-1-methyl-1H-pyrazole-5-carboxamide (Example 67), N-[5-({2-[(cyclopropylcarbonyl)amino][1,2,4]triazolo[1,5-a]pyridin-6-yl}oxy)-2-fluorophenyl]-1-ethyl-3-methyl-1H-pyrazole-5-carboxamide (Example 72), N-[2-chloro-5-({2-[(cyclopropylcarbonyl)amino][1,2,4]triazolo[1,5-a]pyridin-6-yl}oxy)phenyl]-1,3-dimethyl-1H-pyrazole-5-carboxamide (Example 83), N-[2-chloro-5-({2-[(cyclopropylcarbonyl)amino][1,2,4]triazolo[1,5-a]pyridin-6-yl}oxy)phenyl]-1,3-dimethyl-1H-pyrazole-4-carboxamide (Example 84), N-[3-({2-[(cyclopropylcarbonyl)amino][1,2,4]triazolo[1,5-a]pyridin-6-yl}oxy)phenyl]-1-methyl-4-(trifluoromethyl)-1H-pyrazole-3-carboxamide (Example 110), and salts thereof and the like are preferable, and N-[3-({2-[(cyclopropylcarbonyl)amino][1,2,4]triazolo[1,5-a]pyridin-6-yl}oxy)phenyl]-1,3-dimethyl-1H-pyrazole-5-carboxamide (Example 16), N-[5-({2-[(cyclopropylcarbonyl)amino][1,2,4]triazolo[1,5-a]pyridin-6-yl}oxy)-2-methylphenyl]-1,3-dimethyl-1H-pyrazole-5-carboxamide (Example 17-2), N-[3-({2-[(cyclopropylcarbonyl)amino][1,2,4]triazolo[1,5-a]pyridin-6-yl}oxy)phenyl]-2-methyl-5-(trifluoromethyl)-1,3-oxazole-4-carboxamide (Example 22), N-[5-({2-[(cyclopropylcarbonyl)amino][1,2,4]triazolo[1,5-a]pyridin-6-yl}oxy)-2-fluorophenyl]-1,3-dimethyl-1H-pyrazole-5-carboxamide (Example 23-2), N-[5-({2-[(cyclopropylcarbonyl)amino][1,2,4]triazolo[1,5-a]pyridin-6-yl}oxy)-2-fluorophenyl]-1-ethyl-3-methyl-1H-pyrazole-5-carboxamide (Example 72), and salts thereof are particularly preferable.

[Compound (Ic)]

1,2,4-triazolo[1,5-a]pyridine derivative

A compound represented by the formula

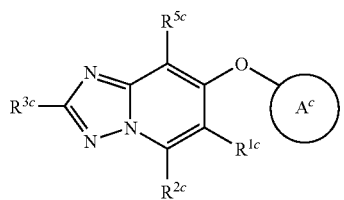

(Ic)

wherein $R^{1c}$ and $R^{2c}$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;

$R^{3c}$ is an amino optionally having substituent(s);

$R^{5c}$ is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom; and a group represented by the formula

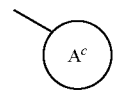

is a cyclic group optionally having substituent(s), or a salt thereof.

As $R^{1c}$, a hydrogen atom is preferable.

As $R^{2c}$, a hydrogen atom is preferable.

As $R^{3c}$, an amino optionally monosubstituted by an acyl is preferable. Here, acyl is the formula —C(O)$R^{7c}$ wherein $R^{7c}$ is (1) a mono-$C_{1-6}$ alkylamino, (2) a di-$C_{1-6}$ alkylamino, (3) a mono($C_{1-6}$ alkyl-carbonyl)amino optionally having 1 to 3 halogen atoms, (4) a mono($C_{3-6}$ cycloalkyl-carbonyl)amino, (5) a mono($C_{6-10}$ aryl-carbonyl)amino optionally having 1 to 3 halogen atoms, (6) a mono(5- or 6-membered monocyclic aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (7) a mono(8- to 12-membered fused aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (8) a mono(3- to 8-membered non-aromatic heterocyclyl-carbonyl)amino, (9) a $C_{1-5}$ alkyl optionally having 1 to 3 substituents selected from the aforementioned substituent group A, (10) a $C_{3-6}$ cycloalkyl optionally having 1 to 3 substituents selected from the aforementioned substituent group A, (11) a $C_{3-6}$ cycloalkyl-$C_{1-3}$ alkyl optionally having 1 to 3 substituents selected from the aforementioned substituent group A, (12) a $C_{3-6}$ cycloalkenyl optionally having 1 to 3 substituents selected from the aforementioned substituent group A, (13) a $C_{3-6}$ cycloalkenyl-$C_{1-3}$ alkyl optionally having 1 to 3 substituents selected from the aforementioned substituent group A, (14) a $C_{6-10}$ aryl optionally having 1 to 3 substituents selected from the aforementioned substituent group A or (15) a $C_{6-10}$ aryl-$C_{1-3}$ alkyl optionally having 1 to 3 substituents selected from the aforementioned substituent group A, or the formula —S(O)$_2$$R^{8c}$ wherein $R^{8c}$ is a group bonded via a carbon atom.

Of these, as $R^{3c}$, an amino optionally monosubstituted by a $C_{3-6}$ cycloalkyl-carbonyl optionally having 1 to 3 substituents selected from the aforementioned substituent group A is preferable. Particularly, an amino or a $C_{3-6}$ cycloalkyl-carbonylamino (particularly cyclopropylcarbonylamino) is preferable.

As $R^{5c}$, a hydrogen atom is preferable.

As a group represented by the formula

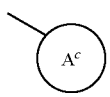

a $C_{6-10}$ aryl optionally having 1 to 3 substituents selected from a $C_{1-6}$ alkyl optionally having 1 to 3 halogen atoms and the substituent group A is preferable. Of these, a $C_{6-10}$ aryl optionally having 1 to 3 substituents selected from a mono (5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkyl-oxy (e.g., methoxy, ethoxy, propoxy etc.) and (d) a $C_{3-6}$ cycloalkyl (e.g., cyclopropyl, cyclobutyl, cyclopentyl, cyclohexyl etc.) is preferable.

Particularly, a $C_{6-10}$ aryl (particularly phenyl) optionally having 1 to 3 mono(5- or 6-membered monocyclic aromatic heterocyclyl-carbonyl)amino (particularly pyrazolylcarbonylamino) optionally having 1 to 3 $C_{1-6}$ alkyl (particularly methyl) is preferable.

As compound (Ic), a compound wherein
$R^{1c}$ is a hydrogen atom;
$R^{2c}$ is a hydrogen atom;
$R^{3c}$ is an amino optionally monosubstituted by an acyl;
$R^{5c}$ is a hydrogen atom; and
a group represented by

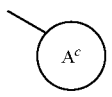

is a $C_{6-10}$ aryl optionally having 1 to 3 substituents selected from a $C_{1-6}$ alkyl optionally having 1 to 3 halogen atoms and the substituent group A is preferable.

Of these, as compound (Ic), a compound wherein
$R^{1c}$ is a hydrogen atom;
$R^{2c}$ is a hydrogen atom;
$R^{3c}$ is an amino optionally monosubstituted by a $C_{3-6}$ cycloalkyl-carbonyl optionally having 1 to 3 substituents selected from the aforementioned substituent group A;
$R^{5c}$ is a hydrogen atom; and
a group represented by

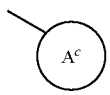

is a $C_{6-10}$ aryl optionally having one mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents selected from (1) a halogen atom, (2) a $C_{1-6}$ alkyl (e.g., methyl, ethyl, propyl etc.) optionally having 1 to 3 halogen atoms, (3) a $C_{1-6}$ alkoxy (e.g., methoxy, ethoxy, propoxy etc.) and (4) a $C_{3-6}$ cycloalkyl (e.g., cyclopropyl, cyclobutyl, cyclopentyl, cyclohexyl etc.) is preferable.

Particularly, as compound (Ic), a compound wherein
$R^{1c}$ is a hydrogen atom;
$R^{2c}$ is a hydrogen atom;
$R^{3c}$ is an amino or a $C_{3-6}$ cycloalkyl-carbonylamino (particularly cyclopropylcarbonylamino);
$R^{5c}$ is a hydrogen atom; and
a group represented by

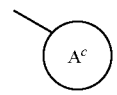

is a $C_{6-10}$ aryl (particularly phenyl) optionally having 1 to 3 mono(5- or 6-membered monocyclic aromatic heterocyclyl-carbonyl)amino (particularly pyrazolylcarbonylamino) optionally having 1 to 3 $C_{1-6}$ alkyl (particularly methyl) is preferable.

As compound (Ic), more specifically, N-[3-({2-[(cyclopropylcarbonyl)amino][1,2,4]triazolo[1,5-a]pyridine-7-yl}oxy)phenyl]-1,3-dimethyl-1H-pyrazole-5-carboxamide (Example 96-4), a salt thereof and the like are preferable.

[Compound (Id)]

1,3-benzothiazole derivative

A compound represented by the formula

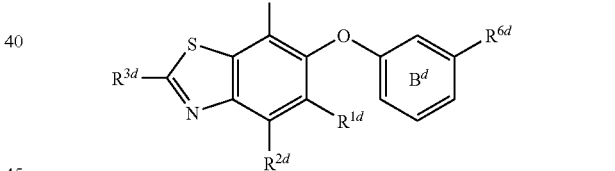

(Id)

wherein $R^{1d}$ and $R^{2d}$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;
$R^{3d}$ is an amino optionally having substituent(s);
$R^{5d}$ is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;
$R^{6d}$ is (1) an amino, (2) a mono-$C_{1-6}$ alkylamino, (3) a di-$C_{1-6}$ alkylamino, (4) a mono($C_{1-6}$ alkyl-carbonyl)amino optionally having 1 to 3 halogen atoms, (5) a mono($C_{3-6}$ cycloalkyl-carbonyl)amino, (6) a mono($C_{3-6}$ cycloalkenyl-carbonyl)amino, (7) a mono($C_{6-10}$ aryl-carbonyl)amino optionally having 1 to 3 halogen atoms, (8) a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (9) a mono(8- to 12-membered fused aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, (10) a mono(3- to 8-membered non-aromatic heterocyclyl-carbonyl)amino, (11) a mono-$C_{1-6}$ alkoxy-carbonylamino, (12) a $C_{1-6}$ alkyl-aminocarbonyl, (13) a di-$C_{1-6}$ alkyl-aminocarbonyl or (14) a nitro, ring $B^d$ is a benzene ring further optionally having substituent(s), or a salt thereof.

Examples of the substituent that ring $B^d$ may further have include substituents selected from a $C_{1-6}$ alkyl optionally having 1 to 3 halogen atoms and the substituent group A, and the ring $B^d$ may further have 1 or 2 substituents.

As $R^{1d}$, a hydrogen atom is preferable.

As $R^{2d}$, a hydrogen atom is preferable.

As $R^{3d}$, an amino optionally monosubstituted by an acyl is preferable. Here, acyl is the formula —C(O)$R^{7d}$ wherein $R^{7d}$ is (1) a mono-$C_{1-6}$ alkylamino, (2) a di-$C_{1-6}$ alkylamino, (3) a mono($C_{1-6}$ alkyl-carbonyl)amino optionally having 1 to 3 halogen atoms, (4) a mono($C_{3-6}$ cycloalkyl-carbonyl)amino, (5) a mono($C_{6-10}$ aryl-carbonyl)amino optionally having 1 to 3 halogen atoms, (6) a mono(5- or 6-membered monocyclic aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (7) a mono(8- to 12-membered fused aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (8) a mono(3- to 8-membered non-aromatic heterocyclyl-carbonyl)amino, (9) a $C_{1-5}$ alkyl optionally having 1 to 3 substituents selected from the aforementioned substituent group A, (10) a $C_{3-6}$ cycloalkyl optionally having 1 to 3 substituents selected from the aforementioned substituent group A, (11) a $C_{3-6}$ cycloalkyl-$C_{1-3}$ alkyl optionally having 1 to 3 substituents selected from the aforementioned substituent group A, (12) a $C_{3-6}$ cycloalkenyl optionally having 1 to 3 substituents selected from the aforementioned substituent group A, (13) a $C_{3-6}$ cycloalkenyl-$C_{1-3}$ alkyl optionally having 1 to 3 substituents selected from the aforementioned substituent group A, (14) a $C_{6-10}$ aryl optionally having 1 to 3 substituents selected from the aforementioned substituent group A or (15) a $C_{6-10}$ aryl-$C_{1-3}$ alkyl optionally having 1 to 3 substituents selected from the aforementioned substituent group A, or the formula —S(O)$_2R^{8d}$ wherein $R^{8d}$ is a group bonded via a carbon atom.

Of these, as $R^{3d}$, an amino optionally monosubstituted by a $C_{3-6}$ cycloalkyl-carbonyl optionally having 1 to 3 substituents selected from the aforementioned substituent group A is preferable. Particularly, a $C_{3-6}$ cycloalkyl-carbonylamino (particularly cyclopropylcarbonylamino) is preferable.

As $R^{5d}$, a hydrogen atom is preferable.

As $R^{6d}$, a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl is preferable. Particularly, a mono(5- or 6-membered monocyclic aromatic heterocyclyl-carbonyl) amino (particularly pyrazolylcarbonylamino) optionally having 1 to 3 $C_{1-6}$ alkyl (particularly methyl) is preferable.

As ring $B^d$, a benzene ring free of a substituent other than $R^{6d}$ is preferable.

As compound (Id), a compound wherein
$R^{1d}$ is a hydrogen atom;
$R^{2d}$ is a hydrogen atom;
$R^{3d}$ is an amino optionally monosubstituted by an acyl;
$R^{5d}$ is a hydrogen atom;
$R^{6d}$ is a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, particularly, a mono(5- or 6-membered monocyclic aromatic heterocyclyl-carbonyl) amino (particularly pyrazolylcarbonylamino) optionally having 1 to 3 $C_{1-6}$ alkyl (particularly methyl); and ring $B^d$ is a benzene ring free of a substituent other than $R^{6d}$ is preferable.

Of these, as compound (Id), a compound wherein
$R^{1d}$ is a hydrogen atom;
$R^{2d}$ is a hydrogen atom;
$R^{3d}$ is an amino optionally monosubstituted by a $C_{3-6}$ cycloalkyl-carbonyl optionally having 1 to 3 substituents selected from the aforementioned substituent group A;
$R^{5d}$ is a hydrogen atom;
$R^{6d}$ is a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, particularly, a mono(5- or 6-membered monocyclic aromatic heterocyclyl-carbonyl) amino (particularly pyrazolylcarbonylamino) optionally having 1 to 3 $C_{1-6}$ alkyl (particularly methyl); and ring $B^d$ is a benzene ring free of a substituent other than $R^{6d}$ is preferable.

Particularly, as compound (Id), a compound wherein
$R^{1d}$ is a hydrogen atom;
$R^{2d}$ is a hydrogen atom;
$R^{3d}$ is a $C_{3-6}$ cycloalkyl-carbonylamino (particularly cyclopropylcarbonylamino);
$R^{5d}$ is a hydrogen atom;
$R^{6d}$ is a mono(5- or 6-membered monocyclic aromatic heterocyclyl-carbonyl)amino optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-6}$ cycloalkyl, particularly, a mono(5- or 6-membered monocyclic aromatic heterocyclyl-carbonyl) amino (particularly pyrazolylcarbonylamino) optionally having 1 to 3 $C_{1-6}$ alkyl (particularly methyl); and ring $B^d$ is a benzene ring free of a substituent other than $R^{6d}$ is preferable.

As compound (Id), specifically, N-[3-({2-[(cyclopropylcarbonyl)amino]-1,3-benzothiazol-6-yl}oxy)phenyl]-1,3-dimethyl-1H-pyrazole-5-carboxamide (Example 97-2), a salt thereof and the like are preferable.

[Compound (Ie)]

1,3-thiazolo[5,4-b]pyridine derivative

A compound represented by the formula

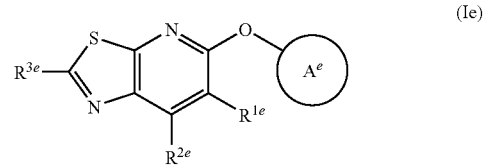

wherein $R^{1e}$ and $R^{2e}$ are the same or different and each is (1) a hydrogen atom, (2) a halogen atom, (3) a group bonded via a carbon atom, (4) a group bonded via a nitrogen atom, (5) a group bonded via an oxygen atom or (6) a group bonded via a sulfur atom;

$R^{3e}$ is an amino optionally having substituent(s); and a group represented by the formula

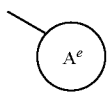

is an aromatic cyclic group having substituent(s), or a salt thereof.

As $R^{1e}$, a hydrogen atom is preferable.

As $R^{2e}$, a hydrogen atom is preferable.

As $R^{3e}$, an amino optionally monosubstituted by an acyl is preferable. Here, acyl is the formula —C(O)$R^{7e}$ wherein $R^{7e}$ is (1) a mono-$C_{1-6}$ alkylamino, (2) a di-$C_{1-6}$ alkylamino, (3) a mono($C_{1-6}$ alkyl-carbonyl)amino optionally having 1 to 3 halogen atoms, (4) a mono($C_{3-6}$ cycloalkyl-carbonyl)amino, (5) a mono($C_{6-10}$ aryl-carbonyl)amino optionally having 1 to 3 halogen atoms, (6) a mono(5- or 6-membered monocyclic aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (7) a mono(8- to 12-membered fused aromatic heterocyclyl-carbonyl)amino optionally having 1 to 3 substituents selected from (a) a halogen atom, (b) a $C_{1-6}$ alkyl (e.g., methyl, ethyl, propyl etc.) optionally having 1 to 3 halogen atoms, (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (8) a mono(3- to 8-membered non-aromatic heterocyclyl-carbonyl)amino, (9) a $C_{1-5}$ alkyl optionally having 1 to 3 substituents selected from the aforementioned substituent group A, (10) a $C_{3-6}$ cycloalkyl optionally having 1 to 3 substituents selected from the aforementioned substituent group A, (11) a $C_{3-6}$ cycloalkyl-$C_{1-3}$ alkyl optionally having 1 to 3 substituents selected from the aforementioned substituent group A, (12) a $C_{3-6}$ cycloalkenyl optionally having 1 to 3 substituents selected from the aforementioned substituent group A, (13) a $C_{3-6}$ cycloalkenyl-$C_{1-3}$ alkyl optionally having 1 to 3 substituents selected from the aforementioned substituent group A, (14) a $C_{6-10}$ aryl optionally having 1 to 3 substituents selected from the aforementioned substituent group A or (15) a $C_{6-10}$ aryl-$C_{1-3}$ alkyl optionally having 1 to 3 substituents selected from the aforementioned substituent group A, or the formula —S(O)$_2$$R^{8e}$ wherein $R^{8e}$ is a group bonded via a carbon atom.

Of these, as $R^{3e}$, an amino optionally monosubstituted by (1) a $C_{1-5}$ alkyl-carbonyl optionally having 1 to 3 substituents selected from the aforementioned substituent group A or (2) a $C_{3-6}$ cycloalkyl-carbonyl optionally having 1 to 3 substituents selected from the aforementioned substituent group A is preferable. Particularly, an amino, a $C_{1-5}$ alkyl-carbonylamino (particularly methylcarbonylamino) or a $C_{3-6}$ cycloalkyl-carbonylamino (particularly cyclopropylcarbonylamino) is preferable.

As a group represented by the formula

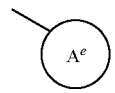

a $C_{6-10}$ aryl optionally having 1 to 3 substituents selected from a $C_{1-6}$ alkyl optionally having 1 to 3 halogen atoms and the substituent group A is preferable. Of these, a $C_{6-10}$ aryl optionally having 1 to 3 substituents selected from (1) a mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents selected from (a) a halogen atom, (b) a $C_{1-6}$ alkyl optionally having 1 to 3 halogen atoms (e.g., methyl, ethyl, propyl, isopropyl, trifluoromethyl, 2,2,2-trifluoroethyl etc.), (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (2) a carboxy and (3) a $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl etc.) is preferable.

Particularly, a $C_{6-10}$ aryl (particularly phenyl) optionally having 1 to 3 substituents selected from a mono(5- or 6-membered monocyclic aromatic heterocyclyl-carbonyl)amino (particularly pyrazolylcarbonylamino, imidazolylcarbonylamino, pyridylcarbonylamino) optionally having 1 to 3 $C_{1-6}$ alkyl (particularly methyl), a carboxyl and a $C_{1-6}$ alkoxy-carbonyl (particularly methoxycarbonyl) is preferable.

As compound (Ie), a compound wherein
$R^{1e}$ a hydrogen atom;
$R^{2e}$ is a hydrogen atom;
$R^{3e}$ is an amino optionally monosubstituted by an acyl; and
a group represented by the formula

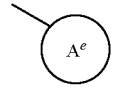

is a $C_{6-10}$ aryl optionally having 1 to 3 substituents selected from a $C_{1-6}$ alkyl optionally having 1 to 3 halogen atoms and the substituent group A is preferable.

Of these, as compound (Ie), a compound wherein
$R^{1e}$ is a hydrogen atom;
$R^{2e}$ is a hydrogen atom;
$R^{3e}$ is an amino optionally monosubstituted by (1) a $C_{1-5}$ alkyl-carbonyl optionally having 1 to 3 substituents selected from the aforementioned substituent group A or (2) a $C_{3-6}$ cycloalkyl-carbonyl optionally having 1 to 3 substituents selected from the aforementioned substituent group A; and
a group represented by the formula

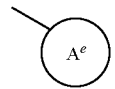

is a $C_{6-10}$ aryl optionally having 1 to 3 substituents selected from (1) a mono(5- or 6-membered monocyclic aromatic heterocyclyl-carbonyl)amino (e.g., furylcarbonylamino, thienylcarbonylamino, pyrrolylcarbonylamino, oxazolylcarbonylamino, isoxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents selected from (a) a halogen atom, (b) a $C_{1-6}$ alkyl optionally having 1 to 3 halogen atoms (e.g., methyl, ethyl, propyl, isopropyl, trifluoromethyl, 2,2,2-trifluoroethyl etc.), (c) a $C_{1-6}$ alkoxy (e.g., methoxy, ethoxy, propoxy etc.) and (d) a $C_{3-6}$ cycloalkyl (e.g., cyclopropyl, cyclobutyl, cyclopentyl, cyclohexyl etc.), (2) a carboxy and (3) a $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl etc.) is preferable.

Particularly, as compound (Ie), a compound wherein
$R^{1e}$ is a hydrogen atom;
$R^{2e}$ is a hydrogen atom;
$R^{3e}$ is an amino, a $C_{1-5}$ alkyl-carbonylamino (particularly methylcarbonylamino) or a $C_{3-6}$ cycloalkyl-carbonylamino (particularly cyclopropylcarbonylamino); and
a group represented by the formula

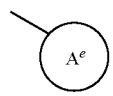

is a $C_{6-10}$ aryl (particularly phenyl) optionally having 1 to 3 substituents selected from a mono(5- or 6-membered monocyclic aromatic heterocyclyl-carbonyl)amino (particularly pyrazolylcarbonylamino, imidazolylcarbonylamino, pyridylcarbonylamino) optionally having 1 to 3 $C_{1-6}$ alkyl (particularly methyl), a carboxyl and a $C_{1-6}$ alkoxy-carbonyl (particularly methoxycarbonyl) is preferable.

As compound (Id), specifically, the compounds of Example 98 to Example 103 and the like are preferable.

Among these, N-[3-({2-[(cyclopropylcarbonyl)amino][1,3]thiazolo[5,4-b]pyridin-5-yl}oxy)phenyl]-1,3-dimethyl-1H-pyrazole-5-carboxamide (Example 99), N-[3-({2-[(cyclopropylcarbonyl)amino][1,3]thiazolo[5,4-b]pyridin-5-yl}oxy)phenyl]-1-methyl-1H-imidazole-2-carboxamide (Example 101-4), N-[3-({2-[(cyclopropylcarbonyl)amino][1,3]thiazolo[5,4-b]pyridin-5-yl}oxy)phenyl]-3-methylpyridine-2-carboxamide (Example 103), or a salt thereof and the like are preferable, and particularly, N-[3-({2-[(cyclopropylcarbonyl)amino][1,3]thiazolo[5,4-b]pyridin-5-yl}oxy)phenyl]-1,3-dimethyl-1H-pyrazole-5-carboxamide (Example 99), and salts thereof are preferable.

Examples of the salt of compound (I) include a metal salt, an ammonium salt, a salt with organic base, a salt with inorganic acid, a salt with organic acid, a salt with basic or acidic amino acid and the like. Preferable examples of the metal salt include alkali metal salts such as sodium salt, potassium salt and the like; alkaline earth metal salts such as calcium salt, magnesium salt, barium salt and the like; aluminum salts and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salt with the inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Of these, pharmaceutically acceptable salts are preferable. For example, when a compound has an acidic functional group, inorganic salts such as alkali metal salts (e.g., sodium salt, potassium salt etc.), alkaline earth metal salts (e.g., calcium salt, magnesium salt etc.) and the like, ammonium salts and the like can be mentioned. Alternatively, when a compound has a basic functional group, for example, salts with inorganic acids such as hydrochloric acid, hydrobromic acid, nitric acid, sulfuric acid, phosphoric acid and the like, salts with organic acids such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

Hereinafter, the production methods of compound (I) of the present invention are explained.

The compound (I) of the present invention can be obtained, for example, according to the methods shown in the following Schemes or a method analogous thereto and the like.

Each compound in the following Schemes includes salts, and as such salts, for example, those similar to the salts of the compound (I) exemplified above and the like can be used.

The compound obtained in each step can be used in the form of a reaction mixture or a crude product for the next reaction. In addition, the compound can be isolated from a reaction mixture according to a conventional method, and can be easily purified by a separation means such as recrystallization, distillation, chromatography and the like.

Schematic reaction formulas are shown in the following, wherein each symbol in the compounds is as defined above.

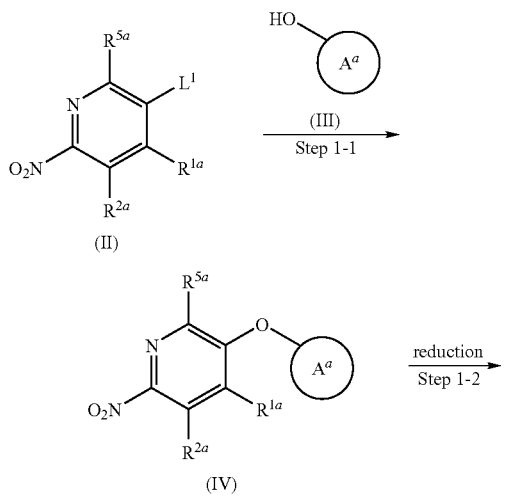

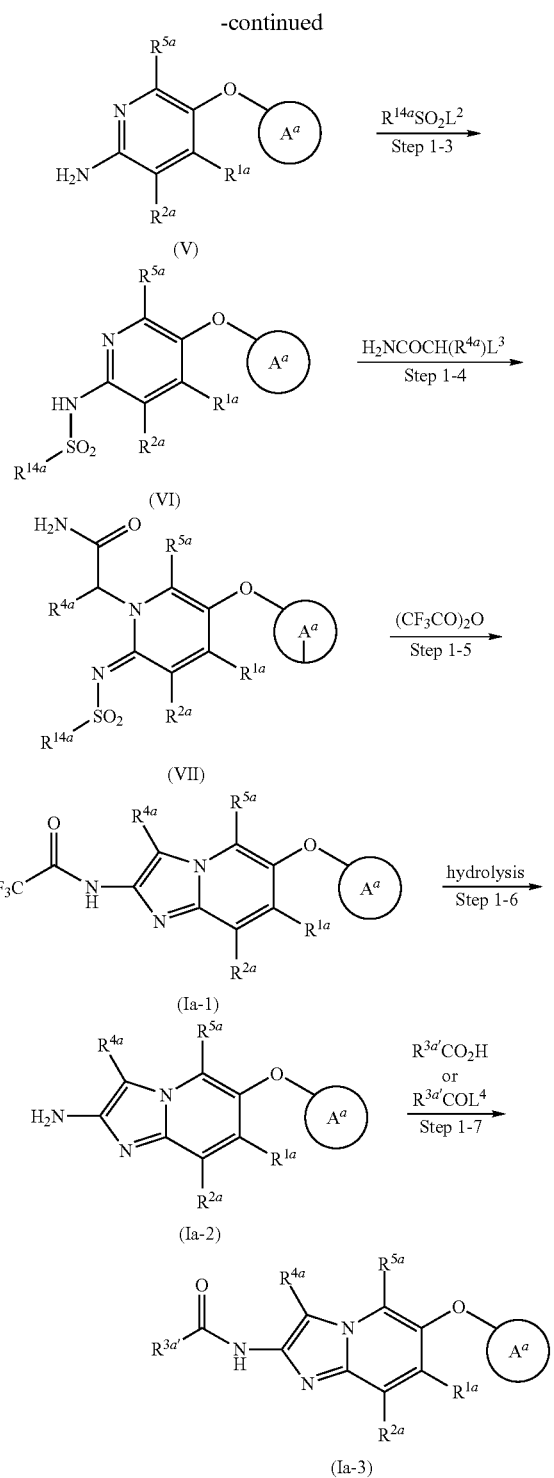

alkyl optionally having 1 to 3 substituents selected from a $C_{1-6}$ alkyl optionally having 1 to 3 halogen atoms and the aforementioned substituent group A, (6) a $C_{3-6}$ cycloalkenyl optionally having 1 to 3 substituents selected from a $C_{1-6}$ alkyl optionally having 1 to 3 halogen atoms and the aforementioned substituent group A, (7) a $C_{3-6}$ cycloalkenyl-$C_{1-3}$ alkyl optionally having 1 to 3 substituents selected from a $C_{1-6}$ alkyl optionally having 1 to 3 halogen atoms and the aforementioned substituent group A, (8) a $C_{6-10}$ aryl-$C_{1-3}$ alkyl optionally having 1 to 3 substituents selected from a $C_{1-6}$ alkyl optionally having 1 to 3 halogen atoms and the aforementioned substituent group A, or (9) a $C_{4-6}$ cycloalkanedienyl optionally having 1 to 3 substituents selected from a $C_{1-6}$ alkyl optionally having 1 to 3 halogen atoms and the aforementioned substituent group A, $R^{14a}$ is an alkyl optionally having substituent(s) or an aryl optionally having substituent(s), and other symbols are as defined above.

Examples of the leaving group for $L^1$ include a halogen atom, an alkylsulfonyl optionally having substituent(s), an alkylsulfonyloxy group optionally having substituent(s), an arylsulfonyloxy optionally having substituent(s) and the like.

Examples of the halogen atom include a fluorine atom, a chlorine atom, a bromine atom and an iodine atom.

Examples of the alkylsulfonyl include a $C_{1-6}$ alkylsulfonyl such as methylsulfonyl, ethylsulfonyl and the like, and the like.

Examples of the alkylsulfonyloxy include a $C_{1-6}$ alkylsulfonyloxy such as methylsulfonyloxy, ethylsulfonyloxy and the like, and the like.

Examples of the arylsulfonyloxy include a $C_{6-14}$ arylsulfonyloxy such as phenylsulfonyloxy and the like, and the like.

Examples of the substituent of the alkylsulfonyl, alkylsulfonyloxy or arylsulfonyloxy include a halogen atom (e.g., a fluorine atom, a chlorine atom, a bromine atom), an optionally halogenated $C_{1-6}$ alkyl (e.g., methyl, ethyl, trifluoromethyl), a nitro and the like.

Examples of the leaving group for $L^2$ include a halogen atom and the like.

Examples of the leaving group for $L^3$ include a halogen atom, an alkylsulfonyloxy optionally having substituent(s), an arylsulfonyloxy optionally having substituent(s) and the like.

Examples of the leaving group for $L^4$ include a halogen atom, an aryloxy optionally having substituent(s), an alkoxy optionally having substituent(s), 1-imidazolyl and the like.

Examples of the aryloxy include a $C_{6-14}$ aryloxy such as phenyloxy and the like, and the like.

Examples of the alkoxy include a $C_{1-6}$ alkoxy such as methyloxy, ethyloxy and the like, and the like.

Examples of the substituent of the aryloxy or alkoxy include a halogen atom (e.g., a fluorine atom, a chlorine atom, a bromine atom), an optionally halogenated $C_{1-6}$ alkyl (e.g., methyl, ethyl, trifluoromethyl), a nitro and the like.

Examples of the "alkyl" of the alkyl optionally having substituent(s) for $R^{14a}$ include a $C_{1-6}$ alkyl such as methyl, ethyl and the like, and the like.

Examples of the "aryl" of the aryl optionally having substituent(s) for $R^{14a}$ include a $C_{6-14}$ aryl such as phenyl and the like, and the like.

Examples of the substituent of the alkyl or aryl include a halogen atom (e.g., a fluorine atom, a chlorine atom, a bromine atom), an optionally halogenated $C_{1-6}$ alkyl (e.g., methyl, ethyl, trifluoromethyl), a nitro and the like.

(Step 1-1):
Compound (IV) can be produced by reacting compound (II) with compound (III). The amount of compound (III) to be wherein $L^1$ to $L^4$ are leaving groups, $R^{3a'}$ is (1) a $C_{1-5}$ alkyl optionally having 1 to 3 substituents selected from the aforementioned substituent group A, (2) a $C_{2-5}$ alkenyl optionally having 1 to 3 substituents selected from the aforementioned substituent group A, (3) a $C_{2-5}$ alkynyl optionally having 1 to 3 substituents selected from the aforementioned substituent group A, (4) a $C_{3-6}$ cycloalkyl optionally having 1 to 3 substituents selected from a $C_{1-6}$ alkyl optionally having 1 to 3 halogen atoms and the aforementioned substituent group A, (5) a $C_{3-6}$ cycloalkyl-$C_{1-3}$ used is about 0.1 to about 10 equivalents, preferably about 0.3 to about 3 equivalents, relative to compound (II). Where necessary, a base may be added. Examples of the base include inorganic bases or organic bases and the like, specifically, sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like. The amount of the base to be used is about 1 to about 30 equivalents, preferably about 1 to about 10 equivalents, relative to compound (II). This reaction is advantageously carried out using a solvent inert to the reaction. While the solvent is not particularly limited as long as the reaction proceeds, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile and the like; sulfoxides such as dimethylsulfoxide and the like; pyridine, water and the like, or a mixed solvent thereof can be used. While the reaction time varies depending on the reagent or solvent to be used, it is generally about 10 min to about 100 hr, preferably about 30 min to about 50 hr. The reaction temperature is generally about −78 to about 200° C., preferably about −20 to about 150° C. The reaction may be carried out using a microwave reaction apparatus.

(Step 1-2):

Compound (V) can be produced by reducing the nitro of compound (IV). The reduction of the nitro can be carried out according to a method known per se, for example, the methods described in "Advanced Organic Chemistry, 4th Ed." (Jerry March), "Comprehensive Organic Transformations, 2nd Ed." (Richard C. Larock), Zikken Kagaku Koza, 4th Ed., vol. 20, pages 279-280 and the like, or a method analogous thereto.

(Step 1-3):

Compound (VI) can be produced by reacting compound (V) with a compound represented by the formula: $R^{14a}SO_2L^2$ in the presence of a base. The amount of $R^{14a}SO_2L^2$ to be used is about 0.1 to about 10 equivalents, preferably about 0.3 to about 3 equivalents, relative to compound (V). As the base, those similar to the base exemplified in Step 1-1 can be used. The amount of the base to be used is about 0.1 to about 10 equivalents, preferably about 0.3 to about 3 equivalents, relative to compound (V). The base may be used as a solvent. This reaction is advantageously carried out using a solvent inert to the reaction. As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about −20 to about 150° C.

(Step 1-4):

Compound (VII) can be produced by reacting compound (VI) with a compound represented by the formula: $H_2NCOCH(R^{4a})L^3$ in the presence of a base. The amount of $H_2NCOCH(R^{4a})L^3$ to be used is 0.1 to 10 equivalents, preferably 0.3 to 3 equivalents, relative to compound (VI). As the base, those similar to the base exemplified in Step 1-1 can be used. The amount of the base to be used is 0.1 to 10 equivalents, preferably 0.3 to 3 equivalents, relative to compound (VI). The base may be used as a solvent. This reaction is advantageously carried out using a solvent inert to the reaction. As the solvent, those similar to the solvent exemplified in Step 1-1 can be used. The reaction time is generally about 10 min to about 100 hr, preferably about 30 min to about 75 hr. The reaction temperature is generally about −78 to about 200° C., preferably about −20 to about 150° C. $H_2NCOCH(R^{4a})L^3$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 1-5):

Compound (Ia-1) can be produced by reacting compound (VII) with trifluoroacetic anhydride. The amount of the trifluoroacetic anhydride to be used is a solvent amount, relative to compound (VII). This reaction is advantageously carried out using a solvent inert to the reaction. As the solvent, those similar to the aforementioned solvent can be used. The reaction time is generally about 10 min to about 100 hr, preferably about 30 min to about 50 hr. The reaction temperature is generally about −78 to about 200° C., preferably about −20 to about 150° C.

(Step 1-6):

Compound (Ia-2) can be produced by subjecting compound (Ia-1) to alkali hydrolysis. This reaction is carried out in an aqueous solvent in the presence of a base. Examples of the base include sodium hydroxide, potassium hydroxide, lithium hydroxide, barium hydroxide, calcium hydroxide, potassium carbonate, sodium carbonate, cesium carbonate, sodium methoxide and the like. The amount of the base to be used is about 1 to about 50 equivalents, preferably about 1 to about 10 equivalents, relative to compound (I-1). Examples of the aqueous solvent include a mixed solvent of water and 1 kind or more solvents selected from methanol, ethanol, tetrahydrofuran, 1,4-dioxane and the like, and the like. The reaction time is generally about 10 min to about 100 hr, preferably about 30 min to about 50 hr. The reaction temperature is generally about −78 to about 200° C., preferably about −20 to about 150° C.

(Step 1-7):

Compound (Ia-3) can be produced by reacting compound (Ia-2) with a carboxylic acid ($R^{3a'}CO_2H$) in the presence of a condensing agent, or by reacting compound (Ia-2) with a reactive derivative ($R^{3a'}COL^4$) of the carboxylic acid.

When compound (Ia-2) is reacted with $R^{3a'}CO_2H$ in the presence of a condensing agent, the amount of $R^{3a'}CO_2H$ to be used is about 0.1 to about 10 equivalents, preferably about 0.3 to about 3 equivalents, relative to compound (Ia-2). Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The amount of the condensing agent to be used is about 1 to about 10 equivalents, preferably about 1 to about 5 equivalents, relative to compound (Ia-2). Where necessary, a suitable condensation promoter (e.g., 1-hydroxybenzotriazole, N-hydroxysuccinimide and the like) can be used. The amount of the condensation promoter to be used is about 0.1 to about 10 equivalents, preferably about 0.3 to about 3 equivalents, relative to compound (Ia-2). This reaction may proceed more smoothly by addition of a base (e.g., triethylamine, N,N-diisopropylethylamine, N-methylmorpholine, 1,8-diazabicyclo[5.4.0]undec-7-ene and the like). The amount of the base to be used is about 0.01 to about 10 equivalents, preferably about 0.03 to about 5 equivalents, relative to compound (Ia-2). This reaction is advantageously carried out using a solvent inert to the reaction. As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about −20 to about 150° C. $R^{3a'}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

When compound (Ia-2) is reacted with a reactive derivative $(R^{3a'}COL^4)$ of the carboxylic acid, The amount of the reactive derivative $(R^{3a'}COL^4)$ of the carboxylic acid to be used is about 0.1 to about 10 equivalents, preferably about 0.3 to about 3 equivalents, relative to compound (Ia-2). This reaction is generally carried out in the presence of a base, which is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The amount of the base to be used is about 0.01 to about 10 equivalents, preferably about 0.03 to about 5 equivalents, relative to compound (Ia-2). This reaction is advantageously carried out using a solvent inert to the reaction. As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about −20 to about 150° C. The reactive derivative $(R^{3a'}COL^4)$ of the carboxylic acid may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 2]

Compound (Ia) wherein ring $A^a$ is substituted by $R^{6a'}CONH$— can also be produced, for example, by the method shown in Scheme 2. Compounds (Ia-4), (Ia-5) and (Ia-6) are encompassed in compound (Ia).

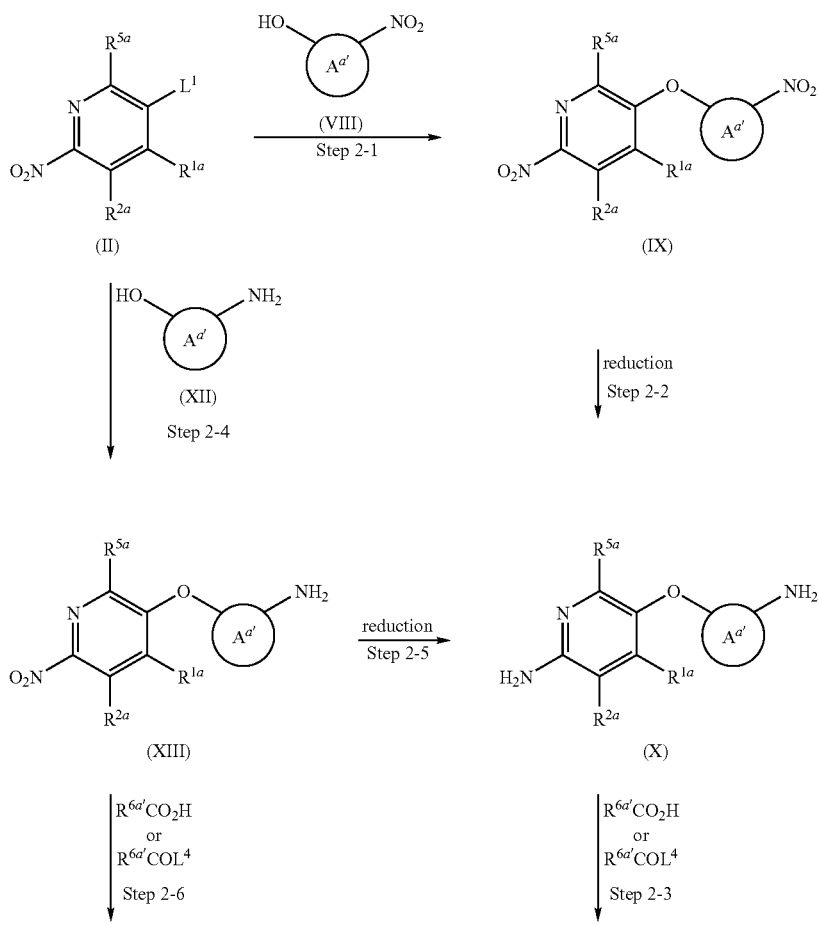

Reaction Scheme 2

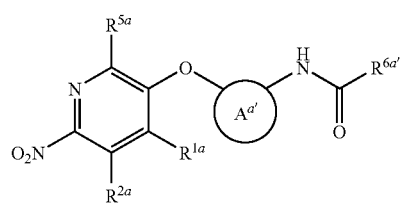
(XIV)

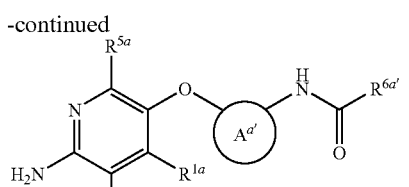
(XI)

-continued

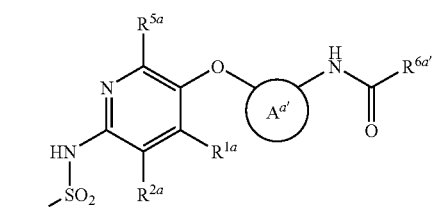
(XV)

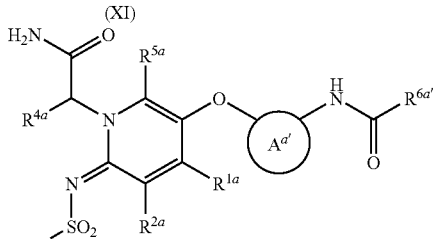
(XVI)

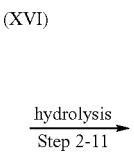

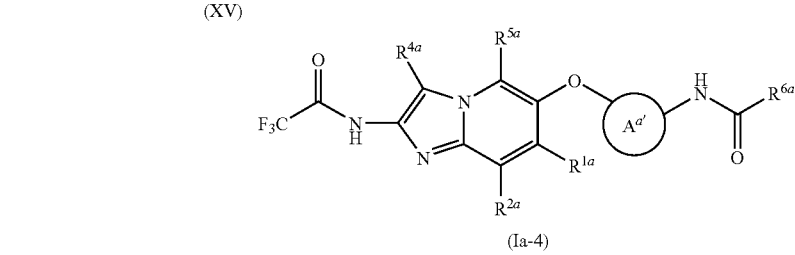
(Ia-4)

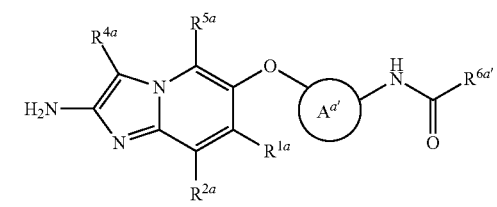
(Ia-5)

(Ia-6)

wherein $R^{6a'}$ is (1) a $C_{1-6}$ alkyl optionally having 1 to 3 halogen atoms, (2) a $C_{3-6}$ cycloalkyl, (3) a $C_{3-6}$ cycloalkenyl, (4) a $C_{6-10}$ aryl optionally having 1 to 3 halogen atoms, (5) a 5- or 6-membered monocyclic aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (6) a 8- to 12-membered fused aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (7) a 3- to 8-membered non-aromatic heterocyclic group or (8) a $C_{1-6}$ alkoxy, ring $A^{a'}$ is a ring further optionally having substituent(s), and other symbols are as defined above.

(Step 2-1):

Compound (IX) can be produced by reacting compound (II) with compound (VIII). The amount of compound (VIII) to be used is about 0.1 to about 10 equivalents, preferably about 0.3 to about 3 equivalents, relative to compound (II). Where necessary, a base may be added. As the base, those similar to the base exemplified in Step 1-1 can be used. The amount of the base to be used is about 1 to about 30 equivalents, preferably about 1 to about 10 equivalents, relative to compound (II). This reaction is advantageously carried out using a solvent inert to the reaction. As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about −20 to about 150° C.

(Step 2-2):

Compound (X) can be produced by reducing the nitro of compound (IX) in the same manner as in Step 1-2.

(Step 2-3):

Compound (XI) can be produced by reacting compound (X) with a carboxylic acid ($R^{6a'}CO_2H$) in the presence of a condensing agent, or by reacting compound (X) with a reactive derivative ($R^{6a'}COL^4$) of the carboxylic acid, in the same manner as in Step 1-7.

(Step 2-4):

Compound (XIII) can be produced by reacting compound (II) with compound (XII) in the presence of a base. The amount of compound (XII) to be used is about 0.1 to about 10 equivalents, preferably about 0.3 to about 3 equivalents, relative to compound (II). As the base, those similar to the base exemplified in Step 1-1 can be used. The amount of the base to be used is about 1 to about 30 equivalents, preferably about 1 to about 10 equivalents, relative to compound (II). This reaction is advantageously carried out using a solvent inert to the reaction. As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about −20 to about 150° C.

(Step 2-5):
Compound (X) can be produced by reducing the nitro of compound (XIII) in the same manner as in Step 1-2.
(Step 2-6):
Compound (XIV) can be produced by reacting compound (XIII) with a carboxylic acid ($R^{6a'}CO_2H$) in the presence of a condensing agent, or by reacting compound (XIII) with a reactive derivative ($R^{6a'}COL^4$) of the carboxylic acid, in the same manner as in Step 1-7.
(Step 2-7):
Compound (XI) can be produced by reducing the nitro of compound (XIV) in the same manner as in Step 1-2.

(Steps 2-8 to 2-12):
Compound (XV), compound (XVI), compound (Ia-4), compound (Ia-5) and compound (Ia-6) can be synthesized from compound (XI) in the same manner as in Steps 1-3 to 1-7.

[Production Method 3]
Compound (Ia) wherein ring $A^a$ is substituted by $^{6a'}$CONH— can also be produced, for example, by the method shown in Scheme 3. Compounds (Ia-7), (Ia-8), (Ia-9), (Ia-10) and (Ia-6) are encompassed in compound (Ia).

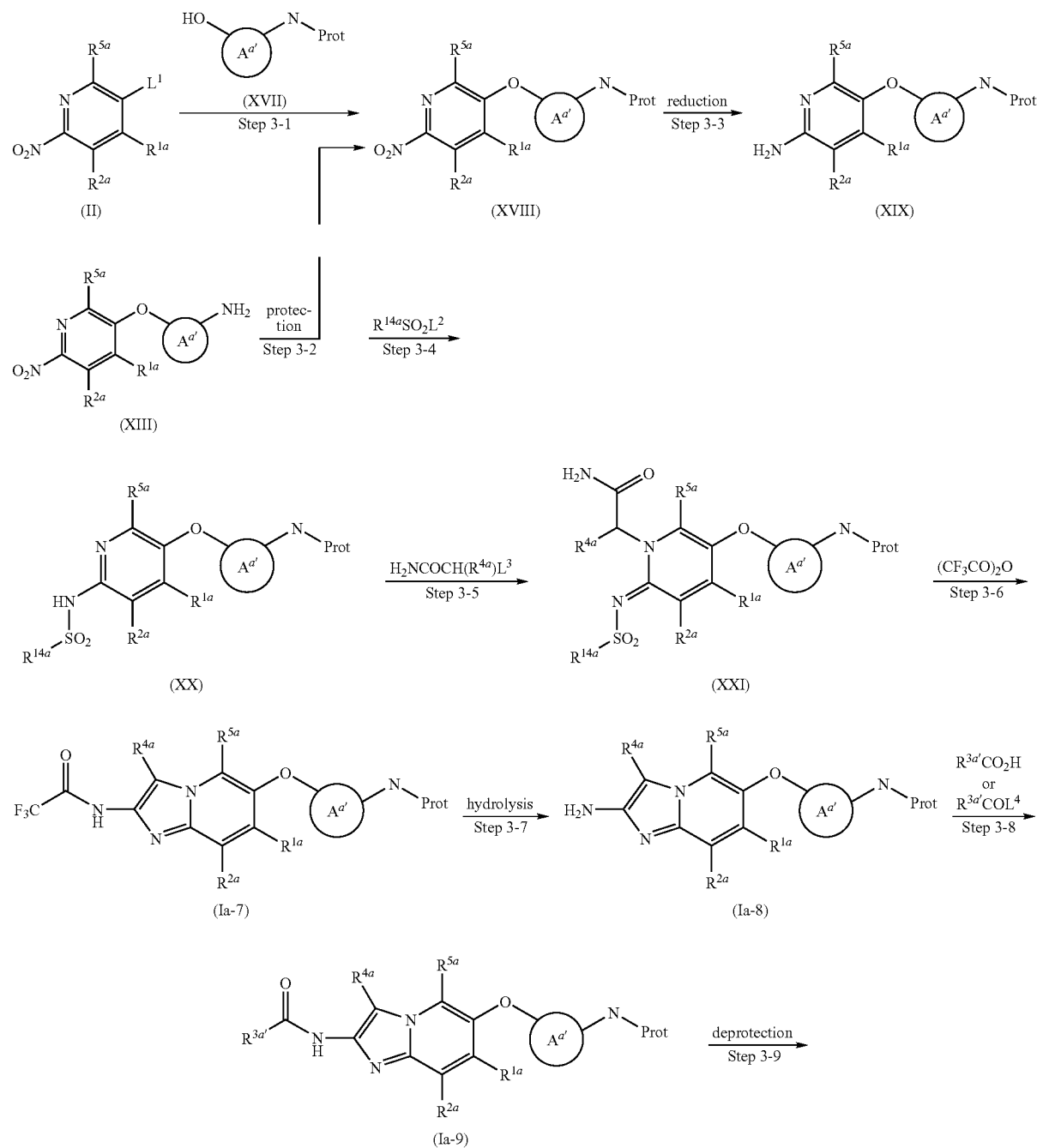

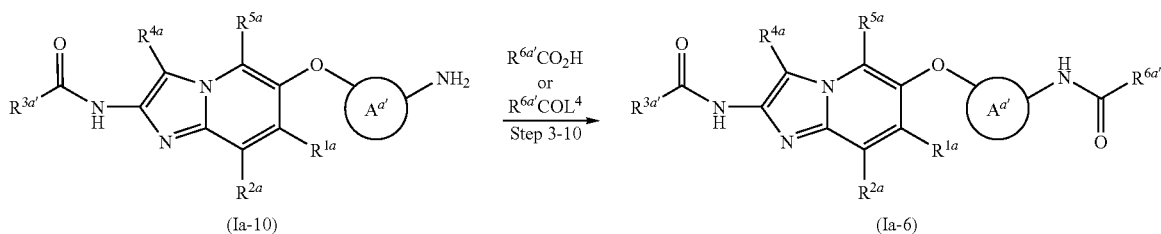

(Ia-10)     (Ia-6)

wherein Prot is an amino-protecting group, and other symbols are as defined above.

Examples of the protecting group for Prot include benzyloxycarbonyl, tert-butyloxycarbonyl and the like.

(Step 3-1):

Compound (XVIII) can be produced by reacting compound (II) with compound (XVII) in the presence of a base. The amount of compound (XVII) to be used is about 0.1 to about 10 equivalents, preferably about 0.3 to about 3 equivalents, relative to compound (II). As the base, those similar to the base exemplified in Step 1-1 can be used. The amount of the base to be used is about 1 to about 30 equivalents, preferably about 1 to about 10 equivalents, relative to compound (II). This reaction is advantageously carried out using a solvent inert to the reaction. As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about −20 to about 150° C.

(Step 3-2):

Compound (XVIII) can be produced by protecting the amino of compound (XIII). The protection of the amino can be carried out according to a method known per se, for example, the methods described in "Protective Groups in Organic Synthesis, 3rd Ed." (Theodora W. Greene) and the like, or a method analogous thereto.

(Steps 3-3 to 3-8):

Compound (XIX), compound (XX), compound (XXI), compound (Ia-7), compound (Ia-8) and compound (Ia-9) can be synthesized from compound (XVIII) in the same manner as in Steps 1-2 to 1-7.

(Step 3-9):

Compound (Ia-10) can be produced by deprotecting the amino-protecting group of compound (Ia-9). The deprotection of the amino-protecting group can be carried out according to a method known per se, for example, the methods described in "Protective Groups in Organic Synthesis, 3rd Ed." (Theodora W. Greene) and the like, or a method analogous thereto.

(Step 3-10):

Compound (Ia-6) can be produced by reacting compound (Ia-10) with a carboxylic acid ($R^{6a'}CO_2H$) in the presence of a condensing agent, or by reacting compound (Ia-10) with a reactive derivative ($R^{6a'}COL^4$) of the carboxylic acid, in the same manner as in Step 1-7.

[Production Method 4]

Compound (Ia) wherein ring $A^a$ is substituted by $R^{6a'}CONH-$ can also be produced, for example, by the method shown in Scheme 4. Compounds (Ia-11), (Ia-12), (Ia-13), (Ia-10) and (Ia-6) are encompassed in compound (Ia).

Reaction Scheme 4

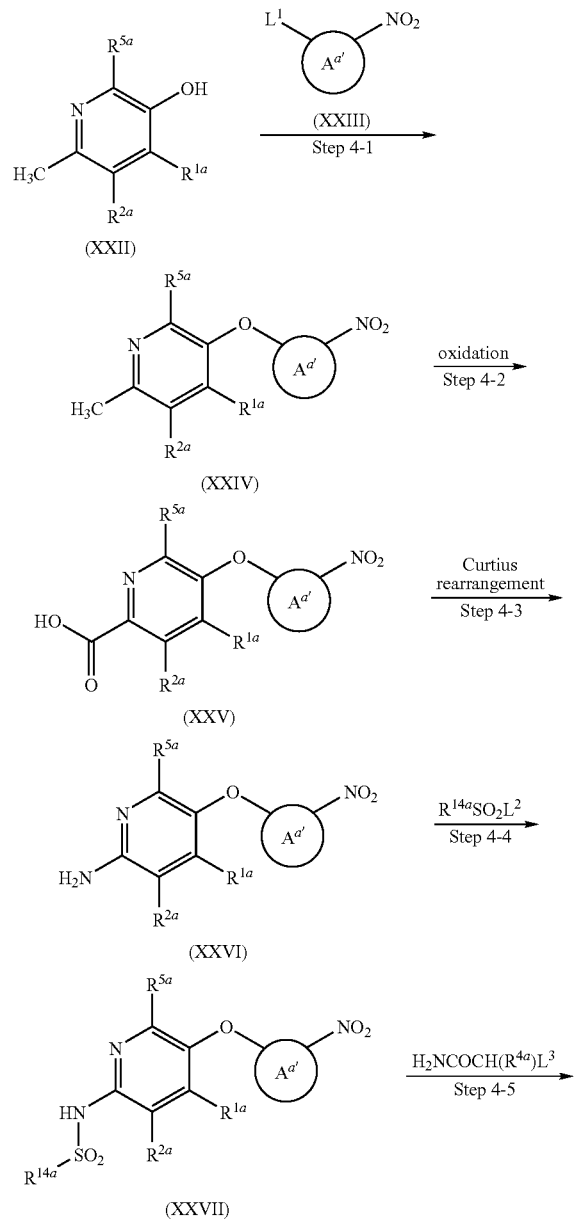

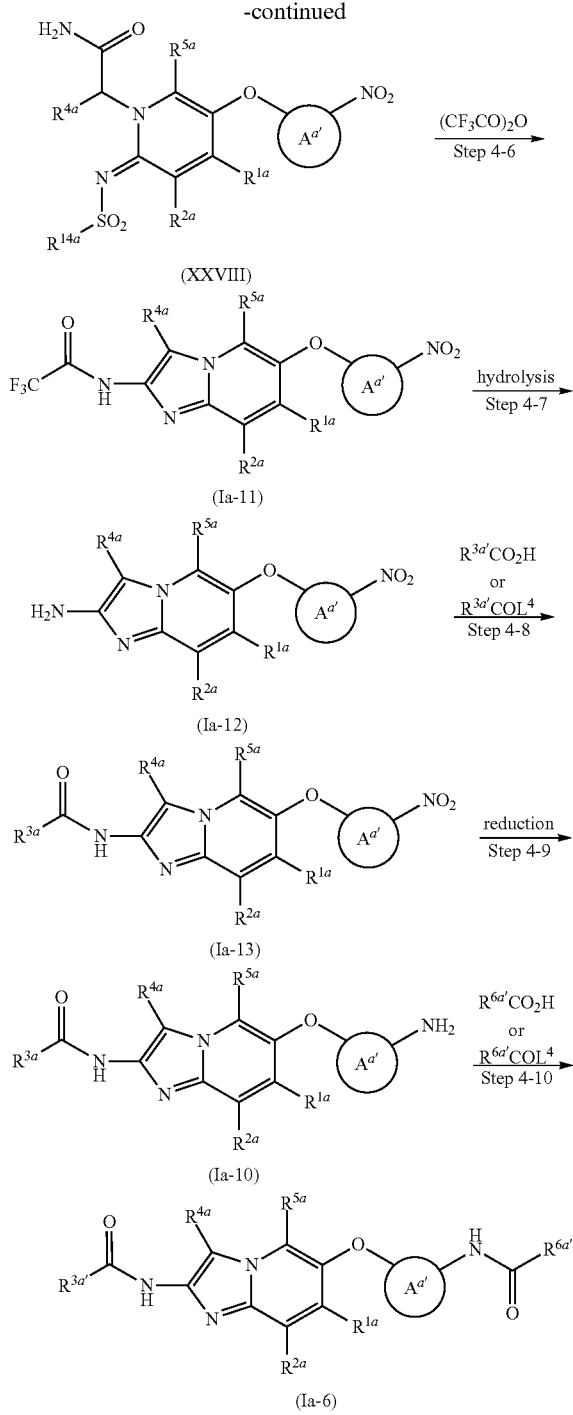

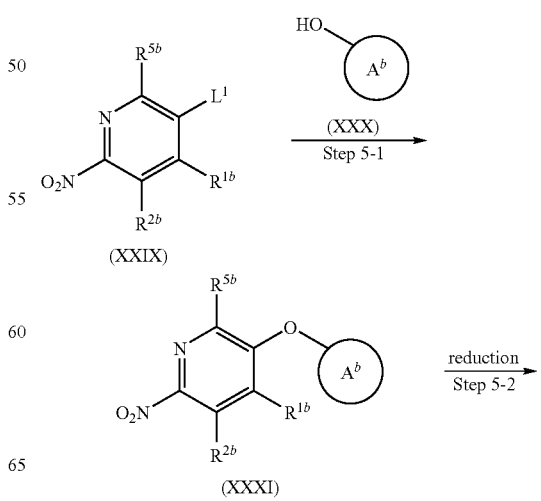

wherein each symbol in the formula is as defined above.

(Step 4-1):

Compound (XXIV) can be produced by reacting compound (XXII) with compound (XXIII) in the presence of a base. The amount of compound (XXIII) to be used is about 0.1 to about 10 equivalents, preferably about 0.3 to about 3 equivalents, relative to compound (XXII). As the base, those similar to the base exemplified in Step 1-1 can be used. The amount of the base to be used is about 1 to about 30 equivalents, preferably about 1 to about 10 equivalents, relative to compound (XXII). This reaction is advantageously carried out using a solvent inert to the reaction. As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about −20 to about 150° C.

(Step 4-2):

Compound (XXV) can be produced by oxidizing the methyl of compound (XXIV). The oxidization of the methyl can be carried out according to a method known per se, for example, the methods described in "Advanced Organic Chemistry, 4th Ed." (Jerry March), "Comprehensive Organic Transformations, 2nd Ed." (Richard C. Larock), Zikken Kagaku Koza, 4th Ed., vol. 23, and the like, or a method analogous thereto.

(Step 4-3):

Compound (XXVI) can be produced by converting the carboxyl of compound (XXV) to an amino according to the Curtius rearrangement and the like. The conversion of the carboxyl to an amino can be carried out according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Steps 4-4 to 4-8):

Compound (XXVII), compound (XXVIII), compound (Ia-11), compound (Ia-12) and compound (Ia-13) can be synthesized from compound (XXVI) in the same manner as in Steps 1-3 to 1-7.

(Step 4-9):

Compound (Ia-10) can be produced by reducing the nitro of compound (Ia-13) in the same manner as in Step 1-2.

(Step 4-10):

Compound (Ia-6) can be produced by reacting compound (Ia-10) with a carboxylic acid ($R^{6a'}CO_2H$) in the presence of a condensing agent, or by reacting compound (Ia-10) with a reactive derivative ($R^{6a'}COL^4$) of the carboxylic acid, in the same manner as in Step 1-7.

[Production Method 5]

Compound (Ib) can be produced, for example, by the method shown in Scheme 5. Compounds (Ib-1) and (Ib-2) are encompassed in compound (Ib).

-continued

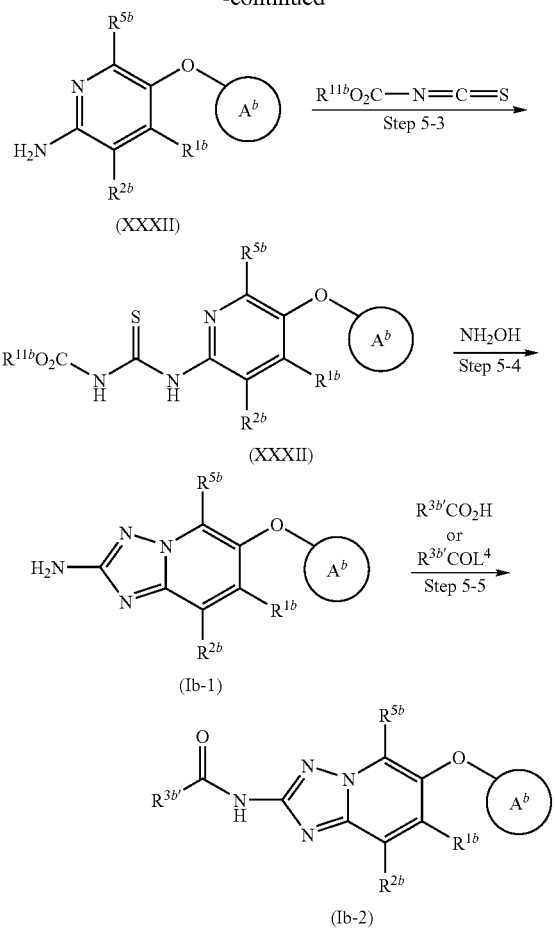

wherein $R^{3b'}$ is (1) a $C_{1-5}$ alkyl optionally having 1 to 3 substituents selected from the aforementioned substituent group A, (2) a $C_{2-5}$ alkenyl optionally having 1 to 3 substituents selected from the aforementioned substituent group A, (3) a $C_{2-5}$ alkynyl optionally having 1 to 3 substituents selected from the aforementioned substituent group A, (4) a $C_{3-6}$ cycloalkyl optionally having 1 to 3 substituents selected from a $C_{1-6}$ alkyl optionally having 1 to 3 halogen atoms and the aforementioned substituent group A, (5) a $C_{3-6}$ cycloalkyl-$C_{1-3}$ alkyl optionally having 1 to 3 substituents selected from a $C_{1-6}$ alkyl optionally having 1 to 3 halogen atoms and the aforementioned substituent group A, (6) a $C_{3-6}$ cycloalkenyl optionally having 1 to 3 substituents selected from a $C_{1-6}$ alkyl optionally having 1 to 3 halogen atoms and the aforementioned substituent group A, (7) a $C_{3-6}$ cycloalkenyl-$C_{1-3}$ alkyl optionally having 1 to 3 substituents selected from a $C_{1-6}$ alkyl optionally having 1 to 3 halogen atoms and the aforementioned substituent group A, (8) a $C_{6-10}$ aryl-$C_{1-3}$ alkyl optionally having 1 to 3 substituents selected from a $C_{1-6}$ alkyl optionally having 1 to 3 halogen atoms and the aforementioned substituent group A, or (9) a $C_{4-6}$ cycloalkanedienyl optionally having 1 to 3 substituents selected from a $C_{1-6}$ alkyl optionally having 1 to 3 halogen atoms and the aforementioned substituent group A, $R^{11b}$ is a $C_{1-6}$ alkyl optionally having 1 to 3 substituents selected from the aforementioned substituent group A, and other symbols are as defined above.

(Step 5-1):

Compound (XXXI) can be produced by reacting compound (XXIX) with compound (XXX). The amount of compound (XXX) to be used is about 0.1 to about 10 equivalents, preferably about 0.3 to about 3 equivalents, relative to compound (XXIX). Where necessary, a base may be added. Examples of the base include inorganic bases, organic bases and the like, specifically, sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like. The amount of the base to be used is about 1 to about 30 equivalents, preferably about 1 to about 10 equivalents, relative to compound (XXIX). This reaction is advantageously carried out using a solvent inert to the reaction. While the solvent is not particularly limited as long as the reaction proceeds, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitrites such as acetonitrile and the like; sulfoxides such as dimethylsulfoxide and the like; pyridine, water and the like, or a mixed solvent thereof can be used. While the reaction time varies depending on the reagent or solvent to be used, it is generally about 10 min to about 100 hr, preferably about 30 min to about 50 hr. The reaction temperature is generally about −78 to about 200° C., preferably about −20 to about 150° C. The reaction may be carried out using a microwave reaction apparatus.

(Step 5-2):

Compound (XXXII) can be produced by reducing the nitro of compound (XXXI). The reduction of the nitro can be carried out according to a method known per se, for example, the methods described in "Advanced Organic Chemistry, 4th Ed." (Jerry March), "Comprehensive Organic Transformations, 2nd Ed." (Richard C. Larock), Zikken Kagaku Koza, 4th Ed., vol. 20, pages 279-280 and the like, or a method analogous thereto.

(Step 5-3):

Compound (XXXIII) can be produced by reacting compound (XXXII) with a compound represented by the formula: $R^{11b}O_2C—N=C=S$. The amount of $R^{11b}O_2C—N=C=S$ to be used is about 0.1 to about 10 equivalents, preferably about 0.3 to about 3 equivalents, relative to compound (XXXII). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C.

(Step 5-4):

Compound (Ib-1) can be produced by reacting compound (XXXIII) with hydroxylamine in the presence of a base. The amount of the hydroxylamine to be used is about 0.1 to about 100 equivalents, preferably about 0.3 to about 30 equivalents, relative to compound (XXXIII). As the base, those similar to the base exemplified in Step 5-1 can be used. The amount of the base to be used is about 0.1 to about 100 equivalents, preferably about 0.3 to about 30 equivalents, relative to compound (XXXIII). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C.

(Step 5-5):

Compound (Ib-2) can be produced by reacting compound (Ib-1) with a carboxylic acid ($R^{3b'}CO_2H$) in the presence of a condensing agent, or by reacting compound (Ib-1) with a reactive derivative ($R^{3b'}COL^4$) of the carboxylic acid.

When compound (Ib-1) is reacted with $R^{3b'}CO_2H$ in the presence of a condensing agent, The amount of $R^{3b'}CO_2H$ to be used is about 0.1 to about 10 equivalents, preferably about 0.3 to about 3 equivalents, relative to compound (1b-1). Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The amount of the condensing agent to be used is about 1 to about 10 equivalents, preferably about 1 to about 5 equivalents, relative to compound (1b-1). Where necessary, a suitable condensation promoter (e.g., 1-hydroxybenzotriazole, N-hydroxysuccinimide and the like) can be used. The amount of the condensation promoter to be used is about 0.1 to about 10 equivalents, preferably about 0.3 to about 3 equivalents, relative to compound (1b-1). This reaction may proceed more smoothly by addition of a base (e.g., triethylamine, N,N-diisopropylethylamine, N-methylmorpholine, 1,8-diazabicyclo[5.4.0]undec-7-ene and the like). The amount of the base to be used is about 0.01 to about 10 equivalents, preferably about 0.03 to about 5 equivalents, relative to compound (1b-1). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C. $R^{3b'}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

When compound (Ib-1) is reacted with the reactive derivative ($R^{3b'}COL^4$) of the carboxylic acid, The amount of the reactive derivative ($R^{3b'}COL^4$) of the carboxylic acid to be used is about 0.1 to about 10 equivalents, preferably about 0.3 to about 3 equivalents, relative to compound (1b-1). This reaction is generally carried out in the presence of a base, which is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The amount of the base to be used is about 0.01 to about 10 equivalents, preferably about 0.03 to about 5 equivalents, relative to compound (1b-1). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C. The reactive derivative ($R^{3b'}COL^4$) of the carboxylic acid may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 6]

Compound (Ib) wherein ring $A^b$ is substituted by $R^{6b'}CONH$— can also be produced, for example, by the method shown in Scheme 6. Compounds (Ib-3) and (Ib-4) are encompassed in compound (Ib).

Reaction Scheme 6

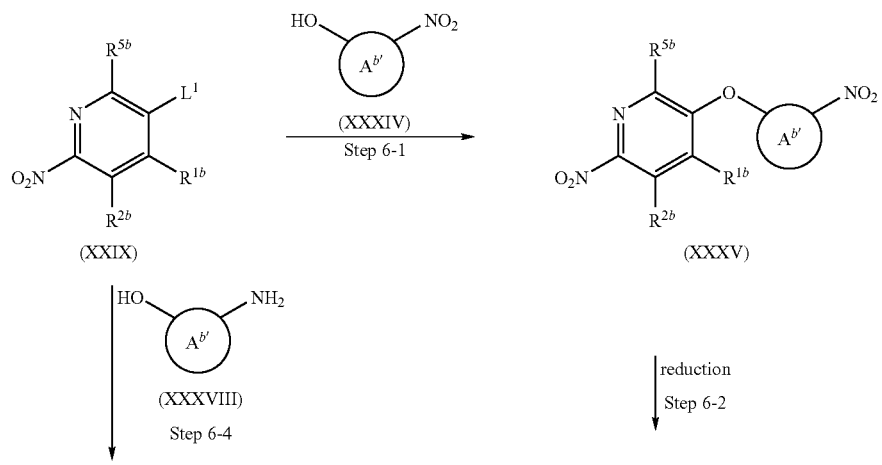

-continued

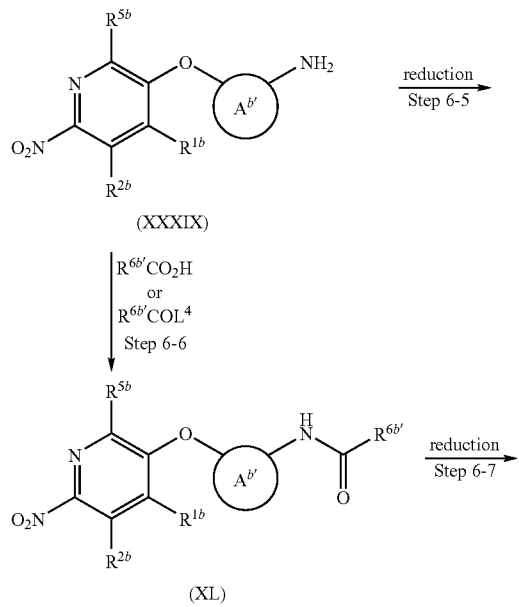

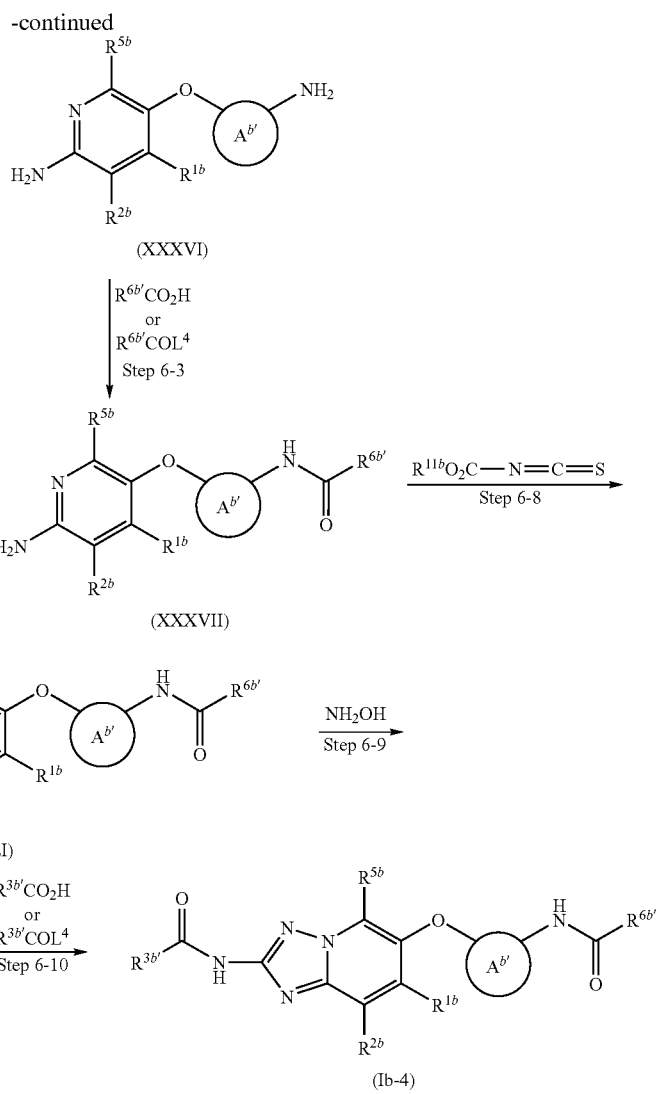

wherein $R^{6b'}$ is (1) a $C_{1-6}$ alkyl optionally having 1 to 3 halogen atoms, (2) a $C_{3-6}$ cycloalkyl, (3) a $C_{3-6}$ cycloalkenyl, (4) a $C_{6-10}$ aryl optionally having 1 to 3 halogen atoms, (5) a 5- or 6-membered monocyclic aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (6) a 8- to 12-membered fused aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (7) a 3- to 8-membered non-aromatic heterocyclic group or (8) a $C_{1-6}$ alkoxy, ring $A^{b'}$ is a ring further optionally having substituent(s), and other symbols are as defined above.

(Step 6-1):

Compound (XXXV) can be produced by reacting compound (XXIX) with compound (XXXIV). The amount of compound (XXXIV) to be used is about 0.1 to about 10 equivalents, preferably about 0.3 to about 3 equivalents, relative to compound (XXIX). Where necessary, a base may be added. As the base, those similar to the base exemplified in Step 5-1 can be used. The amount of the base to be used is about 1 to about 30 equivalents, preferably about 1 to about 10 equivalents, relative to compound (XXIX). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C.

(Step 6-2):

Compound (XXXVI) can be produced by reducing the nitro of compound (XXXV) in the same manner as in Step 5-2.

(Step 6-3):

Compound (XXXVII) can be produced by reacting compound (XXXVI) with a carboxylic acid ($R^{6b'}CO_2H$) in the presence of a condensing agent, or by reacting compound (XXXVI) with a reactive derivative ($R^{6b'}COL^4$) of the carboxylic acid, in the same manner as in Step 5-5.

(Step 6-4):

Compound (XXXIX) can be produced by reacting compound (XXIX) with compound (XXXVIII) in the presence of a base. The amount of compound (XXXVIII) to be used is about 0.1 to about 10 equivalents, preferably about 0.3 to about 3 equivalents, relative to compound (XXIX). As the base, those similar to the base exemplified in Step 5-1 can be used. The amount of the base to be used is about 1 to about 30 equivalents, preferably about 1 to about 10 equivalents, relative to compound (XXIX). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C.

(Step 6-5):

Compound (XXXVI) can be produced by reducing the nitro of compound (XXXIX) in the same manner as in Step 5-2.

(Step 6-6):

Compound (XL) can be produced by reacting compound (XXXIX) with a carboxylic acid ($R^{6b'}CO_2H$) in the presence of a condensing agent, or by reacting compound (XXXIX) with a reactive derivative ($R^{6b'}COL^4$) of the carboxylic acid, in the same manner as in Step 5-5.

(Step 6-7):

Compound (XXXVII) can be produced by reducing the nitro of compound (XL) in the same manner as in Step 5-2.

(Steps 6-8 to 6-10):

Compound (XLI), compound (Ib-3) and compound (Ib-4) can be synthesized from compound (XXXVII) in the same manner as in Steps 5-3 to 5-5.

[Production Method 7]

Compound (Ib) wherein ring $A^b$ is substituted by $R^{6b'}CONH$— can also be produced, for example, by the method shown in Scheme 7. Compounds (Ib-5), (Ib-6), (Ib-7) and (Ib-4) are encompassed in compound (Ib).

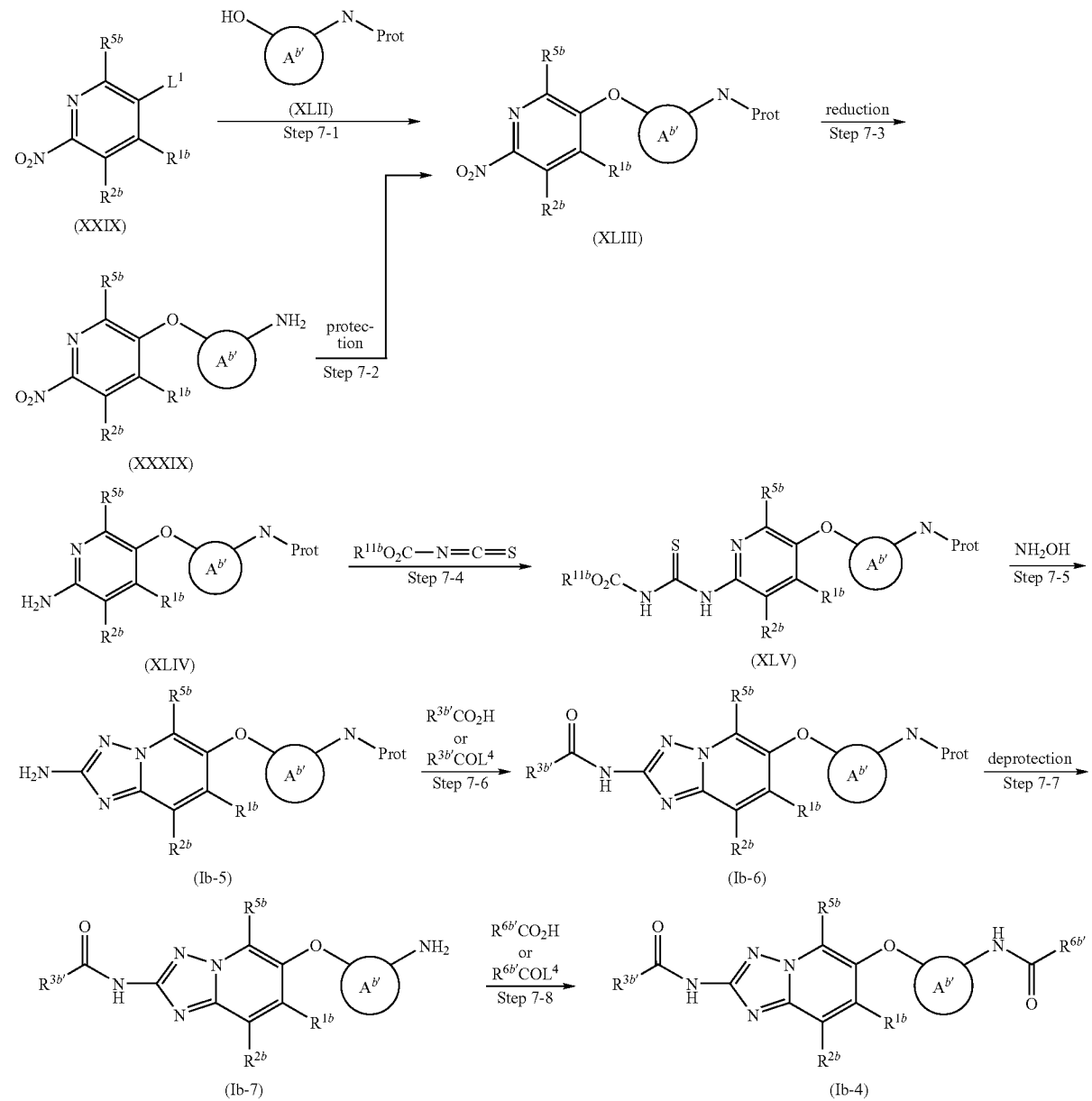

wherein Prot is an amino-protecting group, and other symbols are as defined above.

Examples of the protecting group for Prot include benzyloxycarbonyl, tert-butyloxycarbonyl and the like.

(Step 7-1):

Compound (XLIII) can be produced by reacting compound (XXIX) with compound (XLII) in the presence of a base. The amount of compound (XLII) to be used is about 0.1 to about 10 equivalents, preferably about 0.3 to about 3 equivalents, relative to compound (XXIX). As the base, those similar to the base exemplified in Step 5-1 can be used. The amount of the base to be used is about 1 to about 30 equivalents, preferably about 1 to about 10 equivalents, relative to compound (XXIX). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C.

(Step 7-2):

Compound (XLIII) can be produced by protecting the amino of compound (XXXIX). The protection of the amino can be carried out according to a method known per se, for example, the methods described in "Protective Groups in Organic Synthesis, 3rd Ed." (Theodora W. Greene) and the like, or a method analogous thereto.

(Steps 7-3 to 7-6):

Compound (XLIV), compound (XLV), compound (Ib-5) and compound (Ib-6) can be synthesized from compound (XLIII) in the same manner as in Steps 5-2 to 5-5.

(Step 7-7):

Compound (Ib-7) can be produced by protecting the amino-protecting group of compound (Ib-6). The deprotection of the amino-protecting group can be carried out according to a method known per se, for example, the methods described in "Protective Groups in Organic Synthesis, 3rd Ed." (Theodora W. Greene) and the like, or a method analogous thereto.

(Step 7-8):

Compound (Ib-4) can be produced by reacting compound (Ib-7) with a carboxylic acid ($R^{6b'}CO_2H$) in the presence of a condensing agent, or by reacting compound (Ib-7) with a reactive derivative ($R^{6b'}COL^4$) of the carboxylic acid, in the same manner as in Step 5-5.

[Production Method 8]

Compound (Ib) wherein ring $A^b$ is substituted by $R^{6b'}CONH$— can also be produced, for example, by the method shown in Scheme 8. Compounds (Ib-8), (Ib-9), (Ib-7) and (Ib-4) are encompassed in compound (Ib).

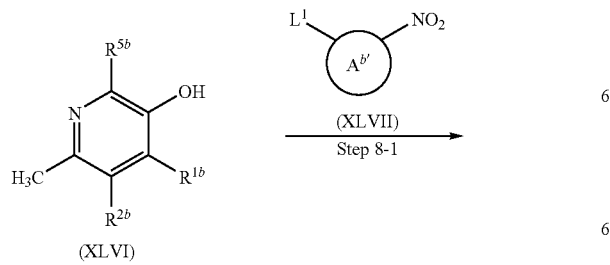

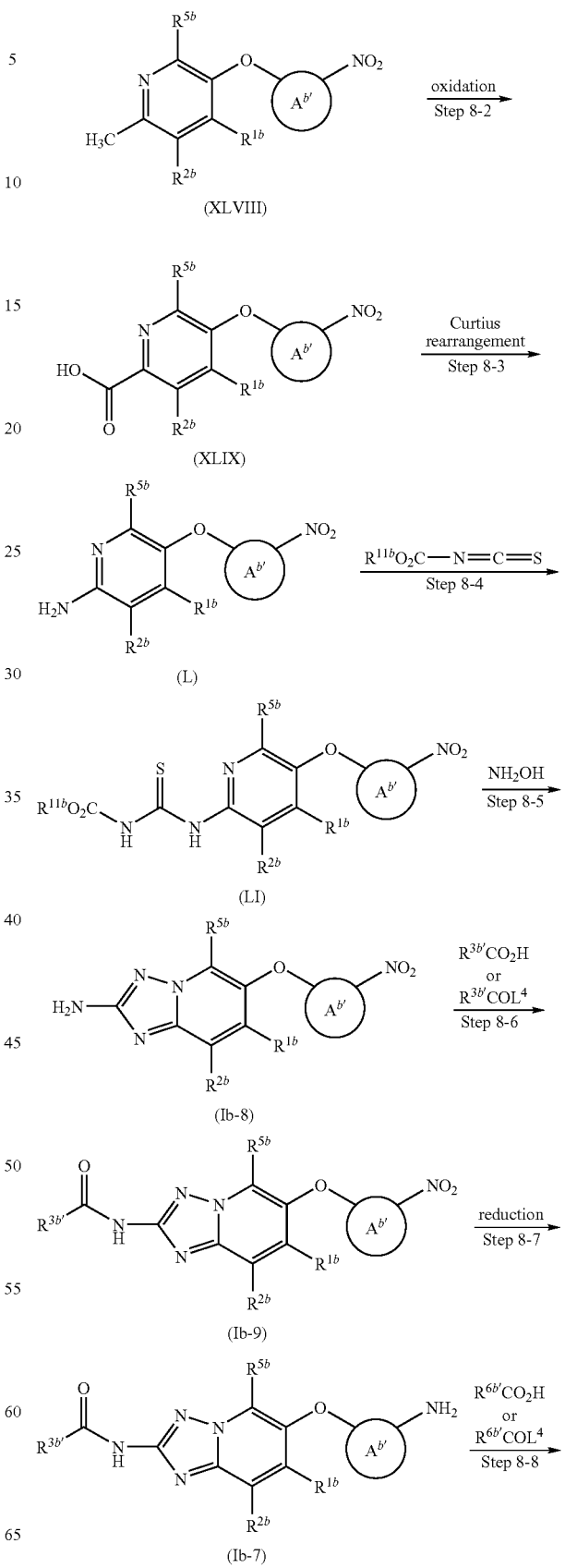

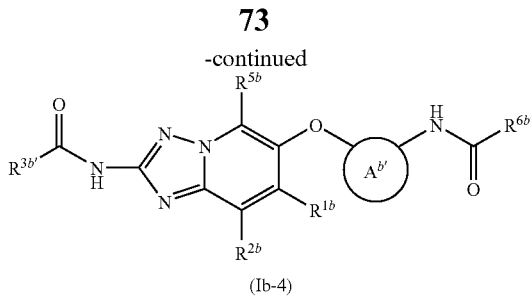

(Ib-4)

wherein each symbol in the formula is as defined above.

(Step 8-1):

Compound (XLVIII) can be produced by reacting compound (XLVI) with compound (XLVII) in the presence of a base. The amount of compound (XLVII) to be used is about 0.1 to about 10 equivalents, preferably about 0.3 to about 3 equivalents, relative to compound (XLVI). As the base, those similar to the base exemplified in Step 5-1 can be used. The amount of the base to be used is about 1 to about 30 equivalents, preferably about 1 to about 10 equivalents, relative to compound (XLVI). This reaction is advantageously carried out using a solvent inert to the reaction. As the solvent, those similar to the solvent exemplified in Step 5-1 can be used. The reaction time is generally about 10 min to about 100 hr, preferably about 30 min to about 50 hr. The reaction temperature is generally about −78 to about 200° C., preferably about −20 to about 150° C.

(Step 8-2):

Compound (XLIX) can be produced by oxidizing the methyl of compound (XLVIII). The oxidization of the methyl can be carried out according to a method known per se, for example, the methods described in "Advanced Organic Chemistry, 4th Ed." (Jerry March), "Comprehensive Organic Transformations, 2nd Ed." (Richard C. Larock), Zikken Kagaku Koza, 4th Ed., vol. 23, and the like, or a method analogous thereto.

(Step 8-3):

Compound (L) can be produced by converting the carboxyl of compound (XLIX) to an amino according to the Curtius rearrangement and the like. The conversion of the carboxyl to an amino can be carried out according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Steps 8-4 to 8-6):

Compound (LI), compound (Ib-8) and compound (Ib-9) can be synthesized from compound (L) in the same manner as in Steps 5-3 to 5-5.

(Step 8-7):

Compound (Ib-7) can be produced by reducing the nitro of compound (Ib-9) in the same manner as in Step 5-2.

(Step 8-8):

Compound (Ib-4) can be produced by reacting compound (Ib-7) with a carboxylic acid ($R^{6b'}CO_2H$) in the presence of a condensing agent, or by reacting compound (Ib-7) with a reactive derivative ($R^{6b'}COL^4$) of the carboxylic acid, in the same manner as in Step 5-5.

[Production Method 9]

Compound (Ib) wherein ring $A^b$ is substituted by $R^{6b'}CONH$— can also be produced, for example, by the method shown in Scheme 9. Compounds (Ib-9), (Ib-7) and (Ib-4) are encompassed in compound (Ib).

Reaction Scheme 9

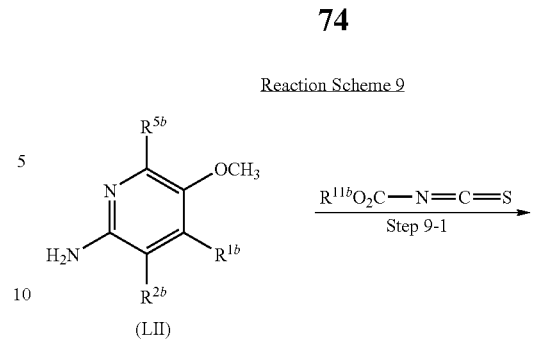

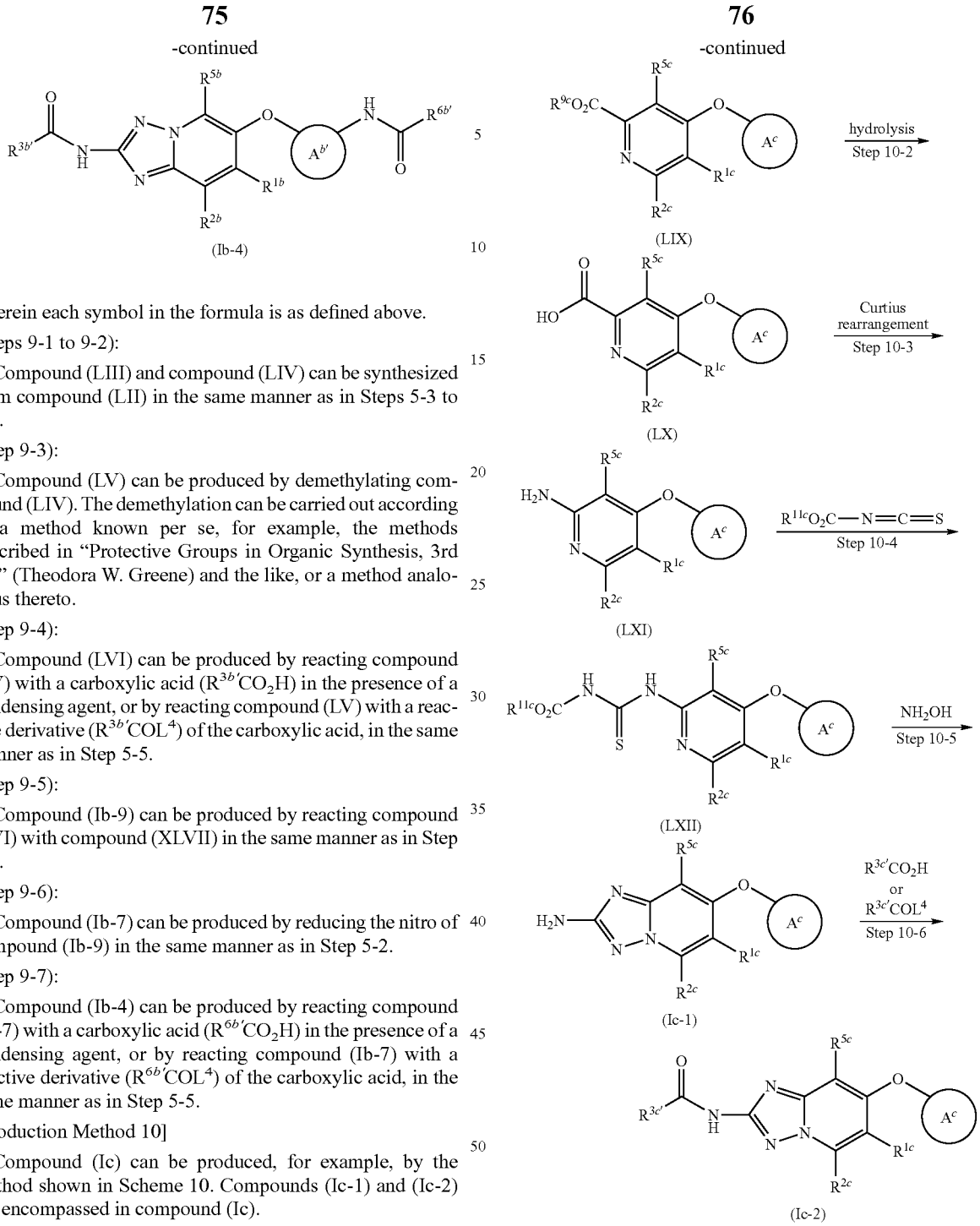

wherein each symbol in the formula is as defined above.

(Steps 9-1 to 9-2):

Compound (LIII) and compound (LIV) can be synthesized from compound (LII) in the same manner as in Steps 5-3 to 5-4.

(Step 9-3):

Compound (LV) can be produced by demethylating compound (LIV). The demethylation can be carried out according to a method known per se, for example, the methods described in "Protective Groups in Organic Synthesis, 3rd Ed." (Theodora W. Greene) and the like, or a method analogous thereto.

(Step 9-4):

Compound (LVI) can be produced by reacting compound (LV) with a carboxylic acid ($R^{3b'}CO_2H$) in the presence of a condensing agent, or by reacting compound (LV) with a reactive derivative ($R^{3b'}COL^4$) of the carboxylic acid, in the same manner as in Step 5-5.

(Step 9-5):

Compound (Ib-9) can be produced by reacting compound (LVI) with compound (XLVII) in the same manner as in Step 8-1.

(Step 9-6):

Compound (Ib-7) can be produced by reducing the nitro of compound (Ib-9) in the same manner as in Step 5-2.

(Step 9-7):

Compound (Ib-4) can be produced by reacting compound (Ib-7) with a carboxylic acid ($R^{6b'}CO_2H$) in the presence of a condensing agent, or by reacting compound (Ib-7) with a reactive derivative ($R^{6b'}COL^4$) of the carboxylic acid, in the same manner as in Step 5-5.

[Production Method 10]

Compound (Ic) can be produced, for example, by the method shown in Scheme 10. Compounds (Ic-1) and (Ic-2) are encompassed in compound (Ic).

Reaction Scheme 10

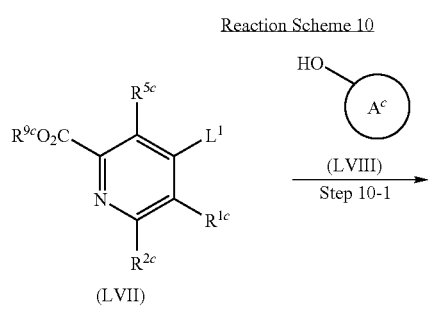

wherein $R^{3c'}$ is (1) a $C_{1-5}$ alkyl optionally having 1 to 3 substituents selected from the aforementioned substituent group A, (2) a $C_{2-5}$ alkenyl optionally having 1 to 3 substituents selected from the aforementioned substituent group A, (3) a $C_{2-5}$ alkynyl optionally having 1 to 3 substituents selected from the aforementioned substituent group A, (4) a $C_{3-6}$ cycloalkyl optionally having 1 to 3 substituents selected from a $C_{1-6}$ alkyl optionally having 1 to 3 halogen atoms and the aforementioned substituent group A, (5) a $C_{3-6}$ cycloalkyl-$C_{1-3}$ alkyl optionally having 1 to 3 substituents selected from a $C_{1-6}$ alkyl optionally having 1 to 3 halogen atoms and the aforementioned substituent group A, (6) a $C_{3-6}$ cycloalkenyl optionally having 1 to 3 substituents selected from a $C_{1-6}$ alkyl optionally having 1 to 3 halogen atoms and the aforementioned substituent group A, (7) a $C_{3-6}$ cycloalkenyl-$C_{1-3}$ alkyl optionally having 1 to 3 substituents selected from a $C_{1-6}$ alkyl optionally having 1 to 3 halogen atoms and the aforementioned substituent group A, (8) a $C_{6-10}$ aryl-$C_{1-3}$ alkyl optionally having 1 to 3 substituents selected from a $C_{1-6}$ alkyl optionally having 1 to 3 halogen atoms and the aforementioned substituent group A, or (9) a $C_{4-6}$ cycloalkanedienyl optionally having 1 to 3 substituents selected from a $C_{1-6}$ alkyl optionally having 1 to 3 halogen atoms and the aforementioned substituent group A, $R^{11c}$ is a $C_{1-6}$ alkyl optionally having 1 to 3 substituents selected from the aforementioned substituent group A, $R^{9c}$ is a $C_{1-6}$ alkyl optionally having 1 to 3 substituents selected from the aforementioned substituent group A, and other symbols are as defined above.

(Step 10-1):

Compound (LIX) can be produced by reacting compound (LVII) with compound (LVIII). The amount of the compound (LVIII) to be used is about 0.1 to about 10 equivalents, preferably about 0.3 to about 3 equivalents, relative to compound (LVII). Where necessary, a base may be added. Examples of the base include inorganic bases or organic bases and the like, specifically, sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like. The amount of the base to be used is about 1 to about 30 equivalents, preferably about 1 to about 10 equivalents, relative to compound (LVII). This reaction is advantageously carried out using a solvent inert to the reaction. While the solvent is not particularly limited as long as the reaction proceeds, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitriles such as acetonitrile and the like; sulfoxides such as dimethylsulfoxide and the like; pyridine, water and the like, or a mixed solvent thereof can be used. While the reaction time varies depending on the reagent or solvent to be used, it is generally about 10 min to about 100 hr, preferably about 30 min to about 50 hr. The reaction temperature is generally about −78 to about 200° C., preferably about −20 to about 150° C. The reaction may be carried out using a microwave reaction apparatus.

(Step 10-2):

Compound (LX) can be produced by subjecting compound (LIX) to alkali hydrolysis. This reaction is carried out in an aqueous solvent in the presence of a base. Examples of the base include sodium hydroxide, potassium hydroxide, lithium hydroxide, barium hydroxide, calcium hydroxide, potassium carbonate, sodium carbonate, cesium carbonate, sodium methoxide and the like. The amount of the base to be used is about 1 to about 50 equivalents, preferably about 1 to about 10 equivalents, relative to compound (LIX). Examples of the aqueous solvent include a mixed solvent of water and 1 kind or more solvents selected from methanol, ethanol, tetrahydrofuran, 1,4-dioxane and the like, and the like. The reaction time is generally about 10 min to about 100 hr, preferably about 30 min to about 50 hr. The reaction temperature is generally about −78 to about 200° C., preferably about −20 to about 150° C.

(Step 10-3):

Compound (LXI) can be produced by converting the carboxyl of compound (LX) to an amino according to the Curtius rearrangement and the like. The conversion of the carboxyl to an amino can be carried out according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 10-4):

Compound (LXII) can be produced by reacting compound (LXI) with a compound represented by the formula: $R^{11c}O_2C-N=C=S$. The amount of $R^{11c}O_2C-N=C=S$ to be used is about 0.1 to about 10 equivalents, preferably about 0.3 to about 3 equivalents, relative to compound (LXI). This reaction is advantageously carried out using a solvent inert to the reaction. As the solvent, those similar to the solvent exemplified in Step 10-1 can be used. The reaction time is generally about 10 min to about 100 hr, preferably about 30 min to about 50 hr. The reaction temperature is generally about −78 to about 200° C., preferably about −20 to about 150° C.

(Step 10-5):

Compound (Ic-1) can be produced by reacting compound (LXII) with hydroxylamine in the presence of a base. The amount of the hydroxylamine to be used is about 0.1 to about 100 equivalents, preferably about 0.3 to about 30 equivalents, relative to compound (LXII). As the base, those similar to the base exemplified in Step 10-1 can be used. The amount of the base to be used is about 0.1 to about 100 equivalents, preferably about 0.3 to about 30 equivalents, relative to compound (LXII). This reaction is advantageously carried out using a solvent inert to the reaction. As the solvent, those similar to the solvent exemplified in Step 10-1 can be used. The reaction time is generally about 10 min to about 100 hr, preferably about 30 min to about 50 hr. The reaction temperature is generally about −78 to about 200° C., preferably about −20 to about 150° C.

(Step 10-6):

Compound (Ic-2) can be produced by reacting compound (Ic-1) with a carboxylic acid ($R^{3c'}CO_2H$) in the presence of a condensing agent, or by reacting compound (Ic-1) with a reactive derivative ($R^{3c'}COL^4$) of the carboxylic acid.

When compound (Ic-1) is reacted with $R^{3c'}CO_2H$ in the presence of a condensing agent, the amount of $R^{3c'}CO_2H$ to be used is about 0.1 to about 10 equivalents, preferably about 0.3 to about 3 equivalents, relative to compound (Ic-1). Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The amount of the condensing agent to be used is about 1 to about 10 equivalents, preferably about 1 to about 5 equivalents, relative to compound (Ic-1). Where necessary, a suitable condensation promoter (e.g., 1-hydroxybenzotriazole, N-hydroxysuccinimide and the like) can be used. The amount of the condensation promoter to be used is about 0.1 to about 10 equivalents, preferably about 0.3 to about 3 equivalents, relative to compound (Ic-1). This reaction may proceed more smoothly by addition of a base (e.g., triethylamine, N,N-diisopropylethylamine, N-methylmorpholine, 1,8-diazabicyclo[5.4.0]undec- 7-ene and the like). The amount of the base to be used is about 0.01 to about 10 equivalents, preferably about 0.03 to about 5 equivalents, relative to compound (Ic-1). This reaction is advantageously carried out using a solvent inert to the reaction. As the solvent, those similar to the solvent exemplified in Step 10-1 can be used. The reaction time is generally about 10 min to about 100 hr, preferably about 30 min to about 50 hr. The reaction temperature is generally about −78 to about 200° C., preferably about −20 to about 150° C. $R^{3c'}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

When compound (Ic-1) is reacted with a reactive derivative ($R^{3c'}COL^4$) of the carboxylic acid, the amount of the reactive derivative ($R^{3c'}COL^4$) of the carboxylic acid to be used is about 0.1 to about 10 equivalents, preferably about 0.3 to about 3 equivalents, relative to compound (Ic-1). This reaction is generally carried out in the presence of a base, which is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The amount of the base to be used is about 0.01 to about 10 equivalents, preferably about 0.03 to about 5 equivalents, relative to compound (Ic-1). This reaction is advantageously carried out using a solvent inert to the reaction. As the solvent, those similar to the solvent exemplified in Step 10-1 can be used. The reaction time is generally about 10 min to about 100 hr, preferably about 30 min to about 50 hr. The reaction temperature is generally about −78 to about 200° C., preferably about −20 to about 150° C. The reactive derivative ($R^{3c'}COL^4$) of the carboxylic acid may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 11]

Compound (Ic) wherein ring $A^c$ is substituted by $R^{6c'}CONH-$ can also be produced, for example, by the method shown in Scheme 11. Compounds (Ic-3), (Ic-4), (Ic-5) and (Ic-6) are encompassed in compound (Ic).

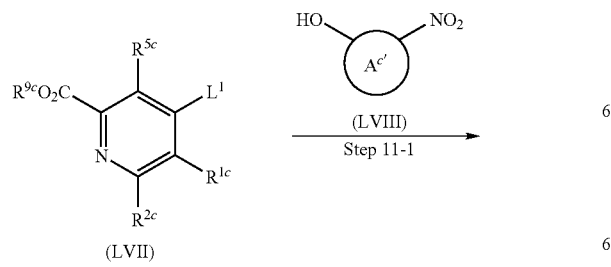

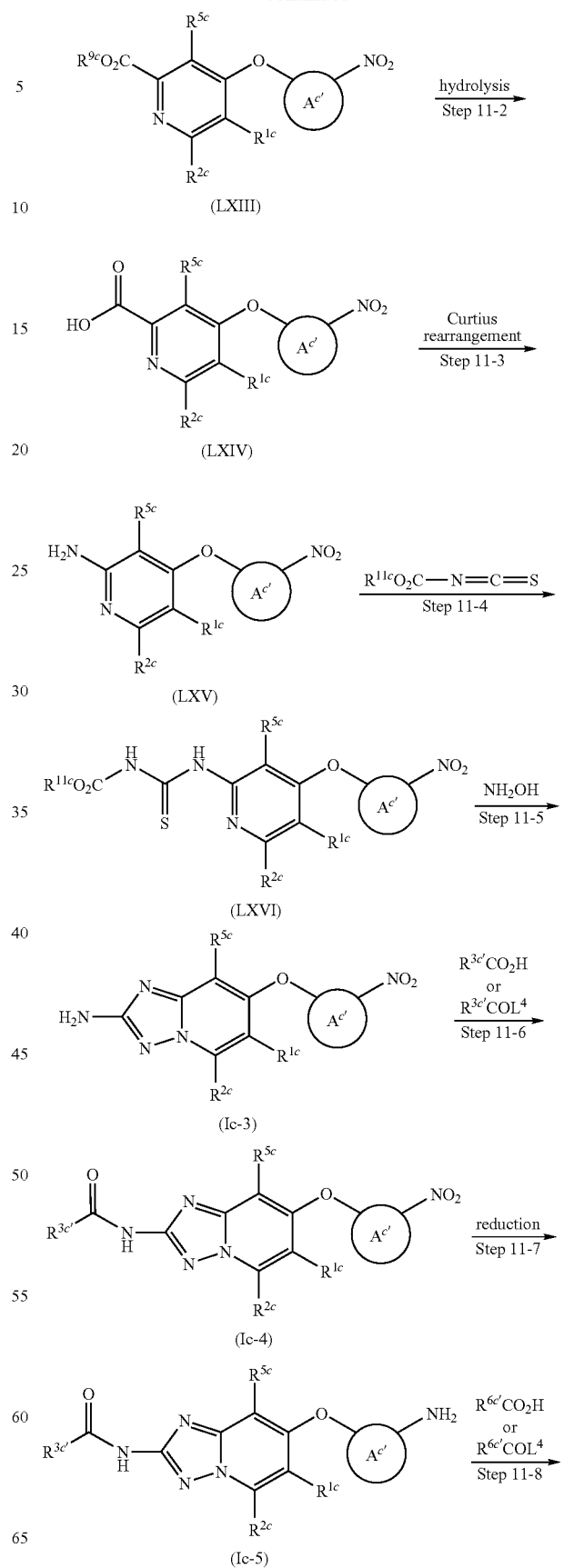

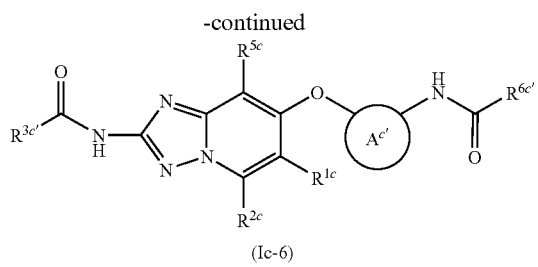

(Ic-6)

wherein $R^{6c'}$ is (1) a $C_{1-6}$ alkyl optionally having 1 to 3 halogen atoms, (2) a $C_{3-6}$ cycloalkyl, (3) a $C_{3-6}$ cycloalkenyl, (4) a $C_{6-10}$ aryl optionally having 1 to 3 halogen atoms, (5) a 5- or 6-membered monocyclic aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (6) a 8- to 12-membered fused aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (7) a 3- to 8-membered non-aromatic heterocyclic group or (8) a $C_{1-6}$ alkoxy, ring $A^c$ is a ring further optionally having substituent(s), and other symbols are as defined above.

(Steps 11-1 to 11-6):

Compound (LXIII), compound (LXIV), compound (LXV), compound (LXVI), compound (Ic-3) and compound (Ic-4) can be synthesized using compound (LVII) and compound (LVIII) in the same manner as in Steps 10-1 to 10-6.

(Step 11-7):

Compound (Ic-5) can be produced by reducing the nitro of compound (Ic-4). The reduction of the nitro can be carried out according to a method known per se, for example, the methods described in "Advanced Organic Chemistry, 4th Ed." (Jerry March), "Comprehensive Organic Transformations, 2nd Ed." (Richard C. Larock), Zikken Kagaku Koza, 4th Ed., vol. 20, pages 279-280 and the like, or a method analogous thereto.

(Step 11-8):

Compound (Ic-6) can be produced by reacting compound (Ic-5) with a carboxylic acid ($R^{6c'}CO_2H$) in the presence of a condensing agent, or by reacting compound (Ic-5) with a reactive derivative ($R^{6c'}COL^4$) of the carboxylic acid, in the same manner as in Step 10-6.

[Production Method 12]

Compound (1d) can be produced, for example, by the method shown in Scheme 12. Compound (1d-1) is encompassed in compound (1d).

Reaction Scheme 12

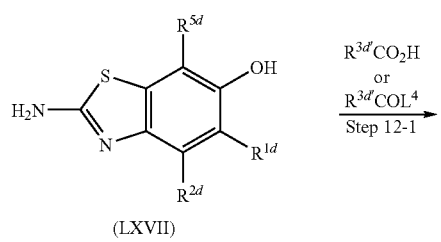

(LXVII)

$R^{3d'}CO_2H$
or
$R^{3d'}COL^4$
———————→
Step 12-1

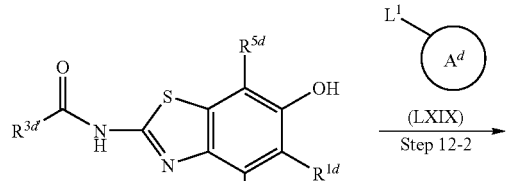

(LXVIII)

(LXIX)
———————→
Step 12-2

(Id-1)

wherein $R^{3d'}$ is (1) a $C_{1-5}$ alkyl optionally having 1 to 3 substituents selected from the aforementioned substituent group A, (2) a $C_{2-5}$ alkenyl optionally having 1 to 3 substituents selected from the aforementioned substituent group A, (3) a $C_{2-5}$ alkynyl optionally having 1 to 3 substituents selected from the aforementioned substituent group A, (4) a $C_{3-6}$ cycloalkyl optionally having 1 to 3 substituents selected from a $C_{1-6}$ alkyl optionally having 1 to 3 halogen atoms and the aforementioned substituent group A, (5) a $C_{3-6}$ cycloalkyl-$C_{1-3}$ alkyl optionally having 1 to 3 substituents selected from a $C_{1-6}$ alkyl optionally having 1 to 3 halogen atoms and the aforementioned substituent group A, (6) a $C_{3-6}$ cycloalkenyl optionally having 1 to 3 substituents selected from a $C_{1-6}$ alkyl optionally having 1 to 3 halogen atoms and the aforementioned substituent group A, (7) a $C_{3-6}$ cycloalkenyl-$C_{1-3}$ alkyl optionally having 1 to 3 substituents selected from a $C_{1-6}$ alkyl optionally having 1 to 3 halogen atoms and the aforementioned substituent group A, (8) a $C_{6-10}$ aryl-$C_{1-3}$ alkyl optionally having 1 to 3 substituents selected from a $C_{1-6}$ alkyl optionally having 1 to 3 halogen atoms and the aforementioned substituent group A, or (9) a $C_{4-6}$ cycloalkanedienyl optionally having 1 to 3 substituents selected from a $C_{1-6}$ alkyl optionally having 1 to 3 halogen atoms and the aforementioned substituent group A, and other symbols are as defined above.

(Step 12-1):

Compound (LXVIII) can be produced by reacting compound (LXVII) with a carboxylic acid ($R^{3d'}CO_2H$) in the presence of a condensing agent, or by reacting compound (LXVII) with a reactive derivative ($R^{3d'}COL^4$) of the carboxylic acid.

When compound (LXVII) is reacted with $R^{3d'}CO_2H$ in the presence of a condensing agent, the amount of $R^{3d'}CO_2H$ to be used is about 0.1 to about 10 equivalents, preferably about 0.3 to about 3 equivalents, relative to compound (LXVII). Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The amount of the condensing agent to be used is about 1 to about 10 equivalents, preferably about 1 to about 5 equivalents, relative to compound (LXVII). Where necessary, a suitable condensation promoter (e.g., 1-hydroxybenzotriazole, N-hydroxysuccinimide and the like) can be used. The amount of the condensation promoter to be used is about 0.1 to about 10 equivalents, preferably about 0.3 to about 3 equivalents, relative to compound (LXVII). This reaction may proceed more smoothly by addition of a base (e.g., triethylamine, N,N-diisopropylethylamine, N-methylmorpholine, 1,8-diazabicyclo[5.4.0]undec-7-ene and the like). The amount of the base to be used is about 0.01 to about 10 equivalents, preferably about 0.03 to about 5 equivalents, relative to compound (LXVII). This reaction is advantageously carried out using a solvent inert to the reaction. While the solvent is not particularly limited as long as the reaction proceeds, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitrites such as acetonitrile and the like; sulfoxides such as dimethylsulfoxide and the like; pyridine, water and the like, or a mixed solvent thereof can be used. While the reaction time varies depending on the reagent or solvent to be used, it is generally about 10 min to about 100 hr, preferably about 30 min to about 50 hr. The reaction temperature is generally about −78 to about 200° C., preferably about −20 to about 150° C. $R^{3d'}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

When compound (LXVII) is reacted with a reactive derivative ($R^{3d'}COL^4$) of the carboxylic acid, the amount of the reactive derivative ($R^{3d'}COL^4$) of the carboxylic acid to be used is about 0.1 to about 10 equivalents, preferably about 0.3 to about 3 equivalents, relative to compound (LXVII). This reaction is generally carried out in the presence of a base, which is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The amount of the base to be used is about 0.01 to about 10 equivalents, preferably about 0.03 to about 5 equivalents, relative to compound (LXVII). This reaction is advantageously carried out using a solvent inert to the reaction. As the solvent, those similar to the aforementioned solvent can be used. The reaction time is generally about 10 min to about 100 hr, preferably about 30 min to about 50 hr. The reaction temperature is generally about −78 to about 200° C., preferably about −20 to about 150° C. The reactive derivative ($R^{3d'}COL^4$) of the carboxylic acid may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.
(Step 12-2):

Compound (Id-1) can be produced by reacting compound (LXVIII) with compound (LXIX). The amount of compound (LXIX) to be used is about 0.1 to about 10 equivalents, preferably about 0.3 to about 3 equivalents, relative to compound (LXVIII). Where necessary, a base may be added. Examples of the base include inorganic bases, organic bases and the like, specifically, for example, sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like can be mentioned. The amount of the base to be used is about 1 to about 30 equivalents, preferably about 1 to about 10 equivalents, relative to compound (LXVIII). This reaction is advantageously carried out using a solvent inert to the reaction. As the solvent, those similar to the solvent exemplified in Step 12-1 can be used. The reaction time is generally about 10 min to about 100 hr, preferably about 30 min to about 50 hr. The reaction temperature is generally about −78 to about 200° C., preferably about −20 to about 150° C. The reaction may be carried out using a microwave reaction apparatus.
[Production Method 13]

Compound (Id) wherein ring $A^d$ is substituted by $R^{6d'}CONH$— can also be produced, for example, by the method shown in Scheme 13. Compounds (Id-2), (Id-3) and (Id-4) are encompassed in compound (Id).

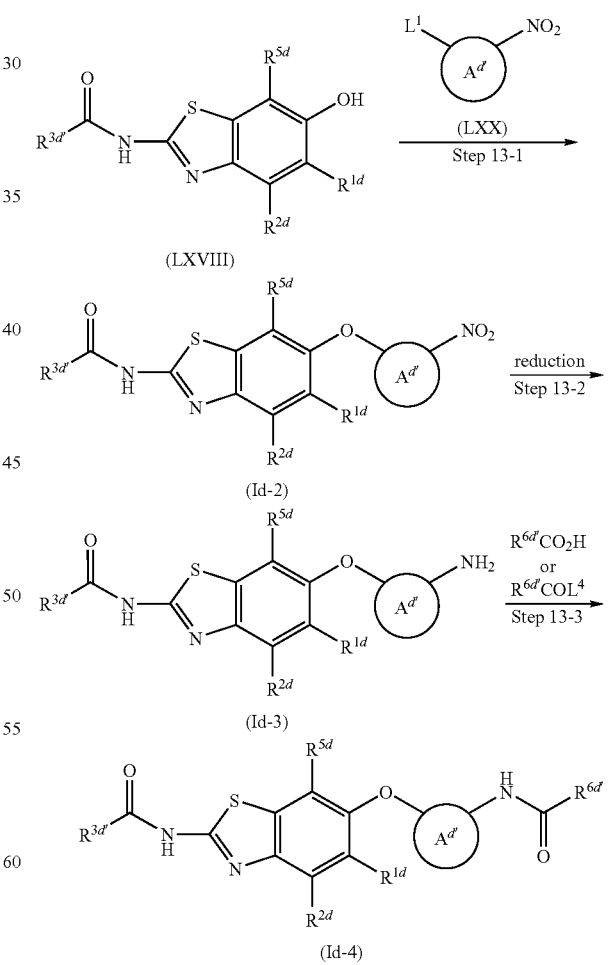

wherein $R^{6d'}$ is (1) a $C_{1-6}$ alkyl optionally having 1 to 3 halogen atoms, (2) a $C_{3-6}$ cycloalkyl, (3) a $C_{3-6}$ cycloalkenyl, (4) a $C_{6-10}$ aryl optionally having 1 to 3 halogen atoms, (5) a 5- or 6-membered monocyclic aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (6) a 8- to 12-membered fused aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (7) a 3- to 8-membered non-aromatic heterocyclic group or (8) a $C_{1-6}$ alkoxy, ring $A^{d'}$ is a ring further optionally having substituent(s), and other symbols are as defined above.

(Step 13-1):

Compound (Id-2) can be produced by reacting compound (LXVIII) with compound (LXX) in the same manner as in Step 12-2.

(Step 13-2):

Compound (Id-3) can be produced by reducing the nitro of compound (Id-2). The reduction of the nitro can be carried out according to a method known per se, for example, the methods described in "Advanced Organic Chemistry, 4th Ed." (Jerry March), "Comprehensive Organic Transformations, 2nd Ed." (Richard C. Larock), Zikken Kagaku Koza, 4th Ed., vol. 20, pages 279-280 and the like, or a method analogous thereto.

(Step 13-3):

Compound (Id-4) can be produced by reacting compound (Id-3) with a carboxylic acid ($R^{6d'}CO_2H$) in the presence of a condensing agent, or by reacting compound (Id-3) with a reactive derivative ($R^{6d'}COL^4$) of the carboxylic acid, in the same manner as in Step 12-1.

[Production Method 14]

Compound (Ie) can be produced, for example, by the method shown in Scheme 14. Compounds (Ie-1) and (Ie-2) are encompassed in compound (Ie).

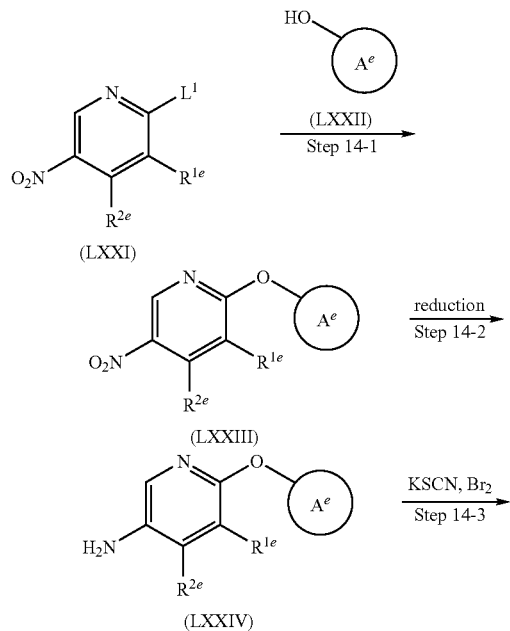

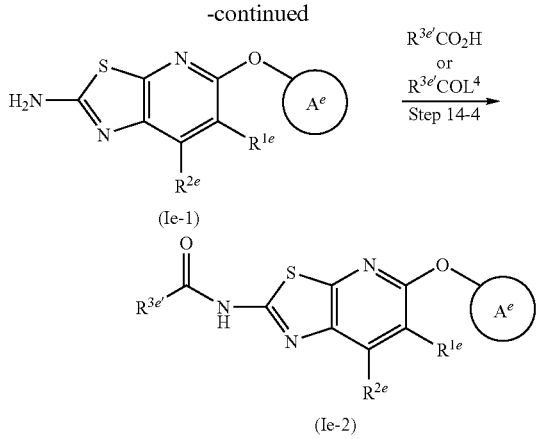

wherein $R^{3e'}$ is (1) a $C_{1-5}$ alkyl optionally having 1 to 3 substituents selected from the aforementioned substituent group A, (2) a $C_{2-5}$ alkenyl optionally having 1 to 3 substituents selected from the aforementioned substituent group A, (3) a $C_{2-5}$ alkynyl optionally having 1 to 3 substituents selected from the aforementioned substituent group A, (4) a $C_{3-6}$ cycloalkyl optionally having 1 to 3 substituents selected from a $C_{1-6}$ alkyl optionally having 1 to 3 halogen atoms and the aforementioned substituent group A, (5) a $C_{3-6}$ cycloalkyl-$C_{1-3}$ alkyl optionally having 1 to 3 substituents selected from a $C_{1-6}$ alkyl optionally having 1 to 3 halogen atoms and the aforementioned substituent group A, (6) a $C_{3-6}$ cycloalkenyl optionally having 1 to 3 substituents selected from a $C_{1-6}$ alkyl optionally having 1 to 3 halogen atoms and the aforementioned substituent group A, (7) a $C_{3-6}$ cycloalkenyl-$C_{1-3}$ alkyl optionally having 1 to 3 substituents selected from a $C_{1-6}$ alkyl optionally having 1 to 3 halogen atoms and the aforementioned substituent group A, (8) a $C_{6-10}$ aryl-$C_{1-3}$ alkyl optionally having 1 to 3 substituents selected from a $C_{1-6}$ alkyl optionally having 1 to 3 halogen atoms and the aforementioned substituent group A, or (9) a $C_{4-6}$ cycloalkanedienyl optionally having 1 to 3 substituents selected from a $C_{1-6}$ alkyl optionally having 1 to 3 halogen atoms and the aforementioned substituent group A, and other symbols are as defined above.

(Step 14-1):

Compound (LXXIII) can be produced by reacting compound (LXXI) with compound (LXXII). The amount of compound (LXXII) to be used is about 0.1 to about 10 equivalents, preferably about 0.3 to about 3 equivalents, relative to compound (LXXI). Where necessary, a base may be added. Examples of the base include inorganic bases or organic bases and the like, specifically, for example, sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline, sodium methoxide, sodium ethoxide, potassium tert-butoxide, sodium hydride, sodium amide, lithium diisopropylamide and the like. The amount of the base to be used is about 1 to about 30 equivalents, preferably about 1 to about 10 equivalents, relative to compound (LXXI). This reaction is advantageously carried out using a solvent inert to the reaction. While the solvent is not particularly limited as long as the reaction proceeds, for example, alcohols such as methanol, ethanol, 2-propanol, 2-methyl-2-propanol and the like; ethers such as diethyl ether, tetrahydrofuran, 1,4-dioxane, 1,2-dimethoxyethane and the like; hydrocarbons such as benzene, toluene, cyclohexane, hexane and the like; esters such as ethyl acetate and the like; amides such as N,N-dimethylformamide, N,N-dimethylacetamide, 1-methyl-2-pyrrolidone and the like; halogenated hydrocarbons such as dichloromethane, chloroform, carbon tetrachloride, 1,2-dichloroethane and the like; nitrites such as acetonitrile and the like; sulfoxides such as dimethylsulfoxide and the like; pyridine, water and the like, or a mixed solvent thereof can be used. While the reaction time varies depending on the reagent or solvent to be used, it is generally about 10 min to about 100 hr, preferably about 30 min to about 50 hr. The reaction temperature is generally about −78 to about 200° C., preferably about −20 to about 150° C. The reaction may be carried out using a microwave reaction apparatus.

(Step 14-2):

Compound (LXIV) can be produced by reducing the nitro of compound (LXXIII). The reduction of the nitro can be carried out according to a method known per se, for example, the methods described in "Advanced Organic Chemistry, 4th Ed." (Jerry March), "Comprehensive Organic Transformations, 2nd Ed." (Richard C. Larock), Zikken Kagaku Koza, 4th Ed., vol. 20, pages 279-280 and the like, or a method analogous thereto.

(Step 14-3):

Compound (Ie-1) can be produced by reacting compound (LXXIV) with potassium thiocyanate and bromine. The amount of the potassium thiocyanate to be used is about 1 to about 100 equivalents, preferably about 1 to about 30 equivalents, relative to compound (LXXIV). The amount of the bromine to be used is about 1 to about 30 equivalents, preferably about 1 to about 10 equivalents, relative to compound (LXXIV). Examples of the solvent include acetic acid and the like. The reaction time is generally about 10 min to about 100 hr, preferably about 30 min to about 50 hr. The reaction temperature is generally about −78 to about 200° C., preferably about −20 to about 150° C.

(Step 14-4):

Compound (Ie-2) can be produced by reacting compound (Ie-1) with a carboxylic acid ($R^{3e'}CO_2H$) in the presence of a condensing agent, or by reacting compound (Ie-1) with a reactive derivative ($R^{3e'}COL^4$) of the carboxylic acid.

When compound (Ie-1) is reacted with $R^{3e'}CO_2H$ in the presence of a condensing agent, the amount of $R^{3e'}CO_2H$ to be used is about 0.1 to about 10 equivalents, preferably about 0.3 to about 3 equivalents, relative to compound (Ie-1). Examples of the condensing agent include 1-ethyl-1-(3-dimethylaminopropyl)carbodiimide hydrochloride, 1,3-dicyclohexylcarbodiimide, diethyl cyanophosphate, diphenylphosphoryl azide, 1,1'-carbonyldiimidazole, benzotriazol-1-yloxytripyrrolidinophosphonium hexafluorophosphate, O-(7-azabenzotriazol-1-yl)-N,N,N',N'-tetramethyluronium hexafluorophosphate and the like. The amount of the condensing agent to be used is about 1 to about 10 equivalents, preferably about 1 to about 5 equivalents, relative to compound (Ie-1). Where necessary, a suitable condensation promoter (e.g., 1-hydroxybenzotriazole, N-hydroxysuccinimide and the like) can be used. The amount of the condensation promoter to be used is about 0.1 to about 10 equivalents, preferably about 0.3 to about 3 equivalents, relative to compound (Ie-1). This reaction may proceed more smoothly by addition of a base (e.g., triethylamine, N,N-diisopropylethylamine, N-methylmorpholine, 1,8-diazabicyclo[5.4.0]undec-7-ene and the like). The amount of the base to be used is about 0.01 to about 10 equivalents, preferably about 0.03 to about 5 equivalents, relative to compound (Ie-1). This reaction is advantageously carried out using a solvent inert to the reaction. As the solvent, those similar to the solvent exemplified in Step 14-1 can be used. The reaction time is generally about 10 min to about 100 hr, preferably about 30 min to about 50 hr. The reaction temperature is generally about −78 to about 200° C., preferably about −20 to about 150° C. $R^{3e'}CO_2H$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

When compound (Ie-1) is reacted with a reactive derivative ($R^{3e'}COL^4$) of the carboxylic acid, the amount of the reactive derivative ($R^{3e'}COL^4$) of the carboxylic acid to be used is about 0.1 to about 10 equivalents, preferably about 0.3 to about 3 equivalents, relative to compound (Ie-1). This reaction is generally carried out in the presence of a base, which is not always essential. Examples of the base include sodium hydroxide, potassium hydroxide, sodium carbonate, potassium carbonate, cesium carbonate, sodium hydrogen carbonate, triethylamine, N,N-diisopropylethylamine, N-methylmorpholine, 1,8-diazabicyclo[5.4.0]undec-7-ene, pyridine, 4-(dimethylamino)pyridine, N,N-dimethylaniline and the like. The amount of the base to be used is about 0.01 to about 10 equivalents, preferably about 0.03 to about 5 equivalents, relative to compound (Ie-1). This reaction is advantageously carried out using a solvent inert to the reaction. As the solvent, those similar to the solvent exemplified in Step 14-1 can be used. The reaction time is generally about 10 min to about 100 hr, preferably about 30 min to about 50 hr. The reaction temperature is generally about −78 to about 200° C., preferably about −20 to about 150° C. The reactive derivative ($R^{3e'}COL^4$) of the carboxylic acid may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 15]

Compound (Ie) wherein ring $A^e$ is substituted by $R^{6e'}CONH$— can also be produced, for example, by the method shown in Scheme 15. Compounds (Ie-3), (Ie-4), (Ie-5), (Ie-6) and (Ie-7) are encompassed in compound (Ie).

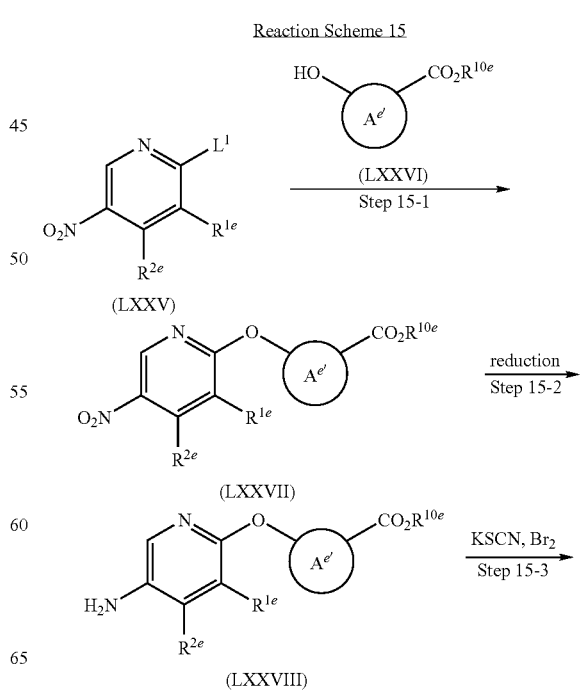

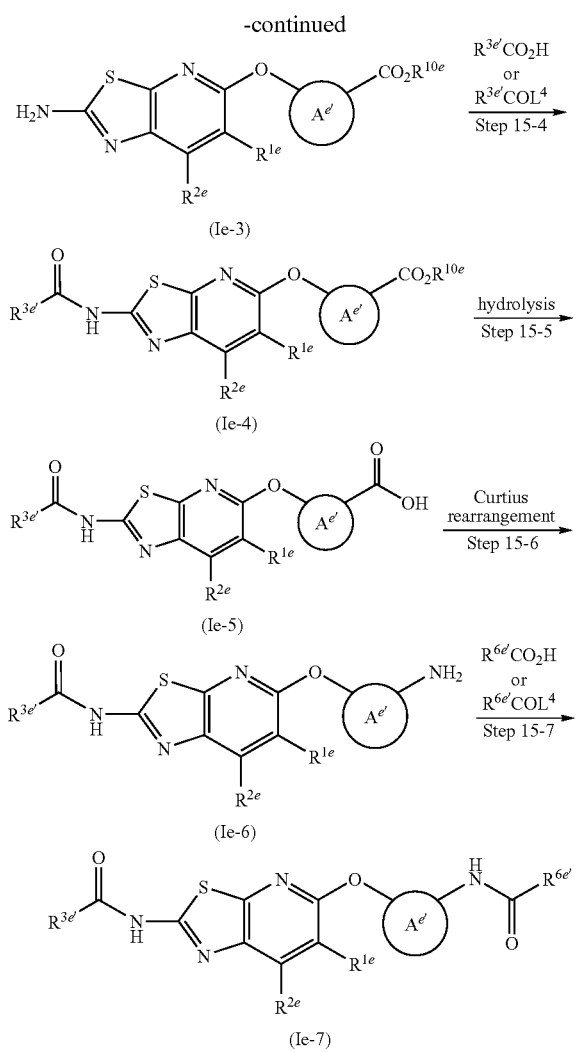

ally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (7) a 3- to 8-membered non-aromatic heterocyclic group or (8) a $C_{1-6}$ alkoxy, $R^{10e}$ is a $C_{1-6}$ alkyl optionally having 1 to 3 substituents selected from the aforementioned substituent group A, ring $A^{e'}$ is a ring further optionally having substituent(s), and other symbols are as defined above.

(Steps 15-1 to 15-4):

Compound (LXXVII), compound (LXXVIII), compound (Ie-3) and compound (Ie-4) can be synthesized using compound (LXXV) and compound (LXXVI) in the same manner as in Steps 14-1 to 14-4.

(Step 15-5):

Compound (Ie-5) can be produced by subjecting compound (Ie-4) to alkali hydrolysis. This reaction is carried out in an aqueous solvent in the presence of a base. Examples of the base include sodium hydroxide, potassium hydroxide, lithium hydroxide, barium hydroxide, calcium hydroxide, potassium carbonate, sodium carbonate, cesium carbonate, sodium methoxide and the like. The amount of the base to be used is about 1 to about 50 equivalents, preferably about 1 to about 10 equivalents, relative to compound (1e-4). Examples of the aqueous solvent include a mixed solvent of water and 1 kind or more solvents selected from methanol, ethanol, tetrahydrofuran, 1,4-dioxane and the like, and the like. The reaction time is generally about 10 min to about 100 hr, preferably about 30 min to about 50 hr. The reaction temperature is generally about −78 to about 200° C., preferably about −20 to about 150° C.

(Step 15-6):

Compound (Ie-6) can be produced by converting the carboxyl of compound (Ie-5) to an amino according to the Curtius rearrangement and the like. The conversion of the carboxyl to an amino can be carried out according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 15-7):

Compound (Ie-7) can be produced by reacting compound (Ie-6) with a carboxylic acid ($R^{6e'}CO_2H$) in the presence of a condensing agent, or by reacting compound (Ie-6) with a reactive derivative ($R^{6e'}COL^4$) of the carboxylic acid, in the same manner as in Step 14-4.

[Production Method 16]

Compound (Ia) wherein $R^{3a}$ is $R^{3a'}NHCONH—$, $R^{3a'}SO_2NH—$ or $R^{13a}NH—$ can also be produced, for example, by the method shown in Scheme 16. Compounds (Ia-14), (Ia-15) and (Ia-16) are encompassed in compound (Ia).

wherein $R^{6e'}$ is (1) a $C_{1-6}$ alkyl optionally having 1 to 3 halogen atoms, (2) a $C_{3-6}$ cycloalkyl, (3) a $C_{3-6}$ cycloalkenyl, (4) a $C_{6-10}$ aryl optionally having 1 to 3 halogen atoms, (5) a 5- or 6-membered monocyclic aromatic heterocyclic group optionally having 1 to 3 substituents selected from (a) a halogen atom, (b) a $C_{1-6}$ alkyl optionally having 1 to 3 halogen atoms, (c) a $C_{1-6}$ alkoxy and (d) a $C_{3-8}$ cycloalkyl, (6) a 8- to 12-membered fused aromatic heterocyclic group option-

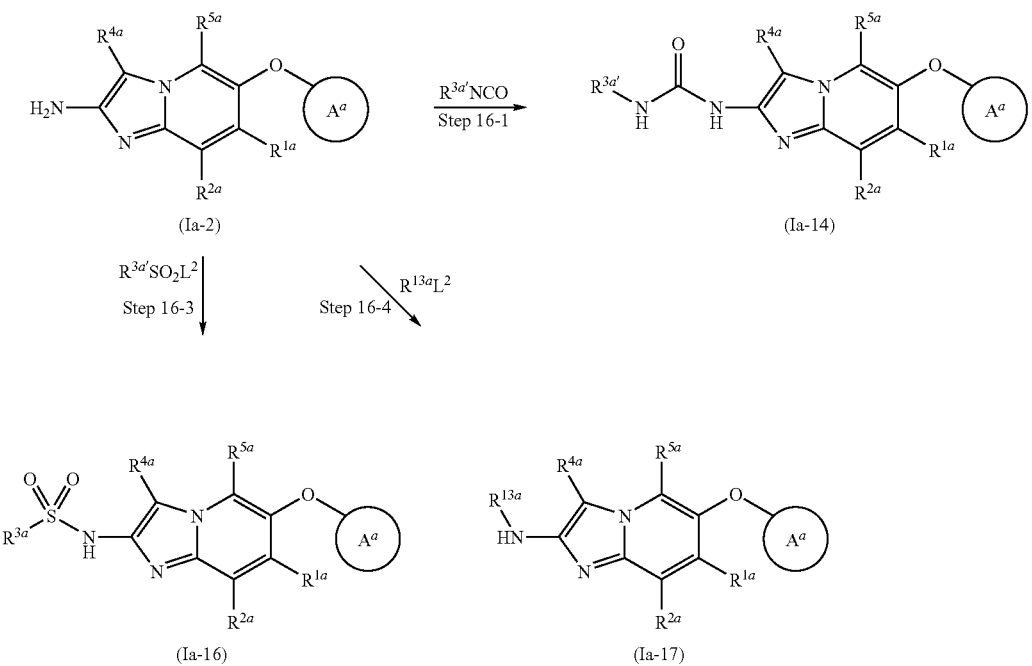

wherein $R^{12a}$ is a $C_{1-6}$ alkyl optionally having 1 to 3 halogen atoms, $R^{13a}$ is a group bonded via a carbon atom, and other symbols are as defined above.

(Step 16-1):

Compound (Ia-14) can be produced by reacting compound (Ia-2) with an isocyanate derivative ($R^{3a'}$NCO). The amount of the isocyanate derivative ($R^{3a'}$NCO) to be used is about 1 to about 20 equivalents, preferably about 1 to about 10 equivalents, relative to compound (Ia-2). The amount of the base to be used is about 0.01 to about 10 equivalents, preferably about 0.01 to about 3 equivalents, relative to compound (Ia-2). This reaction may proceed more smoothly when a base (e.g., triethylamine, N,N-diisopropylethylamine, N-methylmorpholine, 1,8-diazabicyclo[5.4.0]undec-7-ene and the like) is added. As the solvent, those similar to the solvent exemplified in Step 1-1 can be used. The reaction time is generally about 30 min to about 24 hr, preferably about 30 min to about 8 hr. The reaction temperature is generally about −78 to about 200° C., preferably about 0 to about 150° C. The isocyanate derivative ($R^{3a'}$NCO) may be commercially available, or can be produced according to a method known per se.

(Step 16-2):

Compound (Ia-14) can also be produced by reacting compound (Ia-2) with a compound represented by the formula: $R^{12a}$OC(O)$L^2$ to give compound (Ia-15), and then reacting compound (Ia-15) with an amine derivative ($R^{3a'}$NH$_2$). The amount of the compound represented by the formula: $R^{2a}$OC(O)$L^2$ to be used is about 1 to about 5 equivalents, preferably about 1 to about 2 equivalents, relative to compound (Ia-2). The amount of the base to be used is about 0.01 to about 10 equivalents, preferably about 0.01 to about 3 equivalents, relative to compound (Ia-2). This reaction may proceed more smoothly when a base (e.g., triethylamine, N,N-diisopropylethylamine, N-methylmorpholine, 1,8-diazabicyclo[5.4.0]undec-7-ene and the like) is added. As the solvent, those similar to the solvent exemplified in Step 1-1 can be used. The reaction time is generally about 30 min to about 24 hr, preferably about 30 min to about 8 hr. The reaction temperature is generally about −78 to about 200° C., preferably about 0 to about 150° C. The compound represented by the formula: $R^{12a}$OC(O)$L^2$ may be commercially available, or can be produced according to a method known per se. While the obtained compound (Ia-15) can be used for the next reaction in the form of a reaction mixture or a crude product, it can be isolated and purified from the reaction mixture according to a conventional method and then used for the next reaction. The amount of the amine derivative ($R^{3a'}$NH$_2$) to be used is about 1 to about 5 equivalents, preferably about 1 to about 2 equivalents, relative to compound (Ia-2). The amount of the base to be used is about 0.01 to about 10 equivalents, preferably about 0.01 to about 3 equivalents, relative to compound (Ia-2). This reaction may proceed more smoothly when a base (e.g., triethylamine, N,N-diisopropylethylamine, N-methylmorpholine, 1,8-diazabicyclo[5.4.0]undec-7-ene and the like) is added. As the solvent, those similar to the solvent exemplified in Step 1-1 can be used. The reaction time is generally about 30 min to about 24 hr, preferably about 30 min to about 8 hr. The reaction temperature is generally about −78 to about 200° C., preferably about 0 to about 150° C. The amine derivative ($R^{3a'}NH_2$) may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 16-3):

Compound (Ia-16) can be produced by reacting compound (Ia-2) with a reactive derivative ($R^{3a'}SO_2L^2$) of sulfonic acid. The amount of the reactive derivative ($R^{3a'}SO_2L^2$) of sulfonic acid to be used is about 0.1 to about 10 equivalents, preferably about 0.3 to about 3 equivalents, relative to compound (Ia-2). This reaction is generally carried out in the presence of a base, which is not always essential. As the base, those similar to the base exemplified in Step 1-1 can be used. The amount of the base to be used is about 0.01 to about 10 equivalents, preferably about 0.03 to about 5 equivalents, relative to compound (Ia-2). As the solvent, those similar to the solvent exemplified in Step 1-1 can be used. The reaction time is generally about 10 min to about 100 hr, preferably about 30 min to about 24 hr. The reaction temperature is generally about −78 to about 200° C., preferably about 0 to about 150° C. The reactive derivative ($R^{3a'}SO_2L^2$) of sulfonic acid may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

(Step 16-4):

Compound (Ia-17) can be produced by reacting compound (Ia-2) with a compound represented by the formula: $R^{13a}L^2$ in the presence of a base. The amount of the compound represented by the formula: $R^{13a}L^2$ to be used is about 0.1 to about 10 equivalents, preferably about 0.3 to about 3 equivalents, relative to compound (Ia-2). As the base, those similar to the base exemplified in Step 1-1 can be used. The amount of the base to be used is about 0.01 to about 10 equivalents, preferably about 0.03 to about 5 equivalents, relative to compound (Ia-2). As the solvent, those similar to the solvent exemplified in Step 1-1 can be used. The reaction time is generally about 10 min to about 100 hr, preferably about 30 min to about 50 hr. The reaction temperature is generally −78 to 200° C., preferably 0 to 150° C. The compound represented by the formula: $R^{13a}L^2$ may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 17]

Compounds (Ia-18), (Ia-19), (Ia-20), (Ia-21) and (Ia-22) can be produced using compound (Ia-10) produced in Production method 3. Compounds (Ia-18), (Ia-19), (Ia-20), (Ia-21) and (Ia-22) are encompassed in compound (Ia).

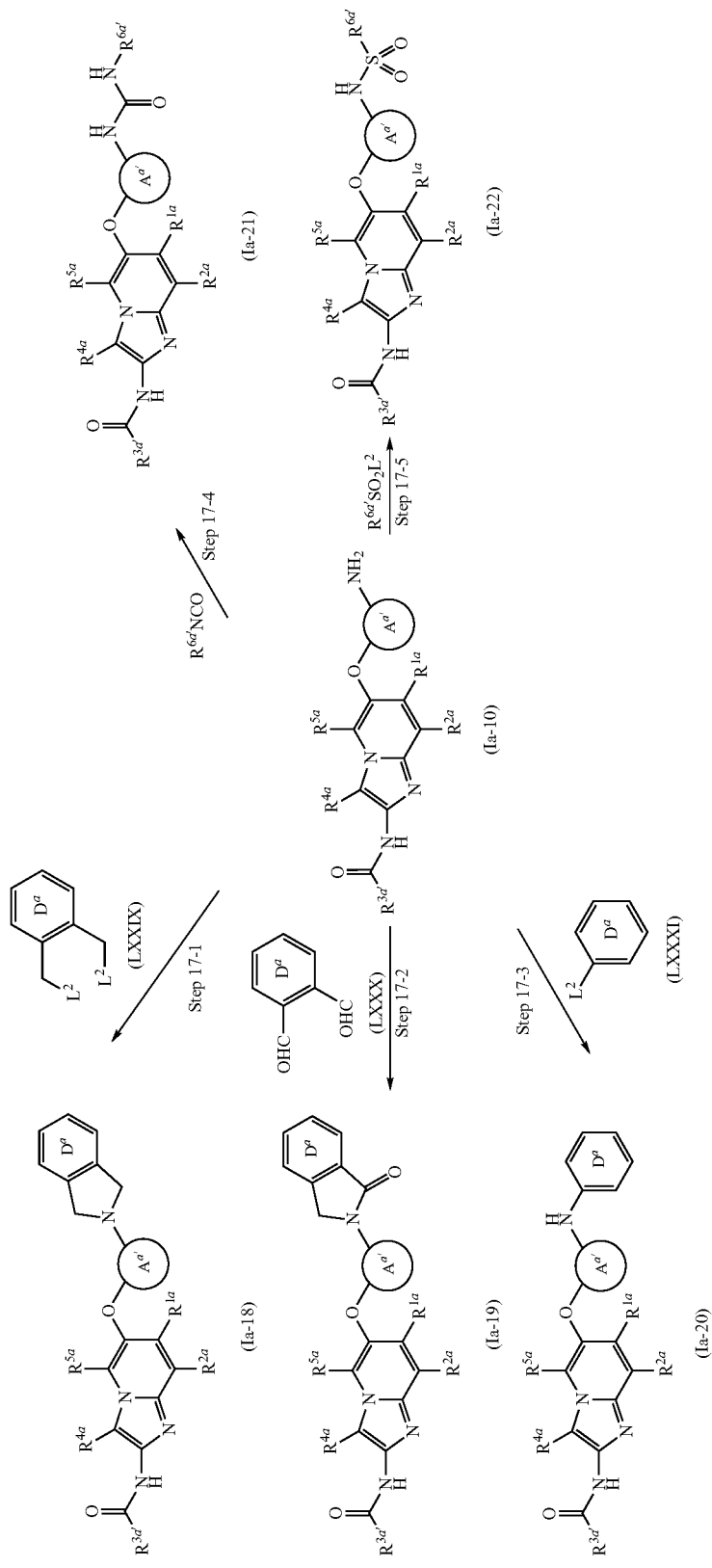

wherein ring $D^a$ is a benzene ring optionally having substituent(s) or a pyridine ring optionally having substituent(s), and other symbols are as defined above.

(Step 17-1):

Compound (Ia-18) can be produced by reacting compound (Ia-10) with compound (LXXIX). The amount of compound (LXXIX) to be used is about 1 to about 20 equivalents, preferably about 1 to about 10 equivalents, relative to compound (Ia-10). The amount of the base to be used is about 0.01 to about 10 equivalents, preferably about 0.01 to about 3 equivalents, relative to compound (Ia-2). This reaction may proceed more smoothly when a base (e.g., triethylamine, N,N-diisopropylethylamine, N-methylmorpholine, 1,8-diazabicyclo[5.4.0]undec-7-ene and the like) is added. As the solvent, those similar to the solvent exemplified in Step 1-1 can be used. The reaction time is generally about 30 min to about 100 hr, preferably about 30 min to about 50 hr. The reaction temperature is generally about −78 to about 200° C., preferably about 0 to about 150° C. Compound (LXXIX) may be commercially available, or can be produced according to a method known per se.

(Step 17-2):

Compound (Ia-19) can be produced by reacting compound (Ia-10) with compound (LXXX). The amount of compound (LXXX) to be used is about 1 to about 20 equivalents, preferably about 1 to about 10 equivalents, relative to compound (Ia-10). Examples of the solvent include acetic acid and the like. The reaction time is generally about 30 min to about 48 hr, preferably about 30 min to about 24 hr. The reaction temperature is generally about −78 to about 200° C., preferably about 0 to about 150° C.

(Step 17-3):

Compound (Ia-20) can be produced by reacting compound (Ia-10) with compound (LXXXI) in the presence of a palladium catalyst and a ligand. The amount of compound (LXXXI) to be used is about 1 to about 20 equivalents, preferably about 1 to about 10 equivalents, relative to compound (Ia-10). The amount of the palladium catalyst (e.g., palladium acetate, tris(dibenzylideneacetone)dipalladium(0)) to be used is about 0.01 to about 5 equivalents, preferably about 0.05 to about 1 equivalent, relative to compound (Ia-10). Examples of the ligand to be used for the reaction include tris(ortho-tolyl)phosphine, BINAP, 1,1-bis(diphenylphosphino)ferrocene, 4,5-bis(diphenylphosphino)-9,9-dimethylxanthene and the like. The amount of the ligand to be used is about 0.01 to about 5 equivalents, preferably about 0.05 to about 1 equivalent, relative to compound (Ia-10). A base may be used in an amount of about 0.1 to about 10 equivalents, preferably about 0.1 to about 5 equivalents, relative to compound (Ia-10). As the base, those similar to the base exemplified in Step 1-1 can be used. As the solvent, those similar to the solvent exemplified in Step 1-1 can be used. The reaction time is generally about 30 min to about 100 hr, preferably about 30 min to about 48 hr. The reaction temperature is generally about −78 to about 200° C., preferably about 0 to about 150° C.

(Step 17-4):

Compound (Ia-21) can be produced by reacting compound (Ia-10) with an isocyanate derivative ($R^{6a'}$NCO). The amount of the isocyanate derivative ($R^{6a'}$NCO) to be used is about 1 to about 20 equivalents, preferably about 1 to about 10 equivalents, relative to compound (Ia-10). In addition, a base may be used. This reaction may proceed more smoothly when a base (e.g., triethylamine, N,N-diisopropylethylamine, N-methylmorpholine, 1,8-diazabicyclo[5.4.0]undec-7-ene and the like) is added. The amount of the base to be used is about 0.01 to about 10 equivalents, preferably about 0.03 to about 5 equivalents, relative to compound (Ia-10). As the solvent, those similar to the solvent exemplified in Step 1-1 can be used. The reaction time is generally about 30 min to about 100 hr, preferably about 30 min to about 50 hr. The reaction temperature is generally about −78 to about 200° C., preferably about 0 to about 150° C. The isocyanate derivative ($R^{6a'}$NCO) may be commercially available, or can be produced according to a method known per se.

(Step 17-5):

Compound (Ia-22) can be produced by reacting compound (Ia-10) with a reactive derivative ($R^{6a'}SO_2L^2$) of sulfonic acid. The amount of the reactive derivative ($R^{6a'}SO_2L^2$) of sulfonic acid to be used is about 0.1 to about 10 equivalents, preferably about 0.3 to about 3 equivalents, relative to compound (Ia-10). This reaction is generally carried out in the presence of a base, which is not always essential. As the base, those similar to the base exemplified in Step 1-1 can be used. The amount of the base to be used is about 0.01 to about 10 equivalents, preferably about 0.03 to about 5 equivalents, relative to compound (Ia-10). As the solvent, those similar to the solvent exemplified in Step 1-1 can be used. The reaction time is generally about 10 min to about 100 hr, preferably about 30 min to about 24 hr. The reaction temperature is generally about −78 to about 200° C., preferably about 0 to about 150° C. The reactive derivative ($R^{6a'}SO_2L^2$) of sulfonic acid may be commercially available, or can be produced according to a method known per se, for example, the methods described in "Advanced Organic Chemistry, 4th Ed." (Jerry March), "Comprehensive Organic Transformations, 2nd Ed." (Richard C. Larock) and the like, or a method analogous thereto.

[Production Method 18]

Compound (Ia-23) can be produced using compound (Ia-6) produced in Production method 2. Compound (Ia-23) is encompassed in compound (Ia).

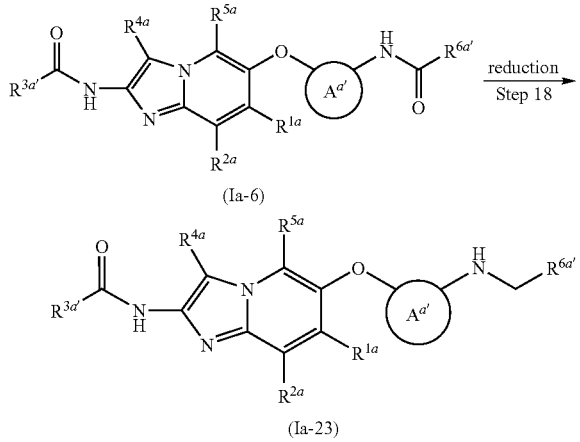

(Step 18):

Compound (Ia-23) can be produced by subjecting compound (Ia-6) to borane reduction. The amount of the borane solution (e.g., borane/tetrahydrofuran solution, borane-dimethylsulfide/tetrahydrofuran solution and the like) to be used is about 0.01 to about 100 equivalents, preferably about 0.1 to about 50 equivalents, relative to compound (Ia-6). As the solvent, those similar to the solvent exemplified in Step 1-1 can be used. The reaction time is generally about 10 min to about 100 hr, preferably about 30 min to about 50 hr. The reaction temperature is generally about −78 to about 200° C., preferably about 0 to about 150° C.

In the above-mentioned each reaction, when the starting material compound has amino, carboxyl or hydroxyl as a substituent, such group may be protected by a protecting group generally used in peptide chemistry and the like. In this case, the object compound can be obtained by removing, as necessary, the protecting group after the reaction. The protecting group can be introduced or removed according to a method known per se, for example, the method described in Wiley-Interscience, 1999, "Protective Groups in Organic Synthesis, 3rd Ed." (edited by Theodora W. Greene, Peter G. M. Wuts) and the like.

When desired further, Compound (I) can also be produced by performing known hydrolysis, deprotection, acylation reaction, alkylation reaction, oxidation reaction, cyclization reaction, carbon chain extension reaction or substituent exchange reaction alone or in a combination of two or more kinds thereof.

Compound (I) can be isolated and purified by a means known per se, such as phase transfer, concentration, solvent extraction, fractionation, liquid conversion, crystallization, recrystallization, chromatography and the like. When compound (I) is obtained as a free compound, it can be converted to a desired salt by a method known per se or a method analogous thereto. Conversely, when the compound is obtained as a salt, it can be converted to a free form or other desired salt by a method known per se or a method analogous thereto.

Compound (I) may be used as a prodrug. A prodrug of compound (I) means a compound converted to compound (I) by a reaction due to an enzyme, a gastric acid, etc. under the physiological condition in the living body, that is, a compound converted to compound (I) by oxidation, reduction, hydrolysis, etc. due to an enzyme, a compound converted to compound (I) by hydrolysis etc. due to gastric acid, and the like.

A prodrug of compound (I) may be a compound obtained by subjecting an amino in compound (I) to an acylation, alkylation or phosphorylation (e.g., a compound obtained by subjecting an amino in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in compound (I) to acylation, alkylation, phosphorylation or boration (e.g., a compound obtained by subjecting hydroxy in compound (I) to acetylation, palmitoylation, propanoylation, pivaloylation, succinylation, fumarylation, alanylation or dimethylaminomethylcarbonylation); a compound obtained by subjecting carboxy in compound (I) to esterification or amidation (e.g., a compound obtained by subjecting carboxy in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from compound (I) by a method known per se.

A prodrug of compound (I) may also be a compound converted into compound (I) under physiological conditions, such as those described in IYAKUHIN no KAIHATSU (Development of Pharmaceuticals), Vol. 7, Design of Molecules, p. 163-198, Published by HIROKAWA SHOTEN (1990).

When compound (I) has an isomer such as optical isomer, stereoisomer, positional isomer, rotational isomer and the like, any isomer and a mixture thereof are encompassed in compound (I). For example, when compound (I) has an optical isomer, an optical isomer separated from a racemate is also encompassed in compound (I). Such isomers can be obtained as independent products by a synthesis means or a separation means (concentration, solvent extraction, column chromatography, recrystallization and the like) known per se.

The compound (I) may be a crystal, and both a single crystal and crystal mixtures are encompassed in compound (I). Crystals can be produced by crystallization according to crystallization methods known per se.

The compound (I) may be a solvate (e.g., hydrate etc.) or a non-solvate, both of which are encompassed in compound (I).

A compound labeled with an isotope (e.g., $^3$H, $^{14}$C, $^{35}$S, $^{125}$I etc.) is also encompassed in compound (I).

Compound (I) of the present invention, a salt thereof and a prodrug thereof (hereinafter sometimes to be abbreviated as the compound of the present invention) have, for example, phosphorylation-inhibitory activity against a kinase having such phosphorylating action. As used herein, kinase encompasses not only a substance having a phosphorylating action by itself as a whole, but also a substance a part of which has a phosphorylating action. The phosphorylating action possessed by kinases encompasses both a phosphorylating action on its own and that on other substances.

Examples of kinase include vascular endothelial growth factor receptor (VEGFR), platelet-derived growth factor receptor (PDGFR), Raf and the like. Examples of vascular endothelial growth factor receptor (VEGFR) include vascular endothelial growth factor receptor 1 (VEGFR1, Flt-1), vascular endothelial growth factor receptor 2 (VEGFR2, KDR, Flk-1), vascular endothelial growth factor receptor 3 (VEGFR3, Flt-4) and the like. Of these, vascular endothelial growth factor receptor 2 (VEGFR2) is preferable. Examples of platelet-derived growth factor receptor (PDGFR) include platelet-derived growth factor receptor α (PDGFRα), platelet-derived growth factor receptor β (PDGFRβ) and the like. Examples of Raf include A-Raf, B-Raf, C-Raf and the like. Particularly, as kinase, vascular endothelial growth factor receptor 2 (VEGFR2), platelet-derived growth factor receptor (PDGFR) and Raf are preferable.

Besides these, as kinase, tyrosine Kinase with Ig and EGF homology domains 2 (TIE2), fibroblast growth factor receptor 1 (FGFR1), fibroblast growth factor receptor 2 (FGFR2), fibroblast growth factor receptor 3 (FGFR3), fibroblast growth factor receptor 4 (FGFR4), stem cell factor receptor (c-Kit), Aurora A, Aurora B, CDK, MEK1, MEK2, Akt, ERK, MAPK, Src, MET, epidermal growth factor receptor (EGFR), human epidermal growth factor receptor 2 (HER2), human epidermal growth factor receptor 4 (HER4), Abl, Fgr, Fms and the like can also be used.

For example, the vascular endothelial growth factor receptor 2 inhibitory activity of the compound of the present invention can be determined according to Test Example 1, the vascular endothelial cell growth inhibitory activity can be determined according to Test Example 2, the antitumor activity can be determined according to Test Example 3, the platelet-derived growth factor receptor α (PDGFRα) kinase inhibitory activity can be determined according to Test Example 4, the platelet-derived growth factor receptor β (PDGFRβ) kinase inhibitory activity can be determined according to Test Example 5, the B-Raf (V600E) kinase inhibitory activity can be determined according to Test Example 6, the colon cancer cell HT-29 intracellular MEK phosphorylation inhibitory action in vitro can be determined according to Test Example 7, and the colon cancer cell HT-29 growth suppressive action in vitro can be determined according to Test Example 8.

The compound of the present invention particularly shows potent inhibitory activity for vascular endothelial growth factor receptor (VEGFR), and specifically high selectivity for vascular endothelial growth factor receptor 2 (VEGFR2, KDR, Flk-1) and potent kinase inhibitory activity for VEGFR1 and PDGFR. Furthermore, the compound of the present invention particularly shows potent inhibitory activity for Raf, particularly B-Raf. In addition, since the compound of the present invention is also superior in the efficacy, pharmacokinetics (absorption, distribution, metabolism, excretion etc.), solubility (water-solubility etc.), interaction with other pharmaceutical products, safety (acute toxicity, chronic toxicity, genetic toxicity, reproductive toxicity, cardiotoxicity, carcinogenicity etc.) and stability (chemical stability, stability to enzyme etc.), it is useful as a pharmaceutical agent.

Accordingly, the compound of the present invention is useful as a kinase inhibitor, preferably a vascular endothelial growth factor receptor (VEGFR) inhibitor, a platelet-derived growth factor receptor (PDGFR) inhibitor, more preferably a vascular endothelial growth factor receptor 2 (VEGFR2, KDR, Flk-1) inhibitor for a mammal (e.g., mouse, rat, hamster, rabbit, cat, dog, bovine, sheep, monkey, human etc.). In addition, the compound of the present invention is useful as an angiogenesis inhibitor or a vascular endothelial cell growth inhibitor. Furthermore, the compound of the present invention is also useful as Raf inhibitor. The compound of the present invention is used as a pharmaceutical agent such as an agent for the prophylaxis or treatment of diseases possibly affected by a vascular endothelial growth factor or Raf-related diseases, for example, cancer [e.g., colorectal cancer (e.g., familial colorectal cancer, hereditary nonpolyposis colorectal cancer, gastrointestinal stromal tumor, etc.), lung cancer (e.g., non-small cell lung cancer, small cell lung cancer, malignant mesothelioma, etc.), mesothelioma, pancreatic cancer (e.g., pancreatic duct cancer, etc.), gastric cancer (e.g., papillary adenocarcinoma, mucinous adenocarcinoma, adenosquamous cancer, etc.), breast cancer (e.g., invasive ductal carcinoma, ductal cancer in situ, inflammatory breast cancer, etc.), ovarian cancer (e.g., ovarian epithelial cancer, extragonadal germ cell tumor, ovarian germ cell tumor, ovarian low malignant potential tumor, etc.), prostate cancer (e.g., hormone-dependent prostate cancer, non-hormone dependent prostate cancer, etc.), liver cancer (e.g., primary liver cancer, extrahepatic bile duct cancer, etc.), thyroid cancer (e.g., medullary thyroid cancer, etc.), kidney cancer (e.g., renal cell carcinoma, renal pelvis and ureter transitional cell cancer, etc.), uterine cancer, brain tumor (e.g., pineal astrocytoma, pilocytic astrocytoma, diffuse astrocytoma, anaplastic astrocytoma, etc.), melanoma, sarcoma, bladder cancer, blood cancer including multiple myeloma etc.], diabetic retinopathy, rheumatoid arthritis, psoriasis, atherosclerosis, Kaposi's sarcoma, COPD, pain, asthma, endometriosis, nephritis, inflammation such as osteoarthritis and the like and hypertension, a cancer growth inhibitor, a cancer metastasis suppressor, an apoptosis promoter and the like. Of these, it is effective, for example, for colorectal cancer, lung cancer, pancreatic cancer, gastric cancer, breast cancer, ovary cancer, prostate cancer, liver cancer, thyroid cancer, kidney cancer, cerebral tumor, melanoma, bladder cancer and blood cancer. Particularly, the compound of the present invention is effective for patients with lung cancer, colorectal cancer, ovary cancer, prostate cancer or kidney cancer.

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet), pill, granule, powder, capsule (including soft capsule, microcapsule), syrup, emulsion, suspension and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the compound of the present invention in the above-mentioned dosage form, a known production method generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pertinent field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogencarbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a coloring agent, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable dissolution aids, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with dissolution aids such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be mentioned. A prepared injection is generally filled in an ampoule.

While the content of the compound of the present invention in the pharmaceutical agent of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the pharmaceutical agent of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, pharmaceutical agents inhibiting the action of cell growth factors or cell growth factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, episteride, and the like), aderenal cortex hormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine, and the like), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell growth factors" in the "pharmaceutical agents inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα, and the like], (2) insulin or substances possessing substantially the same activity as insulin [e.g., insulin, IGF (insulin-like growth factor)-1, IGF-2, and the like], (3) FGF (fibroblast growth factor) or substances possessing substantially the same activity as FGF [e.g., acidic FGF, basic FGF, KGF (keratinocyte growth factor), FGF-10, and the like], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin, and the like].

Examples of the "cell growth factor receptors" include any receptors capable of binding to the aforementioned growth factors, including EGF receptor, heregulin receptor (HER3, etc.), insulin receptor, IGF receptor-1, IGF receptor-2, FGF receptor-1 or FGF receptor-2, VEGF receptor, angiopoietin receptor (Tie2 etc.), PDGF receptor, and the like.

As the "pharmaceutical agents inhibiting the action of cell growth factors or cell growth factor receptors", EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor and the like are used. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, Imatinib, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R),3-dihydroxypropoxy]-3,4-difluoro-2-(2-fluoro-4-iodophenylamino)benzamide (PD-0325901) and the like are used.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), other angiogenesis inhibitors (e.g., humagillin, shark extract, COX-2 inhibitor, and the like), α-blockers (e.g., tamsulosin hydrochloride, and the like), bisphosphonic acids (pamidronate, zoledronate, and the like), thalidomide, 5 azacytidine, decitabine, bortezomib, antitumor antibody such as anti-CD20 antibody and the like, toxin labeled antibody and the like can also be used.

By combining the compound of the present invention and a concomitant drug, a superior effect such as (1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer,
(4) a sustained treatment effect can be designed,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the administration amount clinically set, and can be appropriately selected depending on the administration subject, administration route, disease, combination and the like.

Examples of the administration mode of the combined use of the compound of the present invention and the concomitant drug include the following methods: (1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (for example, the compound of the present invention and the concomitant drug are administered in this order, or in the reverse order). The dose of the concomitant drug is determined in accordance with its clinical dose. And the ratio of the compound of the present invention and the concomitant drug is determined depending on the subject, administration route, disease, symptom, combination, and the like. For example, when the subject is human, the concomitant drug is used in 0.01 to 100 (w/w), relative to the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous, and the like). An injection can be administered directly to the lesion by intravenous, intramuscular, subcutaneous or intra-tissue administration.

As a pharmacologically acceptable carrier which may be used for preparing a preparation of the combination agent of the present invention, those similar to the aforementioned pharmacologically acceptable carriers, that can be used for the production of the pharmaceutical agent of the present invention, can be mentioned. Where necessary, the aforementioned additives that can be used for the production of the pharmaceutical agent of the present invention, such as preservatives, antioxidants, coloring agents, sweetening agents, adsorbents, wetting agents and the like can also be used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the preparation.

The content of additives in the combination agent of the present invention varies depending on the dosage form, and is usually from about 1 to 99.99% by weight, preferably from about 10 to 90% by weight, based on the preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH adjusting agent (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and the like and prepared into an oily injection, whereby an injection is afforded.

In addition, an excipient (e.g., lactose, sucrose, starch and the like), a disintegrating agent (e.g., starch, calcium carbonate and the like), a binder (e.g., starch, gum arabic, carboxymethylcellulose, polyvinylpyrrolidone, hydroxypropylcellulose and the like), a lubricant (e.g., talc, magnesium stearate, polyethylene glycol 6000 and the like) and the like may be added to the compound of the present invention or the concomitant drug according to a method known per se, and the mixture can be compression-molded, then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid-acrylic acid copolymer, manufactured by Rohm, DE), pigment (e.g., iron oxide red, titanium dioxide, etc.) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acid [e.g., cacao butter, Witepsols (manufactured by Dynamit Nobel, Germany), etc.], glycerides of medium chain fatty acid [e.g., Miglyols (manufactured by Dynamit Nobel, Germany), etc.], or vegetable oils (e.g., sesame oil, soybean oil, cotton seed oil and the like), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se.

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal, which is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., β-lactam type such as pansporin and the like, macrolide type such as clarithromycin and the like etc.) for the complication with various infectious diseases, (ii) administration of total parenteral nutrition, amino acid preparation or general vitamin preparation for the improvement of malnutrition, (iii) administration of morphine for pain mitigation, (iv) administration of a pharmaceutical agent for improving side effects such as nausea, vomiting, anorexia, diarrhea, leucopenia, thrombocytopenia, decreased hemoglobin concentration, hair loss, hepatopathy, renopathy, DIC, fever and the like and (v) administration of a pharmaceutical agent for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

EXAMPLES

The present invention is more specifically explained in the following by way of Reference Examples, Examples, Formulation Examples, Experimental Examples and Test Examples, which are not to be construed as limitative.

The LC/MS analysis in the Examples was performed under the following conditions.
measurement tool: Waters Corporation ZQ
column: manufactured by Shiseido Co., Ltd. CAPCELL PAK C18 UG120 S-3 3 μm, 35×1.5 mm
solvent: SOLUTION A; 5 mM aqueous ammonium acetate/acetonitrile=98/2
SOLUTION B; 100 mM aqueous ammonium acetate/acetonitrile=5/95
gradient cycle: 0.00 min (SOLUTION A/SOLUTION B=100/0), 2.00 min (SOLUTION A/SOLUTION B=0/100), 3.00 min (SOLUTION A/SOLUTION B=0/100), 3.01 min (SOLUTION A/SOLUTION B=100/0), 3.80 min (SOLUTION A/SOLUTION B=100/0)
flow rate: 0.5 mL/min, Column temperature was room temperature with no temperature control.
ionization method: Electron Spray Ionization, ESI positive and negative ion peaks were detected.

The percentage of the peak area detected at UV: 220 nm of the resultant product peak was taken as the purity of the compound.

In the Examples, preparative HPLC was performed as in the following.

Preparative HPLC tools: Gilson, Inc. High-Throughput purification system column: YMC Combiprep Hydrosphere C18 S-5 5 μm, 12 nM, 50×20 mm solvent: SOLUTION A; water SOLUTION B; acetonitrile gradient cycle: 0.00 min (SOLUTION A/SOLUTION B=98/2), 1.10 min (SOLUTION A/SOLUTION B=98/2), 5.00 min (SOLUTION A/SOLUTION B=0/100), 6.40 min (SOLUTION A/SOLUTION B=0/100), 6.50 min (SOLUTION A/SOLUTION B=2/98), 6.52 min (SOLUTION A/SOLUTION B=2/98)

flow rate: 25 mL/min, detection method: UV 220 nm

Unless otherwise specified, the elution by column chromatography was performed under observation by TLC (thin layer chromatography) in Reference Examples and Examples. For TLC observation, 60F254 manufactured by Merck, or NH TLC plate manufactured by Fuji Silysia Chemical Ltd. was used as a TLC plate, and the solvent used as an eluent in column chromatography was used as a developing solvent. For detection, moreover, a UV detector was employed. As the silica gel for column chromatography, silica gel 60 (70-230 mesh) manufactured by Merck, silica gel (spherical silica gel 60 μM) manufactured by Fuji Silysia Chemical Ltd., NH silica gel (spherical silica gel 60 μM) manufactured by Fuji Silysia Chemical Ltd., NH silica gel (100-200 mesh) manufactured by Fuji Silysia Chemical Ltd. and the like were used. The room temperature generally means from about 10° C. to 35° C. For drying the extract, anhydrous sodium sulfate or anhydrous magnesium sulfate was used.

In Formulation Examples, the Japanese Pharmacopoeia 14th Edition or Japanese Pharmaceutical Excipients 2003 compatible products are used as the preparation additives (e.g., lactose, cornstarch, magnesium stearate, microcrystalline cellulose).

Abbreviations in the Examples and Reference Examples mean the following.

DMSO: dimethyl sulfoxide

HATU: O-(7-azabenzotriazol-1-yl)-N,N,N',N'-tetramethyluronium hexafluorophosphate Reference Example 1

2-nitro-5-(3-nitrophenoxy)pyridine

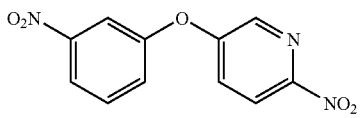

A mixture of 3-nitrophenol (7.76 g, 55.8 mmol), 5-bromo-2-nitropyridine (10.3 g, 50.7 mmol), cesium carbonate (24.8 g, 76.1 mmol) and N,N-dimethylformamide (150 mL) was stirred at 50° C. for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, hexane/ethyl acetate=100/0→0/100) to give the title compound (4.37 g, 33%) as a yellow solid.

$^1$H-NMR (DMSO-$d_6$, 300 MHz) δ 7.73-7.85 (3H, m), 8.10 (1H, t, J=2.1 Hz), 8.15-8.19 (1H, m), 8.38 (1H, dd, J=9.0, 0.6 Hz), 8.52-8.54 (1H, m).

Reference Example 2

5-(3-aminophenoxy)pyridin-2-amine

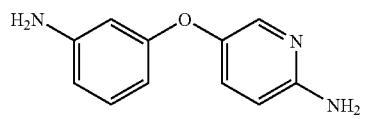

To a solution of 2-nitro-5-(3-nitrophenoxy)pyridine (1.33 g, 5.07 mmol) in methanol (10 mL) was added palladium carbon (50% water-containing product, 100 mg), and the mixture was stirred under a hydrogen atmosphere at room temperature for 12 hr. The reaction mixture was filtered through celite, and the filtrate was concentrated under reduced pressure and dried to give the title compound (980 mg, 96%) as a yellow oil.

$^1$H-NMR (DMSO-$d_6$, 300 MHz) δ 5.15 (2H, br s), 5.82 (2H, br s), 6.00-6.04 (2H, m), 6.18-6.22 (1H, m), 6.47 (1H, d, J=8.9 Hz), 6.90 (1H, t, J=7.7 Hz), 7.14 (1H, dd, J=8.9, 3.0 Hz), 7.69 (1H, d, J=3.0 Hz).

Reference Example 3

N-{3-[(6-aminopyridin-3-yl)oxy]phenyl}-1,3-dimethyl-1H-pyrazole-5-carboxamide

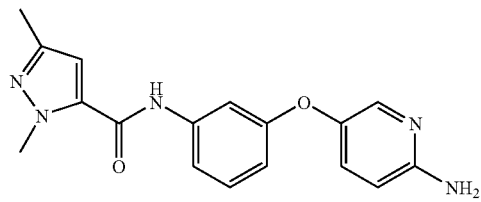

To a solution of 5-(3-aminophenoxy)pyridin-2-amine (975 mg, 4.85 mmol) and pyridine (410 μL, 5.09 mmol) in tetrahydrofuran (10 mL) was added dropwise with stirring under ice-cooling a solution of 1,3-dimethyl-1H-pyrazole-5-carbonyl chloride (807 mg, 5.09 mmol) in tetrahydrofuran (10 mL), and the mixture was stirred at room temperature for 2 hr. The reaction mixture was diluted with water, extracted with ethyl acetate (×3), and the organic layer was washed with saturated brine, dried over anhydrous magnesium sulfate and filtrated. The filtrate was concentrated under reduced pressure, and the residue was purified by column chromatography (silica gel, hexane/ethyl acetate=80/20→40/100) and recrystallized from ethyl acetate-hexane to give the title compound (964 mg, 61%) as a white solid.

1H-NMR (DMSO-$d_6$, 300 MHz) δ 2.18 (3H, s), 3.96 (3H, s), 5.91 (2H, br s), 6.50 (1H, d, J=8.9 Hz), 6.65-6.68 (1H, m), 6.78 (1H, s), 7.11 (1H, dd, J=8.9, 3.0 Hz), 7.24-7.30 (2H, m), 7.43-7.47 (1H, m), 7.75 (1H, d, J=3.0 Hz), 10.10 (1H, br s).

Reference Example 4

1,3-dimethyl-N-{3-[(6-{[(4-methylphenyl)sulfonyl] amino}pyridin-3-yl)oxy]phenyl}-1H-pyrazole-5-carboxamide

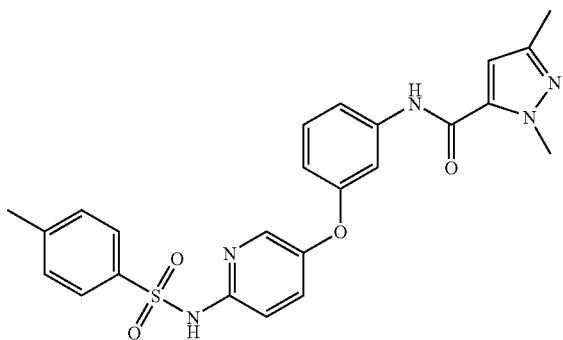

A mixture of N-{3-[(6-aminopyridin-3-yl)oxy]phenyl}-1, 3-dimethyl-1H-pyrazole-5-carboxamide (750 mg, 2.32 mmol), p-toluenesulfonyl chloride (486 mg, 2.55 mmol) and pyridine (6 mL) was stirred at 80° C. for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure and dried to give the title compound (1.13 g, 99%) as a colorless oil.

$^1$H-NMR (DMSO-d$_6$, 300 MHz) δ 2.18 (3H, s), 2.35 (3H, s), 3.33 (3H, s), 6.71-6.77 (2H, s), 7.13 (1H, d, J=8.7 Hz), 7.29-7.53 (6H, m), 7.78 (2H, d, J=8.4 Hz), 8.01 (1H, d, J=3.0 Hz), 10.14 (1H, s), 11.06 (1H, br s).

Reference Example 5

N-{3-[(1-(2-amino-2-oxoethyl)-6-{[(4-methylphenyl)sulfonyl]imino}-1,6-dihydropyridin-3-yl)oxy] phenyl}-1,3-dimethyl-1H-pyrazole-5-carboxamide

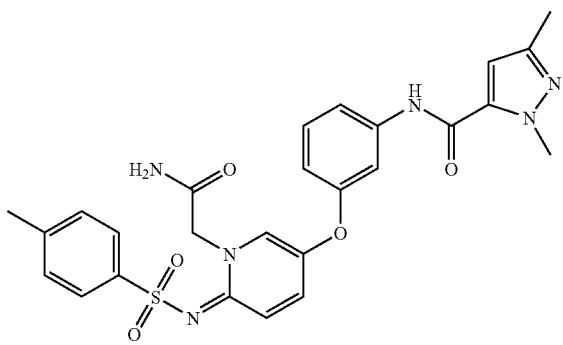

A mixture of 1,3-dimethyl-N-{3-[(6-{[(4-methylphenyl) sulfonyl]amino}pyridin-3-yl)oxy]phenyl}-1H-pyrazole-5-carboxamide (1.11 g, 2.32 mmol), N,N-diisopropylethylamine (424 μL, 2.44 mmol) and N,N-dimethylformamide (7 mL) was stirred at room temperature for 2 hr, iodoacetamide (451 mg, 2.44 mmol) was added and the mixture was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give the title compound (883 mg, 71%) as a white solid.

$^1$H-NMR (DMSO-d$_6$, 300 MHz) δ 2.19 (3H, s), 2.34 (3H, s), 3.97 (3H, s), 4.83 (2H, s), 6.72-6.79 (2H, m), 7.26-7.43 (6H, m), 7.52-7.56 (1H, m), 7.66-7.77 (4H, m), 8.12 (1H, d, J=2.7 Hz), 10.18 (1H, s).

Reference Example 6

5-(4-chloro-3-nitrophenoxy)-2-nitropyridine

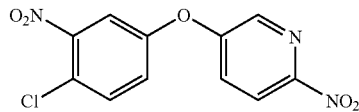

In the same manner as in Reference Example 1 and using 4-chloro-3-nitrophenol (4.70 g, 27.1 mmol), 5-bromo-2-nitropyridine (5.00 g, 24.6 mmol), cesium carbonate (12.0 g, 36.9 mmol) and N,N-dimethylformamide (50 mL) as starting materials, the title compound (3.81 g, 52%) was obtained as a yellow solid.

$^1$H-NMR (DMSO-d$_6$, 300 MHz) δ 7.62-7.66 (1H, m), 7.88-7.92 (2H, m), 8.08 (1H, d, J=3.0 Hz), 8.39 (1H, d, J=9.0 Hz), 8.56 (1H, d, J=2.7 Hz).

Reference Example 7

5-(3-amino-4-chlorophenoxy)pyridin-2-amine

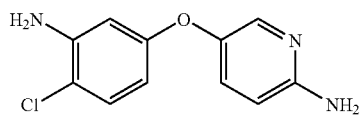

A mixture of 5-(4-chloro-3-nitrophenoxy)-2-nitropyridine (3.80 g, 12.9 mmol), reduced iron (4.84 g, 86.7 mmol), 6N hydrochloric acid (2 mL), ethanol (20 mL) and water (4 mL) was stirred at 85° C. for 2 hr. The reaction mixture was filtered through celite, and the filtrate was concentrated under reduced pressure. The residue was collected by filtration and washed with ethyl acetate-hexane to give the title compound (2.02 g, 66%) as a gray solid.

$^1$H-NMR (DMSO-d$_6$, 300 MHz) δ 5.40 (2H, s), 5.87 (2H, s), 6.10 (1H, dd, J=8.8, 2.8 Hz), 6.27 (1H, d, J=2.8 Hz), 6.48 (1H, d, J=8.7 Hz), 7.08 (1H, d, J=8.8 Hz), 7.17 (1H, dd, J=8.7, 3.0 Hz), 7.71 (1H, d, J=3.0 Hz).

Reference Example 8

N-{5-[(6-aminopyridin-3-yl)oxy]-2-chlorophenyl}-1,3-dimethyl-1H-pyrazole-5-carboxamide

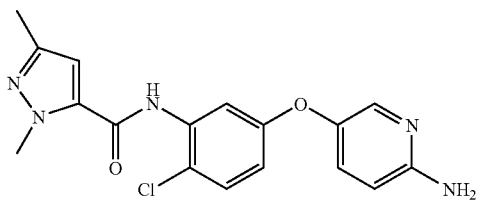

In the same manner as in Reference Example 3 and using 5-(3-amino-4-chlorophenoxy)pyridin-2-amine (2.01 g, 8.55 mmol), pyridine (725 μL, 8.98 mmol), 1,3-dimethyl-1H-pyrazole-5-carbonyl chloride (1.42 g, 8.98 mmol) and tetrahydrofuran (50 mL) as starting materials, the title compound (306 mg, 10%) was obtained as a white solid.

$^1$H-NMR (DMSO-$d_6$, 300 MHz) δ 2.18 (3H, s), 3.96 (3H, s), 5.95 (2H, br s), 6.50 (1H, d, J=8.8 Hz), 6.80 (1H, s), 6.84 (1H, dd, J=8.7, 3.0 Hz), 7.10 (1H, d, J=3.0 Hz), 7.23 (1H, dd, J=8.8, 2.9 Hz), 7.47 (1H, d, J=8.7 Hz), 7.77 (1H, d, J=2.9 Hz), 9.85 (1H, s).

Reference Example 9

N-{2-chloro-5-[(6-{[(4-methylphenyl)sulfonyl]amino}pyridin-3-yl)oxy]phenyl}-1,3-dimethyl-1H-pyrazole-5-carboxamide

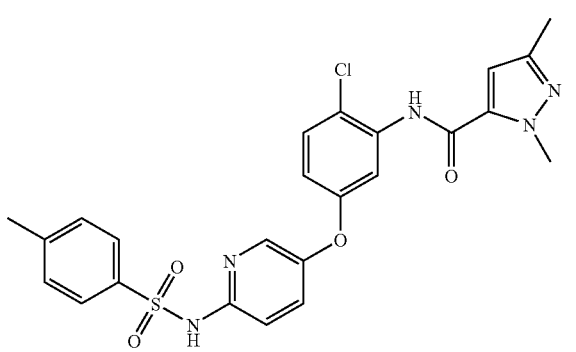

In the same manner as in Reference Example 4 and using N-{5-[(6-aminopyridin-3-yl)oxy]-2-chlorophenyl}-1,3-dimethyl-1H-pyrazole-5-carboxamide (300 mg, 0.838 mmol), p-toluenesulfonyl chloride (176 mg, 0.922 mmol) and pyridine (4 mL) as starting materials, the title compound (368 mg, 86%) was obtained as a white solid.

$^1$H-NMR (DMSO-$d_6$, 300 MHz) δ 2.19 (3H, s), 2.34 (3H, s), 3.96 (3H, s), 6.81 (1H, s), 6.91 (1H, dd, J=8.7, 3.0 Hz), 7.14 (1H, d, J=9.0 Hz), 7.19 (1H, d, J=3.0 Hz), 7.35 (2H, d, J=8.4 Hz), 7.48-7.53 (2H, m), 7.77 (2H, d, J=8.4 Hz), 8.03 (1H, d, J=3.0 Hz), 9.89 (1H, s), 11.05 (1H, br s).

Reference Example 10

N-{5-[(1-(2-amino-2-oxoethyl)-6-{[(4-methylphenyl)sulfonyl]imino}-1,6-dihydropyridin-3-yl)oxy]-2-chlorophenyl}-1,3-dimethyl-1H-pyrazole-5-carboxamide

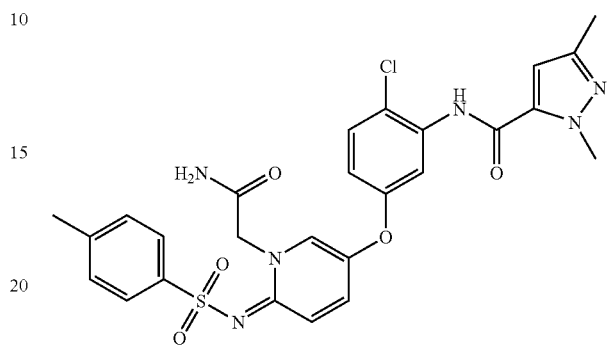

In the same manner as in Reference Example 5 and using N-{2-chloro-5-[(6-{[(4-methylphenyl)sulfonyl]amino}pyridin-3-yl)oxy]phenyl}-1,3-dimethyl-1H-pyrazole-5-carboxamide (364 mg, 0.711 mmol), N,N-diisopropylethylamine (161 μl, 0.924 mmol), iodoacetamide (171 mg, 0.924 mmol) and N,N-dimethylformamide (5 mL) as starting materials, the title compound (305 mg, 75%) was obtained as a white solid.

$^1$H-NMR (DMSO-$d_6$, 300 MHz) δ 2.19 (3H, s), 2.34 (3H, s), 3.97 (3H, s), 4.81 (2H, s), 6.82 (1H, s), 6.95 (1H, dd, J=8.8, 3.0 Hz), 7.25-7.28 (3H, m), 7.36-7.42 (2H, m), 7.53 (1H, d, J=8.8 Hz), 7.65-7.78 (4H, m), 8.16 (1H, d, J=3.0 Hz), 9.94 (1H, s).

Reference Example 11

N-(5-hydroxy-2-methylphenyl)-1,3-dimethyl-1H-pyrazole-5-carboxamide

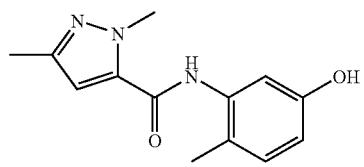

To a solution of 3-amino-4-methylphenol (3.71 g, 30.1 mmol) and triethylamine (4.38 mL, 31.6 mmol) in tetrahydrofuran (30 mL) was added dropwise with stirring under ice-cooling a solution of 1,3-dimethyl-1H-pyrazole-5-carbonyl chloride (5.02 g, 31.6 mmol) in tetrahydrofuran (10 mL), and the mixture was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give the title compound (4.67 g, 63%) as a white solid.

$^1$H-NMR (DMSO-$d_6$, 300 MHz) δ 2.09 (3H, s), 2.19 (3H, s), 3.98 (3H, s), 6.57 (1H, dd, J=8.5, 2.4 Hz), 6.76-6.79 (2H, m), 7.02 (1H, d, J=8.5 Hz), 9.26 (1H, br s), 9.59 (1H, s).

Reference Example 12

1,3-dimethyl-N-{2-methyl-5-[(6-nitropyridin-3-yl)oxy]phenyl}-1H-pyrazole-5-carboxamide

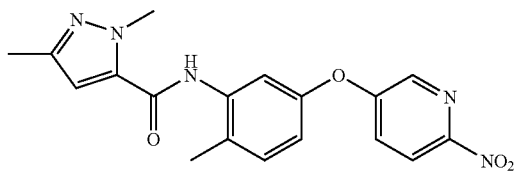

A mixture of N-(5-hydroxy-2-methylphenyl)-1,3-dimethyl-1H-pyrazole-5-carboxamide (4.67 g, 19.0 mmol), 5-bromo-2-nitropyridine (3.68 g, 18.1 mmol), cesium carbonate (9.29 g, 28.5 mmol) and N,N-dimethylformamide (20 mL) was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=80/20→0/100) and then column chromatography (NH silica gel, hexane/ethyl acetate=80/20→0/100) to give the title compound (3.38 g, 44%) as a white solid.

$^1$H-NMR (DMSO-d$_6$, 300 MHz) δ 2.20 (3H, s), 2.27 (3H, s), 3.98 (3H, s), 6.82 (1H, s), 7.09 (1H, dd, J=8.3, 2.5 Hz), 7.31 (1H, d, J=2.5 Hz), 7.41 (1H, d, J=8.3 Hz), 7.62 (1H, dd, J=8.8, 2.8 Hz), 8.36 (1H, d, J=8.8 Hz), 8.42 (1H, d, J=2.8 Hz), 9.82 (1H, s).

Reference Example 13

N-{5-[(6-aminopyridin-3-yl)oxy]-2-methylphenyl}-1,3-dimethyl-1H-pyrazole-5-carboxamide

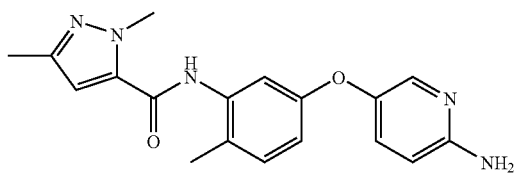

To a solution of 1,3-dimethyl-N-{2-methyl-5-[(6-nitropyridin-3-yl)oxy]phenyl}-1H-pyrazole-5-carboxamide (3.38 g, 9.20 mmol) in methanol (20 mL) was added palladium carbon (50% water-containing product, 300 mg), and the mixture was stirred under a hydrogen atmosphere at room temperature for 4 hr. The reaction mixture was filtered through celite, and the filtrate was concentrated under reduced pressure. The residue was collected by filtration and washed with ethyl acetate-hexane to give the title compound (2.94 g, 95%) as a white solid.

$^1$H-NMR (DMSO-d$_6$, 300 MHz) δ 2.15 (3H, s), 2.18 (3H, s), 3.97 (3H, s), 5.88 (2H, br s), 6.49 (1H, dd, J=9.0, 0.6 Hz), 6.73-6.78 (2H, m), 6.88 (1H, d, J=2.4 Hz), 7.17-7.22 (2H, m), 7.73-7.75 (1H, m), 9.71 (1H, br s).

Reference Example 14

1,3-dimethyl-N-{2-methyl-5-[(6-{[(4-methylphenyl)sulfonyl]amino}pyridin-3-yl)oxy]phenyl}-1H-pyrazole-5-carboxamide

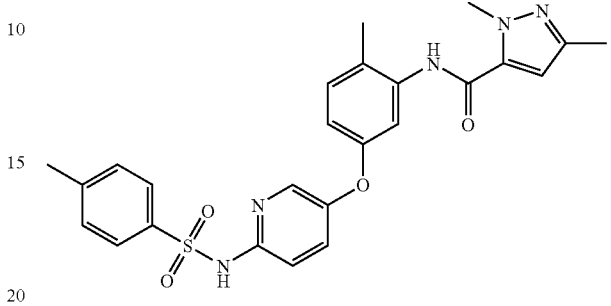

In the same manner as in Reference Example 4 and using N-{5-[(6-aminopyridin-3-yl)oxy]-2-methylphenyl}-1,3-dimethyl-1H-pyrazole-5-carboxamide (2.61 g, 7.75 mmol), p-toluenesulfonyl chloride (1.77 g, 9.31 mmol) and pyridine (15 mL) as starting materials, the title compound (2.92 g, 77%) was obtained as a white solid.

$^1$H-NMR (DMSO-d$_6$, 300 MHz) δ 2.19 (6H, s), 2.34 (3H, s), 3.97 (3H, s), 6.78-6.84 (2H, m), 6.98 (1H, d, J=2.7 Hz), 7.13 (1H, d, J=8.9 Hz), 7.25 (1H, d, J=8.7 Hz), 7.36 (2H, d, J=8.1 Hz), 7.44 (1H, dd, J=8.9, 3.0 Hz), 7.77 (2H, d, J=8.1 Hz), 7.97 (1H, d, J=3.0 Hz), 9.73 (1H, s), 11.02 (1H, br s).

Reference Example 15

N-{5-[(1-(2-amino-2-oxoethyl)-6-{[(4-methylphenyl)sulfonyl]imino}-1,6-dihydropyridin-3-yl)oxy]-2-methylphenyl}-1,3-dimethyl-1H-pyrazole-5-carboxamide

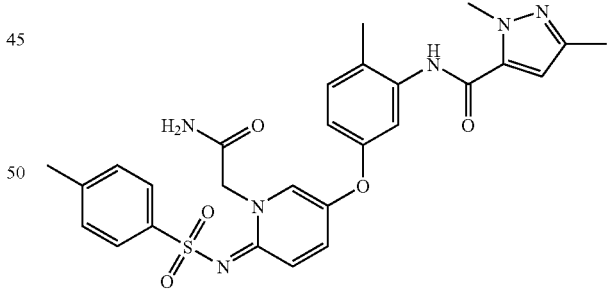

In the same manner as in Reference Example 5 and using 1,3-dimethyl-N-{2-methyl-5-[(6-{[(4-methylphenyl)sulfonyl]amino}pyridin-3-yl)oxy]phenyl}-1H-pyrazole-5-carboxamide (2.91 g, 5.92 mmol), N,N-diisopropylethylamine (1.34 mL, 7.70 mmol), iodoacetamide (1.42 g, 7.70 mmol) and N,N-dimethylformamide (15 mL) as starting materials, the title compound (2.35 g, 72%) was obtained as a white solid.

$^1$H-NMR (DMSO-d$_6$, 300 MHz) δ 2.17 (3H, s), 2.19 (3H, s), 2.34 (3H, s), 3.98 (3H, s), 4.82 (2H, s), 6.79 (1H, s), 6.84 (1H, dd, J=8.3, 2.6 Hz), 7.04 (1H, d, J=2.6 Hz), 7.24-7.29

(3H, m), 7.37-7.42 (2H, m), 7.65-7.71 (3H, m), 7.76 (1H, br s), 8.10 (1H, d, J=3.0 Hz), 9.77 (1H, s).

Reference Example 16

2-methyl-5-(3-nitrophenoxy)pyridine

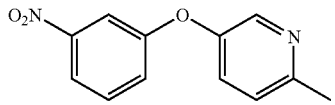

A mixture of 6-methylpyridin-3-ol (17.6 g, 161 mmol), 1-fluoro-3-nitrobenzene (25.0 g, 177 mmol), potassium carbonate (66.8 g, 483 mmol) and N,N-dimethylformamide (200 mL) was stirred at 90° C. for 13 hr, 120° C. for 5 hr and 140° C. for 4 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was dried to give the title compound (28.6 g, 77%) as a yellow oil.

$^1$H-NMR (DMSO-$d_6$, 300 MHz) δ 2.50 (3H, s), 7.35 (1H, d, J=8.4 Hz), 7.48-7.55 (2H, m), 7.65-7.72 (2H, m), 7.97-8.01 (1H, m), 8.35 (1H, d, J=3.0 Hz).

Reference Example 17

5-(3-nitrophenoxy)pyridine-2-carboxylic acid

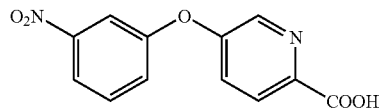

To a mixture of 2-methyl-5-(3-nitrophenoxy)pyridine (25.0 g, 109 mmol), water (250 mL) and pyridine (250 mL) was added with stirring potassium permanganate (87.0 g, 551 mmol) at 85° C. over 12 hr. The reaction mixture was filtered through celite, and the filtrate was concentrated under reduced pressure. The residue was dissolved in water (200 mL) and neutralized with 6N hydrochloric acid. The precipitated solid was collected by filtration and washed with water to give the title compound (11.6 g, 41%) as a white solid.

$^1$H-NMR (DMSO-$d_6$, 300 MHz) δ 7.50-7.64 (2H, m), 7.73 (1H, t, J=8.4 Hz), 7.90 (1H, t, J=2.3 Hz), 7.99-8.10 (2H, m), 8.47 (1H, d, J=2.3 Hz).

Reference Example 18

5-(3-nitrophenoxy)pyridin-2-amine

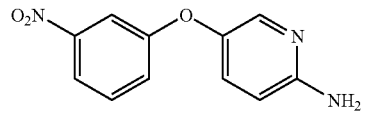

A mixture of 5-(3-nitrophenoxy)pyridine-2-carboxylic acid (10.4 g, 40.0 mmol), diphenylphosphoryl azide (10.8 mL, 50.0 mmol), triethylamine (6.92 mL, 50.0 mmol) and tert-butanol (200 mL) was stirred at room temperature for 3 hr, and then stirred with heating under reflux for 15 hr. The reaction mixture was concentrated under reduced pressure, trifluoroacetic acid (20 mL) was added to the residue, and the mixture was stirred at room temperature for 1 hr. The reaction mixture was concentrated under reduced pressure, 8N aqueous sodium hydroxide solution (70 mL) was added to the residue, and the mixture was stirred with heating under refluxing conditions for 3 hr. After extraction with ethyl acetate (×3), the organic layer was washed with saturated brine, dried over anhydrous magnesium sulfate and filtrated. The filtrate was concentrated under reduced pressure, and the residue was dried to give the title compound (5.80 g, 63%) as a white solid.

$^1$H-NMR (DMSO-$d_6$, 300 MHz) δ 6.03 (2H, br s), 6.52-6.55 (1H, m), 7.30 (1H, dd, J=9.0, 3.0 Hz), 7.39-7.43 (1H, m), 7.57 (1H, t, J=2.4 Hz), 7.63 (1H, t, J=8.4 Hz), 7.84 (1H, d, J=3.0 Hz), 7.89-7.93 (1H, m).

Reference Example 19

2-[2-{[(4-methylphenyl)sulfonyl]imino}-5-(3-nitrophenoxy)pyridin-1(2H)-yl]acetamide

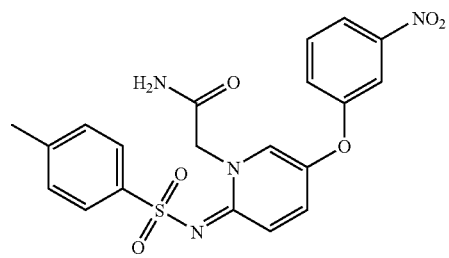

A mixture of 5-(3-nitrophenoxy)pyridin-2-amine (2.70 g, 11.7 mmol), p-toluenesulfonyl chloride (2.67 g, 14.0 mmol) and pyridine (20 mL) was stirred at 80° C. for 2 hr. The reaction mixture was diluted with water and extracted with ethyl acetate (×3). The organic layer was washed with saturated brine, dried over anhydrous magnesium sulfate and filtrated. The filtrate was concentrated under reduced pressure. The residue was collected by filtration and washed with ethyl acetate-hexane to give 4-methyl-N-[5-(3-nitrophenoxy)pyridin-2-yl]benzenesulfonamide (4.15 g, 92%) as a white solid. A mixture of 4-methyl-N-[5-(3-nitrophenoxy)pyridin-2-yl]benzenesulfonamide (4.15 g, 10.7 mmol) thus-obtained, N,N-diisopropylethylamine (2.44 mL, 14.0 mmol) and N,N-dimethylformamide (20 mL) was stirred at room temperature for 2 hr, iodoacetamide (2.59 g, 14.0 mmol) was added, and the mixture was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give the title compound (5.28 g, 99%) as a white solid.

$^1$H-NMR (DMSO-$d_6$, 300 MHz) δ 2.34 (3H, s), 4.82 (2H, s), 7.29 (2H, d, J=8.4 Hz), 7.40 (1H, br s), 7.44 (1H, d, J=9.6 Hz), 7.51-7.55 (1H, m), 7.65-7.71 (3H, m), 7.77-7.82 (3H, m), 7.98-8.02 (1H, m), 8.21 (1H, d, J=2.7 Hz).

Reference Example 20

N-(2-fluoro-5-hydroxyphenyl)-1,3-dimethyl-1H-pyrazole-5-carboxamide

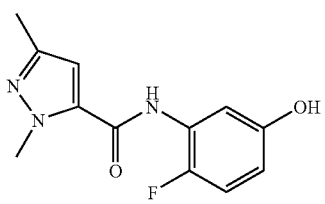

To a solution of 3-amino-4-fluorophenol (5.05 g, 39.7 mmol) and triethylamine (5.77 mL, 41.7 mmol) in tetrahydrofuran (30 mL) was added dropwise with stirring under ice-cooling a solution of 1,3-dimethyl-1H-pyrazole-5-carbonyl chloride (6.61 g, 41.7 mmol) in tetrahydrofuran (10 mL), and the mixture was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give the title compound (9.89 g, 99%) as a white solid.

$^1$H-NMR (DMSO-$d_6$, 300 MHz) δ 2.19 (3H, s), 3.98 (3H, s), 6.58-6.64 (1H, m), 6.83 (1H, s), 6.97-7.09 (2H, m), 9.87 (1H, s).

Reference Example 21

N-{5-[(6-aminopyridin-3-yl)oxy]-2-fluorophenyl}-1,3-dimethyl-1H-pyrazole-5-carboxamide

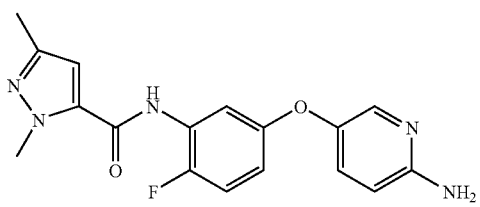

A mixture of N-(2-fluoro-5-hydroxyphenyl)-1,3-dimethyl-1H-pyrazole-5-carboxamide (9.80 g, 39.3 mmol), 5-bromo-2-nitropyridine (7.14 g, 35.1 mmol), cesium carbonate (14.8 g, 45.3 mmol) and N,N-dimethylformamide (80 mL) was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=90/10→0/100) to give N-{2-fluoro-5-[(6-nitropyridin-3-yl)oxy]phenyl}-1,3-dimethyl-1H-pyrazole-5-carboxamide (7.68 g, 59%) as a white solid. To a solution of N-{2-fluoro-5-[(6-nitropyridin-3-yl)oxy]phenyl}-1,3-dimethyl-1H-pyrazole-5-carboxamide (7.68 g, 20.7 mmol) thus-obtained in methanol (50 mL) was added palladium carbon (50% water-containing product, 700 mg), and the mixture was stirred under a hydrogen atmosphere at room temperature for 2 hr. The reaction mixture was filtered through celite, and the filtrate was concentrated under reduced pressure. The residue was collected by filtration and washed with ethyl acetate-hexane to give the title compound (6.20 g, 88%) as a white solid.

$^1$H-NMR (DMSO-$d_6$, 300 MHz) δ 2.18 (3H, s), 3.96 (3H, s), 5.90 (2H, s), 6.50 (1H, d, J=9.0 Hz), 6.76-6.85 (2H, m), 7.10 (1H, dd, J=6.2, 3.2 Hz), 7.16-7.28 (2H, m), 7.76 (1H, d, J=3.0 Hz), 9.97 (1H, s).

Reference Example 22

N-{2-fluoro-5-[(6-{[(4-methylphenyl)sulfonyl]amino}pyridin-3-yl)oxy]phenyl}-1,3-dimethyl-1H-pyrazole-5-carboxamide

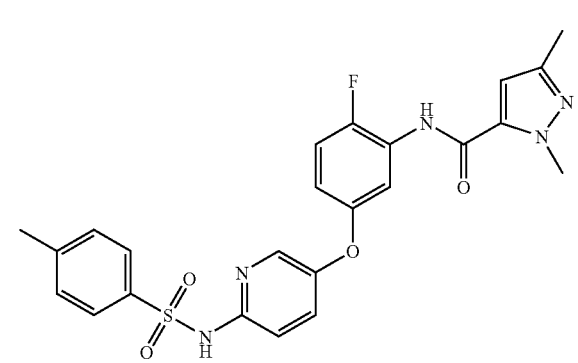

In the same manner as in Reference Example 4 and using N-{5-[(6-aminopyridin-3-yl)oxy]-2-fluorophenyl}-1,3-dimethyl-1H-pyrazole-5-carboxamide (6.20 g, 18.1 mmol), p-toluenesulfonyl chloride (3.80 g, 19.9 mmol) and pyridine (20 mL) as starting materials, the title compound (7.27 g, 81%) was obtained as a white solid.

$^1$H-NMR (DMSO-$d_6$, 300 MHz) δ 2.19 (3H, s), 2.34 (3H, s), 3.96 (3H, s), 6.82 (1H, s), 6.87-6.93 (1H, m), 7.14 (1H, d, J=9.0 Hz), 7.20-7.38 (4H, m), 7.47 (1H, dd, J=9.0, 3.0 Hz), 7.78 (2H, d, J=8.4 Hz), 8.00 (1H, d, J=2.7 Hz), 10.02 (1H, s), 11.04 (1H, s).

Reference Example 23

N-{5-[(1-(2-amino-2-oxoethyl)-6-{[(4-methylphenyl)sulfonyl]imino}-1,6-dihydropyridin-3-yl)oxy]-2-fluorophenyl}-1,3-dimethyl-1H-pyrazole-5-carboxamide

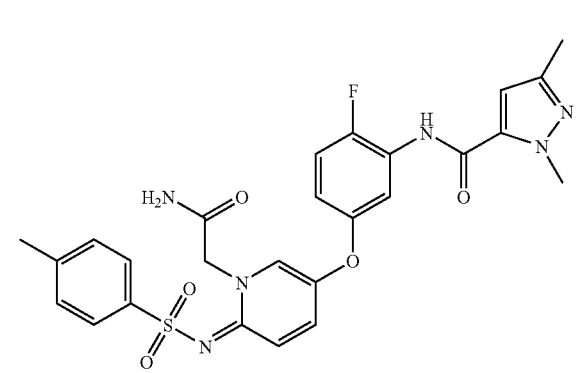

In the same manner as in Reference Example 5 and using N-{2-fluoro-5-[(6-{[(4-methylphenyl)sulfonyl]amino}pyridin-3-yl)oxy]phenyl}-1,3-dimethyl-1H-pyrazole-5-carboxamide (7.25 g, 14.6 mmol), N,N-diisopropylethylamine (3.31 mL, 19.0 mmol), N,N-dimethylformamide (30 mL) and iodoacetamide (3.51 g, 19.0 mmol) as starting materials, the title compound (5.86 g, 73%) was obtained as a white solid.

¹H-NMR (DMSO-d₆, 300 MHz) δ 2.19 (3H, s), 2.34 (3H, s), 3.97 (3H, s), 4.82 (2H, s), 6.82 (1H, s), 6.82-6.95 (1H, m), 7.26-7.43 (6H, m), 7.65-7.76 (4H, s), 8.12 (1H, d, J=2.7 Hz), 10.06 (1H, s).

Reference Example 24

1-methyl-1H-tetrazole-5-carboxylic acid and 2-methyl-2H-tetrazole-5-carboxylic acid

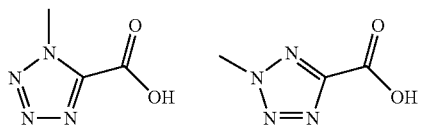

A mixture of ethyl 1H-tetrazole-5-carboxylate sodium salt (5.18 g, 31.6 mmol), potassium carbonate (6.54 g, 47.3 mmol), iodomethane (2.36 mL, 37.9 mmol) and acetonitrile (200 mL) was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, ethyl acetate). Ethanol (30 mL) and 8N aqueous sodium hydroxide solution (5 mL) were added to the purification product, and the mixture was stirred at room temperature for 2 hr. The reaction mixture was concentrated under reduced pressure, and ethanol was evaporated. The mixture was adjusted to pH 4 with 1N hydrochloric acid, and extracted with ethyl acetate-tetrahydrofuran. The organic layer was washed with water and saturated brine, dried over anhydrous magnesium sulfate and filtrated. The filtrate was concentrated under reduced pressure, and the residue was collected by filtration and washed with ethyl acetate-hexane to give a mixture of (1) 1-methyl-1H-tetrazole-5-carboxylic acid and (2) 2-methyl-2H-tetrazole-5-carboxylic acid ((1):(2)≈1:1, 750 mg, 18%) as a white solid.

¹H-NMR (DMSO-d₆, 300 MHz) δ 4.18 (1.5H, s), 4.30 (1.5H, s).

Reference Example 25

N-(3-hydroxy-5-methylphenyl)-1,3-dimethyl-1H-pyrazole-5-carboxamide

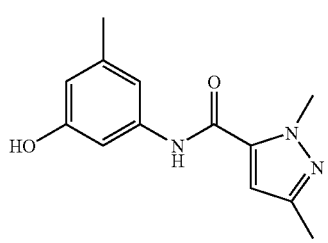

To a solution of 3-amino-5-methylphenol (4.32 g, 35.1 mmol) and triethylamine (5.20 mL, 37.4 mmol) in tetrahydrofuran (40 mL) was added dropwise with stirring under ice-cooling a solution of 1,3-dimethyl-1H-pyrazole-5-carbonyl chloride (5.85 g, 36.9 mmol) in tetrahydrofuran (10 mL), and the mixture was stirred at room temperature for 10 hr. Methanol (40 mL), water (40 mL) and saturated aqueous sodium carbonate solution (20 mL) were added to the reaction mixture, and the mixture was stirred at room temperature for 7 hr. The reaction solution was concentrated under reduced pressure. Ethyl acetate was added to the residue, and the mixture was washed with saturated brine, dried over anhydrous magnesium sulfate and filtrated. The filtrate was concentrated under reduced pressure, and the residue was purified by column chromatography (silica gel, hexane/ethyl acetate=100/0→50/50) to give the title compound (8.30 g, 96%) as a pale-yellow oil.

¹H-NMR (CDCl₃, 300 MHz) δ 2.29 (3H, s), 2.30 (3H, s), 4.13 (3H, s), 5.58 (1H, s), 6.39 (1H, s), 6.49 (1H, s), 6.80 (1H, s), 7.13 (1H, t, J=2.0 Hz), 7.55 (1H, s).

Reference Example 26

1,3-dimethyl-N-{3-methyl-5-[(6-nitropyridin-3-yl)oxy]phenyl}-1H-pyrazole-5-carboxamide

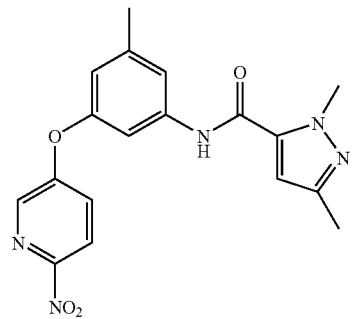

In the same manner as in Reference Example 12 and using N-(3-hydroxy-5-methylphenyl)-1,3-dimethyl-1H-pyrazole-5-carboxamide (8.30 g, 33.8 mmol), cesium carbonate (16.5 g, 50.8 mmol), 5-bromo-2-nitropyridine (6.54 g, 32.2 mmol) and N,N-dimethylformamide (40 mL) as starting materials, the title compound (7.68 g, 54%) was obtained as a pale-yellow oil.

¹H-NMR (CDCl₃, 300 MHz) δ 2.29 (3H, s), 2.39 (3H, s), 4.12 (3H, s), 6.73 (1H, s), 7.19 (1H, s), 7.43 (1H, t, J=2.0 Hz), 7.46 (1H, dd, J=8.8, 3.0 Hz), 7.74 (1H, s), 8.01 (1H, s), 8.25 (1H, d, J=8.8 Hz), 8.34 (1H, d, J=3.0 Hz).

Reference Example 27

N-{3-[(6-aminopyridin-3-yl)oxy]-5-methylphenyl}-1,3-dimethyl-1H-pyrazole-5-carboxamide

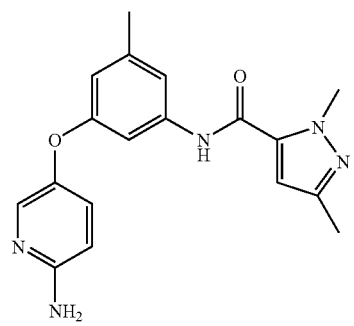

In the same manner as in Reference Example 13 and using 1,3-dimethyl-N-{3-methyl-5-[(6-nitropyridin-3-yl)oxy]phenyl}-1H-pyrazole-5-carboxamide (7.63 g, 17.3 mmol), palladium carbon (50% water-containing product, 1.88 g) and methanol (50 mL) as starting materials, the title compound (6.25 g, 88%) was obtained as a pale-yellow oil.

¹H-NMR (CDCl₃, 300 MHz) δ 2.28 (3H, s), 2.31 (3H, s), 4.12 (3H, s), 4.40 (2H, s), 6.40 (1H, s), 6.50-6.57 (2H, m), 6.92 (1H, t, J=2.0 Hz), 7.17 (1H, s), 7.21 (1H, dd, J=8.6, 2.6 Hz), 7.65 (1H, s), 7.89-7.92 (1H, m).

Reference Example 28

1,3-dimethyl-N-{3-methyl-5-[(6-{[(4-methylphenyl)sulfonyl]amino}pyridin-3-yl)oxy]phenyl}-1H-pyrazole-5-carboxamide

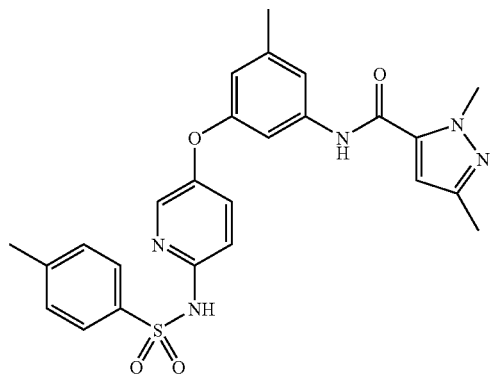

In the same manner as in Reference Example 4 and using N-{3-[(6-aminopyridin-3-yl)oxy]-5-methylphenyl}-1,3-dimethyl-1H-pyrazole-5-carboxamide (4.02 g, 9.79 mmol), p-toluenesulfonyl chloride (2.29 g, 12.0 mmol) and pyridine (30 mL) as starting materials, the title compound (3.88 g, 81%) was obtained as a colorless oil.

¹H-NMR (CDCl₃, 300 MHz) δ 2.27 (3H, s), 2.33 (3H, s), 2.38 (3H, s), 4.11 (3H, s), 6.40 (1H, s), 6.58 (1H, s), 7.05 (1H, t, J=1.9 Hz), 7.19-7.26 (3H, m), 7.32-7.38 (1H, m), 7.40-7.44 (1H, m), 7.65-7.68 (2H, m), 7.69-7.71 (1H, m), 8.17 (1H, d, J=2.3 Hz), 9.55 (1H, s).

Reference Example 29

N-{3-[(1-(2-amino-2-oxoethyl)-6-{[(4-methylphenyl)sulfonyl]imino}-1,6-dihydropyridin-3-yl)oxy]-5-methylphenyl}-1,3-dimethyl-1H-pyrazole-5-carboxamide

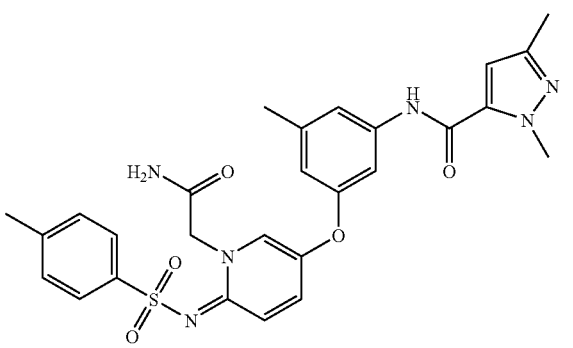

In the same manner as in Reference Example 5 and using 1,3-dimethyl-N-{3-methyl-5-[(6-{[(4-methylphenyl)sulfonyl]amino}pyridin-3-yl)oxy]phenyl}-1H-pyrazole-5-carboxamide (3.88 g, 7.89 mmol), iodoacetamide (1.90 g, 10.27 mmol), N,N-diisopropylethylamine (1.80 mL, 10.3 mmol) and N,N-dimethylformamide (20 mL) as starting materials, the title compound (3.23 g, 75%) was obtained as a pale-yellow oil.

¹H-NMR (CDCl₃, 300 MHz) δ 2.14 (3H, s), 2.28 (3H, s), 2.30 (3H, s), 4.06 (3H, s), 4.78 (2H, s), 6.28 (1H, s), 6.49 (1H, s), 6.54 (1H, s), 6.79 (1H, s), 7.14 (2H, d, J=8.3 Hz), 7.32 (2H, dd, J=9.8, 2.6 Hz), 7.38-7.50 (3H, m), 7.70 (2H, d, J=8.3 Hz), 8.52 (1H, s).

Reference Example 30 ethyl ({[5-(3-{[(1,3-dimethyl-1H-pyrazol-5-yl)carbonyl]amino}phenoxy)pyridin-2-yl]amino}carbonothioyl)carbamate To a solution of N-{3-[(6-aminopyridin-3-yl)oxy]phenyl}-1,3-dimethyl-1H-pyrazole-5-carboxamide (184 mg, 0.569 mmol) in DMSO (4 mL) was added ethyl isothiocyanatoformate (89.6 mg, 0.682 mmol), and the mixture was stirred for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was dried to give the title compound (268 mg, 99%) as a colorless oil.

¹H-NMR (DMSO-d₆, 300 MHz) δ 1.26 (3H, t, J=7.1 Hz), 2.18 (3H, s), 3.97 (3H, s), 4.22 (2H, q, J=7.1 Hz), 6.79-6.85 (2H, m), 7.37 (1H, t, J=8.1 Hz), 7.46 (1H, t, J=2.1 Hz), 7.55-7.58 (1H, m), 7.64 (1H, dd, J=9.0, 3.0 Hz), 8.25 (1H, d, J=3.0 Hz), 8.68 (1H, s), 10.18 (1H, s), 11.55 (1H, s), 12.14 (1H, s).

Reference Example 31 ethyl ({[5-(3-{[(1,3-dimethyl-1H-pyrazol-5-yl)carbonyl]amino}-4-fluorophenoxy)pyridin-2-yl]amino}carbonothioyl)carbamate To a solution of N-{5-[(6-aminopyridin-3-yl)oxy]-2-fluorophenyl}-1,3-dimethyl-1H-pyrazole-5-carboxamide (860 mg, 2.51 mmol) in DMSO (5 mL) was added ethyl isothiocyanatoformate (428 mg, 3.27 mmol), and the mixture was stirred for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was dried to give the title compound (1.16 g, 98%) as a yellow oil.

$^1$H-NMR (DMSO-$d_6$, 300 MHz) δ 1.29 (3H, t, J=7.2 Hz), 2.19 (3H, s), 3.97 (3H, s), 4.23 (2H, q, J=7.2 Hz), 6.83 (1H, s), 6.98-7.04 (1H, m), 7.32-7.38 (2H, m), 7.62 (1H, dd, J=9.3, 2.9 Hz), 8.23 (1H, d, J=2.9 Hz), 8.64 (1H, br s), 10.05 (1H, s), 11.54 (1H, br s), 12.13 (1H, br s).

Reference Example 32 tert-butyl (3-hydroxy-4-methylphenyl)carbamate

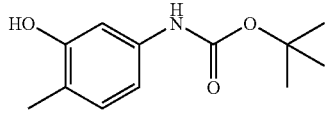

To a solution of 5-amino-2-methylphenol (10.0 g, 81.2 mmol) and triethylamine (16.9 mL, 122 mmol) in tetrahydrofuran (75 mL) was added dropwise with stirring under ice-cooling a solution of di-tert-butyl-dicarbonate (19.5 g, 89.3 mmol) in tetrahydrofuran (25 mL), and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=95/5→50/50) to give the title compound (3.25 g, 18%) as a colorless oil.

$^1$H-NMR (DMSO-$d_6$, 300 MHz) δ 1.46 (9H, s), 2.02 (3H, s), 6.71 (1H, dd, J=8.2, 1.8 Hz), 6.87 (1H, d, J=8.2 Hz), 7.07 (1H, d, J=1.8 Hz), 9.09 (1H, s), 9.16 (1H, s).

Reference Example 33 tert-butyl {4-methyl-3-[(6-nitropyridin-3-yl)oxy]phenyl}carbamate

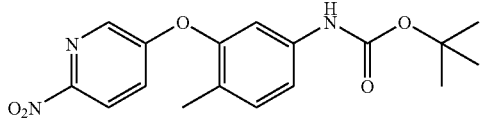

A mixture of tert-butyl (3-hydroxy-4-methylphenyl)carbamate (3.14 g, 14.1 mmol), 5-bromo-2-nitropyridine (2.38 g, 11.7 mmol), cesium carbonate (5.72 g, 17.6 mmol) and N,N-dimethylformamide (25 mL) was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, hexane/ethyl acetate=80/20→0/100) to give the title compound (1.86 g, 44%) as a colorless oil.

$^1$H-NMR (DMSO-$d_6$, 300 MHz) δ 1.45 (9H, s), 2.06 (3H, s), 7.24-7.34 (3H, m), 7.45 (1H, dd, J=9.2, 2.9 Hz), 8.32 (1H, d, J=9.2 Hz), 8.38 (1H, d, J=2.9 Hz), 9.50 (1H, s).

Reference Example 34 tert-butyl {3-[(6-aminopyridin-3-yl)oxy]-4-methylphenyl}carbamate

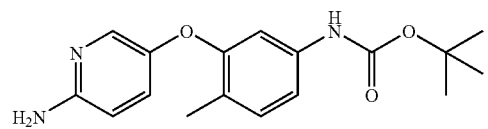

To a solution of tert-butyl {4-methyl-3-[(6-nitropyridin-3-yl)oxy]phenyl}carbamate (1.85 g, 5.35 mmol) in methanol (10 mL) was added palladium carbon (50% water-containing product, 100 mg), and the mixture was stirred under a hydrogen atmosphere at room temperature for 3 hr. The reaction mixture was filtered through celite, and the filtrate was concentrated under reduced pressure. The residue was dried to give the title compound (1.69 g, 99%) as a colorless oil.

$^1$H-NMR (DMSO-$d_6$, 300 MHz) δ 1.40 (9H, s), 2.16 (3H, s), 5.80 (2H, s), 6.46 (1H, d, J=9.0 Hz), 6.89 (1H, s), 7.01-7.13 (3H, m), 7.66 (1H, d, J=3.0 Hz), 9.50 (1H, s).

Reference Example 35-1 ethyl {[(5-methoxypyridin-2-yl)amino]carbonothioyl}carbamate

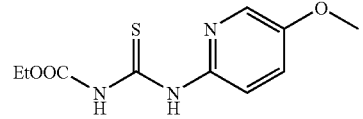

In the same manner as in Reference Example 30 and using 5-methoxypyridin-2-amine (1.05 g, 8.43 mmol), DMSO (5 mL) and ethyl isothiocyanatoformate (1.44 g, 11.0 mmol) as starting materials, the title compound (1.34 g, 62%) was obtained as a white solid.

$^1$H-NMR (DMSO-$d_6$, 300 MHz) δ 1.26 (3H, t, J=7.2 Hz), 3.84 (3H, s), 4.22 (2H, q, J=7.2 Hz), 7.51 (1H, dd, J=9.0, 3.0 Hz), 8.12 (1H, d, J=3.0 Hz), 8.54 (1H, br s), 11.38 (1H, br s), 12.04 (1H, br s).

Reference Example 35-2

6-methoxy[1,2,4]triazolo[1,5-a]pyridin-2-amine

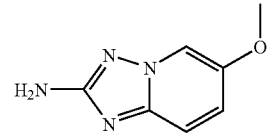

In the same manner as in the below-mentioned Example 23-1 and using ethyl {[(5-methoxypyridin-2-yl)amino]carbonothioyl}carbamate (1.34 g, 5.25 mmol), hydroxylammonium chloride (2.55 g, 36.7 mmol), N,N-diisopropylethylamine (4.57 mL, 26.2 mmol), ethanol (15 mL) and methanol (15 mL) as starting materials, the title compound (790 mg, 92%) was obtained as a yellow oil.

$^1$H-NMR (DMSO-$d_6$, 300 MHz) δ 3.78 (3H, s), 5.79 (2H, br s), 7.18 (1H, dd, J=9.6, 2.4 Hz), 7.27 (1H, d, J=9.6 Hz), 8.28 (1H, d, J=2.4 Hz).

Reference Example 35-3

2-amino[1,2,4]triazolo[1,5-a]pyridin-6-ol hydrobromide

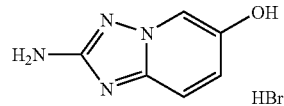

A mixture of 6-methoxy[1,2,4]triazolo[1,5-a]pyridin-2-amine (780 mg, 4.75 mmol) and 48% hydrobromic acid (3 mL) was stirred under refluxing conditions for 7 hr. 48% Hydrobromic acid (2 mL) was further added, and the mixture was stirred with heating under reflux for 3 hr. The mixture was concentrated under reduced pressure, and diisopropyl ether (2 mL) and ethanol (1 mL) were added to the residue. The precipitate was collected by filtration and washed with diisopropyl ether to give the title compound (984 mg, 89%) as a brown solid.

$^1$H-NMR (DMSO-$d_6$, 300 MHz) δ 7.53-7.61 (2H, m), 8.34 (1H, dd, J=1.8, 0.9 Hz), 10.57 (1H, br s).

Reference Example 35-4

N-(6-hydroxy[1,2,4]triazolo[1,5-a]pyridin-2-yl)cyclopropanecarboxamide

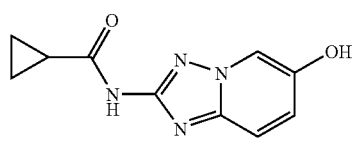

To a solution of 2-amino[1,2,4]triazolo[1,5-a]pyridin-6-ol hydrobromide (1.50 g, 4.22 mmol) in N,N-dimethylacetamide (5 mL) was added with stirring under ice-cooling cyclopropanecarbonyl chloride (1.15 mL, 12.7 mmol), and the mixture was stirred at room temperature for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (1.59 g, 89%) as a white solid.

$^1$H-NMR (DMSO-$d_6$, 300 MHz) δ 0.79-0.82 (4H, m), 1.96-2.05 (1H, m), 7.28 (1H, dd, J=9.4, 2.4 Hz), 7.52 (1H, d, J=9.4 Hz), 8.20 (1H, d, J=2.4 Hz), 10.01 (1H, br s), 10.82 (1H, s).

Reference Example 36 ethyl ({[5-(3-{[(1,3-dimethyl-1H-pyrazol-5-yl)carbonyl]amino}-5-methylphenoxy)pyridin-2-yl]amino}carbonothioyl)carbamate

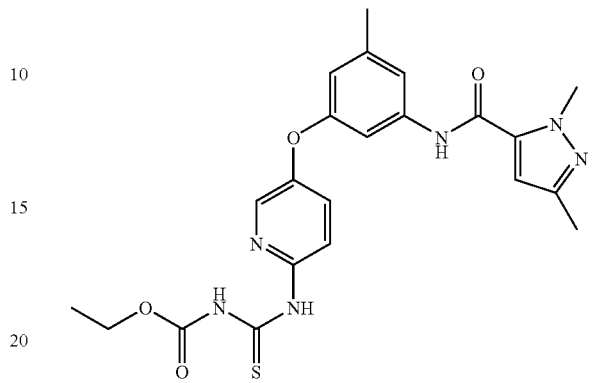

To a solution of N-{3-[(6-aminopyridin-3-yl)oxy]-5-methylphenyl}-1,3-dimethyl-1H-pyrazole-5-carboxamide (2.23 g, 5.43 mmol) in DMSO (30 mL) was added ethyl isothiocyanatoformate (770 µL, 6.52 mmol), and the mixture was stirred at room temperature for 12 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=100/0→50/50) to give the title compound (2.65 g, 88%) as a pale-yellow oil.

$^1$H-NMR (CDCl$_3$, 300 MHz) δ 1.35 (3H, t, J=7.0 Hz), 2.28 (3H, s), 2.35 (3H, s), 4.12 (3H, s), 4.31 (2H, q, J=7.0 Hz), 6.40 (1H, s), 6.64 (1H, s), 7.08 (1H, s), 7.22 (1H, s), 7.40 (1H, dd, J=9.1, 2.8 Hz), 7.58 (1H, s), 8.05 (1H, s), 8.19 (1H, d, J=2.8 Hz), 8.76 (1H, d, J=9.1 Hz), 12.03 (1H, s).

Reference Example 37

1-ethyl-4-(trifluoromethyl)-1H-pyrrole-3-carboxylic acid

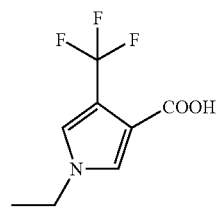

To a mixture of 60% sodium hydride (212 mg, 5.31 mmol) and N,N-dimethylformamide (25 mL) was added with stirring at 0° C. ethyl 4-(trifluoromethyl)-1H-pyrrole-3-carboxylate (1.00 g, 4.83 mmol), and the mixture was stirred at room temperature for 30 min. Iodoethane (581 µL, 7.24 mmol) was added, and the mixture was stirred at room temperature for 3 hr. The reaction mixture was diluted with water and extracted with ethyl acetate, and the organic layer was washed with water and saturated brine, dried over anhydrous magnesium sulfate and filtrated. The filtrate was concentrated under reduced pressure, ethanol (4 mL) and 8N aqueous sodium hydroxide solution (2 mL) were added to the residue, and the mixture was stirred at room temperature for 2 hr and at 60° C.

for 15 hr. The reaction mixture was neutralized with 1N hydrochloric acid, and the precipitated solid was collected by filtration and washed with water to give the title compound (710 mg, 71%) as a white solid.

¹H-NMR (DMSO-d₆, 300 MHz) δ 1.34 (3H, t, J=7.3 Hz), 3.99 (2H, q, J=7.3 Hz), 7.46 (1H, d, J=2.4 Hz), 7.61 (1H, d, J=2.4 Hz), 12.18 (1H, br s).

Reference Example 38

1-ethyl-4-methyl-1H-pyrrole-3-carboxylic acid

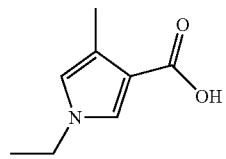

In the same manner as in Reference Example 37 and using 60% sodium hydride (340 mg, 8.62 mmol), N,N-dimethylformamide (25 mL), methyl 4-methyl-1H-pyrrole-3-carboxylate (1.00 g, 7.19 mmol), iodoethane (860 μL, 10.8 mmol), ethanol (6 mL) and 8N aqueous sodium hydroxide solution (1.8 mL) as starting materials, the title compound (805 mg, 73%) was obtained as a white solid.

¹H-NMR (DMSO-d₆, 300 MHz) δ 1.29 (3H, t, J=7.3 Hz), 2.13 (3H, s), 3.85 (2H, q, J=7.3 Hz), 6.58-6.60 (1H, m), 7.29 (1H, d, J=2.4 Hz), 11.46 (1H, br s).

Reference Example 39 tert-butyl (5-hydroxy-2-methylphenyl)carbamate

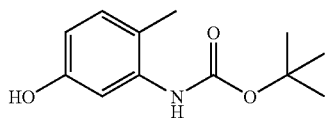

A mixture of 3-amino-4-methylphenol (22.3 g, 0.181 mol), di-tert-butyl dicarbonate (39.7 g, 0.182 mol), tetrahydrofuran (400 mL) and saturated aqueous sodium carbonate solution (100 mL) was stirred at room temperature for 3 days. The reaction mixture was diluted with water and extracted with ethyl acetate. The organic layer was washed with water, saturated aqueous sodium hydrogen carbonate solution and saturated brine, dried over anhydrous magnesium sulfate and filtrated. The filtrate was concentrated under reduced pressure, and the residue was recrystallized from ethyl acetate-hexane to give the title compound (37.4 g, 93%) as a white solid.

¹H-NMR (CDCl₃, 300 MHz) δ 1.52 (9H, s), 2.16 (3H, s), 5.26 (1H, s), 6.30 (1H, s), 6.49 (1H, dd, J=8.3, 2.7 Hz), 6.94-7.01 (1H, m), 7.48 (1H, d, J=1.1 Hz).

Reference Example 40 tert-butyl {2-methyl-5-[(6-nitropyridin-3-yl)oxy]phenyl}carbamate

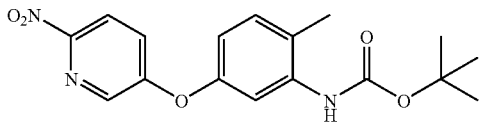

In the same manner as in Reference Example 33 and using tert-butyl (5-hydroxy-2-methylphenyl)carbamate (18.9 g, 85.0 mmol), cesium carbonate (41.8 g, 0.128 mol), N,N-dimethylformamide (100 mL) and 5-bromo-2-nitropyridine (16.4 g, 80.7 mmol) as starting materials, the title compound (19.5 g, 53%) was obtained as a pale-yellow oil.

¹H-NMR (CDCl₃, 300 MHz) δ 1.51 (9H, s), 2.28 (3H, s), 6.40 (1H, s), 6.72 (1H, dd, J=8.3, 2.6 Hz), 7.20 (1H, d, J=8.3 Hz), 7.40 (1H, dd, J=9.0, 2.6 Hz), 7.84 (1H, d, J=1.9 Hz), 8.22 (1H, d, J=9.0 Hz), 8.31 (1H, d, J=2.6 Hz).

Reference Example 41 tert-butyl {5-[(6-aminopyridin-3-yl)oxy]-2-methylphenyl}carbamate

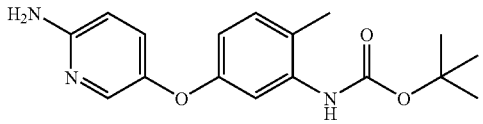

To a solution of tert-butyl {2-methyl-5-[(6-nitropyridin-3-yl)oxy]phenyl}carbamate (19.5 g, 45.3 mmol) in methanol (200 mL) was added palladium carbon (50% water-containing product, 2.99 g), and the mixture was stirred under a hydrogen atmosphere at room temperature for 16 hr. The reaction mixture was filtered through celite, and the filtrate was concentrated under reduced pressure to give the title compound (17.5 g, 98%) as a pale-yellow oil.

¹H-NMR (CDCl₃, 300 MHz) δ 1.50 (9H, s), 2.20 (3H, s), 6.30 (1H, s), 6.55 (1H, dd, J=8.3, 2.7 Hz), 6.60 (1H, d, J=8.7 Hz), 7.05 (1H, d, J=8.3 Hz), 7.25-7.31 (1H, m), 7.59 (1H, s), 7.75 (1H, d, J=2.7 Hz), 8.02 (2H, s).

Reference Example 42 ethyl {[(5-{3-[(tert-butoxycarbonyl)amino]-4-methylphenoxy}pyridin-2-yl)amino]carbonothioyl}carbamate

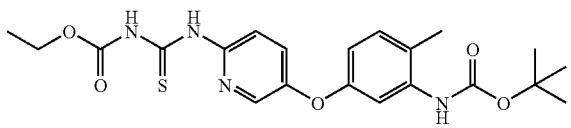

In the same manner as in Reference Example 30 and using tert-butyl {5-[(6-aminopyridin-3-yl)oxy]-2-methylphenyl}carbamate (17.5 g, 44.5 mmol), DMSO (100 mL) and ethyl isothiocyanatoformate (6.50 mL, 55.0 mmol) as starting materials, the title compound (11.5 g, 49%) was obtained as a white solid.

$^1$H-NMR (CDCl$_3$, 300 MHz) δ 1.35 (3H, t, J=7.2 Hz), 1.51 (9H, s), 2.23 (3H, s), 4.30 (2H, q, J=7.2 Hz), 6.32 (1H, s), 6.63 (1H, dd, J=8.3, 2.6 Hz), 7.10 (1H, d, J=8.3 Hz), 7.34 (1H, dd, J=9.0, 3.0 Hz), 7.68-7.79 (1H, m), 8.03 (1H, s), 8.16 (1H, d, J=3.0 Hz), 8.69 (1H, d, J=9.0 Hz), 11.98 (1H, s).

Reference Example 43 tert-butyl {3-[(6-nitropyridin-3-yl)oxy]phenyl}carbamate

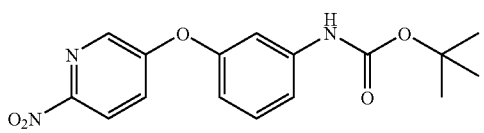

In the same manner as in Reference Example 33 and using tert-butyl (3-hydroxyphenyl)carbamate (18.9 g, 90.3 mmol), 5-bromo-2-nitropyridine (15.3 g, 75.3 mmol), cesium carbonate (36.9 g, 113 mmol) and N,N-dimethylformamide (150 mL) as starting materials, the title compound (16.5 g, 66%) was obtained as a yellow oil.

$^1$H-NMR (DMSO-d$_6$, 300 MHz) δ 1.46 (9H, s), 6.80-6.86 (1H, m), 7.26-7.43 (3H, m), 7.60-7.66 (1H, m), 8.32-8.37 (1H, m), 8.41-8.44 (1H, m), 9.61 (1H, s).

Reference Example 44 tert-butyl {3-[(6-aminopyridin-3-yl)oxy]phenyl}carbamate

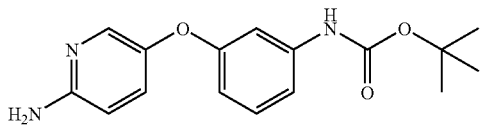

In the same manner as in Reference Example 34 and using tert-butyl {3-[(6-nitropyridin-3-yl)oxy]phenyl}carbamate (16.4 g, 49.5 mmol), palladium carbon (50% water-containing product, 1.50 g) and methanol (100 mL) as starting materials, the title compound (15.9 g, quant.) was obtained as a yellow oil.

$^1$H-NMR (DMSO-d$_6$, 300 MHz) δ 1.44 (9H, s), 6.20 (2H, br s), 6.46-6.51 (1H, m), 6.54 (1H, d, J=8.7 Hz), 7.08-7.29 (4H, m), 7.73 (1H, d, J=2.7 Hz), 9.36 (1H, s).

Reference Example 45

3-[(tert-butoxycarbonyl)amino]-4-fluorophenyl tert-butyl carbonate

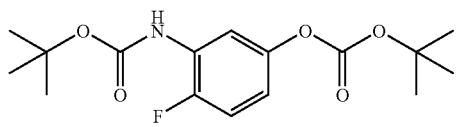

To a mixture of 3-amino-4-fluorophenol (18.7 g, 147 mmol), 10% aqueous sodium carbonate solution (148 mL) and tetrahydrofuran (300 mL) was added di-tert-butyldicarbonate (38.5 g, 176 mmol), and the mixture was stirred at room temperature for 4 hr, and at 80° C. for 14 hr. di-tert-Butyldicarbonate (122 g, 559 mmol) was added over 8 hr. The reaction mixture was diluted with ethyl acetate, washed with water and saturated brine, dried over anhydrous magnesium sulfate and filtrated. The filtrate was concentrated under reduced pressure, and the residue was collected by filtration and washed with ethyl acetate-hexane. The filtrate was concentrated under reduced pressure, and the residue was purified by column chromatography (silica gel, hexane/ethyl acetate=95/5→70/30) to give the title compound (33.5 g, 70%) as a white solid.

$^1$H-NMR (DMSO-d$_6$, 300 MHz) δ 1.46 (9H, s), 1.49 (9H, s), 6.88-6.93 (1H, m), 7.22 (1H, dd, J=10.5, 8.7 Hz), 7.50 (1H, dd, J=6.8, 2.9 Hz), 9.14 (1H, br s).

Reference Example 46 tert-butyl (2-fluoro-5-hydroxyphenyl)carbamate

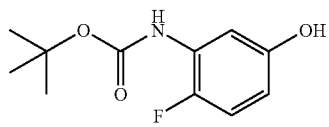

A mixture of 3-[(tert-butoxycarbonyl)amino]-4-fluorophenyl tert-butyl carbonate (33.1 g, 101 mmol), sodium methoxide (6.55 g, 121 mmol) and methanol (500 mL) was stirred at 40° C. for 15 hr. The reaction mixture was concentrated under reduced pressure, and ethyl acetate and water were added to the residue. The organic layer was separated, washed with water and saturated brine, dried over anhydrous magnesium sulfate and filtrated. The filtrate was concentrated under reduced pressure, and the residue was dried to give the title compound (22.8 g, quant.) as a yellow oil.

$^1$H-NMR (DMSO-d$_6$, 300 MHz) δ 1.45 (9H, s), 6.38-6.43 (1H, m), 6.94 (1H, dd, J=10.7, 8.9 Hz), 7.09 (1H, dd, J=6.9, 3.0 Hz), 8.78 (1H, s), 9.33 (1H, br s).

Reference Example 47 tert-butyl {2-fluoro-5-[(6-nitropyridin-3-yl)oxy]phenyl}carbamate

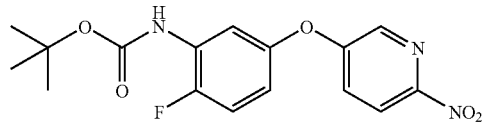

In the same manner as in Reference Example 33 and using tert-butyl (2-fluoro-5-hydroxyphenyl)carbamate (22.4 g, 98.4 mmol), 5-bromo-2-nitropyridine (16.7 g, 82.0 mmol), cesium carbonate (40.1 g, 123 mmol) and N,N-dimethylformamide (140 mL) as starting materials, the title compound (14.2 g, 50%) was obtained as a yellow oil.

¹H-NMR (DMSO-d₆, 300 MHz) δ 1.44 (9H, s), 6.95 (1H, m), 7.34 (1H, dd, J=10.5, 9.0 Hz), 7.58-7.63 (2H, m), 8.33 (1H, d, J=8.7 Hz), 8.41 (1H, d, J=2.7 Hz), 9.27 (1H, br s).

Reference Example 48 tert-butyl {5-[(6-aminopyridin-3-yl)oxy]-2-fluorophenyl}carbamate

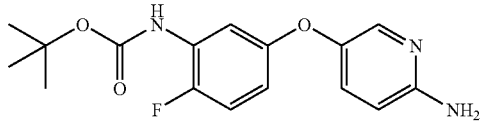

To a solution of tert-butyl {2-fluoro-5-[(6-nitropyridin-3-yl)oxy]phenyl}carbamate (14.2 g, 49.5 mmol) in methanol (200 mL)/ethyl acetate (200 mL) was added palladium carbon (50% water-containing product, 1.50 g), and the mixture was stirred under a hydrogen atmosphere at room temperature for 12 hr. The reaction mixture was filtered through celite, and the filtrate was concentrated under reduced pressure. The residue was purified by column chromatography (silica gel, ethyl acetate) to give the title compound (9.69 g, 75%) as a white solid.

¹H-NMR (DMSO-d₆, 300 MHz) δ 1.43 (9H, s), 5.87 (2H, br s), 6.48 (1H, d, J=9.0 Hz), 6.56-6.62 (1H, m), 7.09-7.28 (3H, m), 7.72 (1H, d, J=3.3 Hz), 8.99 (1H, s).

Reference Example 49 ethyl {[(5-{3-[(tert-butoxycarbonyl)amino]-4-fluorophenoxy}pyridin-2-yl)amino]carbonothioyl}carbamate

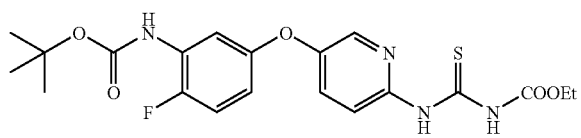

In the same manner as in Reference Example 30 and using tert-butyl {5-[(6-aminopyridin-3-yl)oxy]-2-fluorophenyl}carbamate (9.60 g, 30.1 mmol), DMSO (60 mL) and ethyl isothiocyanatoformate (4.73 g, 36.1 mmol) as starting materials, the title compound (10.8 g, 80%) was obtained as a white solid.

¹H-NMR (DMSO-d₆, 300 MHz) δ 1.26 (3H, t, J=7.3 Hz), 1.43 (9H, s), 4.10 (2H, q, J=7.3 Hz), 6.76-6.82 (1H, m), 7.23 (1H, dd, J=10.5, 9.0 Hz), 7.44 (1H, dd, J=6.6, 3.0 Hz), 7.56 (1H, dd, J=8.9, 2.9 Hz), 8.19 (1H, d, J=3.0 Hz), 8.60 (1H, br s), 9.13 (1H, s), 11.54 (1H, br s), 12.10 (1H, br s).

Reference Example 50

3-cyclopropyl-1-methyl-1H-pyrazole-4-carboxylic acid (1)

5-cyclopropyl-1-methyl-1H-pyrazole-4-carboxylic acid (2)

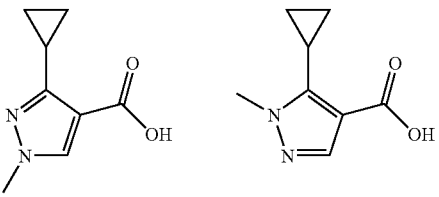

A mixture of methyl 3-cyclopropyl-3-oxopropanoate (10.0 g, 70.4 mmol) and 1,1-dimethoxy-N,N-dimethylmethanamine (10.1 g, 84.4 mmol) was stirred for 1 hr. The reaction mixture was concentrated under reduced pressure, and the residue was dissolved in diethyl ether (25 mL). A solution of methylhydrazine (3.56 g, 77.4 mmol) in diethyl ether (25 mL) was added dropwise with stirring under ice-cooling, and the mixture was stirred for 1 hr. The reaction mixture was diluted with ethyl acetate, washed with water and saturated brine, dried over anhydrous magnesium sulfate and filtrated. The filtrate was concentrated under reduced pressure, ethanol (35 mL) and 8N aqueous sodium hydroxide solution (17.5 mL) were added to the residue, and the mixture was stirred at room temperature for 15 hr. The reaction mixture was neutralized with 1N hydrochloric acid, and the precipitated solid was collected by filtration and washed with water to give a mixture (8.71 g, 75%) of 3-cyclopropyl-1-methyl-1H-pyrazole-4-carboxylic acid (1) and 5-cyclopropyl-1-methyl-1H-pyrazole-4-carboxylic acid (2) as a white solid.

¹H-NMR (DMSO-d₆, 300 MHz) δ 0.74-1.26 (4H, m), 1.83-1.93 (0.3H, m), 2.44-2.53 (0.7H, m), 3.73 (2.1H, s), 3.84 (0.9H, s), 7.67 (0.3H, s), 8.04 (0.7H, s), 12.10 (1H, br s).

Reference Example 51 ethyl 1-ethyl-4-methyl-1H-pyrazole-3-carboxylate

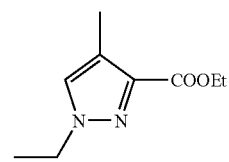

To trichloroacetyl chloride (29.4 mL, 262 mmol) was added dropwise with stirring under ice-cooling a solution of 1-ethoxyprop-1-en (25.0 g, 290 mmol) in pyridine (21.2 mL) over 30 min, diethyl ether (100 mL) was added, and the mixture was stirred at room temperature for 17 hr. 0.2N Hydrochloric acid (200 mL) was added to the reaction mixture, and the organic layer was separated, washed with water and saturated brine, dried over anhydrous magnesium sulfate and filtrated. The filtrate was concentrated under reduced pressure, and the residue was dissolved in ethanol (130 mL). A solution of ethylhydrazine (17.4 g, 290 mmol) in ethanol (130 mL) was added over 10 min, and the mixture was stirred at 80° C. for 2 hr. The reaction mixture was concentrated under reduced pressure, and ethyl acetate and saturated aqueous sodium hydrogen carbonate solution were added to the residue. The organic layer was separated, washed with water and saturated brine, dried over anhydrous magnesium sulfate and filtrated. The filtrate was concentrated under reduced pressure, and the residue was purified by column chromatography (silica gel, hexane/ethyl acetate=95/5→50/50) to give the title compound (8.82 g, 18%) as a colorless oil.

$^1$H-NMR (DMSO-d$_6$, 300 MHz) δ 1.25-1.38 (6H, m), 2.18 (3H, d, J=0.8 Hz), 4.12 (2H, q, J=7.3 Hz), 4.23 (2H, q, J=7.2 Hz), 7.65 (1H, d, J=0.8 Hz).

Reference Example 52

1-ethyl-4-methyl-1H-pyrazole-3-carboxylic acid

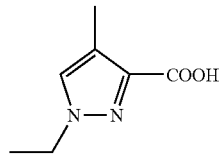

A mixture of ethyl 1-ethyl-4-methyl-1H-pyrazole-3-carboxylate (8.60 g, 47.2 mmol), 8N aqueous sodium hydroxide solution (11.8 mL) and ethanol (30 mL) was stirred at room temperature for 15 hr. The reaction mixture was neutralized with 1N hydrochloric acid, diluted with water, and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (5.19 g, 71%) as a white solid.

$^1$H-NMR (DMSO-d$_6$, 300 MHz) δ 1.35 (3H, t, J=7.3 Hz), 2.16 (3H, d, J=0.8 Hz), 4.10 (2H, q, J=7.3 Hz), 7.61 (1H, d, J=0.8 Hz), 12.41 (1H, br s).

Reference Example 53 ethyl 4-ethyl-1-methyl-1H-pyrazole-3-carboxylate

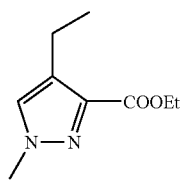

In the same manner as in Reference Example 51 and using 1-ethoxybut-1-en (25.0 g, 250 mmol), pyridine (18.2 mL), trichloroacetyl chloride (25.3 mL, 226 mmol), diethyl ether (100 mL), 0.2N hydrochloric acid (200 mL), methylhydrazine (12.6 g, 273 mmol) and ethanol (220 mL) as starting materials, the title compound (470 mg, 1.1%) was obtained as a colorless oil.

$^1$H-NMR (DMSO-d$_6$, 300 MHz) δ 1.12 (3H, t, J=7.5 Hz), 1.27 (3H, t, J=7.1 Hz), 2.59-2.68 (2H, m), 3.84 (3H, s), 4.23 (2H, q, J=7.1 Hz), 7.62 (1H, s).

Reference Example 54

4-ethyl-1-methyl-1H-pyrazole-3-carboxylic acid

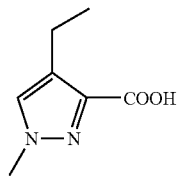

In the same manner as in Reference Example 52 and using ethyl 4-ethyl-1-methyl-1H-pyrazole-3-carboxylate (460 mg, 2.50 mmol), 8N aqueous sodium hydroxide solution (620 μL) and ethanol (3 mL) as starting materials, the title compound (200 mg, 53%) was obtained as a white solid.

$^1$H-NMR (CDCl$_3$, 300 MHz) δ 1.21 (3H, t, J=7.4 Hz), 2.78 (2H, q, J=7.4 Hz), 3.95 (3H, s), 7.24 (1H, s).

Reference Example 55 tert-butyl {2-chloro-5-[(6-nitropyridin-3-yl)oxy]phenyl}carbamate

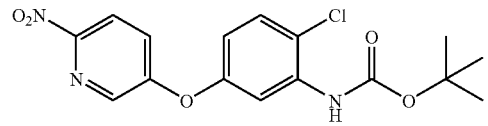

5-Bromo-2-nitropyridine (14.0 g, 69.0 mmol) was added to a mixture of 3-amino-4-chlorophenol (9.44 g, 65.7 mmol), cesium carbonate (32.2 g, 99.0 mmol) and N,N-dimethylformamide (70 mL) at 0° C., and the mixture was stirred at room temperature for 17 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was dissolved in acetonitrile (100 mL). di-tert-Butyl dicarbonate (24.0 g, 110 mmol), 4-dimethylaminopyridine (8.04 g, 65.8 mmol) and acetonitrile (150 mL) were added, and the mixture was stirred at room temperature for 30 min. tert-Butyl alcohol (11.0 mL, 115 mmol) was added to the reaction mixture, and the mixture was stirred at 80° C. for 68 hr. The reaction solution was concentrated under reduced pressure, and ethyl acetate was added to the residue. The mixture was washed with saturated aqueous sodium hydrogen carbonate solution and saturated brine, dried over anhydrous magnesium sulfate and filtrated. The filtrate was concentrated under reduced pressure, and the residue was purified by column chromatography (silica gel, hexane/ethyl acetate=100/0→80/20) to give the title compound (13.0 g, 54%) as a pale-yellow oil.

$^1$H-NMR (CDCl$_3$, 300 MHz) δ 1.52 (9H, s), 6.73 (1H, dd, J=8.8, 2.8 Hz), 7.38-7.47 (2H, m), 8.10 (1H, d, J=2.6 Hz), 8.18 (1H, d, J=1.5 Hz), 8.25 (1H, d, J=8.8 Hz), 8.32 (1H, d, J=2.6 Hz).

Reference Example 56 tert-butyl {5-[(6-aminopyridin-3-yl)oxy]-2-chlorophenyl}carbamate

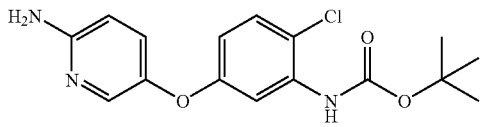

To a solution of tert-butyl {2-chloro-5-[(6-nitropyridin-3-yl)oxy]phenyl}carbamate (13.5 g, 36.9 mmol) in methanol (500 mL) was added palladium carbon (50% water-containing product, 2.96 g), and the mixture was stirred under a hydrogen atmosphere at room temperature for 17 hr. The reaction mixture was filtered through celite, and the filtrate was concentrated under reduced pressure. The residue was purified by column chromatography (silica gel, hexane/ethyl acetate=100/0→75/25) to give the title compound (7.29 g, 59%) as a pale-yellow oil.

$^1$H-NMR (CDCl$_3$, 300 MHz) δ 1.51 (9H, s), 4.37 (2H, s), 6.45-6.55 (2H, m), 6.99 (1H, s), 7.15-7.25 (2H, m), 7.85-7.91 (2H, m).

Reference Example 57 ethyl {[(5-{3-[(tert-butoxycarbonyl)amino]-4-chlorophenoxy}pyridin-2-yl)amino]carbonothioyl}carbamate

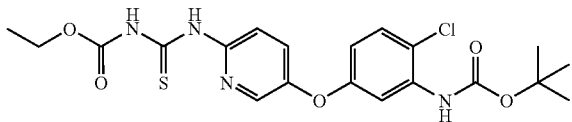

In the same manner as in Reference Example 30 and using tert-butyl {5-[(6-aminopyridin-3-yl)oxy]-2-chlorophenyl}carbamate (10.8 g, 32.3 mmol), ethyl isothiocyanatoformate (4.60 mL, 38.9 mmol) and DMSO (60 mL) as starting materials, the title compound (14.6 g, 97%) was obtained as a pale-yellow oil.

$^1$H-NMR (CDCl$_3$, 300 MHz) δ 1.35 (3H, t, J=7.2 Hz), 1.51 (9H, s), 4.31 (2H, q, J=7.2 Hz), 6.61 (1H, dd, J=8.7, 3.0 Hz), 7.04 (1H, s), 7.30 (1H, d, J=8.7 Hz), 7.37 (1H, dd, J=9.0, 2.8 Hz), 8.00 (1H, d, J=2.8 Hz), 8.05 (1H, s), 8.17 (1H, d, J=3.0 Hz), 8.75 (1H, d, J=9.0 Hz), 12.03 (1H, s).

Reference Example 58

4-(3-nitrophenoxy)pyridin-2-amine

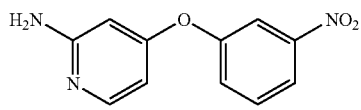

A mixture of 3-nitrophenol (3.65 g, 26.2 mmol), potassium tert-butoxide (3.23 g, 28.8 mmol) and N,N-dimethylformamide (20 mL) was stirred at room temperature for 30 min. After stirring, methyl 4-chloropyridine-2-carboxylate (3.00 g, 17.5 mmol) and potassium carbonate (10.9 g, 78.6 mmol) were added, and the mixture was stirred at 120° C. for 3 hr. The reaction mixture was diluted with water and extracted with ethyl acetate. The organic layer was washed with water and saturated brine, dried over anhydrous magnesium sulfate and filtrated. The filtrate was concentrated under reduced pressure, ethanol (20 mL) and 8N aqueous sodium hydroxide solution (3 mL) were added to the residue, and the mixture was stirred at room temperature for 2 hr. The reaction mixture was neutralized with 1N hydrochloric acid, and the precipitated solid was collected by filtration and washed with water to give 4-(3-nitrophenoxy)pyridine-2-carboxylic acid (345 mg, 8.0%) as a white solid. A mixture of 4-(3-nitrophenoxy)pyridine-2-carboxylic acid (339 mg, 1.24 mmol) thus-obtained, diphenylphosphoryl azide (333 μL, 1.55 mmol), triethylamine (215 μL, 1.55 mmol), N,N-dimethylformamide (5 mL) and water (5 mL) was stirred at 100° C. for 15 hr. The reaction mixture was diluted with water and extracted with ethyl acetate. The organic layer was washed with water and saturated brine, dried over anhydrous magnesium sulfate and filtrated. The filtrate was concentrated under reduced pressure. The residue was collected by filtration and washed with ethyl acetate-hexane to give the title compound (253 mg, 8.8%) as a white solid.

$^1$H-NMR (DMSO-d$_6$, 300 MHz) δ 5.95 (1H, d, J=2.1 Hz), 6.04 (2H, s), 6.21 (1H, dd, J=5.7, 2.1 Hz), 7.59-7.64 (1H, m), 7.74 (1H, t, J=8.1 Hz), 7.85-7.91 (2H, m), 8.07-8.11 (1H, m).

Reference Example 59

N-(6-hydroxy-1,3-benzothiazol-2-yl)cyclopropanecarboxamide

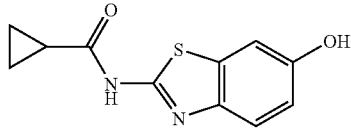

To a solution of 2-amino-1,3-benzothiazol-6-ol (9.03 g, 54.3 mmol) and triethylamine (8.27 mL, 59.7 mmol) in tetrahydrofuran (100 mL) was added with stirring under ice-cooling a solution of cyclopropanecarbonyl chloride (5.19 mL, 57.0 mmol) in tetrahydrofuran (25 mL), and the mixture was stirred at room temperature for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was collected by filtration and washed with hexane-ethyl acetate to give the title compound (12.3 g, 97%) as a white solid.

$^1$H-NMR (DMSO-d$_6$, 300 MHz) δ 0.95-1.05 (4H, m), 1.84-1.99 (1H, m), 6.93 (1H, dd, J=8.8, 2.6 Hz), 7.29 (1H, d, J=8.8 Hz), 7.45-7.50 (3H, m).

Reference Example 60

N-(3-hydroxyphenyl)-1,3-dimethyl-1H-pyrazole-5-carboxamide

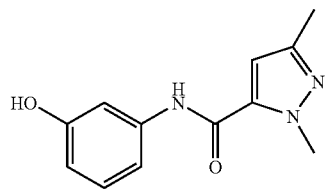

In the same manner as in Reference Example 11 and using 3-aminophenol (2.11 g, 19.3 mmol), triethylamine (2.81 mL, 20.3 mmol), 1,3-dimethyl-1H-pyrazole-5-carbonyl chloride (3.07 g, 19.4 mmol) and tetrahydrofuran (30 mL) as starting materials, the title compound (4.00 g, 90%) was obtained as a white solid.

$^1$H-NMR (DMSO-d$_6$, 300 MHz) δ 2.19 (3H, s), 3.98 (3H, s), 6.47-6.53 (1H, m), 6.79 (1H, s), 7.08-7.13 (2H, m), 7.28 (1H, s), 9.41 (1H, s), 9.97 (1H, s).

Reference Example 61

1,3-dimethyl-N-{3-[(5-nitropyridin-2-yl)oxy]phenyl}-1H-pyrazole-5-carboxamide

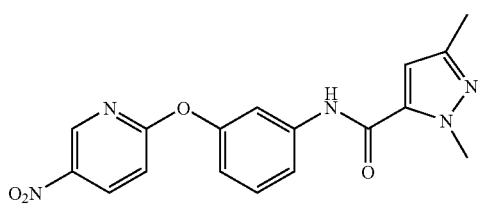

A mixture of N-(3-hydroxyphenyl)-1,3-dimethyl-1H-pyrazole-5-carboxamide (1.58 g, 6.83 mmol), 2-chloro-5-nitropyridine (1.03 g, 6.51 mmol), potassium carbonate (1.42 g, 10.2 mmol) and N,N-dimethylformamide (10 mL) was stirred at 60° C. for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (hexane/ethyl acetate=70/30→0/100) to give the title compound (2.26 g, 94%) as a white solid.

$^1$H-NMR (DMSO-d$_6$, 300 MHz) δ 2.20 (3H, s), 3.98 (3H, s), 6.83 (1H, s), 6.96-7.00 (1H, m), 7.28 (1H, d, J=9.3 Hz), 7.44 (1H, t, J=8.3 Hz), 7.58-7.62 (1H, m), 7.69 (1H, t, J=2.1 Hz), 8.61-8.65 (1H, m), 9.04 (1H, d, J=3.3 Hz), 10.27 (1H, s).

Reference Example 62

N-{3-[(5-aminopyridin-2-yl)oxy]phenyl}-1,3-dimethyl-1H-pyrazole-5-carboxamide

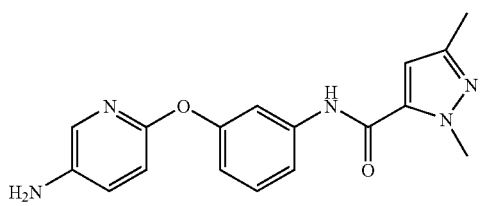

To a solution of 1,3-dimethyl-N-{3-[(5-nitropyridin-2-yl)oxy]phenyl}-1H-pyrazole-5-carboxamide (2.26 g, 6.40 mmol) in methanol (20 mL) was added palladium carbon (50% water-containing product, 200 mg), and the mixture was stirred under a hydrogen atmosphere at room temperature for 5 hr. The reaction mixture was filtered through celite, and the filtrate was concentrated under reduced pressure. The residue was collected by filtration and washed with ethyl acetate-hexane to give the title compound (1.77 g, 86%) as a white solid.

$^1$H-NMR (DMSO-d$_6$, 300 MHz) δ 2.19 (3H, s), 3.97 (3H, s), 5.14 (2H, s), 6.67-6.71 (1H, m), 6.76-7.00 (2H, m), 7.08 (1H, dd, J=8.4, 3.0 Hz), 7.28 (1H, t, J=8.1 Hz), 7.36 (1H, t, J=2.1 Hz), 7.43-7.47 (1H, m), 7.56 (1H, d, J=3.0 Hz), 11.10 (1H, s).

Reference Example 63 methyl 3-[(5-nitropyridin-2-yl)oxy]benzoate

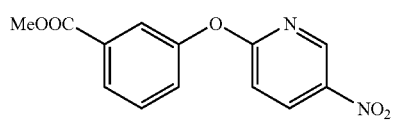

A mixture of methyl 3-hydroxybenzoate (8.14 g, 53.5 g), 2-chloro-5-nitropyridine (8.08 g, 51.0 mmol), potassium carbonate (11.1 g, 80.3 mmol) and N,N-dimethylformamide (100 mL) was stirred at 60° C. for 3 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (14.4 g, 98%) as a white solid.

$^1$H-NMR (DMSO-d$_6$, 300 MHz) δ 3.86 (3H, s), 7.33 (1H, d, J=9.0 Hz), 7.53-7.57 (1H, m), 7.64 (1H, t, J=7.8 Hz), 7.73-7.75 (1H, m), 7.86-7.90 (1H, m), 8.64 (1H, dd, J=9.0, 2.7 Hz), 9.02 (1H, d, J=2.7 Hz).

Reference Example 64 methyl 3-[(5-aminopyridin-2-yl)oxy]benzoate

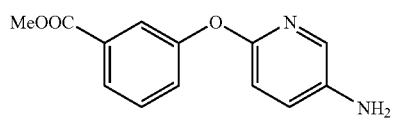

To a solution of methyl 3-[(5-nitropyridin-2-yl)oxy]benzoate (14.4 g, 52.5 mmol) in methanol (100 mL) was added palladium carbon (50% water-containing product, 1.40 g), and the mixture was stirred under a hydrogen atmosphere at room temperature for 6 hr. The reaction mixture was filtered through celite, and the filtrate was concentrated under reduced pressure, and the residue was dried to give the title compound (12.9 g, quant.) as a yellow oil.

$^1$H-NMR (DMSO-d$_6$, 300 MHz) δ 3.83 (3H, s), 5.19 (2H, s), 6.84 (1H, d, J=8.4 Hz), 7.12 (1H, dd, J=8.4, 3.0 Hz), 7.25-7.31 (1H, m), 7.42-7.52 (2H, m), 7.58 (1H, d, J=3.0 Hz), 7.65-7.69 (1H, m).

Reference Example 65 ethyl 1-ethyl-3-(trifluoromethyl)-1H-pyrazole-4-carboxylate and ethyl 1-ethyl-4-(trifluoromethyl)-1H-pyrazole-3-carboxylate

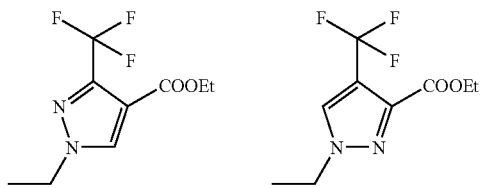

A mixture of ethyl 4,4,4-trifluorobut-2-ynoate (2.00 g, 12.0 mmol), 3-ethyl-1,2,3-oxadiazol-3-ium-5-olate (1.37 g, 12.0 mmol) and o-xylene (8 mL) was stirred at 100° C. for 7 hr. The reaction mixture was concentrated under reduced pressure, ethyl acetate and saturated aqueous sodium hydrogen carbonate solution were added to the residue, and the organic layer was separated. The organic layer was washed with water and saturated brine, dried over anhydrous magnesium sulfate and filtrated. The filtrate was concentrated under reduced pressure, and the residue was purified by column chromatography (hexane/ethyl acetate=90/10→30/70) to give a mixture (990 mg, 35%) of ethyl 1-ethyl-3-(trifluoromethyl)-1H-pyrazole-4-carboxylate (1) and ethyl 1-ethyl-4-(trifluoromethyl)-1H-pyrazole-3-carboxylate (2) as a colorless oil.

$^1$H-NMR (DMSO-$d_6$, 300 MHz) δ 1.24-1.44 (6H, m), 4.20-4.32 (4H, m), 8.53 (0.6H, s), 8.60 (0.4H, s).

Reference Example 66

1-ethyl-3-(trifluoromethyl)-1H-pyrazole-4-carboxylic acid and 1-ethyl-4-(trifluoromethyl)-1H-pyrazole-3-carboxylic acid

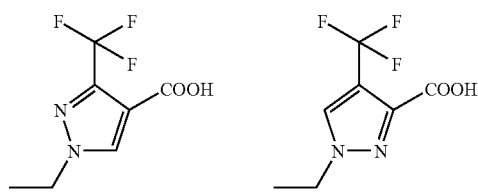

To a solution of a mixture of ethyl 1-ethyl-3-(trifluoromethyl)-1H-pyrazole-4-carboxylate and ethyl 1-ethyl-4-(trifluoromethyl)-1H-pyrazole-3-carboxylate (970 mg, 4.11 mmol) in ethanol (6 mL) was added 8N aqueous sodium hydroxide solution (1.5 mL), and the mixture was stirred at room temperature for 15 hr. The reaction mixture was adjusted to pH 4 with 1N hydrochloric acid, and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give a mixture (781 mg, 91%) of 1-ethyl-3-(trifluoromethyl)-1H-pyrazole-4-carboxylic acid (1) and 1-ethyl-4-(trifluoromethyl)-1H-pyrazole-3-carboxylic acid (2) as a white solid.

$^1$H-NMR (DMSO-$d_6$, 300 MHz) δ 1.37-1.43 (3H, m), 4.19-4.26 (2H, m), 8.47 (0.6H, s), 8.50 (0.4H, s), 13.05 (1H, br s).

Reference Example 67 ethyl 2-ethyl-5-(trifluoromethyl)-1,3-oxazole-4-carboxylate

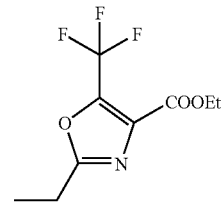

To a mixture of rhodium acetate (100 mg) and propionitrile (15 mL) was added ethyl 2-diazo-4,4,4-trifluoro-3-oxobutanoate (4.20 g, 20.0 mmol) over 12 hr, and the mixture was stirred at 80° C. for 5 days. The reaction mixture was filtered through celite, and the filtrate was concentrated under reduced pressure. The residue was purified by column chromatography (hexane/ethyl acetate=90/10→0/100) to give the title compound (2.03 g, 43%) as a yellow oil.

$^1$H-NMR (DMSO-$d_6$, 300 MHz) δ 1.25-1.32 (6H, m), 2.86-2.94 (2H, m), 4.34 (2H, q, J=7.5 Hz).

Reference Example 68

2-ethyl-5-(trifluoromethyl)-1,3-oxazole-4-carboxylic acid

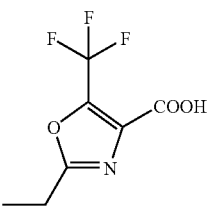

To a solution of ethyl 2-ethyl-5-(trifluoromethyl)-1,3-oxazole-4-carboxylate (2.00 g, 8.43 mmol) in ethanol (10 mL) was added 8N aqueous sodium hydroxide solution (3 mL), and the mixture was stirred at 50° C. for 1.5 hr. The reaction mixture was adjusted to pH 4 with 1N hydrochloric acid, and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (800 mg, 45%) as a white solid.

$^1$H-NMR (DMSO-$d_6$, 300 MHz) δ 1.27 (3H, t, J=7.6 Hz), 2.88 (2H, q, J=7.6 Hz)

Reference Example 69

N-{3-[(6-aminopyridin-3-yl)oxy]phenyl}-3-methylpyridine-2-carboxamide

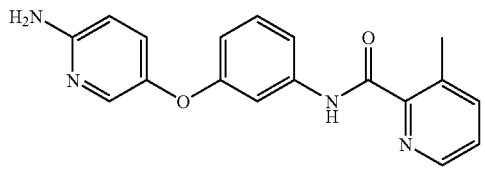

To a solution of 3-methylpyridine-2-carboxylic acid (1.38 g, 10.1 mmol) in tetrahydrofuran (100 mL) were added N,N-dimethylformamide (2 drops) and oxalyl chloride (1.75 mL, 20.2 mmol) at 0° C., and the mixture was stirred at room temperature for 3 hr. The reaction mixture was concentrated under reduced pressure, and the residue was dissolved in N,N-dimethylacetamide (50 mL). A solution of 5-(3-aminophenoxy)pyridin-2-amine (1.83 g, 9.09 mmol) in N,N-dimethylacetamide (5 mL) was added with stirring at room temperature, and the mixture was stirred at room temperature for 13 hr. The reaction mixture was diluted with aqueous sodium hydrogen carbonate solution and extracted with ethyl acetate. The organic layer was washed with saturated brine, dried over anhydrous magnesium sulfate and filtrated. The filtrate was concentrated under reduced pressure and washed with ethyl acetate-hexane to give the title compound (1.84 g, 57%) as a pale-brown solid.

$^1$H-NMR (CDCl$_3$, 400 MHz) δ 2.80 (3H, s), 4.39 (2H, br s), 6.54 (1H, d, J=8.8 Hz), 6.69 (1H, dd, J=8.3, 2.4 Hz), 7.24 (1H, dd, J=8.8, 2.9 Hz), 7.28-7.31 (1H, m), 7.34-7.40 (2H, m), 7.48 (1H, dd, J=7.8, 1.5 Hz), 7.64 (1H, d, J=7.8 Hz), 7.95 (1H, d, J=2.7 Hz), 8.45 (1H, dd, J=4.6, 1.5 Hz), 10.24 (1H, br s).

Reference Example 70 ethyl {[5-(3-{[(3-methylpyridin-2-yl) carbonyl]amino}phenoxy)pyridin-2-yl]carbamothioyl}carbamate

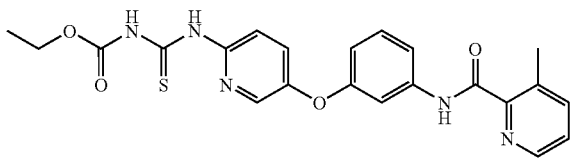

To a solution of N-{3-[(6-aminopyridin-3-yl)oxy]phenyl}-3-methylpyridine-2-carboxamide (1.84 g, 5.75 mmol) in DMSO (20 mL) was added dropwise with stirring under ice-cooling ethyl isothiocyanatoformate (0.75 mL, 6.35 mmol), and the mixture was stirred at room temperature for 12 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by silica gel column chromatography (25%→40% ethyl acetate-hexane) to give the title compound (2.00 g, 77%) as a white solid.

$^1$H-NMR (CDCl$_3$, 400 MHz) δ 1.35 (3H, t, J=7.2 Hz), 2.81 (3H, s), 4.31 (2H, q, J=7.2 Hz), 6.79 (1H, dd, J=8.1, 2.2 Hz), 7.30-7.45 (3H, m), 7.48-7.54 (1H, m), 7.58 (1H, t, J=2.0 Hz), 7.65 (1H, d, J=7.8 Hz), 8.02 (1H, s), 8.22 (1H, d, J=2.9 Hz), 8.45 (1H, d, J=4.6 Hz), 8.75 (1H, d, J=9.0 Hz), 10.32 (1H, s), 12.03 (1H, s).

Reference Example 71

3-methyl-N-{3-[(6-{[(4-methylphenyl)sulfonyl]amino}pyridin-3-yl) oxy]phenyl}pyridine-2-carboxamide

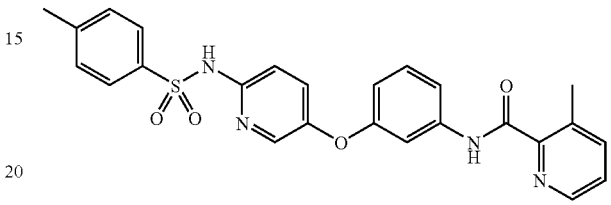

A mixture of N-{3-[(6-aminopyridin-3-yl)oxy]phenyl}-6-methylpyridine-2-carboxamide (8.25 g, 25.8 mmol), p-toluenesulfonyl chloride (5.41 g, 28.4 mmol) and pyridine (50 mL) was stirred at 80° C. for 2 hr. The reaction solution was concentrated under reduced pressure, and ethyl acetate was added to the residue. The mixture was washed with aqueous sodium hydrogen carbonate solution, water and saturated brine, dried over anhydrous magnesium sulfate and filtrated. The filtrate was concentrated under reduced pressure, and the residue was washed with ethyl acetate-hexane to give the title compound (12.1 g, 99%) as a pale-brown solid.

$^1$H-NMR (CDCl$_3$, 400 MHz) δ 2.38 (3H, s), 2.80 (3H, s), 6.71 (1H, dd, J=8.1, 2.4 Hz), 7.24 (3H, d, J=8.6 Hz), 7.28-7.40 (3H, m), 7.41-7.47 (2H, m), 7.56 (1H, t, J=2.2 Hz), 7.65 (1H, d, J=7.8 Hz), 7.71 (2H, d, J=8.3 Hz), 8.18 (1H, d, J=2.9 Hz), 8.45 (1H, d, J=3.9 Hz), 10.30 (1H, s).

Reference Example 72

N-(3-{[1-(2-amino-2-oxoethyl)-6-{[(4-methylphenyl)sulfonyl]imino}-1,6-dihydropyridin-3-yl]oxy}phenyl)-3-methylpyridine-2-carboxamide

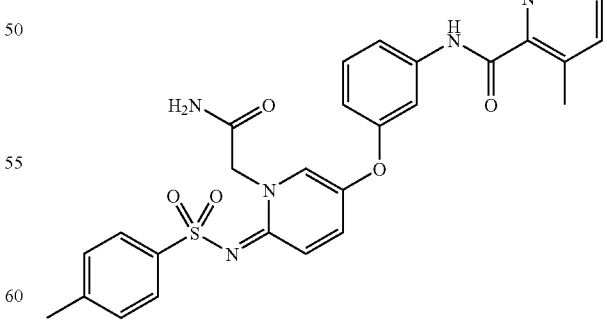

A mixture of 3-methyl-N-{3-[(6-{[(4-methylphenyl)sulfonyl]amino}pyridin-3-yl)oxy]phenyl}pyridine-2-carboxamide (12.4 g, 26.2 mmol), N,N-diisopropylethylamine (6.00 mL, 34.4 mmol) and N,N-dimethylformamide (100 mL) was stirred at room temperature for 1 hr. Iodoacetamide (6.29 g, 34.0 mmol) was added, and the mixture was stirred at room temperature for 71 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was recrystallized from ethanol to give the title compound (9.72 g, 70%) as a white solid.

$^1$H-NMR (DMSO-$d_6$, 400 MHz) δ 2.34 (3H, s), 2.55 (3H, s), 4.83 (2H, s), 6.73 (1H, dd, J=8.2, 2.3 Hz), 7.28 (2H, d, J=8.3 Hz), 7.34 (1H, t, J=8.2 Hz), 7.37-7.44 (2H, m), 7.52 (1H, dd, J=7.8, 4.6 Hz), 7.57 (1H, t, J=2.1 Hz), 7.64-7.70 (3H, m), 7.71-7.85 (3H, m), 8.13 (1H, d, J=2.7 Hz), 8.53 (1H, d, J=3.9 Hz), 10.65 (1H, s).

Reference Example 73

N-{3-[(6-aminopyridin-3-yl)oxy]phenyl}-6-methylpyridine-2-carboxamide

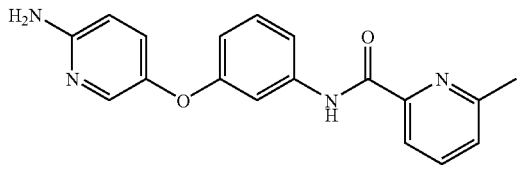

To a solution of 6-methylpyridine-2-carboxylic acid (5.66 g, 41.3 mmol) in tetrahydrofuran (300 mL) were added N,N-dimethylformamide (5 drops) and oxalyl chloride (7.20 mL, 83.0 mmol) at 0° C., and the mixture was stirred at room temperature for 2 hr. The reaction mixture was concentrated under reduced pressure, and the residue was dissolved in N,N-dimethylacetamide (200 mL). A solution of 5-(3-aminophenoxy)pyridin-2-amine (7.90 g, 39.3 mmol) in N,N-dimethylacetamide (20 mL) was added with stirring at room temperature, and the mixture was stirred at room temperature for 65 hr. The reaction mixture was diluted with aqueous sodium hydrogen carbonate solution and extracted with ethyl acetate. The organic layer was washed with water and saturated brine, dried over anhydrous magnesium sulfate and filtrated. The filtrate was concentrated under reduced pressure, and the residue was washed with ethyl acetate-hexane to give the title compound (10.4 g, 83%) as a pale-brown solid.

$^1$H-NMR (DMSO-$d_6$, 400 MHz) δ 2.89 (3H, s), 6.19 (2H, s), 6.79 (1H, d, J=9.1 Hz), 6.96 (1H, dd, J=8.1, 2.5 Hz), 7.51 (1H, dd, J=8.9, 2.5 Hz), 7.58 (1H, t, J=8.2 Hz), 7.77-7.84 (2H, m), 7.86 (1H, t, J=2.0 Hz), 8.06 (1H, d, J=2.9 Hz), 8.17-8.23 (2H, m), 10.74 (1H, s).

Reference Example 74

6-methyl-N-{3-[(6-{[(4-methylphenyl)sulfonyl]amino}pyridin-3-yl)oxy]phenyl}pyridine-2-carboxamide

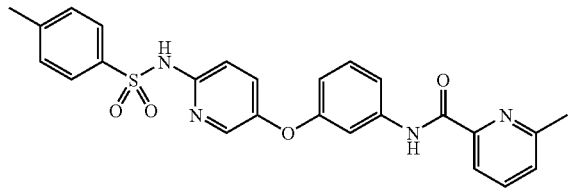

A mixture of N-{3-[(6-aminopyridin-3-yl)oxy]phenyl}-6-methylpyridine-2-carboxamide (10.41 g, 32.5 mmol), p-toluenesulfonyl chloride (6.83 g, 35.8 mmol) and pyridine (75 mL) was stirred at 80° C. for 2 hr. The reaction solution was concentrated under reduced pressure, and ethyl acetate was added to the residue. The mixture was washed with aqueous sodium hydrogen carbonate solution, water and saturated brine, dried over anhydrous magnesium sulfate and filtrated. The filtrate was concentrated under reduced pressure, and the residue was washed with ethyl acetate-hexane to give the title compound (14.8 g, 96%) as a pale-brown solid.

$^1$H-NMR (CDCl$_3$, 400 MHz) δ 2.38 (3H, s), 2.63 (3H, s), 6.73 (1H, dd, J=8.2, 2.3 Hz), 7.17-7.28 (3H, m), 7.30-7.39 (3H, m), 7.41-7.49 (2H, m), 7.61 (1H, t, J=2.2 Hz), 7.72 (2H, d, J=8.1 Hz), 7.79 (1H, t, J=7.8 Hz), 8.08 (1H, d, J=7.8 Hz), 8.18 (1H, d, J=2.7 Hz), 10.11 (1H, s).

Reference Example 75

N-(3-{[1-(2-amino-2-oxoethyl)-6-{[(4-methylphenyl)sulfonyl]imino}-1,6-dihydropyridin-3-yl]oxy}phenyl)-6-methylpyridine-2-carboxamide

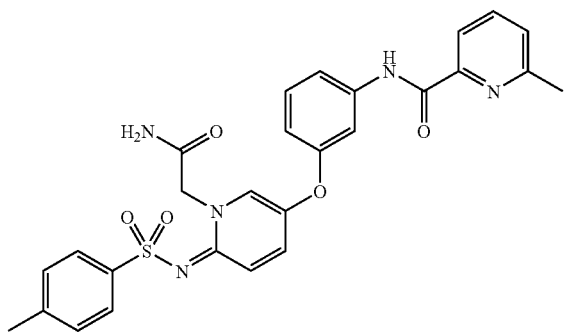

A mixture of 6-methyl-N-{3-[(6-{[(4-methylphenyl)sulfonyl]amino}pyridin-3-yl)oxy]phenyl}pyridine-2-carboxamide (14.8 g, 31.2 mmol), N,N-diisopropylethylamine (7.10 mL, 40.7 mmol) and N,N-dimethylformamide (100 mL) was stirred at room temperature for 20 min. After stirring, iodoacetamide (7.51 g, 40.6 mmol) was added, and the mixture was stirred at room temperature for 16 hr. The reaction mixture was diluted with aqueous sodium hydrogen carbonate solution and extracted with ethyl acetate. The organic layer was washed with water and saturated brine, dried over anhydrous magnesium sulfate and filtrated. The filtrate was concentrated under reduced pressure, and the residue was purified by silica gel column chromatography (0%→100% ethyl acetate-hexane→10% methanol-ethyl acetate) to give the title compound (14.6 g, 88%) as a pale-yellow oil.

$^1$H-NMR (CDCl$_3$, 400 MHz) δ 2.37 (3H, s), 2.63 (3H, s), 4.81 (2H, s), 5.69 (1H, br s), 6.73 (1H, dd, J=8.3, 2.4 Hz), 7.10 (1H, br s), 7.24 (2H, d, J=8.3 Hz), 7.30-7.36 (2H, m), 7.39-7.49 (3H, m), 7.59-7.65 (2H, m), 7.75-7.84 (3H, m), 8.07 (1H, d, J=7.8 Hz), 10.13 (1H, s).

Example 1-1

1,3-dimethyl-N-[3-({2-[(trifluoroacetyl)amino]imidazo[1,2-a]pyridin-6-yl}oxy)phenyl]-1H-pyrazole-5-carboxamide

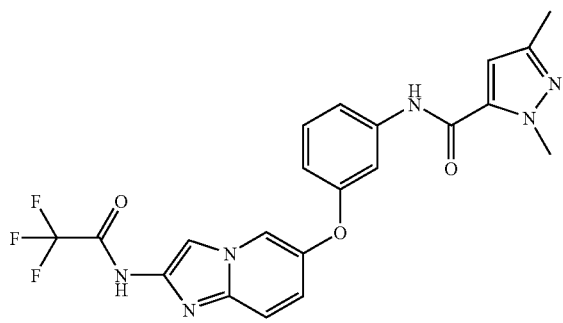

A mixture of N-{3-[(1-(2-amino-2-oxoethyl)-6-{[(4-methylphenyl)sulfonyl]amino}-1,6-dihydropyridin-3-yl)oxy]phenyl}-1,3-dimethyl-1H-pyrazole-5-carboxamide (882 mg, 1.65 mmol), trifluoroacetic anhydride (6 mL) and dichloromethane (8 mL) was stirred at room temperature for 2.5 hr. The reaction solution was concentrated under reduced pressure, saturated aqueous sodium hydrogen carbonate solution was added to the residue, and the mixture was extracted with ethyl acetate (×3). The organic layer was washed with saturated brine, dried over anhydrous magnesium sulfate and filtrated. The filtrate was concentrated under reduced pressure, and the residue was purified by column chromatography (silica gel, hexane/ethyl acetate=70/30→0/100) to give the title compound (338 mg, 45%) as a white solid.

$^1$H-NMR (DMSO-d$_6$, 300 MHz) δ 2.17 (3H, s), 3.95 (3H, s), 6.77-6.84 (2H, m), 7.20 (1H, dd, J=9.6, 2.4 Hz), 7.35 (1H, t, J=8.1 Hz), 7.43 (1H, d, J=2.1 Hz), 7.53-7.60 (2H, m), 8.26 (1H, s), 8.64 (1H, d, J=2.4 Hz), 10.14 (1H, s), 12.48 (1H, s).

Example 1-2

N-{3-[(2-aminoimidazo[1,2-a]pyridin-6-yl)oxy]phenyl}-1,3-dimethyl-1H-pyrazole-5-carboxamide

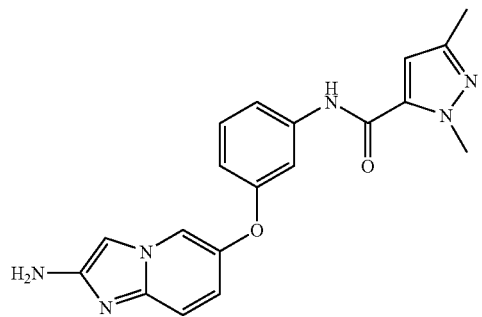

A mixture of 1,3-dimethyl-N-[3-({2-[(trifluoroacetyl)amino]imidazo[1,2-a]pyridin-6-yl}oxy)phenyl]-1H-pyrazole-5-carboxamide (328 mg, 0.715 mmol), 1N aqueous sodium hydroxide solution (3 mL) and ethanol (3 mL) was stirred at 40° C. for 2 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was purified by column chromatography (silica gel, methanol/ethyl acetate=0/100→20/80) to give the title compound (205 mg, 79%) as a white solid.

$^1$H-NMR (DMSO-d$_6$, 300 MHz) δ 2.17 (3H, s), 3.96 (3H, s), 5.09 (2H, s), 6.75-6.78 (2H, m), 6.86 (1H, dd, J=9.4, 2.0 Hz), 7.01 (1H, s), 7.22 (1H, d, J=9.4 Hz), 7.32 (1H, d, J=8.3 Hz), 7.37 (1H, t, J=2.3 Hz), 7.50-7.60 (1H, m), 8.33 (1H, d, J=2.0 Hz), 10.12 (1H, s).

Example 2

N-[3-({2-[(cyclopropylcarbonyl)amino]imidazo[1,2-a]pyridin-6-yl}oxy)phenyl]-1,3-dimethyl-1H-pyrazole-5-carboxamide

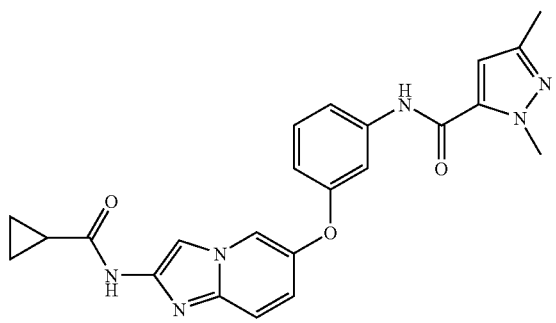

To a solution of N-{3-[(2-aminoimidazo[1,2-a]pyridin-6-yl)oxy]phenyl}-1,3-dimethyl-1H-pyrazole-5-carboxamide (270 mg, 0.745 mmol) and triethylamine (310 μL, 2.24 mmol) in tetrahydrofuran (5 mL) was added with stirring under ice-cooling cyclopropanecarbonyl chloride (88.0 μL, 0.969 mmol), and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=50/50→0/100) and recrystallized from ethyl acetate-hexane to give the title compound (191 mg, 60%) as a white solid.

$^1$H-NMR (DMSO-d$_6$, 300 MHz) δ 0.79-0.81 (4H, m), 1.89-1.97 (1H, m), 2.17 (3H, s), 3.95 (3H, s), 6.77-6.81 (2H, m), 7.08 (1H, dd, J=9.8, 2.4 Hz), 7.33 (1H, t, J=8.3 Hz), 7.39 (1H, t, J=2.1 Hz), 7.46-7.56 (2H, m), 8.06 (1H, s), 8.58 (1H, d, J=2.4 Hz), 10.12 (1H, s), 10.97 (1H, s).

Example 3

N-[2-chloro-5-({2-[(cyclopropylcarbonyl)amino]imidazo[1,2-a]pyridin-6-yl}oxy)phenyl]-1,3-dimethyl-1H-pyrazole-5-carboxamide

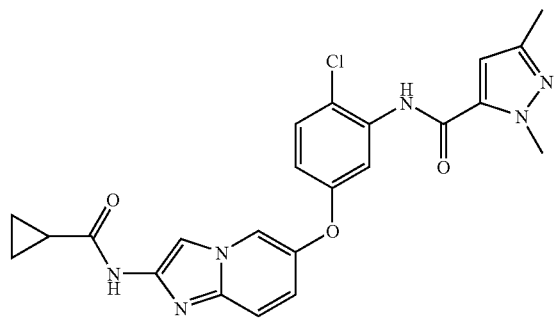

A mixture of N-{5-[(1-(2-amino-2-oxoethyl)-6-{[(4-methylphenyl)sulfonyl]amino}-1,6-dihydropyridin-3-yl)oxy]-2-chlorophenyl}-1,3-dimethyl-1H-pyrazole-5-carboxamide (300 mg, 0.527 mmol), trifluoroacetic anhydride (2 mL) and dichloromethane (2.5 mL) was stirred at room temperature for 5 hr. The reaction solution was concentrated under reduced pressure, saturated aqueous sodium hydrogen carbonate solution was added to the residue, and the mixture was extracted with ethyl acetate (×3). The organic layer was washed with saturated brine, dried over anhydrous magnesium sulfate and filtrated. The filtrate was concentrated under reduced pressure, 1N aqueous sodium hydroxide solution (10 mL) and ethanol (10 mL) were added to the residue, and the mixture was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was purified by column chromatography (NH silica gel, ethyl acetate) and recrystallized from ethyl acetate-hexane to give N-{5-[(2-aminoimidazo[1,2-a]pyridin-6-yl)oxy]-2-chlorophenyl}-1,3-dimethyl-1H-pyrazole-5-carboxamide (134 mg, 64%) as a white solid. To a solution of N-{5-[(2-aminoimidazo[1,2-a]pyridin-6-yl)oxy]-2-chlorophenyl}-1,3-dimethyl-1H-pyrazole-5-carboxamide (130 mg, 0.328 mmol) thus-obtained and triethylamine (136 µL, 0.984 mmol) in tetrahydrofuran (4 mL) was added with stirring under ice-cooling cyclopropanecarbonyl chloride (38.7 µL, 0.426 mmol), and the mixture was stirred at room temperature for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=50/50→0/100) and recrystallized from ethyl acetate-tetrahydrofuran to give the title compound (83.0 mg, 54%) as a white solid.

$^1$H-NMR (DMSO-$d_6$, 300 MHz) δ 0.78-0.81 (4H, m), 1.91-1.95 (1H, m), 2.18 (3H, s), 3.95 (3H, s), 6.80 (1H, s), 6.98 (1H, dd, J=9.2, 3.0 Hz), 7.09 (1H, dd, J=9.6, 2.2 Hz), 7.25 (1H, d, J=3.0 Hz), 7.46-7.54 (2H, m), 8.06 (1H, s), 8.61 (1H, d, J=2.2 Hz), 9.89 (1H, s), 10.97 (1H, s).

Example 4

N-[5-({2-[(cyclopropylcarbonyl)amino]imidazo[1,2-a]pyridin-6-yl}oxy)-2-methylphenyl]-1,3-dimethyl-1H-pyrazole-5-carboxamide

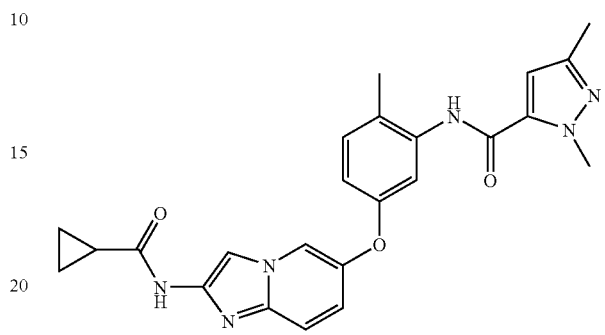

A mixture of N-{5-[(1-(2-amino-2-oxoethyl)-6-{[(4-methylphenyl)sulfonyl]amino}-1,6-dihydropyridin-3-yl)oxy]-2-methylphenyl}-1,3-dimethyl-1H-pyrazole-5-carboxamide (2.34 g, 4.27 mmol), trifluoroacetic anhydride (15 mL) and dichloromethane (20 mL) was stirred at room temperature for 5 hr. The reaction solution was concentrated under reduced pressure, 1N aqueous sodium hydroxide solution (20 mL) and ethanol (20 mL) were added to the residue and the mixture was stirred at room temperature for 1 hr. 8N Aqueous sodium hydroxide solution (4 mL) was further added and the mixture was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give N-{5-[(2-aminoimidazo[1,2-a]pyridin-6-yl)oxy]-2-methylphenyl}-1,3-dimethyl-1H-pyrazole-5-carboxamide (1.10 g, 68%) as a white solid. To a solution of N-{5-[(2-aminoimidazo[1,2-a]pyridin-6-yl)oxy]-2-methylphenyl}-1,3-dimethyl-1H-pyrazole-5-carboxamide (1.10 g, 2.92 mmol) thus-obtained and triethylamine (1.21 mL, 8.76 mmol) in tetrahydrofuran (15 mL) was added with stirring under ice-cooling cyclopropanecarbonyl chloride (345 µL, 3.80 mmol), and the mixture was stirred at room temperature for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=70/30→40/100) and recrystallized from ethyl acetate-hexane to give the title compound (863 mg, 60%) as a white solid.

$^1$H-NMR (DMSO-$d_6$, 300 MHz) δ 0.78-0.81 (4H, m), 1.91-1.94 (1H, m), 2.18 (3H, s), 2.19 (3H, s), 3.96 (3H, s), 6.78 (1H, s), 6.88 (1H, dd, J=8.5, 2.9 Hz), 7.02-7.08 (2H, m), 7.26 (1H, d, J=8.5 Hz), 7.46 (1H, d, J=9.4 Hz), 8.06 (1H, s), 8.53-8.55 (1H, m), 9.74 (1H, s), 10.97 (1H, s).

Example 5

N-[3-({2-[(cyclopropylcarbonyl)amino]imidazo[1,2-a]pyridin-6-yl}oxy)phenyl]-1,3-dimethyl-1H-pyrazole-5-carboxamide p-toluenesulfonate

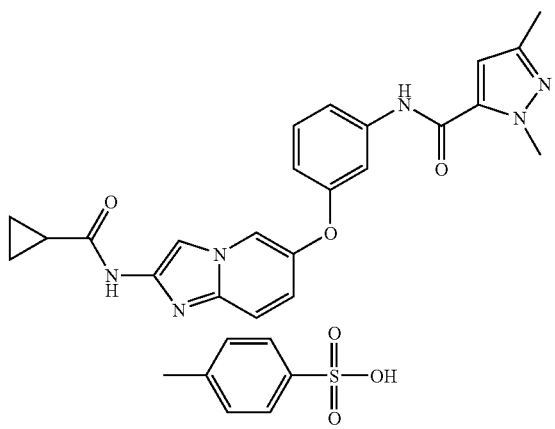

To a solution of N-[3-({2-[(cyclopropylcarbonyl)amino]imidazo[1,2-a]pyridin-6-yl}oxy)phenyl]-1,3-dimethyl-1H-pyrazole-5-carboxamide (204 mg, 0.474 mmol) in ethanol (8 mL) was added a solution of p-toluenesulfonic acid monohydrate (94.7 mg, 0.498 mmol) in ethyl acetate (1.10 mL), and the mixture was stirred at 0° C. for 2 hr and at room temperature for 2 days. The precipitated solid was collected by filtration and washed with ethanol to give the title compound (192 mg, 67%) as a white solid.

$^1$H-NMR (DMSO-$d_6$, 300 MHz) δ 0.89-0.95 (4H, m), 1.86-1.92 (1H, m), 1.99 (3H, s), 2.18 (3H, s), 3.97 (3H, s), 6.81 (1H, s), 6.84-6.88 (1H, m), 7.10-7.13 (2H, m), 7.37-7.57 (6H, m), 7.75 (1H, d, J=9.9 Hz), 8.09 (1H, s), 8.70 (1H, d, J=1.8 Hz), 10.21 (1H, s), 11.49 (1H, s).

Example 6

N-[3-({2-[(cyclopropylcarbonyl)amino]imidazo[1,2-a]pyridin-6-yl}oxy)phenyl]-1,3-dimethyl-1H-pyrazole-5-carboxamide hydrochloride

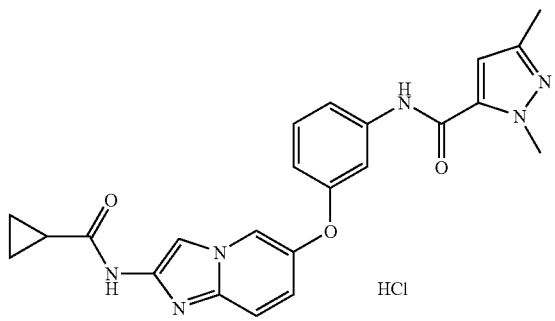

To a solution of N-[3-({2-[(cyclopropylcarbonyl)amino]imidazo[1,2-a]pyridin-6-yl}oxy)phenyl]-1,3-dimethyl-1H-pyrazole-5-carboxamide (318 mg, 0.739 mmol) in ethanol (15 mL) was added 1N hydrogen chloride-ethyl acetate solution (886 µL), and the mixture was stirred at room temperature for 2 days. The precipitated solid was collected by filtration and washed with ethanol to give the title compound (256 mg, 74%) as a white solid.

$^1$H-NMR (DMSO-$d_6$, 300 MHz) δ 0.87-0.90 (4H, m), 1.92-2.00 (1H, m), 2.18 (3H, s), 3.96 (3H, s), 6.82-6.86 (2H, m), 7.37 (1H, t, J=8.1 Hz), 7.44-7.58 (3H, m), 7.72 (1H, d, J=9.3 Hz), 8.10 (1H, s), 8.69 (1H, d, J=2.1 Hz), 10.23 (1H, s), 11.65 (1H, s).

Example 7-1

6-(3-nitrophenoxy)imidazo[1,2-a]pyridin-2-amine

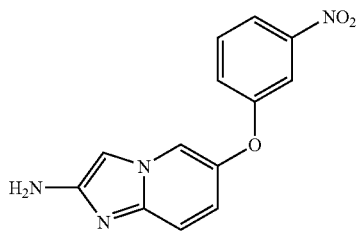

A mixture of 2-[2-{[(4-methylphenyl)sulfonyl]amino}-5-(3-nitrophenoxy)pyridin-1(2H)-yl]acetamide (4.70 g, 10.6 mmol), trifluoroacetic anhydride (30 mL) and dichloromethane (40 mL) was stirred at room temperature for 5 hr. The reaction solution was concentrated under reduced pressure, saturated aqueous sodium hydrogen carbonate solution was added to the residue and the mixture was extracted with ethyl acetate (×3). The organic layer was washed with saturated brine, dried over anhydrous magnesium sulfate and filtrated. The filtrate was concentrated under reduced pressure, 8N aqueous sodium hydroxide solution (10 mL) and ethanol (30 mL) were added to the residue and the mixture was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was purified by column chromatography (silica gel, ethyl acetate) to give the title compound (1.40 g, 49%) as a white solid.

$^1$H-NMR (DMSO-$d_6$, 300 MHz) δ 5.16 (2H, br s), 6.92 (1H, dd, J=9.4, 2.3 Hz), 7.02 (1H, s), 7.25 (1H, d, J=9.4 Hz), 7.47-7.51 (1H, m), 7.62-7.70 (2H, m), 7.93-7.97 (1H, m), 8.42 (1H, d, J=2.3 Hz).

Example 7-2

N-[6-(3-nitrophenoxy)imidazo[1,2-a]pyridin-2-yl]cyclopropanecarboxamide

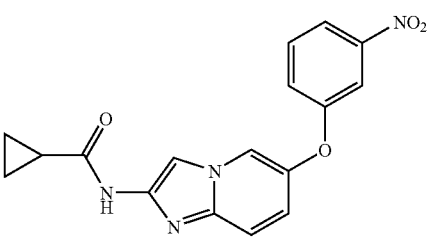

To a solution of 6-(3-nitrophenoxy)imidazo[1,2-a]pyridin-2-amine (1.40 g, 5.18 mmol) in pyridine (6 mL) was added with stirring under ice-cooling cyclopropanecarbonyl chloride (706 μL, 7.77 mmol), and the mixture was stirred at room temperature for 3 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was dissolved in methanol (50 mL). Sodium carbonate (1.00 g) and water (5 mL) were added, and the mixture was stirred at 60° C. for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, ethyl acetate) to give the title compound (622 mg, 35%) as a white solid.

$^1$H-NMR (DMSO-$d_6$, 300 MHz) δ 0.79-0.82 (4H, m), 1.89-1.96 (1H, m), 7.15 (1H, dd, J=9.6, 2.1 Hz), 7.49-7.55 (2H, m), 7.66 (1H, t, J=8.3 Hz), 7.75 (1H, t, J=2.4 Hz), 7.96-7.99 (1H, m), 8.07 (1H, s), 8.65-8.66 (1H, m), 10.99 (1H, s).

Example 7-3

N-[6-(3-aminophenoxy)imidazo[1,2-a]pyridin-2-yl]cyclopropanecarboxamide

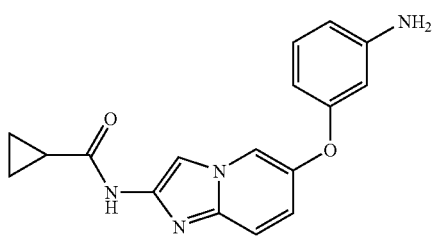

To a solution of N-[6-(3-nitrophenoxy)imidazo[1,2-a]pyridin-2-yl]cyclopropanecarboxamide (622 mg, 1.84 mmol) in methanol (10 mL) was added palladium carbon (50% water-containing product, 50 mg), and the mixture was stirred under a hydrogen atmosphere at room temperature for 4 hr. The reaction mixture was filtered through celite, and the filtrate was concentrated under reduced pressure. The residue was dissolved in methanol (20 mL), and ammonium chloride (300 mg, 5.61 mmol) and zinc (360 mg, 5.51 mmol) were added. The mixture was stirred under refluxing conditions for 2 hr. The reaction mixture was filtered through celite, and the filtrate was concentrated under reduced pressure. The residue was purified by column chromatography (NH silica gel, ethyl acetate) to give the title compound (275 mg, 49%) as a white solid.

$^1$H-NMR (DMSO-$d_6$, 300 MHz) δ 0.75-0.81 (4H, m), 1.88-1.93 (1H, m), 5.20 (2H, s), 6.10-6.14 (2H, m), 6.25-6.29 (1H, m), 6.93-7.04 (2H, m), 7.42 (1H, d, J=9.6 Hz), 8.03 (1H, s), 8.47-8.48 (1H, m), 10.93 (1H, s).

Example 7-4

N-[3-({2-[(cyclopropylcarbonyl)amino]imidazo[1,2-a]pyridin-6-yl}oxy)phenyl]-3-methylpyridine-2-carboxamide

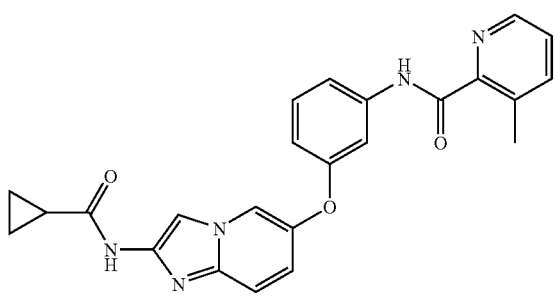

To a solution of 3-methylpyridine-2-carboxylic acid (53.5 mg, 0.390 mmol) in tetrahydrofuran (3 mL) were added oxalyl chloride (68.0 μL, 0.780 mmol) and N,N-dimethylformamide (1 drop), and the mixture was stirred at room temperature for 1 hr. The reaction mixture was concentrated under reduced pressure, the residue was dissolved in N,N-dimethylacetamide (3 mL). N-[6-(3-Aminophenoxy)imidazo[1,2-a]pyridin-2-yl]cyclopropanecarboxamide (60.0 mg, 0.195 mmol) was added with stirring under ice-cooling, and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, ethyl acetate) and recrystallized from ethyl acetate to give the title compound (58.0 mg, 70%) as a white solid.

$^1$H-NMR (DMSO-$d_6$, 300 MHz) δ 0.78-0.81 (4H, m), 1.89-1.97 (1H, m), 2.50 (3H, s), 6.75-6.79 (1H, m), 7.09 (1H, dd, J=9.6, 2.0 Hz), 7.33 (1H, t, J=8.0 Hz), 7.45-7.51 (2H, m), 7.55 (1H, t, J=2.3 Hz), 7.61-7.64 (1H, m), 7.76-7.82 (1H, m), 8.06 (1H, s), 8.49 (1H, dd, J=4.8, 1.2 Hz), 8.57 (1H, d, J=2.0 Hz), 10.58 (1H, s), 10.96 (1H, s).

Example 8

N-[3-({2-[(cyclopropylcarbonyl)amino]imidazo[1,2-a]pyridin-6-yl}oxy)phenyl]-1-methyl-1H-pyrazole-5-carboxamide

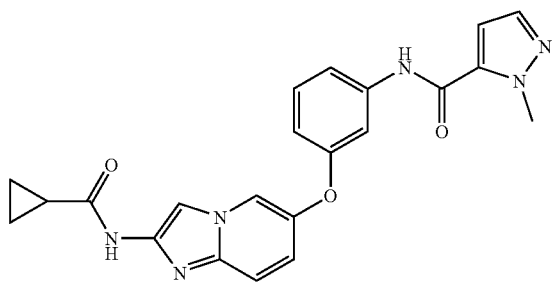

In the same manner as in Example 7-4 and using 1-methyl-1H-pyrazole-5-carboxylic acid (73.6 mg, 0.584 mmol), oxalyl chloride (102 μL, 1.17 mmol), tetrahydrofuran (5 mL), N,N-dimethylformamide (1 drop) and N-[6-(3-aminophenoxy)imidazo[1,2-a]pyridin-2-yl]cyclopropanecarboxamide (60.0 mg, 0.195 mmol) as starting materials, the title compound (41.0 mg, 50%) was obtained as a white solid.

$^1$H-NMR (DMSO-d$_6$, 300 MHz) δ 0.78-0.81 (4H, m), 1.89-1.97 (1H, m), 4.04 (3H, s), 6.79-6.82 (1H, m), 7.00 (1H, d, J=2.1 Hz), 7.08 (1H, dd, J=9.8, 2.0 Hz), 7.34 (1H, t, J=8.3 Hz), 7.39 (1H, t, J=2.1 Hz), 7.46-7.56 (3H, m), 8.06 (1H, s), 8.57 (1H, d, J=2.1 Hz), 10.20 (1H, s), 10.96 (1H, s).

Example 9-1

N-{5-[(2-aminoimidazo[1,2-a]pyridin-6-yl)oxy]-2-fluorophenyl}-1,3-dimethyl-1H-pyrazole-5-carboxamide

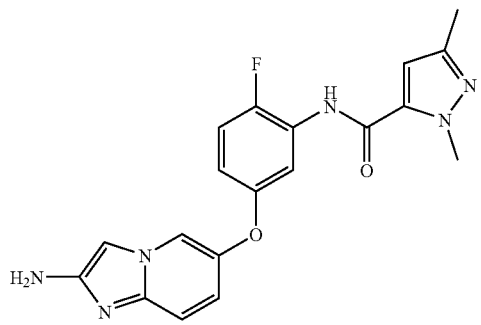

A mixture of N-{5-[(1-(2-amino-2-oxoethyl)-6-{[(4-methylphenyl)sulfonyl]amino}-1,6-dihydropyridin-3-yl)oxy]-2-fluorophenyl}-1,3-dimethyl-1H-pyrazole-5-carboxamide (5.85 g, 10.6 mmol), trifluoroacetic anhydride (40 mL) and dichloromethane (40 mL) was stirred at room temperature for 6 hr. The reaction solution was concentrated under reduced pressure, ethyl acetate (50 mL) and saturated aqueous sodium hydrogen carbonate solution (50 mL) were added to the residue and the mixture was stirred for 10 min. The organic layer was washed with saturated brine, dried over anhydrous magnesium sulfate and filtrated. The filtrate was concentrated under reduced pressure, 8N aqueous sodium hydroxide solution (15 mL) and ethanol (60 mL) were added to the residue. The mixture was stirred at room temperature for 2 hr and at 60° C. for 2 hr. The reaction mixture was diluted with water and extracted with ethyl acetate/tetrahydrofuran (×3). The organic layer was washed with saturated brine, dried over anhydrous magnesium sulfate and filtrated. The filtrate was concentrated under reduced pressure, and the residue was purified by column chromatography (NH silica gel, ethyl acetate) and recrystallized from ethyl acetate-hexane to give the title compound (730 mg, 18%) as a white solid.

$^1$H-NMR (DMSO-d$_6$, 300 MHz) δ 2.18 (3H, s), 3.96 (3H, s), 6.01 (2H, s), 6.81 (1H, s), 6.92-6.98 (1H, m), 7.24-7.42 (5H, m), 8.60-8.61 (1H, m), 10.01 (1H, s).

Example 9-2

N-[5-({2-[(cyclopropylcarbonyl)amino]imidazo[1,2-a]pyridin-6-yl}oxy)-2-fluorophenyl]-1,3-dimethyl-1H-pyrazole-5-carboxamide

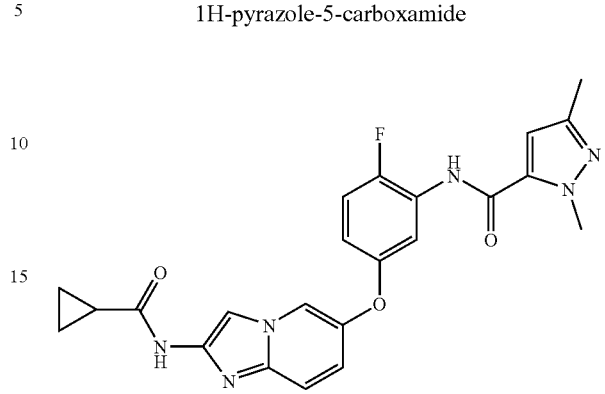

To a solution of N-{5-[(2-aminoimidazo[1,2-a]pyridin-6-yl)oxy]-2-fluorophenyl}-1,3-dimethyl-1H-pyrazole-5-carboxamide (730 mg, 1.92 mmol) in N,N-dimethylacetamide (7 mL) was added with stirring under ice-cooling cyclopropanecarbonyl chloride (262 μL, 2.88 mmol), and the mixture was stirred at room temperature for 2 hr. The reaction mixture was neutralized with saturated aqueous sodium hydrogen carbonate solution, diluted with water, and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, ethyl acetate) and recrystallized from ethyl acetate-ethanol to give the title compound (529 mg, 61%) as a white solid.

$^1$H-NMR (DMSO-d$_6$, 300 MHz) δ 0.75-0.81 (4H, m), 1.88-1.94 (1H, m), 2.18 (3H, s), 3.96 (3H, s), 6.81 (1H, s), 6.93-6.99 (1H, m), 7.09 (1H, dd, J=9.6, 2.2 Hz), 7.25-7.34 (2H, m), 7.48 (1H, d, J=9.6 Hz), 8.06 (1H, s), 8.56 (1H, dd, J=2.2, 0.8 Hz), 10.01 (1H, s), 10.97 (1H, s).

Example 10

N-{5-[(2-{[(ethylamino)carbonyl]amino}imidazo[1,2-a]pyridin-6-yl) oxy]-2-fluorophenyl}-1,3-dimethyl-1H-pyrazole-5-carboxamide

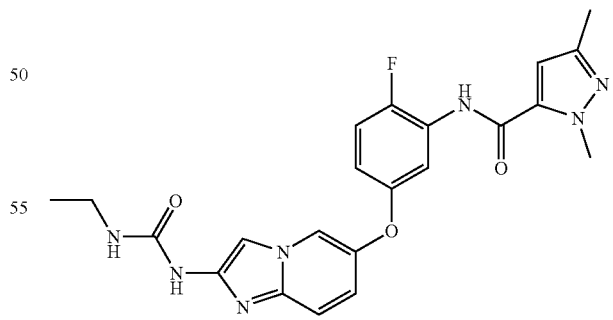

To a solution of N-{5-[(2-aminoimidazo[1,2-a]pyridin-6-yl) oxy]-2-fluorophenyl}-1,3-dimethyl-1H-pyrazole-5-carboxamide (70.0 mg, 0.184 mmol) in tetrahydrofuran (3 mL) was added ethyl isocyanate (17.5 μL, 0.221 mmol), and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, ethyl acetate) and recrystallized from ethyl acetate-ethanol to give the title compound (21.0 mg, 25%) as a white solid.

$^1$H-NMR (DMSO-$d_6$, 300 MHz) δ 1.06 (3H, t, J=7.1 Hz), 2.17 (3H, s), 3.09-3.18 (2H, m), 3.95 (3H, s), 6.61 (1H, br s), 6.80 (1H, s), 6.91-7.00 (1H, m), 7.02 (1H, dd, J=9.6, 2.4 Hz), 7.22-7.33 (2H, m), 7.40 (1H, d, J=9.6 Hz), 7.76 (1H, s), 8.52 (1H, d, J=1.5 Hz), 8.86 (1H, s), 10.00 (1H, s).

Example 11

N-[3-({2-[(cyclopropylcarbonyl)amino]imidazo[1,2-a]pyridin-6-yl}oxy)phenyl]-2-methyl-2H-tetrazole-5-carboxamide

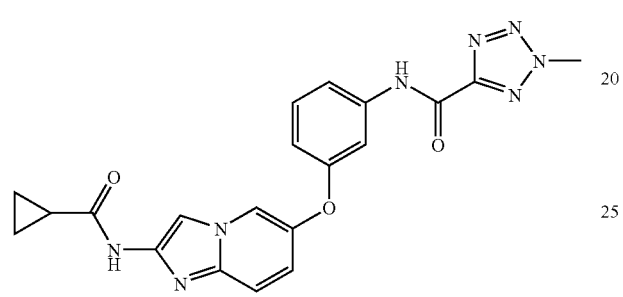

In the same manner as in Example 7-4 and using a mixture of 1-methyl-1H-tetrazole-5-carboxylic acid (1) and 2-methyl-2H-tetrazole-5-carboxylic acid (2) ((1):(2)≈1:1, 200 mg, 1.56 mmol), oxalyl chloride (141 μL, 1.72 mmol), N-[6-(3-aminophenoxy)imidazo[1,2-a]pyridin-2-yl]cyclopropanecarboxamide (70.0 mg, 0.227 mmol), tetrahydrofuran (10 mL), N,N-dimethylformamide (1 drop) and N,N-dimethylacetamide (3 mL) as starting materials, the title compound (51.5 mg, 54%) was obtained as a white solid.

$^1$H-NMR (DMSO-$d_6$, 300 MHz) δ 0.78-0.81 (4H, m), 1.90-1.95 (1H, m), 4.47 (3H, s), 6.83 (1H, dd, J=8.2, 0.7 Hz), 7.10 (1H, dd, J=9.5, 2.3 Hz), 7.36 (1H, t, J=8.2 Hz), 7.45-7.52 (2H, m), 7.64-7.68 (1H, m), 8.06 (1H, s), 8.58-8.59 (1H, m), 10.96 (1H, s), 10.97 (1H, s).

Example 12-1

N-{3-[(2-aminoimidazo[1,2-a]pyridin-6-yl) oxy]-5-methylphenyl}-1,3-dimethyl-1H-pyrazole-5-carboxamide

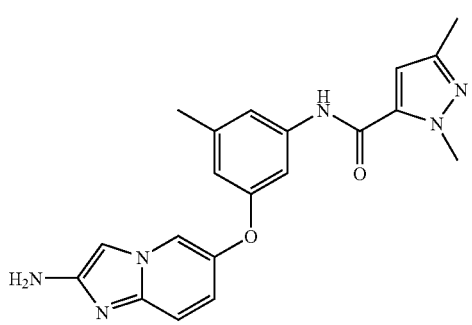

A mixture of N-{3-[(1-(2-amino-2-oxoethyl)-6-{[(4-methylphenyl)sulfonyl]imino}-1,6-dihydropyridin-3-yl)oxy]-5-methylphenyl}-1,3-dimethyl-1H-pyrazole-5-carboxamide (3.20 g, 5.82 mmol), trifluoroacetic anhydride (20 mL) and dichloromethane (30 mL) was stirred at room temperature for 4 hr. The reaction solution was concentrated under reduced pressure, ethanol (30 mL), water (15 mL) and 8N aqueous sodium hydroxide solution (15 mL) were added to the residue, and the mixture was stirred at room temperature for 60 hr. The reaction solution was concentrated under reduced pressure and ethyl acetate was added to the residue. The mixture was washed with water and saturated brine, dried over anhydrous magnesium sulfate and filtrated. The filtrate was concentrated under reduced pressure, and the residue was collected by filtration and washed with diethyl ether to give the title compound (1.22 g, 56%) as a pale-brown solid.

$^1$H-NMR (CDCl$_3$, 300 MHz) δ 2.24 (3H, s), 2.33 (3H, s), 4.11 (3H, s), 6.38 (1H, s), 6.60 (1H, s), 6.84-6.94 (3H, m), 7.00 (1H, t, J=1.9 Hz), 7.22-7.31 (3H, m), 7.78 (1H, dd, J=2.3, 0.8 Hz), 7.96 (1H, s).

Example 12-2

N-[3-({2-[(cyclopropylcarbonyl)amino]imidazo[1,2-a]pyridin-6-yl}oxy)-5-methylphenyl]-1,3-dimethyl-1H-pyrazole-5-carboxamide

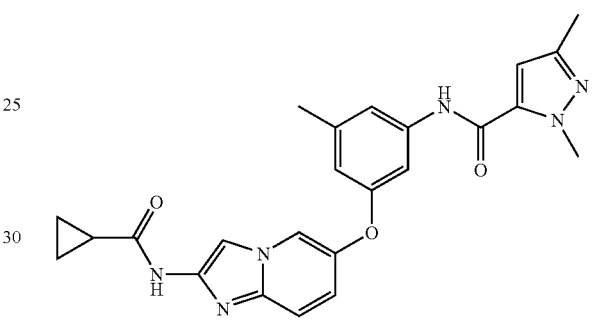

In the same manner as in Example 9-2 and using N-{3-[(2-aminoimidazo[1,2-a]pyridin-6-yl)oxy]-5-methylphenyl}-1,3-dimethyl-1H-pyrazole-5-carboxamide (300 mg, 0.797 mmol), cyclopropanecarbonyl chloride (72.0 μL, 0.797 mmol) and N,N-dimethylacetamide (10 mL) as starting materials, the title compound (111 mg, 31%) was obtained as a pale-yellow solid.

$^1$H-NMR (DMSO-$d_6$, 300 MHz) δ 0.76-0.84 (4H, m), 1.90-1.95 (1H, m), 2.17 (3H, s), 2.28 (3H, s), 3.96 (3H, s), 6.63 (1H, s), 6.77 (1H, s), 7.07 (1H, dd, J=9.7, 2.4 Hz), 7.18 (1H, t, J=1.8 Hz), 7.40 (1H, s), 7.48 (1H, d, J=9.7 Hz), 8.07 (1H, s), 8.56 (1H, d, J=1.8 Hz), 10.04 (1H, s), 10.97 (1H, s).

Example 13

N-{3-[(3-ethyl-2,4-dioxo-1,2,3,4-tetrahydropyrido[2,1-f]purin-7-yl)oxy]-5-methylphenyl}-1,3-dimethyl-1H-pyrazole-5-carboxamide

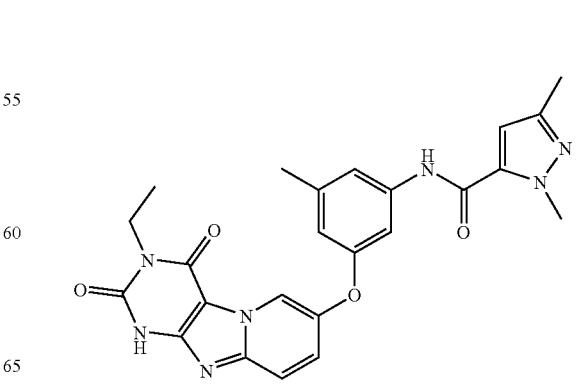

A mixture of N-{3-[(2-aminoimidazo[1,2-a]pyridin-6-yl)oxy]-5-methylphenyl}-1,3-dimethyl-1H-pyrazole-5-carboxamide (300 mg, 0.797 mmol), ethyl isocyanate (314 μL, 3.98 mmol) and pyridine (10 mL) was stirred at 60-70° C. for 15 hr. The mixture was concentrated under reduced pressure and ethyl acetate was added to the residue. The mixture was washed with saturated aqueous sodium hydrogen carbonate solution and saturated brine, dried over anhydrous magnesium sulfate and filtrated. The filtrate was concentrated under reduced pressure, and the residue was purified by column chromatography (silica gel, hexane/ethyl acetate=100/0→0/100) and recrystallized from ethanol to give the title compound (69.0 mg, 18%) as a white solid.

$^1$H-NMR (DMSO-d$_6$, 300 MHz) δ 1.13 (3H, t, J=7.0 Hz), 2.18 (3H, s), 2.30 (3H, s), 3.90 (2H, q, J=7.0 Hz), 3.96 (3H, s), 6.73 (1H, s), 6.79 (1H, s), 7.32 (1H, t, J=2.1 Hz), 7.44 (1H, s), 7.53-7.62 (1H, m), 7.78 (1H, d, J=8.7 Hz), 8.66 (1H, d, J=1.5 Hz), 10.10 (1H, s), 12.16 (1H, s).

Example 14

N-{3-[(2-{[(ethylamino)carbonyl]amino}imidazo[1,2-a]pyridin-6-yl)oxy]-5-methylphenyl}-1,3-dimethyl-1H-pyrazole-5-carboxamide

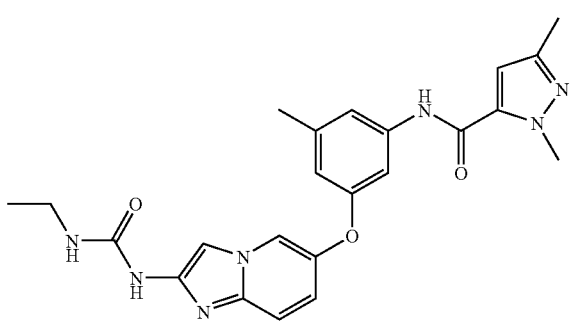

A mixture of N-{3-[(2-aminoimidazo[1,2-a]pyridin-6-yl)oxy]-5-methylphenyl}-1,3-dimethyl-1H-pyrazole-5-carboxamide (301 mg, 0.800 mmol), ethyl isocyanate (100 μL, 1.27 mmol) and pyridine (10 mL) was stirred at 50° C. for 18 hr. The mixture was concentrated under reduced pressure and ethyl acetate was added to the residue. The mixture was washed with saturated aqueous sodium hydrogen carbonate solution and saturated brine, dried over anhydrous magnesium sulfate and filtrated. The filtrate was concentrated under reduced pressure, and the residue was purified by column chromatography (silica gel, hexane/ethyl acetate=100/0→0/100) and recrystallized from ethyl acetate-hexane to give the title compound (78.0 mg, 22%) as a pale-yellow solid.

$^1$H-NMR (DMSO-d$_6$, 300 MHz) δ 1.07 (3H, t, J=7.2 Hz), 2.17 (3H, s), 2.28 (3H, s), 3.07-3.21 (2H, m), 3.95 (3H, s), 6.63 (1H, s), 6.65-6.74 (1H, m), 6.78 (1H, s), 7.08-7.16 (1H, m), 7.19-7.23 (1H, m), 7.40 (1H, s), 7.48 (1H, d, J=9.4 Hz), 7.80 (1H, s), 8.56 (1H, d, J=1.5 Hz), 9.05 (1H, s), 10.05 (1H, s).

Example 15

N-{3-[(2-amino[1,2,4]triazolo[1,5-a]pyridin-6-yl)oxy]phenyl}-1,3-dimethyl-1H-pyrazole-5-carboxamide

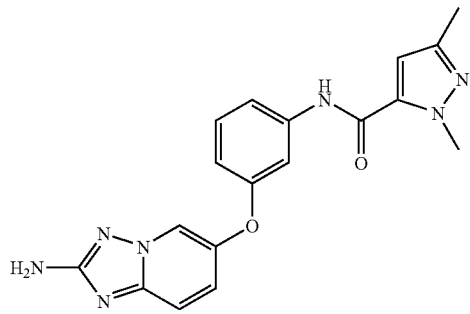

A mixture of ethyl ({[5-(3-{[(1,3-dimethyl-1H-pyrazol-5-yl)carbonyl]amino}phenoxy)pyridin-2-yl]amino}carbonothioyl)carbamate (238 mg, 0.524 mmol), hydroxylammonium chloride (364 mg, 5.24 mmol), N,N-diisopropylethylamine (548 μL, 3.14 mmol), ethanol (3 mL) and methanol (3 mL) was stirred at 60° C. for 5 hr and at 80° C. for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate/methanol=50/50/0→40/100/0→40/90/10) and recrystallized from ethyl acetate-hexane to give the title compound (131 mg, 69%) as a white solid.

$^1$H-NMR (DMSO-d$_6$, 300 MHz) δ 2.18 (3H, s), 3.96 (3H, s), 6.03 (2H, s), 6.78-6.82 (2H, m), 7.30-7.43 (4H, m), 7.52-7.57 (1H, m), 8.65 (1H, d, J=2.4 Hz), 10.13 (1H, s).

Example 16

N-[3-({2-[(cyclopropylcarbonyl)amino][1,2,4]triazolo[1,5-a]pyridin-6-yl}oxy)phenyl]-1,3-dimethyl-1H-pyrazole-5-carboxamide

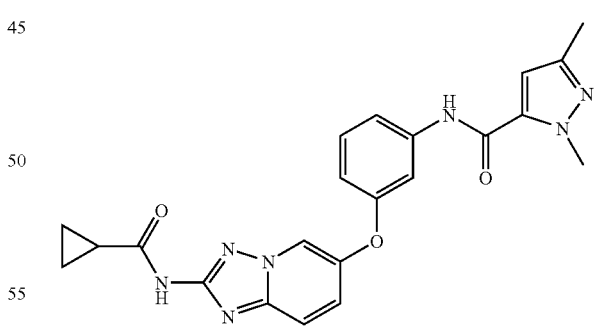

To a solution of N-{3-[(2-amino[1,2,4]triazolo[1,5-a]pyridin-6-yl)oxy]phenyl}-1,3-dimethyl-1H-pyrazole-5-carboxamide (117 mg, 0.322 mmol) and triethylamine (134 μL, 0.966 mmol) in tetrahydrofuran (5 mL) was added with stirring under ice-cooling cyclopropanecarbonyl chloride (38.0 μL, 0.419 mmol), and the mixture was stirred at room temperature for 12 hr. Cyclopropanecarbonyl chloride (29.3 μL, 0.322 mmol) was further added and the mixture was stirred for 3 hr. The reaction mixture was diluted with water and extracted with ethyl acetate. The organic layer was washed with water and saturated brine, dried over anhydrous magnesium sulfate and filtrated. The filtrate was concentrated under reduced pressure, sodium carbonate (100 mg), methanol (2 mL) and water (100 µL) were added to the residue, and the mixture was stirred at 50° C. for 30 min. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, ethyl acetate) and recrystallized from ethyl acetate to give the title compound (112 mg, 60%) as a white solid.

$^1$H-NMR (DMSO-$d_6$, 300 MHz) δ 0.80-0.85 (4H, m), 2.00-2.01 (1H, m), 2.17 (3H, s), 3.96 (3H, s), 6.77-6.85 (2H, m), 7.35 (1H, t, J=8.3 Hz), 7.40 (1H, t, J=2.1 Hz), 7.51-7.58 (2H, m), 7.74 (1H, d, J=9.3 Hz), 8.94 (1H, d, J=2.4 Hz), 10.14 (1H, s), 11.05 (1H, s).

Example 17-1

N-{5-[(2-amino[1,2,4]triazolo[1,5-a]pyridin-6-yl)oxy]-2-methylphenyl}-1,3-dimethyl-1H-pyrazole-5-carboxamide

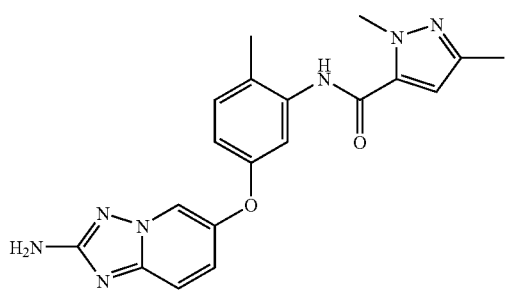

A mixture of N-{5-[(6-aminopyridin-3-yl)oxy]-2-methylphenyl}-1,3-dimethyl-1H-pyrazole-5-carboxamide (214 mg, 0.634 mmol), ethyl isothiocyanatoformate (108 mg, 0.824 mmol) and DMSO (5 mL) was stirred at room temperature for 15 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give ethyl ({[5-(3-{[(1,3-dimethyl-1H-pyrazol-5-yl) carbonyl]amino}-4-methylphenoxy)pyridin-2-yl]amino}carbonothioyl)carbamate (280 mg, 94%) as a white solid. A mixture of ethyl ({[5-(3-{[(1,3-dimethyl-1H-pyrazol-5-yl)carbonyl]amino}-4-methylphenoxy)pyridin-2-yl]amino}carbonothioyl)carbamate (270 mg, 0.576 mmol) thus-obtained, hydroxylammonium chloride (280 mg, 4.03 mmol), N,N-diisopropylethylamine (502 µL, 2.88 mmol), ethanol (10 mL) and methanol (10 mL) was stirred at 80° C. for 8 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give the title compound (164 mg, 75%) as a white solid.

$^1$H-NMR (DMSO-$d_6$, 300 MHz) δ 2.18 (6H, s), 3.96 (3H, s), 5.99 (2H, s), 6.77 (1H, s), 6.87 (1H, dd, J=8.6, 2.6 Hz), 7.02 (1H, d, J=2.6 Hz), 7.23-7.29 (2H, m), 7.38 (1H, d, J=9.3 Hz), 8.55 (1H, d, J=1.8 Hz), 9.73 (1H, s).

Example 17-2

N-[5-({2-[(cyclopropylcarbonyl)amino][1,2,4]triazolo[1,5-a]pyridin-6-yl}oxy)-2-methylphenyl]-1,3-dimethyl-1H-pyrazole-5-carboxamide

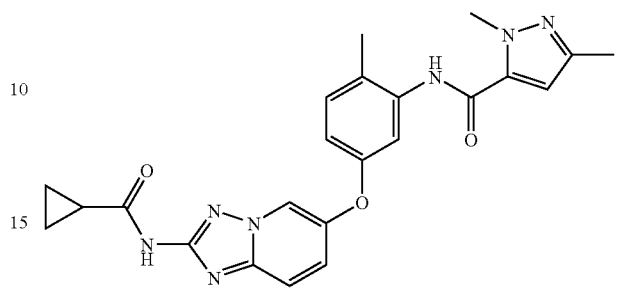

To a solution of N-{5-[(2-amino[1,2,4]triazolo[1,5-a]pyridin-6-yl)oxy]-2-methylphenyl}-1,3-dimethyl-1H-pyrazole-5-carboxamide (158 mg, 0.419 mmol) and triethylamine (63.8 µL, 0.461 mmol) in tetrahydrofuran (5 mL) was added with stirring under ice-cooling cyclopropanecarbonyl chloride (41.9 µL, 0.461 mmol), and the mixture was stirred at room temperature for 1 hr. Cyclopropanecarbonyl chloride (83.8 µL, 0.922 mmol) was further added and the mixture was stirred for 1 hr. The reaction mixture was diluted with water and extracted with ethyl acetate. The organic layer was washed with water and saturated brine, dried over anhydrous magnesium sulfate and filtrated. The filtrate was concentrated under reduced pressure, sodium carbonate (200 mg), methanol (3 mL) and water (100 µL) were added to the residue, and the mixture was stirred at 50° C. for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (hexane/ethyl acetate=50/50→0/100) and recrystallized from ethyl acetate to give the title compound (112 mg, 60%) as a white solid.

$^1$H-NMR (DMSO-$d_6$, 300 MHz) δ 0.81-0.83 (4H, m), 1.98-2.10 (1H, m), 2.18 (3H, s), 2.19 (3H, s), 3.96 (3H, s), 6.78 (1H, s), 6.92 (1H, dd, J=8.4, 2.6 Hz), 7.07 (1H, d, J=2.6 Hz), 7.27 (1H, d, J=8.4 Hz), 7.49 (1H, dd, J=9.5, 2.3 Hz), 7.71 (1H, d, J=9.5 Hz), 8.53 (1H, d, J=2.3 Hz), 9.76 (1H, s), 11.04 (1H, s)

Example 18-1

6-(3-nitrophenoxy)[1,2,4]triazolo[1,5-a]pyridin-2-amine

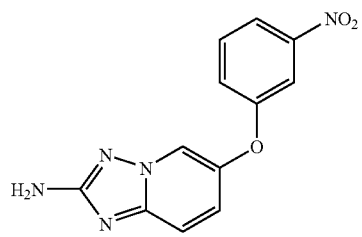

In the same manner as in Example 17-1 and using 5-(3-nitrophenoxy)pyridin-2-amine (3.10 g, 13.4 mmol), ethyl isothiocyanatoformate (2.29 g, 17.4 mmol), hydroxylammonium chloride (4.00 g, 57.6 mmol), N,N-diisopropylethylamine (7.20 mL, 41.3 mmol), DMSO (20 mL), ethanol (25 mL) and methanol (25 mL) as starting materials, the title compound (3.50 g, 96%) was obtained as a white solid.

¹H-NMR (DMSO-d₆, 300 MHz) δ 6.07 (2H, s), 7.36-7.46 (2H, m), 7.50-7.53 (1H, m), 7.66 (1H, t, J=8.1 Hz), 7.75 (1H, t, J=2.1 Hz), 7.95-7.99 (1H, m), 8.75-8.76 (1H, m).

Example 18-2

N-[6-(3-nitrophenoxy)[1,2,4]triazolo[1,5-a]pyridin-2-yl]cyclopropanecarboxamide

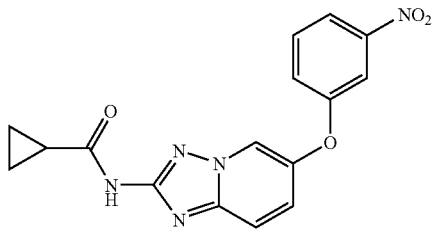

To a solution of 6-(3-nitrophenoxy)[1,2,4]triazolo[1,5-a]pyridin-2-amine (3.49 g, 12.9 mmol) in N,N-dimethylacetamide (20 mL) was added with stirring under ice-cooling cyclopropanecarbonyl chloride (2.46 mL, 27.0 mmol), and the mixture was stirred at room temperature for 15 hr. Water (40 mL) was added to the reaction mixture, and the precipitated solid was collected by filtration, washed with water and dried to give the title compound (3.86 g, 88%) as a white solid.

¹H-NMR (DMSO-d₆, 300 MHz) δ 0.81-0.84 (4H, m), 1.99-2.08 (1H, m), 7.55-7.62 (2H, m), 7.70 (1H, t, J=8.4 Hz), 7.74-7.78 (1H, m), 7.83 (1H, t, J=2.4 Hz), 7.97-8.02 (1H, m), 9.03-9.05 (1H, m), 11.07 (1H, s).

Example 18-3

N-[6-(3-aminophenoxy)[1,2,4]triazolo[1,5-a]pyridin-2-yl]cyclopropanecarboxamide

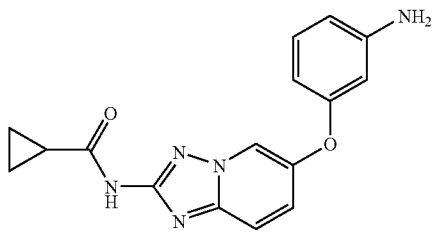

A mixture of N-[6-(3-nitrophenoxy)[1,2,4]triazolo[1,5-a]pyridin-2-yl]cyclopropanecarboxamide (3.84 g, 11.3 mmol), zinc (5.17 g, 79.1 mmol), hydroxylammonium chloride (3.02 g, 56.5 mmol) and methanol (30 mL) was stirred under refluxing conditions for 3 hr. The reaction mixture was filtered through celite, and the filtrate was concentrated under reduced pressure. The residue was dissolved in ethanol (50 mL), and reduced iron (5.00 g, 89.5 mmol), concentrated hydrochloric acid (5 mL) and water (50 mL) were added. The mixture was stirred under refluxing conditions for 1 hr. The reaction mixture was filtered through celite, and the filtrate was concentrated under reduced pressure. The residue was collected by filtration and washed with ethyl acetate to give the title compound (862 mg, 25%) as a white solid.

¹H-NMR (DMSO-d₆, 300 MHz) δ 0.81-0.84 (4H, m), 1.99-2.08 (1H, m), 5.22 (2H, s), 6.13-6.17 (2H, m), 6.29-6.33 (1H, m), 6.95-7.02 (1H, m), 7.46 (1H, dd, J=9.6, 2.4 Hz), 7.69 (1H, dd, J=9.6, 0.3 Hz), 8.78-8.79 (1H, m), 11.00 (1H, s).

Example 18-4

N-[3-({2-[(cyclopropylcarbonyl)amino][1,2,4]triazolo[1,5-a]pyridin-6-yl}oxy)phenyl]-1-methyl-1H-pyrrole-2-carboxamide

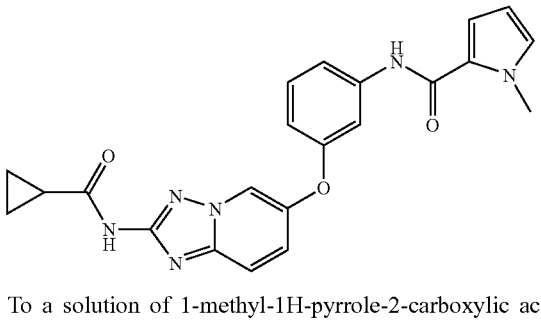

To a solution of 1-methyl-1H-pyrrole-2-carboxylic acid (121 mg, 0.970 mmol) in tetrahydrofuran (5 mL) were added oxalyl chloride (169 μL, 1.94 mmol) and N,N-dimethylformamide (1 drop), and the mixture was stirred at room temperature for 1 hr. The reaction mixture was concentrated under reduced pressure, and the residue was dissolved in N,N-dimethylacetamide (3 mL). N-[6-(3-Aminophenoxy)[1,2,4]triazolo[1,5-a]pyridin-2-yl]cyclopropanecarboxamide (100 mg, 0.323 mmol) was added thereto with stirring under ice-cooling, and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, ethyl acetate) and recrystallized from ethyl acetate to give the title compound (56.0 mg, 14%) as a white solid.

¹H-NMR (DMSO-d₆, 300 MHz) δ 0.81-0.84 (4H, m), 1.99-2.08 (1H, m), 3.84 (3H, s), 6.06 (1H, dd, J=3.8, 2.9 Hz), 6.73-6.78 (1H, m), 6.96-6.99 (2H, m), 7.30 (1H, t, J=8.1 Hz), 7.43-7.44 (1H, m), 7.50-7.58 (2H, m), 7.71-7.75 (1H, m), 8.90 (1H, d, J=2.1 Hz), 9.77 (1H, s), 11.03 (1H, s).

Example 19

N-[3-({2-[(cyclopropylcarbonyl)amino][1,2,4]triazolo[1,5-a]pyridin-6-yl}oxy)phenyl]-2,4-dimethyl-1,3-thiazole-5-carboxamide

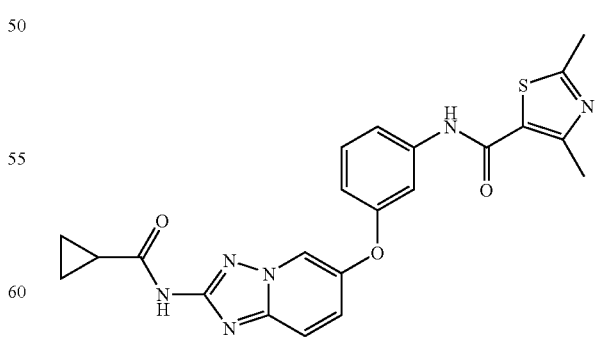

In the same manner as in Example 18-4 and using 2,4-dimethyl-1,3-thiazole-5-carboxylic acid (107 mg, 0.678 mmol), tetrahydrofuran (8 mL), oxalyl chloride (118 μL, 1.36 mmol), N-[6-(3-aminophenoxy)[1,2,4]triazolo[1,5-a]pyridin-2-yl]cyclopropanecarboxamide (70.0 mg, 0.226 mmol), N,N-dimethylformamide (1 drop) and N,N-dimethylacetamide (5 mL) as starting materials, the title compound (27.0 mg, 27%) was obtained as a white solid.

$^1$H-NMR (DMSO-$d_6$, 300 MHz) δ 0.81-0.84 (4H, m), 1.99-2.08 (1H, m), 2.52 (3H, s), 2.73 (3H, s), 6.79-6.84 (1H, m), 7.31-7.39 (2H, m), 7.45-7.49 (1H, m), 7.52 (1H, dd, J=9.6, 2.4 Hz), 7.71-7.75 (1H, m), 8.90 (1H, d, J=1.8 Hz), 10.12 (1H, s), 11.03 (1H, s).

Example 20

N-[3-({2-[(cyclopropylcarbonyl)amino][1,2,4]triazolo[1,5-a]pyridin-6-yl}oxy)phenyl]-1-methyl-1H-pyrazole-5-carboxamide

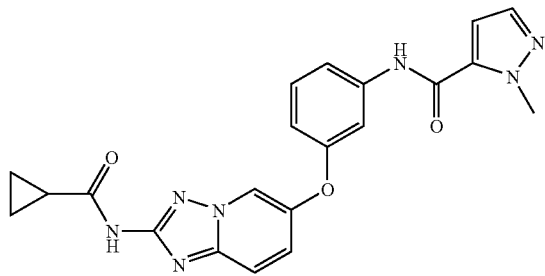

In the same manner as in Example 18-4 and using 1-methyl-1H-pyrazole-5-carboxylic acid (114 mg, 0.904 mmol), tetrahydrofuran (8 mL), oxalyl chloride (118 μL, 1.36 mmol), N-[6-(3-aminophenoxy)[1,2,4]triazolo[1,5-a]pyridin-2-yl]cyclopropanecarboxamide (70.0 mg, 0.226 mmol), N,N-dimethylformamide (1 drop) and N,N-dimethylacetamide (5 mL) as starting materials, the title compound (71.0 mg, 75%) was obtained as a white solid.

$^1$H-NMR (DMSO-$d_6$, 300 MHz) δ 0.81-0.84 (4H, m), 1.99-2.08 (1H, m), 4.05 (3H, s), 6.82-6.86 (1H, m), 7.00 (1H, d, J=2.4 Hz), 7.36 (1H, t, J=8.1 Hz), 7.42 (1H, t, J=2.1 Hz), 7.49-7.59 (3H, m), 7.72-7.76 (1H, m), 8.92 (1H, d, J=1.8 Hz), 10.22 (1H, s), 11.03 (1H, s).

Example 21

N-[3-({2-[(cyclopropylcarbonyl)amino][1,2,4]triazolo[1,5-a]pyridin-6-yl}oxy)phenyl]-1-methyl-5-(trifluoromethyl)-1H-pyrazole-4-carboxamide

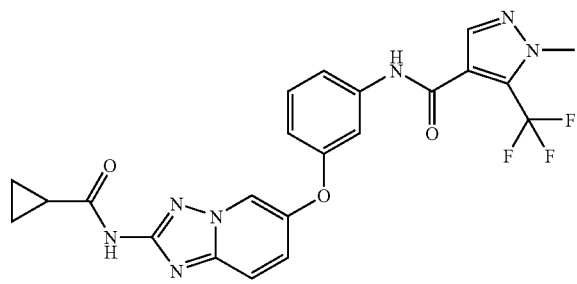

In the same manner as in Example 18-4 and using 1-methyl-5-(trifluoromethyl)-1H-pyrazole-4-carboxylic acid (175 mg, 0.904 mmol), tetrahydrofuran (8 mL), oxalyl chloride (118 μL, 1.36 mmol), N-[6-(3-aminophenoxy)[1,2,4]triazolo[1,5-a]pyridin-2-yl]cyclopropanecarboxamide (70.0 mg, 0.226 mmol), N,N-dimethylformamide (1 drop) and N,N-dimethylacetamide (5 mL) as starting materials, the title compound (71.0 mg, 65%) was obtained as a white solid.

$^1$H-NMR (DMSO-$d_6$, 300 MHz) δ 0.81-0.84 (4H, m), 1.99-2.08 (1H, m), 3.96 (3H, s), 6.78-6.83 (1H, m), 7.30-7.37 (2H, m), 7.51-7.55 (2H, m), 7.74 (1H, dd, J=9.6, 0.9 Hz), 8.47 (1H, s), 8.92 (1H, d, J=1.8 Hz), 10.14 (1H, s), 11.03 (1H, s).

Example 22

N-[3-({2-[(cyclopropylcarbonyl)amino][1,2,4]triazolo[1,5-a]pyridin-6-yl}oxy)phenyl]-2-methyl-5-(trifluoromethyl)-1,3-oxazole-4-carboxamide

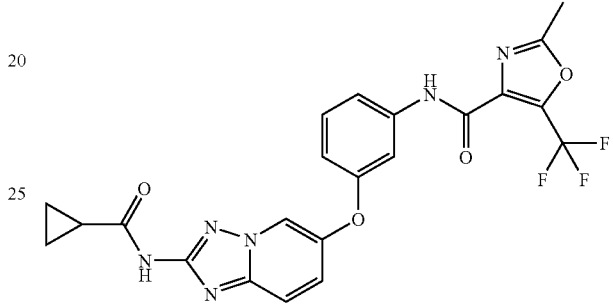

In the same manner as in Example 18-4 and using 2-methyl-5-(trifluoromethyl)-1,3-oxazole-4-carboxylic acid (110 mg, 0.564 mmol), tetrahydrofuran (8 mL), oxalyl chloride (98.0 μL, 1.13 mmol), N-[6-(3-aminophenoxy)[1,2,4]triazolo[1,5-a]pyridin-2-yl]cyclopropanecarboxamide (70.0 mg, 0.226 mmol), N,N-dimethylformamide (1 drop) and N,N-dimethylacetamide (5 mL) as starting materials, the title compound (74.0 mg, 67%) was obtained as a white solid.

$^1$H-NMR (DMSO-$d_6$, 300 MHz) δ 0.81-0.84 (4H, m), 1.99-2.08 (1H, m), 2.59 (3H, s), 6.82-6.87 (1H, m), 7.35 (1H, t, J=8.3 Hz), 7.50-7.54 (2H, m), 7.67-7.75 (2H, m), 8.92 (1H, d, J=2.1 Hz), 10.59 (1H, s), 11.03 (1H, s).

Example 23-1

N-{5-[(2-amino[1,2,4]triazolo[1,5-a]pyridin-6-yl)oxy]-2-fluorophenyl}-1,3-dimethyl-1H-pyrazole-5-carboxamide

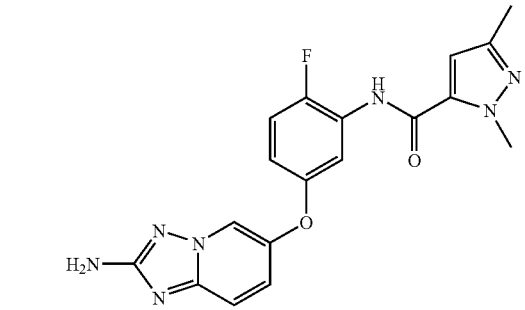

A mixture of ethyl ({[5-(3-{[(1,3-dimethyl-1H-pyrazol-5-yl)carbonyl]amino}-4-fluorophenoxy)pyridin-2-yl]amino}carbonothioyl)carbamate (1.15 g, 2.43 mmol), hydroxylammonium chloride (1.18 g, 17.0 mmol), N,N-diisopropylethylamine (2.12 mL, 12.2 mmol), ethanol (10 mL) and methanol (10 mL) was stirred at 80° C. for 8 hr. The reaction mixture was diluted with water and extracted with ethyl acetate (×3). The organic layer was washed with saturated brine, dried over anhydrous magnesium sulfate and filtrated. The filtrate was concentrated under reduced pressure, and the residue was collected by filtration and washed with ethyl acetate-hexane to give the title compound (650 mg, 70%) as a yellow solid.

$^1$H-NMR (DMSO-$d_6$, 300 MHz) δ 2.18 (3H, s), 3.96 (3H, s), 6.02 (2H, s), 6.82 (1H, s), 6.92-6.98 (1H, m), 7.23-7.33 (3H, m), 7.40 (1H, dd, J=9.3, 0.6 Hz), 8.61 (1H, dd, J=2.1, 0.6 Hz), 10.01 (1H, s).

Example 23-2

N-[5-({2-[(cyclopropylcarbonyl)amino][1,2,4]triazolo[1,5-a]pyridin-6-yl}oxy)-2-fluorophenyl]-1,3-dimethyl-1H-pyrazole-5-carboxamide

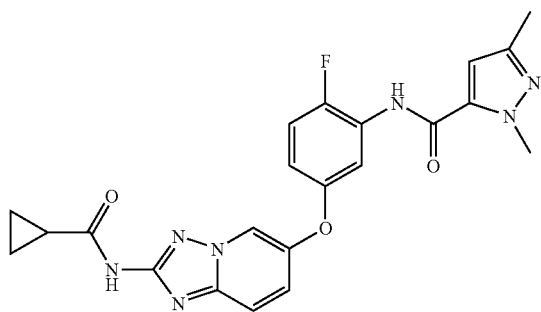

To a solution of N-{5-[(2-amino[1,2,4]triazolo[1,5-a]pyridin-6-yl)oxy]-2-fluorophenyl}-1,3-dimethyl-1H-pyrazole-5-carboxamide (581 mg, 1.52 mmol) in N,N-dimethylacetamide (5 mL) was added with stirring under ice-cooling cyclopropanecarbonyl chloride (166 μL, 1.83 mmol), and the mixture was stirred at room temperature for 1 hr. Cyclopropanecarbonyl chloride (492 μL, 0.966 mmol) was further added and the mixture was stirred for 15 hr. The reaction mixture was diluted with saturated aqueous sodium hydrogen carbonate solution, and extracted with ethyl acetate. The organic layer was washed with water and saturated brine, dried over anhydrous magnesium sulfate and filtrated. The filtrate was concentrated under reduced pressure, and the residue was purified by column chromatography (silica gel, ethyl acetate) and recrystallized from ethyl acetate to give the title compound (485 mg, 71%) as a white solid.

$^1$H-NMR (DMSO-$d_6$, 300 MHz) δ 0.81-0.84 (4H, m), 1.99-2.08 (1H, m), 2.18 (3H, s), 3.96 (3H, s), 6.81 (1H, s), 6.98-7.03 (1H, m), 7.29-7.35 (2H, m), 7.52 (1H, dd, J=9.6, 2.4 Hz), 7.73 (1H, d, J=9.6 Hz), 8.87 (1H, d, J=2.4 Hz), 10.02 (1H, s), 11.02 (1H, s).

Example 24

N-[3-({2-[(cyclopropylcarbonyl)amino][1,2,4]triazolo[1,5-a]pyridin-6-yl}oxy)phenyl]-2,5-dimethyl-1,3-oxazole-4-carboxamide

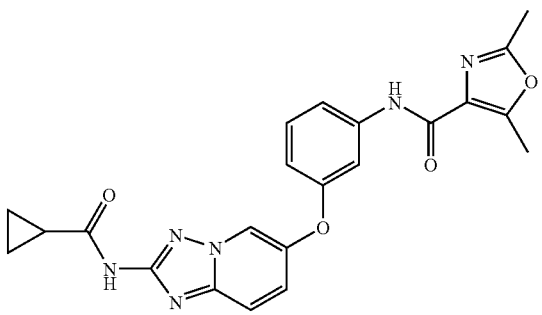

To a solution of N-[6-(3-aminophenoxy)[1,2,4]triazolo[1,5-a]pyridin-2-yl]cyclopropanecarboxamide (70.0 mg, 0.226 mmol) in N,N-dimethylacetamide (5 mL) was added with stirring under ice-cooling 2,5-dimethyl-1,3-oxazole-4-carbonyl chloride (108 mg, 0.678 mmol), and the mixture was stirred at room temperature for 1 hr. The reaction mixture was diluted with saturated aqueous sodium hydrogen carbonate solution and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, ethyl acetate) and recrystallized from ethyl acetate to give the title compound (68.6 mg, 70%) as a white solid.

$^1$H-NMR (DMSO-$d_6$, 300 MHz) δ 0.82-0.84 (4H, m), 1.99-2.08 (1H, m), 2.42 (3H, s), 2.55 (3H, s), 6.77-6.81 (1H, m), 7.31 (1H, t, J=8.1 Hz), 7.49-7.58 (2H, m), 7.65-7.75 (2H, m), 8.89 (1H, dd, J=2.3, 0.8 Hz), 10.02 (1H, s), 11.03 (1H, s).

Example 25

N-[3-({2-[(cyclopropylcarbonyl)amino][1,2,4]triazolo[1,5-a]pyridin-6-yl}oxy)phenyl]-5-methyl-2-(trifluoromethyl)-3-furamide

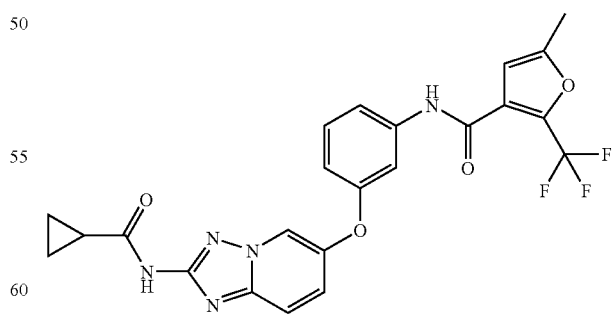

In the same manner as in Example 18-4 and using 5-methyl-2-(trifluoromethyl)-3-furoic acid (175 mg, 0.904 mmol), tetrahydrofuran (8 mL), oxalyl chloride (118 μL, 1.36 mmol), N-[6-(3-aminophenoxy)[1,2,4]triazolo[1,5-a]pyridin-2-yl]cyclopropanecarboxamide (70.0 mg, 0.226 mmol), N,N-dimethylformamide (1 drop) and N,N-dimethylacetamide (3 mL) as starting materials, the title compound (72.0 mg, 66%) was obtained as a white solid.

¹H-NMR (DMSO-d₆, 300 MHz) δ 0.81-0.84 (4H, m), 1.99-2.08 (1H, m), 2.38 (3H, s), 6.75 (1H, s), 6.81-6.85 (1H, m), 7.32-7.38 (2H, m), 7.49-7.55 (2H, m), 7.74 (1H, dd, J=9.6, 0.7 Hz), 8.92 (1H, dd, J=2.3, 0.7 Hz), 10.38 (1H, s), 11.03 (1H, s).

Example 26

N-[3-({2-[(cyclopropylcarbonyl)amino][1,2,4]triazolo[1,5-a]pyridin-6-yl}oxy)phenyl]-2,4-dimethyl-1,3-oxazole-5-carboxamide

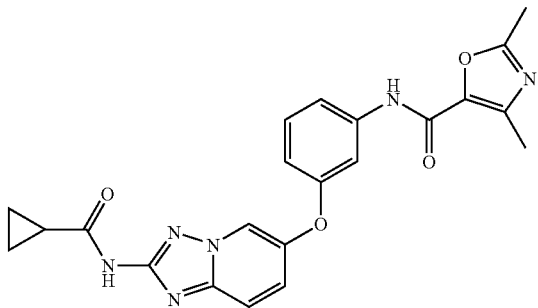

In the same manner as in Example 18-4 and using 2,4-dimethyl-1,3-oxazole-5-carboxylic acid (127 mg, 0.904 mmol), tetrahydrofuran (8 mL), oxalyl chloride (118 μL, 1.36 mmol), N-[6-(3-aminophenoxy)[1,2,4]triazolo[1,5-a]pyridin-2-yl]cyclopropanecarboxamide (70.0 mg, 0.226 mmol), N,N-dimethylformamide (1 drop) and N,N-dimethylacetamide (3 mL) as starting materials, the title compound (69.2 mg, 71%) was obtained as a white solid.

¹H-NMR (DMSO-d₆, 300 MHz) δ 0.82-0.84 (4H, m), 1.99-2.08 (1H, m), 2.35 (3H, s), 2.47 (3H, s), 6.80-6.84 (1H, m), 7.33 (1H, t, J=8.3 Hz), 7.45 (1H, t, J=2.1 Hz), 7.52 (1H, dd, J=9.6, 2.4 Hz), 7.60-7.63 (1H, m), 7.72-7.76 (1H, m), 8.92 (1H, d, J=2.1 Hz), 10.16 (1H, s), 11.04 (1H, s).

Example 27

N-[3-({2-[(cyclopropylcarbonyl)amino][1,2,4]triazolo[1,5-a]pyridin-6-yl}oxy)phenyl]-1-methyl-3-(trifluoromethyl)-1H-pyrazole-4-carboxamide

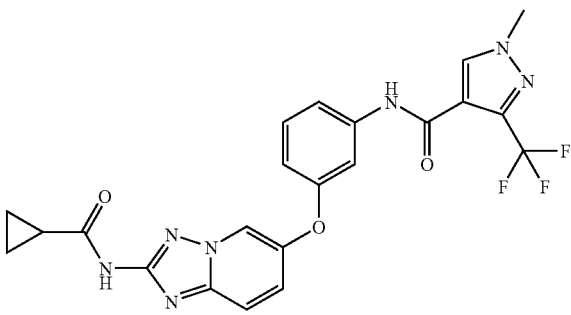

In the same manner as in Example 18-4 and using 1-methyl-3-(trifluoromethyl)-1H-pyrazole-4-carboxylic acid (175 mg, 0.904 mmol), tetrahydrofuran (8 mL), oxalyl chloride (118 μL, 1.36 mmol), N-[6-(3-aminophenoxy)[1,2,4]triazolo[1,5-a]pyridin-2-yl]cyclopropanecarboxamide (70.0 mg, 0.226 mmol), N,N-dimethylformamide (1 drop) and N,N-dimethylacetamide (3 mL) as starting materials, the title compound (76.5 mg, 70%) was obtained as a white solid.

¹H-NMR (DMSO-d₆, 300 MHz) δ 0.81-0.84 (4H, m), 1.99-2.08 (1H, m), 3.95 (3H, s), 6.78-6.83 (2H, m), 7.30-7.37 (2H, m), 7.53 (1H, dd, J=9.6, 2.1 Hz), 7.74 (1H, dd, J=9.6, 0.6 Hz), 8.47 (1H, s), 8.91-8.93 (1H, m), 10.14 (1H, s), 11.03 (1H, s).

Example 28-1 tert-butyl {3-[(2-amino[1,2,4]triazolo[1,5-a]pyridin-6-yl)oxy]-4-methylphenyl}carbamate

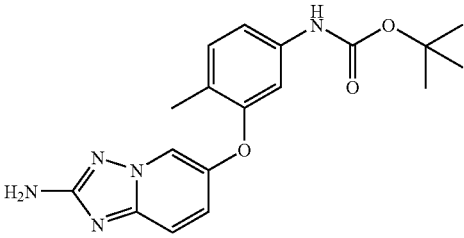

In the same manner as in Example 17-1 and using tert-butyl {3-[(6-aminopyridin-3-yl)oxy]-4-methylphenyl}carbamate (1.69 g, 5.35 mmol), DMSO (5 mL), ethyl isothiocyanatoformate (843 mg, 6.42 mmol), ethanol (20 mL), methanol (20 mL), hydroxylammonium chloride (2.43 g, 35.0 mmol) and N,N-diisopropylethylamine (4.35 mL, 25.0 mmol) as starting materials, the title compound (1.55 g, 87%) was obtained as a white solid.

¹H-NMR (DMSO-d₆, 300 MHz) δ 1.39 (9H, s), 2.19 (3H, s), 6.00 (2H, s), 6.98 (1H, s), 7.12-7.18 (2H, m), 7.24 (1H, dd, J=9.5, 2.3 Hz), 7.39 (1H, dd, J=9.5, 0.3 Hz), 8.43 (1H, d, J=1.8 Hz), 9.23 (1H, s).

Example 28-2 tert-butyl [3-({2-[(cyclopropylcarbonyl)amino][1,2,4]triazolo[1,5-a]pyridin-6-yl}oxy)-4-methylphenyl]carbamate

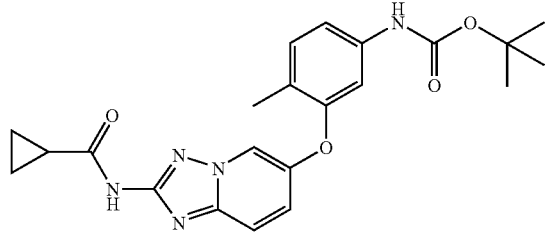

To a solution of tert-butyl {3-[(2-amino[1,2,4]triazolo[1,5-a]pyridin-6-yl)oxy]-4-methylphenyl}carbamate (1.50 g, 4.22 mmol) in N,N-dimethylacetamide (5 mL) was added with stirring under ice-cooling cyclopropanecarbonyl chloride (1.15 mL, 12.7 mmol), and the mixture was stirred at room temperature for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (1.59 g, 89%) as a white solid.

¹H-NMR (DMSO-d₆, 300 MHz) δ 0.81-0.84 (4H, m), 1.39 (9H, s), 1.99-2.08 (1H, m), 2.19 (3H, s), 7.03 (1H, s), 7.16-7.22 (2H, m), 7.45 (1H, dd, J=9.6, 2.1 Hz), 7.72 (1H, dd, J=9.6, 0.6 Hz), 8.68 (1H, d, J=2.4 Hz), 9.26 (1H, s), 11.03 (1H, s).

Example 29

N-[6-(5-amino-2-methylphenoxy)[1,2,4]triazolo[1,5-a]pyridin-2-yl]cyclopropanecarboxamide

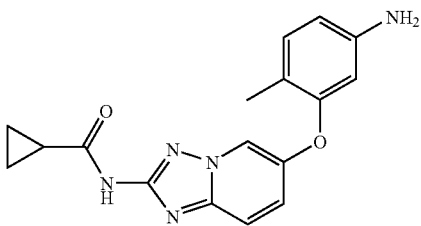

A mixture of tert-butyl [3-({2-[(cyclopropylcarbonyl)amino][1,2,4]triazolo[1,5-a]pyridin-6-yl}oxy)-4-methylphenyl]carbamate (1.50 g, 3.54 mmol) and trifluoroacetic acid (5 mL) was stirred at 0° C. for 30 min. The solvent was evaporated under reduced pressure, and the residue was dissolved in water, neutralized with saturated aqueous sodium hydrogen carbonate solution, and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (1.04 g, 91%) as a white solid.

¹H-NMR (DMSO-d₆, 300 MHz) δ 0.81-0.84 (4H, m), 1.99-2.08 (1H, m), 2.09 (3H, s), 5.09 (2H, br s), 6.08 (1H, d, J=2.1 Hz), 6.30 (1H, dd, J=8.2, 2.1 Hz), 6.93 (1H, d, J=8.2 Hz), 7.42 (1H, dd, J=9.6, 2.3 Hz), 7.69 (1H, d, J=9.6 Hz), 8.61 (1H, d, J=2.3 Hz), 10.98 (1H, s).

Example 30

N-[3-({2-[(cyclopropylcarbonyl)amino][1,2,4]triazolo[1,5-a]pyridin-6-yl}oxy)-4-methylphenyl]-1,3-dimethyl-1H-pyrazole-5-carboxamide

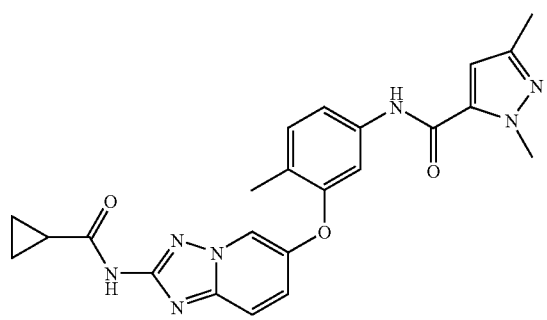

In the same manner as in Example 24 and using N-[6-(5-amino-2-methylphenoxy)[1,2,4]triazolo[1,5-a]pyridin-2-yl]cyclopropanecarboxamide (265 mg, 0.820 mmol), 1,3-dimethyl-1H-pyrazole-5-carbonyl chloride (260 mg, 1.64 mmol) and N,N-dimethylacetamide (5 mL) as starting materials, the title compound (333 mg, 91%) was obtained as a white solid.

¹H-NMR (DMSO-d₆, 300 MHz) δ 0.81-0.84 (4H, m), 1.99-2.08 (1H, m), 2.15 (3H, s), 2.27 (3H, s), 3.93 (3H, s), 6.72 (1H, s), 7.21-7.30 (2H, m), 7.48-7.56 (2H, m), 7.74 (1H, dd, J=9.5, 0.7 Hz), 8.78-8.80 (1H, m), 10.02 (1H, s), 11.04 (1H, s).

Example 31

N-{5-[(2-{[(2,2-difluorocyclopropyl)carbonyl]amino}[1,2,4]triazolo[1,5-a]pyridin-6-yl)oxy]-2-fluorophenyl}-1,3-dimethyl-1H-pyrazole-5-carboxamide

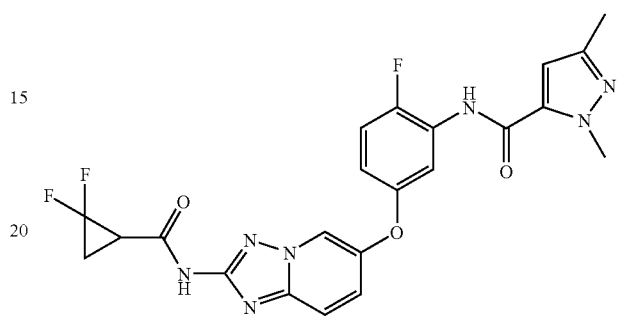

To a solution of 2,2-difluorocyclopropanecarboxylic acid (104 mg, 0.850 mmol) in tetrahydrofuran (1 mL) were added oxalyl chloride (74.3 μL, 0.850 mmol) and N,N-dimethylformamide (1 drop), and the mixture was stirred at room temperature for 1 hr. The reaction mixture was concentrated under reduced pressure, and the residue was dissolved in N,N-dimethylacetamide (3 mL). N-{5-[(2-Amino[1,2,4]triazolo[1,5-a]pyridin-6-yl)oxy]-2-fluorophenyl}-1,3-dimethyl-1H-pyrazole-5-carboxamide (65.0 mg, 0.170 mmol) was added with stirring under ice-cooling, and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=80/20→0/100) and recrystallized from ethyl acetate to give the title compound (22.0 mg, 27%) as a white solid.

¹H-NMR (DMSO-d₆, 300 MHz) δ 1.97-2.08 (2H, m), 2.18 (3H, s), 3.96 (3H, s), 6.81 (1H, s), 6.98-7.04 (2H, m), 7.29-7.36 (2H, m), 7.55 (1H, dd, J=9.8, 2.4 Hz), 7.76 (1H, dd, J=9.8, 0.5 Hz), 8.89-8.91 (1H, m), 10.09 (1H, br s), 11.30 (1H, br s).

Example 32-1

N-[6-(3-fluoro-5-nitrophenoxy)[1,2,4]triazolo[1,5-a]pyridin-2-yl]cyclopropanecarboxamide

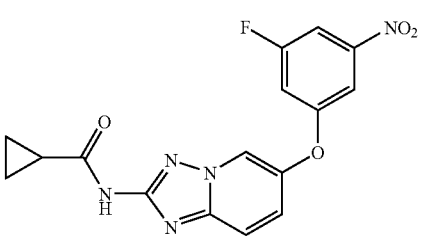

A mixture of N-(6-hydroxy[1,2,4]triazolo[1,5-a]pyridin-2-yl)cyclopropanecarboxamide (200 mg, 0.917 mmol), 1,3-difluoro-5-nitrobenzene (437 mg, 2.75 mmol), potassium carbonate (380 mg, 2.75 mmol) and N,N-dimethylformamide (6 mL) was stirred at 140° C. for 6 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (1.59 g, 89%) as a yellow solid.

$^1$H-NMR (DMSO-d$_6$, 300 MHz) δ 0.82-0.84 (4H, m), 1.99-2.08 (1H, m), 7.57-7.63 (2H, m), 7.72-7.79 (2H, m), 7.86-7.91 (1H, m), 9.07-9.08 (1H, m), 11.06 (1H, s).

Example 32-2

N-[3-({2-[(cyclopropylcarbonyl)amino][1,2,4]triazolo[1,5-a]pyridin-6-yl}oxy)-5-fluorophenyl]-1,3-dimethyl-1H-pyrazole-5-carboxamide

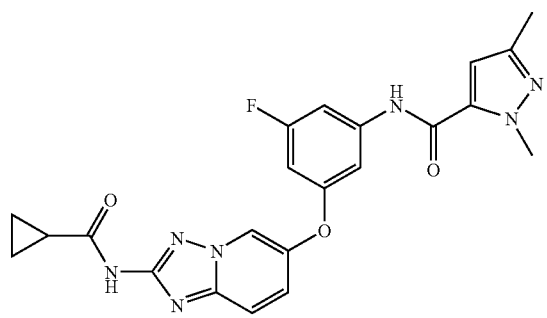

A mixture of N-[6-(3-fluoro-5-nitrophenoxy)[1,2,4]triazolo[1,5-a]pyridin-2-yl]cyclopropanecarboxamide (130 mg, 0.364 mmol), reduced iron (150 mg), concentrated hydrochloric acid (300 μL), ethanol (3 mL) and water (3 mL) was stirred under refluxing conditions for 1 hr. The reaction mixture was filtered through celite, and the filtrate was concentrated under reduced pressure. The residue was dissolved in N,N-dimethylacetamide (3 mL). 1,3-Dimethyl-1H-pyrazole-5-carbonyl chloride (69.3 mg, 0.437 mmol) was added thereto with stirring under ice-cooling, and the mixture was stirred at room temperature for 15 hr. The reaction mixture was diluted with saturated aqueous sodium hydrogen carbonate solution and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, ethyl acetate) and recrystallized from ethyl acetate to give the title compound (45.0 mg, 28%) as a white solid.

$^1$H-NMR (DMSO-d$_6$, 300 MHz) δ 0.82-0.84 (4H, m), 1.99-2.08 (1H, m), 2.17 (3H, s), 3.96 (3H, s), 6.73-6.79 (2H, m), 7.14 (1H, s), 7.49-7.59 (2H, m), 7.76 (1H, d, J=9.6 Hz), 9.02 (1H, d, J=2.4 Hz), 10.24 (1H, br s), 11.05 (1H, br s).

Example 33

N-[3-({2-[(cyclopropylcarbonyl)amino][1,2,4]triazolo[1,5-a]pyridin-6-yl}oxy)phenyl]-1,4-dimethyl-1H-pyrazole-3-carboxamide

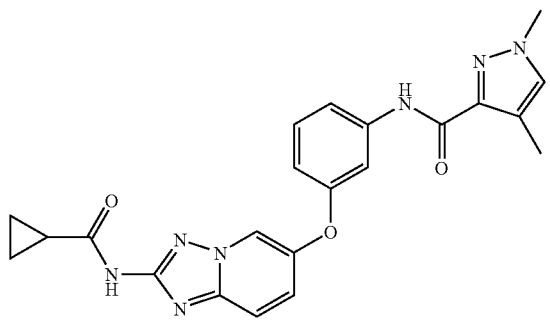

In the same manner as in Example 18-4 and using 1,4-dimethyl-1H-pyrazole-3-carboxylic acid (127 mg, 0.904 mmol), tetrahydrofuran (8 mL), oxalyl chloride (86.7 μL, 0.994 mmol), N-[6-(3-aminophenoxy)[1,2,4]triazolo[1,5-a]pyridin-2-yl]cyclopropanecarboxamide (60.0 mg, 0.194 mmol), N,N-dimethylformamide (1 drop) and N,N-dimethylacetamide (3 mL) as starting materials, the title compound (57.7 mg, 69%) was obtained as a white solid.

$^1$H-NMR (DMSO-d$_6$, 300 MHz) δ 0.81-0.84 (4H, m), 1.99-2.08 (1H, m), 2.20 (3H, s), 3.86 (3H, s), 6.74-6.78 (1H, m), 7.30 (1H, t, J=8.1 Hz), 7.49-7.74 (5H, m), 8.89 (1H, dd, J=2.4, 0.6 Hz), 9.96 (1H, s), 11.02 (1H, s).

Example 34

N-[3-({2-[(cyclopropylcarbonyl)amino][1,2,4]triazolo[1,5-a]pyridin-6-yl}oxy)phenyl]-1,4-dimethyl-1H-pyrrole-3-carboxamide

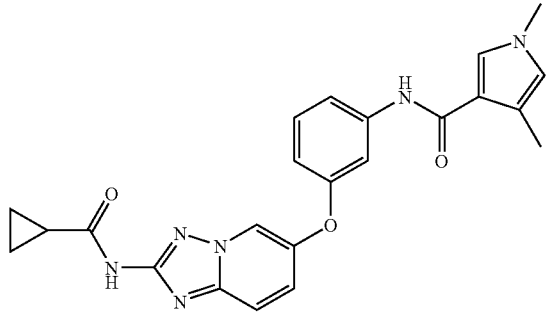

In the same manner as in Example 18-4 and using 1,4-dimethyl-1H-pyrrole-3-carboxylic acid (270 mg, 1.94 mmol), tetrahydrofuran (7 mL), oxalyl chloride (203 μL, 2.32 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (79.2 mg, 28%) was obtained as a white solid.

$^1$H-NMR (DMSO-d$_6$, 300 MHz) δ 0.80-0.85 (4H, m), 2.00-2.10 (1H, m), 2.14 (3H, s), 3.58 (3H, s), 6.52-6.56 (1H, m), 6.72 (1H, dd, J=8.3, 2.6 Hz), 7.29 (1H, t, J=8.3 Hz), 7.40-7.43 (2H, m), 7.50-7.57 (2H, m), 7.74 (1H, dd, J=9.6, 0.7 Hz), 8.90 (1H, dd, J=2.3, 0.7 Hz), 9.43 (1H, s), 11.04 (1H, s).

Example 35

N-[3-({2-[(cyclopropylcarbonyl)amino][1,2,4]triazolo[1,5-a]pyridin-6-yl}oxy)phenyl]-3-methyl-1-(2,2,2-trifluoroethyl)-1H-pyrazole-5-carboxamide

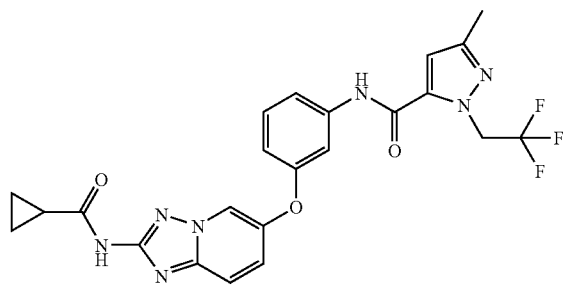

In the same manner as in Example 18-4 and using 3-methyl-1-(2,2,2-trifluoroethyl)-1H-pyrazole-5-carboxylic acid (269 mg, 1.29 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (278 mg, 86%) was obtained as a white solid.

$^1$H-NMR (DMSO-d$_6$, 300 MHz) δ 0.80-0.85 (4H, m), 2.00-2.10 (1H, m), 2.23 (3H, s), 5.39 (2H, q, J=9.1 Hz), 6.83-6.88 (1H, m), 6.95 (1H, s), 7.34-7.40 (2H, m), 7.52-7.60 (2H, m), 7.75 (1H, dd, J=9.6, 0.8 Hz), 8.95 (1H, dd, J=2.3, 0.8 Hz), 10.35 (1H, br s), 11.05 (1H, br s).

Example 36

N-[3-({2-[(cyclopropylcarbonyl)amino][1,2,4]triazolo[1,5-a]pyridin-6-yl}oxy)phenyl]-1-ethyl-3-methyl-1H-pyrazole-5-carboxamide

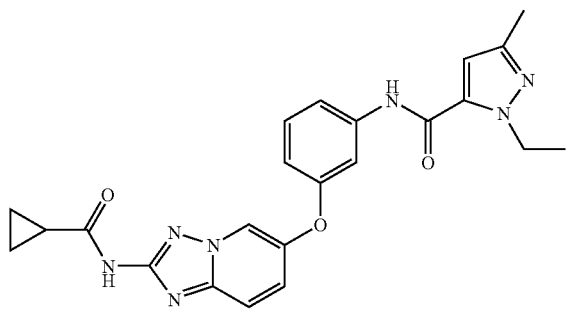

In the same manner as in Example 18-4 and using 1-ethyl-3-methyl-1H-pyrazole-5-carboxylic acid (180 mg, 1.17 mmol), tetrahydrofuran (7 mL), oxalyl chloride (152 μL, 1.74 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (242 mg, 84%) was obtained as a white solid.

$^1$H-NMR (DMSO-d$_6$, 300 MHz) δ 0.80-0.85 (4H, m), 1.29 (3H, t, J=7.1 Hz), 2.00-2.10 (1H, m), 2.19 (3H, s), 4.39 (2H, q, J=7.1 Hz), 6.77 (1H, s), 6.81-6.86 (1H, m), 7.33-7.44 (2H, m), 7.51-7.62 (2H, m), 7.75 (1H, dd, J=9.6, 0.7 Hz), 8.93 (1H, dd, J=2.6, 0.7 Hz), 10.15 (1H, br s), 11.05 (1H, br s).

Example 37

N-[3-({2-[(cyclopropylcarbonyl)amino][1,2,4]triazolo[1,5-a]pyridin-6-yl}oxy)phenyl]-1,3-dimethyl-1H-pyrazole-4-carboxamide

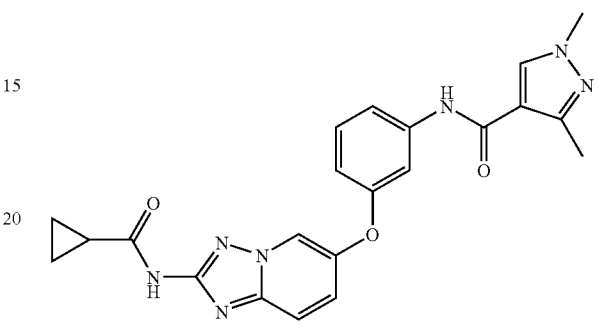

In the same manner as in Example 18-4 and using 1,3-dimethyl-1H-pyrazole-4-carboxylic acid (269 mg, 1.92 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (217 mg, 78%) was obtained as a white solid.

$^1$H-NMR (DMSO-d$_6$, 300 MHz) δ 0.80-0.85 (4H, m), 2.00-2.10 (1H, m), 2.31 (3H, s), 3.79 (3H, s), 6.77 (1H, dd, J=8.3, 2.3 Hz), 7.32 (1H, t, J=8.3 Hz), 7.39 (1H, t, J=2.3 Hz), 7.50-7.58 (2H, m), 7.75 (1H, dd, J=9.6, 0.9 Hz), 8.24 (1H, s), 8.90-8.95 (1H, m), 9.70 (1H, s), 11.05 (1H, br s).

Example 38

N-[3-({2-[(cyclopropylcarbonyl)amino][1,2,4]triazolo[1,5-a]pyridin-6-yl}oxy)phenyl]-1-ethyl-1H-pyrazole-5-carboxamide

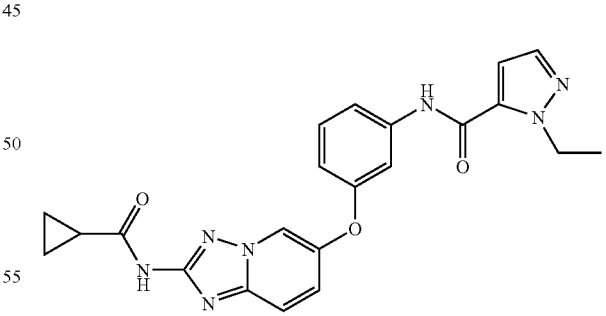

In the same manner as in Example 18-4 and using 1-ethyl-1H-pyrazole-5-carboxylic acid (269 mg, 1.92 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (231 mg, 83%) was obtained as a white solid.

$^1$H-NMR (DMSO-d$_6$, 300 MHz) δ 0.80-0.85 (4H, m), 1.32 (3H, t, J=7.1 Hz), 2.00-2.10 (1H, m), 4.48 (2H, q, J=7.1 Hz), 6.83-6.87 (1H, m), 7.00 (1H, d, J=2.1 Hz), 7.34-7.43 (2H, m), 7.52-7.61 (3H, m), 7.75 (1H, dd, J=9.6, 0.8 Hz), 8.93 (1H, dd, J=2.3, 0.8 Hz), 10.24 (1H, br s), 11.06 (1H, br s).

Example 39

N-[3-({2-[(cyclopropylcarbonyl)amino][1,2,4]triazolo[1,5-a]pyridin-6-yl}oxy)phenyl]-1,4-dimethyl-1H-pyrrole-2-carboxamide

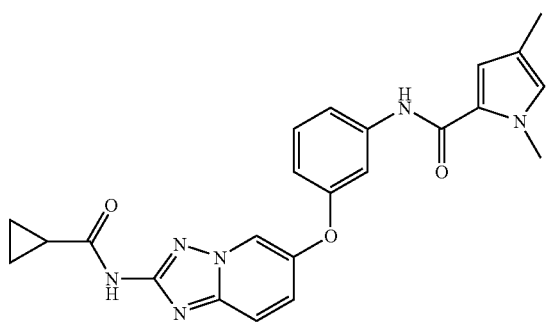

In the same manner as in Example 18-4 and using 1,4-dimethyl-1H-pyrrole-2-carboxylic acid (225 mg, 1.62 mmol), tetrahydrofuran (7 mL), oxalyl chloride (212 μL, 1.67 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (228 mg, 82%) was obtained as a white solid.

$^1$H-NMR (DMSO-d$_6$, 300 MHz) δ 0.80-0.85 (4H, m), 1.99-2.10 (4H, m), 3.77 (3H, s), 6.73-6.83 (3H, m), 7.30 (1H, t, J=8.3 Hz), 7.44 (1H, t, J=2.0 Hz), 7.50-7.58 (2H, m), 7.74 (1H, d, J=9.6 Hz), 8.90-8.92 (1H, m), 9.68 (1H, s), 11.05 (1H, br s).

Example 40-1

N-{3-[(2-amino[1,2,4]triazolo[1,5-a]pyridin-6-yl)oxy]-5-methylphenyl}-1,3-dimethyl-1H-pyrazole-5-carboxamide

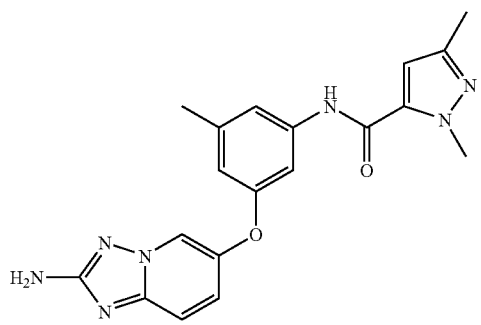

A mixture of ethyl ({[5-(3-{[(1,3-dimethyl-1H-pyrazol-5-yl)carbonyl]amino}-5-methylphenoxy)pyridin-2-yl]amino}carbonothioyl)carbamate (2.65 g, 4.76 mmol), hydroxylammonium chloride (2.96 g, 42.5 mmol), N,N-diisopropylethylamine (5.00 mL, 28.7 mmol), ethanol (100 mL) and methanol (100 mL) was stirred at 80° C. for 14 hr. The reaction solution was concentrated under reduced pressure. Ethyl acetate was added to the residue, and the mixture was washed with water and saturated brine, dried over anhydrous magnesium sulfate and filtrated. The filtrate was concentrated under reduced pressure and washed with ethanol-ethyl acetate to give the title compound (1.29 g, 72%) as a white solid.

$^1$H-NMR (DMSO-d$_6$, 300 MHz) δ 2.17 (3H, s), 2.28 (3H, s), 3.96 (3H, s), 6.01 (2H, s), 6.63 (1H, s), 6.77 (1H, s), 7.17 (1H, t, J=1.9 Hz), 7.25-7.34 (1H, m), 7.36-7.45 (2H, m), 8.61 (1H, d, J=1.9 Hz), 10.03 (1H, s).

Example 40-2

N-[3-({2-[(cyclopropylcarbonyl)amino][1,2,4]triazolo[1,5-a]pyridin-6-yl}oxy)-5-methylphenyl]-1,3-dimethyl-1H-pyrazole-5-carboxamide

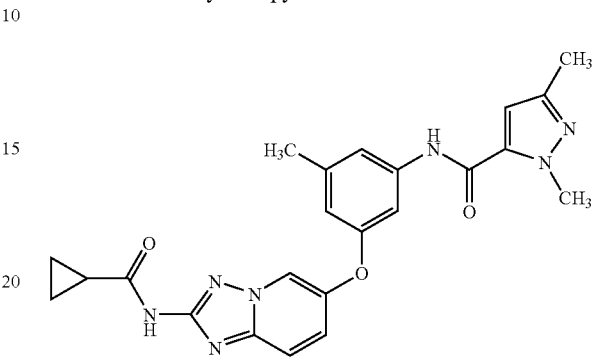

In the same manner as in Example 28-2 and using N-{3-[(2-amino[1,2,4]triazolo[1,5-a]pyridin-6-yl)oxy]-5-methylphenyl}-1,3-dimethyl-1H-pyrazole-5-carboxamide (303 mg, 0.803 mmol), cyclopropanecarbonyl chloride (74.0 μL, 0.815 mmol) and N,N-dimethylacetamide (10 mL) as starting materials, the title compound (188 mg, 53%) was obtained as a white solid.

$^1$H-NMR (DMSO-d$_6$, 300 MHz) δ 0.77-0.87 (4H, m), 1.96-2.10 (1H, m), 2.17 (3H, s), 2.29 (3H, s), 3.96 (3H, s), 6.67 (1H, s), 6.78 (1H, s), 7.21 (1H, t, J=1.9 Hz), 7.43 (1H, s), 7.52 (1H, dd, J=9.6, 2.3 Hz), 7.74 (1H, d, J=9.6 Hz), 8.91 (1H, d, J=2.3 Hz), 10.05 (1H, s), 11.04 (1H, s).

Example 41

N-{3-[(2-{[(ethylamino)carbonyl]amino}[1,2,4]triazolo[1,5-a]pyridin-6-yl)oxy]-5-methylphenyl}-1,3-dimethyl-1H-pyrazole-5-carboxamide

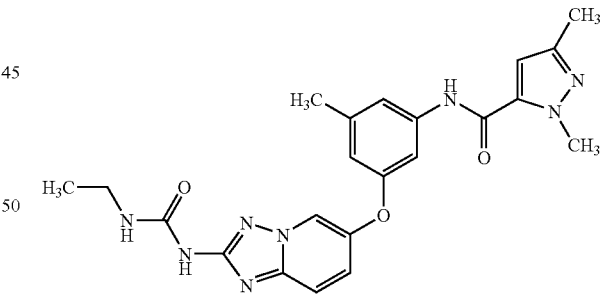

A mixture of N-{3-[(2-amino[1,2,4]triazolo[1,5-a]pyridin-6-yl)oxy]-5-methylphenyl}-1,3-dimethyl-1H-pyrazole-5-carboxamide (304 mg, 0.805 mmol), ethyl isocyanate (314 μL, 3.98 mmol) and pyridine (10 mL) was stirred at 50° C. for 18 hr. The reaction solution was concentrated under reduced pressure and ethyl acetate was added to the residue. The mixture was washed with saturated aqueous sodium hydrogen carbonate solution and saturated brine, dried over anhydrous magnesium sulfate and filtrated. The filtrate was concentrated under reduced pressure, and the residue was purified by column chromatography (silica gel, hexane/ethyl acetate=100/0→0/100) and recrystallized from ethyl acetate-hexane to give the title compound (151 mg, 42%) as a white solid.

¹H-NMR (DMSO-d₆, 300 MHz) δ 1.12 (3H, t, J=7.2 Hz), 2.18 (3H, s), 2.29 (3H, s), 3.18-3.31 (2H, m), 3.96 (3H, s), 6.67 (1H, s), 6.78 (1H, s), 7.19-7.26 (1H, m), 7.42 (1H, s), 7.53 (1H, dd, J=9.6, 2.3 Hz), 7.72 (1H, d, J=9.6 Hz), 8.17 (1H, t, J=5.5 Hz), 8.86 (1H, d, J=1.9 Hz), 9.89 (1H, s), 10.06 (1H, s).

Example 42

N-[3-({2-[(cyclopropylcarbonyl)amino][1,2,4]triazolo[1,5-a]pyridin-6-yl}oxy)phenyl]-3-ethyl-1-methyl-1H-pyrazole-5-carboxamide

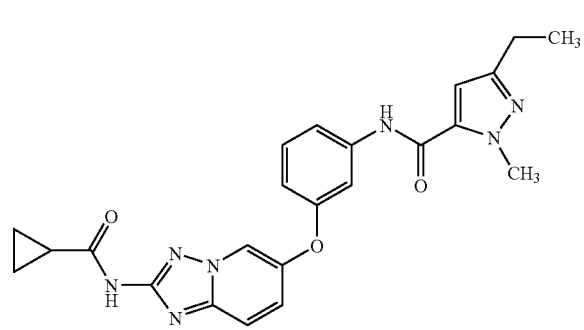

In the same manner as in Example 18-4 and using 3-ethyl-1-methyl-1H-pyrazole-5-carboxylic acid (212 mg, 1.37 mmol), tetrahydrofuran (10 mL), oxalyl chloride (180 μL, 2.07 mmol), N-[6-(3-aminophenoxy)[1,2,4]triazolo[1,5-a]pyridin-2-yl]cyclopropanecarboxamide (296 mg, 0.950 mmol), N,N-dimethylformamide (2 drops) and N,N-dimethylacetamide (10 mL) as starting materials, the title compound (261 mg, 61%) was obtained as a white solid.

¹H-NMR (DMSO-d₆, 300 MHz) δ 0.80-0.87 (4H, m), 1.18 (3H, J=7.2 Hz), 1.99-2.12 (1H, m), 2.51-2.61 (2H, m), 3.98 (3H, s), 6.83 (1H, s), 6.85 (1H, d, J=2.6 Hz), 7.36 (1H, t, J=8.1 Hz), 7.42 (1H, t, J=2.1 Hz), 7.50-7.62 (2H, m), 7.75 (1H, d, J=10.2 Hz), 8.93 (1H, d, J=1.5 Hz), 10.16 (1H, s), 11.05 (1H, s).

Example 43

N-[3-({2-[(cyclopropylcarbonyl)amino][1,2,4]triazolo[1,5-a]pyridin-6-yl}oxy)phenyl]-4-methyl-1,3-thiazole-5-carboxamide

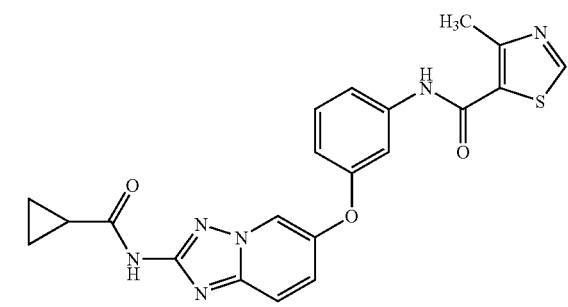

In the same manner as in Example 18-4 and using 4-methyl-1,3-thiazole-5-carboxylic acid (531 mg, 3.70 mmol), tetrahydrofuran (10 mL), oxalyl chloride (477 μL, 5.49 mmol), N-[6-(3-aminophenoxy)[1,2,4]triazolo[1,5-a]pyridin-2-yl]cyclopropanecarboxamide (295 mg, 0.954 mmol), N,N-dimethylformamide (2 drops) and N,N-dimethylacetamide (10 mL) as starting materials, the title compound (253 mg, 61%) was obtained as a white solid.

¹H-NMR (DMSO-d₆, 300 MHz) δ 0.83 (4H, m), 1.96-2.12 (1H, m), 2.58 (3H, s), 6.83 (1H, dd, J=8.1, 2.5 Hz), 7.30-7.43 (2H, m), 7.45-7.58 (2H, m), 7.74 (1H, d, J=9.4 Hz), 8.93 (1H, d, J=2.3 Hz), 9.12 (1H, s), 10.28 (1H, s), 11.04 (1H, s).

Example 44

N-[3-({2-[(cyclopropylcarbonyl)amino][1,2,4]triazolo[1,5-a]pyridin-6-yl}oxy)phenyl]-4-methyl-1,3-oxazole-5-carboxamide

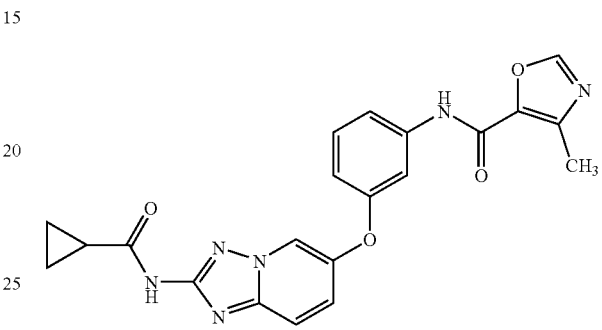

In the same manner as in Example 18-4 and using 4-methyl-1,3-oxazole-5-carboxylic acid (410 mg, 3.22 mmol), tetrahydrofuran (10 mL), oxalyl chloride (420 μL, 4.84 mmol), N-[6-(3-aminophenoxy)[1,2,4]triazolo[1,5-a]pyridin-2-yl]cyclopropanecarboxamide (200 mg, 0.647 mmol), N,N-dimethylformamide (2 drops) and N,N-dimethylacetamide (10 mL) as starting materials, the title compound (102 mg, 38%) was obtained as a white solid.

¹H-NMR (DMSO-d₆, 300 MHz) δ 0.80-0.87 (4H, m), 1.96-2.13 (1H, m), 2.40 (3H, s), 6.80-6.87 (1H, m), 7.35 (1H, t, J=8.3 Hz), 7.48 (1H, t, J=2.3 Hz), 7.53 (1H, dd, J=9.6, 2.5 Hz), 7.59-7.64 (1H, m), 7.72-7.77 (1H, m), 8.51 (1H, s), 8.93 (1H, dd, J=2.3, 0.8 Hz), 10.31 (1H, s), 11.05 (1H, s).

Example 45

N-[3-({2-[(cyclopropylcarbonyl)amino][1,2,4]triazolo[1,5-a]pyridin-6-yl}oxy)phenyl]-1,3-oxazole-4-carboxamide

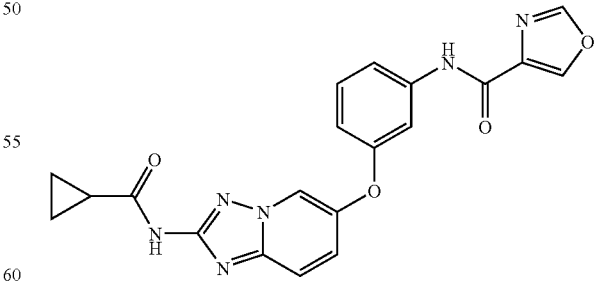

In the same manner as in Example 18-4 and using 1,3-oxazole-4-carboxylic acid (146 mg, 1.29 mmol), tetrahydrofuran (10 mL), oxalyl chloride (168 μL, 1.93 mmol), N-[6-(3-aminophenoxy)[1,2,4]triazolo[1,5-a]pyridin-2-yl]cyclopropanecarboxamide (200 mg, 0.647 mmol), N,N-dimethylformamide (2 drops) and N,N-dimethylacetamide (10 mL) as starting materials, the title compound (120 mg, 46%) was obtained as a white solid.

¹H-NMR (DMSO-d₆, 300 MHz) δ 0.78-0.87 (4H, m), 1.95-2.12 (1H, m), 6.79-6.86 (1H, m), 7.35 (1H, t, J=8.2 Hz), 7.49-7.59 (2H, m), 7.64-7.70 (1H, m), 7.71-7.77 (1H, m), 8.61 (1H, d, J=0.8 Hz), 8.79 (1H, d, J=0.8 Hz), 8.93 (1H, d, J=1.9 Hz), 10.26 (1H, s), 11.05 (1H, s).

Example 46

N-[3-({2-[(cyclopropylcarbonyl)amino][1,2,4]triazolo[1,5-a]pyridin-6-yl}oxy)phenyl]-1-methyl-1H-indazole-3-carboxamide

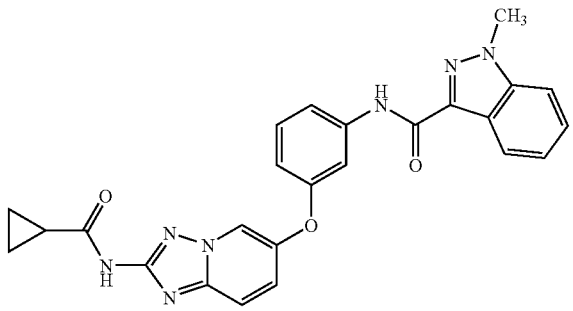

In the same manner as in Example 18-4 and using 1-methyl-1H-indazole-3-carboxylic acid (300 mg, 1.70 mmol), tetrahydrofuran (10 mL), oxalyl chloride (222 μL, 2.55 mmol), N-[6-(3-aminophenoxy)[1,2,4]triazolo[1,5-a]pyridin-2-yl]cyclopropanecarboxamide (200 mg, 0.647 mmol), N,N-dimethylformamide (2 drops) and N,N-dimethylacetamide (10 mL) as starting materials, the title compound (85.0 mg, 28%) was obtained as a white solid.

¹H-NMR (DMSO-d₆, 300 MHz) δ 0.79-0.87 (4H, m), 1.98-2.13 (1H, m), 4.18 (3H, s), 6.77-6.86 (1H, m), 7.27-7.40 (2H, m), 7.46-7.59 (2H, m), 7.64 (1H, t, J=2.3 Hz), 7.71-7.81 (3H, m), 8.17-8.23 (1H, m), 8.93 (1H, d, J=1.9 Hz), 10.41 (1H, s), 11.04 (1H, s).

Example 47

N-[3-({2-[(cyclopropylcarbonyl)amino][1,2,4]triazolo[1,5-a]pyridin-6-yl}oxy)phenyl]-3-methoxy-1-methyl-1H-pyrazole-5-carboxamide

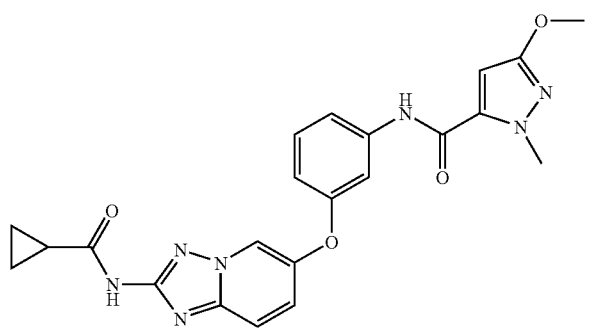

In the same manner as in Example 18-4 and using 3-methoxy-1-methyl-1H-pyrazole-5-carboxylic acid (201 mg, 1.29 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (265 mg, 92%) was obtained as a white solid.

¹H-NMR (DMSO-d₆, 300 MHz) δ 0.82-0.84 (4H, m), 1.99-2.10 (1H, m), 3.79 (3H, s), 3.90 (3H, s), 6.43 (1H, s), 6.83-6.87 (1H, m), 7.34-7.41 (2H, m), 7.52-7.58 (2H, m), 7.74-7.77 (1H, m), 8.93-8.94 (1H, m), 10.16 (1H, br s), 11.06 (1H, br s).

Example 48

N-[3-({2-[(cyclopropylcarbonyl)amino][1,2,4]triazolo[1,5-a]pyridin-6-yl}oxy)phenyl]-1-isopropyl-3-methyl-1H-pyrazole-5-carboxamide

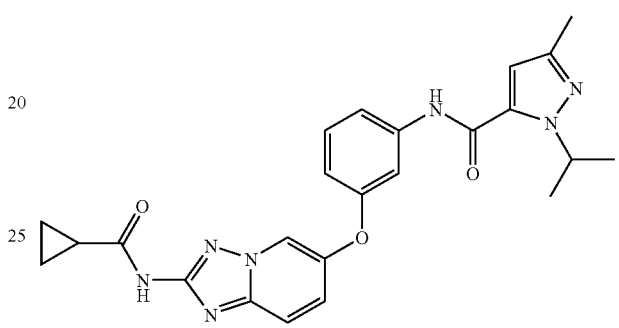

In the same manner as in Example 18-4 and using 1-isopropyl-3-methyl-1H-pyrazole-5-carboxylic acid (218 mg, 1.29 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (264 mg, 89%) was obtained as a white solid.

¹H-NMR (DMSO-d₆, 300 MHz) δ 0.81-0.84 (4H, m), 1.36 (6H, d, J=6.3 Hz), 2.00-2.10 (1H, m), 2.20 (3H, s), 5.21-5.30 (1H, m), 6.68 (1H, s), 6.81-6.84 (1H, m), 7.35 (1H, t, J=8.1 Hz), 7.42 (1H, t, J=2.3 Hz), 7.50-7.57 (2H, m), 7.24 (1H, d, J=9.6 Hz), 8.92 (1H, d, J=2.4 Hz), 10.18 (1H, br s), 11.03 (1H, br s).

Example 49

N-[3-({2-[(cyclopropylcarbonyl)amino][1,2,4]triazolo[1,5-a]pyridin-6-yl}oxy)phenyl]-1-ethyl-4-(trifluoromethyl)-1H-pyrrole-3-carboxamide

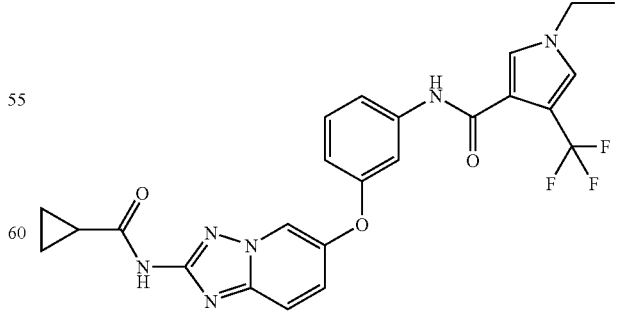

In the same manner as in Example 18-4 and using 1-ethyl-4-(trifluoromethyl)-1H-pyrrole-3-carboxylic acid (268 mg, 1.29 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (238 mg, 74%) was obtained as a white solid.

¹H-NMR (DMSO-d₆, 300 MHz) δ 0.81-0.85 (4H, m), 1.37 (3H, t, J=7.2 Hz), 1.99-2.10 (1H, m), 3.99 (2H, q, J=7.2 Hz), 6.74-6.78 (1H, m), 7.28-7.35 (2H, m), 7.46-7.57 (3H, m), 7.68-7.75 (2H, m), 8.89-8.91 (1H, m), 9.80 (1H, s), 11.03 (1H, br s).

Example 50

N-[3-({2-[(cyclopropylcarbonyl)amino][1,2,4]triazolo[1,5-a]pyridin-6-yl}oxy)phenyl]-1-ethyl-4-methyl-1H-pyrrole-3-carboxamide

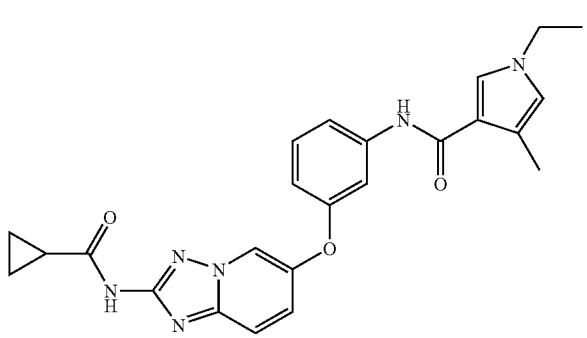

In the same manner as in Example 18-4 and using 1-ethyl-4-methyl-1H-pyrrole-3-carboxylic acid (198 mg, 1.29 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (67.0 mg, 23%) was obtained as a white solid.

¹H-NMR (DMSO-d₆, 300 MHz) δ 0.82-0.84 (4H, m), 1.32 (3H, t, J=7.3 Hz), 1.99-2.15 (4H, m), 3.85 (2H, q, J=7.3 Hz), 6.60-6.61 (1H, m), 6.69-6.73 (1H, m), 7.28 (1H, t, J=8.3 Hz), 7.41 (1H, t, J=2.1 Hz), 7.47-7.55 (3H, m), 7.73 (1H, d, J=10.2 Hz), 8.88-8.89 (1H, m), 9.42 (1H, s), 11.03 (1H, br s).

Example 51

N-[3-({2-[(cyclopropylcarbonyl)amino][1,2,4]triazolo[1,5-a]pyridin-6-yl}oxy)phenyl]-1-ethyl-3-methyl-1H-pyrazole-4-carboxamide

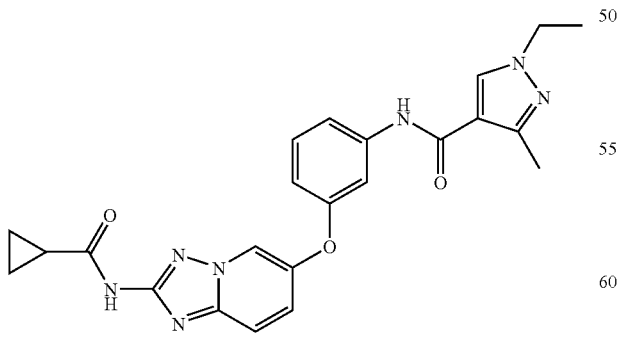

In the same manner as in Example 18-4 and using 1-ethyl-3-methyl-1H-pyrazole-4-carboxylic acid (198 mg, 1.28 mmol), tetrahydrofuran (7 mL), oxalyl chloride (169 μL, 1.94 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (3 mL) as starting materials, the title compound (230 mg, 80%) was obtained as a white solid.

¹H-NMR (DMSO-d₆, 300 MHz) δ 0.81-0.84 (4H, m), 1.37 (3H, t, J=7.1 Hz), 1.99-2.10 (1H, m), 2.32 (3H, s), 4.07 (2H, q, J=7.1 Hz), 6.74-6.77 (1H, m), 7.31 (1H, t, J=8.3 Hz), 7.37 (1H, t, J=2.1 Hz), 7.50-7.54 (2H, m), 7.74 (1H, dd, J=9.6, 0.6 Hz), 8.28 (1H, s), 8.90-8.91 (1H, m), 9.68 (1H, s), 11.03 (1H, br s).

Example 52

5-chloro-N-[3-({2-[(cyclopropylcarbonyl)amino][1,2,4]triazolo[1,5-a]pyridin-6-yl}oxy)phenyl]-1-methyl-1H-pyrazole-4-carboxamide

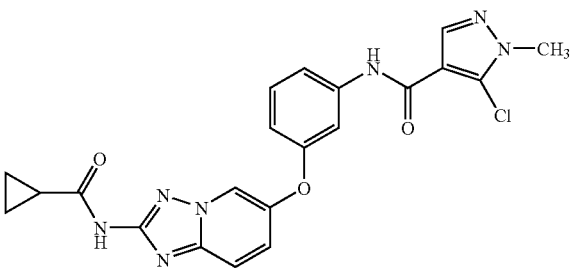

In the same manner as in Example 18-4 and using 5-chloro-1-methyl-1H-pyrazole-4-carboxylic acid (291 mg, 1.81 mmol), tetrahydrofuran (10 mL), oxalyl chloride (236 μL, 2.72 mmol), N-[6-(3-aminophenoxy)[1,2,4]triazolo[1,5-a]pyridin-2-yl]cyclopropanecarboxamide (200 mg, 0.647 mmol), N,N-dimethylformamide (2 drops) and N,N-dimethylacetamide (10 mL) as starting materials, the title compound (25.0 mg, 9%) was obtained as a white solid.

¹H-NMR (DMSO-d₆, 300 MHz) δ 0.76-0.91 (4H, m), 1.95-2.12 (1H, m), 3.83 (3H, s), 6.81 (1H, dd, J=8.1, 2.5 Hz), 7.35 (1H, t, J=8.1 Hz), 7.41 (1H, t, J=2.3 Hz), 7.48-7.58 (2H, m), 7.75 (1H, d, J=9.4 Hz), 8.15 (1H, s), 8.93 (1H, d, J=2.3 Hz), 9.93 (1H, s), 11.05 (1H, s).

Example 53-1 tert-butyl {5-[(2-amino[1,2,4]triazolo[1,5-a]pyridin-6-yl)oxy]-2-methylphenyl}carbamate

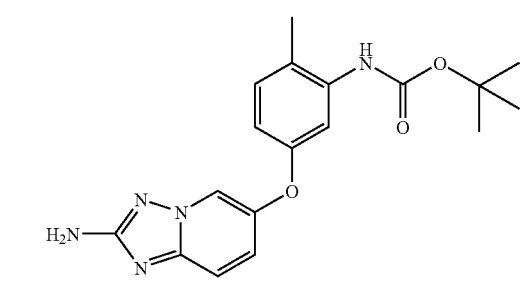

A mixture of ethyl {[(5-{3-[(tert-butoxycarbonyl)amino]-4-methylphenoxy}pyridin-2-yl)amino]carbonothioyl}carbamate (11.5 g, 15.4 mmol), hydroxylammonium chloride (15.4 g, 0.223 mol), N,N-diisopropylethylamine (23.0 mL, 0.132 mol), ethanol (200 mL) and methanol (200 mL) was stirred at 80° C. for 12 hr. The reaction solution was concentrated under reduced pressure and ethyl acetate was added to the residue. The mixture was washed with water and saturated brine, dried over anhydrous magnesium sulfate and filtrated. The filtrate was concentrated under reduced pressure, and the residue was recrystallized from ethyl acetate-hexane to give the title compound (9.18 g, 100%) as a white solid.

¹H-NMR (CDCl₃, 300 MHz) δ 1.50 (9H, s), 2.22 (3H, s), 4.42 (2H, s), 6.32 (1H, s), 6.61 (1H, dd, J=8.3, 2.7 Hz), 7.09 (1H, d, J=8.3 Hz), 7.23 (1H, d, J=2.3 Hz), 7.32-7.38 (1H, m), 7.70 (1H, d, J=1.9 Hz), 8.07 (1H, d, J=1.9 Hz).

Example 53-2 tert-butyl [5-({2-[(cyclopropylcarbonyl)amino][1,2,4]triazolo[1,5-a]pyridin-6-yl}oxy)-2-methylphenyl]carbamate

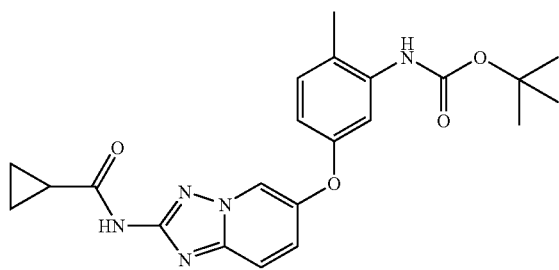

To a solution of tert-butyl {5-[(2-amino[1,2,4]triazolo[1,5-a]pyridin-6-yl)oxy]-2-methylphenyl}carbamate (3.52 g, 8.92 mmol) in N,N-dimethylacetamide (30 mL) was added cyclopropanecarbonyl chloride (0.811 mL, 8.93 mmol) at 0° C., and the mixture was stirred at room temperature for 84 hr. The reaction mixture was diluted with saturated aqueous sodium hydrogen carbonate solution, and extracted with ethyl acetate. The organic layer was washed with saturated aqueous sodium hydrogen carbonate solution and saturated brine, dried over anhydrous magnesium sulfate and filtrated. The filtrate was concentrated under reduced pressure, and the residue was purified by column chromatography (silica gel, hexane/ethyl acetate=100/0→425/75) to give the title compound (3.87 g, 97%) as a colorless oil.

¹H-NMR (CDCl₃, 300 MHz) δ 0.88-0.97 (2H, m), 1.15-1.22 (2H, m), 1.50 (9H, s), 2.00-2.10 (1H, m), 2.24 (3H, s), 6.35 (1H, s), 6.64 (1H, dd, J=8.2, 2.5 Hz), 7.12 (1H, d, J=8.2 Hz), 7.38 (1H, dd, J=9.4, 2.3 Hz), 7.50-7.58 (1H, m), 7.73-7.79 (1H, m), 8.21 (1H, d, J=1.9 Hz), 9.00 (1H, s).

Example 53-3

N-[6-(3-amino-4-methylphenoxy)[1,2,4]triazolo[1,5-a]pyridin-2-yl]cyclopropanecarboxamide

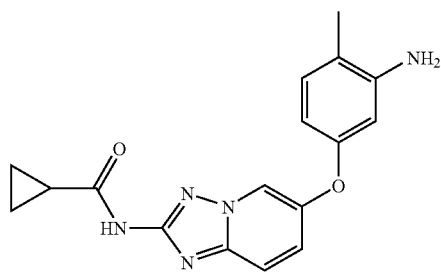

In the same manner as in Example 29 and using tert-butyl [5-({2-[(cyclopropylcarbonyl)amino][1,2,4]triazolo[1,5-a]pyridin-6-yl}oxy)-2-methylphenyl]carbamate (3.78 g, 8.48 mmol) and trifluoroacetic acid (20 mL) as starting materials, the title compound (2.43 g, 89%) was obtained as a white solid.

¹H-NMR (CDCl₃, 300 MHz) δ 0.87-0.97 (2H, m), 1.15-1.23 (2H, m), 1.65 (1H, s), 2.14 (3H, s), 3.70 (2H, s), 6.29-6.39 (2H, m), 7.01 (1H, d, J=7.5 Hz), 7.33-7.41 (1H, m), 7.55 (1H, dd, J=9.8, 0.8 Hz), 8.27 (1H, d, J=1.9 Hz), 9.56 (1H, s).

Example 53-4

N-[5-({2-[(cyclopropylcarbonyl)amino][1,2,4]triazolo[1,5-a]pyridin-6-yl}oxy)-2-methylphenyl]-1-ethyl-3-methyl-1H-pyrazole-5-carboxamide

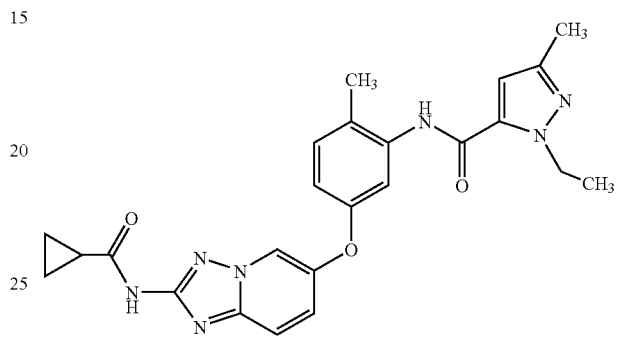

In the same manner as in Example 18-4 and using 1-ethyl-3-methyl-1H-pyrazole-5-carboxylic acid (572 mg, 3.71 mmol), tetrahydrofuran (10 mL), oxalyl chloride (536 µL, 6.17 mmol), N-[6-(3-amino-4-methylphenoxy)[1,2,4]triazolo[1,5-a]pyridin-2-yl]cyclopropanecarboxamide (200 mg, 0.619 mmol), N,N-dimethylformamide (1 drop) and N,N-dimethylacetamide (10 mL) as starting materials, the title compound (153 mg, 54%) was obtained as a pale-yellow solid.

¹H-NMR (DMSO-d₆, 300 MHz) δ 0.76-0.87 (4H, m), 1.28 (3H, t, J=7.2 Hz), 1.95-2.11 (1H, m), 2.19 (6H, s), 4.40 (2H, q, J=7.2 Hz), 6.77 (1H, s), 6.93 (1H, dd, J=8.6, 2.8 Hz), 7.10 (1H, d, J=2.6 Hz), 7.28 (1H, d, J=8.6 Hz), 7.50 (1H, dd, J=9.5, 2.5 Hz), 7.72 (1H, d, J=9.5 Hz), 8.83 (1H, d, J=1.5 Hz), 9.77 (1H, s), 11.03 (1H, s).

Example 54

N-[5-({2-[(cyclopropylcarbonyl)amino][1,2,4]triazolo[1,5-a]pyridin-6-yl}oxy)-2-methylphenyl]-2-methyl-5-(trifluoromethyl)-1,3-oxazole-4-carboxamide

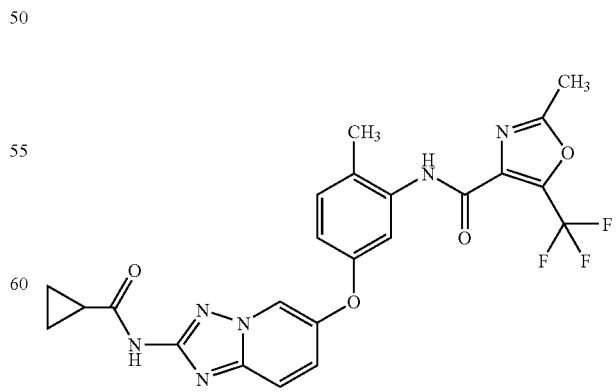

To a solution of 2-methyl-5-(trifluoromethyl)-1,3-oxazole-4-carboxylic acid (241 mg, 1.23 mmol) in tetrahydrofuran (5 mL) were added N,N-dimethylformamide (2 drops) and oxalyl chloride (268 μL, 3.08 mmol), and the mixture was stirred at room temperature for 3 hr. The reaction mixture was concentrated under reduced pressure, and the residue was dissolved in N,N-dimethylacetamide (6 mL). The mixture was stirred at room temperature, N-[6-(3-amino-4-methylphenoxy)[1,2,4]triazolo[1,5-a]pyridin-2-yl]cyclopropanecarboxamide (200 mg, 0.619 mmol) was added thereto, and the mixture was stirred at room temperature for 62 hr. Methanol (5 mL), tetrahydrofuran (5 mL), water (5 mL) and sodium carbonate solution (2 mL) were added to the reaction mixture, and the mixture was stirred at room temperature for 2 hr. The reaction solution was concentrated under reduced pressure, and ethyl acetate was added to the residue. A white precipitate was collected by filtration, and the filtrate was washed with saturated aqueous sodium hydrogen carbonate solution and saturated brine, dried over anhydrous magnesium sulfate and filtrated. The filtrate was concentrated under reduced pressure, and a white precipitate obtained above was added to the residue. The mixture was recrystallized from ethanol to give the title compound (252 mg, 81%) as a white solid.

$^1$H-NMR (DMSO-$d_6$, 300 MHz) δ 0.75-0.89 (4H, m), 1.96-2.11 (1H, m), 2.21 (3H, s), 2.60 (3H, s), 6.91 (1H, dd, J=8.3, 2.7 Hz), 7.20-7.33 (2H, m), 7.50 (1H, dd, J=9.5, 2.3 Hz), 7.68-7.75 (1H, m), 8.83 (1H, d, J=1.9 Hz), 10.00 (1H, s), 11.01 (1H, s).

Example 55

N-[5-({2-[(cyclopropylcarbonyl)amino][1,2,4]triazolo[1,5-a]pyridin-6-yl}oxy)-2-methylphenyl]-2,5-dimethyl-1,3-thiazole-4-carboxamide

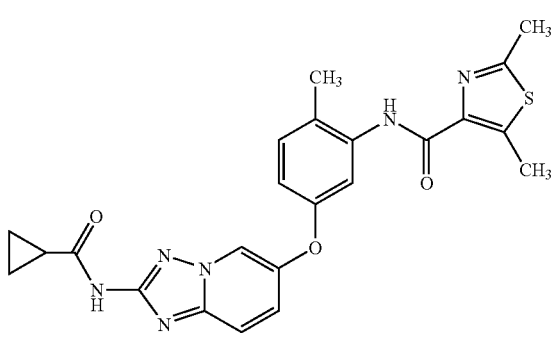

To a solution of 2,5-dimethyl-1,3-thiazole-4-carboxylic acid (107 mg, 0.681 mmol) in tetrahydrofuran (5 mL) were added N,N-dimethylformamide (2 drops) and thionyl chloride (118 μL, 1.36 mmol), and the mixture was stirred at room temperature for 2 hr. The reaction mixture was concentrated under reduced pressure, and the residue was dissolved in N,N-dimethylacetamide (6 mL). N-[6-(3-Amino-4-methylphenoxy)[1,2,4]triazolo[1,5-a]pyridin-2-yl]cyclopropanecarboxamide (200 mg, 0.619 mmol) was added thereto, and the mixture was stirred at room temperature for 2 hr. The reaction mixture was diluted with saturated aqueous sodium hydrogen carbonate solution, and extracted with ethyl acetate. The organic layer was washed with saturated aqueous sodium hydrogen carbonate solution and saturated brine, dried over anhydrous magnesium sulfate and filtrated. The filtrate was concentrated under reduced pressure, the residue was and recrystallized from ethanol to give the title compound (248 mg, 87%) as a white solid.

$^1$H-NMR (DMSO-$d_6$, 300 MHz) δ 0.78-0.86 (4H, m), 1.97-2.10 (1H, m), 2.23 (3H, s), 2.65 (3H, s), 2.70 (3H, s), 6.82 (1H, dd, J=8.5, 2.7 Hz), 7.27 (1H, d, J=8.5 Hz), 7.50 (1H, dd, J=9.5, 2.3 Hz), 7.66 (1H, d, J=2.7 Hz), 7.69-7.75 (1H, m), 8.82 (1H, dd, J=2.3, 0.8 Hz), 9.66 (1H, s), 11.02 (1H, s).

Example 56

N-[5-({2-[(cyclopropylcarbonyl)amino][1,2,4]triazolo[1,5-a]pyridin-6-yl}oxy)-2-methylphenyl]-1-methyl-1H-pyrazole-5-carboxamide

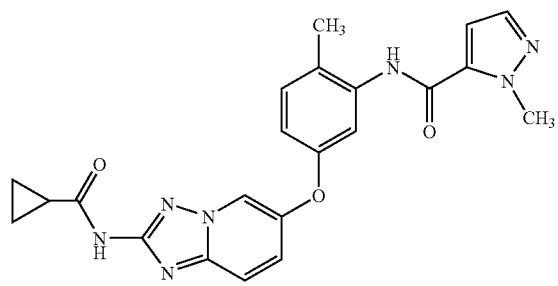

In the same manner as in Example 55 and using 1-methyl-1H-pyrazole-5-carboxylic acid (86.0 mg, 0.686 mmol), tetrahydrofuran (5 mL), thionyl chloride (118 μL, 1.36 mmol), N,N-dimethylformamide (2 drops), N-[6-(3-amino-4-methylphenoxy)[1,2,4]triazolo[1,5-a]pyridin-2-yl]cyclopropanecarboxamide (200 mg, 0.619 mmol) and N,N-dimethylacetamide (6 mL) as starting materials, the title compound (125 mg, 47%) was obtained as a white solid.

$^1$H-NMR (DMSO-$d_6$, 300 MHz) δ 0.78-0.87 (4H, m), 1.97-2.11 (1H, m), 2.20 (3H, s), 4.05 (3H, s), 6.94 (1H, dd, J=8.5, 2.7 Hz), 7.02 (1H, d, J=1.9 Hz), 7.09 (1H, d, J=2.7 Hz), 7.29 (1H, d, J=8.5 Hz), 7.46-7.53 (2H, m), 7.72 (1H, dd, J=9.8, 0.8 Hz), 8.82-8.85 (1H, d, J=2.3, 0.8 Hz), 9.86 (1H, s), 11.02 (1H, s).

Example 57

N-[5-({2-[(cyclopropylcarbonyl)amino][1,2,4]triazolo[1,5-a]pyridin-6-yl}oxy)-2-methylphenyl]-3-ethyl-1-methyl-1H-pyrazole-5-carboxamide

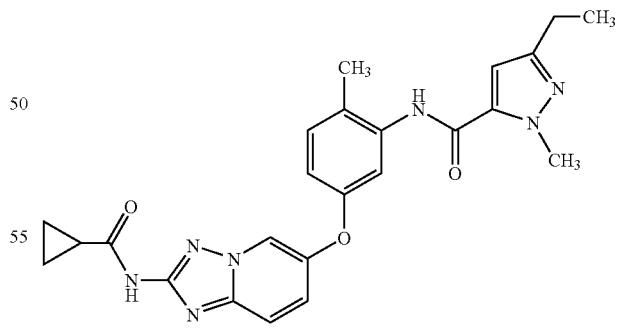

In the same manner as in Example 55 and using 3-ethyl-1-methyl-1H-pyrazole-5-carboxylic acid (98.0 mg, 0.632 mmol), tetrahydrofuran (5 mL), thionyl chloride (109 μL, 1.25 mmol), N,N-dimethylformamide (2 drops), N-[6-(3-amino-4-methylphenoxy)[1,2,4]triazolo[1,5-a]pyridin-2-yl] cyclopropanecarboxamide (185 mg, 0.572 mmol) and N,N-dimethylacetamide (6 mL) as starting materials, the title compound (160 mg, 61%) was obtained as a white solid.

¹H-NMR (DMSO-d₆, 300 MHz) δ 0.78-0.88 (4H, m), 1.18 (3H, t, J=7.6 Hz), 1.95-2.10 (1H, m), 2.20 (3H, s), 2.56 (2H, q, J=7.6 Hz), 3.98 (3H, s), 6.83 (1H, s), 6.93 (1H, dd, J=8.5, 2.6 Hz), 7.08 (1H, d, J=2.6 Hz), 7.28 (1H, d, J=8.5 Hz), 7.50 (1H, dd, J=9.8, 2.3 Hz), 7.69-7.76 (1H, m), 8.81-8.85 (1H, m), 9.78 (1H, s), 11.03 (1H, s).

Example 58

N-(6-{4-methyl-3-[(3-methylbutanoyl)amino]phenoxy}[1,2,4]triazolo[1,5-a]pyridin-2-yl)cyclopropanecarboxamide

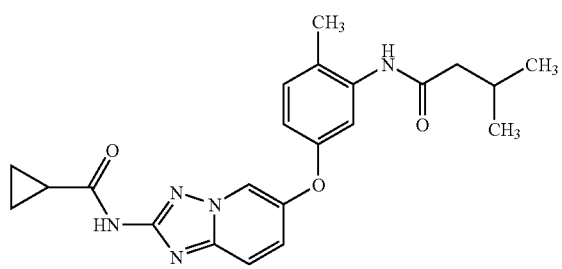

To a solution of N-[6-(3-amino-4-methylphenoxy)[1,2,4]triazolo[1,5-a]pyridin-2-yl]cyclopropanecarboxamide (185 mg, 0.572 mmol) in N,N-dimethylacetamide (5 mL) was added 3-methylbutanoyl chloride (71.0 μL, 0.579 mmol), and the mixture was stirred at room temperature for 12 hr. The reaction mixture was diluted with saturated aqueous sodium hydrogen carbonate solution, and extracted with ethyl acetate. The organic layer was washed with saturated aqueous sodium hydrogen carbonate solution and saturated brine, dried over anhydrous magnesium sulfate and filtrated. The filtrate was concentrated under reduced pressure, and the residue was recrystallized from ethanol to give the title compound (176 mg, 72%) as a white solid.

¹H-NMR (DMSO-d₆, 300 MHz) δ 0.79-0.85 (4H, m), 0.93 (6H, d, J=6.4 Hz), 1.96-2.11 (2H, m), 2.16-2.23 (5H, m), 6.79 (1H, dd, J=8.3, 2.7 Hz), 7.17-7.25 (2H, m), 7.47 (1H, dd, J=9.6, 2.4 Hz), 7.71 (1H, dd, J=9.6, 0.8 Hz), 8.79 (1H, dd, J=2.4, 0.8 Hz), 9.21 (1H, s), 11.01 (1H, s).

Example 59

N-[5-({2-[(cyclopropylcarbonyl)amino][1,2,4]triazolo[1,5-a]pyridin-6-yl}oxy)-2-methylphenyl]-2,5-dimethyl-3-furamide

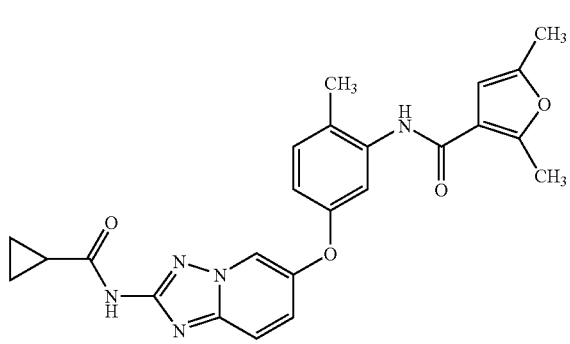

In the same manner as in Example 58 and using 2,5-dimethyl-3-furoyl chloride (84.0 μL, 0.630 mmol), N,N-dimethylacetamide (5 mL) and N-[6-(3-amino-4-methylphenoxy)[1,2,4]triazolo[1,5-a]pyridin-2-yl] cyclopropanecarboxamide (185 mg, 0.572 mmol) as starting materials, the title compound (150 mg, 56%) was obtained as a white solid.

¹H-NMR (DMSO-d₆, 300 MHz) δ 0.78-0.87 (4H, m), 1.97-2.10 (1H, m), 2.18 (3H, s), 2.24 (3H, s), 2.46 (3H, s), 6.56 (1H, s), 6.89 (1H, dd, J=8.8, 2.7 Hz), 7.11 (1H, d, J=2.7 Hz), 7.26 (1H, d, J=8.8 Hz), 7.49 (1H, dd, J=9.4, 2.3 Hz), 7.72 (1H, dd, J=9.4, 0.8 Hz), 8.81 (1H, dd, J=2.3, 0.8 Hz), 9.21 (1H, s), 11.02 (1H, s).

Example 60

N-[5-({2-[(cyclopropylcarbonyl)amino][1,2,4]triazolo[1,5-a]pyridin-6-yl}oxy)-2-methylphenyl]cyclopent-3-en-1-carboxamide

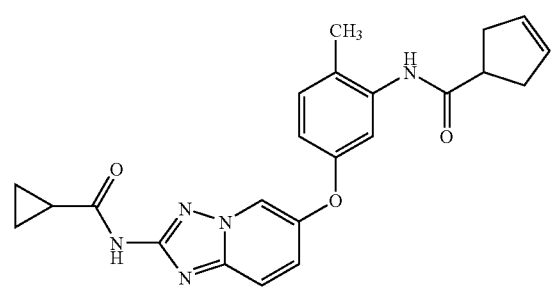

In the same manner as in Example 55 and using cyclopenta-3-en-1-carboxylic acid (66.0 mg, 0.592 mmol), tetrahydrofuran (5 mL), thionyl chloride (100 μL, 1.15 mmol), N,N-dimethylformamide (2 drops), N-[6-(3-amino-4-methylphenoxy)[1,2,4]triazolo[1,5-a]pyridin-2-yl]cyclopropanecarboxamide (170 mg, 0.526 mmol) and N,N-dimethylacetamide (5 mL) as starting materials, the title compound (130 mg, 59%) was obtained as a white solid.

¹H-NMR (DMSO-d₆, 300 MHz) δ 0.78-0.86 (4H, m), 1.95-2.11 (1H, m), 2.18 (3H, s), 2.53-2.60 (4H, m), 3.19-3.29 (1H, m), 5.65 (2H, s), 6.81 (1H, dd, J=8.5, 2.8 Hz), 7.17-7.25 (2H, m), 7.44-7.50 (1H, m), 7.71 (1H, dd, J=9.4, 0.8 Hz), 8.80 (1H, dd, J=2.3, 0.8 Hz), 9.27 (1H, s), 11.02 (1H, s).

Example 61

4-chloro-N-[5-({2-[(cyclopropylcarbonyl)amino][1,2,4]triazolo[1,5-a]pyridin-6-yl}oxy)-2-methylphenyl]-1-methyl-1H-pyrazole-3-carboxamide

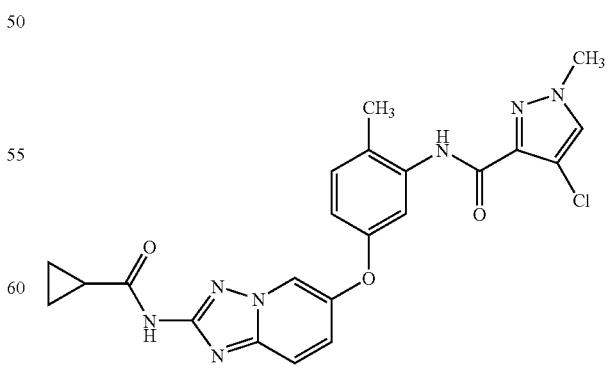

In the same manner as in Example 55 and using 4-chloro-1-methyl-1H-pyrazole-3-carboxylic acid (83.0 mg, 0.519 mmol), tetrahydrofuran (5 mL), thionyl chloride (89.0 μL, 1.02 mmol), N,N-dimethylformamide (2 drops), N-[6-(3-amino-4-methylphenoxy)[1,2,4]triazolo[1,5-a]pyridin-2-yl]cyclopropanecarboxamide (150 mg, 0.464 mmol) and N,N-dimethylacetamide (6 mL) as starting materials, the title compound (155 mg, 72%) was obtained as a white solid.

$^1$H-NMR (DMSO-$d_6$, 300 MHz) δ 0.78-0.87 (4H, m), 1.95-2.12 (1H, m), 2.23 (3H, s), 3.92 (3H, s), 6.85 (1H, dd, J=8.6, 2.7 Hz), 7.26 (1H, d, J=8.6 Hz), 7.38 (1H, d, J=2.7 Hz), 7.50 (1H, dd, J=9.6, 2.3 Hz), 7.72 (1H, dd, J=9.6, 0.8 Hz), 8.11 (1H, s), 8.83 (1H, d, J=1.5 Hz), 9.49 (1H, s), 11.02 (1H, s).

Example 62

3-chloro-N-[5-({2-[(cyclopropylcarbonyl)amino][1,2,4]triazolo[1,5-a]pyridin-6-yl}oxy)-2-methylphenyl]-4-methylthiophene-2-carboxamide

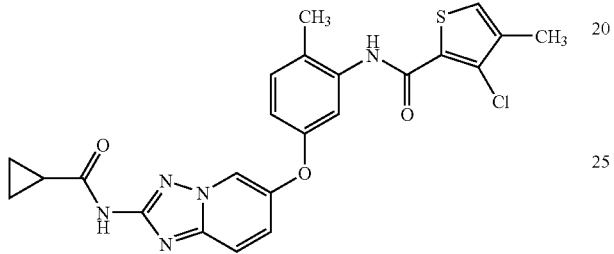

In the same manner as in Example 55 and using 3-chloro-4-methylthiophene-2-carboxylic acid (90.0 mg, 0.510 mmol), tetrahydrofuran (5 mL), thionyl chloride (89.0 μL, 1.02 mmol), N,N-dimethylformamide (2 drops), N-[6-(3-amino-4-methylphenoxy)[1,2,4]triazolo[1,5-a]pyridin-2-yl]cyclopropanecarboxamide (150 mg, 0.464 mmol) and N,N-dimethylacetamide (6 mL) as starting materials, the title compound (174 mg, 78%) was obtained as a pale-yellow solid.

$^1$H-NMR (DMSO-$d_6$, 300 MHz) δ 0.79-0.86 (4H, m), 1.96-2.11 (1H, m), 2.20 (3H, d, J=1.1 Hz), 2.27 (3H, s), 6.89 (1H, dd, J=8.5, 2.6 Hz), 7.28 (1H, d, J=8.5 Hz), 7.42 (1H, d, J=2.6 Hz), 7.50 (1H, dd, J=9.8, 2.3 Hz), 7.66 (1H, d, J=1.1 Hz), 7.69-7.76 (1H, m), 8.84 (1H, dd, J=2.3, 0.8 Hz), 9.54 (1H, s), 10.96-11.09 (1H, m).

Example 63

N-[5-({2-[(cyclopropylcarbonyl)amino][1,2,4]triazolo[1,5-a]pyridin-6-yl}oxy)-2-methylphenyl]-1,3-dimethyl-1H-pyrazole-4-carboxamide

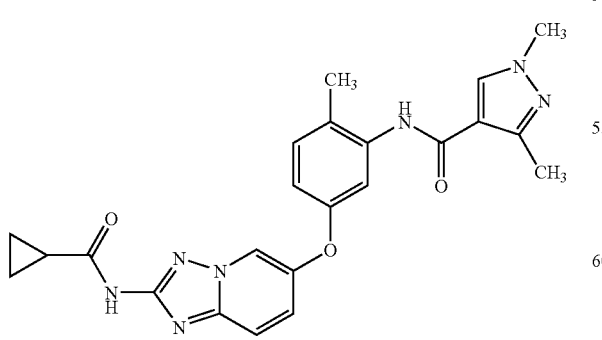

In the same manner as in Example 55 and using 1,3-dimethyl-1H-pyrazole-4-carboxylic acid (67.0 mg, 0.478 mmol), tetrahydrofuran (5 mL), thionyl chloride (83.0 μL, 0.957 mmol), N,N-dimethylformamide (2 drops), N-[6-(3-amino-4-methylphenoxy)[1,2,4]triazolo[1,5-a]pyridin-2-yl]cyclopropanecarboxamide (140 mg, 0.433 mmol) and N,N-dimethylacetamide (6 mL) as starting materials, the title compound (112 mg, 58%) was obtained as a pale-brown solid.

$^1$H-NMR (DMSO-$d_6$, 300 MHz) δ 0.79-0.86 (4H, m), 1.97-2.09 (1H, m), 2.20 (3H, s), 2.32 (3H, s), 3.79 (3H, s), 6.86 (1H, dd, J=8.6, 2.7 Hz), 7.17 (1H, d, J=2.7 Hz), 7.25 (1H, d, J=8.6 Hz), 7.49 (1H, dd, J=9.5, 2.4 Hz), 7.72 (1H, dd, J=9.5, 0.8 Hz), 8.23 (1H, s), 8.81 (1H, dd, J=2.4, 0.8 Hz), 9.16 (1H, s), 11.03 (1H, s).

Example 64

N-[5-({2-[(cyclopropylcarbonyl)amino][1,2,4]triazolo[1,5-a]pyridin-6-yl}oxy)-2-methylphenyl]tetrahydrofuran-3-carboxamide

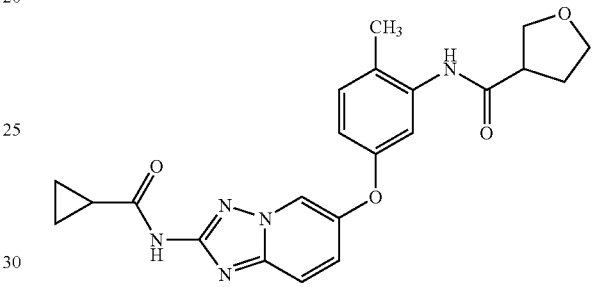

In the same manner as in Example 55 and using tetrahydrofuran-3-carboxylic acid (57.0 mg, 0.491 mmol), tetrahydrofuran (5 mL), thionyl chloride (83.0 μL, 0.957 mmol), N,N-dimethylformamide (2 drops), N-[6-(3-amino-4-methylphenoxy)[1,2,4]triazolo[1,5-a]pyridin-2-yl]cyclopropanecarboxamide (140 mg, 0.433 mmol) and N,N-dimethylacetamide (6 mL) as starting materials, the title compound (106 mg, 58%) was obtained as a white solid.

$^1$H-NMR (DMSO-$d_6$, 300 MHz) δ 0.75-0.89 (4H, m), 1.94-2.11 (3H, m), 2.17 (3H, s), 3.14-3.28 (1H, m), 3.62-3.81 (3H, m), 3.91 (1H, t, J=8.3 Hz), 6.82 (1H, dd, J=8.3, 2.7 Hz), 7.16-7.28 (2H, m), 7.47 (1H, dd, J=9.5, 2.3 Hz), 7.71 (1H, d, J=9.5 Hz), 8.79 (1H, d, J=2.3 Hz), 9.36 (1H, s), 11.01 (1H, s).

Example 65

N-[5-({2-[(cyclopropylcarbonyl)amino][1,2,4]triazolo[1,5-a]pyridin-6-yl}oxy)-2-methylphenyl]cyclobutanecarboxamide

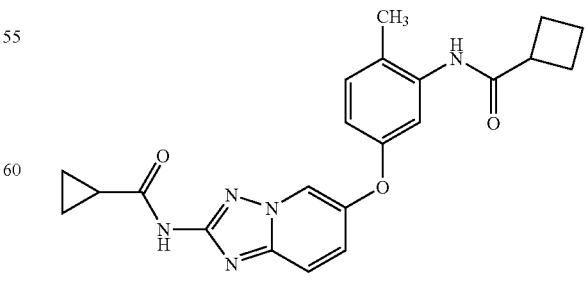

In the same manner as in Example 24 and using cyclobutanecarbonyl chloride (56.0 μL, 0.489 mmol), N,N-dimethylacetamide (5 mL) and N-[6-(3-amino-4-methylphenoxy)[1,2,4]triazolo[1,5-a]pyridin-2-yl]cyclopropanecarboxamide (140 mg, 0.433 mmol) as starting materials, the title compound (83.5 mg, 45%) was obtained as a white solid.

¹H-NMR (DMSO-d₆, 300 MHz) δ 0.78-0.87 (4H, m), 1.72-1.85 (1H, m), 1.85-1.98 (1H, m), 1.98-2.14 (3H, m), 2.15 (3H, s), 2.17-2.27 (2H, m), 3.21-3.35 (1H, m), 6.80 (1H, dd, J=8.5, 2.7 Hz), 7.20 (1H, d, J=8.5 Hz), 7.25 (1H, d, J=1.9 Hz), 7.47 (1H, dd, J=9.5, 2.3 Hz), 7.66-7.74 (1H, m), 8.76-8.80 (1H, m), 9.05 (1H, s), 11.01 (1H, s).

Example 66-1 tert-butyl {3-[(2-amino[1,2,4]triazolo[1,5-a]pyridin-6-yl)oxy]phenyl}carbamate

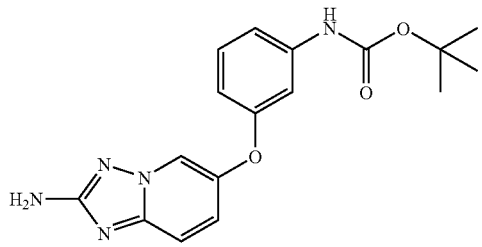

In the same manner as in Example 17-1 and using tert-butyl {3-[(6-aminopyridin-3-yl)oxy]phenyl}carbamate (15.0 g, 49.8 mmol), ethyl isothiocyanatoformate (7.18 g, 54.8 mmol), DMSO (50 mL), hydroxylammonium chloride (11.8 g, 170 mmol), N,N-diisopropylethylamine (21.2 mL, 122 mmol), ethanol (70 mL) and methanol (70 mL) as starting materials, the title compound (10.5 g, 94%) was obtained as a white solid.

¹H-NMR (DMSO-d₆, 300 MHz) δ 1.43 (9H, s), 6.00 (2H, br s), 6.57-6.61 (1H, m), 7.15-7.29 (4H, m), 7.38 (1H, d, J=9.3 Hz), 8.57 (1H, d, J=2.4 Hz), 9.39 (1H, s).

Example 66-2

N-[6-(3-aminophenoxy)[1,2,4]triazolo[1,5-a]pyridin-2-yl]cyclopropanecarboxamide

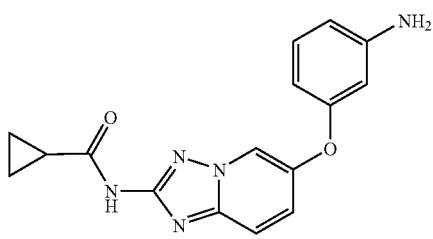

To a solution of tert-butyl {3-[(2-amino[1,2,4]triazolo[1,5-a]pyridin-6-yl)oxy]phenyl}carbamate (10.5 g, 30.8 mmol) in N,N-dimethylacetamide (40 mL) was added with stirring under ice-cooling cyclopropanecarbonyl chloride (8.39 mL, 92.4 mmol), and the mixture was stirred at room temperature for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, trifluoroacetic acid (50 mL) was added to the residue, and the mixture was stirred at 0° C. for 30 min. The solvent was evaporated under reduced pressure, and the residue was dissolved in water. The mixture was neutralized with saturated aqueous sodium hydrogen carbonate solution and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (7.44 g, 78%) as a white solid.

¹H-NMR (DMSO-d₆, 300 MHz) δ 0.81-0.84 (4H, m), 2.00-2.10 (1H, m), 5.24 (2H, br s), 6.14-6.18 (2H, m), 6.29-6.33 (1H, m), 6.96-7.02 (1H, m), 7.46 (1H, dd, J=9.5, 2.3 Hz), 7.69 (1H, dd, J=9.5, 0.7 Hz), 8.78 (1H, dd, J=2.3, 0.7 Hz), 11.00 (1H, s).

Example 67

N-[5-({2-[(cyclopropylcarbonyl)amino][1,2,4]triazolo[1,5-a]pyridin-6-yl}oxy)-2-fluorophenyl]-3-ethyl-1-methyl-1H-pyrazole-5-carboxamide

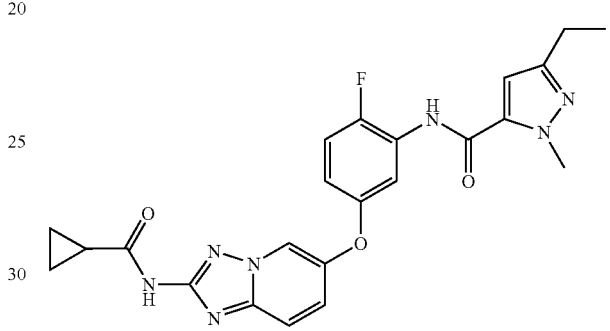

In the same manner as in Example 18-4 and using 3-ethyl-1-methyl-1H-pyrazole-5-carboxylic acid (188 mg, 1.22 mmol), tetrahydrofuran (7 mL), oxalyl chloride (160 μL, 1.83 mmol), N-[6-(3-amino-4-fluorophenoxy)[1,2,4]triazolo[1,5-a]pyridin-2-yl]cyclopropanecarboxamide (200 mg, 0.611 mmol), N,N-dimethylformamide (1 drop) and N,N-dimethylacetamide (3 mL) as starting materials, the title compound (230 mg, 81%) was obtained as a white solid.

¹H-NMR (DMSO-d₆, 300 MHz) δ 0.81-0.83 (4H, m), 1.18 (3H, t, J=7.5 Hz), 1.95-2.10 (1H, m), 2.51-2.59 (2H, m), 3.70 (3H, s), 6.86 (1H, s), 6.97-7.03 (1H, m), 7.29-7.35 (2H, m), 7.52 (1H, dd, J=9.5, 2.1 Hz), 7.72 (1H, dd, J=9.5, 0.8 Hz), 8.88 (1H, dd, J=2.1, 0.8 Hz), 10.04 (1H, br s), 11.03 (1H, br s).

Example 68-1 tert-butyl {5-[(2-amino[1,2,4]triazolo[1,5-a]pyridin-6-yl)oxy]-2-fluorophenyl}carbamate

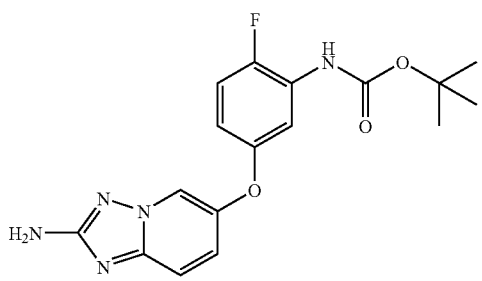

In the same manner as in Example 23-1 and using ethyl{[(5-{3-[(tert-butoxycarbonyl)amino]-4- fluorophenoxy}pyridin-2-yl)amino]carbonothioyl}carbamate (13.5 g, 30.0 mmol), hydroxylammonium chloride (14.7 g, 212 mmol), N,N-diisopropylethylamine (26.2 mL, 150 mmol), ethanol (75 mL) and methanol (75 mL) as starting materials, the title compound (9.00 g, 84%) was obtained as a white solid.

¹H-NMR (DMSO-d₆, 300 MHz) δ 1.42 (9H, s), 6.00 (2H, br s), 6.70-6.75 (1H, m), 7.18 (1H, dd, J=10.4, 9.2 Hz), 7.27 (1H, dd, J=9.5, 2.6 Hz), 7.34-7.39 (2H, m), 8.55 (1H, d, J=2.1 Hz), 9.07 (1H, br s).

Example 68-2

N-[6-(3-amino-4-fluorophenoxy)[1,2,4]triazolo[1,5-a]pyridin-2-yl]cyclopropanecarboxamide

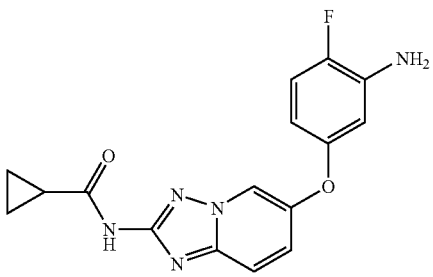

In the same manner as in Example 66-2 and using tert-butyl {5-[(2-amino[1,2,4]triazolo[1,5-a]pyridin-6-yl)oxy]-2-fluorophenyl}carbamate (8.99 g, 25.0 mmol), cyclopropanecarbonyl chloride (3.82 mL, 42.0 mmol), N,N-dimethylacetamide (60 mL) and trifluoroacetic acid (50 mL) as starting materials, the title compound (6.32 g, 77%) was obtained as a white solid.

¹H-NMR (DMSO-d₆, 300 MHz) δ 0.81-0.84 (4H, m), 1.95-2.10 (1H, m), 5.31 (2H, br s), 6.15-6.20 (1H, m), 6.40 (1H, dd, J=7.5, 3.0 Hz), 6.96 (1H, dd, J=11.0, 8.9 Hz), 7.46 (1H, dd, J=8.4, 2.4 Hz), 7.69 (1H, dd, J=9.6, 0.6 Hz), 8.77 (1H, dd, J=2.4, 0.6 Hz), 11.00 (1H, br s).

Example 69

3-cyclopropyl-N-[3-({2-[(cyclopropylcarbonyl)amino][1,2,4]triazolo[1,5-a]pyridin-6-yl}oxy)phenyl]-1-methyl-1H-pyrazole-4-carboxamide

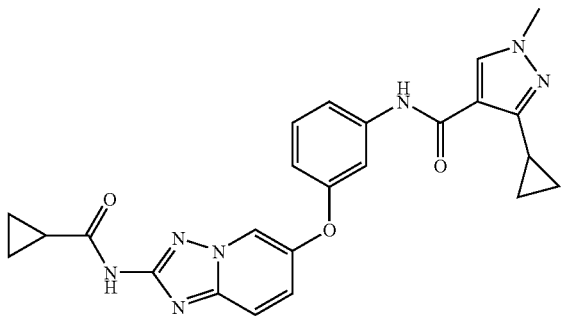

To a mixture of 3-cyclopropyl-1-methyl-1H-pyrazole-4-carboxylic acid and 5-cyclopropyl-1-methyl-1H-pyrazole-4-carboxylic acid (430 mg, 2.59 mmol) in tetrahydrofuran (7 mL) were added oxalyl chloride (338 μL, 3.87 mmol) and N,N-dimethylformamide (1 drop), and the mixture was stirred at room temperature for 1 hr. The reaction mixture was concentrated under reduced pressure, and the residue was dissolved in N,N-dimethylacetamide (3 mL). N-[6-(3-Aminophenoxy)[1,2,4]triazolo[1,5-a]pyridin-2-yl]cyclopropanecarboxamide (400 mg, 1.29 mmol) was added with stirring under ice-cooling, and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, hexane/ethyl acetate=70/30→0/100), and then by column chromatography (silica gel, ethyl acetate/methanol=95/5) and recrystallized from ethyl acetate to give the title compound (120 mg, 20%) as a white solid.

¹H-NMR (DMSO-d₆, 300 MHz) δ 0.73-0.85 (8H, m), 1.99-2.10 (2H, m), 3.75 (3H, s), 6.77 (1H, dd, J=7.5, 2.1 Hz), 7.31 (1H, t, J=8.1 Hz), 7.40 (1H, t, J=2.1 Hz), 7.50-7.55 (2H, m), 7.74 (1H, d, J=9.6 Hz), 8.19 (1H, s), 8.91-8.92 (1H, m), 9.69 (1H, s), 11.03 (1H, br s).

Example 70

N-[5-({2-[(cyclopropylcarbonyl)amino][1,2,4]triazolo[1,5-a]pyridin-6-yl}oxy)-2-fluorophenyl]-1,4-dimethyl-1H-pyrazole-3-carboxamide

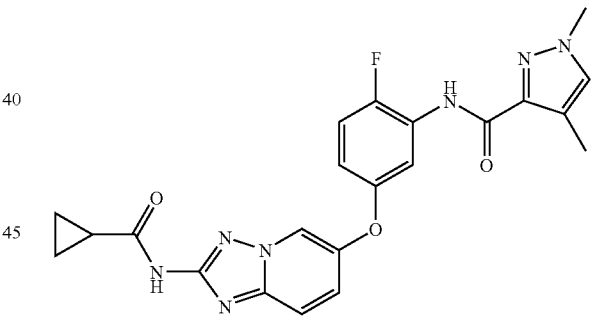

In the same manner as in Example 18-4 and using 1,4-dimethyl-1H-pyrazole-3-carboxylic acid (171 mg, 1.22 mmol), tetrahydrofuran (7 mL), oxalyl chloride (160 μL, 1.83 mmol), N-[6-(3-amino-4-fluorophenoxy)[1,2,4]triazolo[1,5-a]pyridin-2-yl]cyclopropanecarboxamide (200 mg, 0.611 mmol), N,N-dimethylformamide (1 drop) and N,N-dimethylacetamide (3 mL) as starting materials, the title compound (229 mg, 83%) was obtained as a white solid.

¹H-NMR (DMSO-d₆, 300 MHz) δ 0.81-0.84 (4H, m), 1.95-2.10 (1H, m), 2.20 (3H, s), 3.88 (3H, s), 6.84-6.90 (1H, m), 7.31 (1H, dd, J=10.4, 9.2 Hz), 7.52 (1H, dd, J=9.6, 2.4 Hz), 7.64 (1H, d, J=0.6 Hz), 7.72 (1H, d, J=9.6 Hz), 7.80 (1H, dd, J=6.5, 3.2 Hz), 8.87 (1H, d, J=2.4 Hz), 9.34 (1H, br s), 11.03 (1H, br s).

Example 71

N-[5-({2-[(cyclopropylcarbonyl)amino][1,2,4]triazolo[1,5-a]pyridin-6-yl}oxy)-2-fluorophenyl]-2-methyl-5-(trifluoromethyl)-1,3-oxazole-4-carboxamide

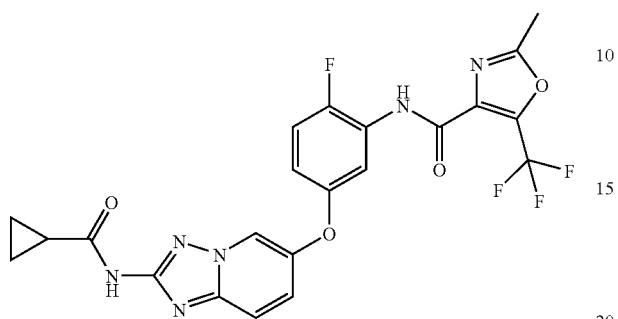

In the same manner as in Example 18-4 and using 2-methyl-5-(trifluoromethyl)-1,3-oxazole-4-carboxylic acid (238 mg, 1.22 mmol), tetrahydrofuran (7 mL), oxalyl chloride (160 μL, 1.83 mmol), N-[6-(3-amino-4-fluorophenoxy)[1,2,4]triazolo[1,5-a]pyridin-2-yl]cyclopropanecarboxamide (200 mg, 0.611 mmol), N,N-dimethylformamide (1 drop) and N,N-dimethylacetamide (3 mL) as starting materials, the title compound (276 mg, 90%) was obtained as a white solid.

$^1$H-NMR (DMSO-d$_6$, 300 MHz) δ 0.81-0.83 (4H, m), 1.99-2.10 (1H, m), 2.60 (3H, s), 6.95-7.01 (1H, m), 7.33 (1H, dd, J=10.2, 9.0 Hz), 7.47-7.54 (2H, m), 7.72 (1H, dd, J=9.6, 0.8 Hz), 8.87 (1H, dd, J=2.4, 0.8 Hz), 10.16 (1H, br s), 11.02 (1H, br s).

Example 72

N-[5-({2-[(cyclopropylcarbonyl)amino][1,2,4]triazolo[1,5-a]pyridin-6-yl}oxy)-2-fluorophenyl]-1-ethyl-3-methyl-1H-pyrazole-5-carboxamide

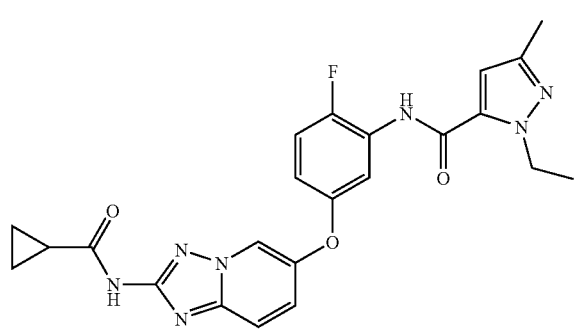

To a solution of 1-ethyl-3-methyl-1H-pyrazole-5-carboxylic acid (188 mg, 1.22 mmol) in tetrahydrofuran (7 mL) were added oxalyl chloride (160 μL, 1.83 mmol) and N,N-dimethylformamide (1 drop), and the mixture was stirred at room temperature for 1 hr. The reaction mixture was concentrated under reduced pressure, and the residue was dissolved in N,N-dimethylacetamide (3 mL). N-[6-(3-Amino-4-fluorophenoxy)[1,2,4]triazolo[1,5-a]pyridin-2-yl]cyclopropanecarboxamide (200 mg, 0.611 mmol) was added with stirring under ice-cooling, and the mixture was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (NH silica gel, ethyl acetate) and recrystallized from ethyl acetate to give the title compound (254 mg, 90%) as a white solid.

$^1$H-NMR (DMSO-d$_6$, 300 MHz) δ 0.81-0.86 (4H, m), 1.28 (3H, t, J=7.1 Hz), 1.95-2.10 (1H, m), 2.19 (3H, s), 4.71 (2H, q, J=7.1 Hz), 6.79 (1H, s), 6.97-7.03 (1H, m), 7.28-7.35 (2H, m), 7.52 (1H, dd, J=9.6, 2.3 Hz), 7.72 (1H, dd, J=9.6, 0.8 Hz), 8.88 (1H, dd, J=2.3, 0.8 Hz), 10.03 (1H, br s), 11.03 (1H, br s).

Example 73

N-[5-({2-[(cyclopropylcarbonyl)amino][1,2,4]triazolo[1,5-a]pyridin-6-yl}oxy)-2-fluorophenyl]-3-methyl-1-(2,2,2-trifluoroethyl)-1H-pyrazole-5-carboxamide

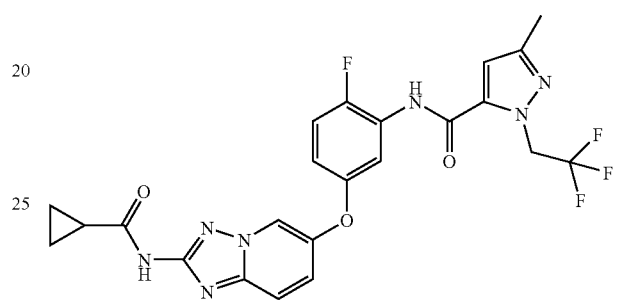

In the same manner as in Example 18-4 and using 3-methyl-1-(2,2,2-trifluoroethyl)-1H-pyrazole-5-carboxylic acid (254 mg, 1.22 mmol), tetrahydrofuran (7 mL), oxalyl chloride (160 μL, 1.83 mmol), N-[6-(3-amino-4-fluorophenoxy)[1,2,4]triazolo[1,5-a]pyridin-2-yl]cyclopropanecarboxamide (200 mg, 0.611 mmol), N,N-dimethylformamide (1 drop) and N,N-dimethylacetamide (3 mL) as starting materials, the title compound (264 mg, 84%) was obtained as a white solid.

$^1$H-NMR (DMSO-d$_6$, 300 MHz) δ 0.81-0.83 (4H, m), 1.95-2.10 (1H, m), 2.23 (3H, s), 5.37-5.39 (2H, m), 6.97 (1H, s), 6.99-7.04 (1H, m), 7.26-7.36 (2H, m), 7.53 (1H, dd, J=9.6, 2.5 Hz), 7.72 (1H, dd, J=9.6, 0.8 Hz), 8.88 (1H, dd, J=2.5, 0.8 Hz), 10.28 (1H, br s), 11.03 (1H, br s).

Example 74

N-[3-({2-[(cyclopropylcarbonyl)amino][1,2,4]triazolo[1,5-a]pyridin-6-yl}oxy)phenyl]-1-ethyl-4-methyl-1H-pyrazole-3-carboxamide

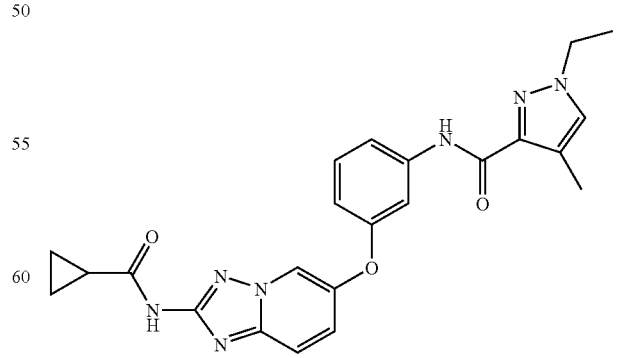

In the same manner as in Example 18-4 and using 1-ethyl-4-methyl-1H-pyrazole-3-carboxylic acid (150 mg, 0.970 mmol), tetrahydrofuran (7 mL), oxalyl chloride (93.0 μL, 1.07 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (5 mL) as starting materials, the title compound (150 mg, 52%) was obtained as a white solid.

$^1$H-NMR (DMSO-d$_6$, 300 MHz) δ 0.81-0.84 (4H, m), 1.39 (3H, t, J=7.3 Hz), 1.99-2.08 (1H, m), 2.20 (3H, s), 4.15 (2H, q, J=7.3 Hz), 6.74-6.78 (1H, m), 7.30 (1H, t, J=8.3 Hz), 7.49-7.56 (2H, m), 7.64-7.75 (3H, m), 8.89-8.91 (1H, m), 9.92 (1H, s), 11.04 (1H, s).

Example 75

N-[3-({2-[(cyclopropylcarbonyl)amino][1,2,4]triazolo[1,5-a]pyridin-6-yl}oxy)phenyl]-4-ethyl-1-methyl-1H-pyrazole-3-carboxamide

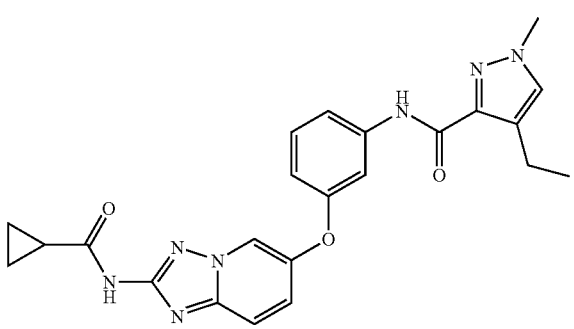

In the same manner as in Example 18-4 and using 4-ethyl-1-methyl-1H-pyrazole-3-carboxylic acid (150 mg, 0.970 mmol), tetrahydrofuran (7 mL), oxalyl chloride (93.0 μL, 1.07 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (5 mL) as starting materials, the title compound (184 mg, 64%) was obtained as a white solid.

$^1$H-NMR (DMSO-d$_6$, 300 MHz) δ 0.82-0.84 (4H, m), 1.12 (3H, t, J=7.5 Hz), 1.99-2.08 (1H, m), 2.68 (2H, q, J=7.5 Hz), 3.87 (3H, s), 6.74-6.78 (1H, m), 7.30 (1H, t, J=8.1 Hz), 7.49-7.56 (2H, m), 7.63-7.75 (3H, m), 8.89-8.91 (1H, m), 9.98 (1H, s), 11.05 (1H, s).

Example 76

N-[5-({2-[(cyclopropylcarbonyl)amino][1,2,4]triazolo[1,5-a]pyridin-6-yl}oxy)-2-methylphenyl]-2,5-dimethylthiophene-3-carboxamide

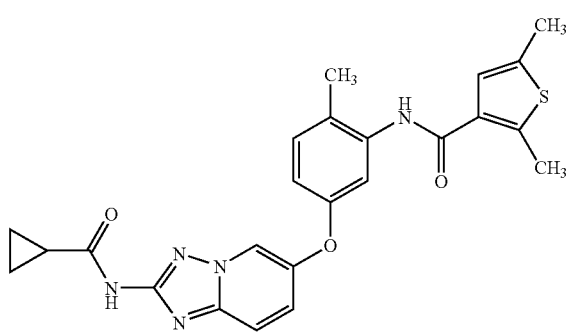

In the same manner as in Example 55 and using 2,5-dimethylthiophene-3-carboxylic acid (71.0 mg, 0.454 mmol), tetrahydrofuran (5 mL), thionyl chloride (77.0 μL, 0.888 mmol), N,N-dimethylformamide (2 drops), N-[6-(3-amino-4-methylphenoxy)[1,2,4]triazolo[1,5-a]pyridin-2-yl]cyclopropanecarboxamide (129 mg, 0.399 mmol) and N,N-dimethylacetamide (6 mL) as starting materials, the title compound (137 mg, 74%) was obtained as a white solid.

$^1$H-NMR (DMSO-d$_6$, 300 MHz) δ 0.78-0.87 (4H, m), 1.96-2.11 (1H, m), 2.21 (3H, s), 2.38 (3H, s), 2.56 (3H, s), 6.88 (1H, dd, J=8.3, 2.7 Hz), 7.11 (1H, s), 7.15 (1H, d, J=2.7 Hz), 7.25 (1H, d, J=8.3 Hz), 7.49 (1H, dd, J=9.6, 2.3 Hz), 7.72 (1H, d, J=9.6 Hz), 8.82 (1H, d, J=2.3 Hz), 9.39 (1H, s), 11.02 (1H, s).

Example 77

N-[5-({2-[(cyclopropylcarbonyl)amino][1,2,4]triazolo[1,5-a]pyridin-6-yl}oxy)-2-methylphenyl]-2,5-dimethyl-1,3-oxazole-4-carboxamide

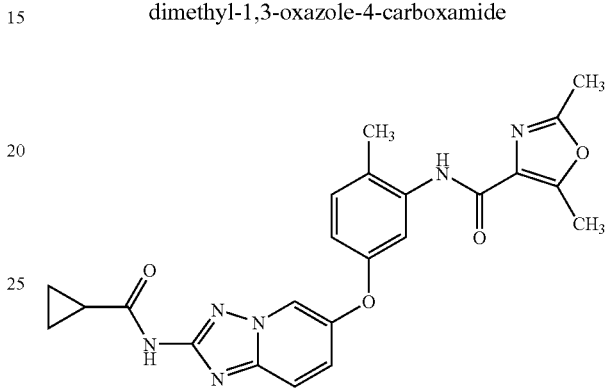

In the same manner as in Example 55 and using 2,5-dimethyl-1,3-oxazole-4-carboxylic acid (65.0 mg, 0.462 mmol), tetrahydrofuran (5 mL), thionyl chloride (77.0 μL, 0.888 mmol), N,N-dimethylformamide (2 drops), N-[6-(3-amino-4-methylphenoxy)[1,2,4]triazolo[1,5-a]pyridin-2-yl]cyclopropanecarboxamide (129 mg, 0.399 mmol) and N,N-dimethylacetamide (6 mL) as starting materials, the title compound (148 mg, 83%) was obtained as a white solid.

$^1$H-NMR (DMSO-d$_6$, 300 MHz) δ 0.78-0.87 (4H, m), 1.95-2.12 (1H, m), 2.23 (3H, s), 2.44 (3H, s), 2.54 (3H, s), 6.84 (1H, dd, J=8.4, 2.8 Hz), 7.26 (1H, d, J=8.4 Hz), 7.46-7.53 (2H, m), 7.69-7.75 (1H, m), 8.78-8.86 (1H, m), 9.33 (1H, s), 11.03 (1H, s).

Example 78

N-[5-({2-[(cyclopropylcarbonyl)amino][1,2,4]triazolo[1,5-a]pyridin-6-yl}oxy)-2-methylphenyl]-1-methyl-3-(trifluoromethyl)-1H-pyrazole-4-carboxamide

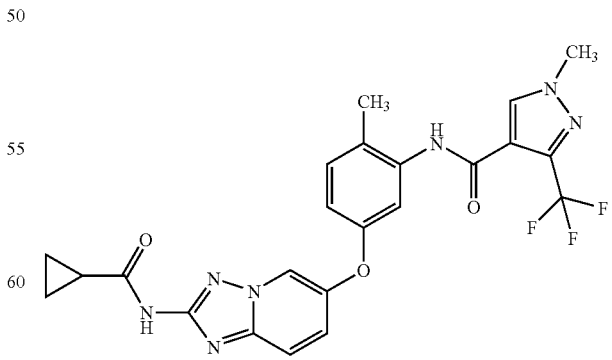

In the same manner as in Example 55 and using 1-methyl-3-(trifluoromethyl)-1H-pyrazole-4-carboxylic acid (85.2 mg, 0.439 mmol), tetrahydrofuran (5 mL), thionyl chloride (77.0 μL, 0.888 mmol), N,N-dimethylformamide (2 drops), N-[6-

(3-amino-4-methylphenoxy)[1,2,4]triazolo[1,5-a]pyridin-2-yl]cyclopropanecarboxamide (129 mg, 0.399 mmol) and N,N-dimethylacetamide (6 mL) as starting materials, the title compound (119 mg, 60%) was obtained as a white solid.

$^1$H-NMR (DMSO-d$_6$, 300 MHz) δ 0.77-0.86 (4H, m), 1.94-2.11 (1H, m), 2.19 (3H, s), 3.97 (3H, s), 6.90 (1H, dd, J=8.6, 2.6 Hz), 7.12 (1H, d, J=2.6 Hz), 7.27 (1H, d, J=8.6 Hz), 7.50 (1H, dd, J=9.6, 2.5 Hz), 7.68-7.75 (1H, m), 8.48 (1H, s), 8.81-8.86 (1H, m), 9.67 (1H, s), 11.03 (1H, s).

Example 79

N-[5-({2-[(cyclopropylcarbonyl)amino][1,2,4]triazolo[1,5-a]pyridin-6-yl}oxy)-2-methylphenyl]-1-methyl-1H-pyrazole-3-carboxamide

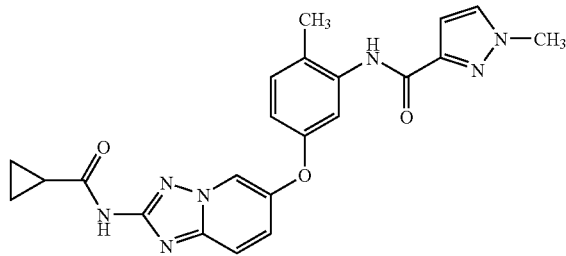

In the same manner as in Example 55 and using 1-methyl-1H-pyrazole-3-carboxylic acid (55.5 mg, 0.440 mmol), tetrahydrofuran (5 mL), thionyl chloride (77.0 μL, 0.888 mmol), N,N-dimethylformamide (2 drops), N-[6-(3-amino-4-methylphenoxy)[1,2,4]triazolo[1,5-a]pyridin-2-yl]cyclopropanecarboxamide (129 mg, 0.399 mmol) and N,N-dimethylacetamide (6 mL) as starting materials, the title compound (100 mg, 58%) was obtained as a white solid.

$^1$H-NMR (DMSO-d$_6$, 300 MHz) δ 0.78-0.87 (4H, m), 1.96-2.12 (1H, m), 2.23 (3H, s), 3.95 (3H, s), 6.72 (1H, d, J=2.3 Hz), 6.83 (1H, dd, J=8.5, 2.6 Hz), 7.25 (1H, d, J=8.5 Hz), 7.45 (1H, d, J=2.6 Hz), 7.50 (1H, dd, J=9.6, 2.5 Hz), 7.68-7.76 (1H, m), 7.84 (1H, d, J=2.3 Hz), 8.81-8.86 (1H, m), 9.40 (1H, s), 11.03 (1H, s).

Example 80

N-[5-({2-[(cyclopropylcarbonyl)amino][1,2,4]triazolo[1,5-a]pyridin-6-yl}oxy)-2-methylphenyl]-5-methyl-1,3-thiazole-4-carboxamide

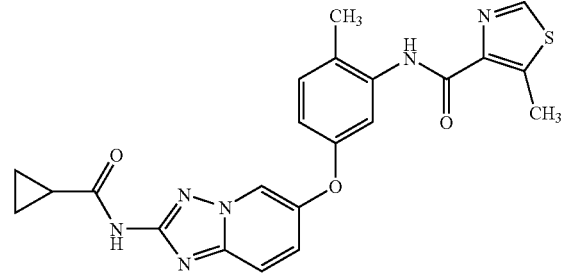

In the same manner as in Example 55 and using 5-methyl-1,3-thiazole-4-carboxylic acid (63.1 mg, 0.441 mmol), tetrahydrofuran (5 mL), thionyl chloride (77.0 μL, 0.888 mmol), N,N-dimethylformamide (2 drops), N-[6-(3-amino-4-methylphenoxy)[1,2,4]triazolo[1,5-a]pyridin-2-yl]cyclopropanecarboxamide (129 mg, 0.399 mmol) and N,N-dimethylacetamide (6 mL) as starting materials, the title compound (140 mg, 78%) was obtained as a white solid.

$^1$H-NMR (DMSO-d$_6$, 300 MHz) δ 0.78-0.87 (4H, m), 1.95-2.12 (1H, m), 2.26 (3H, s), 2.77 (3H, s), 6.83 (1H, dd, J=8.5, 2.6 Hz), 7.28 (1H, d, J=8.5 Hz), 7.51 (1H, dd, J=9.6, 2.3 Hz), 7.66 (1H, d, J=2.6 Hz), 7.72 (1H, dd, J=9.6, 0.8 Hz), 8.83 (1H, dd, J=2.3, 0.8 Hz), 9.01 (1H, s), 9.76 (1H, s), 11.03 (1H, s).

Example 81

N-[5-({2-[(cyclopropylcarbonyl)amino][1,2,4]triazolo[1,5-a]pyridin-6-yl}oxy)-2-methylphenyl]-1-ethyl-3-methyl-1H-pyrazole-4-carboxamide

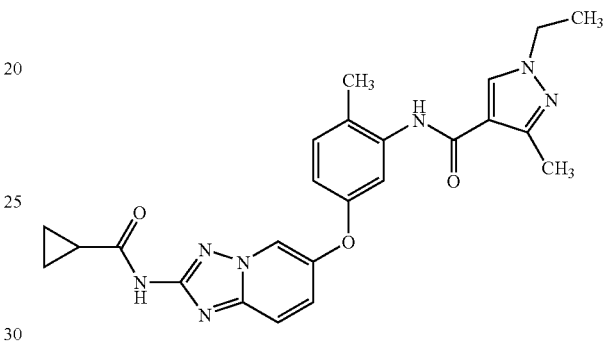

In the same manner as in Example 55 and using 1-ethyl-3-methyl-1H-pyrazole-4-carboxylic acid (69.1 mg, 0.448 mmol), tetrahydrofuran (5 mL), thionyl chloride (78.0 μL, 0.899 mmol), N,N-dimethylformamide (2 drops), N-[6-(3-amino-4-methylphenoxy)[1,2,4]triazolo[1,5-a]pyridin-2-yl]cyclopropanecarboxamide (132 mg, 0.408 mmol) and N,N-dimethylacetamide (6 mL) as starting materials, the title compound (102 mg, 55%) was obtained as a white solid.

$^1$H-NMR (DMSO-d$_6$, 300 MHz) δ 0.78-0.87 (4H, m), 1.37 (3H, t, J=7.2 Hz), 1.95-2.12 (1H, m), 2.20 (3H, s), 2.33 (3H, s), 4.08 (2H, q, J=7.2 Hz), 6.86 (1H, dd, J=8.5, 2.6 Hz), 7.16 (1H, d, J=2.6 Hz), 7.25 (1H, d, J=8.5 Hz), 7.49 (1H, dd, J=9.8, 2.3 Hz), 7.72 (1H, dd, J=9.8, 0.8 Hz), 8.29 (1H, s), 8.82 (1H, dd, J=2.3, 0.8 Hz), 9.16 (1H, s), 11.03 (1H, s).

Example 82

N-[2-chloro-5-({2-[(cyclopropylcarbonyl)amino][1,2,4]triazolo[1,5-a]pyridin-6-yl}oxy)phenyl]-2-methyl-5-(trifluoromethyl)-1,3-oxazole-4-carboxamide

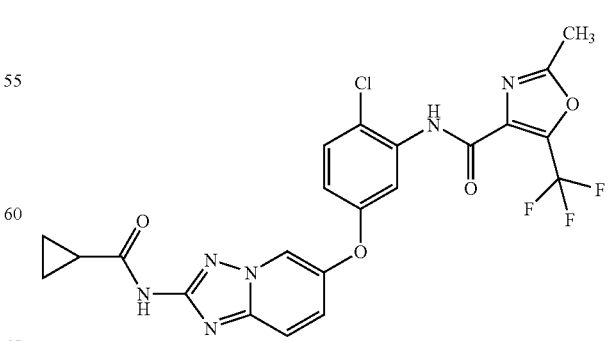

In the same manner as in Example 55 and using 2-methyl-5-(trifluoromethyl)-1,3-oxazole-4-carboxylic acid (110 mg, 0.564 mmol), tetrahydrofuran (5 mL), thionyl chloride (97.2 μL, 1.12 mmol), N,N-dimethylformamide (2 drops), N-[6-(3-amino-4-chlorophenoxy)[1,2,4]triazolo[1,5-a]pyridin-2-yl]cyclopropanecarboxamide (170 mg, 0.495 mmol) and N,N-dimethylacetamide (6 mL) as starting materials, the title compound (124 mg, 48%) was obtained as a white solid.

¹H-NMR (DMSO-d₆, 300 MHz) δ 0.79-0.86 (4H, m), 1.95-2.12 (1H, m), 2.61 (3H, s), 6.97 (1H, dd, J=8.7, 3.0 Hz), 7.52-7.56 (1H, m), 7.56-7.59 (1H, m), 7.72-7.78 (2H, m), 8.96 (1H, dd, J=2.3, 0.8 Hz), 9.95 (1H, s), 11.04 (1H, s).

Example 83

N-[2-chloro-5-({2-[(cyclopropylcarbonyl)amino][1,2,4]triazolo[1,5-a]pyridin-6-yl}oxy)phenyl]-1,3-dimethyl-1H-pyrazole-5-carboxamide

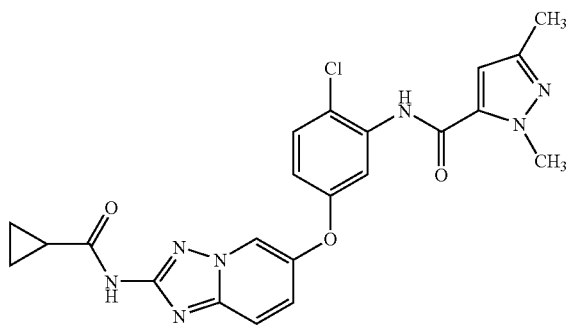

In the same manner as in Example 24 and using 1,3-dimethyl-1H-pyrazole-5-carbonyl chloride (89.2 mg, 0.562 mmol), N,N-dimethylacetamide (5 mL) and N-[6-(3-amino-4-chlorophenoxy)[1,2,4]triazolo[1,5-a]pyridin-2-yl]cyclopropanecarboxamide (170 mg, 0.495 mmol) as starting materials, the title compound (92.2 mg, 40%) was obtained as a white solid.

¹H-NMR (DMSO-d₆, 300 MHz) δ 0.78-0.88 (4H, m), 1.97-2.12 (1H, is m), 2.18 (3H, s), 3.97 (3H, s), 6.81 (1H, s), 7.04 (1H, dd, J=9.3, 3.0 Hz), 7.32 (1H, d, J=3.0 Hz), 7.50-7.59 (2H, m), 7.75 (1H, d, J=9.3 Hz), 8.96 (1H, d, J=2.3 Hz), 9.92 (1H, s), 11.04 (1H, s).

Example 84

N-[2-chloro-5-({2-[(cyclopropylcarbonyl)amino][1,2,4]triazolo[1,5-a]pyridin-6-yl}oxy)phenyl]-1,3-dimethyl-1H-pyrazole-4-carboxamide

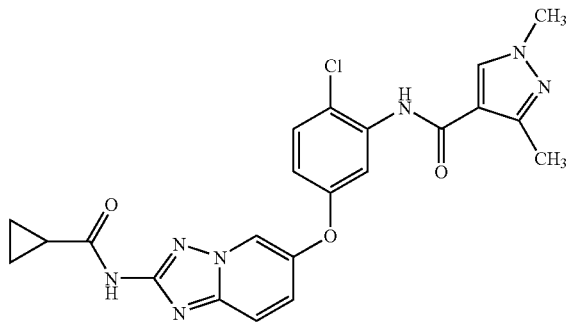

In the same manner as in Example 55 and using 1,3-dimethyl-1H-pyrazole-4-carboxylic acid (58.2 mg, 0.415 mmol), tetrahydrofuran (5 mL), thionyl chloride (71.7 μL, 0.826 mmol), N,N-dimethylformamide (2 drops), N-[6-(3-amino-4-chlorophenoxy)[1,2,4]triazolo[1,5-a]pyridin-2-yl]cyclopropanecarboxamide (129 mg, 0.375 mmol) and N,N-dimethylacetamide (6 mL) as starting materials, the title compound (42.5 mg, 24%) was obtained as a white solid.

¹H-NMR (DMSO-d₆, 300 MHz) δ 0.79-0.87 (4H, m), 1.95-2.12 (1H, m), 2.33 (3H, s), 3.80 (3H, s), 6.95 (1H, dd, J=9.2, 3.0 Hz), 7.45-7.58 (3H, m), 7.74 (1H, dd, J=9.2, 0.8 Hz), 8.30 (1H, s), 8.95 (1H, dd, J=2.3, 0.8 Hz), 9.24 (1H, s), 11.06 (1H, s).

Example 85

N-[5-({2-[(cyclopropylcarbonyl)amino][1,2,4]triazolo[1,5-a]pyridin-6-yl}oxy)-2-methylphenyl]-1-ethyl-1H-pyrazole-5-carboxamide

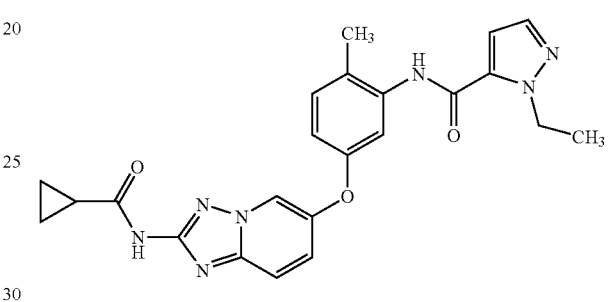

In the same manner as in Example 55 and using 1-ethyl-1H-pyrazole-5-carboxylic acid (56.0 mg, 0.400=mol), tetrahydrofuran (5 mL), thionyl chloride (69.1 μL, 0.796 mmol), N,N-dimethylformamide (2 drops), N-[6-(3-amino-4-methylphenoxy)[1,2,4]triazolo[1,5-a]pyridin-2-yl]cyclopropanecarboxamide (117 mg, 0.362 mmol) and N,N-dimethylacetamide (6 mL) as starting materials, the title compound (93.5 mg, 58%) was obtained as a white solid.

¹H-NMR (DMSO-d₆, 300 MHz) δ 0.77-0.86 (4H, m), 1.31 (3H, t, J=7.2 Hz), 1.95-2.11 (1H, m), 2.20 (3H, s), 4.49 (2H, q, J=7.2 Hz), 6.94 (1H, dd, J=8.5, 2.6 Hz), 7.01 (1H, d, J=2.3 Hz), 7.09 (1H, d, J=2.6 Hz), 7.30 (1H, d, J=8.5 Hz), 7.45-7.56 (2H, m), 7.72 (1H, dd, J=9.4, 0.8 Hz), 8.83 (1H, dd, J=2.3, 0.8 Hz), 9.88 (1H, s), 11.03 (1H, s).

Example 86

N-[5-({2-[(cyclopropylcarbonyl)amino][1,2,4]triazolo[1,5-a]pyridin-6-yl}oxy)-2-methylphenyl]-3-methyl-1-(2,2,2-trifluoroethyl)-1H-pyrazole-5-carboxamide

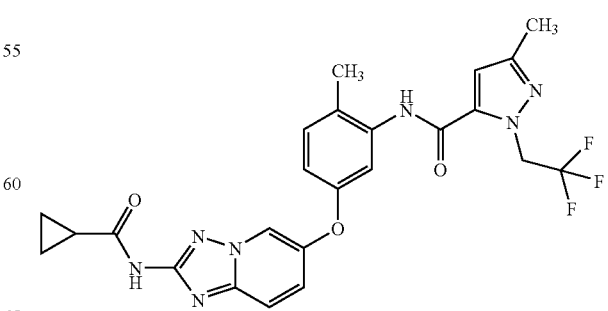

In the same manner as in Example 55 and using 3-methyl-1-(2,2,2-trifluoroethyl)-1H-pyrazole-5-carboxylic acid (82.8 mg, 0.398=mol), tetrahydrofuran (5 mL), thionyl chloride (69.1 μL, 0.796 mmol), N,N-dimethylformamide (2 drops), N-[6-(3-amino-4-methylphenoxy)[1,2,4]triazolo[1,5-a]pyridin-2-yl]cyclopropanecarboxamide (117 mg, 0.362 mmol) and N,N-dimethylacetamide (6 mL) as starting materials, the title compound (151 mg, 81%) was obtained as a white solid.

¹H-NMR (DMSO-d₆, 300 MHz) δ 0.76-0.88 (4H, m), 1.96-2.11 (1H, m), 2.18 (3H, s), 2.23 (3H, s), 5.39 (2H, q, J=8.8 Hz), 6.90-6.99 (2H, m), 7.04 (1H, d, J=2.6 Hz), 7.29 (1H, d, J=8.8 Hz), 7.50 (1H, dd, J=9.4, 2.3 Hz), 7.72 (1H, dd, J=9.4, 0.8 Hz), 8.84 (1H, dd, J=2.3, 0.8 Hz), 10.04 (1H, s), 11.03 (1H, s).

Example 87

N-[5-({2-[(cyclopropylcarbonyl)amino][1,2,4]triazolo[1,5-a]pyridin-6-yl}oxy)-2-methylphenyl]-3-methoxy-1-methyl-1H-pyrazole-5-carboxamide

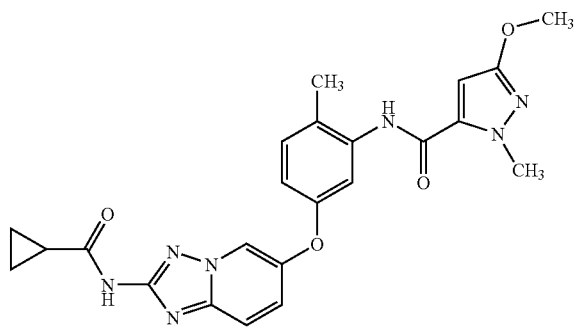

In the same manner as in Example 55 and using 3-methoxy-1-methyl-1H-pyrazole-5-carboxylic acid (62.5 mg, 0.400 mmol), tetrahydrofuran (5 mL), thionyl chloride (69.1 μL, 0.796 mmol), N,N-dimethylformamide (2 drops), N-[6-(3-amino-4-methylphenoxy)[1,2,4]triazolo[1,5-a]pyridin-2-yl]cyclopropanecarboxamide (117 mg, 0.362 mmol) and N,N-dimethylacetamide (6 mL) as starting materials, the title compound (137 mg, 82%) was obtained as a white solid.

¹H-NMR (DMSO-d₆, 300 MHz) δ 0.76-0.89 (4H, m), 1.95-2.12 (1H, m), 2.19 (3H, s), 3.79 (3H, s), 3.90 (3H, s), 6.43 (1H, s), 6.94 (1H, dd, J=8.5, 2.6 Hz), 7.07 (1H, d, J=2.6 Hz), 7.29 (1H, d, J=8.5 Hz), 7.50 (1H, dd, J=9.4, 2.3 Hz), 7.72 (1H, dd, J=9.4, 0.8 Hz), 8.84 (1H, dd, J=2.3, 0.8 Hz), 9.81 (1H, s), 11.03 (1H, s).

Example 88

N-[5-({2-[(cyclopropylcarbonyl)amino][1,2,4]triazolo[1,5-a]pyridin-6-yl}oxy)-2-methylphenyl]-2,4-dimethyl-1,3-oxazole-5-carboxamide

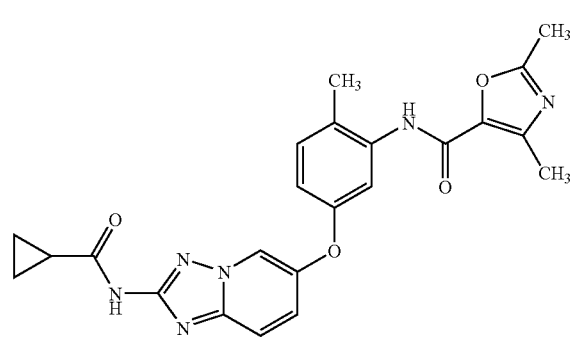

In the same manner as in Example 55 and using 2,4-dimethyl-1,3-oxazole-5-carboxylic acid (56.6 mg, 0.401 mmol), tetrahydrofuran (5 mL), thionyl chloride (69.1 μL, 0.796 mmol), N,N-dimethylformamide (2 drops), N-[6-(3-amino-4-methylphenoxy)[1,2,4]triazolo[1,5-a]pyridin-2-yl]cyclopropanecarboxamide (117 mg, 0.362 mmol) and N,N-dimethylacetamide (6 mL) as starting materials, the title compound (104 mg, 64%) was obtained as a pale-brown solid.

¹H-NMR (DMSO-d₆, 300 MHz) δ 0.76-0.88 (4H, m), 1.94-2.11 (1H, m), 2.19 (3H, s), 2.33 (3H, s), 2.46 (3H, s), 6.91 (1H, dd, J=8.5, 2.7 Hz), 7.11 (1H, d, J=2.7 Hz), 7.27 (1H, d, J=8.5 Hz), 7.49 (1H, dd, J=9.6, 2.3 Hz), 7.72 (1H, d, J=9.6 Hz), 8.83 (1H, d, J=2.3 Hz), 9.67 (1H, s), 11.03 (1H, s).

Example 89-1 tert-butyl {5-[(2-amino[1,2,4]triazolo[1,5-a]pyridin-6-yl)oxy]-2-chlorophenyl}carbamate

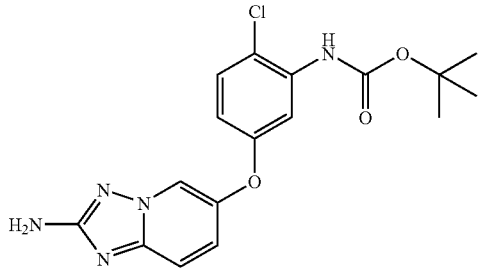

In the same manner as in Example 23-1 and using ethyl{[(5-{3-[(tert-butoxycarbonyl)amino]-4-chlorophenoxy}pyridin-2-yl)amino]carbonothioyl}carbamate (7.23 g, 15.5 mmol), hydroxylammonium chloride (7.64 g, 0.110 mol), N,N-diisopropylethylamine (13.5 mL, 77.4 mmol), ethanol (50 mL) and methanol (50 mL) as starting materials, the title compound (5.49 g, 92%) was obtained as a white solid.

¹H-NMR (DMSO-d₆, 300 MHz) δ 1.42 (9H, s), 6.03 (2H, s), 6.78 (1H, dd, J=9.0, 3.0 Hz), 7.27-7.36 (2H, m), 7.36-7.45 (2H, m), 8.56-8.67 (2H, m).

Example 89-2 tert-butyl [2-chloro-5-({2-[(cyclopropylcarbonyl)amino][1,2,4]triazolo[1,5-a]pyridin-6-yl}oxy)phenyl]carbamate

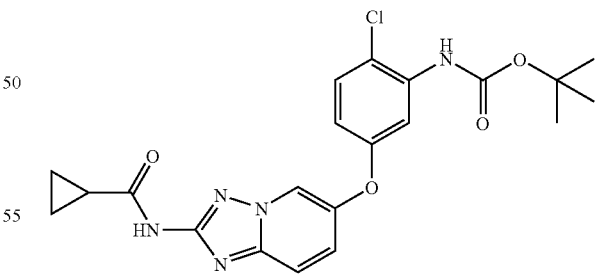

To a solution of tert-butyl {5-[(2-amino[1,2,4]triazolo[1,5-a]pyridin-6-yl)oxy]-2-chlorophenyl}carbamate (5.49 g, 14.60 mmol) in N,N-dimethylacetamide (40 mL) was added cyclopropanecarbonyl chloride (1.50 mL, 16.5 mmol) at 0° C., and the mixture was stirred at room temperature for 14 hr. The reaction mixture was diluted with saturated aqueous sodium hydrogen carbonate solution, and extracted with ethyl acetate. The organic layer was washed with saturated aqueous sodium hydrogen carbonate solution and saturated brine, dried over anhydrous magnesium sulfate and filtrated. The filtrate was concentrated under reduced pressure, and the residue was washed with ethyl acetate-hexane to give the title compound (5.61 g, 87%) as a white solid.

$^1$H-NMR (DMSO-d$_6$, 300 MHz) δ 0.79-0.86 (4H, m), 1.42 (9H, s), 1.97-2.12 (1H, m), 6.84 (1H, dd, J=8.8, 3.0 Hz), 7.39 (1H, d, J=3.0 Hz), 7.44 (1H, d, J=8.8 Hz), 7.49-7.56 (1H, m), 7.70-7.77 (1H, m), 8.65 (1H, s), 8.93 (1H, dd, J=2.3, 0.8 Hz), 11.05 (1H, s).

Example 89-3

N-[6-(3-amino-4-chlorophenoxy)[1,2,4]triazolo[1,5-a]pyridin-2-yl]cyclopropanecarboxamide

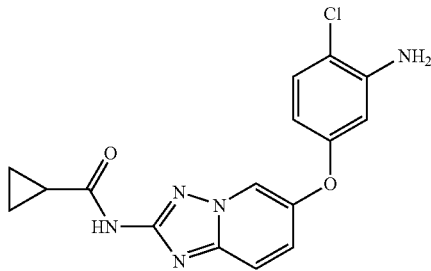

Trifluoroacetic acid (30 mL) was added to tert-butyl [2-chloro-5-({2-[(cyclopropylcarbonyl)amino][1,2,4]triazolo[1,5-a]pyridin-6-yl}oxy)phenyl]carbamate (5.59 g, 12.6 mmol), and the mixture was stirred at room temperature for 30 min. The reaction solution was concentrated under reduced pressure, and ethyl acetate was added to the residue. The mixture was washed with saturated aqueous sodium hydrogen carbonate solution and saturated brine, dried over anhydrous magnesium sulfate and filtrated. The filtrate was concentrated under reduced pressure, and the residue was washed with ethyl acetate-hexane to give the title compound (3.58 g, 83%) as a white solid.

$^1$H-NMR (DMSO-d$_6$, 300 MHz) δ 0.79-0.88 (4H, m), 1.93-2.12 (1H, m), 5.48 (2H, s), 6.25 (1H, dd, J=8.4, 2.7 Hz), 6.41 (1H, d, J=2.7 Hz), 7.16 (1H, d, J=8.4 Hz), 7.49 (1H, dd, J=9.6, 2.4 Hz), 7.72 (1H, dd, J=9.6, 0.8 Hz), 8.88 (1H, dd, J=2.4, 0.8 Hz), 11.03 (1H, s).

Example 89-4

N-[2-chloro-5-({2-[(cyclopropylcarbonyl)amino][1,2,4]triazolo[1,5-a]pyridin-6-yl}oxy)phenyl]-3-ethyl-1-methyl-1H-pyrazole-5-carboxamide

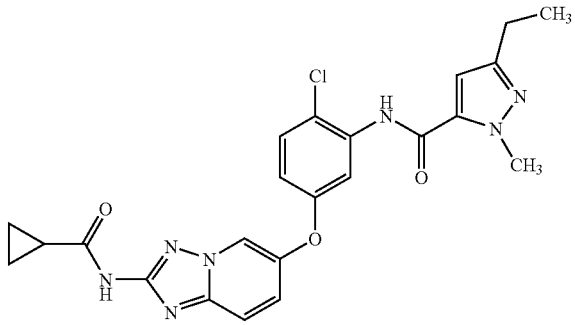

In the same manner as in Example 55 and using 3-ethyl-1-methyl-1H-pyrazole-5-carboxylic acid (56.5 mg, 0.366 mmol), tetrahydrofuran (5 mL), thionyl chloride (63.3 µL, 0.730 mmol), N,N-dimethylformamide (2 drops), N-[6-(3-amino-4-chlorophenoxy)[1,2,4]triazolo[1,5-a]pyridin-2-yl]cyclopropanecarboxamide (114 mg, 0.332 mmol) and N,N-dimethylacetamide (6 mL) as starting materials, the title compound (48.9 mg, 28%) was obtained as a white solid.

$^1$H-NMR (DMSO-d$_6$, 300 MHz) δ 0.78-0.87 (4H, m), 1.18 (3H, t, J=7.6 Hz), 1.95-2.13 (1H, m), 2.56 (2H, q, J=7.6 Hz), 3.98 (3H, s), 6.86 (1H, s), 7.04 (1H, dd, J=8.9, 2.9 Hz), 7.30 (1H, d, J=2.9 Hz), 7.51-7.58 (2H, m), 7.71-7.79 (1H, m), 8.97 (1H, dd, J=2.3, 0.8 Hz), 9.95 (1H, s), 11.05 (1H, s).

Example 90

N-[2-chloro-5-({2-[(cyclopropylcarbonyl)amino][1,2,4]triazolo[1,5-a]pyridin-6-yl}oxy)phenyl]-1-ethyl-3-methyl-1H-pyrazole-4-carboxamide

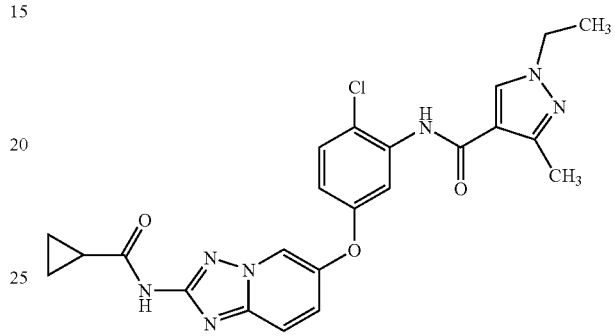

In the same manner as in Example 55 and using 1-ethyl-3-methyl-1H-pyrazole-4-carboxylic acid (56.5 mg, 0.366 mmol), tetrahydrofuran (5 mL), thionyl chloride (63.3 µL, 0.730 mmol), N,N-dimethylformamide (2 drops), N-[6-(3-amino-4-chlorophenoxy)[1,2,4]triazolo[1,5-a]pyridin-2-yl]cyclopropanecarboxamide (114 mg, 0.332 mmol) and N,N-dimethylacetamide (6 mL) as starting materials, the title compound (68.0 mg, 43%) was obtained as a white solid.

$^1$H-NMR (DMSO-d$_6$, 300 MHz) δ 0.79-0.87 (4H, m), 1.37 (3H, t, J=7.3 Hz), 1.95-2.12 (1H, m), 2.34 (3H, s), 4.09 (2H, q, J=7.3 Hz), 6.95 (1H, dd, J=9.2, 3.0 Hz), 7.46 (1H, d, J=3.0 Hz), 7.48-7.58 (2H, m), 7.75 (1H, dd, J=9.2, 0.8 Hz), 8.35 (1H, s), 8.96 (1H, dd, J=2.3, 0.8 Hz), 9.25 (1H, s), 11.06 (1H, s).

Example 91

N-[2-chloro-5-({2-[(cyclopropylcarbonyl)amino][1,2,4]triazolo[1,5-a]pyridin-6-yl}oxy)phenyl]-1-ethyl-3-methyl-1H-pyrazole-5-carboxamide

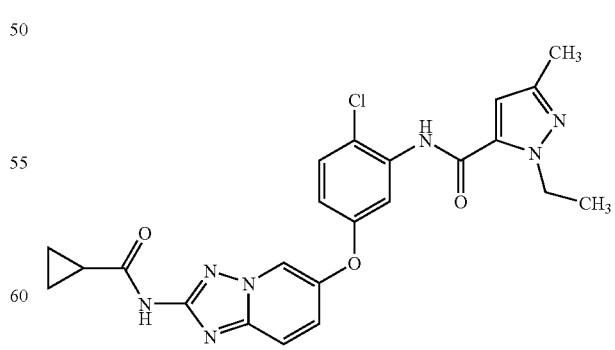

In the same manner as in Example 55 and using 1-ethyl-3-methyl-1H-pyrazole-5-carboxylic acid (56.2 mg, 0.365 mmol), tetrahydrofuran (5 mL), thionyl chloride (63.3 µL, 0.730 mmol), N,N-dimethylformamide (2 drops), N-[6-(3- amino-4-chlorophenoxy)[1,2,4]triazolo[1,5-a]pyridin-2-yl]cyclopropanecarboxamide (114 mg, 0.332 mmol) and N,N-dimethylacetamide (6 mL) as starting materials, the title compound (65.2 mg, 41%) was obtained as a white solid.

¹H-NMR (DMSO-d₆, 300 MHz) δ 0.79-0.87 (4H, m), 1.24-1.31 (3H, m), 1.95-2.13 (1H, m), 2.19 (3H, s), 4.35-4.45 (2H, m), 6.80 (1H, s), 7.03 (1H, dd, J=9.0, 3.0 Hz), 7.33 (1H, d, J=3.0 Hz), 7.50-7.58 (2H, m), 7.69-7.79 (1H, m), 8.92-9.00 (1H, m), 9.94 (1H, s), 11.05 (1H, s).

Example 92

N-[2-chloro-5-({2-[(cyclopropylcarbonyl)amino][1,2,4]triazolo[1,5-a]pyridin-6-yl}oxy)phenyl]-2,4-dimethyl-1,3-oxazole-5-carboxamide

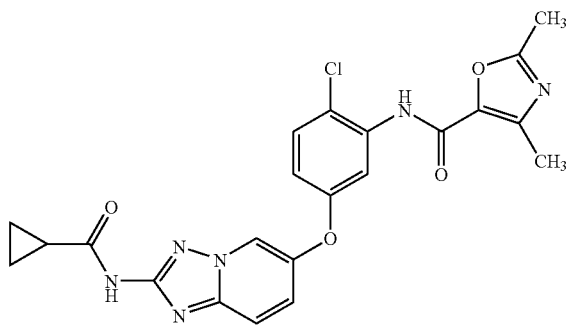

In the same manner as in Example 55 and using 2,4-dimethyl-1,3-oxazole-5-carboxylic acid (51.8 mg, 0.367 mmol), tetrahydrofuran (5 mL), thionyl chloride (63.3 μL, 0.730 mmol), N,N-dimethylformamide (2 drops), N-[6-(3-amino-4-chlorophenoxy)[1,2,4]triazolo[1,5-a]pyridin-2-yl]cyclopropanecarboxamide (114 mg, 0.332 mmol) and N,N-dimethylacetamide (6 mL) as starting materials, the title compound (98.4 mg, 63%) was obtained as a pale-brown solid.

¹H-NMR (DMSO-d₆, 400 MHz) δ 0.79-0.86 (4H, m), 1.94-2.13 (1H, m), 2.34 (3H, s), 2.48 (3H, s), 7.00 (1H, dd, J=8.9, 3.0 Hz), 7.46 (1H, d, J=3.0 Hz), 7.52-7.58 (2H, m), 7.75 (1H, d, J=9.5 Hz), 8.98 (1H, d, J=2.2), 9.67 (1H, s), 11.08 (1H, s).

Example 93

N-[2-chloro-5-({2-[(cyclopropylcarbonyl)amino][1,2,4]triazolo[1,5-a]pyridin-6-yl}oxy)phenyl]-1-methyl-1H-pyrazole-5-carboxamide

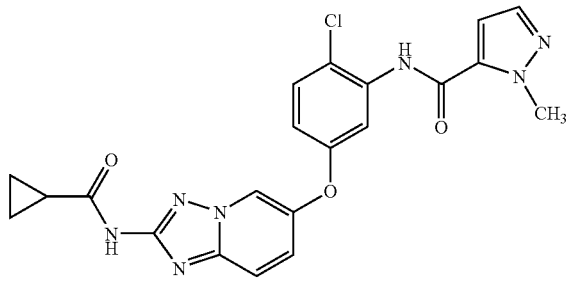

In the same manner as in Example 55 and using 1-methyl-1H-pyrazole-5-carboxylic acid (46.1 mg, 0.366 mmol), tet-rahydrofuran (5 mL), thionyl chloride (63.3 μL, 0.730 mmol), N,N-dimethylformamide (2 drops), N-[6-(3-amino-4-chlorophenoxy)[1,2,4]triazolo[1,5-a]pyridin-2-yl]cyclopropanecarboxamide (114 mg, 0.332 mmol) and N,N-dimethylacetamide (6 mL) as starting materials, the title compound (69.5 mg, 46%) was obtained as a white solid.

¹H-NMR (DMSO-d₆, 300 MHz) δ 0.79-0.86 (4H, m), 1.95-2.11 (1H, m), 4.05 (3H, s), 7.01-7.08 (2H, m), 7.31 (1H, d, J=3.0 Hz), 7.49-7.59 (3H, m), 7.75 (1H, dd, J=9.4, 0.8 Hz), 8.97 (1H, dd, J=2.3, 0.8 Hz), 10.05 (1H, s), 11.05 (1H, s).

Example 94

N-[2-chloro-5-({2-[(cyclopropylcarbonyl)amino][1,2,4]triazolo[1,5-a]pyridin-6-yl}oxy)phenyl]-1-methyl-3-(trifluoromethyl)-1H-pyrazole-4-carboxamide

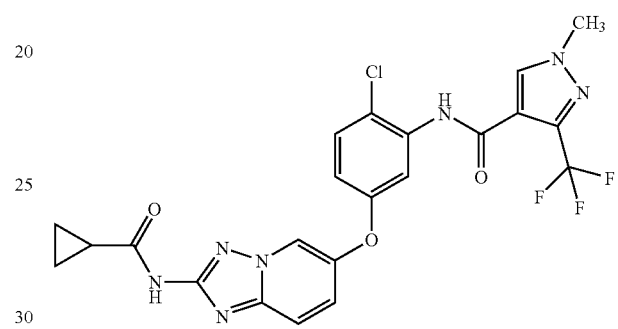

In the same manner as in Example 55 and using 1-methyl-3-(trifluoromethyl)-1H-pyrazole-4-carboxylic acid (70.8 mg, 0.365 mmol), tetrahydrofuran (5 mL), thionyl chloride (63.3 μL, 0.730 mmol), N,N-dimethylformamide (2 drops), N-[6-(3-amino-4-chlorophenoxy)[1,2,4]triazolo[1,5-a]pyridin-2-yl]cyclopropanecarboxamide (112 mg, 0.326 mmol) and N,N-dimethylacetamide (6 mL) as starting materials, the title compound (63.6 mg, 38%) was obtained as a white solid.

¹H-NMR (DMSO-d₆, 300 MHz) δ 0.78-0.88 (4H, m), 1.95-2.13 (1H, m), 3.97 (3H, s), 6.99 (1H, dd, J=8.9, 2.9 Hz), 7.37 (1H, d, J=2.9 Hz), 7.49-7.59 (2H, m), 7.71-7.78 (1H, m), 8.53 (1H, s), 8.93-8.99 (1H, m), 9.83 (1H, s), 11.05 (1H, s).

Example 95

4-chloro-N-[3-({2-[(cyclopropylcarbonyl)amino][1,2,4]triazolo[1,5-a]pyridin-6-yl}oxy)phenyl]-1-methyl-1H-pyrazole-3-carboxamide

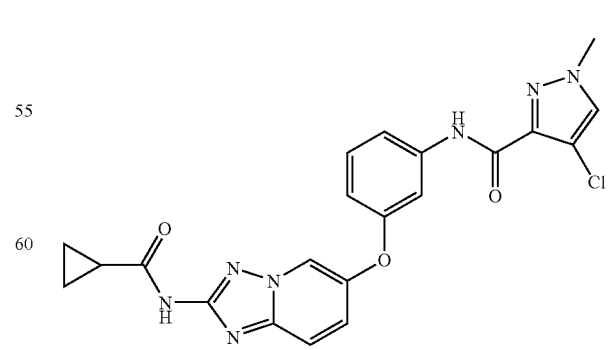

In the same manner as in Example 18-4 and using 4-chloro-1-methyl-1H-pyrazole-3-carboxylic acid (156 mg, 0.970 mmol), tetrahydrofuran (7 mL), oxalyl chloride (93.0 μL, 1.07 mmol), N-[6-(3-aminophenoxy)[1,2,4]triazolo[1,5-a]pyridin-2-yl]cyclopropanecarboxamide (200 mg, 0.646 mmol), N,N-dimethylformamide (1 drop) and N,N-dimethylacetamide (5 mL) as starting materials, the title compound (132 mg, 45%) was obtained as a white solid.

¹H-NMR (DMSO-d₆, 300 MHz) δ 0.82-0.84 (4H, m), 1.99-2.08 (1H, m), 3.90 (3H, s), 6.77-6.81 (1H, m), 7.32 (1H, t, J=8.1 Hz), 7.50-7.54 (2H, m), 7.62-7.66 (1H, m), 7.73 (1H, d, J=9.6 Hz), 8.09 (1H, s), 8.91 (1H, dd, J=2.3, 0.8 Hz), 10.21 (1H, s), 11.04 (1H, s).

Example 96-1

7-(3-nitrophenoxy)[1,2,4]triazolo[1,5-a]pyridin-2-amine

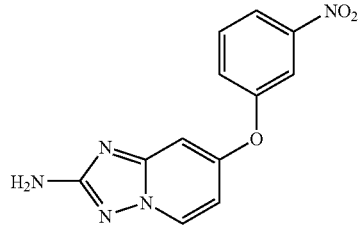

In the same manner as in Example 17-1 and using 4-(3-nitrophenoxy)pyridin-2-amine (250 mg, 1.08 mmol), ethyl isothiocyanatoformate (184 mg, 1.41 mmol), DMSO (5 mL), hydroxylammonium chloride (525 mg, 7.56 mmol), N,N-diisopropylethylamine (940 μL, 5.40 mmol), ethanol (10 mL) and methanol (10 mL) as starting materials, the title compound (113 mg, 39%) was obtained as a white solid.

¹H-NMR (DMSO-d₆, 300 MHz) δ 6.00 (2H, s), 6.70 (1H, dd, J=7.3, 2.5 Hz), 6.90 (1H, d, J=2.5 Hz), 7.62-7.67 (1H, m), 7.73 (1H, t, J=8.1 Hz), 7.94 (1H, t, J=2.4 Hz), 8.06-8.10 (1H, m), 8.56 (1H, d, J=7.3 Hz).

Example 96-2

N-[7-(3-nitrophenoxy)[1,2,4]triazolo[1,5-a]pyridin-2-yl]cyclopropanecarboxamide

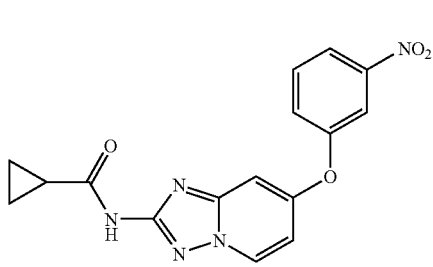

In the same manner as in Example 18-2 and using 7-(3-nitrophenoxy)[1,2,4]triazolo[1,5-a]pyridin-2-amine (112 mg, 0.413 mmol), cyclopropanecarbonyl chloride (135 μL, 0.496 mmol) and N,N-dimethylacetamide (5 mL) as starting materials, the title compound (134 mg, 96%) was obtained as a white solid.

¹H-NMR (DMSO-d₆, 300 MHz) δ 0.81-0.84 (4H, m), 1.99-2.08 (1H, m), 6.98 (1H, dd, J=7.3, 2.5 Hz), 7.15 (1H, d, J=2.5 Hz), 7.68-7.72 (1H, m), 7.76 (1H, t, J=7.8 Hz), 8.02 (1H, t, J=2.0 Hz), 8.10-8.14 (1H, m), 8.86 (1H, d, J=7.3 Hz), 11.00 (1H, s).

Example 96-3

N-[7-(3-aminophenoxy)[1,2,4]triazolo[1,5-a]pyridin-2-yl]cyclopropanecarboxamide

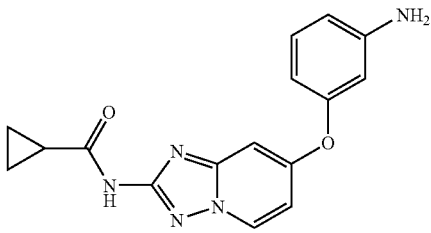

A mixture of N-[7-(3-nitrophenoxy)[1,2,4]triazolo[1,5-a]pyridin-2-yl]cyclopropanecarboxamide (125 mg, 0.368 mmol), reduced iron (500 mg), concentrated hydrochloric acid (500 μL) and ethanol (5 mL) was stirred under refluxing conditions for 1 hr. The reaction mixture was diluted with saturated aqueous sodium hydrogen carbonate solution, and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate to give the title compound (40.0 mg, 32%) as a white solid.

¹H-NMR (DMSO-d₆, 300 MHz) δ 0.79-0.82 (4H, m), 1.99-2.08 (1H, m), 5.36 (2H, s), 6.26-6.33 (2H, m), 6.33-6.48 (1H, m), 6.83-6.86 (2H, m), 7.09 (1H, t, J=8.3 Hz), 8.74-8.77 (1H, m), 10.96 (1H, s).

Example 96-4

N-[3-({2-[(cyclopropylcarbonyl)amino][1,2,4]triazolo[1,5-a]pyridin-7-yl}oxy)phenyl]-1,3-dimethyl-1H-pyrazole-5-carboxamide

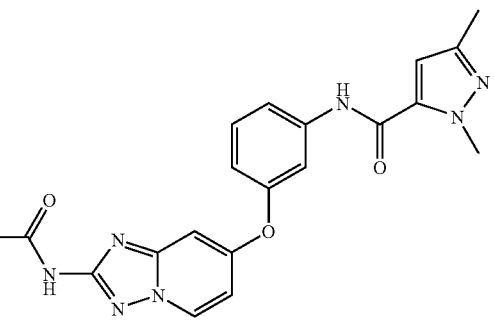

In the same manner as in Example 24 and using N-[7-(3-aminophenoxy)[1,2,4]triazolo[1,5-a]pyridin-2-yl]cyclopropanecarboxamide (40.0 mg, 0.129 mmol), 1,3-dimethyl-H-pyrazole-5-carbonyl chloride (30.8 mg, 0.194 mmol) and N,N-dimethylacetamide (3 mL) as starting materials, the title compound (53.6 mg, 96%) was obtained as a white solid.

¹H-NMR (DMSO-d₆, 300 MHz) δ 0.80-0.83 (4H, m), 1.99-2.08 (1H, m), 2.19 (3H, s), 3.97 (3H, s), 6.81 (1H, s), 6.91 (1H, dd, J=7.4, 2.7 Hz), 6.95-6.99 (2H, m), 7.46 (1H, t, J=8.9 Hz), 7.62-7.65 (2H, m), 8.81 (1H, d, J=7.4 Hz), 10.25 (1H, s), 10.98 (1H, s).

Example 97-1

N-[6-(3-nitrophenoxy)-1,3-benzothiazol-2-yl]cyclopropanecarboxamide

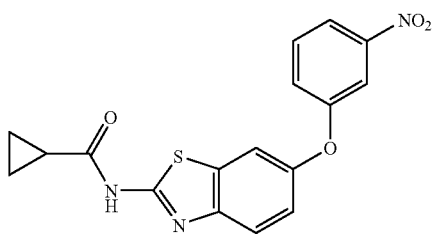

A mixture of N-(6-hydroxy-1,3-benzothiazol-2-yl)cyclopropanecarboxamide (3.54 g, 15.1 mmol), 1-fluoro-3-nitrobenzene (2.24 g, 15.9 mmol), potassium carbonate (6.26 g, 45.3 mmol) and N,N-dimethylformamide (30 mL) was stirred at 150° C. for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (1.82 g, 37%) as a white solid.

$^1$H-NMR (DMSO-d$_6$, 300 MHz) δ 0.95-0.99 (4H, m), 1.96-2.05 (1H, m), 7.24 (1H, dd, J=8.7, 2.7 Hz), 7.47-7.51 (1H, m), 7.63-7.70 (2H, m), 7.78-7.83 (2H, m), 7.94-7.99 (1H, m), 12.67 (1H, s).

Example 97-2

N-[3-({2-[(cyclopropylcarbonyl)amino]-1,3-benzothiazol-6-yl}oxy)phenyl]-1,3-dimethyl-1H-pyrazole-5-carboxamide

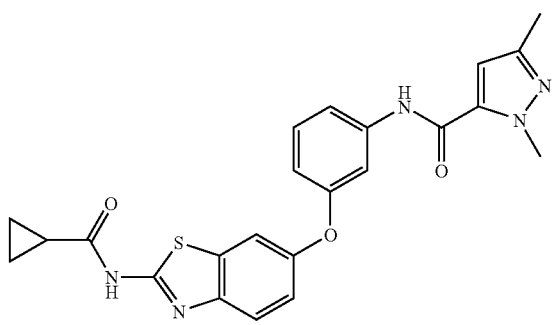

To a solution of N-[6-(3-nitrophenoxy)-1,3-benzothiazol-2-yl]cyclopropanecarboxamide (1.80 g, 5.53 mmol) in methanol (20 mL) was added palladium carbon (50% water-containing product, 100 mg), and the mixture was stirred at room temperature for 5 hr under a hydrogen atmosphere. The reaction mixture was filtered through celite, and the filtrate was concentrated under reduced pressure. Reduced iron (309 mg), calcium chloride (613 mg, 5.53 mmol), ethanol (10 mL) and water (2 mL) were added to the residue, and the mixture was stirred for 2 hr. The reaction mixture was filtered through celite, and the filtrate was diluted with water and extracted with ethyl acetate. The organic layer was washed with water and saturated brine, dried over anhydrous magnesium sulfate and filtrated. The filtrate was concentrated under reduced pressure, and the residue was dissolved in tetrahydrofuran (10 mL). Triethylamine (192 μL) and 1,3-dimethyl-1H-pyrazole-5-carbonyl chloride (220 mg, 1.39 mmol) were added with stirring under ice-cooling, and the mixture was stirred at room temperature for 3 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=70/30→0/100) and recrystallized from ethyl acetate-tetrahydrofuran to give the title compound (126 mg, 5.1%) as a white solid.

$^1$H-NMR (DMSO-d$_6$, 300 MHz) δ 0.94-0.97 (4H, m), 1.96-2.05 (1H, m), 2.17 (3H, s), 3.95 (3H, s), 6.76-6.80 (2H, m), 7.15 (1H, dd, J=8.6, 2.6 Hz), 7.34 (1H, t, J=8.1 Hz), 7.40 (1H, t, J=2.3 Hz), 7.51-7.56 (1H, m), 7.70-7.77 (2H, m), 10.13 (1H, s), 12.62 (1H, s).

Example 98

N-{3-[(2-amino[1,3]thiazolo[5,4-b]pyridin-5-yl)oxy]phenyl}-1,3-dimethyl-1H-pyrazole-5-carboxamide

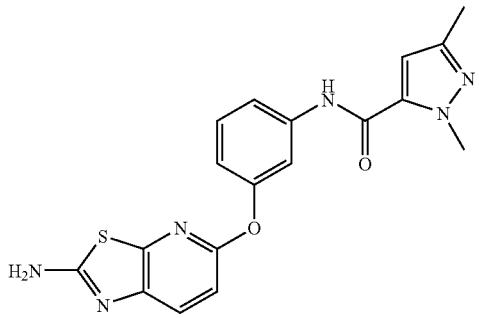

To a suspension of N-{3-[(5-aminopyridin-2-yl)oxy]phenyl}-1,3-dimethyl-1H-pyrazole-5-carboxamide (1.75 g, 5.41 mmol) and potassium thiocyanate (4.21 g, 43.3 mmol) in acetic acid (10 mL) was added dropwise with stirring under ice-cooling a solution of bromine (1 mL) in acetic acid (4 mL), and the mixture was stirred at 0° C. for 2 hr and at room temperature for 15 hr. Water (10 mL) was added to the reaction mixture, and the mixture was heated to 80° C. and filtered through celite. The filtrate was neutralized with 8N aqueous sodium hydroxide solution, and the precipitated solid was collected by filtration and washed with water to give the title compound (1.05 g, 51%) as a white solid.

$^1$H-NMR (DMSO-d$_6$, 300 MHz) δ 2.19 (3H, s), 3.98 (3H, s), 6.81-6.86 (2H, m), 6.92 (1H, d, J=8.1 Hz), 7.35 (1H, t, J=8.1 Hz), 7.50 (1H, t, J=2.1 Hz), 7.57 (1H, br d, J=8.1 Hz), 7.68-7.74 (3H, m), 10.31 (1H, s).

Example 99

N-[3-({2-[(cyclopropylcarbonyl)amino][1,3]thiazolo[5,4-b]pyridin-5-yl}oxy)phenyl]-1,3-dimethyl-1H-pyrazole-5-carboxamide

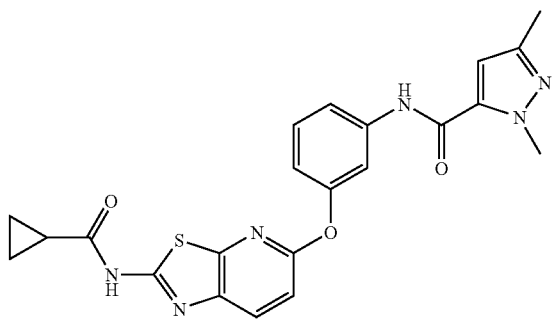

To a solution of N-{3-[(2-amino[1,3]thiazolo[5,4-b]pyridin-5-yl)oxy]phenyl}-1,3-dimethyl-1H-pyrazole-5-carboxamide (1.03 g, 2.71 mmol) and triethylamine (563 μL, 4.07 mmol) in tetrahydrofuran (15 mL) was added with stirring under ice-cooling cyclopropanecarbonyl chloride (295 μL, 3.25 mmol), and the mixture was stirred at room temperature for 2 hr. Cyclopropanecarbonyl chloride (500 μL, 5.51 mmol) was further added thereto, and the mixture was stirred for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, sodium carbonate (750 mg), methanol (15 mL) and water (100 μL) were added to the residue, and the mixture was stirred at 70° C. for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=60/40→0/100) and recrystallized from ethanol-ethyl acetate-hexane to give the title compound (675 mg, 56%) as a white solid.

$^1$H-NMR (DMSO-$d_6$, 300 MHz) δ 0.94-0.98 (4H, m), 1.96-2.05 (1H, m), 2.19 (3H, s), 3.97 (3H, s), 6.81 (1H, s), 6.89-6.94 (1H, m), 7.14 (1H, d, J=8.9 Hz), 7.40 (1H, t, J=8.4 Hz), 7.57-7.61 (2H, m), 8.17 (1H, d, J=8.9 Hz), 10.20 (1H, s), 12.70 (1H, s).

Example 100

N-(3-{[2-(acetylamino)[1,3]thiazolo[5,4-b]pyridin-5-yl]oxy}phenyl)-1,3-dimethyl-1H-pyrazole-5-carboxamide

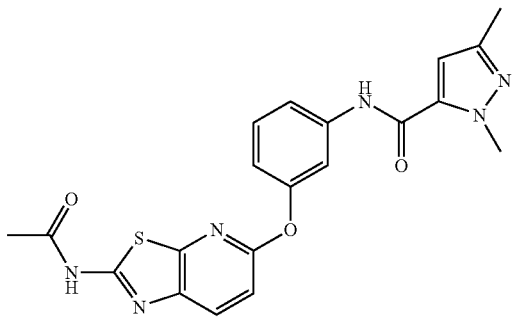

In the same manner as in Example 28-2 and using N-{3-[(2-amino[1,3]thiazolo[5,4-b]pyridin-5-yl)oxy]phenyl}-1,3-dimethyl-1H-pyrazole-5-carboxamide (199 mg, 0.523 mmol), N,N-dimethylacetamide (2 mL) and acetyl chloride (89.2 μL, 1.26 mmol) as starting materials, the title compound (125 mg, 57%) was obtained as a white solid.

$^1$H-NMR (DMSO-$d_6$, 300 MHz) δ 2.19 (3H, s), 2.20 (3H, s), 3.98 (3H, s), 6.82 (1H, s), 6.90-6.94 (1H, m), 7.14 (1H, d, J=8.9 Hz), 7.41 (1H, t, J=8.3 Hz), 7.58-7.62 (2H, m), 8.18 (1H, d, J=8.9 Hz), 10.21 (1H, s), 12.41 (1H, s).

Example 101-1 methyl 3-[(2-amino[1,3]thiazolo[5,4-b]pyridin-5-yl)oxy]benzoate

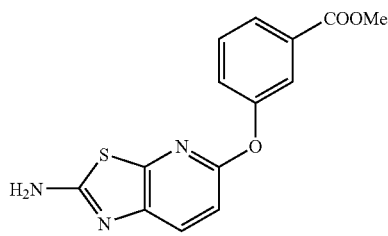

In the same manner as in Example 98 and using methyl 3-[(5-aminopyridin-2-yl)oxy]benzoate (12.5 g, 51.2 mmol), potassium thiocyanate (34.8 g, 358 mmol), bromine (8.2 mL) and acetic acid (125 mL) as starting materials, the title compound (7.25 g, 47%) was obtained as a yellow solid.

$^1$H-NMR (DMSO-$d_6$, 300 MHz) δ 3.85 (3H, s), 6.98 (1H, d, J=8.4 Hz), 7.39-7.43 (1H, m), 7.54-7.59 (2H, m), 7.66 (2H, s), 7.73-7.80 (2H, m).

Example 101-2

3-({2-[(cyclopropylcarbonyl)amino][1,3]thiazolo[5,4-b]pyridin-5-yl}oxy)benzoic acid

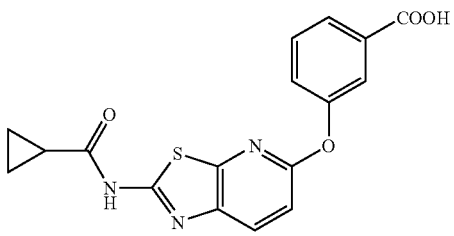

To a solution of methyl 3-[(2-amino[1,3]thiazolo[5,4-b]pyridin-5-yl)oxy]benzoate (4.20 g, 13.9 mmol) and triethylamine (3.47 μL, 25.1 mmol) in tetrahydrofuran (40 mL) was added with stirring under ice-cooling cyclopropanecarbonyl chloride (1.52 mL, 16.7 mmol), and the mixture was stirred at room temperature for 2 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was dissolved in ethanol (50 mL). 8N Aqueous sodium hydroxide solution (7 mL) was added thereto, and the mixture was stirred at room temperature for 3 hr. The reaction mixture was adjusted to pH 4 with 6N hydrochloric acid, and the precipitated solid was collected by filtration and washed with water to give the title compound (3.90 g, 79%) as a white solid.

¹H-NMR (DMSO-d₆, 300 MHz) δ 0.94-1.01 (4H, m), 1.96-2.04 (1H, m), 7.18 (1H, d, J=8.7 Hz), 7.42-7.47 (1H, m), 7.57 (1H, t, J=7.8 Hz), 7.63 (1H, t, J=2.0 Hz), 7.78-7.82 (1H, m), 8.19 (1H, d, J=8.7 Hz), 12.71 (1H, s), 13.20 (1H, br s).

Example 101-3

N-[5-(3-aminophenoxy)[1,3]thiazolo[5,4-b]pyridin-2-yl]cyclopropanecarboxamide

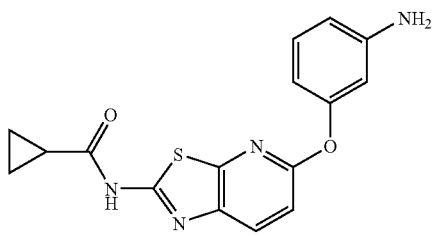

A mixture of 3-({2-[(cyclopropylcarbonyl)amino][1,3]thiazolo[5,4-b]pyridin-5-yl}oxy)benzoic acid (3.90 g, 11.0 mmol), diphenylphosphoryl azide (3.55 mL, 16.5 mmol), triethylamine (2.28 mL, 16.5 mmol) and N,N-dimethylformamide (80 mL) was stirred at room temperature for 3 hr, and water (20 mL) was added and the mixture was stirred at 100° C. for 15 hr. The precipitation solid was collected by filtration. 6N Hydrochloric acid (100 mL), ethyl acetate (30 mL) and tetrahydrofuran (10 mL) were added to the solid, and the mixture was stirred at room temperature for 30 min. The insoluble material was filtered off, and the aqueous layer was separated from the filtrate, neutralized with 8N aqueous sodium hydroxide solution, and extracted with ethyl acetate. The organic layer was washed with water and saturated brine, dried over anhydrous magnesium sulfate and filtrated. The filtrate was concentrated under reduced pressure, and the residue was collected by filtration and washed with ethyl acetate-hexane to give the title compound (1.13 g, 31%) as a white solid.

¹H-NMR (DMSO-d₆, 300 MHz) δ 0.94-1.01 (4H, m), 1.95-2.04 (1H, m), 5.24 (2H, s), 6.23 (1H, dd, J=8.0, 2.3 Hz), 6.28 (1H, t, J=2.1 Hz), 6.39 (1H, dd, J=8.0, 2.0 Hz), 7.00-7.05 (2H, m), 8.01 (1H, d, J=8.4 Hz), 12.66 (1H, s).

Example 101-4

N-[3-({2-[(cyclopropylcarbonyl)amino][1,3]thiazolo[5,4-b]pyridin-5-yl}oxy)phenyl]-1-methyl-1H-imidazole-2-carboxamide

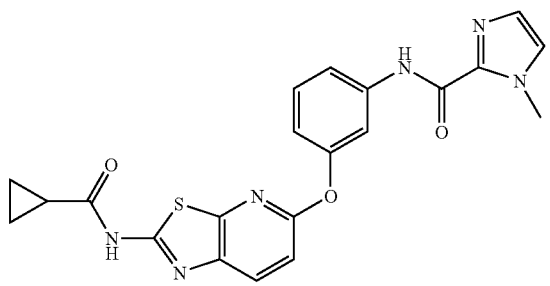

A mixture of N-[5-(3-aminophenoxy)[1,3]thiazolo[5,4-b]pyridin-2-yl]cyclopropanecarboxamide (175 mg, 0.536 mmol), 1-methyl-1H-imidazole-2-carboxylic acid (101 mg, 0.804 mmol), HATU (367 mg, 0.965 mmol), N,N-diisopropylethylamine (420 μL, 2.41 mmol) and N,N-dimethylformamide (5 mL) was stirred at room temperature for 15 hr. The reaction mixture was diluted with water and extracted with ethyl acetate. The organic layer was washed with water and saturated brine, dried over anhydrous magnesium sulfate and filtrated. The filtrate was concentrated under reduced pressure, and the residue was purified by column chromatography (silica gel, hexane/ethyl acetate=50/50→0/100) and recrystallized from ethyl acetate-tetrahydrofuran to give the title compound (152 mg, 65%) as a white solid.

¹H-NMR (DMSO-d₆, 300 MHz) δ 0.94-1.01 (4H, m), 1.95-2.04 (1H, m), 3.97 (3H, s), 6.86-6.91 (1H, m), 7.07-7.15 (2H, m), 7.38 (1H, t, J=8.1 Hz), 7.44 (1H, d, J=0.3 Hz), 7.67-7.74 (2H, m), 8.18 (1H, d, J=9.0 Hz), 10.47 (1H, s), 12.70 (1H, s).

Example 102

N-[3-({2-[(cyclopropylcarbonyl)amino][1,3]thiazolo[5,4-b]pyridin-5-yl}oxy)phenyl]-1-methyl-1H-imidazole-5-carboxamide

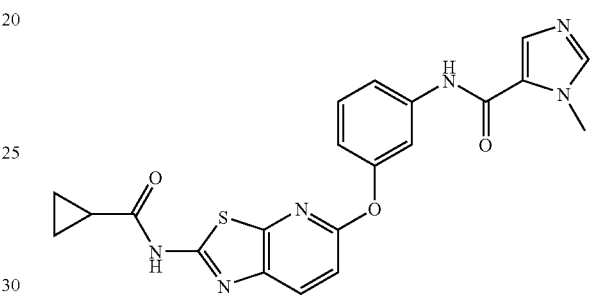

In the same manner as in Example 101-4 and using N-[5-(3-aminophenoxy)[1,3]thiazolo[5,4-b]pyridin-2-yl]cyclopropanecarboxamide (124 mg, 0.280 mmol), 1-methyl-1H-imidazole-5-carboxylic acid (71.9 mg, 0.570 mmol), HATU (260 mg, 0.684 mmol), N,N-diisopropylethylamine (298 μL, 1.71 mmol) and N,N-dimethylformamide (4 mL) as starting materials, the title compound (107 mg, 65%) was obtained as a white solid.

¹H-NMR (DMSO-d₆, 300 MHz) δ 0.94-1.01 (4H, m), 1.95-2.04 (1H, m), 3.83 (3H, s), 6.86-6.90 (1H, m), 7.13 (1H, d, J=8.9 Hz), 7.38 (1H, t, J=8.4 Hz), 7.54-7.57 (2H, m), 7.77-7.82 (2H, m), 8.16 (1H, d, J=8.9 Hz), 10.10 (1H, s), 12.69 (1H, s).

Example 103

N-[3-({2-[(cyclopropylcarbonyl)amino][1,3]thiazolo[5,4-b]pyridin-5-yl}oxy)phenyl]-3-methylpyridine-2-carboxamide

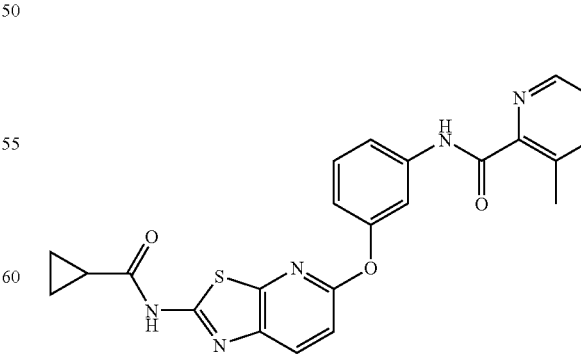

In the same manner as in Example 18-4 and using 3-methylpyridine-2-carboxylic acid (132 mg, 0.965 mmol), tetrahydrofuran (8 mL), oxalyl chloride (169 μL, 1.93 mmol), N-[5-(3-aminophenoxy)[1,3]thiazolo[5,4-b]pyridin-2-yl]cyclopropanecarboxamide (210 mg, 0.643 mmol), N,N-dimethylformamide (1 drop) and N,N-dimethylacetamide (5 mL) as starting materials, the title compound (220 mg, 77%) was obtained as a white solid.

$^1$H-NMR (DMSO-d$_6$, 300 MHz) δ 0.94-1.01 (4H, m), 1.95-2.04 (1H, m), 2.55 (3H, s), 6.88-6.92 (1H, m), 7.13 (1H, d, J=8.6 Hz), 7.39 (1H, t, J=8.1 Hz), 7.50 (1H, dd, J=7.7, 4.7 Hz), 7.66-7.81 (3H, m), 8.17 (1H, d, J=8.6 Hz), 8.50-8.53 (1H, m), 10.64 (1H, s), 12.68 (1H, s).

Example 104

N-[5-({2-[(cyclopropylcarbonyl)amino][1,2,4]triazolo[1,5-a]pyridin-6-yl}oxy)-2-fluorophenyl]-1-methyl-1H-pyrazole-5-carboxamide

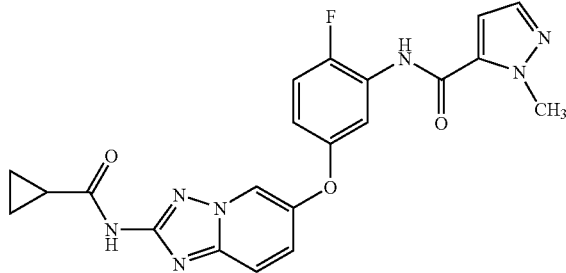

In the same manner as in Example 55 and using 1-methyl-1H-pyrazole-5-carboxylic acid (50.9 mg, 0.404 mmol), tetrahydrofuran (5 mL), thionyl chloride (70.0 μL, 0.807 mmol), N,N-dimethylformamide (2 drops), N-[6-(3-amino-4-fluorophenoxy)[1,2,4]triazolo[1,5-a]pyridin-2-yl]cyclopropanecarboxamide (120 mg, 0.367 mmol) and N,N-dimethylacetamide (5 mL) as starting materials, the title compound (107 mg, 67%) was obtained as a white solid.

$^1$H-NMR (DMSO-d$_6$, 300 MHz) δ 0.79-0.88 (4H, m), 1.95-2.10 (1H, m), 4.05 (3H, s), 6.99-7.08 (2H, m), 7.29-7.39 (2H, m), 7.50-7.57 (2H, m), 7.71-7.77 (1H, m), 8.87-8.92 (1H, m), 10.15 (1H, s), 11.05 (1H, s).

Example 105

N-[5-({2-[(cyclopropylcarbonyl)amino][1,2,4]triazolo[1,5-a]pyridin-6-yl}oxy)-2-fluorophenyl]-1-ethyl-3-methyl-1H-pyrazole-4-carboxamide

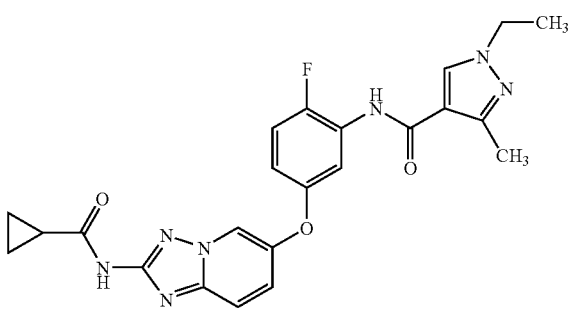

In the same manner as in Example 55 and using 1-ethyl-3-methyl-1H-pyrazole-4-carboxylic acid (62.6 mg, 0.406 mmol), tetrahydrofuran (5 mL), thionyl chloride (70.0 μL, 0.807 mmol), N,N-dimethylformamide (2 drops), N-[6-(3-amino-4-fluorophenoxy)[1,2,4]triazolo[1,5-a]pyridin-2-yl]cyclopropanecarboxamide (120 mg, 0.367 mmol) and N,N-dimethylacetamide (5 mL) as starting materials, the title compound (60.4 mg, 36%) was obtained as a white solid.

$^1$H-NMR (DMSO-d$_6$, 300 MHz) δ 0.79-0.86 (4H, m), 1.37 (3H, t, J=7.3 Hz), 1.96-2.11 (1H, m), 2.32 (3H, s), 4.08 (2H, q, J=7.3 Hz), 6.87-6.95 (1H, m), 7.29 (1H, dd, J=10.2, 9.1 Hz), 7.44-7.56 (2H, m), 7.69-7.76 (1H, m), 8.36 (1H, s), 8.87 (1H, dd, J=2.3, 0.8 Hz), 9.48 (1H, s), 11.03 (1H, s).

Example 106

N-[5-({2-[(cyclopropylcarbonyl)amino][1,2,4]triazolo[1,5-a]pyridin-6-yl}oxy)-2-fluorophenyl]-1,3-dimethyl-1H-pyrazole-4-carboxamide

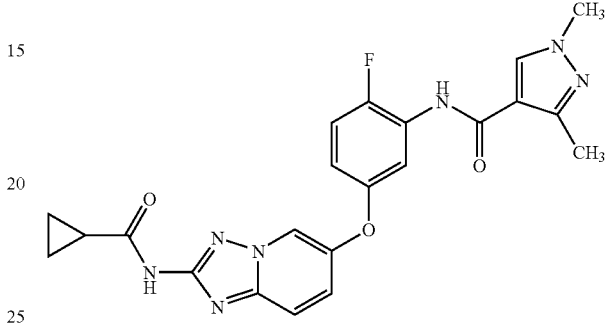

In the same manner as in Example 55 and using 1,3-dimethyl-1H-pyrazole-4-carboxylic acid (56.4 mg, 0.402 mmol), tetrahydrofuran (5 mL), thionyl chloride (70.0 μL, 0.807 mmol), N,N-dimethylformamide (2 drops), N-[6-(3-amino-4-fluorophenoxy)[1,2,4]triazolo[1,5-a]pyridin-2-yl]cyclopropanecarboxamide (120 mg, 0.367 mmol) and N,N-dimethylacetamide (5 mL) as starting materials, the title compound (92.4 mg, 56%) was obtained as a white solid.

$^1$H-NMR (DMSO-d$_6$, 300 MHz) δ 0.79-0.87 (4H, m), 1.96-2.10 (1H, m), 2.31 (3H, s), 3.80 (3H, s), 6.88-6.95 (1H, m), 7.29 (1H, dd, J=10.2, 9.0 Hz), 7.48 (1H, dd, J=6.4, 3.0 Hz), 7.52 (1H, dd, J=9.4, 2.3 Hz), 7.73 (1H, dd, J=9.4, 0.8 Hz), 8.30 (1H, s), 8.87 (1H, dd, J=2.3, 0.8 Hz), 9.48 (1H, s), 11.04 (1H, s).

Example 107

N-[5-({2-[(cyclopropylcarbonyl)amino][1,2,4]triazolo[1,5-a]pyridin-6-yl}oxy)-2-fluorophenyl]-1-methyl-3-(trifluoromethyl)-1H-pyrazole-4-carboxamide

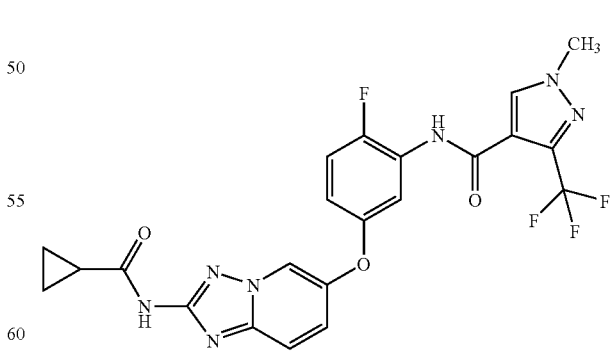

In the same manner as in Example 55 and using 1-methyl-3-(trifluoromethyl)-1H-pyrazole-4-carboxylic acid (78.6 mg, 0.405 mmol), tetrahydrofuran (5 mL), thionyl chloride (70.0 μL, 0.807 mmol), N,N-dimethylformamide (2 drops), N-[6-(3-amino-4-fluorophenoxy)[1,2,4]triazolo[1,5-a]pyridin-2-yl]cyclopropanecarboxamide (120 mg, 0.367 mmol) and N,N-dimethylacetamide (5 mL) as starting materials, the title compound (132 mg, 72%) was obtained as a white solid.

$^1$H-NMR (DMSO-d$_6$, 300 MHz) δ 0.78-0.87 (4H, m), 1.97-2.11 (1H, m), 3.97 (3H, s), 6.91-7.00 (1H, m), 7.32 (1H, dd, J=10.2, 9.0 Hz), 7.46 (1H, dd, J=6.4, 3.0 Hz), 7.53 (1H, dd, J=9.8, 2.3 Hz), 7.69-7.77 (1H, m), 8.52 (1H, s), 8.88 (1H, dd, J=2.3, 0.8 Hz), 10.01 (1H, s), 11.03 (1H, s).

Example 108

N-[5-({2-[(cyclopropylcarbonyl)amino][1,2,4]triazolo[1,5-a]pyridin-6-yl}oxy)-2-fluorophenyl]-2,4-dimethyl-1,3-oxazole-5-carboxamide

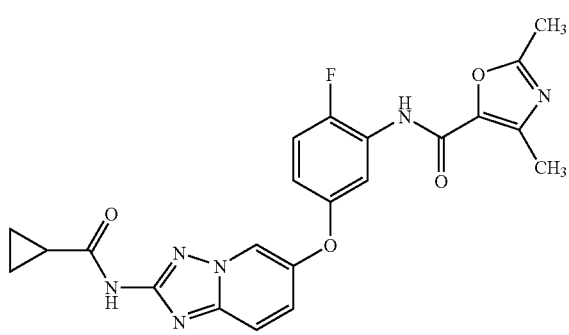

In the same manner as in Example 55 and using 2,4-dimethyl-1,3-oxazole-5-carboxylic acid (57.2 mg, 0.405 mmol), tetrahydrofuran (5 mL), thionyl chloride (70.0 μL, 0.807 mmol), N,N-dimethylformamide (2 drops), N-[6-(3-amino-4-fluorophenoxy)[1,2,4]triazolo[1,5-a]pyridin-2-yl]cyclopropanecarboxamide (120 mg, 0.367 mmol) and N,N-dimethylacetamide (5 mL) as starting materials, the title compound (114 mg, 69%) was obtained as a pale-brown solid.

$^1$H-NMR (DMSO-d$_6$, 300 MHz) δ 0.79-0.87 (4H, m), 1.96-2.12 (1H, m), 2.33 (3H, s), 2.47 (3H, s), 6.95-7.04 (1H, m), 7.26-7.39 (2H, m), 7.53 (1H, dd, J=9.8, 2.3 Hz), 7.70-7.77 (1H, m), 8.89 (1H, dd, J=2.3, 0.8 Hz), 9.88 (1H, s), 11.04 (1H, s).

Example 109

N-[3-({2-[(cyclopropylcarbonyl)amino][1,2,4]triazolo[1,5-a]pyridin-6-yl}oxy)phenyl]-1-ethyl-3-(trifluoromethyl)-1H-pyrazole-4-carboxamide(1) and
N-[3-({2-[(cyclopropylcarbonyl)amino][1,2,4]triazolo[1,5-a]pyridin-6-yl}oxy)phenyl]-1-ethyl-4-(trifluoromethyl)-1H-pyrazole-3-carboxamide(2)

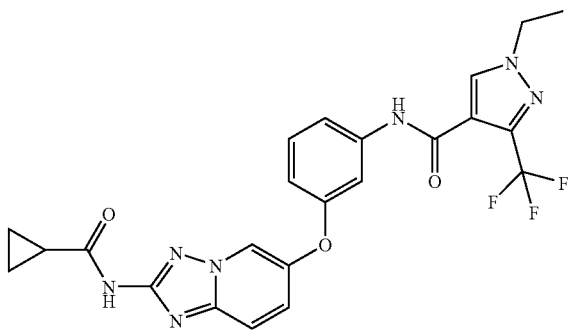

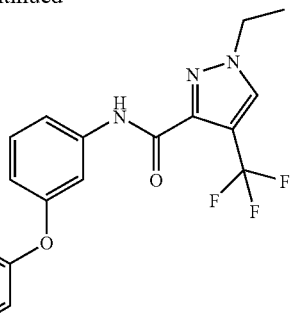

In the same manner as in Example 18-4 and using a mixture (303 mg, 1.45 mmol) of 1-ethyl-3-(trifluoromethyl)-1H-pyrazole-4-carboxylic acid and 1-ethyl-4-(trifluoromethyl)-1H-pyrazole-3-carboxylic acid, tetrahydrofuran (7 mL), oxalyl chloride (139 μL, 1.60 mmol), N-[6-(3-aminophenoxy)[1,2,4]triazolo[1,5-a]pyridin-2-yl]cyclopropanecarboxamide (300 mg, 0.970 mmol), N,N-dimethylformamide (1 drop) and N,N-dimethylacetamide (5 mL) as starting materials, N-[3-({2-[(cyclopropylcarbonyl)amino][1,2,4]triazolo[1,5-a]pyridin-6-yl}oxy)phenyl]-1-ethyl-3-(trifluoromethyl)-1H-pyrazole-4-carboxamide (1, 123 mg) and N-[3-({2-[(cyclopropylcarbonyl)amino][1,2,4]triazolo[1,5-a]pyridin-6-yl}oxy)phenyl]-1-ethyl-4-(trifluoromethyl)-1H-pyrazole-3-carboxamide (2, 157 mg) were each obtained as a white solid.

(1): $^1$H-NMR (DMSO-d$_6$, 300 MHz) δ 0.81-0.85 (4H, m), 1.44 (3H, t, J=7.3 Hz), 1.99-2.07 (1H, m), 4.26 (2H, q, J=7.3 Hz), 6.79-6.83 (1H, m), 7.33 (1H, t, J=8.3 Hz), 7.47-7.55 (2H, m), 7.66-7.75 (2H, m), 8.53 (1H, s), 8.92 (1H, d, J=2.4 Hz), 10.35 (1H, s), 11.06 (1H, s).

(2): $^1$H-NMR (DMSO-d$_6$, 300 MHz) δ 0.81-0.86 (4H, m), 1.42 (3H, t, J=7.4 Hz), 1.99-2.07 (1H, m), 4.24 (2H, q, J=7.4 Hz), 6.79-6.83 (1H, m), 7.29-7.37 (2H, m), 7.51-7.55 (2H, m), 7.75 (1H, d, J=9.9 Hz), 8.53 (1H, s), 8.94 (1H, d, J=2.4 Hz), 10.16 (1H, s), 11.06 (1H, s).

Example 110

N-[3-({2-[(cyclopropylcarbonyl)amino][1,2,4]triazolo[1,5-a]pyridin-6-yl}oxy)phenyl]-1-methyl-4-(trifluoromethyl)-1H-pyrazole-3-carboxamide

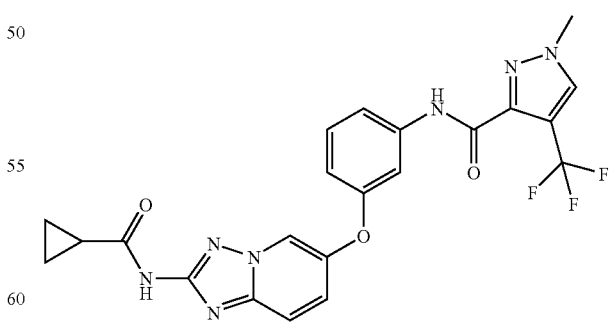

In the same manner as in Example 18-4 and using 1-methyl-4-(trifluoromethyl)-1H-pyrazole-3-carboxylic acid (194 mg, 1.00 mmol), tetrahydrofuran (7 mL), oxalyl chloride (95.6 μL, 1.10 mmol), N-[6-(3-aminophenoxy)[1,2,4]triazolo[1,5-a]pyridin-2-yl]cyclopropanecarboxamide (281 mg, 0.910 mmol), N,N-dimethylformamide (1 drop) and N,N-dimethylacetamide (5 mL) as starting materials, the title compound (211 mg, 48%) was obtained as a white solid.

$^1$H-NMR (DMSO-d$_6$, 300 MHz) δ 0.82-0.85 (4H, m), 1.99-2.07 (1H, m), 3.97 (3H, s), 6.78-6.83 (1H, m), 7.38 (1H, t, J=8.1 Hz), 7.48-7.55 (2H, m), 7.66-7.75 (2H, m), 8.47 (1H, s), 8.92 (1H, dd, J=2.3, 0.8 Hz), 10.41 (1H, s), 11.05 (1H, s).

Example 111

N-[3-({2-[(cyclopropylcarbonyl)amino][1,2,4]triazolo[1,5-a]pyridin-6-yl}oxy)phenyl]-2-ethyl-5-(trifluoromethyl)-1,3-oxazole-4-carboxamide

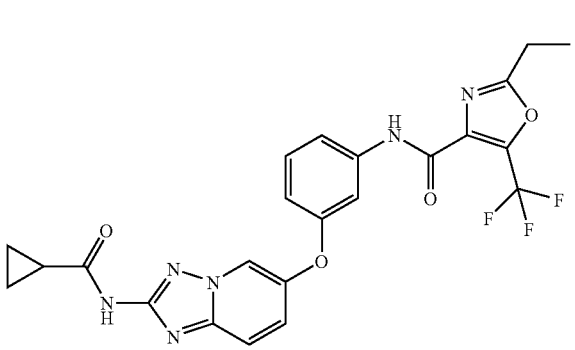

In the same manner as in Example 18-4 and using 2-ethyl-5-(trifluoromethyl)-1,3-oxazole-4-carboxylic acid (314 mg, 1.50 mmol), tetrahydrofuran (7 mL), oxalyl chloride (143 μL, 1.65 mmol), N-[6-(3-aminophenoxy)[1,2,4]triazolo[1,5-a]pyridin-2-yl]cyclopropanecarboxamide (309 mg, 1.00 mmol), N,N-dimethylformamide (1 drop) and N,N-dimethylacetamide (5 mL) as starting materials, the title compound (244 mg, 49%) was obtained as a white solid.

$^1$H-NMR (DMSO-d$_6$, 300 MHz) δ 0.81-0.84 (4H, m), 1.30 (3H, t, J=7.6 Hz), 1.99-2.07 (1H, m), 2.93 (2H, q, J=7.6 Hz), 6.83-6.87 (1H, m), 7.35 (1H, t, J=8.1 Hz), 7.48-7.55 (2H, m), 7.65-7.76 (2H, m), 8.93 (1H, d, J=2.1 Hz), 10.56 (1H, s), 11.12 (1H, s).

Example 112

N-[3-({2-[(cyclopropylcarbonyl)amino][1,2,4]triazolo[1,5-a]pyridin-6-yl}oxy)phenyl]-2,5-dimethyl-1,3-thiazole-4-carboxamide

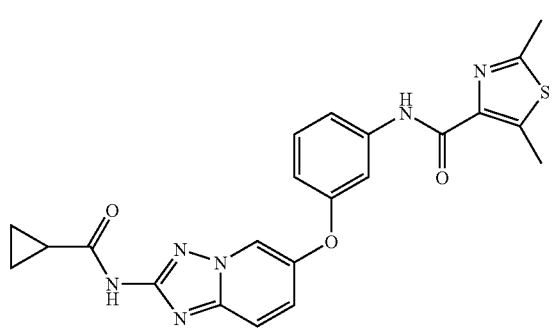

In the same manner as in Example 18-4 and using 2,5-dimethyl-1,3-thiazole-4-carboxylic acid (314 mg, 2.00 mmol), tetrahydrofuran (50 mL), oxalyl chloride (191 μL, 2.20 mmol), N-[6-(3-aminophenoxy)[1,2,4]triazolo[1,5-a]pyridin-2-yl]cyclopropanecarboxamide (309 mg, 1.00 mmol), N,N-dimethylformamide (1 drop) and N,N-dimethylacetamide (6 mL) as starting materials, the title compound (283 mg, 63%) was obtained as a white solid.

$^1$H-NMR (DMSO-d$_6$, 300 MHz) δ 0.81-0.84 (4H, m), 1.99-2.07 (1H, m), 2.64 (3H, s), 2.69 (3H, s), 6.78-6.82 (1H, m), 7.32 (1H, t, J=8.1 Hz), 7.50-7.57 (2H, m), 7.64-7.75 (2H, m), 8.91 (1H, d, J=1.5 Hz), 10.13 (1H, s), 11.05 (1H, s).

Example 113

N-{3-[(2-amino[1,2,4]triazolo[1,5-a]pyridin-6-yl)oxy]phenyl}-3-methylpyridine-2-carboxamide

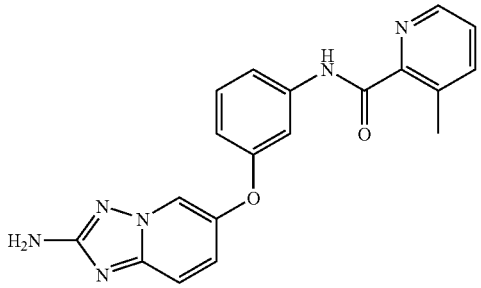

A mixture of ethyl{[5-(3-{[(3-methylpyridin-2-yl)carbonyl]amino}phenoxy)pyridin-2-yl]carbamothioyl}carbamate (2.00 g, 4.43 mmol), hydroxylammonium chloride (3.13 g, 45.0 mmol), N,N-diisopropylethylamine (4.70 mL, 26.9 mmol), ethanol (50 mL) and methanol (50 mL) was stirred at 80° C. for 5 hr. The reaction solution was concentrated under reduced pressure, and ethyl acetate was added to the residue. The mixture was washed with aqueous sodium hydrogen carbonate solution and saturated brine, dried over anhydrous magnesium sulfate and filtrated. The filtrate was concentrated under reduced pressure, and the residue was washed with ethyl acetate to give the title compound (1.35 g, 84%) as a white solid.

$^1$H-NMR (DMSO-d$_6$, 400 MHz) δ 2.54 (3H, s), 6.04 (2H, s), 6.77 (1H, dd, J=8.3, 2.4 Hz), 7.29-7.37 (2H, m), 7.38-7.44 (1H, m), 7.48-7.55 (2H, m), 7.65 (1H, d, J=8.3 Hz), 7.80 (1H, d, J=7.6 Hz), 8.51 (1H, d, J=4.6 Hz), 8.64 (1H, d, J=2.2 Hz), 10.61 (1H, s).

Example 114

N-[3-({2-[(cyclopropylcarbonyl)amino][1,2,4]triazolo[1,5-a]pyridin-6-yl}oxy)phenyl]-3-methylpyridine-2-carboxamide

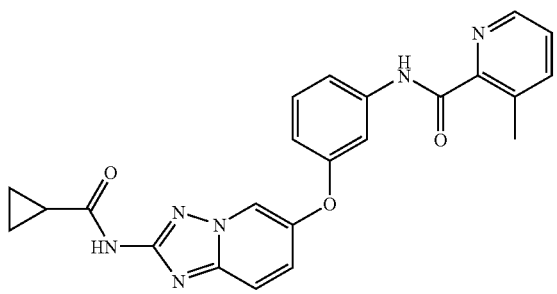

To a solution of N-{3-[(2-amino[1,2,4]triazolo[1,5-a]pyridin-6-yl)oxy]phenyl}-3-methylpyridine-2-carboxamide (120 mg, 0.333 mmol) in N,N-dimethylacetamide (5 mL) was added cyclopropanecarbonyl chloride (30.5 μL, 0.336 mmol), and the mixture was stirred at room temperature for 12 hr. The reaction mixture was diluted with aqueous sodium hydrogen carbonate solution, and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (110 mg, 77%) as a white solid.

$^1$H-NMR (DMSO-d$_6$, 400 MHz) δ 0.81-0.86 (4H, m), 1.97-2.10 (1H, m), 2.54 (3H, s), 6.82 (1H, dd, J=8.3, 2.4 Hz), 7.36 (1H, t, J=8.3 Hz), 7.48-7.57 (2H, m), 7.58 (1H, t, J=2.2 Hz), 7.66-7.72 (1H, m), 7.75 (1H, d, J=9.8 Hz), 7.80 (1H, d, J=7.8 Hz), 8.51 (1H, d, J=3.7 Hz), 8.94 (1H, d, J=2.2 Hz), 10.63 (1H, s), 11.07 (1H, br s).

Example 115

N-(3-{[2-(acetylamino)[1,2,4]triazolo[1,5-a]pyridin-6-yl]oxy}phenyl)-3-methylpyridine-2-carboxamide

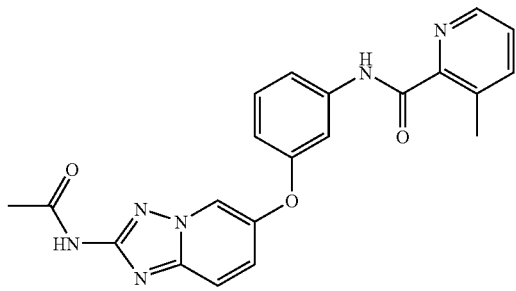

To a solution of N-{3-[(2-amino[1,2,4]triazolo[1,5-a]pyridin-6-yl)oxy]phenyl}-3-methylpyridine-2-carboxamide (120 mg, 0.333 mmol) in N,N-dimethylacetamide (5 mL) was added acetyl chloride (24.0 μL, 0.338 mmol), and the mixture was stirred at room temperature for 2 hr. The reaction mixture was diluted with aqueous sodium hydrogen carbonate solution, and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (89.1 mg, 66%) as a white solid.

$^1$H-NMR (DMSO-d$_6$, 400 MHz) δ2.14 (3H, br s), 2.54 (3H, s), 6.82 (1H, dd, J=8.3, 2.5 Hz), 7.36 (1H, t, J=8.3 Hz), 7.48-7.57 (2H, m), 7.58 (1H, t, J=2.2 Hz), 7.66-7.71 (1H, m), 7.75 (1H, d, J=9.5 Hz), 7.80 (1H, d, J=7.8 Hz), 8.49-8.53 (1H, m), 8.95 (1H, d, J=2.5 Hz), 10.62 (1H, s), 10.80 (1H, br s).

Example 116

3-methyl-N-(3-{[2-(propanoylamino)[1,2,4]triazolo[1,5-a]pyridin-6-yl]oxy}phenyl)pyridine-2-carboxamide

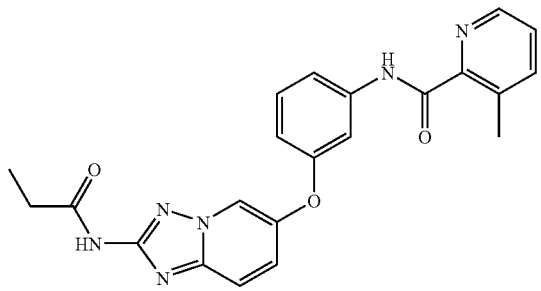

To a solution of N-{3-[(2-amino[1,2,4]triazolo[1,5-a]pyridin-6-yl)oxy]phenyl}-3-methylpyridine-2-carboxamide (120 mg, 0.333 mmol) in N,N-dimethylacetamide (5 mL) was added propionylchloride (29.2 μL, 0.336 mmol), and the mixture was stirred at room temperature for 1 hr. The reaction mixture was diluted with aqueous sodium hydrogen carbonate solution, and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (101 mg, 73%) as a white solid.

$^1$H-NMR (DMSO-d$_6$, 400 MHz) δ 1.07 (3H, t, J=7.6 Hz), 2.42-2.48 (2H, m), 2.54 (3H, s), 6.82 (1H, dd, J=8.2, 2.5 Hz), 7.36 (1H, t, J=8.2 Hz), 7.48-7.57 (2H, m), 7.58 (1H, t, J=2.1 Hz), 7.66-7.71 (1H, m), 7.74 (1H, d, J=9.8 Hz), 7.81 (1H, d, J=7.8 Hz), 8.49-8.53 (1H, m), 8.95 (1H, d, J=2.5 Hz), 10.63 (1H, s), 10.74 (1H, s).

Example 117

N-[3-({2-[(trifluoroacetyl)amino]imidazo[1,2-a]pyridin-6-yl}oxy)phenyl]-3-(trifluoromethyl)benzamide

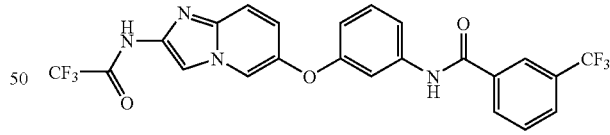

(i) 5-(3-aminophenoxy)pyridin-2-amine dihydrochloride

To a solution of 2-nitro-5-(3-nitrophenoxy)pyridine (14.0 g, 53.6 mmol) in methanol (1000 mL)/tetrahydrofuran (200 mL)/ethyl acetate (200 mL) was added 10% palladium-carbon (1.4 g), and the mixture was stirred at room temperature for 20 hr under a hydrogen atmosphere (1.0 atm). The insoluble material was removed by filtration, and the filtrate was concentrated. The obtained residue was diluted with ethyl acetate (300 mL), and 4N hydrochloric acid/ethyl acetate (30 mL) was slowly added dropwise thereto. The obtained colorless precipitated product was collected by filtration, washed with diisopropyl ether and hexane on a filter paper and dried to give the title compound (15.2 g, quantitative) as a colorless powder. The obtained compound was used in the next reaction without further purification.

$^1$H-NMR (DMSO-$d_6$, 300 MHz) δ 6.69-6.83 (2H, m), 6.85-6.95 (1H, m), 7.09 (1H, d, J=9.6 Hz), 7.33 (1H, t, J=8.0 Hz), 7.86 (1H, dd, J=9.6, 2.7 Hz), 7.98 (1H, d, J=2.7 Hz), 8.15 (3H, br s), 10.02 (3H, br s).

(ii) N-{3-[(6-aminopyridin-3-yl)oxy]phenyl}-3-(trifluoromethyl)benzamide

To a solution of 5-(3-aminophenoxy)pyridin-2-amine dihydrochloride (3.5 g, 12.7 mmol) in N,N-dimethylacetamide (30 mL) was added 3-(trifluoromethyl)benzoylchloride (2.80 g, 13.4 mmol), and the mixture was stirred at room temperature for 6 hr. The reaction mixture was concentrated under reduced pressure, 5% aqueous sodium hydrogen carbonate solution (100 mL) was added to the residue, and the mixture was extracted with ethyl acetate (200 mL). The organic layer was washed with water (100 mL) and saturated brine (100 mL), and dried over anhydrous sodium sulfate. The insoluble material was filtered off, and the filtrate was concentrated under reduced pressure. Ethyl acetate (30 mL)/hexane (20 mL) was added to the obtained residue, the precipitated product was collected by filtration and dried with air to give the title compound (3.95 g, 83%) as a colorless powder.

$^1$H-NMR (DMSO-$d_6$, 300 MHz) δ 5.90 (2H, s), 6.51 (1H, d, J=8.9 Hz), 6.71 (1H, dd, J=2.4, 8.1 Hz), 7.23 (1H, dd, J=3.0, 8.9 Hz), 7.31 (1H, t, J=8.1 Hz), 7.36 (1H, t, J=2.1 Hz), 7.51 (1H, d, J=8.1 Hz), 7.69-7.83 (2H, m), 7.96 (1H, d, J=7.5 Hz), 8.15-8.29 (2H, m), 10.47 (1H, s).

(iii) N-{3-[(6-{[(4-methylphenyl)sulfonyl]amino}pyridin-3-yl)oxy]phenyl}-3-(trifluoromethyl)benzamide To a solution of N-{3-[(6-aminopyridin-3-yl)oxy]phenyl}-3-(trifluoromethyl)benzamide (2.00 g, 5.36 mmol) in pyridine (60 mL) was added under ice-cooling 4-methylbenzenesulfonyl chloride (1.12 g, 5.89 mmol), and the mixture was stirred with heating at 80° C. for 2 days. The reaction mixture was cooled to room temperature, water (200 mL) was added thereto and the mixture was extracted with ethyl acetate (300 mL). The organic layer was washed with saturated brine (300 mL), and dried over anhydrous sodium sulfate. The insoluble material was removed by filtration, and the filtrate was concentrated under reduced pressure to give the title compound (2.75 g, 99%) as a yellow oil. The obtained compound was used in the next reaction without further purification.

$^1$H-NMR (DMSO-$d_6$, 300 MHz) δ 2.34 (3H, s), 6.72-6.80 (1H, m), 7.14 (1H, d, J=9.0 Hz), 7.29-7.44 (4H, m), 7.50 (1H, dd, J=9.0, 2.4 Hz), 7.53-7.60 (1H, m), 7.75-7.83 (3H, m), 7.96 (1H, d, J=7.8 Hz), 8.02 (1H, d, J=2.4 Hz), 8.16-8.27 (2H, m), 10.50 (1H, s), 11.07 (1H, br s).

(iv) N-{3-[(1-(2-amino-2-oxoethyl)-6-{[(4-methylphenyl)sulfonyl]imino}-1,6-dihydropyridin-3-yl)oxy]phenyl}-3-(trifluoromethyl)benzamide To a solution of N-{3-[(6-{[(4-methylphenyl)sulfonyl]amino}pyridin-3-yl)oxy]phenyl}-3-(trifluoromethyl)benzamide (2.7 g, 5.12 mmol) in N,N-dimethylformamide (18 mL) was added N,N-diisopropylethylamine (0.94 mL, 5.38 mmol), and the mixture was stirred at room temperature for 15 min. 2-Iodoacetamide (995 mg, 5.38 mmol) was added to the reaction mixture, and the mixture was stirred at room temperature for 18 hr. Water (200 mL) was added to the reaction mixture, and the mixture was extracted with ethyl acetate (300 mL). The organic layer was washed with water (100 mL) and saturated brine (100 mL), and dried over anhydrous sodium sulfate. The insoluble material was filtered off, and the filtrate was concentrated under reduced pressure. The obtained residue was purified by silica gel column chromatography (hexane/ethyl acetate=60/40→0/100) and recrystallized from ethyl acetate and hexane to give the title compound (1.84 g, 61%) as a colorless solid.

$^1$H-NMR (DMSO-$d_6$, 300 MHz) δ 2.34 (3H, s), 4.83 (2H, s), 6.78 (1H, dd, J=8.4, 2.7 Hz), 7.28 (2H, d, J=8.4 Hz), 7.32-7.45 (3H, m), 7.47 (1H, t, J=2.1 Hz), 7.60 (1H, d, J=8.4 Hz), 7.68 (2H, d, J=8.4 Hz), 7.71-7.85 (3H, m), 7.98 (1H, d, J=7.8 Hz), 8.15 (1H, d, J=2.7 Hz), 8.19-8.30 (2H, m), 10.56 (1H, s).

(v) N-[3-({2-[(trifluoroacetyl)amino]imidazo[1,2-a]pyridin-6-yl}oxy)phenyl]-3-(trifluoromethyl)benzamide To a solution of N-{3-[(1-(2-amino-2-oxoethyl)-6-{[(4-methylphenyl)sulfonyl]imino}-1,6-dihydropyridin-3-yl)oxy]phenyl}-3-(trifluoromethyl)benzamide (1.00 g, 1.71 mmol) in dichloromethane (8.0 mL) was added trifluoroacetic anhydride (6.0 mL), and the mixture was stirred at room temperature for 4 hr. The reaction mixture was concentrated under reduced pressure, 5% aqueous sodium hydrogen carbonate solution (150 mL) was added to the residue, and the mixture was extracted with ethyl acetate (300 mL). The organic layer was washed with saturated brine (150 mL), and dried over anhydrous sodium sulfate. The insoluble material was collected by filtration, and the filtrate was concentrated under reduced pressure. The obtained residue was purified by silica gel column chromatography (hexane/ethyl acetate=70/30→40/60) and recrystallized from ethyl acetate and hexane to give the title compound (0.55 g, 64%) as a colorless solid.

$^1$H-NMR (DMSO-$d_6$, 300 MHz) δ 6.86 (1H, dd, J=1.8, 8.1 Hz), 7.22 (1H, dd, J=9.6, 2.1 Hz), 7.39 (1H, t, J=8.2 Hz), 7.50 (1H, t, J=2.1 Hz), 7.55-7.67 (2H, m), 7.76 (1H, t, J=7.8 Hz), 7.96 (1H, d, J=7.8 Hz), 8.15-8.33 (3H, m), 8.66 (1H, d, J=2.1 Hz), 10.51 (1H, s), 12.49 (1H, br s).

Example 118-1

N-{3-[(2-aminoimidazo[1,2-a]pyridin-6-yl)oxy]phenyl}-3-methylpyridine-2-carboxamide

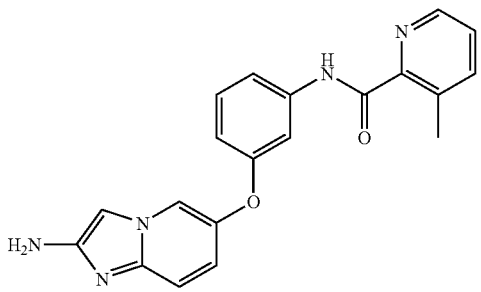

A mixture of N-(3-{[1-(2-amino-2-oxoethyl)-6-{[(4-methylphenyl)sulfonyl]imino}-1,6-dihydropyridin-3-yl]oxy}phenyl)-3-methylpyridine-2-carboxamide (9.68 g, 18.2 mmol), trifluoroacetic anhydride (30 mL) and tetrahydrofuran (250 mL) was stirred at room temperature for 2 hr. The reaction solution was concentrated under reduced pressure, ethanol (200 mL) and 4M aqueous sodium hydroxide solution (60 mL) were added to the residue, and the mixture was stirred at room temperature for 19 hr. The reaction solution was concentrated under reduced pressure, and ethyl acetate was added to the residue. The mixture was washed with water and saturated brine, dried over anhydrous magnesium sulfate and filtrated. The filtrate was concentrated under reduced pressure, and the residue was purified by silica gel column chromatography (NH silica gel, 0%→100% ethyl acetate-hexane) to give the title compound (4.52 g, 69%) as a pale-yellow oil.

$^1$H-NMR (DMSO-$d_6$, 400 MHz) δ 2.53 (3H, s), 5.09 (2H, s), 6.74 (1H, dd, J=8.1, 2.4 Hz), 6.87 (1H, dd, J=9.5, 2.2 Hz), 7.01 (1H, s), 7.21 (1H, d, J=9.5 Hz), 7.32 (1H, t, J=8.2 Hz), 7.50 (1H, dd, J=7.8, 4.6 Hz), 7.54 (1H, t, J=2.1 Hz), 7.60 (1H, d, J=8.1 Hz), 7.80 (1H, d, J=7.8 Hz), 8.33 (1H, d, J=2.4 Hz), 8.50 (1H, d, J=3.7 Hz), 10.60 (1H, s).

Example 118-2

3-methyl-N-(3-{[2-(propanoylamino)imidazo[1,2-a]pyridin-6-yl]oxy}phenyl)pyridine-2-carboxamide

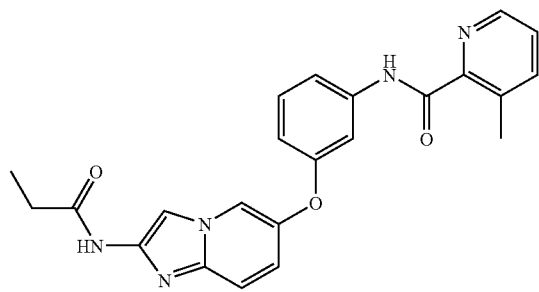

To a solution of N-{3-[(2-aminoimidazo[1,2-a]pyridin-6-yl)oxy]phenyl}-3-methylpyridine-2-carboxamide (129 mg, 0.359 mmol) in N,N-dimethylacetamide (6 mL) was added propionylchloride (34.3 μL, 0.395 mmol), and the mixture was stirred at room temperature for 22 hr. Methanol, tetrahydrofuran and aqueous sodium carbonate solution were added to the reaction mixture, and the mixture was stirred at 60° C. for 22 hr. The reaction mixture was concentrated under reduced pressure, diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (61.4 mg, 41%) as a white solid.

$^1$H-NMR (DMSO-$d_6$, 400 MHz) δ 1.08 (3H, t, J=7.6 Hz), 2.37 (2H, q, J=7.6 Hz), 2.53 (3H, s), 6.78 (1H, dd, J=8.1, 2.4 Hz), 7.10 (1H, dd, J=9.4, 2.4 Hz), 7.34 (1H, t, J=8.1 Hz), 7.44-7.54 (2H, m), 7.56 (1H, t, J=2.1 Hz), 7.63 (1H, d, J=7.8 Hz), 7.80 (1H, d, J=7.8 Hz), 8.12 (1H, s), 8.50 (1H, d, J=4.2 Hz), 8.60 (1H, d, J=2.2 Hz), 10.61 (1H, s), 10.66 (1H, s).

Example 119

3-methyl-N-[3-({2-[(morpholin-4-ylacetyl)amino]imidazo[1,2-a]pyridin-6-yl}oxy)phenyl]pyridine-2-carboxamide

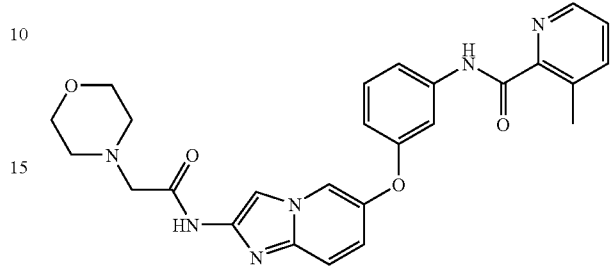

A mixture of N-{3-[(2-aminoimidazo[1,2-a]pyridin-6-yl)oxy]phenyl}-3-methylpyridine-2-carboxamide (129 mg, 0.359 mmol), morpholin-4-ylacetic acid (56.8 mg, 0.391 mmol), N-[3-(dimethylamino)propyl]-N'-ethylcarbodiimide hydrochloride (97.8 mg, 0.510 mmol), 1H-benzotriazol-1-ol (50.7 mg, 0.375 mmol), N,N-diisopropylethylamine (123 μL, 0.719 mmol) and N,N-dimethylacetamide (5 mL) was stirred at room temperature for 21 hr. The reaction mixture was diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (NH silica gel, 0%→75% ethyl acetate-hexane) to give the title compound (82.8 mg, 47%) as a pale-yellow solid.

$^1$H-NMR (DMSO-$d_6$, 400 MHz) δ 2.44-2.49 (4H, m), 2.54 (3H, s), 3.40 (2H, s), 3.52-3.65 (4H, m), 6.81 (1H, dd, J=8.3, 2.4 Hz), 7.26 (2H, br s), 7.35 (1H, t, J=8.2 Hz), 7.41-7.53 (3H, m), 7.58 (1H, s), 7.66 (1H, d, J=8.2 Hz), 7.80 (1H, d, J=7.6 Hz), 8.51 (1H, d, J=4.2 Hz), 9.46 (1H, brs), 10.62 (1H, s).

Example 120

N-[3-({2-[(cyclopropylcarbamoyl)amino]imidazo[1,2-a]pyridin-6-yl}oxy)phenyl]-3-methylpyridine-2-carboxamide

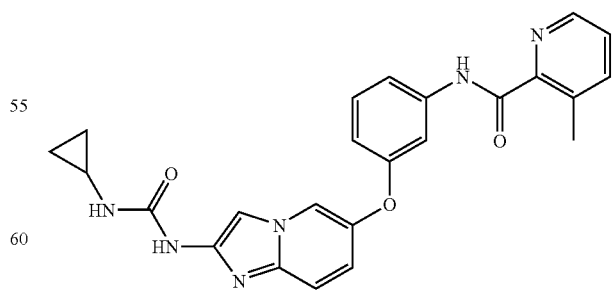

To a solution of N-{3-[(2-aminoimidazo[1,2-a]pyridin-6-yl)oxy]phenyl}-3-methylpyridine-2-carboxamide (129 mg, 0.359 mmol) and N,N-diisopropylethylamine (184 μL, 1.075 mmol) in tetrahydrofuran (5 mL) was added 2,2,2-trichloroethyl chlorocarbonate (52.0 μL, 0.378 mmol), and the mixture was stirred at room temperature for 30 min. Cyclopropaneamine (150 μL, 2.17 mmol) and N,N-dimethylacetamide (5 mL) were added to the reaction mixture, and the mixture was stirred at 80° C. for 22 hr. The reaction mixture was concentrated under reduced pressure, diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (20.3 mg, 13%) as a white solid.

$^1$H-NMR (DMSO-d$_6$, 400 MHz) δ 0.38-0.44 (2H, m), 0.61-0.68 (2H, m), 2.53 (3H, s), 2.54-2.59 (1H, m), 6.77 (1H, dd, J=8.2, 2.6 Hz), 6.83 (1H, br s), 7.05 (1H, dd, J=9.4, 2.1 Hz), 7.33 (1H, t, J=8.1 Hz), 7.41 (1H, d, J=9.3 Hz), 7.50 (1H, dd, J=7.8, 4.6 Hz), 7.55 (1H, t, J=2.2 Hz), 7.62 (1H, d, J=8.1 Hz), 7.77-7.82 (2H, m), 8.51 (1H, d, J=4.4 Hz), 8.56 (1H, d, J=2.2 Hz), 8.79 (1H, s), 10.61 (1H, s).

Example 121

3-methyl-N-[3-({2-[(pyridin-3-ylcarbonyl)amino]imidazo[1,2-a]pyridin-6-yl}oxy)phenyl]pyridine-2-carboxamide

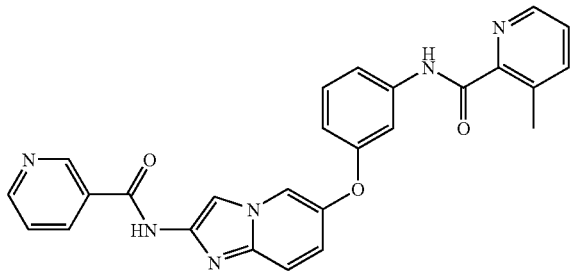

A mixture of N-{3-[(2-aminoimidazo[1,2-a]pyridin-6-yl)oxy]phenyl}-3-methylpyridine-2-carboxamide (150 mg, 0.625 mmol), pyridine-3-carboxylic acid (76.9 mg, 0.625 mmol), N-[3-(dimethylamino)propyl]-N'-ethylcarbodiimide hydrochloride (132 mg, 0.689 mmol), 1H-benzotriazol-1-ol (58.0 mg, 0.429 mmol), N,N-diisopropylethylamine (143 μL, 0.835 mmol) and N,N-dimethylacetamide (5 mL) was stirred at room temperature for 13 hr. The reaction mixture was diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (NH silica gel, 0%→75% ethyl acetate-hexane) to give the title compound (89.0 mg, 46%) as a pale-yellow solid.

$^1$H-NMR (DMSO-d$_6$, 400 MHz) δ 2.55 (3H, s), 5.89 (2H, br s.), 6.82 (1H, dd, J=8.2, 2.6 Hz), 7.36 (1H, t, J=8.2 Hz), 7.46-7.54 (5H, m), 7.61 (1H, t, J=2.1 Hz), 7.67 (1H, d, J=8.3 Hz), 7.81 (1H, d, J=7.8 Hz), 7.99 (1H, dt, J=7.8, 1.8 Hz), 8.52 (1H, d, J=4.4 Hz), 8.72 (1H, dd, J=4.8, 1.3 Hz), 8.75 (1H, d, J=2.2 Hz), 10.65 (1H, s).

Example 122

N-[3-({2-[(cyclopropylcarbonyl)amino]imidazo[1,2-a]pyridin-6-yl}oxy)phenyl]-3-(trifluoromethyl)pyridine-2-carboxamide

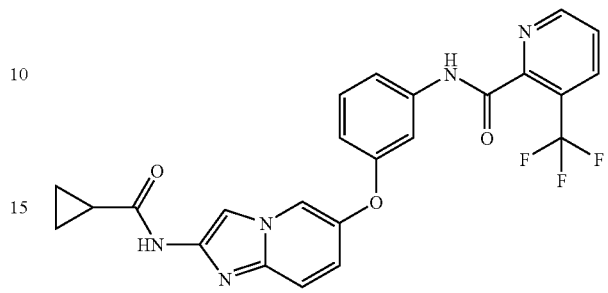

To a solution of 3-(trifluoromethyl)pyridine-2-carboxylic acid (47.5 mg, 0.249 mmol) in tetrahydrofuran (5 mL) were added N,N-dimethylformamide (2 drops) and oxalyl chloride (43.2 μL, 0.498 mmol), and the mixture was stirred at room temperature for 3 hr. The reaction mixture was concentrated under reduced pressure, the residue was dissolved in N,N-dimethylacetamide (6 mL), and the solution was stirred at room temperature. N-[6-(3-Aminophenoxy)imidazo[1,2-a]pyridin-2-yl]cyclopropanecarboxamide (66 mg, 0.214 mmol) was added thereto, and the mixture was stirred at room temperature for 3 days. The reaction mixture was diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (72.5 mg, 70%) as a white solid.

$^1$H-NMR (DMSO-d$_6$, 400 MHz) δ 0.74-0.85 (4H, m), 1.87-1.98 (1H, m), 6.81 (1H, dd, J=8.3, 2.4 Hz), 7.12 (1H, dd, J=9.7, 2.3 Hz), 7.32-7.40 (2H, m), 7.48 (1H, d, J=9.5 Hz), 7.54 (1H, d, J=8.1 Hz), 7.80 (1H, dd, J=8.3, 4.9 Hz), 8.07 (1H, s), 8.38 (1H, d, J=7.8 Hz), 8.61 (1H, d, J=2.2 Hz), 8.91 (1H, d, J=4.4 Hz), 10.78 (1H, s), 10.99 (1H, s).

Example 123

N-[3-({2-[(cyclopropylsulfonyl)amino]imidazo[1,2-a]pyridin-6-yl}oxy)phenyl]-3-methylpyridine-2-carboxamide

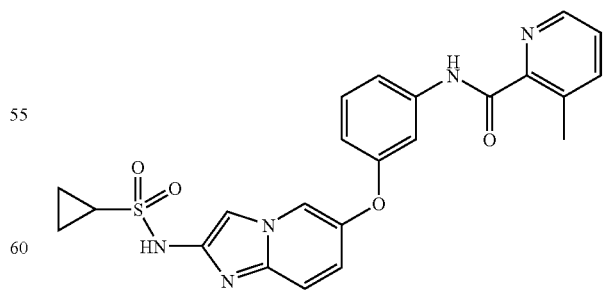

To N-{3-[(2-aminoimidazo[1,2-a]pyridin-6-yl)oxy]phenyl}-3-methylpyridine-2-carboxamide (150 mg, 0.417 mmol), tetrahydrofuran (10 mL) and aqueous sodium hydrogen carbonate solution (5 mL) was added cyclopropanesulfonyl chloride (348 μL, 2.48 mmol), and the mixture was stirred

Example 124

N-[3-({2-[(methoxyacetyl)amino]imidazo[1,2-a]pyridin-6-yl}oxy)phenyl]-3-methylpyridine-2-carboxamide

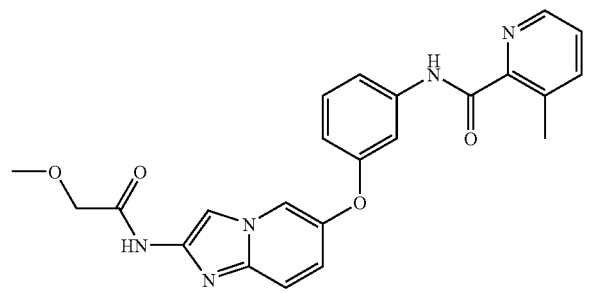

To a solution of N-{3-[(2-aminoimidazo[1,2-a]pyridin-6-yl)oxy]phenyl}-3-methylpyridine-2-carboxamide (148 mg, 0.412 mmol) in N,N-dimethylacetamide (5 mL) was added methoxyacetyl chloride (37.8 μL, 0.413 mmol), and the mixture was stirred at room temperature for 81 hr. Methanol, tetrahydrofuran and aqueous sodium carbonate solution were added to the reaction mixture, and the mixture was stirred at 60° C. for 8 hr. The reaction mixture was concentrated under reduced pressure, diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→90% ethyl acetate-hexane) to give the title compound (40.6 mg, 23%) as a pale-yellow solid.

$^1$H-NMR (DMSO-d$_6$, 400 MHz) δ 2.53 (3H, s), 3.36 (3H, s), 4.07 (2H, s), 6.79 (1H, dd, J=8.2, 2.5 Hz), 7.12 (1H, dd, J=9.7, 2.3 Hz), 7.34 (1H, t, J=8.2 Hz), 7.47-7.53 (2H, m), 7.57 (1H, t, J=2.1 Hz), 7.64 (1H, d, J=8.1 Hz), 7.80 (1H, d, J=7.8 Hz), 8.17 (1H, s), 8.50 (1H, d, J=3.4 Hz), 8.61 (1H, d, J=2.5 Hz), 10.46 (1H, s), 10.61 (1H, s).

Example 125

N-[3-({2-[(2-chloropyrimidin-4-yl)amino]imidazo[1,2-a]pyridin-6-yl}oxy)phenyl]-3-methylpyridine-2-carboxamide

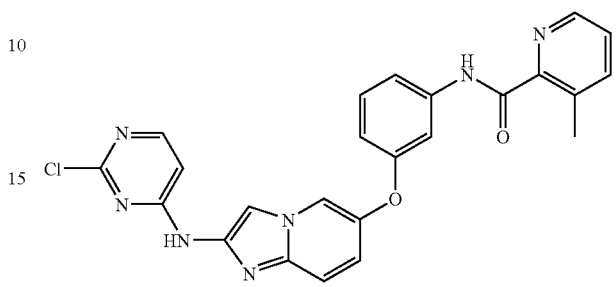

A mixture of N-{3-[(2-aminoimidazo[1,2-a]pyridin-6-yl)oxy]phenyl}-3-methylpyridine-2-carboxamide (150 mg, 0.417 mmol), 2,4-dichloropyrimidine (63.8 mg, 0.428 mmol) and N,N-dimethylacetamide (5 mL) was stirred at room temperature for 20 hr. The reaction mixture was diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (NH silica gel, 0%→100% ethyl acetate-hexane→2% methanol-ethyl acetate) to give the title compound (38.8 mg, 20%) as a white solid.

$^1$H-NMR (DMSO-d$_6$, 400 MHz) δ 2.53 (3H, s), 6.59 (2H, s), 6.85 (1H, dd, J=8.1, 2.4 Hz), 7.33-7.42 (2H, m), 7.44-7.53 (2H, m), 7.61-7.70 (3H, m), 7.80 (1H, d, J=7.6 Hz), 8.46 (1H, d, J=5.9 Hz), 8.51 (1H, d, J=3.7 Hz), 9.52 (1H, d, J=2.4 Hz), 10.63 (1H, s).

Example 126

N-[3-({2-[(hydroxyacetyl)amino]imidazo[1,2-a]pyridin-6-yl}oxy)phenyl]-3-methylpyridine-2-carboxamide

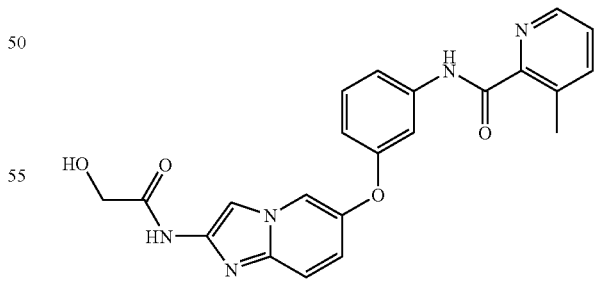

To a solution of N-{3-[(2-aminoimidazo[1,2-a]pyridin-6-yl)oxy]phenyl}-3-methylpyridine-2-carboxamide (150 mg, 0.417 mmol) in N,N-dimethylacetamide (5 mL) was added 2-chloro-2-oxoethylacetate (45.0 μL, 0.419 mmol), and the mixture was stirred at room temperature for 2 hr. Methanol, tetrahydrofuran and aqueous sodium carbonate solution were added to the reaction mixture, and the mixture was stirred at 60° C. for 5 hr. The reaction mixture was concentrated under reduced pressure, diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (NH silica gel, 0%→100% ethyl acetate-hexane→2% methanol-ethyl acetate) to give the title compound (70.1 mg, 40%) as a pale-yellow solid.

$^1$H-NMR (DMSO-$d_6$, 400 MHz) δ 2.53 (3H, s), 4.06 (2H, d, J=6.1 Hz), 5.57 (1H, t, J=6.1 Hz), 6.79 (1H, dd, J=8.1, 2.4 Hz), 7.13 (1H, dd, J=9.7, 2.3 Hz), 7.34 (1H, t, J=8.2 Hz), 7.48-7.53 (2H, m), 7.56 (1H, t, J=2.2 Hz), 7.64 (1H, d, J=1.7 Hz), 7.80 (1H, d, J=7.6 Hz), 8.18 (1H, s), 8.50 (1H, d, J=3.2 Hz), 8.62 (1H, d, J=2.2 Hz), 10.08 (1H, s), 10.61 (1H, s).

Example 127-1

N-{3-[(2-aminoimidazo[1,2-a]pyridin-6-yl)oxy]phenyl}-6-methylpyridine-2-carboxamide

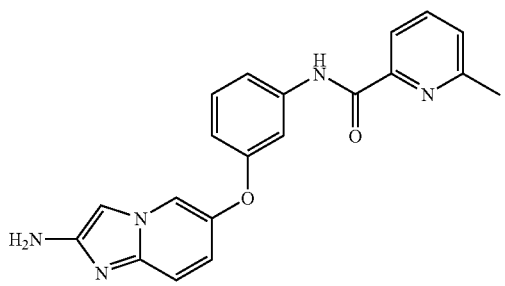

A mixture of N-(3-{[1-(2-amino-2-oxoethyl)-6-{[(4-methylphenyl)sulfonyl]imino}-1,6-dihydropyridin-3-yl]oxy}phenyl)-6-methylpyridine-2-carboxamide (14.6 g, 27.5 mmol), trifluoroacetic anhydride (31 mL) and tetrahydrofuran (300 mL) was stirred at room temperature for 1 hr. The reaction solution was concentrated under reduced pressure, and ethyl acetate was added to the residue. The mixture was washed with aqueous sodium hydrogen carbonate solution and saturated brine, dried over anhydrous magnesium sulfate and filtrated. The filtrate was concentrated under reduced pressure, ethanol (200 mL) and 4M aqueous sodium hydroxide solution (80 mL) were added to the residue, and the mixture was stirred at 60° C. for 24 hr. The reaction solution was concentrated under reduced pressure, and ethyl acetate was added to the residue. The mixture was washed with water and saturated brine, dried over anhydrous magnesium sulfate and filtrated. The filtrate was concentrated under reduced pressure, and the residue was purified by silica gel column chromatography (NH silica gel, 0%→100% ethyl acetate-hexane) to give the title compound (2.22 g, 22%) as a pale-brown solid.

$^1$H-NMR (DMSO-$d_6$, 400 MHz) δ 2.61 (3H, s), 5.20 (2H, s), 6.77 (1H, dd, J=8.3, 2.4 Hz), 6.88 (1H, dd, J=9.5, 2.2 Hz), 7.02 (1H, s), 7.20 (1H, dd, J=9.5 Hz), 7.34 (1H, t, J=8.2 Hz), 7.51 (1H, dd, J=5.6, 2.9 Hz), 7.59-7.67 (2H, m), 7.89-7.94 (2H, m), 8.34 (1H, d, J=2.2 Hz), 10.49 (1H, s).

Example 127-2

N-[3-({2-[(cyclopropylcarbonyl)amino]imidazo[1,2-a]pyridin-6-yl}oxy)phenyl]-6-methylpyridine-2-carboxamide

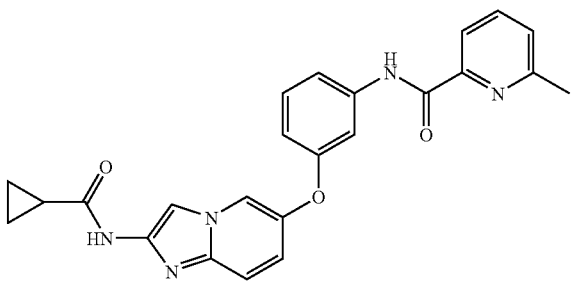

To a solution of N-{3-[(2-aminoimidazo[1,2-a]pyridin-6-yl)oxy]phenyl}-6-methylpyridine-2-carboxamide (300 mg, 0.835 mmol) in N,N-dimethylacetamide (5 mL) was added cyclopropanecarbonyl chloride (76.0 μL, 0.836 mmol), and the mixture was stirred at room temperature for 10 hr. The reaction mixture was diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (103 mg, 29%) as a white solid.

$^1$H-NMR (DMSO-$d_6$, 400 MHz) δ 0.75-0.85 (4H, m), 1.90-1.97 (1H, m), 2.60 (3H, s), 6.79-6.84 (1H, m), 7.11 (1H, dd, J=9.5, 2.2 Hz), 7.36 (1H, t, J=8.4 Hz), 7.46-7.53 (2H, m), 7.63-7.69 (2H, m), 7.92 (2H, d, J=3.2 Hz), 8.07 (1H, s), 8.60 (1H, d, J=2.2 Hz), 10.50 (1H, s), 11.00 (1H, s).

Example 128

6-methyl-N-(3-{[2-(propanoylamino)imidazo[1,2-a]pyridin-6-yl]oxy}phenyl)pyridine-2-carboxamide

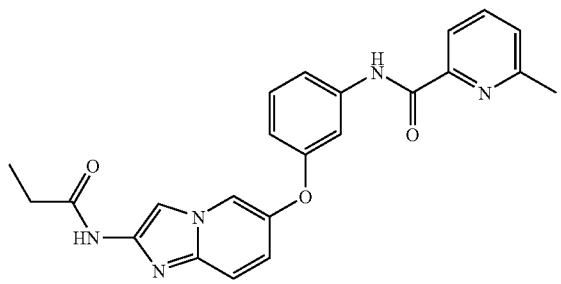

To a solution of N-{3-[(2-aminoimidazo[1,2-a]pyridin-6-yl)oxy]phenyl}-6-methylpyridine-2-carboxamide (300 mg, 0.835 mmol) in N,N-dimethylacetamide (5 mL) was added propionyl chloride (72.6 μL, 0.836 mmol), and the mixture was stirred at room temperature for 10 hr. The reaction mixture was diluted with aqueous sodium hydrogen carbonate solution and extracted with ethyl acetate. The organic layer was washed with aqueous sodium hydrogen carbonate solu-

Example 129

N-[3-({2-[(cyclopropylcarbamoyl)amino]imidazo[1,2-a]pyridin-6-yl}oxy)phenyl]-6-methylpyridine-2-carboxamide

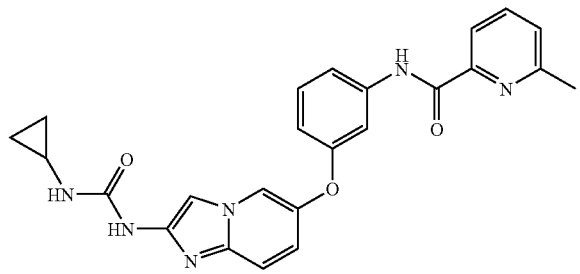

To a solution of N-{3-[(2-aminoimidazo[1,2-a]pyridin-6-yl)oxy]phenyl}-6-methylpyridine-2-carboxamide (300 mg, 0.835 mmol) and N,N-diisopropylethylamine (286 μL, 1.67 mmol) in tetrahydrofuran (5 mL) was added 2,2,2-trichloroethylchlorocarbonate (130 μL, 0.944 mmol), and the mixture was stirred at room temperature for 50 min. N,N-Dimethylformamide (5 mL) and cyclopropaneamine (290 μL, 4.19 mmol) were added to the reaction mixture, and the mixture was stirred at 80° C. for 11 hr. The reaction mixture was concentrated under reduced pressure, diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (51.0 mg, 14%) as a white solid.

$^1$H-NMR (DMSO-d$_6$, 400 MHz) δ 0.37-0.45 (2H, m), 0.61-0.68 (2H, m), 2.54-2.58 (1H, m), 2.61 (3H, s), 6.77-6.87 (2H, m), 7.06 (1H, dd, J=9.5, 2.2 Hz), 7.36 (1H, t, J=8.3 Hz), 7.42 (1H, d, J=9.5 Hz), 7.52 (1H, dd, J=6.0, 2.6 Hz), 7.62-7.68 (2H, m), 7.80 (1H, s), 7.92 (2H, d, J=3.7 Hz), 8.57 (1H, d, J=2.2 Hz), 8.80 (1H, s), 10.50 (1H, s).

Example 130

N-[3-({2-[(methoxyacetyl)amino]imidazo[1,2-a]pyridin-6-yl}oxy)phenyl]-6-methylpyridine-2-carboxamide

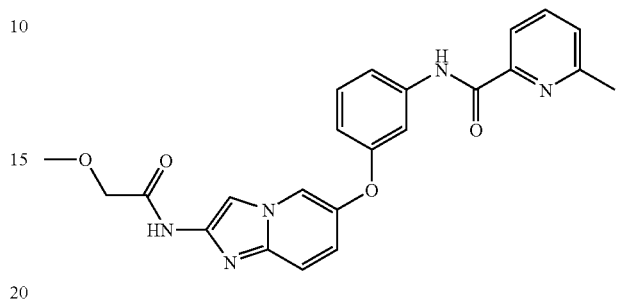

To a solution of N-{3-[(2-aminoimidazo[1,2-a]pyridin-6-yl)oxy]phenyl}-6-methylpyridine-2-carboxamide (300 mg, 0.835 mmol) in N,N-dimethylacetamide (5 mL) was added methoxyacetyl chloride (92.0 μL, 1.01 mmol), and the mixture was stirred at room temperature for 15 hr. Methanol, tetrahydrofuran and aqueous sodium carbonate solution were added to the reaction mixture, and the mixture was stirred at 60° C. for 17 hr. The reaction mixture was concentrated under reduced pressure, diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (NH silica gel, 0%→85% ethyl acetate-hexane) to give the title compound (115 mg, 32%) as a white solid.

$^1$H-NMR (DMSO-d$_6$, 400 MHz) δ 2.60 (3H, s), 3.36 (3H, s), 4.07 (2H, s), 6.79-6.84 (1H, m), 7.13 (1H, dd, J=9.5, 2.2 Hz), 7.37 (1H, t, J=8.6 Hz), 7.48-7.55 (2H, m), 7.64-7.70 (2H, m), 7.89-7.95 (2H, m), 8.18 (1H, s), 8.62 (1H, d, J=2.2 Hz), 10.47 (1H, s), 10.51 (1H, s).

Example 131

N-(3-{[2-(acetylamino)imidazo[1,2-a]pyridin-6-yl]oxy}phenyl)-3-methylpyridine-2-carboxamide

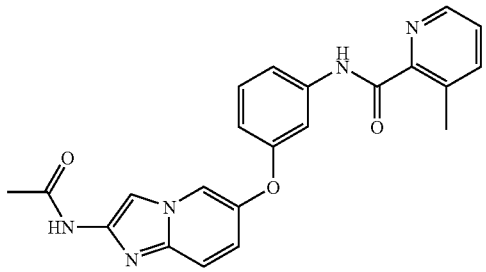

To a solution of N-{3-[(2-aminoimidazo[1,2-a]pyridin-6-yl)oxy]phenyl}-3-methylpyridine-2-carboxamide (130 mg, (Page text of prior example continued at top of left column:)

tion and saturated brine, dried over anhydrous magnesium sulfate and filtrated. The filtrate was concentrated under reduced pressure, and the residue was purified by silica gel column chromatography (NH silica gel, 0%→100% ethyl acetate-hexane) to give the title compound (140 mg, 40%) as a white solid.

$^1$H-NMR (DMSO-d$_6$, 400 MHz) δ 1.08 (3H, t, J=7.6 Hz), 2.37 (2H, q, J=7.6 Hz), 2.60 (3H, s), 6.81 (1H, dd, J=8.8, 2.0 Hz), 7.11 (1H, dd, J=9.7, 2.6 Hz), 7.36 (1H, t, J=8.2 Hz), 7.48 (1H, d, J=9.5 Hz), 7.52 (1H, dd, J=5.9, 2.7 Hz), 7.63-7.69 (2H, m), 7.89-7.93 (2H, m), 8.12 (1H, s), 8.61 (1H, d, J=2.2 Hz), 10.50 (1H, s), 10.67 (1H, s).

0.362 mmol) in N,N-dimethylacetamide (5 mL) was added acetyl chloride (26.0 μL, 0.366 mmol), and the mixture was stirred at room temperature for 3 hr. Methanol, tetrahydrofuran and aqueous sodium carbonate solution were added to the reaction mixture, and the mixture was stirred at 60° C. for 68 hr. The reaction mixture was diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (0%→100% ethyl acetate-hexane) to give the title compound (71.7 mg, 49%) as a white solid.

$^1$H-NMR (DMSO-d$_6$, 400 MHz) δ 2.07 (3H, s), 2.53 (3H, s), 6.78 (1H, dd, J=8.0, 2.3 Hz), 7.10 (1H, dd, J=9.5, 2.4 Hz), 7.34 (1H, t, J=8.2 Hz), 7.45-7.53 (2H, m), 7.55 (1H, t, J=2.2 Hz), 7.64 (1H, d, J=7.1 Hz), 7.80 (1H, d, J=7.8 Hz), 8.12 (1H, s), 8.50 (1H, dd, J=4.5, 1.3 Hz), 8.59 (1H, d, J=2.2 Hz), 10.61 (1H, s), 10.72 (1H, s).

Example 132

N-(3-{[2-(acetylamino)imidazo[1,2-a]pyridin-6-yl]oxy}phenyl)-6-methylpyridine-2-carboxamide

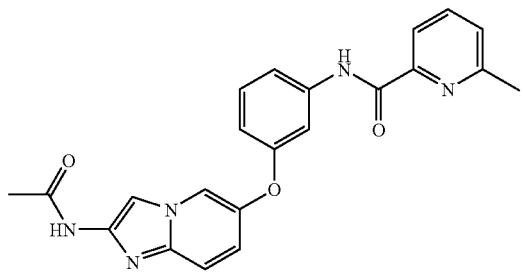

To a solution of N-{3-[(2-aminoimidazo[1,2-a]pyridin-6-yl)oxy]phenyl}-6-methylpyridine-2-carboxamide (300 mg, 0.835 mmol) in N,N-dimethylacetamide (5 mL) was added acetyl chloride (59.4 μL, 0.835 mmol), and the mixture was stirred at room temperature for 11 hr. The reaction mixture was diluted with aqueous sodium hydrogen carbonate solution and extracted with ethyl acetate. The organic layer was washed with aqueous sodium hydrogen carbonate solution and saturated brine, dried over anhydrous magnesium sulfate and filtrated. The filtrate was concentrated under reduced pressure, and the residue was purified by silica gel column chromatography (NH silica gel, 0%→100% ethyl acetate-hexane) to give the title compound (109 mg, 33%) as a pale-yellow solid.

$^1$H-NMR (DMSO-d$_6$, 400 MHz) δ 2.08 (3H, s), 2.60 (3H, s), 6.78-6.84 (1H, m), 7.11 (1H, dd, J=9.7, 2.3 Hz), 7.36 (1H, t, J=8.4 Hz), 7.46-7.54 (2H, m), 7.63-7.69 (2H, m), 7.88-7.95 (2H, m), 8.12 (1H, s), 8.60 (1H, d, J=2.2 Hz), 10.50 (1H, s), 10.73 (1H, s).

Example 133

N-{6-[3-(1,3-dihydro-2H-isoindol-2-yl)phenoxy]imidazo[1,2-a]pyridin-2-yl}cyclopropanecarboxamide

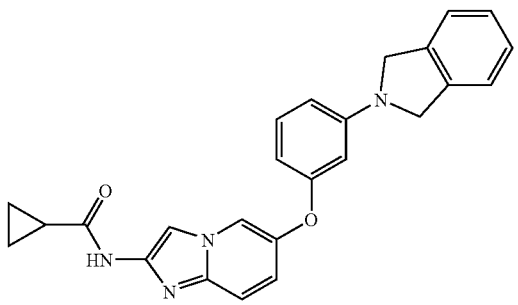

A mixture of N-[6-(3-aminophenoxy)imidazo[1,2-a]pyridin-2-yl]cyclopropanecarboxamide (19.4 mg, 0.063 mmol), 1,2-bis(chloromethyl)benzene (13.5 mg, 0.077 mmol) and N,N-dimethylformamide (2.0 mL) was stirred at 50° C. for 14 hr. Ethyl acetate was added to the reaction mixture, and the mixture was washed with aqueous sodium hydrogen carbonate solution and saturated brine. The organic layer was concentrated, and the residue was purified by preparative HPLC to give the title compound (8.8 mg, 34%).

LC-MS 411 (M+H).

Example 134

N-{6-[3-(1-oxo-1,3-dihydro-2H-isoindol-2-yl)phenoxy]imidazo[1,2-a]pyridin-2-yl}cyclopropanecarboxamide

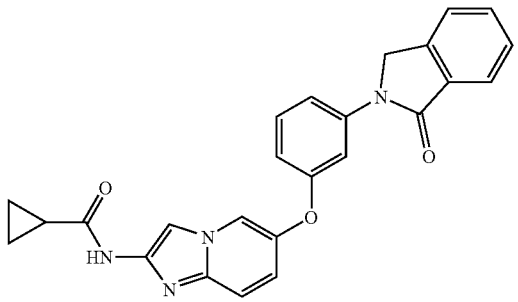

A mixture of N-[6-(3-aminophenoxy)imidazo[1,2-a]pyridin-2-yl]cyclopropanecarboxamide (19.7 mg, 0.064 mmol), benzene-1,2-dicarbaldehyde (10.7 mg, 0.080 mmol) and acetic acid (4.0 mL) was stirred at 100° C. for 13 hr. The reaction mixture was concentrated under reduced pressure, and ethyl acetate was added to the residue. The mixture was washed with aqueous sodium hydrogen carbonate solution and saturated brine. The organic layer was concentrated, and the residue was purified by preparative HPLC to give the title compound (4.8 mg, 18%).

LC-MS 425 (M+H).

Example 135

N-{6-[3-(pyridin-2-ylamino)phenoxy]imidazo[1,2-a]pyridin-2-yl}cyclopropanecarboxamide

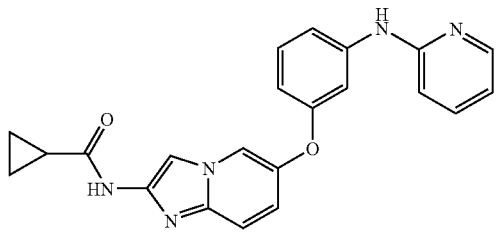

A mixture of N-[6-(3-aminophenoxy)imidazo[1,2-a]pyridin-2-yl]cyclopropanecarboxamide (19.7 mg, 0.064 mmol), 2-bromopyridine (15.4 mg, 0.098 mmol), tris(dibenzylideneacetone)2 palladium(0) (6.1 mg, 0.007 mmol), 5-bis(diphenylphosphino)-9,9-dimethylxanthene (3.9 mg, 0.007 mmol), potassium t-butoxide (18.1 mg, 0.161 mmol) and toluene (4.0 mL) was stirred at 120° C. for 15 hr. The reaction mixture was diluted with aqueous sodium bicarbonate solution and extracted with ethyl acetate. The organic layer was concentrated, and the residue was purified by preparative HPLC to give the title compound (9.9 mg, 40%).
LC-MS 386 (M+H).

Example 136

N-{6-[3-(pyridin-3-ylamino)phenoxy]imidazo[1,2-a]pyridin-2-yl}cyclopropanecarboxamide

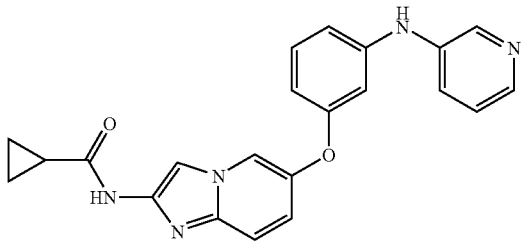

A mixture of N-[6-(3-aminophenoxy)imidazo[1,2-a]pyridin-2-yl]cyclopropanecarboxamide (20.0 mg, 0.065 mmol), 3-bromopyridine (14.4 mg, 0.091 mmol), tris(dibenzylideneacetone)2 palladium(0) (6.8 mg, 0.0074 mmol), 5-bis(diphenylphosphino)-9,9-dimethylxanthene (4.3 mg, 0.007 mmol), potassium t-butoxide (17.2 mg, 0.153 mmol) and toluene (2.0 mL) was stirred at 120° C. for 13 hr. The reaction mixture was diluted with aqueous sodium hydrogen carbonate solution and extracted with ethyl acetate. The organic layer was concentrated, and the residue was purified by preparative HPLC to give the title compound (3.0 mg, 12%).
LC-MS 386 (M+H).

Example 137

N-{6-[3-(benzylamino)phenoxy]imidazo[1,2-a]pyridin-2-yl}cyclopropanecarboxamide

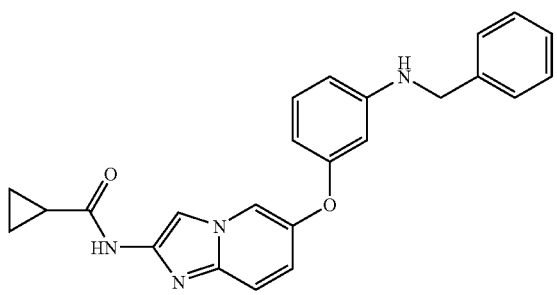

A mixture of N-[6-(3-aminophenoxy)imidazo[1,2-a]pyridin-2-yl]cyclopropanecarboxamide (20.0 mg, 0.065 mmol), benzoic acid (16.5 mg, 0.135 mmol), HATU (42.3 mg, 0.111 mmol), N,N-diisopropylethylamine (35.0 μL, 0.204 mmol) and pyridine (1.5 mL) was stirred at 60° C. for 4 hr. The reaction solution was concentrated under reduced pressure, and ethyl acetate was added to the residue. The mixture was washed with aqueous sodium hydrogen carbonate solution and saturated brine, dried over anhydrous magnesium sulfate and filtrated. The filtrate was concentrated under reduced pressure, the residue was dissolved in tetrahydrofuran (1.0 mL), and the mixture was stirred at room temperature. A solution (2.0 mL, 2.0 mmol) of 1M borane-tetrahydrofuran-complex/tetrahydrofuran was added thereto, and the mixture was stirred at room temperature for 39 hr. The reaction mixture was diluted with aqueous sodium hydrogen carbonate solution and extracted with ethyl acetate. The organic layer was concentrated, and the residue was purified by preparative HPLC to give the title compound (7.7 mg, 30%).
LC-MS 399 (M+H).

In the same manner as in Example 137, compounds of Examples 138 to 140 were synthesized. The compounds of Examples 138 to 140 are shown in Table 1.

TABLE 1

| Example No. | chemical structural formula | MS (m/z) | compound name |
|---|---|---|---|
| 138 | | 414 | N-[6-(3-{[(3-methylpyridin-2-yl)methyl]amino}phenoxy)imidazo[1,2-a]pyridin-2-yl]cyclopropanecarboxamide |

TABLE 1-continued

| Example No. | chemical structural formula | MS (m/z) | compound name |
|---|---|---|---|
| 139 | | 400 | N-(6-{3-[(pyridin-2-ylmethyl)amino]phenoxy}imidazo[1,2-a]pyridin-2-yl)cyclopropanecarboxamide |
| 140 | | 400 | N-(6-{3-[(pyridin-3-ylmethyl)amino]phenoxy}imidazo[1,2-a]pyridin-2-yl)cyclopropanecarboxamide |

Example 141

N-(6-{3-[(phenylsulfonyl)amino]phenoxy}imidazo[1,2-a]pyridin-2-yl)cyclopropanecarboxamide

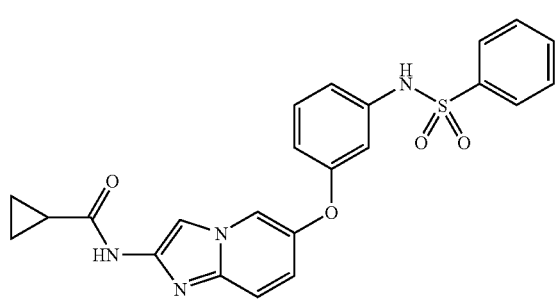

A mixture of N-[6-(3-aminophenoxy)imidazo[1,2-a]pyridin-2-yl]cyclopropanecarboxamide (18.6 mg, 0.060 mmol), benzenesulfonyl chloride (12.8 µL, 0.100 mmol), tetrahydrofuran (3 mL) and aqueous sodium hydrogen carbonate solution (2 mL) was stirred at room temperature for 4 hr. The reaction mixture was extracted with ethyl acetate. The organic layer was concentrated, and the residue was purified by preparative HPLC to give the title compound (10.9 mg, 41%).

LC-MS 449 (M+H).

In the same manner as in Example 141, compounds of Examples 142 to 149 were synthesized. The compounds of Examples 142 to 149 are shown in Table 2.

TABLE 2

| Example No. | chemical structural formula | MS (m/z) | compound name |
|---|---|---|---|
| 142 | | 463 | N-[6-(3-{[(2-methylphenyl)sulfonyl]amino}phenoxy)imidazo[1,2-a]pyridin-2-yl]cyclopropanecarboxamide |
| 143 | | 463 | N[6-(3-{[(3-methylphenyl)sulfonyl]amino}phenoxy)imidazo[1,2-a]pyridin-2-yl]cyclopropanecarboxamide |
| 144 | | 467 | N[6-(3-{[(3-fluorophenyl)sulfonyl]amino}phenoxy)imidazo[1,2-a]pyridin-2-yl]cyclopropanecarboxamide |
| 145 | | 450 | N-(6-{3-[(pyridin-2-ylsulfonyl)amino]phenoxy}imidazo[1,2-a]pyridin-2-yl)cyclopropanecarboxamide |

TABLE 2-continued

| Example No. | chemical structural formula | MS (m/z) | compound name |
|---|---|---|---|
| 146 | | 450 | N-(6-{3-[(pyridin-3-ylsulfonyl) amino] phenoxy}imidazo[1,2-a]pyridin-2-yl) cyclopropanecarboxamide |
| 147 | | 453 | N-[6-(3{[(1-methyl-1H-imidazol-4-yl)sulfonyl]amino}phenoxy) imidazo[1,2-a]pyridin-2-yl] cyclopropanecarboxamide |
| 148 | | 527 | N-{6-[3-({[3-(methylsulfonyl) phenyl] sulfonyl}amino)phenoxy] imidazo[1,2-a]pyridin-2-yl} cyclopropanecarboxamide |
| 149 | | 517 | N-{6-[3-({[3-(trifluoromethyl)phenyl] sulfonyl}amino)phenoxy] imidazo[1,2-a]pyridin-2-yl} cyclopropanecarboxamide |

Example 150

N-[6-(3-{[isopropylcarbamoyl]amino}phenoxy)imidazo[1,2-a]pyridin-2-yl]cyclopropanecarboxamide

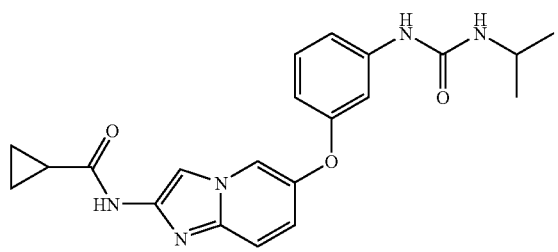

A mixture of N-[6-(3-aminophenoxy)imidazo[1,2-a]pyridin-2-yl]cyclopropanecarboxamide (19.3 mg, 0.063 mmol), 2-isocyanatopropane (25.3 mg, 0.297 mmol) and pyridine (1.5 mL) was stirred at 80° C. for 23 hr. The reaction mixture was diluted with aqueous sodium hydrogen carbonate solution and extracted with ethyl acetate. The organic layer was concentrated, and the residue was purified by preparative HPLC to give the title compound (15.2 mg, 62%).

LC-MS 394 (M+H).

In the same manner as in Example 150, compounds of Examples 151 and 152 were synthesized. The compounds of Examples 151 and 152 are shown in Table 3.

TABLE 3

| Example No. | chemical structural formula | MS (m/z) | compound name |
|---|---|---|---|
| 151 |  | 428 | N-(6-{3-[(phenylcarbamoyl)amino]phenoxy}imidazo [1,2-a]pyridin-2-yl)cyclopropanecarboxamide |
| 152 |  | 429 | N-(6-{3-[(pyridin-3-ylcarbamoyl)amino]phenoxy}imidazo[1,2-a]pyridin-2-yl)cyclopropanecarboxamide |

Example 153

N-(6-{3-[(3-phenylprop-2-ynoyl)amino]phenoxy}imidazo[1,2-a]pyridin-2-yl)cyclopropanecarboxamide

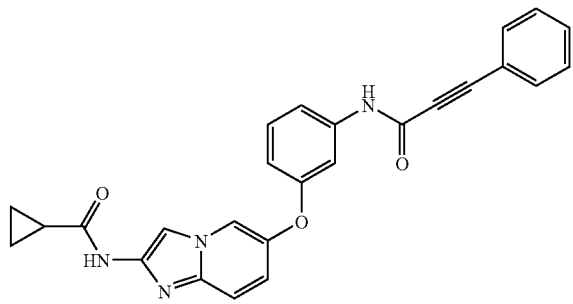

A mixture of N-[6-(3-aminophenoxy)imidazo[1,2-a]pyridin-2-yl]cyclopropanecarboxamide (18.6 mg, 0.060 mmol), 3-phenylprop-2-ynic acid (13.1 mg, 0.090 mmol), HATU (48.7 mg, 0.128 mmol), N,N-diisopropylethylamine (35.1 µL, 0.205 mmol) and pyridine (1.5 mL) was stirred at 80° C. for 13 hr. The reaction mixture was diluted with aqueous sodium hydrogen carbonate solution and extracted with ethyl acetate. The organic layer was concentrated, and the residue was purified by preparative HPLC to give the title compound (4.6 mg, 18%).

LC-MS 437 (M+H).

In the same manner as in Example 153, compounds of Examples 154 to 225 were synthesized. The compounds of Examples 154 to 225 are shown in Tables 4 to 9.

TABLE 4

| Example No. | chemical structural formula | MS (m/z) | compound name |
|---|---|---|---|
| 154 | | 403 | N-[3-({2-[(cyclopropylcarbonyl)amino]imidazo[1,2-a]pyridin-6-yl}oxy)phenyl]furan-2-carboxamide |
| 155 | | 413 | N-[3-({2-[(cyclopropylcarbonyl)amino]imidazo[1,2-a]pyridin-6-yl}oxy)phenyl]benzamide |

TABLE 4-continued

| Example No. | chemical structural formula | MS (m/z) | compound name |
|---|---|---|---|
| 156 | | 419 | N-[3-({2-[(cyclopropylcarbonyl)amino]imidazo[1,2-a]pyridin-6-yl}oxy)phenyl]thiophene-3-carboxamide |
| 157 | | 429 | N-[3-({2-[(cyclopropylcarbonyl)amino]imidazo[1,2-a]pyridin-6-yl}oxy)phenyl]-3-hydroxybenzamide |
| 158 | | 431 | N-[3-({2-[(cyclopropylcarbonyl)amino]imidazo[1,2-a]pyridin-6-yl}oxy)phenyl]-3-fluorobenzamide |
| 159 | | 428 | N-[3-({2-[(cyclopropylcarbonyl)amino]imidazo[1,2-a]pyridin-6-yl}oxy)phenyl]-3-methylpyridine-4-carboxamide |

TABLE 4-continued

| Example No. | chemical structural formula | MS (m/z) | compound name |
|---|---|---|---|
| 160 | | 443 | N-[3-({2-[(cyclopropylcarbonyl)amino]imidazo[1,2-a]pyridin-6-yl}oxy)phenyl]-3-methoxybenzamide |
| 161 | | 457 | N-[3-({2-[(cyclopropylcarbonyl)amino]imidazol[1,2-a]pyridin-6-yl}oxy)phenyl]-1,3-benzodioxole-5-carboxamide |
| 162 | | 470 | 3-(acetylamino)-N-[3-({2-[(cyclopropylcarbonyl)amino]imidazo[1,2-a]pyridin-6-yl}oxy)phenyl]benzamide |
| 163 | | 481 | N-[3-({2-[(cyclopropylcarbonyl)amino]imidazo[1,2-a]pyridin-6-yl}oxy)phenyl]-2-(trifluoromethyl)benzamide |

TABLE 4-continued

| Example No. | chemical structural formula | MS (m/z) | compound name |
|---|---|---|---|
| 164 | | 419 | N-[3-({2-[(cyclopropylcarbonyl)amino]imidazo[1,2-a]pyridin-6-yl}oxy)phenyl]thiophene-2-carboxamide |
| 165 | | 429 | N-[3-({2-[(cyclopropylcarbonyl)amino]imidazo[1,2-a]pyridin-6-yl}oxy)phenyl]-2-hydroxybenzamide |

TABLE 5

| Example No. | chemical structural formula | MS (m/z) | compound name |
|---|---|---|---|
| 166 | | 431 | N-[3-({2-[(cyclopropylcarbonyl)amino]imidazo[1,2-a]pyridin-6-yl}oxy)phenyl]-2-fluorobenzamide |

TABLE 5-continued

| Example No. | chemical structural formula | MS (m/z) | compound name |
|---|---|---|---|
| 167 | | 438 | 3-cyano-N[3-({2-[(cyclopropylcarbonyl)amino]imidazo[1,2-a]pyridin-6-yl}oxy)phenyl]benzamide |
| 168 | | 447 | 2-chloro-N-[3-({2-[(cyclopropylcarbonyl)amino]imidazo[1,2-a]pyridin-6-yl}oxy)phenyl]benzamide |
| 169 | | 403 | N-[3-({2-[(cyclopropylcarbonyl)amino]imidazo[1,2-a]pyridin-6-yl}oxy)phenyl]furan-3-carboxamide |
| 170 | | 427 | N-[3-({2-[(cyclopropylcarbonyl)amino]imidazo[1,2-a]pyridin-6-yl}oxy)phenyl]-2-methylbenzamide |

TABLE 5-continued

| Example No. | chemical structural formula | MS (m/z) | compound name |
|---|---|---|---|
| 171 | | 427 | N-[3-({2-[(cyclopropylcarbonyl)amino]imidazo[1,2-a]pyridin-6-yl}oxy)phenyl]-4-methylbenzamide |
| 172 | | 427 | N-[3-({2-[(cyclopropylcarbonyl)amino]imidazo[1,2-a]pyridin-6-yl}oxy)phenyl]-3-methylbenzamnide |
| 173 | | 443 | N-[3-({2-[(cyclopropylcarbonyl)amino]imidazo[1,2-a]pyridin-6-yl}oxy)phenyl]-2-methoxybenzamide |
| 174 | | 447 | 3-chloro-N-[3-({2-[(cyclopropylcarbonyl)amino]imidazo[1,2-a]pyridin-6-yl}oxy)phenyl]benzamide |

TABLE 5-continued

| Example No. | chemical structural formula | MS (m/z) | compound name |
|---|---|---|---|
| 175 | | 403 | N-[3-({2-[(cyclopropylcarbonyl)amino]imidazo[1,2-a]pyridin-6-yl}oxy)phenyl]-1H-imidazole-4-carboxamide |
| 176 | | 414 | N-[3-({2-[(cyclopropylcarbonyl)amino]imidazo[1,2-a]pyridin-6-yl}oxy)phenyl]pyridine-3-carboxamide |
| 177 | | 414 | N-[3-({2-[(cyclopropylcarbonyl)amino]imidazo[1,2-a]pyridin-6-yl}oxy)phenyl]pyridine-2-carboxamide |

TABLE 6

| Example No. | chemical structural formula | MS (m/z) | compound name |
|---|---|---|---|
| 178 | | 414 | N-[3-({2-[(cyclopropylcarbonyl)amino]imidazo[1,2-a]pyridin-6-yl}oxy)phenyl]pyridine-4-carboxamide |

TABLE 6-continued

| Example No. | chemical structural formula | MS (m/z) | compound name |
|---|---|---|---|
| 179 | 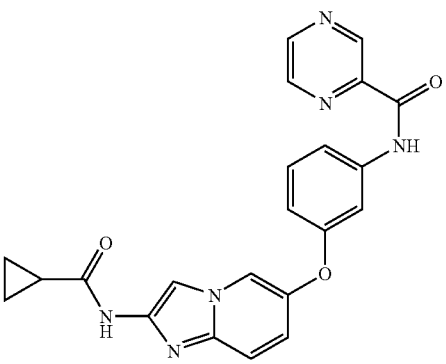 | 415 | N-[3-({2-[(cyclopropylcarbonyl)amino]imidazo[1,2-a]pyridin-6-yl}oxy)phenyl]pyrazine-2-carboxamide |
| 180 | 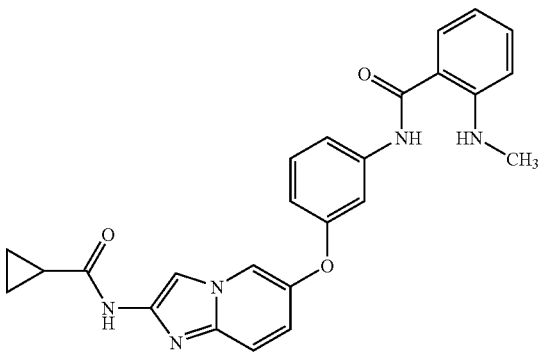 | 442 | N-[3-({2-[(cyclopropylcarbonyl)amino]imidazo[1,2-a]pyridin-6-yl}oxy)phenyl]-2-(methylamino)benzamide |
| 181 | 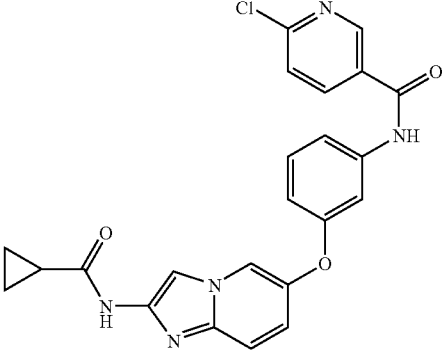 | 448 | 6-chloro-N-[3-({2-[(cyclopropylcarbonyl)amino]imidazo[1,2-a]pyridin-6-yl}oxy)phenyl]pyridine-3-carboxamide |
| 182 | 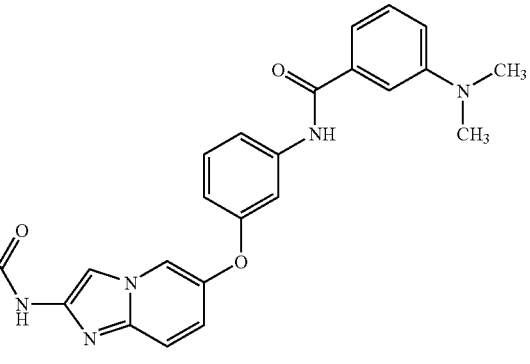 | 456 | N-[3-({2-[(cyclopropylcarbonyl)amino]imidazo[1,2-a]pyridin-6-yl}oxy)phenyl]-3-(dimethylamino)benzamide |

TABLE 6-continued

| Example No. | chemical structural formula | MS (m/z) | compound name |
|---|---|---|---|
| 183 | | 460 | N-[3-({2-[(cyclopropylcarbonyl)amino]imidazo[1,2-a]pyridin-6-yl}oxy)phenyl]-2-(methylsulfanyl)pyridine-3-carboxamide |
| 184 | | 428 | N-(6-{3-[(pyridin-4-ylacetyl)amino]phenoxy}imidazo[1,2-a]pyridin-2-yl)cyclopropanecarboxamide |
| 185 | | 428 | N-(6-{3-[(pyridin-2-ylacetyl)amino]phenoxy}imidazo[1,2-a]pyridin-2-yl)cyclopropanecarboxamide |
| 186 | | 428 | N-(6-{3-[(pyridin-3-ylacetyl)amino]phenoxy}imidazo[1,2-a]pyridin-2-yl)cyclopropanecarboxamide |

TABLE 6-continued

| Example No. | chemical structural formula | MS (m/z) | compound name |
| --- | --- | --- | --- |
| 187 | | 428 | 3-amino-N-[3-({2-[(cyclopropylcarbonyl)amino]imidazo[1,2-a]pyridin-6-yl}oxy)phenyl]benzamide |
| 188 | | 428 | 2-amino-N-[3-({2-[(cyclopropylcarbonyl)amino]imidazo[1,2-a]pyridin-6-yl}oxy)phenyl]benzamide |
| 189 | | 430 | N-[3-({2-[(cyclopropylcarbonyl)amino]imidazo[1,2-a]pyridin-6-yl}oxy)phenyl]-6-hydroxypyridine-2-carboxamide |

TABLE 7

| Example No. | chemical structural formula | MS (m/z) | compound name |
| --- | --- | --- | --- |
| 190 | | 430 | 3-amino-N-[3-({2-[(cyclopropylcarbonyl)amino]imidazo[1,2-a]pyridin-6-yl}oxy)phenyl]pyrazine-2-carboxamide |

TABLE 7-continued

| Example No. | chemical structural formula | MS (m/z) | compound name |
|---|---|---|---|
| 191 | | 448 | 4-chloro-N-[3-({2-[(cyclopropylcarbonyl)amino]imidazo[1,2-a]pyridin-6-yl}oxy)phenyl]pyridine-2-carboxamide |
| 192 | | 448 | 2-chloro-N-[3-({2-[(cyclopropylcarbonyl)amino]imidazo[1,2-a]pyridin-6-yl}oxy)phenyl]pyridine-4-carboxamide |
| 193 | | 432 | N-[3-({2-[(cyclopropylcarbonyl)amino]imidazo[1,2-a]pyridin-6-yl}oxy)phenyl]-2-fluoropyridine-3-carboxamide |
| 194 | | 462 | 2-chloro-N-[3-({2-[(cyclopropylcarbonyl)amino]imidazo[1,2-a]pyridin-6-yl}oxy)phenyl]-6-methylpyridine-3-carboxamide |

TABLE 7-continued

| Example No. | chemical structural formula | MS (m/z) | compound name |
|---|---|---|---|
| 195 | | 429 | N-[3-({2-[(cyclopropylcarbonyl)amino]imidazo[1,2-a]pyridin-6-yl}oxy)phenyl]-5-methylpyrazine-2-carboxamide |
| 196 | | 448 | 6-chloro-N-[3-({2-[(cyclopropylcarbonyl)amino]imidazo[1,2-a]pyridin-6-yl}oxy)phenyl]pyridine-2-carboxamide |
| 197 | | 428 | N-[3-({2-[(cyclopropylcarbonyl)amino]imidazo[1,2-a]pyridin-6-yl}oxy)phenyl]-4-methylpyridine-2-carboxamide |
| 198 | | 442 | N-[3-({2-[(cyclopropylcarbonyl)amino]imidazo[1,2-a]pyridin-6-yl}oxy)phenyl]-4,6-dimethylpyridine-2-carboxamide |

TABLE 7-continued

| Example No. | chemical structural formula | MS (m/z) | compound name |
|---|---|---|---|
| 199 | | 432 | N-[3-({2-[(cyclopropylcarbonyl)amino]imidazo[1,2-a]pyridin-6-yl}oxy)phenyl]-3-fluoropyridine-2-carboxamide |
| 200 | | 432 | N-[3-({2-[(cyclopropylcarbonyl)amino]imidazo[1,2-a]pyridin-6-yl}oxy)phenyl]-6-fluoropyridine-2-carboxamide |
| 201 | | 450 | N-[3-({2-[(cyclopropylcarbonyl)amino]imidazo[1,2-a]pyridin-6-yl}oxy)phenyl]-3,5-difluoropyridine-2-carboxamide |

TABLE 8

| Example No. | chemical structural formula | MS (m/z) | compound name |
|---|---|---|---|
| 202 | | 448 | 2-chloro-N-[3-({2-[(cyclopropylcarbonyl)amino]imidazo[1,2-a]pyridin-6-yl}oxy)phenyl]pyridine-3-carboxamide |

TABLE 8-continued

| Example No. | chemical structural formula | MS (m/z) | compound name |
|---|---|---|---|
| 203 | 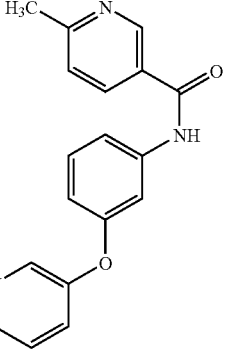 | 428 | N-[3-({2-[(cyclopropylcarbonyl)amino]imidazo[1,2-a]pyridin-6-yl}oxy)phenyl]-6-methylpyridine-3-carboxamide |
| 204 | 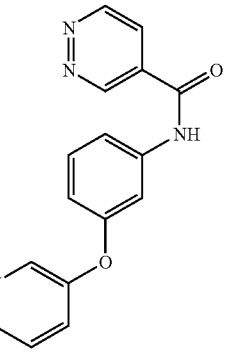 | 415 | N-[3-({2-[(cyclopropylcarbonyl)amino]imidazo[1,2-a]pyridin-6-yl}oxy)phenyl]pyridazine-4-carboxamide |
| 205 | 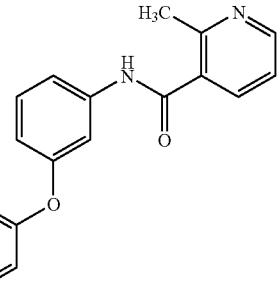 | 428 | N-[3-({2-[(cyclopropylcarbonyl)amino]imidazo[1,2-a]pyridin-6-yl}oxy)phenyl]-2-methylpyridine-3-carboxamide |
| 206 | 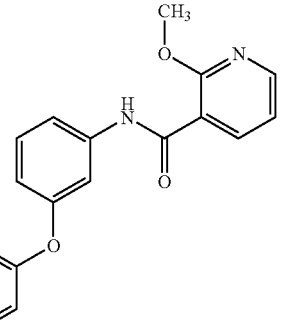 | 444 | N-[3-({2-[(cyclopropylcarbonyl)amino]imidazo[1,2-a]pyridin-6-yl}oxy)phenyl]-2-methoxypyridine-3-carboxamide |

TABLE 8-continued

| Example No. | chemical structural formula | MS (m/z) | compound name |
|---|---|---|---|
| 207 | | 428 | N-[3-({2-[(cyclopropylcarbonyl)amino]imidazo[1,2-a]pyridin-6-yl}oxy)phenyl]-4-methylpyridine-3-carboxamide |
| 208 | | 448 | 3-chloro-N-[3-({2-[(cyclopropylcarbonyl)amino]imidazo[1,2-a]pyridin-6-yl}oxy)phenyl]pyridine-4-carboxamide |
| 209 | | 444 | N-[3-({2-[(cyclopropylcarbonyl)amino]imidazo[1,2-a]pyridin-6-yl}oxy)phenyl]-2-methyoxypyridine-4-carboxamide |
| 210 | | 486 | N-[3-({2-[(cyclopropylcarbonyl)amino]imidazo[1,2-a]pyridin-6-yl}oxy)phenyl]-2-methyl-5-trifluoromethyl)-1,3-oxazole-4-carboxamide |

TABLE 8-continued

| Example No. | chemical structural formula | MS (m/z) | compound name |
|---|---|---|---|
| 211 | 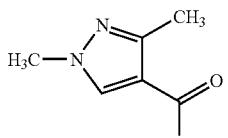 | 431 | N-[3-({2-[(cyclopropylcarbonyl)amino]imidazo[1,2-a]pyridin-6-yl}oxy)phenyl]-1,3-dimethyl-1H-pyrazole-4-carboxamide |
| 212 | 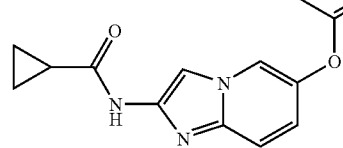 | 445 | N-[3-({2-[(cyclopropylcarbonyl)amino]imidazo[1,2-a]pyridin-6-yl}oxy)phenyl]-3-ethyl-1-methyl-1H-pyrazole-5-carboxamide |
| 213 | 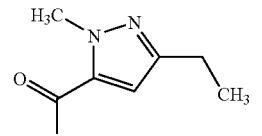 | 445 | N-[3-({2-[(cyclopropylcarbonyl)amino]imidazo[1,2-a]pyridin-6-yl}oxy)phenyl]-1-ethyl-3-methyl-1H-pyrazole-4-carboxamide |

TABLE 9

| Example No. | chemical structural formula | MS (m/z) | compound name |
|---|---|---|---|
| 214 | 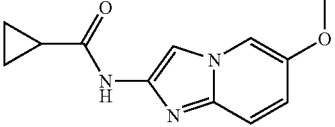 | 445 | N-[3-({2-[(cyclopropylcarbonyl)amino]imidazo[1,2-a]pyridin-6-yl}oxy)phenyl]-1-ethyl-3-methyl-1H-pyrazole-5-carboxamide |

TABLE 9-continued

| Example No. | chemical structural formula | MS (m/z) | compound name |
|---|---|---|---|
| 215 | 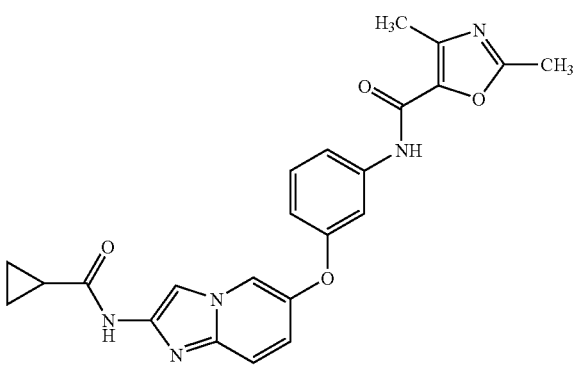 | 432 | N-[3-({2-[(cyclopropylcarbonyl)amino]imidazo[1,2-a]pyridin-6-yl}oxy)phenyl]-2,4-dimethyl-1,3-oxazole-5-carboxamide |
| 216 | 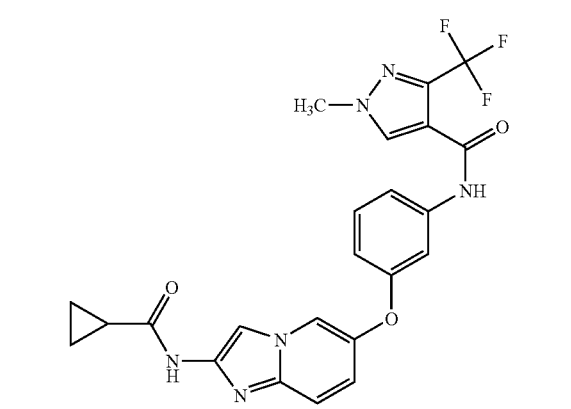 | 485 | N-[3-({2-[(cyclopropylcarbonyl)amino]imidazo[1,2-a]pyridin-6-yl}oxy)phenyl]-1-methyl-3-(trifluoromethyl)-1H-pyrazole-4-carboxamide |
| 217 | 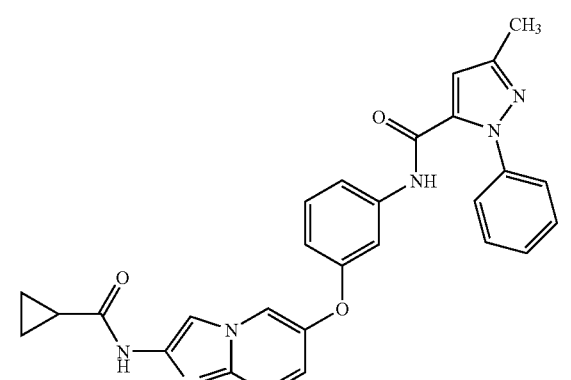 | 493 | N-[3-({2-[(cyclopropylcarbonyl)amino]imidazo[1,2-a]pyridin-6-yl}oxy)phenyl]-3-methyl-1-phenyl-1H-pyrazole-5-carboxamide |
| 218 | 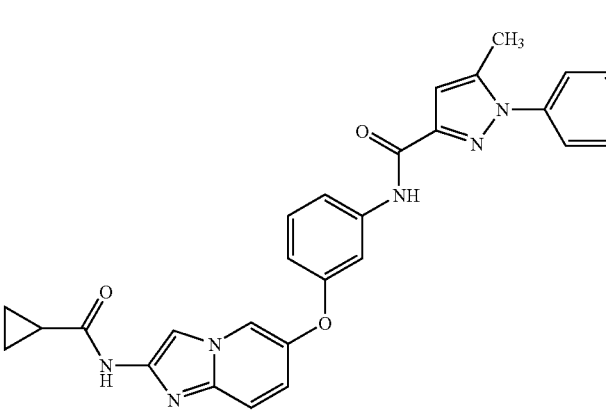 | 493 | N-[3-({2-[(cyclopropylcarbonyl)amino]imidazo[1,2-a]pyridin-6-yl}oxy)phenyl]-5-methyl-1-phenyl-1H-pyrazole-3-carboxamide |

TABLE 9-continued

| Example No. | chemical structural formula | MS (m/z) | compound name |
|---|---|---|---|
| 219 | | 452 | N-[3-({2-[(cyclopropylcarbonyl)amino]imidazo[1,2-a]pyridin-6-yl}oxy)phenyl]-1H-indole-2-carboxamide |
| 220 | | 452 | N-[3-({2-[(cyclopropylcarbonyl)amino]imidazo[1,2-a]pyridin-6-yl}oxy)phenyl]-1H-indole-3-carboxamide |
| 221 | | 470 | 2-(acetylamino)-N-[3-({2-(cyclopropylcarbonyl)amino]imidazo[1,2-a]pyridin-6-yl}oxy)phenyl]benzamide |
| 222 | | 458 | 2-amino-N-[3-({2-[(cyclopropylcarbonyl)amino]imidazo[1,2-a]pyridin-6-yl}oxy)phenyl]-3-methoxybenzamide |

TABLE 9-continued

| Example No. | chemical structural formula | MS (m/z) | compound name |
|---|---|---|---|
| 223 | | 462 | 2-amino-5-chloro-N-[3-({2-[cyclopropylcarbonyl)amino]imidazo[1,2-a]pyridin-6-yl}oxy)phenyl]benzamide |
| 224 | | 458 | N-[3-({2-[(cyclopropylcarbonyl)amino]imidazo[1,2-a]pyridin-6-yl}oxy)phenyl]-2-ethoxypyridine-3-carboxamide |
| 225 | | 428 | N-[3-({2-[(cyclopropylcarbonyl)amino]imidazo[1,2-a]pyridin-6-yl}oxy)phenyl]-5-methylpyridine-3-carboxamide |

Example 226

N-[3-({2-[(cyclopropylcarbonyl)amino]imidazo[1,2-a]pyridin-6-yl}oxy)phenyl]-3-(trifluoromethyl)benzamide

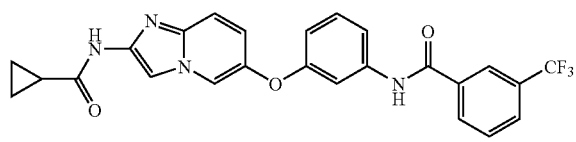

(i) N-{3-[(2-aminoimidazo[1,2-a]pyridin-6-yl)oxy]phenyl}-3-(trifluoromethyl)benzamide To a solution of N-[3-({2-[(trifluoroacetyl)amino]imidazo[1,2-a]pyridin-6-yl}oxy)phenyl]-3-(trifluoromethyl)benzamide (400 mg, 0.787 mmol) in ethanol (4.0 mL) was added 1N aqueous sodium hydroxide solution (8.0 mL), and the mixture was stirred at room temperature for 12 hr. Water (100 mL) was added to the reaction mixture, and the mixture was extracted with ethyl acetate (200 mL). The organic layer was washed with saturated brine (100 mL), and dried over anhydrous sodium sulfate. The insoluble material was removed by filtration, and the filtrate was concentrated under reduced pressure. The obtained residue was purified by silica gel column chromatography (NH silica gel, ethyl acetate/methanol=100/0→80/20), and fractions containing the desired product were concentrated under reduced pressure. The residue was washed with ethyl acetate/diisopropyl ether (1:4) to give the title compound (350 mg, quantitative) as a colorless solid.

$^1$H-NMR (DMSO-$d_6$, 300 MHz) δ 5.09 (2H, br s), 6.80 (1H, dd, J=2.4, 8.1 Hz), 6.88 (1H, dd, J=2.1, 9.6 Hz), 7.02 (1H, s), 7.23 (1H, d, J=9.6 Hz), 7.35 (1H, t, J=8.1 Hz), 7.43 (1H, t, J=2.1 Hz), 7.53-7.60 (1H, m), 7.76 (1H, t, J=7.8 Hz), 7.96 (1H, d, J=7.8 Hz), 8.16-8.26 (2H, m), 8.34 (1H, d, J=2.1 Hz), 10.49 (1H, s).

(ii) N-[3-({2-[(cyclopropylcarbonyl)amino]imidazo[1,2-a]pyridin-6-yl}oxy)phenyl]-3-(trifluoromethyl)benzamide To a solution of N-{3-[(2-aminoimidazo[1,2-a]pyridin-6-yl)oxy]phenyl}-3-(trifluoromethyl)benzamide (300 mg, 0.727 mmol) in N,N-dimethylacetamide (3.0 mL) was added cyclopropanecarbonyl chloride (69 μL, 0.763 mmol), and the mixture was stirred at room temperature for 2 hr. The reaction mixture was diluted with ethyl acetate (200 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The obtained residue was purified by silica gel column chromatography (NH silica gel, hexane/ethyl acetate=60/40→0/100), and fractions containing the desired product were concentrated under reduced pressure. The residue was triturated with ethyl acetate, diisopropyl ether and hexane to give the title compound (145 mg, 42%) as a colorless solid.
$^1$H-NMR (DMSO-$d_6$, 300 MHz) δ 0.57-0.93 (4H, m), 1.77-2.06 (1H, m), 6.83 (1H, dd, J=1.8, 8.1 Hz), 7.10 (1H, dd, J=2.1, 9.6 Hz), 7.37 (1H, t, J=8.2 Hz), 7.42-7.53 (2H, m), 7.58 (1H, d, J=8.4 Hz), 7.76 (1H, t, J=7.8 Hz), 7.95 (1H, d, J=7.8 Hz), 8.07 (1H, s), 8.16-8.30 (2H, m), 8.60 (1H, d, J=2.1 Hz), 10.49 (1H, s), 10.98 (1H, s).

Example 227

3-(1-cyano-1-methylethyl)-N-[3-({2-[(trifluoroacetyl)amino]imidazo[1,2-a]pyridin-6-yl}oxy)phenyl]benzamide

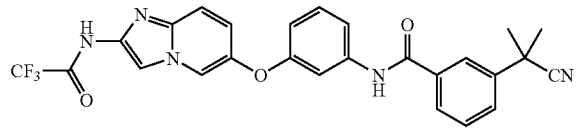

(i) methyl 3-(cyanomethyl)benzoate

To a solution of methyl 3-bromobenzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtered, and the solvent was evaporated under reduced pressure. The residue was purified by silica gel column chromatography (ethyl acetate/hexane=5/95→30/70), and the combined solution was concentrated under reduced pressure to give the title compound (7.0 g, 91%) as a colorless oil.
$^1$H-NMR (DMSO-$d_6$, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

(ii) methyl 3-(1-cyano-1-methylethyl)benzoate

To a solution of methyl 3-(cyanomethyl)benzoate (7.0 g, 40 mmol) in dimethyl sulfoxide (80 mL) was added sodium hydride (60% in oil, 4.8 g, 120 mmol) while cooling the mixture to 25° C. or below but preventing coagulation. The reaction mixture was stirred at room temperature for 20 min. Methyl iodide (7.5 mL, 120 mmol) was added thereto, and the mixture was further stirred at room temperature for 16 hr. The reaction mixture was diluted with water (400 mL) and extracted with ethyl acetate (800 mL). The organic layer was washed with water (400 mL) and saturated brine (400 mL), dried over anhydrous sodium sulfate and filtrated. The solvent was evaporated under reduced pressure, and the residue was purified by silica gel column chromatography (ethyl acetate/hexane=5/95→50/50). The combined eluate was concentrated under reduced pressure to give the title compound (6.4 g, 79%) as a colorless oil.
$^1$H-NMR (DMSO-$d_6$, 300 MHz) δ 1.72 (6H, s), 3.89 (3H, s), 7.61 (1H, t, J=7.8 Hz), 7.84 (1H, ddd, J=1.2, 2.1, 7.8 Hz), 7.95 (1H, dt, J=7.8, 1.2 Hz), 8.08 (1H, t, J=1.5 Hz).

(iii) 3-(1-cyano-1-methylethyl)benzoic acid

To a solution of methyl 3-(1-cyano-1-methylethyl)benzoate (2.8 g, 14 mmol) in tetrahydrofuran (30 mL) were added lithium hydroxide monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). 1N Hydrochloric acid was slowly added to adjust the mixture to pH 3. The resulting white precipitate was collected by filtration, washed with water and dried to give the title compound (2.5 g, 98%) as a white powder.
$^1$H-NMR (DMSO-$d_6$, 300 MHz) δ 1.72 (6H, s), 7.57 (1H, t, J=7.8 Hz), 7.78 (1H, ddd, J=1.2, 2.1, 7.8 Hz), 7.92 (1H, dt, J=7.8, 1.5 Hz), 8.08 (1H, t, J=1.5 Hz), 13.19 (1H, s).

(iv) N-{3-[(6-aminopyridin-3-yl)oxy]phenyl}-3-(1-cyano-1-methylethyl)benzamide

To a solution of 3-(1-cyano-1-methylethyl)benzoic acid (2.66 g, 14.0 mmol) in tetrahydrofuran (28 mL) were added oxalyl chloride (1.63 mL, 19.1 mmol) and N,N-dimethylformamide (about 20 μL), and the mixture was stirred at room temperature for 1 hr. The reaction mixture was concentrated under reduced pressure to give 3-(1-cyano-1-methylethyl)benzoyl chloride as a pale-brown oil.
To a solution of 3-(1-cyano-1-methylethyl)benzoyl chloride synthesized above in N,N-dimethylacetamide (50 mL) was added 5-(3-aminophenoxy)pyridin-2-amine dihydrochloride (3.5 g, 12.7 mmol), and the mixture was stirred at room temperature for 18 hr. 5% Aqueous sodium hydrogen carbonate solution (200 mL) was added to the reaction mixture, and the mixture was extracted with ethyl acetate (300 mL). The organic layer was washed with saturated brine (100 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and triturated with ethyl acetate and hexane to give the title compound (3.44 g, 66%) as a colorless solid.
$^1$H-NMR (DMSO-$d_6$, 300 MHz) δ 1.74 (6H, s), 5.91 (2H, s), 6.51 (1H, d, J=8.9 Hz), 6.66-6.77 (1H, m), 7.23 (1H, dd, J=2.7, 8.9 Hz), 7.30 (1H, t, J=8.1 Hz), 7.38 (1H, t, J=2.1 Hz), 7.43-7.52 (1H, m), 7.58 (1H, t, J=7.8 Hz), 7.68-7.82 (2H, m), 7.84-7.94 (1H, m), 7.99 (1H, t, J=1.8 Hz), 10.33 (1H, s).

(v) 3-(1-cyano-1-methylethyl)-N-{3-[(6-{[(4-methylphenyl)sulfonyl]amino}pyridin-3-yl)oxy]phenyl}benzamide To a solution of N-{3-[(6-aminopyridin-3-yl)oxy]phenyl}-3-(1-cyano-1-methylethyl)benzamide (2.5 g, 6.71 mmol) in pyridine (60 mL) was added 4-methylbenzenesulfonyl chloride (1.34 g, 7.05 mmol) under ice-cooling, and the mixture was stirred with heating at 80° C. for 2 days. The reaction mixture was cooled to room temperature, water (200 mL) was added thereto and the mixture was extracted with ethyl acetate (300 mL). The organic layer was washed with saturated brine (300 mL), and dried over anhydrous sodium sulfate. The insoluble material was filtered off, and the filtrate was concentrated under reduced pressure to give the title compound (3.48 g, 99%) as a colorless powder. The compound was used in the next reaction without further purification.

$^1$H-NMR (DMSO-d$_6$, 300 MHz) δ 1.74 (6H, s), 2.34 (3H, s), 6.75 (1H, dd, J=8.1, 2.4 Hz), 7.15 (1H, d, J=9.0 Hz), 7.27-7.45 (4H, m), 7.46-7.68 (3H, m), 7.71-7.83 (3H, m), 7.89 (1H, d, J=7.8 Hz), 7.99 (1H, s), 8.02 (1H, d, J=3.0 Hz), 10.37 (1H, s), 11.07 (1H, br s).

(vi) N-{3-[(1-(2-amino-2-oxoethyl)-6-{[(4-methylphenyl)sulfonyl]imino}-1,6-dihydropyridin-3-yl)oxy]phenyl}-3-(1-cyano-1-methylethyl)benzamide To a solution of 3-(1-cyano-1-methylethyl)-N-{3-[(6-{[(4-methylphenyl)sulfonyl]amino}pyridin-3-yl)oxy]phenyl}benzamide (3.2 g, 6.08 mmol) in N,N-dimethylformamide (20 mL) was added N,N-diisopropylethylamine (1.11 mL, 6.38 mmol), and the mixture was stirred at room temperature for 15 min. 2-Iodoacetamide (1.18 g, 6.38 mmol) was added to the reaction mixture, and the mixture was stirred at room temperature for 48 hr. The reaction mixture was concentrated under reduced pressure, 5% aqueous sodium hydrogen carbonate solution (150 mL) was added to the residue, and the mixture was extracted with ethyl acetate (300 mL). The organic layer was washed with saturated brine (150 mL), and dried over anhydrous sodium sulfate. The insoluble material was removed by filtration, and the filtrate was concentrated under reduced pressure. The obtained residue was purified by silica gel column chromatography (hexane/ethyl acetate=50/50→0/100), and triturated with ethyl acetate, diisopropyl ether and hexane to give the title compound (2.23 g, 63%) as a colorless solid.

$^1$H-NMR (DMSO-d$_6$, 300 MHz) δ 1.74 (6H, s), 2.34 (3H, s), 4.83 (2H, s), 6.76 (1H, dd, J=2.4, 7.8 Hz), 7.28 (2H, d, J=8.1 Hz), 7.32-7.46 (3H, m), 7.48 (1H, t, J=2.1 Hz), 7.59 (2H, t, J=7.8 Hz), 7.68 (2H, d, J=8.1 Hz), 7.71-7.82 (3H, m), 7.86-7.94 (1H, m), 8.01 (1H, t, J=1.8 Hz), 8.13 (1H, d, J=2.4 Hz), 10.41 (1H, s).

(vii) 3-(1-cyano-1-methylethyl)-N-[3-({2-[(trifluoroacetyl)amino]imidazo[1,2-a]pyridin-6-yl}oxy)phenyl]benzamide To a solution of N-{3-[(1-(2-amino-2-oxoethyl)-6-{[(4-methylphenyl)sulfonyl]imino}-1,6-dihydropyridin-3-yl)oxy]phenyl}-3-(1-cyano-1-methylethyl)benzamide (1.00 g, 1.72 mmol) in dichloromethane (8.0 mL) was added trifluoroacetic anhydride (6.0 mL), and the mixture was stirred at room temperature for 16 hr. The reaction mixture was concentrated under reduced pressure, 5% aqueous sodium hydrogen carbonate solution (150 mL) was added thereto, and the mixture was extracted with ethyl acetate (150 mL). The organic layer was washed with saturated brine (150 mL), and dried over anhydrous sodium sulfate. The insoluble material was filtered off, and the filtrate was concentrated under reduced pressure. The obtained residue was purified by silica gel column chromatography (hexane/ethyl acetate=70/30→40/60), and triturated with diisopropyl ether and hexane to give the title compound (450 mg, 52%) as a colorless solid.

$^1$H-NMR (DMSO-d$_6$, 300 MHz) δ 1.73 (6H, s), 6.84 (1H, dd, J=2.4, 7.5 Hz), 7.22 (1H, dd, J=2.4, 9.6 Hz), 7.38 (1H, t, J=8.1 Hz), 7.51 (1H, t, J=2.4 Hz), 7.54-7.68 (3H, m), 7.70-7.79 (1H, m), 7.89 (1H, d, J=8.1 Hz), 7.99 (1H, t, J=1.8 Hz), 8.27 (1H, s), 8.66 (1H, d, J=2.4 Hz), 10.36 (1H, s), 12.48 (1H, s).

Example 228

3-(1-cyano-1-methylethyl)-N-[3-({2-[(cyclopropylcarbonyl)amino]imidazo[1,2-a]pyridin-6-yl}oxy)phenyl]benzamide

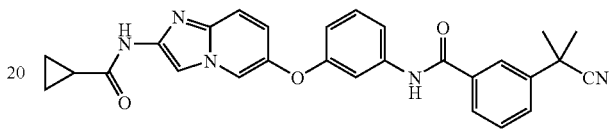

(i) N-{3-[(2-aminoimidazo[1,2-a]pyridin-6-yl)oxy]phenyl}-3-(1-cyano-1-methylethyl)benzamide To a solution of 3-(1-cyano-1-methylethyl)-N-[3-({2-[(trifluoroacetyl)amino]imidazo[1,2-a]pyridin-6-yl}oxy)phenyl]benzamide (400 mg, 0.788 mmol) in ethanol (4.0 mL) was added 1N aqueous sodium hydroxide solution (8.0 mL), and the mixture was stirred at 45° C. for 12 hr. Water (100 mL) was added to the reaction mixture, and the mixture was extracted with ethyl acetate (200 mL). The organic layer was washed with saturated brine (100 mL), and dried over anhydrous sodium sulfate. The insoluble material was removed by filtration, and the filtrate was concentrated under reduced pressure. The obtained residue was purified by silica gel column chromatography (NH silica gel, ethyl acetate/methanol=100/0→80/20), and fractions containing the desired product were concentrated under reduced pressure to give the title compound (0.35 g, quantitative) as a colorless solid.

$^1$H-NMR (DMSO-d$_6$, 300 MHz) δ 1.73 (6H, s), 5.08 (2H, s), 6.78 (1H, dd, J=2.1, 8.1 Hz), 6.87 (1H, dd, J=2.1, 9.6 Hz), 7.01 (1H, s), 7.22 (1H, d, J=9.6 Hz), 7.34 (1H, t, J=8.2 Hz), 7.44 (1H, s), 7.50-7.62 (2H, m), 7.74 (1H, d, J=8.1 Hz), 7.88 (1H, d, J=7.5 Hz), 7.98 (1H, s), 8.34 (1H, d, J=2.1 Hz), 10.34 (1H, s).

(ii) 3-(1-cyano-1-methylethyl)-N-[3-({2-[(cyclopropylcarbonyl)amino]imidazo[1,2-a]pyridin-6-yl}oxy)phenyl]benzamide To a solution of N-{3-[(2-aminoimidazo[1,2-a]pyridin-6-yl)oxy]phenyl}-3-(1-cyano-1-methylethyl)benzamide (200 mg, 0.486 mmol) in N,N-dimethylacetamide (2.0 mL) was added cyclopropanecarbonyl chloride (46 μL, 0.510 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (NH silica gel, hexane/ethyl acetate=50/50→0/100), and fractions containing the desired product were concentrated under reduced pressure. The residue was triturated with ethyl acetate and diisopropyl ether to give the title compound (100 mg, 43%) as a colorless solid.

¹H-NMR (DMSO-d₆, 300 MHz) δ 0.73-0.85 (4H, m), 1.73 (6H, s), 1.86-2.03 (1H, m), 6.81 (1H, dd, J=2.4, 8.1 Hz), 7.10 (1H, dd, J=2.4, 9.6 Hz), 7.36 (1H, t, J=8.1 Hz), 7.44-7.52 (2H, m), 7.57 (2H, t, J=7.8 Hz), 7.69-7.78 (1H, m), 7.89 (1H, d, J=8.4 Hz), 7.98 (1H, t, J=1.5 Hz), 8.07 (1H, s), 8.59 (1H, d, J=2.4 Hz), 10.35 (1H, s), 10.98 (1H, s).

Example 229

3-(1-cyanocyclopropyl)-N-[3-({2-[(cyclopropylcarbonyl)amino]imidazo[1,2-a]pyridin-6-yl}oxy)phenyl]benzamide

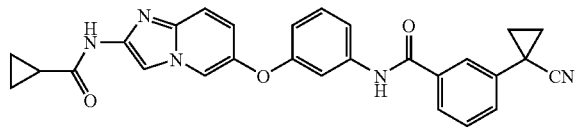

(i) methyl 3-(1-cyanocyclopropyl)benzoate

To a solution of methyl 3-(cyanomethyl)benzoate (1.5 g, 8.6 mmol) in DMSO (30 mL) was added sodium hydride (60% in oil, 1.0 g, 26 mmol) while cooling the mixture to 25° C. or below to prevent precipitation. The reaction mixture was stirred at room temperature for 30 min, 1,2-dibromoethane (2.4 g, 12.8 mmol) was added thereto, and the mixture was further stirred at room temperature for 10 hr. The reaction mixture was diluted with water (100 mL) and extracted with ethyl acetate (300 mL). The organic layer was washed with saturated brine (100 mL) and dried over anhydrous sodium sulfate, and insoluble material was filtered off. The solvent was evaporated under reduced pressure. The residue was purified by silica gel column chromatography (ethyl acetate/hexane=5/95→50/50), and fractions containing the desired product were concentrated under reduced pressure to give the title compound (1.3 g, 76%) as a colorless oil.

¹H-NMR (CDCl₃, 300 MHz) δ 1.38-1.56 (2H, m), 1.74-1.82 (2H, m), 3.93 (3H, s), 7.40-7.49 (1H, m), 7.55-7.62 (1H, m), 7.88 (1H, t, J=1.5 Hz), 7.96 (1H, dt, J=7.8, 1.5 Hz).

(ii) 3-(1-cyanocyclopropyl)benzoic acid

To a solution of methyl 3-(1-cyanocyclopropyl)benzoate (1.3 g, 6.4 mmol) in tetrahydrofuran (12 mL) were added lithium hydroxide monohydrate (0.44 g, 11 mmol), methanol (4.0 mL) and water (6.0 ml), and the mixture was stirred at room temperature for 4 hr. The solvent was evaporated under reduced pressure, and the residue was diluted with water (5.0 mL). 1N Hydrochloric acid was slowly added to the mixture, and the mixture was adjusted to pH 5. The resulting white precipitate was collected by filtration, washed with water and dried to give the title compound (0.73 g, 61%) as a white powder.

¹H-NMR (DMSO-d₆, 300 MHz) δ 1.50-1.62 (2H, m), 1.76-1.86 (2H, m), 7.41-7.59 (2H, m), 7.82-7.97 (2H, m), 13.19 (1H, br s).

(iii) N-{3-[(6-aminopyridin-3-yl)oxy]phenyl}-3-(1-cyanocyclopropyl)benzamide

To a solution of 3-(1-cyanocyclopropyl)benzoic acid (2.6 g, 13.9 mmol) in tetrahydrofuran (60 mL) were added oxalyl chloride (1.63 mL, 19.1 mmol) and N,N-dimethylformamide (about 20 μL), and the mixture was stirred at room temperature for 1 hr. The reaction mixture was concentrated under reduced pressure to give 3-(1-cyanocyclopropyl)benzoyl chloride as a colorless oil.

To a solution of 3-(1-cyanocyclopropyl)benzoyl chloride synthesized above in N,N-dimethylacetamide (50 mL) was added 5-(3-aminophenoxy)pyridin-2-amine dihydrochloride (3.5 g, 12.7 mmol), and the mixture was stirred at room temperature for 18 hr. 5% Aqueous sodium hydrogen carbonate solution (200 mL) was added to the reaction mixture, and the mixture was extracted with ethyl acetate (300 mL). The organic layer was washed with saturated brine (100 mL) and dried over anhydrous sodium sulfate. The insoluble material was filtered off, and the filtrate was concentrated under reduced pressure. The obtained residue was purified by silica gel column chromatography (hexane/ethyl acetate=50/50→0/100), and triturated with ethyl acetate and hexane to give the title compound (3.84 g, 75%) as a colorless solid.

¹H-NMR (DMSO-d₆, 300 MHz) δ 1.56-1.65 (2H, m), 1.75-1.86 (2H, m), 5.91 (2H, s), 6.51 (1H, d, J=8.9 Hz), 6.64-6.73 (1H, m), 7.23 (1H, dd, J=3.0, 8.9 Hz), 7.30 (1H, t, J=8.1 Hz), 7.37 (1H, t, J=2.1 Hz), 7.45-7.52 (1H, m), 7.52-7.60 (2H, m), 7.74-7.81 (2H, m), 7.85 (1H, dt, J=4.2, 2.1 Hz), 10.31 (1H, s).

(iv) 3-(1-cyanocyclopropyl)-N-{3-[(6-{[(4-methylphenyl)sulfonyl]amino}pyridin-3-yl)oxy]phenyl}benzamide To a solution of N-{3-[(6-aminopyridin-3-yl)oxy]phenyl}-3-(1-cyanocyclopropyl)benzamide (2.0 g, 5.4 mmol) in pyridine (60 mL) was added 4-methylbenzenesulfonyl chloride (1.13 g, 5.94 mmol) under ice-cooling, and the mixture was stirred with heating at 80° C. for 2 days. The reaction mixture was cooled to room temperature, water (200 mL) was added thereto, and the mixture was extracted with ethyl acetate (400 mL). The organic layer was washed with saturated brine (200 mL), and dried over anhydrous sodium sulfate. The insoluble material was filtered off, and the filtrate was concentrated under reduced pressure. The obtained residue was washed with ethyl acetate and diisopropyl ether to give the title compound (2.61 g, 92%) as a colorless solid.

¹H-NMR (DMSO-d₆, 300 MHz) δ 1.56-1.65 (2H, m), 1.76-1.85 (2H, m), 2.34 (3H, s), 6.74 (1H, dd, J=2.1, 7.8 Hz), 7.13 (1H, d, J=9.0 Hz), 7.26-7.40 (3H, m), 7.41 (1H, t, J=2.1 Hz), 7.49 (1H, dd, J=3.0, 9.0 Hz), 7.52-7.61 (3H, m), 7.74-7.91 (4H, m), 8.01 (1H, d, J=3.0 Hz), 10.34 (1H, s), 11.05 (1H, br s).

(v) N-{3-[(1-(2-amino-2-oxoethyl)-6-{[(4-methylphenyl)sulfonyl]imino}-1,6-dihydropyridin-3-yl)oxy]phenyl}-3-(1-cyanocyclopropyl)benzamide To a solution of 3-(1-cyanocyclopropyl)-N-{3-[(6-{[(4-methylphenyl)sulfonyl]amino}pyridin-3-yl)oxy]phenyl}benzamide (2.5 g, 4.77 mmol) in N,N-dimethylformamide (15 mL) was added N,N-diisopropylethylamine (0.90 mL, 5.01 mmol), and the mixture was stirred at room temperature for 15 min. 2-Iodoacetamide (927 mg, 5.01 mmol) was added to the reaction mixture, and the mixture was stirred at room temperature for 48 hr. The reaction mixture was concentrated under reduced pressure, water (150 mL) was added to the residue, and the mixture was extracted with ethyl acetate (150 mL). The organic layer was washed with saturated brine (150 mL) and dried over anhydrous magnesium sulfate. The insoluble material was filtered off, and the filtrate was concentrated under reduced pressure. The obtained residue was recrystallized from ethyl acetate and hexane to give the title compound (2.14 g, 77%) as a pale-yellow solid.

$^1$H-NMR (DMSO-d$_6$, 300 MHz) δ 1.52-1.67 (2H, m), 1.76-1.87 (2H, m), 2.29-2.38 (3H, m), 4.83 (2H, s), 6.69-6.79 (1H, m), 7.28 (2H, d, J=8.1 Hz), 7.31-7.50 (4H, m), 7.50-7.62 (3H, m), 7.68 (2H, d, J=8.1 Hz), 7.71-7.91 (4H, m), 8.14 (1H, d, J=3.0 Hz), 10.39 (1H, s).

(vi) 3-(1-cyanocyclopropyl)-N-[3-({2-[(trifluoro-acetyl)amino]imidazo[1,2-a]pyridin-6-yl}oxy)phenyl]benzamide To a solution of N-{3-[(1-(2-amino-2-oxoethyl)-6-{[(4-methylphenyl)sulfonyl]imino}-1,6-dihydropyridin-3-yl)oxy]phenyl}-3-(1-cyanocyclopropyl)benzamide (1.5 g, 2.58 mmol) in dichloromethane (10 mL) was added trifluoroacetic anhydride (10 mL), and the mixture was stirred at room temperature for 12 hr. Water (200 mL) was added to the reaction mixture, and the mixture was extracted with ethyl acetate (200 mL). The organic layer was washed with 5% aqueous sodium hydrogen carbonate solution (200 mL) and saturated brine (200 mL), and dried over anhydrous sodium sulfate. The insoluble material was filtered off, and the filtrate was concentrated under reduced pressure. The obtained residue was purified by silica gel column chromatography (NH silica gel, hexane/ethyl acetate=40/60→0/100), and fractions containing the desired product were concentrated under reduced pressure to give the title compound (977 mg, 75%) as a pale-yellow oil.

$^1$H-NMR (DMSO-d$_6$, 300 MHz) δ 1.50-1.65 (2H, m), 1.76-1.87 (2H, m), 6.84 (1H, dt, J=1.2, 8.1 Hz), 7.22 (1H, dd, J=2.4, 9.6 Hz), 7.38 (1H, t, J=8.1 Hz), 7.50 (1H, t, J=2.1 Hz), 7.52-7.62 (4H, m), 7.75-7.89 (2H, m), 8.27 (1H, s), 8.66 (1H, dd, J=0.9, 2.4 Hz), 10.34 (1H, s), 12.48 (1H, br s).

(vii) 3-(1-cyanocyclopropyl)-N-[3-({2-[(cyclopropylcarbonyl)amino]imidazo[1,2-a]pyridin-6-yl}oxy)phenyl]benzamide To a solution of 3-(1-cyanocyclopropyl)-N-[3-({2-[(trifluoroacetyl)amino]imidazo[1,2-a]pyridin-6-yl}oxy)phenyl]benzamide (450 mg, 0.89 mmol) in ethanol (8.0 mL) was added 1N aqueous sodium hydroxide solution (8.9 mL), and the mixture was stirred at 45° C. for 8 hr. Water (100 mL) was added to the reaction mixture, and the mixture was extracted with ethyl acetate (200 mL). The organic layer was washed with saturated brine (100 mL) and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→80/20), and fractions containing the desired product were concentrated under reduced pressure to give N-{3-[(2-aminoimidazo[1,2-a]pyridin-6-yl)oxy]phenyl}-3-(1-cyanocyclopropyl)benzamide (200 mg, 55%) as a colorless solid.

To a solution of N-{3-[(2-aminoimidazo[1,2-a]pyridin-6-yl)oxy]phenyl}-3-(1-cyanocyclopropyl)benzamide (200 mg, 0.488 mmol) obtained above in N,N-dimethylacetamide (4.0 mL) was added cyclopropanecarbonyl chloride (47 µL, 0.512 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was removed by filtration, and the filtrate was concentrated under reduced pressure. The obtained residue was purified by silica gel column chromatography (hexane/ethyl acetate=60/40→0/100) and further purified by preparative HPLC, and fractions containing the desired product were concentrated under reduced pressure. The residue was diluted with ethyl acetate (100 mL), washed with 5% aqueous sodium hydrogen carbonate solution (100 mL) and saturated brine (100 mL), and dried over anhydrous sodium sulfate. The insoluble material was filtered off, and the filtrate was concentrated under reduced pressure. The residue was recrystallized from tetrahydrofuran and hexane to give the title compound (116 mg, 50%) as a colorless solid.

$^1$H-NMR (DMSO-d$_6$, 300 MHz) δ 0.56-0.89 (4H, m), 1.53-1.66 (2H, m), 1.74-1.87 (2H, m), 1.86-2.02 (1H, m), 6.81 (1H, dd, J=2.4, 8.4 Hz), 7.10 (1H, dd, J=2.4, 9.6 Hz), 7.36 (1H, t, J=8.1 Hz), 7.43-7.63 (5H, m), 7.70-7.89 (2H, m), 8.07 (1H, s), 8.60 (1H, d, J=2.4 Hz), 10.33 (1H, s), 10.99 (1H, s).

Example 230

N-[3-({2-[(cyclopropylcarbonyl)amino][1,2,4]triazolo[1,5-a]pyridin-6-yl}oxy)phenyl]-3-(trifluoromethyl)benzamide

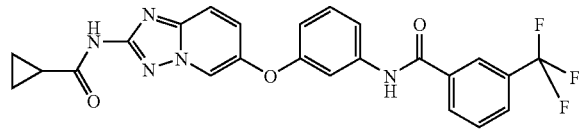

(i) N-{3-[(2-amino[1,2,4]triazolo[1,5-a]pyridin-6-yl)oxy]phenyl}-3-(trifluoromethyl)benzamide To a solution of N-{3-[(6-aminopyridin-3-yl)oxy]phenyl}-3-(trifluoromethyl)benzamide (600 mg, 1.61 mmol) in DMSO (30 mL) was added ethyl isothiocyanatocarbonate (230 µL, 1.95 mmol), and the mixture was stirred at room temperature for 12 hr. Water (150 mL) was slowly added to the reaction mixture, and the mixture was extracted with ethyl acetate (300 mL). The organic layer was washed with water (100 mL) and saturated brine (100 mL), and dried over anhydrous sodium sulfate. The insoluble material was filtered off, and the filtrate was concentrated under reduced pressure to give ethyl ({[5-(3-{[3-(trifluoromethyl)benzoyl]amino}phenoxy)pyridin-2-yl]amino}carbonothioyl)carbamate (485 mg, 59%) as a brown oil.

To a solution of hydroxylamine hydrochloride (400 mg, 5.76 mmol) and N,N-diisopropylethylamine (1.20 mL, 6.88 mmol) in methanol (8.0 mL)/ethanol (8.0 mL) was added ethyl ({[5-(3-{[3-(trifluoromethyl)benzoyl]amino}phenoxy)pyridin-2-yl]amino}carbonothioyl)carbamate (480 mg, 0.95 mmol) obtained above, and the mixture was stirred with heating at 60° C. for 12 hr. The reaction mixture was concentrated under reduced pressure, and the residue was diluted with ethyl acetate (100 mL). The mixture was washed with water (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and fractions containing the desired product were concentrated under reduced pressure to give the title compound (0.48 g, quantitative) as a pale-yellow powder.

¹H-NMR (DMSO-d$_6$, 300 MHz) δ 6.02 (2H, s), 6.83 (1H, dd, J=1.8, 7.8 Hz), 7.24-7.51 (4H, m), 7.59 (1H, dd, J=0.9, 8.1 Hz), 7.77 (1H, t, J=7.8 Hz), 7.96 (1H, d, J=7.8 Hz), 8.11-8.31 (2H, m), 8.65 (1H, d, J=1.8 Hz), 10.50 (1H, s).

(ii) N-[3-({2-[(cyclopropylcarbonyl)amino][1,2,4]triazolo[1,5-a]pyridin-6-yl}oxy)phenyl]-3-(trifluoromethyl)benzamide To a solution of N-{3-[(2-amino[1,2,4]triazolo[1,5-a]pyridin-6-yl)oxy]phenyl}-3-(trifluoromethyl)benzamide (100 mg, 0.24 mmol) in N,N-dimethylacetamide (2.0 mL) was added cyclopropanecarbonyl chloride (33 μL, 0.36 mmol), and the mixture was stirred at room temperature for 4 hr. Cyclopropanecarbonyl chloride (15 μL, 0.17 mmol) was added to the reaction mixture, and the mixture was further stirred at room temperature for 2 hr. The reaction mixture was diluted with ethyl acetate (150 mL), washed with 1N hydrochloric acid (15 mL), 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and fractions containing the desired product were concentrated under reduced pressure and the residue was recrystallized from ethyl acetate, hexane and diisopropyl ether to give the title compound (108 mg, 92%) as a colorless powder.

¹H-NMR (DMSO-d$_6$, 300 MHz) δ 0.78-0.90 (4H, m), 2.03 (1H, br s), 6.87 (1H, dt, J=1.2, 8.1 Hz), 7.39 (1H, t, J=8.1 Hz), 7.49 (1H, t, J=2.1 Hz), 7.55 (1H, dd, J=2.4, 9.6 Hz), 7.61 (1H, dd, J=1.2, 8.1 Hz), 7.70-7.81 (2H, m), 7.96 (1H, d, J=7.8 Hz), 8.17-8.29 (2H, m), 8.95 (1H, d, J=1.8 Hz), 10.51 (1H, br s), 11.05 (1H, br s).

Example 231

3-(1-cyano-1-methylethyl)-N-[3-({2-[(cyclopropylcarbonyl)amino][1,2,4]triazolo[1,5-a]pyridin-6-yl}oxy)phenyl]benzamide

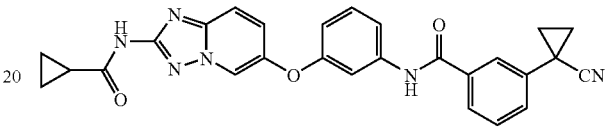

To a solution of 3-(1-cyano-1-methylethyl)benzoic acid (110 mg, 0.582 mmol) in tetrahydrofuran (5.0 mL) were added oxalyl chloride (62 μL, 0.728 mmol) and N,N-dimethylformamide (about 20 μL), and the mixture was stirred at room temperature for 1 hr. The reaction mixture was concentrated under reduced pressure to give 3-(1-cyano-1-methylethyl)benzoyl chloride as a pale-brown oil.

3-(1-Cyano-1-methylethyl)benzoyl chloride synthesized above in N,N-dimethylacetamide (5.0 mL) was added N-[6-(3-aminophenoxy)[1,2,4]triazolo[1,5-a]pyridin-2-yl]cyclopropanecarboxamide (150 mg, 0.485 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=60/40→0/100), and the obtained oil was triturated with ethyl acetate, toluene and diisopropyl ether to give the title compound (117 mg, 42%) as a colorless powder.

¹H-NMR (DMSO-d$_6$, 300 MHz) δ 0.74-0.94 (4H, m), 1.73 (6H, s), 2.00-2.12 (1H, m), 6.85 (1H, dd, J=2.4, 8.1 Hz), 7.38 (1H, t, J=8.1 Hz), 7.47-7.65 (4H, m), 7.69-7.79 (2H, m), 7.90 (1H, d, J=7.8 Hz), 7.99 (1H, s), 8.94 (1H, d, J=2.4 Hz), 10.37 (1H, s), 11.05 (1H, s).

Example 232

3-(1-cyanocyclopropyl)-N-[3-({2-[(cyclopropylcarbonyl)amino][1,2,4]triazolo[1,5-a]pyridin-6-yl}oxy)phenyl]benzamide

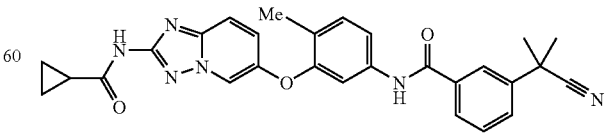

To a solution of 3-(1-cyanocyclopropyl)benzoic acid (109 mg, 0.582 mmol) in tetrahydrofuran (5.0 mL) were added oxalyl chloride (62 μL, 0.728 mmol) and N,N-dimethylformamide (about 20 μL), and the mixture was stirred at room temperature for 1 hr. The reaction mixture was concentrated under reduced pressure to give 3-(1-cyanocyclopropyl)benzoyl chloride as a pale-brown oil.

To a solution of 3-(1-cyanocyclopropyl)benzoyl chloride synthesized above in N,N-dimethylacetamide (5.0 mL) was added N-[6-(3-aminophenoxy)[1,2,4]triazolo[1,5-a]pyridin-2-yl]cyclopropanecarboxamide (150 mg, 0.485 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=60/40→0/100), and the obtained oil was triturated with ethyl acetate, toluene and diisopropyl ether to give the title compound (175 mg, 63%) as a colorless powder.

¹H-NMR (DMSO-d$_6$, 300 MHz) δ 0.72-0.89 (4H, m), 1.55-1.65 (2H, m), 1.76-1.86 (2H, m), 1.97-2.11 (1H, m), 6.77-6.91 (1H, m), 7.38 (1H, t, J=8.1 Hz), 7.49 (1H, t, J=2.1 Hz), 7.51-7.63 (4H, m), 7.71-7.80 (2H, m), 7.80-7.88 (1H, m), 8.94 (1H, d, J=1.5 Hz), 10.35 (1H, s), 11.04 (1H, s).

Example 233

3-(1-cyano-1-methylethyl)-N-[3-({2-[(cyclopropylcarbonyl)amino][1,2,4]triazolo[1,5-a]pyridin-6-yl}oxy)-4-methylphenyl]benzamide To a solution of 3-(1-cyano-1-methylethyl)benzoic acid (53 mg, 0.280 mmol) in tetrahydrofuran (2.0 mL) were added oxalyl chloride (35 μL, 0.42 mmol) and N,N-dimethylformamide (about 20 μL), and the mixture was stirred at room temperature for 1 hr. The reaction mixture was concentrated under reduced pressure to give 3-(1-cyano-1-methylethyl)benzoyl chloride as a pale-brown oil.

3-(1-Cyano-1-methylethyl)benzoyl chloride synthesized above in N,N-dimethylacetamide (2.0 mL) was added N-[6-(5-amino-2-methylphenoxy)[1,2,4]triazolo[1,5-a]pyridin-2-yl]cyclopropanecarboxamide (75 mg, 0.233 mmol), and the mixture was stirred at room temperature for 10 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (NH silica gel, hexane/ethyl acetate=50/50→0/100), and the obtained oil was triturated with ethyl acetate and diisopropyl ether to give the title compound (40.8 mg, 35%) as a colorless powder.

$^1$H-NMR (DMSO-d$_6$, 300 MHz) δ 0.72-0.91 (4H, m), 1.71 (6H, s), 1.95-2.10 (1H, m), 2.28 (3H, s), 7.27-7.36 (2H, m), 7.48-7.60 (3H, m), 7.67-7.79 (2H, m), 7.82-7.89 (1H, m), 7.95 (1H, t, J=1.8 Hz), 8.80 (1H, dd, J=0.6, 2.4 Hz), 10.24 (1H, s), 11.03 (1H, s).

Example 234

3-(1-cyanocyclopropyl)-N-[3-({2-[(cyclopropylcarbonyl)amino][1,2,4]triazolo[1,5-a]pyridin-6-yl}oxy)-4-methylphenyl]benzamide

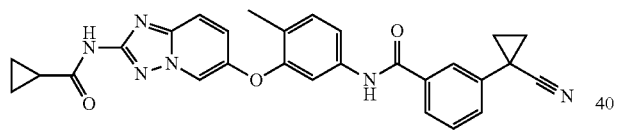

To a solution of 3-(1-cyanocyclopropyl)benzoic acid (139 mg, 0.742 mmol) in tetrahydrofuran (7.0 mL) were added oxalyl chloride (80 μL, 0.929 mmol) and N,N-dimethylformamide (about 20 μL), and the mixture was stirred at room temperature for 1 hr. The reaction mixture was concentrated under reduced pressure to give 3-(1-cyanocyclopropyl)benzoyl chloride as a pale-brown oil.

To a solution of 3-(1-cyanocyclopropyl)benzoyl chloride synthesized above in 1-methylpyrrolidin-2-one (7.0 mL) was added N-[6-(5-amino-2-methylphenoxy)[1,2,4]triazolo[1,5-a]pyridin-2-yl]cyclopropanecarboxamide (200 mg, 0.619 mmol), and the mixture was stirred at room temperature for 8 hr. The reaction mixture was diluted with ethyl acetate (100 mL), washed with 5% aqueous sodium hydrogen carbonate solution (50 mL) and saturated brine (50 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and the obtained oil was triturated with toluene and diisopropyl ether to give the title compound (256 mg, 84%) as a colorless powder.

$^1$H-NMR (DMSO-d$_6$, 300 MHz) δ 0.72-0.90 (4H, m), 1.52-1.63 (2H, m), 1.74-1.83 (2H, m), 1.83-1.97 (1H, m), 2.28 (3H, s), 7.26-7.37 (2H, m), 7.44-7.61 (4H, m), 7.68-7.86 (3H, m), 8.79 (1H, d, J=1.5 Hz), 10.23 (1H, s), 11.02 (1H, s).

Example 235

Production of N-[3-({2-[(cyclopropylcarbonyl)amino][1,2,4]triazolo[1,5-a]pyridin-6-yl}oxy)-4-methylphenyl]-3-(trifluoromethyl)benzamide

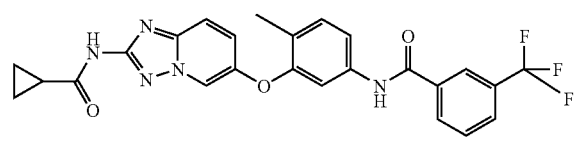

To a solution of N-[6-(3-amino-6-methylphenoxy)[1,2,4]triazolo[1,5-a]pyridin-2-yl]cyclopropanecarboxamide (100 mg, 0.309 mmol) in 1-methylpyrrolidin-2-one (2.0 mL) was added 3-(trifluoromethyl)benzoyl chloride (78 mg, 0.371 mmol), and the mixture was stirred at room temperature for 10 hr. The reaction mixture was concentrated under reduced pressure, the residue was diluted with ethyl acetate (100 mL), washed with 5% aqueous sodium hydrogen carbonate solution (50 mL) and saturated brine (50 mL), and dried over anhydrous sodium sulfate. The insoluble material was removed by filtration, and the filtrate was concentrated under reduced pressure. The obtained residue was purified by silica gel column chromatography (NH silica gel, hexane/ethyl acetate=50/50→0/100), and the obtained oil was triturated with ethyl acetate and hexane to give the title compound (100 mg, 65%) as a colorless powder.

$^1$H-NMR (DMSO-d$_6$, 300 MHz) δ 0.71-0.93 (4H, m), 2.03 (1H, br s), 2.29 (3H, s), 7.24-7.39 (2H, m), 7.52 (1H, dd, J=2.4, 9.6 Hz), 7.58 (1H, dd, J=1.8, 8.4 Hz), 7.68-7.81 (2H, m), 7.93 (1H, d, J=7.8 Hz), 8.10-8.26 (2H, m), 8.81 (1H, d, J=2.1 Hz), 10.39 (1H, s), 11.03 (1H, s).

Example 236

N-{6-[3-({[3-(1-cyano-1-methylethyl)phenyl]carbonyl}amino)phenoxy][1,2,4]triazolo[1,5-a]pyridin-2-yl}-1,3-oxazole-4-carboxamide

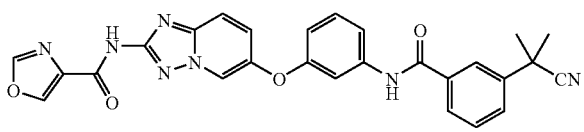

(i) 3-(1-cyano-1-methylethyl)-N-(3-hydroxyphenyl)benzamide

To a solution of 3-(1-cyano-1-methylethyl)benzoic acid (10 g, 52.8 mmol) in tetrahydrofuran (100 mL) were added N,N-dimethylformamide (80 μL) and oxalyl chloride (6.28 mL, 72.0 mmol), and the mixture was stirred at room temperature for 1.5 hr. The reaction mixture was concentrated under reduced pressure to give 3-(cyano-1-methylethyl)benzoyl chloride as a pale-brown oil. To a solution of 3-aminophenol (5.24 g, 48.0 mmol) in tetrahydrofuran (40 mL) was added an aqueous suspension (60 mL) of sodium hydrogen carbonate (6.05 g, 72.0 mmol), and the mixture was vigorously stirred at room temperature. To this mixture was added dropwise a solution of 3-(cyano-1-methylethyl)benzoyl chloride in tetrahydrofuran (60 mL) synthesized above under ice-cooling, and the mixture was stirred at room temperature for 5 hr. The aqueous layer of the reaction mixture was separated, and the organic layer was diluted with ethyl acetate (200 mL) and washed with saturated brine (200 mL). The extract was dried over anhydrous magnesium sulfate and decolored with activated carbon. The insoluble material was filtered off through a pad packed with silica gel and celite in two layers. The solvent was evaporated under reduced pressure, and the obtained solid was washed with ethyl acetate-hexane mixture to give the title compound (13.03 g, 96%) as a colorless powder.

$^1$H-NMR (DMSO-$d_6$, 300 MHz) δ 1.75 (6H, s), 6.49-6.55 (1H, m), 7.08-7.18 (2H, m), 7.30-7.34 (1H, m), 7.59 (1H, t, J=7.8 Hz), 7.72-7.77 (1H, m), 7.88-7.93 (1H, m), 8.01 (1H, t, J=1.7 Hz), 9.43 (1H, s), 10.18 (1H, s).

(ii) 3-(1-cyano-1-methylethyl)-N-{3-[(6-nitropyridin-3-yl)oxy]phenyl}benzamide

To a solution of 5-bromo-2-nitropyridine (4.56 g, 22.4 mmol) and cesium carbonate (10.9 g, 33.6 mmol) in N,N-dimethylformamide (40 mL) was added dropwise a solution of 3-(1-cyano-1-methylethyl)-N-(3-hydroxyphenyl)benzamide (6.92 g, 24.6 mmol) in N,N-dimethylformamide (20 mL) over 30 min, and the mixture was stirred at room temperature for 28 hr. Cesium carbonate (3.63 g, 11.2 mmol) was added to the reaction mixture, and the mixture was further stirred with heating at 60° C. for 15 hr. Water (200 mL) was added to the reaction mixture, and the mixture was extracted with ethyl acetate-hexane mixture (1:1, 200 mL, 3×50 mL). The combined organic layer was washed with saturated brine (30 mL) and dried over anhydrous magnesium sulfate. The insoluble material was removed by filtration, and the filtrate was concentrated under reduced pressure. The obtained residue was purified by silica gel column chromatography (NH silica gel, hexane/ethyl acetate=90/10→50/50), and fractions containing the desired t product were concentrated under reduced pressure to give the title compound (6.01 g, 67%) as a yellow amorphous solid.

$^1$H-NMR (CDCl$_3$, 300 MHz) δ 1.78 (6H, s), 6.90-6.96 (1H, m), 7.35-7.41(1H, m), 7.41-7.59 (3H, m), 7.66-7.74 (1H, m), 7.74-7.82 (2H, m), 7.93 (1H, s), 7.97 (1H, t, J=1.8 Hz), 8.26 (1H, d, J=8.9 Hz), 8.36 (1H, d, J=2.8 Hz).

(iii) N-{3-[(6-aminopyridin-3-yl)oxy]phenyl}-3-(1-cyano-1-methylethyl)benzamide

To a solution of 3-(1-cyano-1-methylethyl)-N-{3-[(6-nitropyridin-3-yl)oxy]phenyl}benzamide (6.00 g, 14.9 mmol) in methanol (150 mL) was added 10% palladium-carbon (790 mg), and the mixture was stirred at room temperature for 20 hr under a hydrogen atmosphere (3.0 atm). The insoluble material was filtered off, and the filtrate was concentrated under reduced pressure. The obtained residue was recrystallized from ethyl acetate and hexane to give the title compound (4.42 g, 79%) as colorless crystals.

$^1$H-NMR (CDCl$_3$, 300 MHz) δ 1.77 (6H, s), 4.37 (2H, s), 6.54 (1H, dd, J=8.7, 0.7 Hz), 6.68-6.80 (1H, m), 7.24 (1H, dd, J=8.7, 3.0 Hz), 7.27-7.34 (3H, m), 7.52 (1H, t, J=7.8 Hz), 7.71 (1H, ddd, J=7.8, 2.0, 1.0 Hz), 7.75 (1H, dt, J=7.8, 1.3 Hz), 7.79 (1H, s), 7.92-7.98 (2H, m).

(iv) N-{3-[(2-amino[1,2,4]triazolo[1,5-a]pyridin-6-yl)oxy]phenyl}-3-(1-cyano-1-methylethyl)benzamide To a solution of N-{3-[(6-aminopyridin-3-yl)oxy]phenyl}-3-(1-cyano-1-methylethyl)benzamide (4.32 g, 11.6 mmol) in DMSO (100 mL) was added ethyl isothiocyanatocarbonate (1.64 mL, 13.9 mmol), and the mixture was stirred at room temperature for 21 hr. Water (300 mL) was added to the reaction mixture, and the mixture was extracted with ethyl acetate (250 mL, 50 mL). The combined organic layer was washed with saturated brine (30 mL) and dried over anhydrous magnesium sulfate. The insoluble material was filtered off, and the filtrate was concentrated under reduced pressure to give ethyl ({5-[3-({[3-(1-cyano-1-methylethyl)phenyl]carbonyl}amino)phenoxy]pyridin-2-yl}carbamothioyl)carbamate as a yellow amorphous solid. The obtained compound was used in the next reaction without further purification.

$^1$H-NMR (CDCl$_3$, 300 MHz) δ 1.34 (3H, t, J=7.2 Hz), 1.77 (6H, s), 4.31 (2H, q, J=7.2 Hz), 6.84 (1H, dt, J=6.9, 2.2 Hz), 7.32-7.47 (4H, m), 7.49-7.57 (1H, m), 7.72 (1H, ddd, J=7.9, 2.2, 1.1 Hz), 7.74-7.79 (1H, m), 7.81 (1H, s), 7.96 (1H, t, J=1.8 Hz), 7.98-8.02 (1H, m), 8.22 (1H, d, J=3.0 Hz), 8.77 (1H, d, J=9.1 Hz), 12.04 (1H, s).

To a solution of the above-mentioned crude product, ethyl ({5-[3-({[3-(1-cyano-1-methylethyl)phenyl]carbonyl}amino)phenoxy]pyridin-2-yl}carbamothioyl)carbamate, in methanol (100 mL)/ethanol (100 mL) were added hydroxylamine hydrochloride (4.84 g, 69.6 mmol) and N,N-diisopropylethylamine (14.6 mL, 83.5 mmol), and the mixture was stirred with heating at 60° C. for 3 hr. The reaction mixture was concentrated under reduced pressure, water (100 mL) was added to the residue, and the mixture was extracted with ethyl acetate (150 mL, 2×50 mL). The combined organic layer was washed with saturated brine (30 mL) and dried over anhydrous sodium sulfate. The insoluble material was filtered off, and the filtrate was concentrated under reduced pressure. The obtained residue was purified by silica gel column chromatography (NH silica gel, hexane/ethyl acetate=30/70→0/100), and fractions containing the desired product were concentrated under reduced pressure to give the title compound (3.65 g, 76%) as a pale-yellow amorphous solid.

$^1$H-NMR (DMSO-$d_6$, 300 MHz) δ 1.73 (6H, s), 6.02 (2H, s), 6.80 (1H, ddd, J=8.2, 2.5, 0.8 Hz), 7.30-7.39 (2H, m), 7.42 (1H, dd, J=9.6, 1.5 Hz), 7.46 (1H, t, J=2.2 Hz), 7.53-7.61 (2H, m), 7.74 (1H, ddd, J=7.8, 2.2, 0.8 Hz), 7.89 (1H, dt, J=7.8, 1.5 Hz), 7.98 (1H, t, J=1.5 Hz), 8.65 (1H, dd, J=2.2, 0.8 Hz), 10.34 (1H, s).

(v) N-{6-[3-({[3-(1-cyano-1-methylethyl)phenyl]carbonyl}amino)phenoxy][1,2,4]triazolo[1,5-a]pyridin-2-yl}-1,3-oxazole-4-carboxamide To a solution of 1,3-oxazole-4-carboxylic acid (145 mg, 1.29 mmol) in tetrahydrofuran (3 mL) were added oxalyl chloride (157 μL, 1.80 mmol) and N,N-dimethylformamide (20 μL), and the mixture was stirred at room temperature for 1 hr. The reaction mixture was concentrated under reduced pressure. The obtained residue and the above-mentioned N-{3-[(2-amino[1,2,4]triazolo[1,5-a]pyridin-6-yl)oxy]phenyl}-3-(1-cyano-1-methylethyl)benzamide (213 mg, 516 μmol) were dissolved in pyridine (8 mL), and the mixture was stirred at room temperature for 25 hr. A saturated aqueous sodium hydrogen carbonate solution (10 mL) was added to the reaction mixture, and the mixture was extracted with ethyl acetate (20 mL, 2×10 mL). The combined organic layer was washed with saturated brine (5 mL) and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→97/3), and fractions containing the desired product were concentrated under reduced pressure. Diisopropyl ether was added to the obtained residue. The obtained precipitate was collected by filtration and dried to give the title compound (211 mg, 81%) as a colorless powder.

$^1$H-NMR (DMSO-d$_6$, 300 MHz) δ 1.73 (6H, s), 6.88 (1H, ddd, J=8.2, 2.5, 0.8 Hz), 7.39 (1H, t, J=8.2 Hz), 7.51 (1H, t, J=2.2 Hz), 7.57-7.64 (3H, m), 7.74 (1H, ddd, J=7.9, 2.0, 1.0 Hz), 7.84 (1H, dd, J=9.5, 0.8 Hz), 7.87-7.94 (1H, m), 8.00 (1H, t, J=1.7 Hz), 8.62 (1H, d, J=0.9 Hz), 8.92 (1H, d, J=0.9 Hz), 9.04 (1H, dd, J=2.2, 0.8 Hz), 10.37 (1H, s), 10.81 (1H, s).

Example 237

3-(1-cyano-1-methylethyl)-N-[3-({2-[(hydroxyacetyl)amino][1,2,4]triazolo[1,5-a]pyridin-6-yl}oxy)phenyl]benzamide

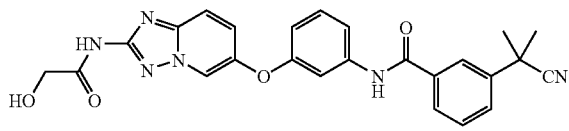

To a solution of N-{3-[(2-amino[1,2,4]triazolo[1,5-a]pyridin-6-yl)oxy]phenyl}-3-(1-cyano-1-methylethyl)benzamide (219 mg, 0.531 mmol) in pyridine (10 mL) was added 2-chloro-2-oxoethyl acetate (171 µL, 1.59 mmol), and the mixture was stirred at room temperature for 18 hr. The reaction solution was concentrated under reduced pressure, and the residue was dissolved in methanol (10 mL). Potassium carbonate (147 mg, 1.06 mmol) was added thereto, and the mixture was stirred at room temperature for 19 hr. Water (30 mL) was added to the reaction mixture, and the mixture was extracted with ethyl acetate (50 mL, 2×10 mL). The combined organic layer was washed with saturated brine (10 mL) and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→90/10), and fractions containing the desired product were concentrated under reduced pressure. Ethyl acetate and diisopropyl ether were added to the obtained residue. The obtained precipitate was collected by filtration, and dried to give the title compound (140 mg, 56%) as a pale-yellow powder.

$^1$H-NMR (DMSO-d$_6$, 300 MHz) δ 1.73 (6H, s), 4.12 (2H, s), 5.47 (1H, br s), 6.83-6.89 (1H, m), 7.39 (1H, t, J=8.2 Hz), 7.50 (1H, t, J=2.1 Hz), 7.54-7.62 (3H, m), 7.71-7.80 (2H, m), 7.87-7.92 (1H, m), 7.99 (1H, t, J=1.6 Hz), 8.98 (1H, dd, J=2.3, 0.8 Hz), 10.36 (1H, s), 10.41 (1H, s).

Example 238

3-(1-cyano-1-methylethyl)-N-{3-[(2-{[(4-methylpiperazin-1-yl)acetyl]amino}[1,2,4]triazolo[1,5-a]pyridin-6-yl)oxy]phenyl}benzamide

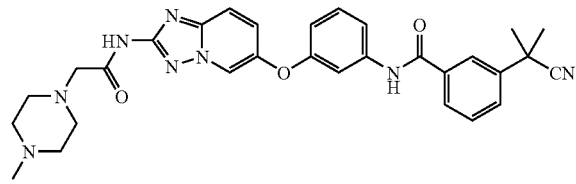

To a solution of N-{3-[(2-amino[1,2,4]triazolo[1,5-a]pyridin-6-yl)oxy]phenyl}-3-(1-cyano-1-methylethyl)benzamide (200 mg, 0.485 mmol) in N,N-dimethylformamide (5 mL) was added chloroacetyl chloride (116 µL, 1.46 mmol), and the mixture was stirred at room temperature for 21 hr. 1N Hydrochloric acid (20 mL) was added to the reaction mixture, and the mixture was extracted with ethyl acetate (30 mL, 2×10 mL). The combined organic layer was washed with saturated aqueous sodium hydrogen carbonate solution (5 mL) and saturated brine (5 mL) and dried over anhydrous sodium sulfate. The insoluble material was removed by filtration, and the filtrate was concentrated under reduced pressure. The residue was dissolved in tetrahydrofuran (5 mL). Triethylamine (202 µL, 1.46 mmol) and 1-methylpiperazine (162 µL, 1.46 mmol) were added thereto, and the mixture was stirred at 60° C. for 19 hr. A saturated aqueous sodium hydrogen carbonate solution (20 mL) was added to the reaction mixture, and the mixture was extracted with ethyl acetate (30 mL, 2×10 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→94/6), and fractions containing the desired product were concentrated under reduced pressure. Diisopropyl ether was added to the obtained residue. The obtained precipitate was collected by filtration and dried to give the title compound (147 mg, 55%) as a pale-yellow powder.

$^1$H-NMR (DMSO-d$_6$, 300 MHz) δ 1.73 (6H, s), 2.19 (3H, s), 2.40 (4H, br s), 2.53 (4H, br s), 3.22 (2H, s), 6.85 (1H, ddd, J=8.2, 2.5, 0.8 Hz), 7.38 (1H, t, J=8.1 Hz), 7.52 (1H, t, J=2.2 Hz), 7.53-7.63 (3H, m), 7.70-7.80 (2H, m), 7.84-7.93 (1H, m), 7.99 (1H, t, J=1.7 Hz), 8.97 (1H, dd, J=2.2, 0.8 Hz), 10.37 (1H, s), 10.42 (1H, s).

Example 239

N-{6-[5-({[3-(1-cyano-1-methylethyl)phenyl]carbonyl}amino)-2-methylphenoxy][1,2,4]triazolo[1,5-a]pyridin-2-yl}-1,3-oxazole-4-carboxamide

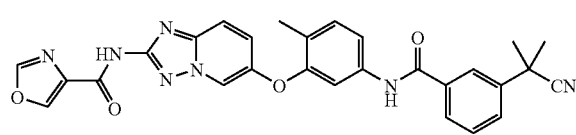

(i) 3-(1-cyano-1-methylethyl)-N-(3-hydroxy-4-methylphenyl)benzamide

To a solution of 3-(1-cyano-1-methylethyl)benzoic acid (5.00 g, 26.4 mmol) in tetrahydrofuran (50 mL) were added N,N-dimethylformamide (40 μL) and oxalyl chloride (3.20 mL, 36.5 mmol), and the mixture was stirred at room temperature for 1.5 hr. The reaction mixture was concentrated under reduced pressure to give 3-(1-cyano-1-methylethyl)benzoyl chloride. To a solution of 5-amino-2-methylphenol (3.00 g, 24.3 mmol) in tetrahydrofuran (20 mL) was added an aqueous suspension (30 mL) of sodium hydrogen carbonate (3.00 g, 36.5 mmol), and the mixture was vigorously stirred at room temperature. To this mixture was added dropwise under ice-cooling a solution of the above-mentioned 3-(1-cyano-1-methylethyl)benzoyl chloride in tetrahydrofuran (30 mL), and the mixture was stirred at room temperature for 5 hr. The aqueous layer of the reaction mixture was separated, and the organic layer was diluted with ethyl acetate (200 mL) and washed with saturated brine (200 mL). The extract was dried over anhydrous magnesium sulfate and decolored with activated carbon. The insoluble material was filtered off through a pad packed with silica gel and celite in two layers. The solvent was evaporated under reduced pressure, and the obtained solid was washed with a mixed solvent of ethyl acetate and hexane to give the title compound (6.75 g, 94%) as a white powder.

$^1$H-NMR (DMSO-$d_6$, 300 MHz) δ 1.75 (6H, s), 2.09 (3H, s), 6.97-7.06 (2H, m), 7.37 (1H, s), 7.58 (1H, t, J=7.7 Hz), 7.73 (1H, d, J=7.7 Hz), 7.90 (1H, d, J=7.7 Hz), 8.00 (1H, t, J=1.6 Hz), 9.36 (1H, s), 10.13 (1H, s).

(ii) 3-(1-cyano-1-methylethyl)-N-{4-methyl-3-[(6-nitropyridin-3-yl)oxy]phenyl}benzamide A solution of 3-(1-cyano-1-methylethyl)-N-(3-hydroxy-4-methylphenyl)benzamide (8.35 g, 28.4 mmol), 5-bromo-2-nitropyridine (5.24 g, 25.8 mmol) and cesium carbonate (16.8 g, 51.6 mmol) in N,N-dimethylformamide (70 mL) was stirred at 60° C. for 4 hr. Water (200 mL) was added to the reaction mixture, and the mixture was extracted with ethyl acetate (100 mL, 2×50 mL). The combined organic layer was washed with saturated brine (30 mL) and dried over anhydrous magnesium sulfate. The insoluble material was filtered off, and the filtrate was concentrated under reduced pressure. The obtained residue was purified by silica gel column chromatography (NH silica gel, hexane/ethyl acetate=90/10→60/40), and fractions containing the desired product were concentrated under reduced pressure to give the title compound (6.70 g, 63%) as a yellow amorphous solid.

$^1$H-NMR (CDCl$_3$, 300 MHz) δ 1.77 (6H, s), 2.20 (3H, s), 7.31-7.33 (2H, m), 7.36 (1H, dd, J=8.9, 2.8 Hz), 7.53 (1H, t, J=7.8 Hz), 7.66 (1H, s), 7.67-7.73 (1H, m), 7.74-7.80 (1H, m), 7.88 (1H, s), 7.96 (1H, t, J=1.7 Hz), 8.24 (1H, d, J=8.9 Hz), 8.36 (1H, d, J=2.8 Hz).

(iii) N-{3-[(6-aminopyridin-3-yl)oxy]-4-methylphenyl}-3-(1-cyano-1-methylethyl)benzamide To a solution of 3-(1-cyano-1-methylethyl)-N-{4-methyl-3-[(6-nitropyridin-3-yl)oxy]phenyl}benzamide (6.68 g, 16.0 mmol) in methanol (150 mL) was added 10% palladium-carbon (850 mg), and the mixture was stirred at room temperature for 16 hr under a hydrogen atmosphere (2.0 atm). The insoluble material was filtered off, and the filtrate was concentrated under reduced pressure. The obtained residue was recrystallized from ethyl acetate and hexane to give the title compound (4.83 g, 78%) as colorless crystals.

$^1$H-NMR (CDCl$_3$, 300 MHz) δ 1.75 (6H, s), 2.30 (3H, s), 4.33 (2H, s), 6.52 (1H, d, J=8.7 Hz), 7.04 (1H, d, J=1.8 Hz), 7.14-7.24 (2H, m), 7.27-7.32 (1H, m), 7.49 (1H, t, J=7.8 Hz), 7.65-7.74 (2H, m), 7.78 (1H, s), 7.87 (1H, d, J=2.8 Hz), 7.92 (1H, t, J=1.8 Hz).

(iv) N-{3-[(2-amino[1,2,4]triazolo[1,5-a]pyridin-6-yl)oxy]-4-methylphenyl}-3-(1-cyano-1-methylethyl)benzamide To a solution of N-{3-[(6-aminopyridin-3-yl)oxy]-4-methylphenyl}-3-(1-cyano-1-methylethyl)benzamide (4.71 g, 12.2 mmol) in dimethyl sulfoxide (100 mL) was added ethyl isothiocyanatocarbonate (1.73 mL, 14.6 mmol), and the mixture was stirred at room temperature for 6 hr. Water (300 mL) was added to the reaction mixture, and the mixture was extracted with ethyl acetate (200 mL, 50 mL). The combined organic layer was washed with saturated brine (50 mL) and dried over anhydrous magnesium sulfate. The insoluble material was filtered off, and the filtrate was concentrated under reduced pressure to give ethyl ({5-[5-({[3-(1-cyano-1-methylethyl)phenyl]carbonyl}amino)-2-methylphenoxy]pyridin-2-yl}carbamothioyl)carbamate as a yellow amorphous solid. The obtained compound was used in the next reaction without further purification.

$^1$H-NMR (CDCl$_3$, 300 MHz) δ 1.35 (3H, t, J=7.2 Hz), 1.77 (6H, s), 2.25 (3H, s), 4.30 (2H, q, J=7.2 Hz), 7.28-7.34 (3H, m), 7.38 (1H, dd, J=8.1, 2.1 Hz), 7.51 (1H, t, J=7.6 Hz), 7.69 (1H, dd, J=2.1, 1.1 Hz), 7.70-7.74 (1H, m), 7.74-7.78 (1H, m), 7.94 (1H, t, J=1.7 Hz), 7.99 (1H, s), 8.16 (1H, d, J=2.8 Hz), 8.71 (1H, d, J=9.1 Hz), 12.00 (1H, s).

To a solution of the above-mentioned crude product, ethyl ({5-[5-({[3-(1-cyano-1-methylethyl)phenyl]carbonyl}amino)-2-methylphenoxy]pyridin-2-yl}carbamothioyl)carbamate, in methanol (100 mL)/ethanol (100 mL) were added hydroxylamine hydrochloride (5.08 g, 73.1 mmol) and N,N-diisopropylethylamine (15.3 mL, 87.8 mmol), and the mixture was stirred with heating at 60° C. for 15 hr. The reaction mixture was concentrated under reduced pressure, water (100 mL) was added to the residue, and the mixture was extracted with ethyl acetate (200 mL, 50 mL). The combined organic layer was washed with saturated brine (20 mL) and dried over anhydrous sodium sulfate. The insoluble material was filtered off, and the filtrate was concentrated under reduced pressure. The obtained residue was purified by basic silica gel column chromatography (NH silica gel, hexane/ethyl acetate=30/70→0/100), and fractions containing the desired product were concentrated under reduced pressure to give the title compound (1.81 g, 35%) as a colorless solid.

$^1$H-NMR (DMSO-$d_6$, 300 MHz) δ 1.71 (6H, s), 2.27 (3H, s), 6.00 (2H, s), 7.25-7.33 (3H, m), 7.41 (1H, dd, J=9.3, 1.5 Hz), 7.50-7.58 (2H, m), 7.71 (1H, ddd, J=7.9, 2.0, 1.0 Hz), 7.85 (1H, dt, J=7.8, 1.3 Hz), 7.95 (1H, t, J=1.7 Hz), 8.54 (1H, dd, J=2.3, 0.8 Hz), 10.22 (1H, s).

(v) N-{6-[5-({[3-(1-cyano-1-methylethyl)phenyl]carbonyl}amino)-2-methylphenoxy][1,2,4]triazolo[1,5-a]pyridin-2-yl}-1,3-oxazole-4-carboxamide To a solution of 1,3-oxazole-4-carboxylic acid (107 mg, 946 μmol) in tetrahydrofuran (3 mL) were added oxalyl chloride (123 μL, 1.42 mmol) and N,N-dimethylformamide (20 μL), and the mixture was stirred at room temperature for 1 hr. The reaction mixture was concentrated under reduced pressure. The obtained residue and N-{3-[(2-amino[1,2,4]triazolo[1,5-a]pyridin-6-yl)oxy]-4-methylphenyl}-3-(1-cyano-1-methylethyl)benzamide (202 mg, 473 μmol) were dissolved in pyridine (5 mL), and the mixture was stirred at room temperature for 15 hr. A saturated aqueous sodium hydrogen carbonate solution (10 mL) was added to the reaction mixture, and the mixture was extracted with ethyl acetate (30 mL, 2×10 mL). The combined organic layer was washed with saturated brine (10 mL) and dried over anhydrous sodium sulfate. The insoluble material was filtered off, and the filtrate was concentrated under reduced pressure. The obtained residue was purified by basic silica gel column chromatography (NH silica gel, ethyl acetate/methanol=100/0→98/2), and fractions containing the desired product were concentrated under reduced pressure. The obtained residue was recrystallized from ethanol to give the title compound (196 mg, 79%) as a colorless powder.

$^1$H-NMR (DMSO-$d_6$, 300 MHz) δ 1.71 (6H, s), 2.29 (3H, s), 7.24-7.38 (2H, m), 7.48-7.62 (3H, m), 7.71 (1H, ddd, J=7.9, 2.0, 0.9), 7.83 (1H, dd, J=9.6, 0.9 Hz), 7.87 (1H, dt, J=7.8, 0.9 Hz), 7.96 (1H, t, J=1.7 Hz), 8.61 (1H, d, J=0.9 Hz), 8.89 (1H, dd, J=2.4, 0.9 Hz), 8.90 (1H, d, J=0.9 Hz), 10.25 (1H, s), 10.79 (1H, s).

Example 240

N-{6-[5-({[3-(1-cyano-1-methylethyl)phenyl]carbonyl}amino)-2-methylphenoxy][1,2,4]triazolo[1,5-a]pyridin-2-yl}-1,3-thiazole-4-carboxamide

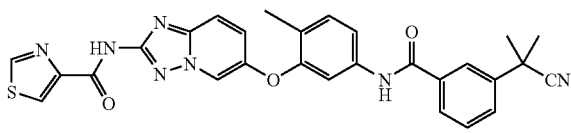

To a solution of 1,3-thiazole-4-carboxylic acid (121 mg, 938 μmol) in tetrahydrofuran (3 mL) were added oxalyl chloride (102 μL, 1.17 mmol) and N,N-dimethylformamide (20 μL) and the mixture was stirred at room temperature for 1 hr. The reaction mixture was concentrated under reduced pressure. The obtained residue and N-{3-[(2-amino[1,2,4]triazolo[1,5-a]pyridin-6-yl)oxy]-4-methylphenyl}-3-(1-cyano-1-methylethyl)benzamide (200 mg, 0.469 mmol) were dissolved in pyridine (5 mL), and the mixture was stirred at room temperature for 16 hr. A saturated aqueous sodium hydrogen carbonate solution (15 mL) was added to the reaction mixture, and the mixture was extracted with ethyl acetate (20 mL, 5 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→99/1), and fractions containing the desired product were concentrated under reduced pressure. Diisopropyl ether was added to the obtained residue. The obtained precipitate was collected by filtration, and dried to give the title compound (206 mg, 82%) as a colorless powder.

$^1$H-NMR (DMSO-$d_6$, 300 MHz) δ 1.71 (6H, s), 2.23 (3H, s), 7.27-7.36 (2H, m), 7.50-7.62 (3H, m), 7.71 (1H, ddd, J=7.9, 2.0, 1.0 Hz), 7.80-7.89 (2H, m), 7.96 (1H, t, J=1.7 Hz), 8.61 (1H, d, J=2.0 Hz), 8.89 (1H, dd, J=2.3, 0.8 Hz), 9.28 (1H, d, J=2.0 Hz), 10.25 (1H, s), 10.72 (1H, s).

Example 241

N-{6-[5-({[3-(1-cyano-1-methylethyl)phenyl]carbonyl}amino)-2-methylphenoxy][1,2,4]triazolo[1,5-a]pyridin-2-yl}pyridine-3-carboxamide

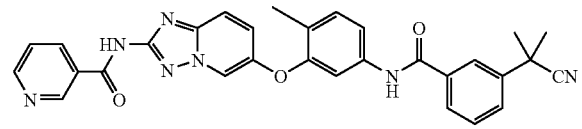

To a solution of N-{3-[(2-amino[1,2,4]triazolo[1,5-a]pyridin-6-yl)oxy]-4-methylphenyl}-3-(1-cyano-1-methylethyl)benzamide (200 mg, 0.469 mmol) in pyridine (5 mL) was added pyridine-3-carbonyl hydrochloride (212 mg, 1.19 mmol), and the mixture was stirred at room temperature for 3 hr. A saturated aqueous sodium hydrogen carbonate solution (20 mL) was added to the reaction mixture, and the mixture was extracted with ethyl acetate (20 mL, 5 mL). The combined organic layer was washed with saturated brine (5 mL) and dried over anhydrous sodium sulfate. The insoluble material was filtered off, and the filtrate was concentrated under reduced pressure. Ethyl acetate was added to the obtained residue. The obtained precipitate was collected by filtration and dried to give the title compound (245 mg, 97%) as a colorless powder.

$^1$H-NMR (DMSO-$d_6$, 300 MHz) δ 1.71 (6H, s), 2.30 (3H, s), 7.28-7.39 (2H, m), 7.49-7.63 (4H, m), 7.72 (1H, ddd, J=8.0, 2.0, 1.0 Hz), 7.80-7.91 (2H, m), 7.96 (1H, t, J=1.7 Hz), 8.34 (1H, ddd, J=8.0, 2.3, 1.7 Hz), 8.78 (1H, dd, J=4.9, 1.7 Hz), 8.90 (1H, dd, J=2.3, 0.6 Hz), 9.14 (1H, dd, J=2.3, 0.9 Hz), 10.26 (1H, s), 11.47 (1H, s).

Example 242

N-{6-[5-({[3-(1-cyano-1-methylethyl)phenyl]carbonyl}amino)-2-methylphenoxy][1,2,4]triazolo[1,5-a]pyridin-2-yl}pyridine-2-carboxamide

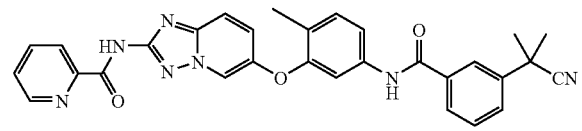

To a solution of pyridine-2-carboxylic acid (234 mg, 1.90 mmol) in tetrahydrofuran (6 mL) were added oxalyl chloride (206 μL, 2.38 mmol) and N,N-dimethylformamide (20 μL), and the mixture was stirred at room temperature for 1 hr. The reaction mixture was concentrated under reduced pressure. The obtained residue and N-{3-[(2-amino[1,2,4]triazolo[1,5-a]pyridin-6-yl)oxy]-4-methylphenyl}-3-(1-cyano-1-methylethyl)benzamide (203 mg, 0.475 mmol) were dissolved in pyridine (7 mL), and the mixture was stirred at room temperature for 23 hr. A saturated aqueous sodium hydrogen carbonate solution (50 mL) was added to the reaction mixture, and the mixture was extracted with ethyl acetate (50 mL, 20 mL). The combined organic layer was washed with saturated brine (10 mL) and dried over anhydrous sodium sulfate. The insoluble material was filtered off, and the filtrate was concentrated under reduced pressure. The obtained residue was purified by silica gel column chromatography (NH silica gel, hexane/ethyl acetate=40/60→20/80), and fractions containing the desired product were concentrated under reduced pressure. The crystals precipitated during concentration were collected by filtration and dried to give the title compound (146 mg, 58%) as colorless crystals.

$^1$H-NMR (DMSO-$d_6$, 300 MHz) δ 1.71 (6H, s), 2.30 (3H, s), 7.28-7.36 (2H, m), 7.52-7.62 (3H, m), 7.68-7.76 (2H, m), 7.80-7.90 (2H, m), 7.96 (1H, t, J=1.7 Hz), 8.10 (1H, dt, J=7.8, 1.8 Hz), 8.18 (1H, dt, J=7.8, 1.2 Hz), 8.76 (1H, ddd, J=4.8, 1.6, 0.9 Hz), 8.90 (1H, dd, J=2.4, 0.7 Hz), 10.25 (1H, s), 10.91 (1H, s).

Example 243

N-{6-[5-({[3-(1-cyano-1-methylethyl)phenyl]carbonyl}amino)-2-methylphenoxy][1,2,4]triazolo[1,5-a]pyridin-2-yl}-6-methylpyridine-3-carboxamide

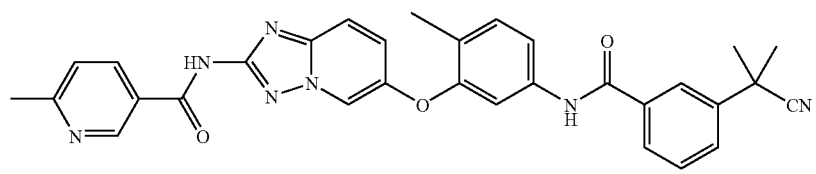

To a solution of 6-methylpyridine-3-carboxylic acid (252 mg, 1.84 mmol) in tetrahydrofuran (6 mL) were added oxalyl chloride (200 μL, 2.30 mmol) and N,N-dimethylformamide (20 μL), and the mixture was stirred at room temperature for 1 hr. The reaction mixture was concentrated under reduced pressure. The obtained residue and N-{3-[(2-amino[1,2,4]triazolo[1,5-a]pyridin-6-yl)oxy]-4-methylphenyl}-3-(1-cyano-1-methylethyl)benzamide (196 mg, 0.460 mmol) were dissolved in pyridine (7 mL), and the mixture was stirred at room temperature for 7 days. A saturated aqueous sodium hydrogen carbonate solution (20 mL) was added to the reaction mixture, and the mixture was extracted with ethyl acetate (30 mL, 10 mL). The combined organic layer was washed with saturated brine (10 mL) and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→99.5/0.5), and fractions containing the desired product were concentrated under reduced pressure. The obtained residue was recrystallized from methanol to give the title compound (124 mg, 49%) as colorless crystals.

$^1$H-NMR (DMSO-$d_6$, 300 MHz) δ 1.71 (6H, s), 2.30 (3H, s), 2.56 (3H, s), 7.29-7.36 (2H, m), 7.41 (1H, d, J=8.1 Hz), 7.50-7.62 (3H, m), 7.72 (1H, ddd, J=7.9, 2.0, 1.0 Hz), 7.82 (1H, dd, J=9.6, 0.6 Hz), 7.87 (1H, dt, J=7.9, 1.2 Hz), 7.96 (1H, t, J=1.8 Hz), 8.24 (1H, dd, J=8.1, 2.3 Hz), 8.89 (1H, dd, J=2.3, 0.6 Hz), 9.03 (1H, d, J=1.8 Hz), 10.26 (1H, s), 11.36 (1H, s).

Example 244

5-bromo-N-{6-[5-({[3-(1-cyano-1-methylethyl)phenyl]carbonyl}amino)-2-methylphenoxy][1,2,4]triazolo[1,5-a]pyridin-2-yl}pyridine-3-carboxamide

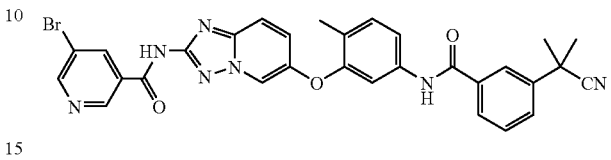

To a solution of 5-bromopyridine-3-carboxylic acid (375 mg, 1.87 mmol) in tetrahydrofuran (6 mL) were added oxalyl chloride (204 μL, 2.34 mmol) and N,N-dimethylformamide (20 μL), and the mixture was stirred at room temperature for 1 hr. The reaction mixture was concentrated under reduced pressure. The obtained residue and N-{3-[(2-amino[1,2,4]triazolo[1,5-a]pyridin-6-yl)oxy]-4-methylphenyl}-3-(1-cyano-1-methylethyl)benzamide (400 mg, 0.937 mmol) were dissolved in pyridine (7 mL), and the mixture was stirred at room temperature for 1 hr. Water (15 mL) was added to the reaction mixture, and the mixture was extracted with ethyl acetate (15 mL, 5 mL). The combined organic layer was washed with saturated aqueous sodium hydrogen carbonate solution (3 mL) and saturated brine (2 mL), and dried over anhydrous sodium sulfate. The insoluble material was filtered off, and the filtrate was concentrated under reduced pressure. To the obtained residue in methanol-tetrahydrofuran mixed solution (2:1, 6 mL) was added potassium carbonate (130 mg, 0.937 mmol), and the mixture was stirred at room temperature for 14 hr. A saturated aqueous sodium hydrogen carbonate solution (15 mL) was added to the reaction mixture, and the mixture was extracted with ethyl acetate (15 mL, 5 mL). The combined organic layer was washed with saturated brine (5 mL) and dried over anhydrous sodium sulfate. The insoluble material was filtered off, and the filtrate was concentrated under reduced pressure. The obtained residue was purified by silica gel column chromatography (NH silica gel, hexane/ethyl acetate=30/70→0/100), and fractions containing the desired product were concentrated under reduced pressure. Diisopropyl ether was added to the obtained residue. The obtained precipitate was collected by filtration and dried to give the title compound (490 mg, 86%) as a colorless powder.

$^1$H-NMR (DMSO-$d_6$, 300 MHz) δ 1.71 (6H, s), 2.30 (3H, s), 7.27-7.38 (2H, m), 7.51-7.61 (3H, m), 7.72 (1H, ddd, J=7.9, 2.0, 1.0 Hz), 7.79-7.89 (2H, m), 7.96 (1H, t, J=1.7 Hz), 8.58 (1H, t, J=2.1 Hz), 8.90 (1H, dd, J=2.4, 0.7 Hz), 8.93 (1H, d, J=2.1 Hz), 9.09 (1H, d, J=1.7 Hz), 10.26 (1H, s), 11.58 (1H, s).

Example 245

3-(1-cyano-1-methylethyl)-N-[3-({2-[(hydroxyacetyl)amino][1,2,4]triazolo[1,5-a]pyridin-6-yl}oxy)-4-methylphenyl]benzamide

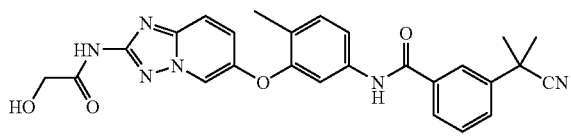

To a solution of N-{3-[(2-amino[1,2,4]triazolo[1,5-a]pyridin-6-yl)oxy]-4-methylphenyl}-3-(1-cyano-1-methylethyl)benzamide (203 mg, 0.477 mmol) in pyridine (10 mL) was added 2-chloro-2-oxoethyl acetate (103 μL, 0.954 mmol), and the mixture was stirred at room temperature for 17 hr. The reaction solution was concentrated under reduced pressure, and the residue was dissolved in methanol (10 mL). Potassium carbonate (132 mg, 0.954 mmol) was added thereto, and the mixture was stirred at room temperature for 1 hr. Water (30 mL) was added to the reaction mixture, and the mixture was extracted with ethyl acetate (50 mL, 2×10 mL). The combined organic layer was washed with saturated brine (10 mL) and dried over anhydrous sodium sulfate. The insoluble material was filtered off, and the filtrate was concentrated under reduced pressure. Ethyl acetate and diisopropyl ether were added to the obtained residue. The obtained precipitate was collected by filtration and dried to give the title compound (182 mg, 79%) as a colorless powder.

$^1$H-NMR (DMSO-$d_6$, 300 MHz) δ 1.71 (6H, s), 2.27 (3H, s), 4.11 (2H, br s), 5.49 (1H, br s), 7.29-7.34 (2H, m), 7.50-7.59 (3H, m), 7.69-7.74 (1H, m), 7.78 (1H, dd, J=9.5, 0.7 Hz), 7.83-7.88 (1H, m), 7.95 (1H, t, J=1.8 Hz), 8.83 (1H, dd, J=2.3, 0.8 Hz), 10.25 (1H, s), 10.40 (1H, s).

Example 246

3-(1-cyano-1-methylethyl)-N-{4-methyl-3-[(2-{[(4-methylpiperazin-1-yl)acetyl]amino}[1,2,4]triazolo[1,5-a]pyridin-6-yl)oxy]phenyl}benzamide

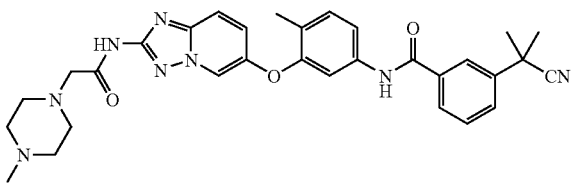

To a solution of N-{3-[(2-amino[1,2,4]triazolo[1,5-a]pyridin-6-yl)oxy]-4-methylphenyl}-3-(1-cyano-1-methylethyl)benzamide (202 mg, 0.474 mmol) in N,N-dimethylformamide (5 mL) was added chloroacetyl chloride (76 μL, 0.948 mmol), and the mixture was stirred at room temperature for 4 hr. Water (15 mL) was added to the reaction mixture, and extracted with ethyl acetate (20 mL, 2×10 mL). The combined organic layer was washed with saturated brine (10 mL), and dried over anhydrous sodium sulfate. The insoluble material was filtered off, and the filtrate was concentrated under reduced pressure. The residue was dissolved in tetrahydrofuran (5 mL). Triethylamine (197 μL, 1.42 mmol) and 1-methylpiperazine (158 μL, 1.42 mmol) were added, and the mixture was stirred at 60° C. for 19 hr. A saturated aqueous sodium hydrogen carbonate solution (10 mL) was added to the reaction mixture, and the mixture was extracted with ethyl acetate (20 mL). The organic layer was washed with saturated brine (10 mL) and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→94/6), and fractions containing the desired product were concentrated under reduced pressure. Diisopropyl ether was added to the obtained residue. The obtained precipitate was collected by filtration and dried to give the title compound (173 mg, 64%) as a colorless powder.

$^1$H-NMR (DMSO-$d_6$, 300 MHz) δ 1.71 (6H, s), 2.16 (3H, s), 2.29 (3H, s), 2.35 (4H, br s), 2.53 (4H, br s), 3.20 (2H, s), 7.27-7.36 (2H, m), 7.49-7.59 (3H, m), 7.72 (1H, ddd, J=7.8, 2.0, 1.0 Hz), 7.77 (1H, dd, J=9.6, 0.8 Hz), 7.86 (1H, dt, J=7.8, 1.3 Hz), 7.96 (1H, t, J=1.7 Hz), 8.83 (1H, dd, J=2.3, 0.8 Hz), 10.25 (1H, s), 10.39 (1H, s).

Example 247

3-(1-cyano-1-methylethyl)-N-[4-methyl-3-({2-[(morpholin-4-ylacetyl)amino][1,2,4]triazolo[1,5-a]pyridin-6-yl}oxy)phenyl]benzamide

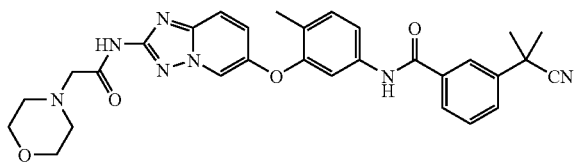

To a solution of N-{3-[(2-amino[1,2,4]triazolo[1,5-a]pyridin-6-yl)oxy]-4-methylphenyl}-3-(1-cyano-1-methylethyl)benzamide (199 mg, 0.468 mmol) in N,N-dimethylformamide (5 mL) was added chloroacetyl chloride (76 μL, 0.842 mmol), and the mixture was stirred at room temperature for 1 hr. Water (15 mL) was added to the reaction mixture, and extracted with ethyl acetate (20 mL, 2×5 mL). The combined organic layer was washed with saturated brine (10 mL), and dried over anhydrous sodium sulfate. The insoluble material was filtered off, and the filtrate was concentrated under reduced pressure. The obtained residue was purified by silica gel column chromatography (hexane/ethyl acetate=40/60→20/80), and fractions containing the desired product were concentrated under reduced pressure. The residue was dissolved in tetrahydrofuran (5 mL). Triethylamine (195 μL, 1.40 mmol) and morpholine (122 μL, 1.40 mmol) were added, and the mixture was stirred at 60° C. for 3 hr. Water (20 mL) was added to the reaction mixture, and the mixture was extracted with ethyl acetate (20 mL, 2×5 mL). The combined organic layer was washed with saturated brine (5 mL), and dried over anhydrous sodium sulfate. The insoluble material was filtered off, and the filtrate was concentrated under reduced pressure. The obtained residue was purified by silica gel column chromatography (NH silica gel, ethyl acetate/methanol=100/0→99/1), and fractions containing the desired product were concentrated under reduced pressure. Diisopropyl ether was added to the obtained residue. The obtained precipitate was collected by filtration and dried over to give the title compound (144 mg, 56%) as a colorless powder.

$^1$H-NMR (DMSO-d$_6$, 300 MHz) δ 1.71 (6H, s), 2.28 (3H, s), 2.48-2.55 (4H, m), 3.23 (2H, s), 3.57-3.65 (4H, m), 7.28-7.36 (2H, m), 7.49-7.58 (3H, m), 7.71 (1H, ddd, J=7.8, 2.0, 0.9 Hz), 7.77 (1H, dd, J=9.5, 0.7 Hz), 7.81-7.90 (1H, m), 7.95 (1H, t, J=1.7 Hz), 8.83 (1H, dd, J=2.4, 0.7 Hz), 10.25 (1H, s), 10.48 (1H, s).

Example 248

3-(1-cyano-1-methylethyl)-N-{4-methyl-3-[(2-{[4-(4-methylpiperazin-1-yl)butanoyl]amino}[1,2,4]triazolo[1,5-a]pyridin-6-yl)oxy]phenyl}benzamide

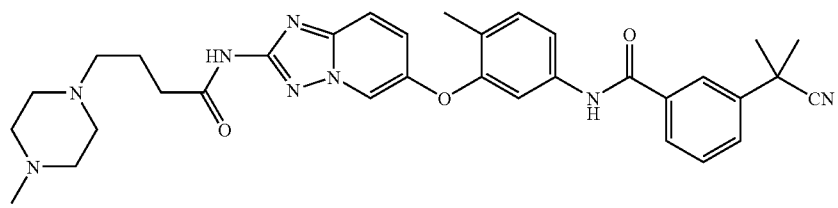

To a solution of N-{3-[(2-amino[1,2,4]triazolo[1,5-a]pyridin-6-yl)oxy]-4-methylphenyl}-3-(1-cyano-1-methylethyl)benzamide (153 mg, 0.359 mmol) in N,N-dimethylformamide (5 mL) was added 4-chlorobutanoyl chloride (81 μL, 0.718 mmol), and the mixture was stirred at room temperature for 1 hr. A saturated aqueous sodium hydrogen carbonate solution (15 mL) was added to the reaction mixture, and the mixture was extracted with ethyl acetate (15 mL, 5 mL). The combined organic layer was washed with saturated brine (5 mL) and dried over anhydrous magnesium sulfate. The insoluble material was filtered off, and the filtrate was concentrated under reduced pressure. The residue was dissolved in tetrahydrofuran (3 mL). Triethylamine (149 μL, 1.08 mmol) and 1-methylpiperazine (120 μL, 1.08 mmol) were added, and the mixture was stirred at 60° C. for 14 hr. 1-Methylpiperazine (399 μL, 3.59 mmol) was added to the reaction mixture, and the mixture was further stirred at 60° C. for 5 hr. Water (15 mL) was added to the reaction mixture, and the mixture was extracted with ethyl acetate (15 mL, 2×5 mL). The combined organic layer was washed with saturated brine (5 mL) and dried over anhydrous sodium sulfate. The insoluble material was filtered off, and the filtrate was concentrated under reduced pressure. The obtained residue was purified by silica gel column chromatography (NH silica gel, hexane/ethyl acetate=30/70→0/100, ethyl acetate/methanol=100/0→95/5), and fractions containing the desired product were concentrated under reduced pressure. The obtained residue was purified by preparative HPLC, and fractions containing the desired product were concentrated under reduced pressure. A saturated aqueous sodium hydrogen carbonate solution (10 mL) was added to the obtained residue, and the mixture was extracted with ethyl acetate (15 mL). The organic layer was washed with saturated brine (5 mL), and dried over anhydrous sodium sulfate. The insoluble material was filtered off, and the filtrate was concentrated under reduced pressure. Ethyl acetate and hexane were added to the obtained residue. The obtained precipitate was collected by filtration, and dried to give the title compound (12 mg, 6%) as a colorless powder.

$^1$H-NMR (DMSO-d$_6$, 300 MHz) δ 1.58-1.85 (8H, m), 2.11 (3H, s), 2.18-2.70 (15H, m), 7.20-7.41 (2H, m), 7.46-7.62 (3H, m), 7.64-7.80 (2H, m), 7.86 (1H, d, J=7.4 Hz), 7.96 (1H, s), 8.80 (1H, s), 10.26 (1H, s), 10.74 (1H, s).

Formulation Example 1

A pharmaceutical agent containing the compound of the present invention as an active ingredient can be produced, for example, according to the following formulation.

| 1. Capsule | |
|---|---|
| (1) compound obtained in Example 1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended, granulated and the rest of (4) are added thereto. The whole mixture is sealed in a gelatin capsule.

| 2. Tablet | |
|---|---|
| (1) compound obtained in Example 2 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4), and ½ of (5) are blended and granulated. The rest of (4) and (5) are added to the granules. The mixture is compression-formed into a tablet.

Formulation Example 2

The compound (50 mg) obtained Example 2 is dissolved in Japanese Pharmacopoeia distilled water for injection (50 mL), and the Japanese Pharmacopoeia distilled water for injection is added to 100 mL. This solution is filtrated under sterile conditions. The solution (1 mL) is taken, filled in a vial for injection under sterile conditions, freeze-dried and sealed.

Experimental Example 1 Human Vascular Endothelial Growth Factor Receptor 2 (VEGFR2) Gene and Preparation of Recombinant Baculovirus Human vascular endothelial growth factor receptor 2 (hereinafter to be referred to as VEGFR2) gene was cloned by PCR using cDNA Libraries Human Placenta (Clontech) as a template. The primer used for PCR was prepared from base sequence (Genbank Accession AF035121) information of VEGFR2 gene by adding a base sequence encoding flag peptide and a recognition sequence of the restriction enzyme to a base sequence (2671-4374 of Genbank Accession AF035121) encoding the VEGFR2 intracellular domain region, so that the protein contains an N-terminal Flag tag. The primer base sequence is shown below.

```
VEGFR2-U:
5'-                                                              (SEQ ID NO: 1)
AATTAAGTCGACATGGACTACAAGGATGACGATGACAAGAAGCGGGCCAATGGAGGGGAACTGAA
GACA-3'
and VEGFR2-L:
5'-AATTAAGCATGCTTAAACAGGAGGAGAGCTCAGTGTGGTCCC-3'                 (SEQ ID NO: 2)
```

The base sequence of primer VEGFR2-U is shown in SEQUENCE LISTING SEQ ID NO:1, and the base sequence of primer VEGFR2-L is shown in SEQUENCE LISTING SEQ ID NO:2.

The PCR reaction was conducted using a KOD-plus kit (TOYOBO). The obtained PCR product was electrophoresed on agarose gel (1%), the DNA fragment amplified by PCR was recovered from the gel, and then digested with restriction enzymes Sal I and Sph I. The DNA treated with the restriction enzymes was electrophoresed on agarose gel (1%), and the obtained DNA fragment was recovered and ligated to plasmid pFASTBAC1 (Invitrogen) digested with restriction enzymes Sal I and Sph I to give expression plasmid pFB-VEGFR2. The base sequence of the insert fragment was confirmed and found to be identical with the base sequence (2671-4374 of Genbank Accession AF035121) of VEGFR2 intracellular domain. Furthermore, using BAC-TO-BAC Baculovirus Expression System (Invitrogen), virus stock BAC-VEGFR2 of recombinant baculovirus was prepared.

Experimental Example 2 VEGF Receptor 2 (VEGFR2) Intracellular Domain Protein

SF-21 cells were sown at $1 \times 10^6$ cells/mL to Sf-900II SEM medium (1 L, Invitrogen) containing 10% fetal bovine serum (trace), 50 mg/L Gentamicin (Invitrogen) and 0.1% Pluronic F-68 (Invitrogen), and shaking culture was performed using a 2 L volume Erlenmeyer flask at 27° C., 100 rpm. After culturing for 24 hrs, recombinant baculovirus BAC-VEGFR2 (13.4 mL) was added to the mixture, and the mixture was further cultured for 3 days. The culture medium was centrifuged at 2,000 rpm for 5 min to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min and filtered with a 0.45 µm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 µg/mL of FLAG peptide. The eluate was concentrated with Vivaspin 20 (Vivascience) having a molecular weight cut off of 30K. The buffer of this concentrate was exchanged using NAP™ 25 column (Amersham Bioscience) equilibrated with buffer A. The fractions containing intracellular domain protein of VEGFR2 were collected, glycerol was added to the final concentration of 50% and cryopreserved at −80° C.

Test Example 1 Determination of VEGF Receptor 2 Kinase Inhibitory Activity

A test compound dissolved in DMSO was diluted with a buffer (50 mM Tris-HCl (pH 7.5), 5 mM $MgCl_2$, 5 mM $MnCl_2$, 2 mM dithiothreitol, 0.01% Tween-20). To this compound solution (5 µL) was added a buffer (10 µL) containing 50 ng/mL of VEGFR2 intracellular domain protein and 250 ng/mL of biotin labeled polypeptide biotinyl-poly-Glu:Tyr (4:1, CIS bio International). To the obtained mixture was added a buffer (10 µL) containing ATP (25 µM), the mixture was allowed to react at 25° C. for 5 min and the reaction was quenched with 25 µL of a stop solution (100 mM EDTA disodium salt, 62.5 mM HEPES buffer (pH 7.4), 250 mM NaCl, 0.1% bovine serum albumin, 10 µg/mL AlphaScreen assay streptavidin donor beads (Streptavidin Donor beads: PerkinElmer), 10 µg/mL AlphaScreen assay anti-phosphotyrosine recognition antibody PY-100 binding acceptor beads (Anti-phosphotyrosine (P-Tyr-100) Acceptor beads: PerkinElmer)). The reaction solution was allowed to stand at 25° C. for 16 hrs, and the wells were counted using a plate reader Fusion™ (PerkinElmer). The kinase inhibitory rate (%) of the test compound was calculated by the following formula:

Inhibitory rate(%)=(1−(count of test compound−blank)÷(control−blank))×100

The count of the solution reacted without addition of the compound was used as a "control", and the count of the solution without the compound and ATP was used as a "blank". The inhibitory rate of the compounds of Examples 2, 7-4, 9-2, 10, 16, 17-2, 22, 23-2, 72, 96-4, 97-2, 99 and 127-2 at 1 µM was not less than 90%.

Test Example 2 Vascular Endothelial Cell Growth Inhibitory Test

Human umbilical vein vascular endothelial cells (HUVEC purchased from KURABO INDUSTRIES LTD.) were cultured in an incubator at 37° C., 5% carbon dioxide in a vascular endothelial cell medium (Invitrogen) containing 3% bovine fetal serum and 2.5 ng/mL basic fibroblast growth factor. To be specific, HUVEC was suspended in a vascular endothelial cell medium containing the aforementioned 3% bovine fetal serum and plated in a 96 well flat bottom plate by 50 µL (3000 cells) each well. After culture overnight, various concentrations of the test substance and 120 ng/mL of vascular endothelial growth factor (VEGF) were dissolved in a vascular endothelial cell medium containing 3% bovine fetal serum and added to each well by 50 µL. After 5 days of culture, a WST-8 reagent (DOJINDO LABORATORIES) was added to each well by 10 µL, and the mixture was reacted in an incubator at 37° C., 5% carbon dioxide for 2-3 hr. The absorbance at 450 nm was measured by a microtiter plate reader and the cell growth inhibitory activity was determined. Using the absorbance with addition of a test substance at each concentration and based on the nonlinear least-squares analysis using a logistic curve of SAS system NLIN procedure, the concentration of the test substance ($IC_{50}$ value) necessary for showing 50% of the value obtained without addition of the test substance was calculated.

As a result, $IC_{50}$ value of the compounds of Examples 2, 7-4, 9-2, 10, 16, 17-2, 22, 23-2, 72, 96-4, 97-2, 99 and 127-2 was not more than 500 nM.

Test Example 3 Antitumor Test

Cancer cells are cultivated in an incubator at 37° C., 5% carbon dioxide in a culture medium containing 10% bovine fetal serum. The cells are isolated by a trypsin treatment, washed with HBSS (HANK's Balanced Saline Solution) and adjusted to cell density of $5 \times 10^7$ cells/mL with HBSS. The cell suspension (0.1 mL, $5 \times 10^6$ cells) is transplanted by subcutaneously injecting into the abdomen of 6-week-old female nude mice (BALB/c nu/nu, CLEA Japan, Inc.). When the tumor volume reached 100-200 mm³, the mice are grouped, and orally administered with various doses of test substance for 14 consecutive days starting from the next day. The major axis length and minor axis length of the tumor are measured over time and the tumor volume is calculated from tumor volume=major axis length×minor axis length×minor axis length×0.5.

Test Example 4 Determination of Platelet-Derived Growth Factor Receptor α (PDGFRα) Kinase Inhibitory Activity A test compound dissolved in dimethyl sulfoxide (DMSO) was diluted with a buffer (50 mM Tris-HCl (pH 7.5), 5 mM $MgCl_2$, 5 mM $MnCl_2$, 2 mM dithiothreitol, 0.01% Tween-20). To this compound solution (5 μL) was added a buffer (10 μL) containing 125 ng/ml of PDGFα intracellular domain protein (UPSTATE) and 250 ng/mL of biotin labeled polypeptide biotinyl-poly-Glu:Tyr (4:1) (CIS bio International). At 5 min after mixing kinase enzyme and the compound and biotin labeled polypeptide, to the obtained mixture was added a buffer (10 μL) containing ATP (25 μM), the mixture was allowed to react at 25° C. for 30 min and the reaction was quenched with 25 μL of a stop solution (100 mM EDTA disodium salt, 62.5 mM HEPES buffer (pH 7.4), 250 mM NaCl, 0.1% bovine serum albumin, 10 μg/mL AlphaScreen assay streptavidin donor beads (Streptavidin Donor beads: PerkinElmer), 10 μg/mL AlphaScreen assay anti-phosphotyrosine recognition antibody PT-66 binding acceptor beads (Anti-phosphotyrosine (P-Tyr-66) Acceptor beads: PerkinElmer)). The reaction solution was allowed to stand at 25° C. for 16 hrs, and the wells were counted using a plate reader Fusion™ (PerkinElmer). The kinase inhibitory rate (%) of the test compound was calculated by the following formula:

Inhibitory rate(%)=(1−(count of test compound−blank)÷(control−blank))×100

The count of the solution reacted without addition of the compound was used as a "control", and the count of the solution without the compound and ATP was used as a "blank".

The $IC_{50}$ value of the compounds of Examples 2, 7-4, 9-2, 10, 16, 17-2, 22, 23-2, 72, 96-4, 97-2, 99 and 127-2 was not more than 500 nM.

Test Example 5 Determination of Platelet-Derived Growth Factor Receptor β (PDGFRβ) Kinase Inhibitory Activity A test compound dissolved in dimethyl sulfoxide (DMSO) was diluted with a buffer (50 mM Tris-HCl (pH 7.5), 5 mM $MgCl_2$, 5 mM $MnCl_2$, 2 mM dithiothreitol, 0.01% Tween-20). To this compound solution (5 μL) was added a buffer (10 μL) containing 125 ng/ml of PDGFRβ intracellular domain protein (UPSTATE) and 250 ng/mL of biotin labeled polypeptide biotinyl-poly-Glu:Tyr (4:1) (CIS bio International). At 5 min after mixing kinase enzyme and the compound and biotin labeled polypeptide, to the obtained mixture was added a buffer (10 μL) containing ATP (50 μM), the mixture was allowed to react at 25° C. for 60 min and the reaction was quenched with 25 μL of a stop solution (100 mM EDTA disodium salt, 62.5 mM HEPES buffer (pH 7.4), 250 mM NaCl, 0.1% bovine serum albumin, 10 μg/mL AlphaScreen assay streptavidin donor beads (Streptavidin Donor Beads: PerkinElmer), 10 μg/mL AlphaScreen assay anti-phosphotyrosine recognition antibody PT-66 binding acceptor beads (Anti-phosphotyrosine (P-Tyr-66) Acceptor beads: PerkinElmer)). The reaction solution was allowed to stand at 25° C. for 16 hr, and the wells were counted using a plate reader Fusion™ (PerkinElmer). The kinase inhibitory rate (%) of the test compound was calculated by the following formula:

Inhibitory rate(%)=(1−(count of test compound−blank)÷(control−blank))×100

The count of the solution reacted without addition of the compound was used as a "control", and the count of the solution without the compound and ATP was used as a "blank".

The $IC_{50}$ value of the compounds of Examples 2, 7-4, 9-2, 10, 16, 17-2, 22, 23-2, 72, 96-4, 97-2, 99 and 127-2 was not more than 500 nM.

Experimental Example 3 Cloning of Human BRAF Gene and Preparation of Recombinant Baculovirus Human BRAF gene was cloned by PCR using human Testis cDNA library (Clontech) as a template. The primer used for PCR was prepared from base sequence (Genbank Accession NM_004333) information of BRAF gene by adding a base sequence encoding flag peptide and a recognition sequence of the restriction enzyme to area encoding the BRAF kinase domain region, so that the protein contains an N-terminal Flag. The primer base sequence is shown below.

BRAF-U:
5'- (SEQ ID NO: 3)

AAAGAATTCACCATGGACTACAAGGACGACGATGACAAGACCCCCCCTGCCTCATTACCTGGCT-

3'
and

BRAF-L:
5'-AAAAGTCGACTCAGTGGACAGGAAACGCACCATAT-3' (SEQ ID NO: 4)

The PCR reaction was conducted using Pyrobest (Takara Shuzo Co., Ltd). The obtained PCR product was electrophoresed on agarose gel (1%), the DNA fragment amplified by PCR was recovered from the gel, and then digested with restriction enzymes EcoRI and SalI. The DNA treated with the restriction enzymes was electrophoresed on agarose gel (1%), and the obtained DNA fragment was recovered. The recovered DNA fragment was ligated to plasmid pFAST-BAC1 (Invitrogen) digested with restriction enzymes EcoRI and SalI to give expression plasmid pFB-BRAF, and the base sequence of the insert fragment was confirmed. In addition, mutation was introduced into V600E using a Quick change Site Directed Mutagenesis kit (Stratagene). The nucleotide sequences of the primers used are shown in the following.

V600E-U:
5'-GGTCTAGCTACAGAGAAATCTCGATGGAG-3'  (SEQ ID NO: 5)
and

V600E-L:
5'-CTCCATCGAGATTTCTCTGTAGCTAGACC-3'  (SEQ ID NO: 6)

The obtained plasmid was sequenced to confirm the introduction of mutation into V600E. The plasmid DNA was digested with restriction enzymes EcoRI and SalI, DNA treated with the restriction enzymes was electrophoresed on agarose gel (1%), and the obtained DNA fragment was recovered. The recovered DNA fragment was ligated to plasmid pFAST-BAC1 (Invitrogen) digested with restriction enzymes EcoRI and SalI to give expression plasmid pFB-V600E.

Using BAC-TO-BAC Baculovirus Expression System (Invitrogen), virus stock BAC-V600E of recombinant baculovirus was prepared.

Experimental Example 4 Preparation of BRAF (V600E) Protein

SF-21 cells were sown at $1 \times 10^6$ cells/mL to Sf-900II SFM medium (1 L, Invitrogen) containing 10% fetal bovine serum (Trace), 50 mg/L Gentamicin (Invitrogen) and 0.1% Pluronic F-68 (Invitrogen), and shaking culture was performed using a 2 L volume Erlenmeyer flask at 27° C., 100 rpm. After culturing for 24 hr, recombinant baculovirus BAC-V600E (13.4 mL) was added to the mixture, and the mixture was further cultured for 3 days. The culture medium was centrifuged at 2,000 rpm for 5 min to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min and filtered with a 0.45 μm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 μg/mL of FLAG peptide. The buffer of this concentrate was exchanged using NAP25 column (Amersham Bioscience) equilibrated with buffer A and the fractions were cryopreserved at −80° C.

Test Example 6

Determination of BRAF (V600E) Kinase Inhibitory Activity

A test compound (2.5 μL) dissolved in dimethyl sulfoxide (DMSO) was added to 37.5 μL of a reaction solution (25 mM HEPES (pH 7.5), 10 mM magnesium acetate, 1 mM dithiothreitol) containing BRAF (V600E) enzyme (30 ng) and recombinant type protein GST-MEK1 (K96R) 250 ng, and the mixture was incubated at room temperature for 10 min. ATP solution (10 μL, 2.5 μM ATP, 0.1 μCi [γ-$^{32}$P]ATP) was added to the obtained mixture, and the mixture was reacted at room temperature for 20 min. The reaction was quenched by adding 50 μL of ice-cooled 20% trichloroacetic acid (Wako Pure Chemical Industries, Ltd.). The reaction solution was allowed to stand at 4° C. for 30 min, and the acid-precipitable fraction was transferred to GF/C filter plate (Millipore Corporation) using cell harvester (PerkinElmer). The plate was dried at 45° C. for 60 min, and 40 μL of MicroScinti 0 (PerkinElmer) was added thereto. The radioactivity was measured using TopCount (PerkinElmer). The kinase inhibitory rate (%) of the test compound was calculated by the following formula:

$$\text{Inhibitory rate}(\%) = (1 - (\text{count of test compound} - \text{blank}) \div (\text{control} - \text{blank})) \times 100$$

The count of the solution reacted without addition of the compound was used as a "control", and the count of the solution without the compound and enzyme was used as a "blank".

The obtained results are shown in Table 10. The results show that the compound of the present invention strongly inhibits an activity of BRAF (V600E) kinase.

TABLE 10

| Example No. (compound No.) | The inhibitory rate of the compounds at 1 μM (%) |
|---|---|
| 226 | 100 |
| 231 | 100 |
| 235 | 100 |

Test Example 7

Colon Cancer Cell HT-29 Intracellular MEK Phosphorylation Inhibitory Action In Vitro A cell suspension (500 μL) of human colon cancer cell HT-29 was plated in a 48-well plate (100,000 cells/well), and the cells were cultured overnight at 37° C. in the presence of 5% $CO_2$, treated with a test compound (250 μL/well) diluted in 3-fold dilution series and cultured for two more hours. After 2 hr, the culture medium containing the test compound was removed, and the cells were lysed with SDS sample buffer (100 μL/well) and heated at 95° C. for 5 min. Thereafter, the cells were applied to SDS-PAGE, and the protein was transferred onto Sequi-Blot™ PVDF Membrane (Bio-Rad, Richmond, Calif.) by the Western blot method. The cells were blocked with a block-Ace solution (Snow Brand Milk Products Co., Ltd) dissolved in phosphate buffer to 5% W/V, and reacted overnight with anti-phosphorylated MEK1/2 (Ser217/221) (Cell signaling #9121) diluted 1000-fold with phosphate buffer containing 0.4% block-Ace. The membrane was washed with phosphate buffer containing 0.1% Tween 20 (Wako Pure Chemical Industries, Ltd.), and reacted at room temperature for 1 hr with HRP labeled rabbit IgG polyclonal antibody (Cell signaling #7074) diluted 1000-fold with phosphate buffer containing 0.4% block-Ace. The membrane was washed in the same manner as above, chemical luminescence of a phosphorylated MEK1/2 protein labeled with the antibody, which was caused by ECL-plus Detection Reagent (Amersham bioscience), was detected by Luminescent Image Analyzer LAS-1000 (FUJIFILM Corporation). Taking the luminescence of the control group free of the test compound as 100%, the concentration ($IC_{50}$ value) of the compound necessary for inhibiting the residual luminescence to 50% of the control group was calculated. The results are shown in Table 11.

TABLE 11

| Example No. (compound No.) | $IC_{50}$ (nM) |
|---|---|
| 228 | <500 |
| 232 | <500 |

Test Example 8

Colon Cancer Cell HT-29 Growth Suppressive Action In Vitro

A cell suspension (100 μL, 3,000 cells/well) of human colon cancer cell HT-29 (purchased from ATCC) was plated in a 96-well plate, and the cells were cultured at 37° C. in a 5% carbon dioxide gas incubator. The next day, 2-fold serial dilution of each test compound solution (diluted from maximum concentration 20 μM) (100 μL) was added, and the cells were cultured for 3 days. The culture medium containing the test compound was removed, and the cells were washed with phosphate buffer (PBS). A 50% trichloroacetic acid solution was added to the final concentration of 10% (v/v), and the mixture was stood overnight at 4° C., whereby the cells were fixed to the plate. Then, a dye SRB 0.4% (W/V) solution (dissolved in 1% acetic acid) was added at 50 μl/well, whereby the cell protein was fixed and stained (Skehan et al., Journal Of National Cancer Institute, vol. 82, pp. 1107-1112, 1990). The cells were washed 3 times with 1% acetic acid solution (200 μL/well), and 100 μL of an extract (10 mM Tris buffer) was added to extract the dye. The absorbance at an absorption wavelength 550 nM was measured, and cell amount was measured as a protein amount. Taking the protein amount of the control group free of the test compound as 100%, the proportion of the residual protein amount of each treatment group was determined and the concentration of the compound necessary for suppressing the residual cell amount to 50% of the control ($IC_{50}$ value) was calculated. The results are shown in Table 12.

TABLE 12

| Example No. (compound No.) | $IC_{50}$ (nM) |
|---|---|
| 228 | <500 |
| 233 | <500 |

SEQUENCE LISTING Free Text

[SEQ ID NO:1]
Designed oligonucleotide primer to amplify DNA encoding human VEGFR2
[SEQ ID NO:2]
Designed oligonucleotide primer to amplify DNA encoding human VEGFR2
[SEQ ID NO:3]
Designed oligonucleotide primer to amplify DNA encoding human BRAF
[SEQ ID NO:4]
Designed oligonucleotide primer to amplify DNA encoding human BRAF
[SEQ ID NO:5]
Designed oligonucleotide primer to amplify DNA encoding human BRAF
[SEQ ID NO:6]
Designed oligonucleotide primer to amplify DNA encoding human BRAF Industrial Applicability The compounds (I), a salt thereof and a prodrug thereof of the present invention show superior inhibitory activity on kinases such as vascular endothelial growth factor receptor and the like. Therefore, a clinically useful agent for the prophylaxis or treatment of diseases related to the action of vascular endothelial growth factor in the living body (e.g., cancer etc.) can be provided. Moreover, since compounds (I), a salt thereof and a prodrug thereof of the present invention are also superior in efficacy expression, pharmacokinetics, solubility, interaction with other pharmaceutical products, safety and stability, they are useful as pharmaceutical agents.

This application is based on patent application Nos. 2007-149781 and 2007-223284 filed in Japan, the contents of which are incorporated in full herein by this reference.

The invention claimed is:

1. A compound represented by the formula (Id):

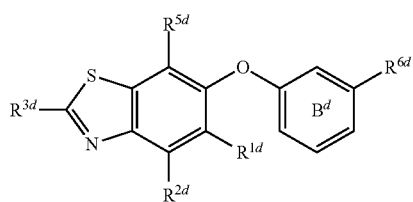

(Id)

wherein
$R^{1d}$ and $R^{2d}$ are a hydrogen atom,
$R^{3d}$ is a $C_{3-6}$ cycloalkyl-carbonylamino,
$R^{5d}$ is a hydrogen atom,
$R^{6d}$ is (1) an amino, (2) a mono-$C_{1-6}$ alkylamino,
(3) a di-$C_{1-6}$ alkylamino,
(4) a mono($C_{1-6}$ alkyl-carbonyl)amino optionally having 1 to 3 halogen atoms,
(5) a mono($C_{3-6}$ cycloalkyl-carbonyl)amino,
(6) a mono($C_{3-6}$ cycloalkenyl-carbonyl)amino,
(7) a mono($C_{6-10}$ aryl-carbonyl)amino optionally having 1 to 3 halogen atoms,
(8) a mono(5- or 6-membered monocyclic aromatic heterocyclyl-carbony)amino optionally having 1 to 3 substituents selected from the group consisting of
  (a) a halogen atom,
  (b) a $C_{1-6}$ alkyl optionally having 1 to 3 halogen atoms,
  (c) a $C_{1-6}$ alkoxy, and
  (d) a $C_{3-6}$ cycloalkyl,
(9) a mono(8- to 12-membered fused aromatic heterocyclyl-carbonyl)amino optionally having 1 to 3 substituents selected from the group consisting of (a) a halogen atom,
(b) a $C_{1-6}$ alkyl optionally having 1 to 3 halogen atoms,
(c) a $C_{1-6}$ alkoxy, and
(d) a $C_{3-6}$ cycloalkyl,
(10) a mono(3- to 8-membered non-aromatic heterocyclyl-carbonyl)amino,
(11) a mono-$C_{1-6}$ alkoxy-carbonylamino,
(12) a $C_{1-6}$ alkyl-aminocarbonyl,
(13) a di-$C_{1-6}$ alkyl-aminocarbonyl, or
(14) a nitro, and ring $B^d$ is a benzene ring optionally further having 1 or 2 $C_{1-6}$ alkyl substituents that optionally have 1 to 3 halogen atoms, or a salt thereof.

2. N-[3-({2-[(Cyclopropylcarbonyl)amino]-1,3-benzothiazol-6-yl}oxy)phenyl]-1,3-dimethyl-1H-pyrazole-5-carboxamide or a salt thereof.

3. A pharmaceutical composition comprising the compound of claim 1 or a salt thereof and a pharmacologically acceptable carrier.

4. The compound of claim 1, wherein $R^{6d}$ is a mono(5- or 6-membered monocycle aromatic heterocyclyl-carbonyl)amino optionally having 1 to 3 substituents selected from the group consisting of (a) a halogen atom, (b) a $C_{1-6}$ alkyl optionally having 1 to 3 halogen atoms, (c) a $C_{1-6}$ alkoxy, and (d) a $C_{3-6}$ cycloalkyl, or a salt thereof.

5. The compound of claim 1, wherein $R^{6d}$ is a mono(5- or 6-membered monocycle aromatic heterocyclyl-carbonyl)amino optionally having 1 to 3 $C_{1-6}$ alkyl, or a salt thereof.

6. N-[6-(3-Nitrophenoxy)-1,3-benzothiazol-2-yl]clcyclopropanecarboxamide or a salt thereof.

* * * * *

UNITED STATES PATENT AND TRADEMARK OFFICE
CERTIFICATE OF CORRECTION

| | |
|---|---|
| PATENT NO. | : 8,304,557 B2 |
| APPLICATION NO. | : 12/133063 |
| DATED | : November 6, 2012 |
| INVENTOR(S) | : Oguro et al. |

It is certified that error appears in the above-identified patent and that said Letters Patent is hereby corrected as shown below:

Title page, Item [75] Inventors: For address of Yuya Oguro, delete "Tsukuba" and insert --Fujisawa--.

Title page, Item [75] Inventors: For address of Shinichi Imamura, delete "Tsukuba" and insert --Fujisawa--.

Signed and Sealed this
Eleventh Day of March, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 69
<212> TYPE: DNA
<213> ORGANISM: Artificial
<220> FEATURE:
<223> OTHER INFORMATION: Designed oligonucleotide primer to amplify DNA
      encoding human VEGFR2

<400> SEQUENCE: 1
aattaagtcg acatggacta caaggatgac gatgacaaga agcgggccaa tggaggggaa       60
ctgaagaca                                                              69

<210> SEQ ID NO 2
<211> LENGTH: 42
<212> TYPE: DNA
<213> ORGANISM: Artificial
<220> FEATURE:
```

-continued

```
<223> OTHER INFORMATION: Designed oligonucleotide primer to amplify DNA
      encoding human VEGFR2

<400> SEQUENCE: 2
aattaagcat gcttaaacag gaggagagct cagtgtggtc cc                    42

<210> SEQ ID NO 3
<211> LENGTH: 64
<212> TYPE: DNA
<213> ORGANISM: Artificial
<220> FEATURE:
<223> OTHER INFORMATION: primer for cloning human BRAF gene

<400> SEQUENCE: 3
aaagaattca ccatggacta caaggacgac gatgacaaga cccccctgc ctcattacct   60 ggct                                                              64

<210> SEQ ID NO 4
<211> LENGTH: 35
<212> TYPE: DNA
<213> ORGANISM: Artificial
<220> FEATURE:
<223> OTHER INFORMATION: primer for cloning human BRAF gene

<400> SEQUENCE: 4
aaaagtcgac tcagtggaca ggaaacgcac catat                            35

<210> SEQ ID NO 5
<211> LENGTH: 29
<212> TYPE: DNA
<213> ORGANISM: Artificial
<220> FEATURE:
<223> OTHER INFORMATION: primer for cloning human BRAF gene

<400> SEQUENCE: 5
ggtctagcta cagagaaatc tcgatggag                                   29

<210> SEQ ID NO 6
<211> LENGTH: 29
<212> TYPE: DNA
<213> ORGANISM: Artificial
<220> FEATURE:
<223> OTHER INFORMATION: primer for cloning human BRAF gene

<400> SEQUENCE: 6
ctccatcgag atttctctgt agctagacc                                   29
```